United States Patent
Nadler et al.

(10) Patent No.: US 9,228,018 B2
(45) Date of Patent: *Jan. 5, 2016

(54) ANTIBODY POLYPEPTIDES THAT ANTAGONIZE CD40L

(71) Applicants: Bristol-Myers Squibb Company, Princeton, NJ (US); Domantis Limited, Brentford, Middlesex (GB)

(72) Inventors: Steven G. Nadler, Princeton, NJ (US); James K. Tamura, Yardley, PA (US); Laura Price, Langhorne, PA (US); Robert P. Rehfuss, North Wales, PA (US); Suzanne J. Suchard, Wilmington, DE (US); Anish Suri, Yardley, PA (US); James William Bryson, Langhorne, PA (US); Aaron Yamniuk, Lawrenceville, NJ (US); Steven Grant, Swaffham Prior (GB); Olga Ignatovich, Cambridge (GB); Philip Drew, Histon (GB)

(73) Assignees: BRISTOL-MYERS SQUIBB COMPANY, Princeton, NJ (US); DOMANTIS LIMITED, Brentford, Middlesex (GB)

(*) Notice: Subject to any disclaimer, the term of this patent is extended or adjusted under 35 U.S.C. 154(b) by 0 days.

This patent is subject to a terminal disclaimer.

(21) Appl. No.: 14/510,474

(22) Filed: Oct. 9, 2014

(65) Prior Publication Data

US 2015/0023976 A1 Jan. 22, 2015

Related U.S. Application Data

(63) Continuation of application No. 13/650,493, filed on Oct. 12, 2012, now Pat. No. 8,895,010.

(60) Provisional application No. 61/546,800, filed on Oct. 13, 2011, provisional application No. 61/655,110, filed on Jun. 4, 2012.

(51) Int. Cl.

| | |
|---|---|
| *A61K 39/395* | (2006.01) |
| *C07K 16/28* | (2006.01) |
| *A61K 45/06* | (2006.01) |
| *C07K 16/46* | (2006.01) |
| *C07K 16/18* | (2006.01) |
| *A61K 39/00* | (2006.01) |
| *A61K 38/00* | (2006.01) |

(52) U.S. Cl.
CPC ......... *C07K 16/2878* (2013.01); *A61K 39/3955* (2013.01); *A61K 45/06* (2013.01); *C07K 16/18* (2013.01); *C07K 16/283* (2013.01); *C07K 16/2833* (2013.01); *C07K 16/2875* (2013.01); *C07K 16/2896* (2013.01); *C07K 16/46* (2013.01); *C07K 16/468* (2013.01); *A61K 38/00* (2013.01); *A61K 2039/505* (2013.01); *A61K 2039/545* (2013.01); *C07K 2317/21* (2013.01); *C07K 2317/31* (2013.01); *C07K 2317/52* (2013.01); *C07K 2317/565* (2013.01); *C07K 2317/567* (2013.01); *C07K 2317/569* (2013.01); *C07K 2317/76* (2013.01); *C07K 2317/92* (2013.01); *C07K 2317/94* (2013.01); *C07K 2319/00* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,876,950 A | 3/1999 | Siadak et al. | |
| 6,001,358 A | 12/1999 | Black et al. | |
| 7,094,874 B2 | 8/2006 | Peach et al. | |
| 7,482,327 B2 | 1/2009 | Hagerty et al. | |
| 8,895,010 B2 * | 11/2014 | Nadler et al. | 424/154.1 |
| 2010/0166774 A1 | 7/2010 | Dali et al. | |

FOREIGN PATENT DOCUMENTS

| | | |
|---|---|---|
| WO | WO-2005003175 A2 | 1/2005 |
| WO | WO-2005035572 A2 | 4/2005 |
| WO | WO-2006030220 A1 | 3/2006 |
| WO | WO-2010023482 A2 | 3/2010 |
| WO | WO-2012115241 A1 | 8/2012 |
| WO | WO-2013118858 A1 | 8/2013 |

OTHER PUBLICATIONS

Borcherding et al., The CD40-CD40L pathway contributes to the proinflammatory function of intestinal epithelial cells in inflammatory bowel disease. Am J Pathol. (2010) 176(4):1816-27. {doi: 102353/ajpath.2010.090461. Epub Feb. 4, 2010}.

Aruffo, et al., "The CD40 Ligand, gp39, Is Defective in Activated T Cells from Patients with X-Linked Hyper-Igm Syndorme," *Cell* (1993) 72:291-300.

Ashokkumar, et al., "Allospecific CD154+ T Cells Associate with Rejection Risk After Pediatric Liver Transplantation," *Amer. J. Transplantation* (2009) 9: 179-191.

Ashokkumar, et al., Allospecific CD154+ T cells identify rejection-prone recipients after pediatric small-bowel transplantation, *Surgery* (2009) 146: 166-173.

(Continued)

*Primary Examiner* — Phillip Gambel
(74) *Attorney, Agent, or Firm* — Drinker Biddle & Reath LLP

(57) ABSTRACT

Antibody polypeptides that specifically bind human CD40L are provided. The antibody polypeptides do not activate platelets. The antibody polypeptides are useful in the treatment of diseases involving CD40L activation, such as graft-related diseases and autoimmune diseases. The antibody polypeptides may be domain antibodies (dAbs) comprising a single $V_H$ or $V_K$ domain. The half-life of the antibody polypeptides may be increased by modifying the antibody polypeptides to be dual specific reagents that can also bind human serum albumin (HSA) or another antigen.

35 Claims, 26 Drawing Sheets
(20 of 26 Drawing Sheet(s) Filed in Color)

(56) References Cited

OTHER PUBLICATIONS

Bartlett, et al., "Analysis of Intragraft Gene and Protein Expression of Costimulatory Molecules, CD80, CD86 and CD154, and Orthotopic Liver Transplant Recipients," *Amer. J. Transplantation* (2003) 3: 1363-1368.

Baumgart, et al., "Exaggerated inflammatory response of primary human myeloid dendritic cells to lipopolysaccharide in patients with inflammatory bowel disease," *Clinical and Experimental Immunology* (2009) 157: 423-436.

Biaconne, et al., "Expression of inducible lymphocyte costimulatory molecules in human renal allograft," *Nephrol. Diall. Transplant.* (1998) 13: 716-722.

Boumpas, et al., "A Short Course of BG9588 (Anti-CD40 Ligand Antibody) Improves Serologic Activity and Decreases Hematuria in Patients With Proliferative Lupus Glomerulonephritis," *Arthritis & Rheumatism* (2003), 48: 719-727.

Danese, et al., "Activated platelets are the source of elevated levels of soluble CD40 ligand and the circulation of inflammatory bowel disease patients," *Gut* (2003) 52: 1435-1441.

Grammer, et al., Abnormal germinal center reactions in systemic lupus erythematosus demonstrated by blockade of CD154-CD40 interactions *J. Clin. Invest.* (2003) 112: 1506-1520.

Kasran, et al., "Safety and tolerability of antagonist anti-human CD40 Mab ch5D12 in patients with moderate to severe Crohn's disease," *Aliment. Pharmacol. Ther.* (2005) 22: 111-122.

Kawai, et al., "CD154 Blockade for Induction of Mixed Chimerism and Prolonged Renal Allograft Survival in Nonhuman Primates," *Amer. J. Transplantation* (2004) 4: 1391-1398.

Kenyon, et al., "Long-term survival and fuction of intrahepatic islet allografts in rhesus monkeys treated with humanized anti-CD154," *Proc. Natl. Acad. Sci. USA* (1999) 96: 8132-8137.

Kimura, et al., "Study of Plasma Levels of Soluble CD40 Ligand in Systemic Lupus Erythematosus Patients Who Have Undergone Plasmapheresis," *Therapeutic Apheriss and Dialysis* (2005) 9: 64-68.

Kirk, et al., "CTLA4-Ig and anti-CD40 ligand prevent renal allograft rejection in primates," *Proc. Natl. Acad. Sci. USA* (1997) 94: 8789-8794.

Komura, et al., "Elevated Circulating CD40 Concentrations in Patients with Systemic Sclerosis," *J. Reumatol.* (2004) 31: 514-519.

Ludwiczek, et al., "Plasma levels of soluble CD40 ligand are elevated in inflammatory bowel diseases," *Int. J. Colorectal Dis.* (2003) 18: 142-147.

Mach, et al., "Reduction of Atherosclerosis in mice by inhibition of CD40 signalling," *Nature* (1998) 394: 200-203.

Menchen, et al., "Matrix metalloproteinase 9 in involved in Crohn's disease associated platelet hyperactivation through th release of soluble CD40 ligand," *Gut* 58: (2009) 920-928.

Mirabet, et al., Platelet pro-aggregatory effects of CD40 monoclonal antibody. *Mol. Immunol.* (2008) 45: 937-44.

Montgomery, et al., "Combination Induction Thereapy With Monoclonal Antibodies Specific for CE80, CD86, and CD154 in Nonhuman Primate Renal Transplantation," *Transplantation* (2002) 74: 1365-1369.

Orozco, et al., "Association of CD40 with rheumatoid arthritis confirmed in a large UK case-control study," *Ann. Rheum. Dis.* (2010) 69: 813-816.

Patel, et al., "The effect of anti-CD40 ligand in immune thrombocytopenic purpura," *British J. Haematology* (2008) 141: 545-548.

Prahalad, et al., "Elevated serum levels of soluble CF154 in children with juvenile idiopathic arthritis." *Pediatric Rheumatology* (2008) 6: 1-8.

Preston, et al., "IDEC-131 (Anti-CD154), Sirolimus and Donor Specific Transfusion Facilitate Operational Tolerance in Non-Human Primates," *Amer. J. Transplantation* (2005) 5: 1032-1041.

Raychaudhuri, et al., "Common variants at CD40 and other loci confer risk of rheumatoid arthritis", *Nature Genetics* (2008) 40: 1216-1223.

Robles-Carrillo, et al., "Anti-CD40L Immune Complexes Potently Activate Platelets In Vitro and Cause Thrombosis in FCGRA2A Transgenic Mice," *The Journal of Immunology* (2010) 185: 1577-1583.

Schönbeck, et al., "Inhibition of CD40 signaling limits evolution of established atherosclerosis in mice," *Proc. Natl. Acad. Sci.* (2000) 97: 7458-7463.

Schuler, et al., "Efficacy and Safety of AB1793, A Novel Human Anti-Human CD154 Monoclonal Antibody, in Cynomolgus Monkey Renal Allotransplantation," *Transplantation* (2004) 77: 717-726.

Vakkalanka, et al., "Elevated Levels and Functional Capacity of Soluble CD40 Ligand in Systemi Lupus Erythematosus Sera,", *Arthritis & Rheumatism* (1999) 42: 871-881.

Xu, et al., "Effects of Dose and Duration of Anti-CD154 Antibody Therapy in Preventing Renal Allograft Rejection in a Nonhuman Primate Model," *Transplantation Proceedings* (2001) 33: 223-224.

Adams, et al., "Development of a Chimeric Anti-CD40 Monoclonal Antibody That Synergizes with LEA29Y to Prolong Islet Allograft Survival" (2005) J. Immunol. 174: 542-550.

Daoussis, et al., "Increased expression of CD154 (CD40L) on stimulated T-cells from patients with psoriatic arthritis", *Rheumatology* (2007) 46: 227-231.

Chapman, et al., "PEGylated antibodies and antibody fragments for improved therapy: a review," *Adv. Drug Deliv. Rev.* (2002) 54(4):531-545.

de Kruif, et al., "Rapid selection of cell subpopulation-specific human monoclonal antibodies from a synthetic phage antibody library", *Proc. Natl. Acad. Sci. USA* (1995) 92: 3938-3942.

Duffau, et al., "Platelet CD154 Potentiates Interferon-α Secretion by Plasmacytoid Dendritic Cells in Systemic Lupus Erythematosus", *Sci. Transl. Med.* (2010) 2: 47: 1-10 (2010).

Durie, et al., "Antibody to the Ligand of CD40, GP39, Blocks the Occurrence of the Acute and Chronic Forms of Graft-vs-Host Disease", *J. Clin. Invest.* (1994) 94: 1333-1338.

Ferroni, et al., "Contribution of Platelet-Derived CD40 Ligand to Inflammation, Thrombosis and Neoangiogenesis". *Curr. Med. Chem.* (2007) 14: 2170-2180.

Garcia, et al., "Monocytic suppressive cells mediate cardiovascular transplantation tolerance in mice", *J. Clin. Inv.* (2010) 120: 2486-2496.

Gilson, et al., "Anti-CD40 Monoclonal Antibody Synergizes with CTLA4-Ig in Promoting Long-Term Graft Survival in Murine Models of Transplantation", *J. Immunol.* (2009) 183: 1625-1635.

Harrison, et al., "Screening of Phage Antibody Libraries", *Meth. Enzymol.* (1996) 267: 83-109.

Hoogenboom, et al., "Multi-subunit proteins on the surface of filamentous phage: methodologies for displaying antibody (Fab) heavy and light chains", *Nucleic Acids Res.* (1991) 19:4133-4137.

Huang, et al., "The Effect of Anti-CD40 Ligand Antibody on B Cells in Human Systemic Lupus Erythematosus", *Arthritis & Reumatism* (2002) 46: 1554-1562.

Im, et al., "Blockade of CD40 Ligand Suppresses Chronic Experimental Myasthenia Gravis by Down-Regulation of Th1 Differentiation and Up-Regulation of CTLA-4", *J. Immunol.* (2001) 166: 6893-6898.

Kanmaz, et al., "Monotherapy with the Novel Human Anti-CD-154 Monoclonal Antibody ABI793 in Rhesus Monkey Renal Transplantation Model", *Transplantation* (2004) 77: 914-920.

Koyama, et al., "Thrombophilia Associated With Anti-CD154 Monoclonal Antibody Treatment and Its Prophylaxis in Nonhuman Primates", Transplantation (2004) 77: 460-461.

Kuwana, et al., "T and B Cell Collaboration Is Essential for the Autoantibody Response to DNA Topoisomerase I in Systemic Sclerosis", *J. Immunol.* (1995) 155: 2703-2714.

Larsen, et al., "Rational Development of LEA29Y (belatacept), a High-Affinity Variant of CTLA4-Ig with Potent Immunosuppressive Properties", *Amer. J. Transplant.* (2005) 5: 443-453.

Lederer, et al., "Reduced CD40L Expression on ex vivo Activated CD4+ T-Lymphocytes from Patients with Execellent Renal Allograft Function Measured with a Rapid Whole Blood Flow Cytometry Procedure", *Int. Arch. Allergy Immunol.* (2004) 133: 276-284.

(56) References Cited

OTHER PUBLICATIONS

Marks, et al., "Human Antibody Fragments Specific for Human Blood Group Antigens from a Phage Display Library", *BioTechnology* (1993) 11: 1145-1149.

Oosterwegel, et al., "CTLA-4 and T cell activation", *Curr. Opin. Immunol.* (1999) 11: 294-300.

Reilly, et al., "Genetic Diversity in Human Fc Receptor II for Immunoglobulin G: Fcγ Receptor IIA Ligand-Binding Polymorphism", *Clin. Diagn. Lab. Immunol.* (1994) 1: 640-644.

Shi, et al., "Differential requirements for CD28 and CD40 ligand in the induction of experimental autoimmune myasthenia gravis", *Eur J. Immunol.* (1998) 28: 3587-3593.

Tomiyama, et al., "Response of Human Platelets to Activating Monoclonal Antibodies: Importance of FcγRII (CD32) Phenotype and Level of Expression", *Blood* (1992) 80: 2261-2268.

Daley et al., "Fc-Disabled Anti-Mouse CD40L Antibodies Retain Efficacy in Promoting Transplantation Tolerance," American Journal of Transplantation, Nov. 1, 2008, vol. 8, No. 11, pp. 2265-2271.

Yan Ge, et al., "Functional expression of chimeric Fab of an anti-CD40L mAb: Vector design an culture condition optimization", Biomedicine & Pharmacotherapy, Sep. 17, 2010, vol. 65, No. 1, pp. 52-59.

Holt, et al., "Domain antibodies: proteins for therapy", Trends in Biotechnology, Nov. 1, 2003, vol. 21, No. 11, pp. 484-490.

Suri, et al., Investigative Studies Demonstrate Reduced Risk for Thromboembolism (TE) by BMS-986004, an Anti-CD40L Domain antibody, Session 71: Novel Approaches to Treatment & Monitoring of Allograft Injury, Jun. 6, 2012, Publication Page No. 518, XP002690660, Abstract.

International Search Report dated Mar. 12, 2013, issued in PCT Application No. PCT/US2012/059977 filed Oct. 12, 2012.

International Preliminary Report on Patentability and Written Opinion of the International Search Authority mailed Apr. 24, 2014 in PCT Application No. PCT/US2012/059977.

\* cited by examiner

FIG. 1A

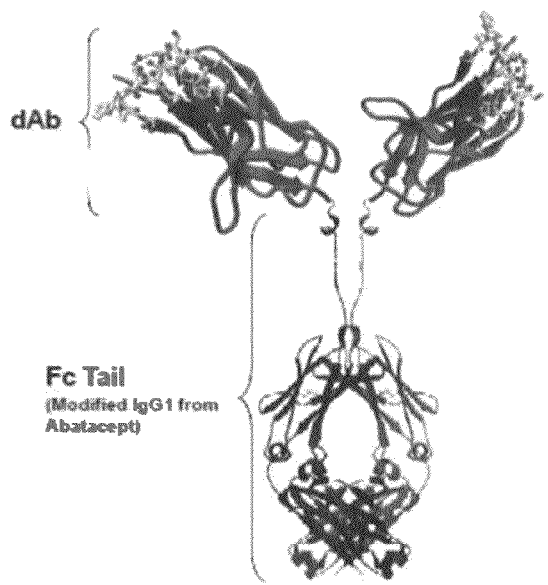

FIG. 1B

EVQLLESGGGLVQPGGSLRLSCAASGFTFNWELMGWARQAPGKGLEWVSGIEGPGDVTYYADSVKGRFTISRDNSKNTLYLQMNSLRAEDTAVYY
CVKVGKDAKSDYRGQGTLVTVSSASTEPKSSDKTHTSPPSPAPELLGGSSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQ
PENNYKTTPPVLDSDGSFFLYSKLTVDKSRWQQGNVFSCSVMHEALHNHYTQKSLSLSPGK
(MW=77,984 daltons)

dAb
Linker
Modified IgG1 Fc from Abatacept (Cys→Ser; Pro→Ser)

FIG. 3

Fc
Domain antibody-[AS]-THTCPPCP...

CT-long
Domain antibody-[AST]-EPKSSDKTHTSPPSP...

CT-short
Domain antibody-[AS]-THTSPPSP...

N297Qlong Fc
Domain antibody-[AST]-EPKSSDKTHTSPPSP...

N297Qshort Fc
Domain antibody-[AS]-THTSPPSP...

Osteonectin signal peptide sequence:
MRAWIFFLLCLAGRALA ^ EVQLLES...(start of Domain antibody)

FIG. 4

BMS2h-572-633-CT-L2

MRAWIFFLLCLAGRALA^EVQLLESGGGLVQPGGSLRLSCAASGFTFNWELMGWARQAPGKGLE
WVSGIEGPGDVTYYADSVKGRFTISRDNSKNTLYLQMNSLRAEDTAVYYCVKVGKDAKSDYRGQ
GTLVTVSS[AST]EPKSSDKTHTSPPSPAPELLGGSSVFLFPPKPKDTLMISRTPEVTCVVVDVSH
EDPEVKFNWYVDGVEVHNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPGK

BMS2h-572-633-CT-S1

MRAWIFFLLCLAGRALA^EVQLLESGGGLVQPGGSLRLSCAASGFTFNWELMGWARQAPGKGLE
WVSGIEGPGDVTYYADSVKGRFTISRDNSKNTLYLQMNSLRAEDTAVYYCVKVGKDAKSDYRGQ
GTLVTVSS[AS]THTSPPSPAPELLGGSSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIEKTISKAK
GQPREPQVYTLPPSRDELTKNQVSLTCLVKGFYPSDIAVEWESNGQPENNYKTTPPVLDSDGSF
FLYSKLTVDKSRWQQGNVFSCSVMHEALHNHYTQKSLSLSPGK

BMS2h-572-633-N297Q long Fc

MRAWIFFLLCLAGRALA^EVQLLESGGGLVQPGGSLRLSCAASGFTFNWELMGWARQAPGKGLE
WVSGIEGPGDVTYYADSVKGRFTISRDNSKNTLYLQMNSLRAEDTAVYYCVKVGKDAKSDYRGQ
GTLVTVSS[AST]EPKSSDKTHTCPPCPAPELLGGPSVFLFPPKPKDTLMISRTPEVTCVVVDVSH
EDPEVKFNWYVDGVEVHNAKTKPREEQYQSTYRVVSVLTVLHQDWLNGKEYKCKVSNKALPAPI
EKTISKAKGQPREPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPGK

BMS2h-572-633-N297Q short Fc

MRAWIFFLLCLAGRALA^EVQLLESGGGLVQPGGSLRLSCAASGFTFNWELMGWARQAPGKGLE
WVSGIEGPGDVTYYADSVKGRFTISRDNSKNTLYLQMNSLRAEDTAVYYCVKVGKDAKSDYRGQ
GTLVTVSS[AS]THTCPPCPAPELLGGPSVFLFPPKPKDTLMISRTPEVTCVVVDVSHEDPEVKFN
WYVDGVEVHNAKTKPREEQYQSTYRVVSVLTVLHQDWLNGKEYKCKVSNKALPAPIEKTISKAK
GQPREPQVYTLPPSRDELTKNQVSLTCLVKGFYPSDIAVEWESNGQPENNYKTTPPVLDSDGSF
FLYSKLTVDKSRWQQGNVFSCSVMHEALHNHYTQKSLSLSPGK

FIG. 14
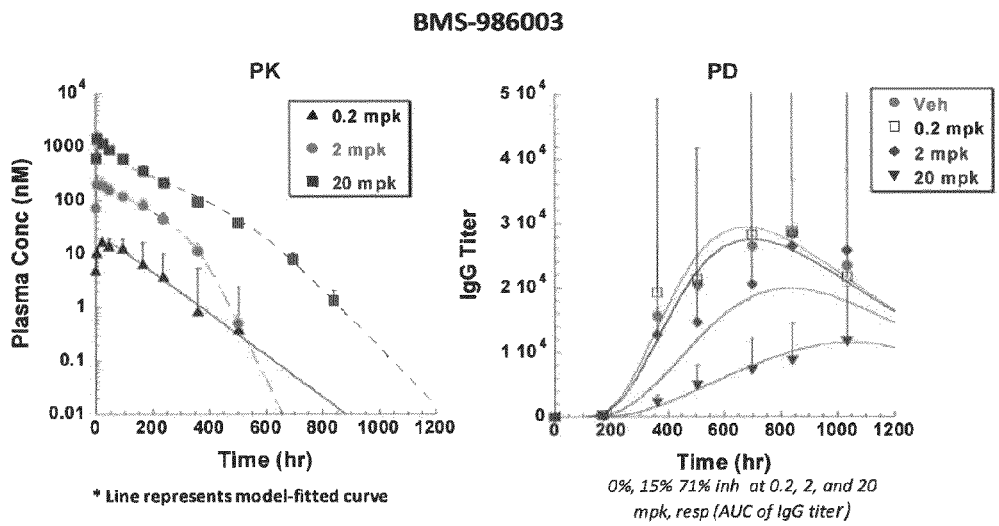
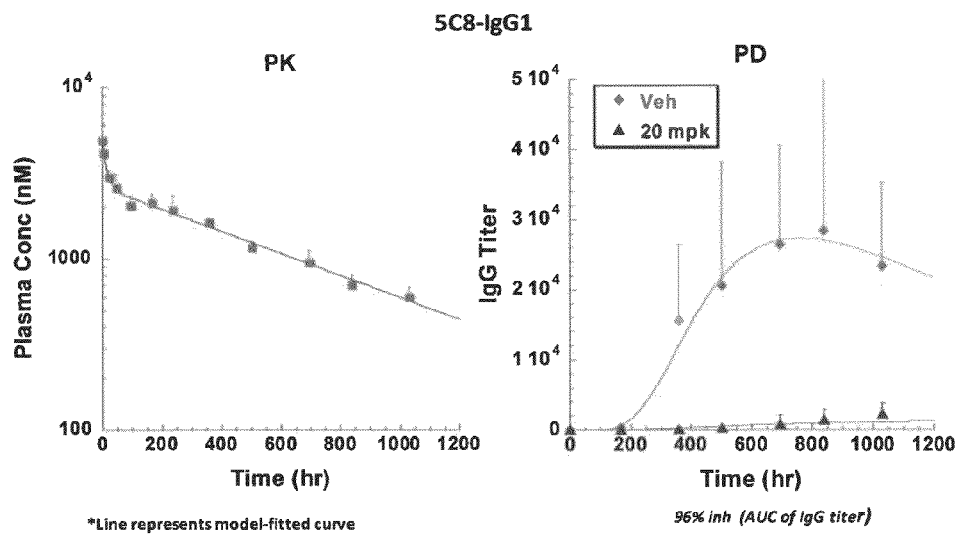

FIG. 21

```
                            CDR1                                              CDR2
BMS2h-572-6    EVQLLESGGGLVQPGGSLRLSCAASGFTFNWQLMGWVRQAPGKGLEWVSGIEGPGDVTYY  60
BMS2h-572-608  EVQLLESGGGLVQPGGSLRLSCAASGFTFNWELMGWARQAPGKGLEWVSGIEGPGDVTYY  60
BMS2h-572-614  EVQLLESGGGLVQPGGSLRLSCAASGFTFNWQLMGWVRQAPGKGLEWVSGIEGPGDVTYY  60
BMS2h-572-619  EVQLLESGGGLVQPGGSLRLSCAASGFTFNWQLMGWVRQAPGKGLEWVSGIEGPGDVTYY  60
BMS2h-572-633  EVQLLESGGGLVQPGGSLRLSCAASGFTFNWELMGWARQAPGKGLEWVSGIEGPGDVTYY  60
BMS2h-572-634  EVQLLESGGGLVQPGGSLRLSCAASGFTFNWELMGWARQAPGKGLEWVSGIEGPGDVTYY  60
BMS2h-572-635  EVQLLESGGGLVQPGGSLRLSCAASGFTFNWELMGWARQAPGKGLEWVSGIEGPGDVTYY  60
               ********************************** ***** ******************

CDR2                                    CDR3
BMS2h-572-6    ADSVKGRFTISRDNSKNTLYLQMNSLRAEDTAVYYCVKVGKESNSDYRGQGTLVTVSS  118
BMS2h-572-608  ADSVKGRFTISRDNSKNTLYLQMNSLRAEDTAVYYCVKVGKESNSDYRGQGTLVTVSS  118
BMS2h-572-614  ADSVKGRFTISRDNSKNTLYLQMNSLRAEDTAVYYCVKVGKDAKSDYRGQGTLVTVSS  118
BMS2h-572-619  ADSVKGRFTISRDNSKNTLYLQMNSLRAEDTAVYYCVKVGKDSRSDYRGQGTLVTVSS  118
BMS2h-572-633  ADSVKGRFTISRDNSKNTLYLQMNSLRAEDTAVYYCVKVGKDAKSDYRGQGTLVTVSS  118
BMS2h-572-634  ADSVKGRFTISRDNSKNTLYLQMNSLRAEDTAVYYCVKVGKDSRSDYRGQGTLVTVSS  118
BMS2h-572-635  ADSVKGRFTISRDNSKNTLYLQMNSLRAEDTAVYYCVKVGKDSKSDYRGQGTLVTVSS  118
               ****************************************  ***************
```

FIG. 22

|  | CDR1 | CDR2 |  |
|---|---|---|---|
| BMS2h-719-2 | EVQLLESGGGLVQPGGSLRLSCAAASGFTFKRYEMMWVRQAPGKGLEWVSSISSDGSFTYY | 60 |
| BMS2h-719-202 | EVQLLESGGGLVQPGGSLRLSCAAASGFTFKKYEMMWVRQAPGKGLEWVSSISSDGSFTYY | 60 |
| BMS2h-719-203 | EVQLLESGGGLVQPGGSLRLSCAAASGFTFNSYEMMWVRQAPGKGLEWVSSISSDGSFTYY | 60 |
| BMS2h-719-213 | EVQLLESGGGLVQPGGSLRLSCAAASGFTFKRYEMMWVRQAPGKGLEWVSSISSDGSFTYY | 60 |
| BMS2h-719-214 | EVQLLESGGGLVQPGGSLRLSCAAASGFTFKRYEMMWVRQAPGKGLEWVSSISSDGSFTYY | 60 |
| BMS2h-719-215 | EVQLLESGGGLVQPGGSLRLSCAAASGFTFKRYEMMWVRQAPGKGLEWVSSISSDGSFTYY | 60 |
| BMS2h-719-218 | EVQLLESGGGLVQPGGSLRLSCAAASGFTFKRYEMMWVRQAPGKGLEWVSSISSDGSFTYY | 60 |
| BMS2h-719-225 | EVQLLESGGGLVQPGGSLRLSCAAASGFTFNTYEMQWVRQAPGKGLEWVSSISSDGSFTYY | 60 |
|  | **** ***************************************** |  |

|  | CDR2 | CDR3 |  |
|---|---|---|---|
| BMS2h-719-2 | ADSVKGRFTISRDNSKNTLYLQMNSLRAEDTAVYYCAEPFTEFDYWGHGTLVTVSS | 116 |
| BMS2h-719-202 | ADSVKGRFTISRDNSKNTLYLQMNSLRAEDTAVYYCAEPFTEFDYWGHGTLVTVSS | 116 |
| BMS2h-719-203 | ADSVKGRFTISRDNSKNTLYLQMNSLRAEDTAVYYCAEPFTEFDYWGHGTLVTVSS | 116 |
| BMS2h-719-213 | ADSVKGRFTISRDNSKNTLYLQMNSLRAEDTAVYYCADPFTEMDYWGHGTLVTVSS | 116 |
| BMS2h-719-214 | ADSVKGRFTISRDNSKNTLYLQMNSLRAEDTAVYYCADPFTEFDYWGHGTLVTVSS | 116 |
| BMS2h-719-215 | ADSVKGRFTISRDNSKNTLYLQMNSLRAEDTAVYYCAEPFTELDYWGHGTLVTVSS | 116 |
| BMS2h-719-218 | AESVKGRFTISRDNSKNTLYLQMNSLRAEDTAVYYCAEPFTEFDYWGHGTLVTVSS | 116 |
| BMS2h-719-225 | ADSVKGRFTISRDNSKNTLYLQMNSLRAEDTAVYYCAEPFTEFDYWGHGTLVTVSS | 116 |
|  | * ******************************** **** *************** |  |

FIG. 23

```
BMS2h-503-1    DIQMTQSPSSLSASVGDRVTITCRASHHIQRYLSWYQQKPGKAPKLLILWGSQLQSGVPS  60
BMS2h-503-2    DIQMTQSPSSLSASVGDRVTITCRASHDIQRYLSWYQQKPGKAPKLLILWGSQLQSGVPS  60
               *************************** ********************************

BMS2h-503-1    RFSGSGSGTDFTLTISSLQPEDFATYYCGQWVAPPQTFGQGTKVEIKR  108
BMS2h-503-2    RFSGSGSGTDFTLTISSLQPEDFATYYCGQWVAPPQTFGQGTKVEIKR  108
               ************************************************
```

FIG. 24

```
BMS2h-116-1312    DIQMTQSPSSLSASVGDRVTITCRASQPIGPDLLWYQQKPGKAPKLLIYQTSILRSGVPS 60
BMS2h-116-1313    DIQMTQSPSSLSASVGDRVTITCRASQPIGPDLLWYQQKPGKAPKLLIYQTSILRSGVPS 60
BMS2h-116-1320    DIQMTQSPSSLSAYVGDRVTITCRASQPIGPDLLWYQQKPGKAPKLLIYQTSILRSGVPS 60
                  ************ *** *******************************************

BMS2h-116-1312    RFSGSGSETDFTLTISNLQPEDLATYYCQQYWAFPVTFGKGTKVVIKR 108
BMS2h-116-1313    RFSGSGSETDFTLTISNLQPEDFATYYCQQYWAFPVTFGRGTKVVIKR 108
BMS2h-116-1320    RFSGSGSETDFTLTISNLQPEDFAKYYCQQYWAFPVTFGQGTKVVIKR 108
                  ********************* * * ************* ********
```

ANTIBODY POLYPEPTIDES THAT ANTAGONIZE CD40L

REFERENCE TO RELATED APPLICATIONS

This application is a continuation of U.S. application Ser. No. 13/650,493, filed Oct. 12, 2012, now U.S. Pat. No. 8,895,010, issued Nov. 25, 2014, which claims the benefit of U.S. Provisional Application No. 61/546,800, filed Oct. 13, 2011, and U.S. Provisional Application No. 61/655,110, filed Jun. 4, 2012, which are herein incorporated by reference in their entirety.

TECHNICAL FIELD

Antibodies and fragments thereof that target CD40L, compositions comprising the same, and methods of using the same for treatment of diseases involving CD40L activity are provided.

SEQUENCE LISTING

The instant application contains a Sequence Listing which has been submitted in ASCII format via EFS-Web and is hereby incorporated by reference in its entirety. Said ASCII copy, created on Oct. 9, 2014, is named 200896-0005-02-518050-SEQLIST.txt and is 1,224,704 bytes in size.

BACKGROUND

CD40 ligand (CD40L), also known as CD154, gp39, TNF-related activation protein (TRAP), 5c8 antigen, or T-BAM, is a trimeric transmembrane protein of the tumor necrosis factor (TNF) superfamily of molecules. CD40L is primarily expressed on activated T cells, as well as on activated leukocytes, eosinophils, basophils, natural killer cells, mast cells, and non-immune cells such as platelets and activated endothelial cells. CD40L also exists in soluble form (sCD40L) that is produced by microsomal stimulus-dependent cleavage of the membrane-bound CD40L. Most of sCD40L in circulation (>90%) is platelet-derived.

CD40L binds CD40, a type I transmembrane glycoprotein belonging to the TNF receptor (TNFR) family. Although all monomeric, dimeric, and trimeric forms of sCD40L can bind to CD40, the trimeric form of sCD40L has the most potent biological activity through oligomerization of cell surface CD40, a common feature of TNFR family. The highest expression of CD40 has been observed on antigen presenting cells (APCs), such as B cells, macrophages, and dendritic cells, while lower expression of this receptor is noted on a variety of other cell types, including stromal cells and thymic epithelium. The CD40-CD40L interaction is essential for normal T-B cell interactions, including increased co-stimulation, T-cell priming, cytokine production, antibody-class switching and affinity maturation, and antibody and autoantibody production.

The crucial role of CD40-CD40L interactions in immune and inflammatory responses has made them a promising target for treatment of pathological immuno-inflammatory processes. Blockade of CD40-CD40L interactions by means of specific CD40L monoclonal antibodies (mAbs) successfully prevents allograft rejection in primates and treats autoimmune diseases and atherosclerosis in animal models. Montgomery et al., *Transplantation* 74: 1365-1369 (2002).

In humans, two different anti-CD40L mAb clones have been used in clinical trials for treatment of different autoimmune diseases. Maribel et al., *Mol. Immunol.* 45: 937-44 (2008). Monoclonal antibodies, however, can display unusually high incidence of thromboembolic (TE) complications, such as atherothrombotic central nervous system events, myocardial infarction, pulmonary embolism, and deep vein thrombosis. For example, the usefulness of the anti-CD40L mAb clone hu5c8 (anti-CD40L mAb, Biogen) is limited by an unusually high incidence of TE complications. TE by these antibodies is thought to result from the formation of higher-order immune complexes (IC) of the mAbs with membrane-bound CD40L on platelets, or sCD40L shed from platelets, that can ligate and thereby aggregate neighboring platelets via their FcgRIIa receptors, resulting in thrombi formation. The risk of thromboembolism has led to a halt in all ongoing clinical trials. Boumpas et al., *Arthritis & Rheumatism* 48: 719-727 (2003).

SUMMARY

Anti-CD40L antibody antagonists that are less likely to cause platelet aggregation and thus cause thromboembolism are still needed in a clinical setting. Novel antibody polypeptides that specifically bind human CD40L are provided. The antibody polypeptides advantageously do not cause platelet aggregation. The antibody polypeptides are useful in the treatment of diseases involving CD40L activation, including autoimmune diseases, transplant rejection, and allergic responses. The antibody polypeptides comprise a variable domain. Exemplary antibody polypeptides are in the form of a domain antibody (dAb) that contains a single variable domain. Alternatively, the dAbs can be bi-specific reagents that comprise a second variable domain that can bind another antigen, such as human serum albumin (HSA), for example.

An antibody polypeptide is provided comprising a first variable domain that specifically binds human CD40L, wherein the first variable domain comprises the amino acid sequence of one of the variable domains selected from the BMS2h lineage. Further provided is an isolated antibody polypeptide comprising a first variable domain that specifically binds human CD40L, wherein CD40L comprises the amino acid sequence of SEQ ID NO: 1, wherein the amino acid sequence of the first variable domain comprises: (a) a CDR1 region which differs from the CDR1 region of BMS2h-572-633 by up to three amino acids, (b) a CDR2 region which differs from the CDR2 region of BMS2h-572-633 by up to three amino acids, (c) a CDR3 region which differs from the CDR3 region of BMS2h-572-633 by up to three amino acids, (d) a FR1 region which differs from the FR1 region of BMS2h-572-633 by up to three amino acids, (e) a FR2 region which differs from the FR2 region of BMS2h-572-633 by up to three amino acids, (f) a FR3 region which differs from the FR3 region of BMS2h-572-633 by up to three amino acids, and (g) a FR4 region which differs from the FR4 region of BMS2h-572-633 by up to three amino acids; and wherein the antibody polypeptide inhibits binding of CD40L to CD40 with an EC50 of 100 pM to 100 nM. Also provided is an antibody polypeptide, wherein the amino acid sequence of the first variable domain comprises: (a) a CDR1 region which differs from the CDR1 region of BMS2h-572-633 by up to three amino acids, (b) a CDR2 region which differs from the CDR2 region of BMS2h-572-633 by up to three amino acids, and (c) a CDR3 region which differs from the CDR3 region of BMS2h-572-633 by up to three amino acids. Alternatively, the amino acid sequence of the first variable domain can differ from the amino acid sequence of BMS2h-572-633 by up to and including 10 amino acids. Furthermore, the amino acid sequence of the first variable domain can differ from the amino acid sequence of BMS2h-

572-633 by up to and including 5 amino acids. The amino acid sequence of the first variable domain can also differ from the amino acid sequence of BMS2h-572-633 by up to and including 2 amino acids. Alternatively, the first variable domain differs from the amino acid sequence of BMS2h-572-633 by 1 amino acid.

Also provided is an antibody polypeptide selected from the lineage group of BMS2h-572, wherein the amino acid sequence of the first variable domain further comprises: (a) a CDR1 region having a sequence Trp-$X_1$-Leu-Met-Gly (SEQ ID NO: 2), wherein $X_1$ is Glu or Gln; (b) a CDR2 region having a sequence Gly-Ile-Glu-Gly-Pro-Gly-Asp-Val-Thr-Tyr-Tyr-Ala-Asp-Ser-Val-Lys-Gly (SEQ ID NO: 3); and (c) a CDR3 region having a sequence Lys-$X_2$-$Y_2$-$Z_2$-Ser-Asp-Tyr (SEQ ID NO: 4), wherein $X_2$ is Asp or Glu, $Y_2$ is Ala or Scr, and $Z_2$ is Lys, Asn, or Arg. Also provided is the antibody polypeptide, wherein the amino acid sequence of the first variable domain further comprises: (a) a FR1 region having a sequence Glu-Val-Gln-Leu-Leu-Glu-Ser-Gly-Gly-Gly-Leu-Val-Gln-Pro-Gly-Gly-Ser-Leu-Arg-Leu-Ser-Cys-Ala-Ala-Ser-Gly-Phe-Thr-Phe-Asn (SEQ ID NO: 5); (b) a FR2 region having a sequence Trp-$X_1$-Arg-Gln-Ala-Pro-Gly-Lys-Gly-Leu-Glu-Trp-Val-Ser (SEQ ID NO: 6), wherein $X_1$ is Ala or Val; (c) a FR3 region having a sequence Arg-Thr-Phe-Ile-Ser-Arg-Asp-Asn-Ser-Lys-Asn-Thr-Leu-Tyr-Leu-Gln-Met-Asn-Ser-Leu-Arg-Ala-Glu-Asp-Thr-Ala-Val-Tyr-Tyr-Cys-Val-Lys-Val-Gly (SEQ ID NO: 7); and (d) a FR4 region having a sequence Arg-Gly-Gln-Gly-Thr-Leu-Val-Thr-Val-Ser-Ser (SEQ ID NO: 8).

Alternatively, the first variable domain of the antibody polypeptide can comprise the amino acid sequence of BMS2h-572-633.

Also provided is an antibody polypeptide selected from the lineage group of BMS2h-719, comprising a first variable domain with the following consensus sequence: Glu-Val-Gln-Leu-Leu-Glu-Ser-Gly-Gly-Gly-Leu-Val-Gln-Pro-Gly-Gly-Ser-Leu-Arg-Leu-Ser-Cys-Ala-Ala-Ser-Gly-Phe-Thr-Phe-$X_1$-$Y_1$-Tyr-Glu-Met-$Z_1$-Trp-Val-Arg-Gln-Ala-Pro-Gly-Lys-Gly-Leu-Glu-Trp-Val-Ser-Ser-Ile-Ser-Ser-Asp-Gly-Ser-Phe-Thr-Tyr-Tyr-Ala-$A_1$-Ser-Val-Lys-Gly-Arg-Phe-Thr-Ile-Ser-Arg-Asp-Asn-Ser-Lys-Asn-Thr-Leu-Tyr-Leu-Gln-Met-Asn-Ser-Leu-Arg-Ala-Glu-Asp-Thr-Ala-Val-Tyr-Tyr-Cys-Ala-$B_1$-Pro-Phe-Thr-Glu-$C_1$-Asp-Tyr-Trp-Gly-His-Gly-Thr-Leu-Val-Thr-Val-Ser-Ser (SEQ ID NO: 9), wherein $X_1$ is Lys or Asn; $Y_1$ is Arg, Lys, Ser, or Thr; $Z_1$ is Met or Gln; $A_1$ is Asp or Glu; $B_1$ is Asp or Glu; and $C_1$ is Phe, Met, or Leu.

Also provided is an antibody polypeptide selected from the lineage group of BMS2h-503, comprising a first variable domain with the following consensus sequence: Asp-Ile-Gln-Met-Thr-Gln-Ser-Pro-Ser-Ser-Leu-Scr-Ala-Ser-Val-Gly-Asp-Arg-Val-Thr-Ile-Thr-Cys-Arg-Ala-Ser-His-$X_1$-Ile-Gln-Arg-Tyr-Leu-Ser-Trp-Tyr-Gln-Gln-Lys-Pro-Gly-Lys-Ala-Pro-Lys-Leu-Leu-Ile-Leu-Trp-Gly-Ser-Gln-Leu-Gln-Ser-Gly-Val-Pro-Ser-Arg-Phe-Ser-Gly-Ser-Gly-Ser-Gly-Thr-Asp-Phe-Thr-Leu-Thr-Ile-Ser-Ser-Leu-Gln-Pro-Glu-Asp-Phe-Ala-Thr-Tyr-Tyr-Cys-Gly-Gln-Trp-Trp-Ala-Pro-Pro-Gln-Thr-Phe-Gly-Gln-Gly-Thr-Lys-Val-Glu-Ile-Lys-Arg (SEQ ID NO: 10), wherein $X_1$ is His or Asp.

Also provided is an antibody polypeptide selected from the lineage group of BMS2h-116, comprising a first variable domain with the following consensus sequence: Asp-Ile-Gln-Met-Thr-Gln-Ser-Pro-Ser-Ser-Leu-Ser-Ala-$X_1$-Val-Gly-Asp-Arg-Val-Thr-Ile-Thr-Cys-Arg-Ala-Ser-Gln-Pro-Ile-Gly-Pro-Asp-Leu-Leu-Trp-Tyr-Gln-Gln-Lys-Pro-Gly-Lys-Ala-Pro-Lys-Leu-Leu-Ile-Tyr-Gln-Thr-Ser-Ile-Leu-Arg-Ser-Gly-Val-Pro-Ser-Arg-Phe-Ser-Gly-Ser-Gly-Ser-Glu-Thr-Asp-Phe-Thr-Leu-Thr-Ile-Ser-Asn-Leu-Gln-Pro-Glu-Asp-$Y_1$-Ala-$Z_1$-Tyr-Tyr-Cys-Gln-Gln-Tyr-Trp-Ala-Phe-Pro-Val-Thr-Phe-Gly-$A^1$-Gly-Thr-Lys-Val-Val-Ile-Lys-Arg (SEQ ID NO: 11), wherein $X_1$ is Ser or Tyr; $Y_1$ is Leu or Phe; $Z_1$ is Thr or Lys; and $A_1$ is Lys, Arg, or Gln.

Also provided is an antibody polypeptide comprising a first variable domain that specifically binds human CD40L, wherein the antibody polypeptide is a domain antibody (dAb). The antibody polypeptide can be a fusion polypeptide comprising the first variable domain and an Fc domain. Alternatively, the fusion polypeptide can comprise an IgG4 Fc domain. The fusion polypeptide also can comprise an IgG1 Fc domain. The fusion polypeptide can also comprise an IgG1 Fc domain. Alternatively, the fusion polypeptide can comprise a CT-Long domain. The fusion polypeptide can also comprise a CT-short domain. Alternatively, the fusion polypeptide can comprise a N297Q Long Fc domain. The fusion polypeptide can alternatively comprise a N297Q Short Fc domain.

Also provided is an antibody polypeptide comprising a first variable domain that specifically binds human CD40L, wherein the antibody polypeptide further comprises a second variable domain that specifically binds a second antigen, wherein the second antigen is an antigen other than human CD40L. The second antigen can be a cluster of differentiation (CD) molecule or a Major Histocompatibility Complex (MHC) Class II molecule. Alternatively, the second antigen can be serum albumin (SA).

Also provided is a nucleic acid encoding any of the antibody polypeptides provided herein. Further contemplated is a vector comprising the nucleic acid. An isolated host cell can comprise such vector.

A pharmaceutical composition is provided comprising a therapeutically-effective amount of the presently provided antibody polypeptide and a pharmaceutically acceptable carrier. The pharmaceutical composition can further comprise an immunosuppressive/immunomodulatory and/or anti-inflammatory agent.

A method of treating an immune disease in a patient in need of such treatment is provided comprising administering to the patient a therapeutically effective amount of the pharmaceutical composition described herein. An exemplary method administers the pharmaceutical composition in combination with an immunosuppressive/immunomodulatory and/or anti-inflammatory agent. The immune disease can be an autoimmune disease or a graft-related disease. Alternatively, the immune disease is a graft-related disease. Furthermore, the graft-related disease can comprise solid organ, tissue and/or cell transplant rejection. Alternatively, the graft-related disease is graft versus host disease (GVHD). The graft-related disease can further be an acute transplant rejection. Alternatively, the graft-related disease can be a chronic transplant rejection.

Also provided is the method of treating a graft-related disease, wherein the pharmaceutical composition is co-administered with a CTLA4 mutant molecule. The CTLA4 mutant molecule can be L104EA29Y-Ig (belatacept).

A method of treating an immune disease in a patient in need of such treatment is also provided comprising administering to the patient a therapeutically effective amount of the pharmaceutical composition provided herein, wherein the immune disease is selected from the group consisting of selected from the group consisting of Addison's disease, allergies, ankylosing spondylitis, asthma, atherosclerosis, autoimmune diseases of the ear, autoimmune diseases of the eye, autoimmune hepatitis, autoimmune parotitis, colitis, coronary heart disease, Crohn's disease, diabetes, including Type 1 and/or Type 2 diabetes, epididymitis, glomerulonephritis, Graves' disease, Guillain-Barre syndrome, Hashimoto's disease, hemolytic anemia, idiopathic thrombocytopenic purpura, inflammatory bowel disease, immune response to recombinant drug products, systemic lupus erythematosus, male infertility, multiple sclerosis, myasthenia gravis, pemphigus, psoriasis, rheumatic fever, rheumatoid arthritis, sarcoidosis, scleroderma, Sjogren's syndrome, spondyloarthropathies, thyroiditis, transplant rejection, vasculitis, AIDS, atopic allergy, bronchial asthma, eczema, leprosy, schizophrenia, inherited depression, transplantation of tissues and organs, chronic fatigue syndrome, Alzheimer's disease, Parkinson's disease, myocardial infarction, stroke, autism, epilepsy, Arthus's phenomenon, anaphylaxis, alcohol addiction, and drug addiction. Alternatively, the immune disease can be myasthenia gravis, idiopathic thrombocytopenic purpura, or systemic sclerosis.

Also provided is a use of an isolated antibody polypeptide disclosed herein for the preparation of a medicament for the treatment of a patient, wherein the patient has or is at risk of having an immune disease. Further provided is a use of an isolated antibody polypeptide disclosed herein for preparation of a medicament for alleviating at least one symptom of an immune disease in a patient in need thereof.

Further provided herein is an isolated antibody polypeptide comprising a first variable domain, wherein said antibody polypeptide specifically binds human CD40L, wherein CD40L comprises the amino acid sequence of SEQ ID NO: 1, wherein the antibody polypeptide competes with the binding of BMS2h-572-633, and wherein the antibody polypeptide inhibits binding of CD40L to CD40 with an EC50 of 100 pM to 100 nM. In one aspect, the first variable domain comprises the amino acid sequence of one of the antibody polypeptides selected from the lineage group consisting of BMS2h-572, BMS2h-719, BMS2h-503, and BMS2h-116. In another aspect, the first variable domain comprises an amino acid sequence at least 95% identical to BMS2h-572-6, BMS2h-572-608, BMS2h-572-614, BMS2h-572-619, BMS2h-572-633, BMS2h-572-634, BMS2h-572-635, BMS2h-719-2, BMS2h-719-202, BMS2h-719-203, BMS2h-719-213, BMS2h-719-214, BMS2h-719-215, BMS2h-719-218, BMS2h-719-225, BMS2h-503-1, BMS2h-503-2, BMS2h-116-1312, BMS2h-116-1313, or BMS2h-116-1320. In yet another aspect, the first variable domain comprises the amino acid sequence of BMS2h-572-6, BMS2h-572-608, BMS2h-572-614, BMS2h-572-619, BMS2h-572-633, BMS2h-572-634, BMS2h-572-635, BMS2h-719-2, BMS2h-719-202, BMS2h-719-203, BMS2h-719-213, BMS2h-719-214, BMS2h-719-215, BMS2h-719-218, BMS2h-719-225, BMS2h-503-1, BMS2h-503-2, BMS2h-116-1312, BMS2h-116-1313, or BMS2h-116-1320.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1A depicts the domain antibody that comprises a $V_H$ variable domain BMS2h-572-633 fused to a modified Fc tail from Abatacept IgG1.

FIG. 1B shows the amino acid sequence (SEQ ID NO: 1355) of the variable domain BMS2h-572-633 (in blue). The Fc fusion protein is a dimer of molecular weight 77,984 Daltons, with each polypeptide chain consisting of 354 amino acids. The variable domain is fused by a linker (green) to the mutated Fc construct of human IgG1, wherein three cysteine residues (shown in purple) are substituted with serine, and one proline (shown in red) is substituted with a serine residue.

FIG. 3 provides sequences (SEQ ID NOS 1356-1361, respectively, in order of appearance) of various Fc domains. Linker regions are shown in boxes.

FIG. 4 shows examples of various Fc-formatted domain antibodies (SEQ ID NOS 1362-1365, respectively, in order of appearance). Linker regions are indicated by boxes.

FIG. 14 demonstrates PK/PD modeling of BMS-986003 and 5c8-IgG1 plasma exposures and anti-KLH antibody response (IgG Titers).

FIGS. 21, 22, 23, and 24 show is ClustalW2 alignments of representative domain antibody polypeptides from lineages BMS2h-572, BMS2h-719, BMS2h-503, and BMS2h-116, respectively. FIG. 21 discloses SEQ ID NOS 243, 251, 257, 262 and 274-276, respectively, in order of appearance, FIG. 22 discloses SEQ ID NOS 352, 354-355 and 357-361, respectively, in order of appearance, FIG. 23 discloses SEQ ID NOS 1087-1088, respectively, in order of appearance, and FIG. 24 discloses SEQ ID NOS 970-971 and 974, respectively, in order of appearance.

DETAILED DESCRIPTION

Figure 2:
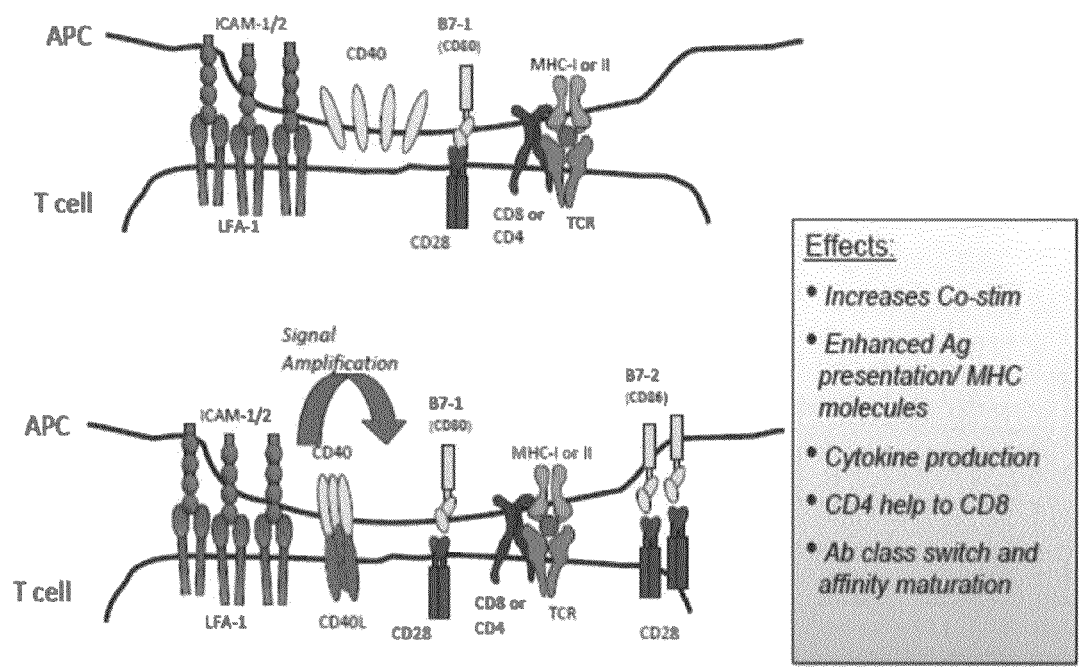
FIG. 2 depicts a working model for the CD40-40L pathway. The top panel demonstrates initial stages of an encounter between a T cell and an APC. The initial encounter driven by T cell receptor (TCR) engagement of pMHC complex (signal 1) coupled with an early CD28-CD80 interaction (signal 2) is sufficient for the cell surface expression of trimeric CD40L (bottom panel). Engagement of CD40 by CD40L results in numerous biological responses outlined in the grey box.

Antibody polypeptides that specifically bind to human CD40L are provided. The antibody polypeptides do not activate platelets, and the antibody polypeptides are useful in the treatment of diseases involving CD40L activation, such as graft-related diseases and autoimmune diseases. The antibody polypeptides may be selected using a primary screen that utilizes cell binding assays, followed by one or more rounds of error-prone or degenerate oligonucleotide-directed affinity maturation. As a result, a genus of antibody polypeptides that specifically bind CD40L are provided.

A "lineage" is a set of related antibody polypeptides that were prepared from a common precursor by error-prone or degenerate oligonucleotide-directed affinity maturation, as disclosed in the examples below, and that are expected to bind CD40L. The nomenclature of the antibody polypeptides is used to designate the various lineages. The nomenclature "BMS2h-572," for example, refers to antibody polypeptides of lineage 572, which were raised against human CD40L. "Lineage BMS2h-572" antibody polypeptides include BMS2h-572-1 through BMS2h-572-19, BMS2h-572-21 through BMS2h-572-24, BMS2h-572-601 through BMS2h-572-627, and BMS2h-572-630 through BMS2h-572-635.

Accordingly, in one aspect, an antibody polypeptide comprises a variable domain that specifically binds human CD40L, where the antibody polypeptide competes with the binding of any one of the domain antibodies (dAbs) listed in TABLE 1 or TABLE 3. For example, the antibody polypeptide may compete with a dAb selected from the 2h lineage. The dAb also may be selected from a lineage selected from the group consisting of BMS2h-116, BMS2h-503, BMS2h-572, and BMS2h-719, such as the dAb BMS2h-572-633, BMS2h-572-608, or BMS2h-572-614, for instance. In another aspect, an antibody polypeptide specifically binds human CD40L as any one of the dAbs listed in TABLE 1 and TABLE 3. For example, the antibody polypeptide may comprise a variable domain that specifically binds human CD40L as the dAb BMS2h-572-633, BMS2h-572-608, or BMS2h-572-614, for instance.

The antibody polypeptides may be a domain antibody containing a single variable domain. The antibody polypeptides also may comprise additional domains, such as an Fc domain. For instance, the antibody polypeptide may comprise a second variable domain that specifically binds human serum albumin (HSA). Such dual specific antibody polypeptides may have an increased half-life, for example.

As used herein, "specific binding" refers to the binding of an antigen by an antibody polypeptide with a dissociation constant ($K_d$) of about 1 µM or lower as measured, for example, by surface plasmon resonance (SPR). Suitable assay systems include the BIAcore™ surface plasmon resonance system and BIAcore™ kinetic evaluation software (e.g., version 2.1). The affinity or $K_d$ for a specific binding interaction may be about 1 µM or lower, about 500 nM or lower or about 300 nM or lower.

The term "about" will be understood by persons of ordinary skill in the art and will vary to some extent on the context in which it is used. Generally, about encompasses a range of values that are plus/minus 10% of a referenced value.

In accordance with this detailed description, the following abbreviations and definitions apply. It must be noted that as used herein, the singular forms "a", "an", and "the" include plural referents unless the context clearly dictates otherwise. Thus, for example, reference to "an antibody" includes a plurality of such antibodies and reference to "the dosage" includes reference to one or more dosages and equivalents thereof known to those skilled in the art, and so forth.

1. CD40L and CD40L Activities

Antibody polypeptides are provided that bind human CD40L. CD40L is also known as CD154, gp39, TNF-related activation protein (TRAP), 5c8 antigen, or T-BAM. Relevant structural information for human CD40L can be found, for example, at UniProt Accession Number P29965. "Human CD40L" refers to the CD40L comprising the following amino acid sequence:

```
                                           (SEQ ID NO: 1)
         10         20         30         40
MIETYNQTSP RSAATGLPIS MKIFMYLLTV FLITQMIGSA 50         60         70         80
LFAVYLHRRL DKIEDERNLH EDFVFMKTIG RCNTGERSLS 90        100        110        120
LLNCEEIKSQ FEGFVKDIML NKEETKKENS FEMQKGDQNP 130        140        150        160
QTAARVISEA SSKTTSVLQW AEKGYYTMSN NLVTLENGKQ 170        180        190        200
LTVKRQGLYY LYAQVTFCSN PEASSQAPFI ASLCLKSPGR 210        220        230        240
FERILLRAAN THSSAKPGGQ QSISLGGVFE LQPGASVFVN 250        260
VTDPSQVSHG TGFTSFGLLK L
```

CD40L has also been sequenced in *Sus scrofa*, *Mus musculus*, *Canis familiaris*, *Bos ffini*, *Macaca mulatta*, *Aotus livirgatus*, *Callithrix jacchus*, *Cercocebus torquatus atys*, *Macaca nemestrina*, *Rattus norvegicus*, *Gallus gallus*, *Felis catus*, and *Sus scrofa*.

Binding of the present antibody polypeptides to CD40L antagonizes CD40L, activity. "CD40L activities" include, but are not limited to, costimulation and activation an APC in association with T cell receptor stimulation by MHC molecules on the APC, secretion of all immunoglobulin isotypes in the presence of cytokines, stimulation of B cell proliferation, cytokine production, antibody class switching and affinity maturation. For example, patients with X-linked hyper-IgM syndrome express functional CD40 on their B cells, but their activated T cells have a defective CD40L protein, resulting in its inability to activate B cells and induce immunoglobulin isotype switching. Aruffo et al., *Cell* 72:291-300 (1993).

CD40L activities can be mediated by interaction with other molecules. "CD40 activities" include the functional interaction between CD40L and the following molecules: CD40 (CD40L receptor), α5β1 integrin, and αIIbβ3. For example, CD40L binds its receptor, CD40, which is expressed on a variety of APCs, such as B cells, macrophages, and dendritic cells, as well as on stromal cells, vascular endothelial cells, and platelets.

As used herein, the terms "activate," "activates," and "activated" refer to an increase in a given measurable CD40L activity by at least 10% relative to a reference, for example, at least 10%, 25%, 50%, 75%, or even 100%, or more. A CD40L activity is "antagonized" if the activity is reduced by at least 10%, and in an exemplary embodiment, at least 20%, 30%, 40%, 50%, 60%, 70%, 80%, 90%, 95%, 97%, or even 100% (i.e., no detectable activity), relative to the absence of the antagonist. For example, an antibody polypeptide may antagonize some or all CD40L activity. In one embodiment, the antibody polypeptide does not activate B cell proliferation. In another embodiment, the antibody polypeptide does not activate cytokine secretion by T cells or dendritic cells (DCs), where the cytokine is at least one cytokine selected from the group consisting of IL-2, IL-6, IL-10, IL-12, IL-13, IL-17, IL-23, TNF-α, and IFNγ.

2. Antibody Polypeptides

The antibody polypeptides comprise a variable domain. In one embodiment, the antibody polypeptides are in the form of a dAb that contains a single variable domain. Antibody polypeptides may be full-length anti-CD40L immunoglobulin molecules comprising two heavy (H) chains and two light (L) chains interconnected by disulfide bonds. In this embodiment, the amino terminal portion of each chain includes a variable domain ($V_L$ or $V_H$) of about 100-120 amino acids. The complementarity determining regions (CDRs) contained therein are primarily responsible for antigen recognition, although framework residues can play a role in epitope binding. The carboxy-terminal "half" of each heavy chain defines a constant region (Fc) primarily responsible for effector function.

Antibody polypeptides also may be "fragments" comprising a portion of the full-length anti-CD40L immunoglobulin molecule that comprises a variable domain that specifically binds CD40L. Thus, the term "antibody polypeptides" includes an antigen-binding heavy chain, light chain, heavy chain-light chain dimer, Fab fragment, F(ab')$_2$ fragment, Fv fragment, single chain Fv (scFv), and dAb, for example. The term "antibody polypeptides" thus includes polypeptides made by recombinant engineering and expression, as well as monoclonal antibodies produced by natural recombination and secretion by hybridoma cell clones.

Light chains are classified as kappa (κ) or lambda (λ), and are characterized by a particular constant region, $C_L$, as known in the art. Heavy chains are classified as γ, μ, α, δ, or ε, and define the isotype of an antibody as IgG, IgM, IgA, IgD, or IgE, respectively. The heavy chain constant region is comprised of three domains (CH1, CH2, and CH3) for IgG, IgD, and IgA; and four domains (CH1, CH2, CH3, and CH4) for IgM and IgE. Anti-CD40L antibodies may have a heavy chain constant region selected from any of the immunoglobulin classes (IgA, IgD, IgG, IgM, and IgE).

Each light chain variable domain ($V_L$) and heavy chain variable domain ($V_H$) is composed of three CDRs and four framework regions (FRs), arranged from amino-terminus to carboxy-terminus in the following order: FR1, CDR1, FR2, CDR2, FR3, CDR3, and FR4. The three CDRs of the light chain are referred to as "LCDR1, LCDR2, and LCDR3" and the three CDRs of the heavy chain are referred to as "HCDR1, HCDR2, and HCDR3."

As used herein, the term "Fc domain" refers to the constant region antibody sequences comprising CH2 and CH3 constant domains as delimited according to Kabat et al., *Sequences of Immunological Interest*, 5$^{th}$ ed., U.S. Dept. Health & Human Services, Washington, D.C. (1991). The Fc domain may be derived from an IgG1 or an IgG4 Fc region, for example.

A variable domain may be fused to an Fc domain. Examples of various Fc-formatted domain antibodies and their potency are provided in TABLE 6. FIG. 3 provides sequences of various Fc domains provided herein. Linker regions are shown in boxes. As used in TABLE 6, "Fc" indicates that the dAb is fused to a human IgG1 short Fc. "CT Long Fc," also called CT-L2, refers to the Fc from CTLA4. The underlined S are cysteine-to-serine point mutations made to eliminate the disulfides in the Fc hinge. "CT Short," also called CT-S1, is shorter than CT Long by 7 amino acids. "N297Q Long Fc," also referred to as N297Q-L4, is the Fc domain of human IgG1 with a N297Q mutation made to eliminate the N-linked carbohydrate in the Fc. "N297Q Short Fc," also called N297Q-S3, is short than N297Q Long Fc by 7 amino acids, and is a human IgG1 with a N297Q point mutation made to eliminate the N-linked carbohydrate in the Fc domain. "CT-Fc SP5" is the CT Long Fc, where SP5 refers to the octeonectin signal peptide used for secretion from the mammalian expression host. Cleavage site is indicated by "^". FIG. 4 further provides examples of various Fc domain formats.

When a variable domain is fused to an Fc domain, the carboxyl terminus of the variable domain (either a $V_L$ or $V_H$ domain, including dAbs) may be linked or fused to the amino terminus of the Fc CH2 domain. Alternatively, the carboxyl terminus of the variable domain may be linked or fused to the amino terminus of a CH1 domain, which itself is fused to the Fc CH2 domain. The protein may comprise the hinge region between the CH1 and CH2 domains in whole or in part.

The CDRs contain most of the residues that form specific interactions with the antigen. In one embodiment, the variable domain of an antibody polypeptide comprises CDR1, CDR2, and CDR3 regions that have the same amino acid sequence as the CDR1, CDR2, and CDR3 regions of one of the dAbs listed in TABLE 1 or TABLE 3 or that each differ from the CDR1, CDR2, and CDR3 regions by one, two, or three amino acids. For example, the antibody polypeptide may comprise CDR1, CDR2, and CDR3 regions that have the same amino acid sequence as the CDR1, CDR2, and CDR3 regions of BMS2h-572-633, BMS2h-572-608, or BMS2h-572-614, for example.

A "domain antibody" (dAb) comprises a single variable ($V_L$ or $V_H$) domain that is capable of specifically and monovalently binding an antigen, such as CD40L. For example, a dAb may have a $V_{HH}$ structure, characteristic of a camelid dAb. A "$V_H$ domain" as used herein is meant to include a $V_{HH}$ structure. In another embodiment, the $V_H$ domains (including all features and combination of features presented as embodiments herein) are other than $V_{HH}$ domains. dAbs may form homo- or heterodimers in solution. While not limited by any particular theory, it is believed that the dAbs disclosed herein do not cause platelet aggregation, because the antibodies containing mutated Fc constructs do not bind FcγRIIa (also known as CD32a) on the platelet surface and do not activate platelets.

As used herein, the term "variable domain" refers to immunoglobulin variable domains defined by Kabat et al., *Sequences of Immunological Interest*, 5th ed., U.S. Dept. Health & Human Services, Washington, D.C. (1991). The numbering and positioning of CDR amino acid residues within the variable domains is in accordance with the well-known Kabat numbering convention.

The term "human," when applied to antibody polypeptides, means that the antibody polypeptide has a sequence, e.g., framework regions and/or CH domains, derived from a human immunoglobulin. A sequence is "derived from" a human immunoglobulin coding sequence when the sequence is either: (a) isolated from a human individual or from a cell or cell line from a human individual; (b) isolated from a library of cloned human antibody gene sequences or of human antibody variable domain sequences; or (c) diversified by mutation and selection from one or more of the polypeptides above. An "isolated" compound as used herein means that the compound is removed from at least one component with which the compound is naturally associated with in nature.

Antibody polypeptides can be administered to human patients while largely avoiding the anti-antibody immune response often provoked by the administration of antibodies from other species, e.g., mouse. For example, murine antibodies can be "humanized" by grafting murine CDRs onto a human variable domain FR, according to procedures well known in the art. Human antibodies as disclosed herein, however, can be produced without the need for genetic manipulation of a murine antibody sequence.

Variable domains may comprise one or more FR with the same amino acid sequence as a corresponding framework region encoded by a human germline antibody gene segment. For example, a domain antibody may comprise the $V_H$ germline gene segments DP47, DP45, or DP38, the $V_\kappa$ germline gene segment DPK9, the $J_H$ segment JH4b, or the $J_\kappa$ segment $J_\kappa 1$.

Changes may be made to antibody polypeptide sequences while retaining the ability to bind CD40L specifically. Specifically, the antibody polypeptides (e.g., a dAb) may comprise a variant variable domain that retains the function of specifically binding CD40L as the dAb BMS2h-572-633. In one embodiment, the variant variable domain may compete with BMS2h-572-633 for specific binding to CD40L. Error-prone affinity maturation, as disclosed in the examples below, provides one exemplary method for making and identifying antibody polypeptides with variant sequences that specifically bind CD40L.

For example, a variant variable domain may differ from one of the variable domains listed in TABLE 1 and TABLE 3 by up to 10 amino acids or any integral value between, where the variant variable domain specifically binds CD40L. Alternatively, the variant variable domain may have at least 90% sequence identity (e.g., at least 91%, 92%, 93%, 94%, 95%, 96%, 97%, 98%, or 99% sequence identity) relative to a sequence listed in the present Sequence Listing. Non-identical amino acid residues or amino acids that differ between two sequences may represent amino acid substitutions, additions, or deletions. Residues that differ between two sequences appear as non-identical positions, when the two sequences are aligned by any appropriate amino acid sequence alignment algorithm, such as BLAST.

In one embodiment, amino acid substitutions may be made to individual FR regions, such that a FR comprises 1, 2, 3, 4, or 5 amino acid differences relative to the amino acid sequence of the corresponding FR encoded by a human germline antibody gene segment. In another embodiment, the variant variable domain may contain one or two amino acid substitutions in a CDR. In other embodiments, amino acid substitutions to FR and CDR regions may be combined. Representative variable domains that specifically bind CD40L are listed in TABLE 1 and TABLE 3.

The information regarding the boundaries of the $V_L$ or $V_H$ domains of heavy and light chain genes may be used to design PCR primers to amplify the variable domain from a cloned heavy or light chain coding sequence encoding an antibody polypeptide known to bind CD40L. The amplified variable domain may be inserted into a suitable expression vector, e.g., pHEN-1 (Hoogenboom et al. (1991) *Nucleic Acids Res.* 19:4133-4137) and expressed, either alone or as a fusion with another polypeptide sequence, using techniques well known in the art. Based on the disclosed amino acid and polynucleotide sequences, the fusion protein can be produced and purified using only ordinary skill in any suitable mammalian host cell line, such as CHO, 293, COS, NS0, and the like, followed by purification using one or a combination of methods, including protein A affinity chromatography, ion exchange, reverse phase techniques, or the like.

In one aspect, the antibody polypeptide is a "dual specific" antibody polypeptide comprising a first variable domain that specifically binds human CD40L. Dual specific antibody polypeptides comprise a second variable domain that specifically binds a second antigen that is other than human CD40L.

In another embodiment, the second antigen may be a cell surface molecule of an immune effector cell or a soluble molecule such as a cytokine, for example. Binding of the dual specificity antibody polypeptide could be used to antagonize CD40L and antagonize a biological activity of the second antigen. Cell surface molecules of immune effector cells include the cluster of differentiation (CD) molecules. Representative CD markers are listed on the Internet at hypertext transfer protocol http://en.wikipedia.org/wiki/List_of_human_clusters_of_differentiation (last modified on Aug. 8, 2012). Cell surface molecules of immune effector cells also include Major Histocompatibility Complex (MHC) Class II molecules. Antibodies against these cell surface molecules are known in the art and can be used a source of a variable domain to construct a dual specific antibody polypeptide.

In one embodiment, antibody polypeptides of a dual specific ligand may be linked by an "amino acid linker" or "linker." For example, a dAb may be fused to the N-terminus of an amino acid linker, and another dAb may be fused to the C-terminus of the linker. Although amino acid linkers can be any length and consist of any combination of amino acids, the linker length may be relatively short (e.g., five or fewer amino acids) to reduce interactions between the linked domains. The amino acid composition of the linker also may be adjusted to reduce the number of amino acids with bulky side chains or amino acids likely to introduce secondary structure. Suitable amino acid linkers include, but are not limited to, those up to 3, 4, 5, 6, 7, 10, 15, 20, or 25 amino acids in length. Representative amino acid linker sequences include $(GGGGS)_n$ (SEQ ID NO: 12), where n may be any integer between 1 and 5. Other suitable linker sequences may be selected from the group consisting of AS, AST, TVAAPS (SEQ ID NO: 13), TVA, and ASTSGPS (SEQ ID NO: 14).

The binding of the second antigen can increase the in vivo half-life of the antibody polypeptide. For example, the second variable domain of the dual specific antibody polypeptide may specifically bind serum albumin (SA), e.g., human serum albumin (HSA). The antibody polypeptide formatted to bind I can have an increased in vivo t-α ("alpha half-life") or t-β ("beta half-life") half-life relative to the same unformatted antibody polypeptide. The t-α and t-β half-lives measure how quickly a substance is distributed in and eliminated from the body. The linkage to I may be accomplished by fusion of the antibody polypeptide with a second variable domain capable of specifically binding I, for example. Anti-human serum albumin antibodies are well-known in the art. See, e.g., Abcam®, Human Serum Albumin antibodies ab10241, ab2406, and ab8940, available on the Internet at hypertext transfer protocol www.abcam.com/index.html, or GenWay, ALB antibody, available on the Internet at hypertext transfer protocol www.genwaybio.com. Variable domains that specifically bind I can be obtained from any of these antibodies, and then fused to an antibody polypeptide of the disclosure using recombinant techniques that are well known in the art.

Alternatively, the linking of the antibody polypeptide to I can be accomplished by directly fusing the antibody polypeptide sequence to an I coding sequence using techniques well known to the skilled artisan. The I coding sequences can be obtained by PCR using primers derived from the cDNA sequence available at GenBank Accession No. NM000477, for example.

In one embodiment, the tα-half-life of the I-linked domain antibody composition is increased by 10% or more. In another embodiment, the tα-half-life of the I-linked domain antibody composition is in the range of 0.25 hours to 6 hours. In another embodiment, the tβ-half-life of the I-linked domain antibody composition is increased by 10% or more. In another embodiment, the tβ-half-life of the I-linked domain antibody composition is in the range of 12 to 48 hours.

In another embodiment, an antibody polypeptide may be formatted to increase its in vivo half-life by PEGylation. In one embodiment, the PEG is covalently linked. In another embodiment, the PEG is linked to the antibody polypeptide at a cysteine or lysine residue. In yet another embodiment, the PEG-linked antibody polypeptide has a hydrodynamic size of at least 24 kD. In yet another embodiment, the total PEG size is from 20 to 60 kD, inclusive. In yet another embodiment, the PEG-linked domain antibody has a hydrodynamic size of at least 200 kD.

PEGylation can be achieved using several PEG attachment moieties including, but not limited to N-hydroxysuccinimide active ester, succinimidyl propionate, maleimide, vinyl sulfone, or thiol. A PEG polymer can be linked to an antibody polypeptide at either a predetermined position, or can be randomly linked to the domain antibody molecule. PEGylation can also be mediated through a peptide linker attached to a domain antibody. That is, the PEG moiety can be attached to a peptide linker fused to an antibody polypeptide, where the linker provides the site (e.g., a free cysteine or lysine) for PEG attachment. Methods of PEGylating antibodies are well known in the art, as disclosed in Chapman, et al., "PEGylated antibodies and antibody fragments for improved therapy: a review," *Adv. Drug Deliv. Rev.* 54(4):531-45 (2002), for example.

Antibody polypeptides also may be designed to form a dimer, trimer, tetramer, or other multimer. Antibody polypeptides, e.g., dAbs, can be linked to form a multimer by several methods known in the art, including, but not limited to, expression of monomers as a fusion protein, linkage of two or more monomers via a peptide linker between monomers, or by chemically joining monomers after translation, either to each other directly, or through a linker by disulfide bonds, or by linkage to a di-, tri- or multivalent linking moiety (e.g., a multi-arm PEG). In one embodiment, the multimer can bind a single molecule of CD40.

3. Pharmaceutical Compositions and Methods of Treatment

A pharmaceutical composition comprises a therapeutically-effective amount of one or more antibody polypeptides and optionally a pharmaceutically acceptable carrier. Pharmaceutically acceptable carriers include, for example, water, saline, phosphate buffered saline, dextrose, glycerol, ethanol and the like, as well as combinations thereof. Pharmaceutically acceptable carriers can further comprise minor amounts of auxiliary substances, such as wetting or emulsifying agents, preservatives, or buffers that enhance the shelf-life or effectiveness of the fusion protein. The compositions can be formulated to provide quick, sustained, or delayed release of the active ingredient(s) after administration. Suitable pharmaceutical compositions and processes for preparing them are well known in the art. See, e.g., Remington, THE SCIENCE AND PRACTICE OF PHARMACY, A. Gennaro, et al., eds., 21$^{st}$ ed., Mack Publishing Co. (2005).

The pharmaceutical composition further may comprise an immunosuppressive/immunomodulatory and/or anti-inflammatory agent. A method of treating an immune disease in a patient in need of such treatment may comprise administering to the patient a therapeutically effective amount of the pharmaceutical composition. Antagonizing CD40L-mediated T cell activation could inhibit undesired T cell responses occurring during autoimmunity, transplant rejection, or allergic responses, for example. Inhibiting CD40L-mediated T cell activation could moderate the progression and/or severity of these diseases.

As used herein, a "patient" means an animal, e.g. mammal, including humans. The patient may be diagnosed with an immune disease. "Treatment" or "treat" or "treating" refers to the process involving alleviating the progression or severity of a symptom, disorder, condition, or disease. An "immune disease" refers to any disease associated with the development of an immune reaction in an individual, including a cellular and/or a humoral immune reaction. Examples of immune diseases include, but are not limited to graft-related disease, inflammation, allergy, and autoimmune disease. The autoimmune disease may be selected from the group consisting of systemic lupus erythematosus, multiple sclerosis, rheumatoid arthritis, diabetes, psoriasis, scleroderma, atherosclerosis, inflammatory bowel disease, and ulcerative colitis.

Diseases that can be treated by administering the pharmaceutical composition may be selected from the group consisting of Addison's disease, allergies, ankylosing spondylitis, asthma, atherosclerosis, autoimmune diseases of the ear, autoimmune diseases of the eye, autoimmune hepatitis, autoimmune parotitis, colitis, coronary heart disease, Crohn's disease, diabetes, including Type 1 and/or Type 2 diabetes, epididymitis, glomerulonephritis, Graves' disease, Guillain-Barre syndrome, Hashimoto's disease, hemolytic anemia, idiopathic thrombocytopenic purpura, inflammatory bowel disease, immune response to recombinant drug products (e.g., Factor VII in hemophiliacs), systemic lupus erythematosus, male infertility, multiple sclerosis, myasthenia gravis, pemphigus, psoriasis, rheumatic fever, rheumatoid arthritis, sarcoidosis, scleroderma, Sjogren's syndrome, spondyloarthropathies, thyroiditis, transplant rejection, and vasculitis. Autoimmune-mediated conditions include, but are not limited to, conditions in which the tissue affected is the primary target, and in some cases, the secondary target. Such conditions include, but are not limited to, AIDS, atopic allergy, bronchial asthma, eczema, leprosy, schizophrenia, inherited depression, transplantation of tissues and organs, chronic fatigue syndrome, Alzheimer's disease, Parkinson's disease, myocardial infarction, stroke, autism, epilepsy, Arthus' phenomenon, anaphylaxis, alcohol addiction, and drug addiction.

Preferred indications for administration of the present pharmaceutical compositions are, for example, immune thrombocytopenic purpura, systemic sclerosis, myasthenia gravis, allograft rejection, and graft-versus-host disease.

The pharmaceutical composition may be administered alone or in combination therapy, (i.e., simultaneously or sequentially) with an immunosuppressive/immunomodulatory and/or anti-inflammatory agent. Different immune diseases can require use of specific auxiliary compounds useful for treating immune diseases, which can be determined on a patient-to-patient basis. For example, the pharmaceutical composition may be administered in combination with one or more suitable adjuvants, e.g., cytokines (IL-10 and IL-13, for example) or other immune stimulators, e.g., chemokines, tumor-associated antigens, and peptides. Suitable adjuvants are known in the art.

For example, the disclosed pharmaceutical composition may be co-administered, concomitantly or sequentially, with a cytotoxic T-lymphocyte antigen 4 (CTLA4) mutant molecule, such as L104EA29Y-Ig (belatacept). CTLA4 binds to CD80 (B7-1) and CD86 (B7-2) with higher avidity than CD28, and it is transiently expressed on T cells following their activation, where it interrupts the interaction between CD28 and CD80/86. Oosterwegel et al., *Curr. Opin. Immunol.* 11: 294-300 (1999). This creates a negative feedback signal for T cell activation.

CTLA4 mutant molecules, including L104EA29Y-Ig, have increased binding avidity to CD80/86 compared to wild-type CTLA4. Intervention of the CD28-CD80/86 pathway by L104EA29Y-Ig has been successfully pursued, for example, to treat graft-related diseases in non-human primate transplant models, alone or in combination with other immunosuppressive agents. Larsen et al., *Amer. J. Transplant.* 5: 443 (2005). U.S. Patent Application number 2010/0166774 describes the structure of L104EA29Y-Ig, methods of producing it, and a formulation comprising a CTLA4 molecule; and the application is herein incorporated by reference. U.S. Pat. Nos. 7,094,874 and 7,482,327 further disclose administration (including co-administration with one or more other drugs) and dosage schedule of L104EA29Y-Ig, and the disclosures of these patents are herein incorporated by reference.

Any suitable method or route can be used to administer the antibody polypeptide or the pharmaceutical composition. Routes of administration include, for example, oral, intravenous, intraperitoneal, subcutaneous, or intramuscular administration. A therapeutically effective dose of administered antibody polypeptide(s) depends on numerous factors, including, for example, the type and severity of the immune disease being treated, the use of combination therapy, the route of administration of the antibody polypeptide(s) or pharmaceutical composition, and the weight of the patient. A non-limiting range for a therapeutically effective amount of a domain antibody is 0.1-20 mg/kg, and in an aspect, 1-10 mg/kg, relative to the body weight of the patient. The dose of antibody polypeptide(s) can be further guided by the amount of antibody polypeptide(s) required for CD40 antagonism in in vitro and/or in vivo models of disease states. Representative models are described below and in the examples.

4. In Vitro and In Vivo Models

The ability of antibody polypeptides of the disclosure to antagonize CD40L can be tested in one of several available in vitro or in vivo model systems. Appropriate human, animal, and cell model systems are described below. Further cell assay systems are described in the examples.

4.1. Immune Thrombocytopenic Purpura (ITP) In Vivo Model:

The potential role of CD40-CD40L in the pathogenesis of ITP is reported by Patel et al., *British J. Haematology* 141: 545-548 (2008). Antiplatelet autoantibodies in patients with ITP bind to circulating platelets and accelerate their destruction. The primary mechanism by which anti-CD40L antibodies are thought to increase the platelet count in ITP is by blocking T-cell based activation of autoreactive B cells that produce anti-platelet antibodies. Anti-CD40L antibodies may also block expression of CD40L on platelets, thus preventing autopresentation of platelet glycoprotein antigens to macrophages. Furthermore, anti-CD40L mAbs inhibit direct interactions between platelet CD40L and other cells, such as plasmacytoid dendritic cells (DCs), which have recently been implicated in driving the type I interferon (IFN) response in human lupus patients. Duffau et al., *Sci. Transl. Med.* 2: 47 (2010).

Patel et al. demonstrated efficacy of two humanized anti-CD40L monoclonal antibodies, hu5c8 and IDEC-131, in 46 human patients with chronic ITP refractory to conventional therapies. The patients had an overall 24% response rate, characterized by increased platelet counts. This demonstrated the potential role of CD40-CD40L in the pathogenesis of ITP.

4.2. Lupus In Vivo and In Vitro Models:

Glomerular and tubular CD40 expression is markedly upregulated in proliferative nephritis. Several studies have reported hyperexpression of CD40L by T cells and elevated soluble sCD40L concentrations in human lupus. Kimura et al., *Therapeutic Apheriss and Dialysis* 9: 64-68 (2005); Vakkalanka et al., *Arthritis & Rheumatism* 42: 871-881 (1999).

Systemic lupus erythematosus (SLE) is a chronic autoimmune disease characterized by the production of multiple autoantibodies and by B cell hyperactivity. Grammer et al., *J. Clin. Invest.* 112: 1506-1520 (2003) reports the results of treatment of patients with SLE with humanized anti-CD40L mAb 5c8 (BG9588). See also Huang et al., *Arthritis & Reumatism* 46: 1554-1562 (2002). Grammer et al. report that CD19+ peripheral B cells were examined before and after treatment with the anti-CD40L mAb. Before treatment, SLE patients manifested activated B cells that expressed CD40L, CD69, CD38, CD5, and CD27. The activated B cells disappeared from the periphery during and post-treatment. Before treatment, active SLE patients had circulating $CD38^{bright}$ Ig-secreting cells that were not found in normal individuals. Disappearance of these plasma cells during treatment was associated with decreases in anti-double stranded DNA (anti-dsDNA) Ab levels, proteinuria, and SLE disease activity index. Consistent with this finding, peripheral B cells cultured in vitro spontaneously proliferated and secreted Ig in a manner that was inhibited by anti-CD40L mAb. The CD38+/++IgD+, CD38+++, and CD38+IgD-B cell subsets present in the peripheral blood of SLE patients also disappeared following treatment with the anti-CD40L mAb. Together, these results suggest that spontaneous CD40L-CD40 interactions in active SLE patients drive B cell activation, proliferation, and differentiation to autoantibody-secreting plasma cells that mediate proteinuria and disease activity.

Proliferative lupus glomerulonephritis is a protracted autoimmune disease with a waxing and waning course, characterized by increased level of anti-dsDNA antibodies, decreased serum C3 concentrations, and hematuria. Boumpas et al, *Arthritis & Rheumatism* 48: 719-727 (2003) report results of a phase II, multicenter, open-label study evaluating the toxicity and efficacy of BG9688, a humanized anti-CD40L monoclonal antibody, in patients with proliferative lupus glomerulonephritis. Although the study had to be terminated prematurely because of thromboembolic events occurring in patients in several BG9588 protocols, a short course of the anti-CD40L antibody treatment in patients with proliferative lupus nephritis reduced anti-dsDNA antibodies, increased C3 concentrations, and decreased hematuria, suggesting that the drug has immunomodulatory function.

4.3. Inflammatory Bowel Disease (IBD) In Vivo Models:

Crohn's disease (CD) and ulcerative colitis (UC) are IBDs that are characterized by leukocytic infiltrates in inflamed intestinal mucosa, which consists primarily of activated CD25+ cells, B cells, and macrophages. Ludwiczek et al., *Int. J. Colorectal Dis.* 18: 142-147 (2003) report that in CD patients, plasma levels of sCD40L were significantly higher than in healthy individuals. Moreover, CD patients with fistulas and/or abscesses had significantly higher levels of sCD40L than patients with uncomplicated CD. It has also been reported that the CD40-CD40L pathway contributes to the proinflammatory function of intestinal epithelial cells in IBD. Borcherding et al., *Am. J. Pathol.* 176: 1816-1827 (2010). Patients with CD also have an increased risk of systemic thromboembolism, and the hyperactive state of platelets from such patients likely results from the enhanced release of sCD40L as a consequence of their higher endogenous content of CD40L. Menchen et al., *Gut* 58: 920-928 (2009); see also Danese et al., *Gut* 52: 1435-1441 (2003).

Kasran et al., *Aliment. Pharmacol. Ther.* 22: 111-122 (2005) investigated the use of a chimeric anti-human CD40 mAb ch5D12 to treat Crohn's disease. The mAb was administered to 18 patients with moderate to severe CD in a single dose, open-label dose escalation phase I/IIa study. Of the 18 patients, 13 (or 72%) experienced a favorable response to the antibody infusion, and 4 patients (or 22%) experienced a remission. Treatment with the anti-CD40 mAb reduced microscopic disease activity and intensity of the lamina propria cell infiltrate, and the mAb was well tolerated.

4.4. Rheumatoid Arthritis (RA), Juvenile Idiopathic Arthritis (JIA), and Psoriatic Arthritis (PsA) In Vivo Models:

Rheumatoid arthritis is a systemic autoimmune disease with intra-articular inflammation as a dominant feature that affects up to 1% of the population. The disease can be subdivided clinically by the presence or absence of autoantibodies (antibodies to cyclic citrullinated peptide (CCP) or rheumatoid factor (RF), both of which are highly correlated to each other. Raychaudhuri et al., *Nature Genetics* 40: 1216-1223 (2008) reported that they conducted a meta-analysis of two published genome-wide association (GWA) studies totaling 3,393 cases and 12,462 controls, in order to identify RA risk loci in European populations. They genotyped 31 top-ranked short nucleotide polymorphisms (SNPs) not previously associated with RA in an independent replication of 3,929 autoantibody-positive RA cases and 5,807 matched controls from eight separate collections. They identified a common variant at the CD40 gene locus, which implied a central role for the CD40 signaling pathway in RA pathogenesis. The strong association of the CD40 gene with susceptibility to RA was robustly replicated in another study in a large UK cohort of 3,962 patients with RA. Orozso et al., *Ann. Rheum. Dis.* 69: 813-816 (2010).

A major role of CD40L has also been found in the pathogenesis of juvenile idiopathic arthritis (JIA). Prahalad et al., *Pediatric Rheumatology* 6: 1-8 (2008). JIA is a heterogeneous group of arthropathies of unknown etiology. It was found that sCD40L was significantly elevated in the serum of children with JIA, along with some cytokines. Logistic regression analysis suggested that sCD40L, as well as IL-6 and TNFα, were positively associated with JIA. sCD40L was elevated in all JIA subtypes, with highest levels among more severe subtypes. These results implicated sCD40L as a potential biomarker for treatment and monitoring of patients with JIA.

It has also been demonstrated that activated T cells from patients with psoriatic arthritis (PsA), and particularly those with active disease, have a significantly increased expression of CD40L. Daoussis et al., *Rheumatology* 46: 227-231 (2007). These results indicate a role of the CD40-CD40L pathway in the pathogenesis of PsA and that a therapy selectively targeting CD40L could benefit PsA patients.

4.5. Systemic Sclerosis In Vivo Models:

Systemic sclerosis (SSc) is an autoimmune connective tissue disorder characterized by fibrous and vascular changes in the skin and internal visceral organs. In a study involving 52 Japanese patients with SSc, serum sCD40L levels were elevated when compared with healthy controls. Komura et al., *J. Reumatol.* 31: 514-519 (2004). Moreover, levels of sCD40L in patients with SSc were higher than in patients with systemic lupus erythematosus (SLE) who had elevated sCD40L levels compared to controls, and sCD40L levels correlated positively with C reactive peptide levels in SSc patients. It has also been reported that blockade of CD40L with anti-CD40L antibody in cultured T and B cells from SSc patients inhibited anti-topoisomerase I antibody production. Kuwana et al., *J. Immunol.* 155: 2703-2714 (1995). These results suggest that inhibition of CD40-CD40L interactions may be potential therapeutic targets in therapy of SSc as well as SLE.

4.6. Atherosclerosis In Vive Models:

Several studies have suggested a role of CD40-CD40L signaling pathway during atherogenesis. Mach et al. demonstrated that in mice, treatment with monoclonal anti-CD40L antibody limited atherosclerosis in mice lacking receptor for low-density lipoprotein that had been fed a high-cholesterol diet for 12 weeks. Nature 394: 200-203 (1998). The antibody reduced the size of aortic atherosclerotic lesions by 59% and their lipid content by 79%. Additionally, atheroma of mice treated with anti-CD40L antibody contained significantly fewer macrophages and T lymphocytes, and exhibited decreased expression of vascular cell adhesion molecule-1.

Anti-CD40L antibody treatment of low-density lipoprotein receptor-deficient mice during the second half of a 26-week regimen of a high-cholesterol diet did not regress, but did significantly reduce further progression of established atherosclerotic lesions within the aortic arch and particularly the thoracic and abdominal aorta, as compared to control treatment. Schonbeck et al., *Proc. Natl. Acad. Sci.* 97: 7458-7463 (2000). Furthermore, anti-CD40L treatment changed the composition of atheroma in manners thought to favor plaque stability, e.g., reduced relative content of macrophages and lipid, as well as increased relative content of smooth muscle cells and collagen. These studies lend support to the importance of the CD40-CD40L signaling pathway in atherosclerosis and its complications, such as coronary artery disease.

4.7. Allograft Rejection In Vivo Models:

Targeting the CD40-CD40L pathway has long been of much interest for prevention of rejection of solid organ transplants (SOT), particularly in light of the promising data from numerous published transplant studies in non-human primates. It has been demonstrated that reduced CD40L expression on ex vivo activated CD4+ T lymphocytes correlates with excellent renal allograft function. Lederer et al., *Int. Arch. Allergy Immunol.* 133: 276-284 (2004). Furthermore, several studies have demonstrated that anti-CD40L mAbs can both prevent and reverse acute allograft rejection in primates. For example, Kirk et al., *Proc. Natl. Acad. Sci. USA* 94: 8789-8794 (1997) reported that, in rhesus monkeys transplanted with renal allografts, anti-CD40L mAb 5C8 alone or in combination with CTLA4-Ig significantly prolonged rejection-free survival. The CD40L-specific mAb hu5c8 alone also allowed for allogeneic islet engraftment and long-term insulin independence in rhesus monkeys that were transplanted an adequate number of viable pancreatic islets. Kenyon et al., *Proc. Natl. Acad. Sci. USA* 96: 8132-8137 (1999). Preston et al., *Amer. J. Transplantation* 5: 1032-1041 (2005) performed renal transplants in MHC-mismatched rhesus monkeys and treated the recipients with combinations of CD40L-specific mAb IDEC-131, and/or sirolimus, and/or pre-transplant donor-specific transfusion. IDEC-131 was highly effective in preventing renal allograft rejection in primates. In cynomolgus monkeys that underwent renal allotransplantation, treatment with anti-CD40L mAb ABI793 effectively prevented graft rejection. Schuler et al., *Transplantation* 77: 717-726 (2004). In addition to preventing allograft rejection, CD40L-specific mAbs induced donor specific tolerance in primate transplant models. Preston et al., *Amer. J. Transplantation* 5: 1032-1041 (2005); Kenyon et al., *Proc. Natl. Acad. Sci. USA* 96: 8132-8137 (1999).

In pediatric human patients that were undergoing acute graft rejection after liver or small-bowel transplantation, a correlation was observed between the expression of CD40L on CD8+ T cells and the risk of transplant rejection. Ashokkumar et al., *Amer. J. Transplantation* 9: 179-191 (2009) and Ashokkumar et al., *Surgery* 146: 166-173 (2009). Similarly, in adult patients that were undergoing allograft rejection following liver or renal transplantation, histological analysis demonstrated an association between CD40L expression and acute or chronic rejection. Bartlett et al., *Amer. J. Transplantation* 3: 1363-1368 (2003) and Biancone et al., *Nephrol. Diall. Transplant.* 13: 716-722 (1998).

Several studies support targeting CD40L over CD40 to achieve better efficacy in transplantation. For example, graft survival is longer and more durable when CD40L is selectively blocked, compared to CD40. Gilson et al., *J. Immunol.* 183: 1625-35 (2009). Furthermore, recent data suggest that CD40L blockade may enhance induction of Tregs and/or suppressor cells to promote graft survival. Garcia et al., *J. Clin. Inv.* 120: 2486-96 (2010). Also, blockade of CD40L, but not CD40, has demonstrated induction of long-lived immunological tolerance resulting in indefinite graft survival, particularly when combined with blockade of the B7 pathway. Kenyon et al., *Proc. Natl. Acad. Sci. USA* 96: 8132-8137 (1999); Kawai et al., *Amer. Transplantation* 4: 1391-1398 (2004); Preston et al., *Amer. J. Transplantation* 5: 1032-1041 (2005); Adams et al., *J. Immunol.* 174: 542-50 (2005). The synergy of blocking CD40-40L and B7-CD28 pathways in enhancing graft survival is especially important, because it presents the presently disclosed domain antibodies as a natural choice for combination with belatacept (CTLA4-Ig) for SOT.

4.8. Graft-Versus-Host Disease In Vivo Model:

Chronic and acute graft-versus-host disease (cGVHD and aGVHD) are complications that can occur after a stem cell or bone marrow transplant in which the transplanted donor cells attack the transplant recipient's body. Acute GVHD in humans takes place withing about 60 days post-transplantation and results in damage to the skin, liver, and gut by the action of cytolytic lymphocytes. Chronic GVHD occurs later and is a systemic autoimmune disease that affects primarily the skin, resulting in the polyclonal activation of B cells and the hyperproduction of Ig and autoantibodies.

CD40L-CD40 interactions appear to be critical in the development of both cGVHD and aGVHD. Durie et al., *J. Clin. Invest.* 94: 1333-1338 (1994). In a mouse in vivo model, anti-CD40L antibodies blocked the following cGVHD-associated phenomena: splenomegaly, in vitro polyclonal Ig production, elevated levels of serum IgE and serum anti-DNA autoantibodies, and the generation of anti-host cytotoxic T cells. Antibody production remained inhibited for extended periods of time after the end of anti-CD40L antibody administration. In mice with aGVHD, which is associated with the induction of a profound antiallogenic cytotoxic T cell (CTL) response, treatment with anti-CD40L prevented the generation of H-2b-derived CTL. The results of the study suggest that CD40L-CD40 interactions are critical in GVHD and that CD40L may be a valuable ligand for targeting immunotherapeutic agents to control GVHD.

4.9. Myasthenia Gravis In Vivo Model:

Myasthenia gravis (MG) and its animal model, experimental autoimmune MG (EAMG), are T-cell dependent autoimmune disorders caused by autoantibodies against the nicotinic acetylcholine receptors (AChR) at the neuromuscular junction of skeletal muscle. The role of CD40-CD40L in EAMG was shown in CD40L (CD40L−/−) knockout mice. Shi et al, *Eur. J. Immunol.* 28: 3587-3593 (1998). The CD40L knockout mice were completely resistant to EAMG induction and had diminished Th1 and Th2 responses as well as severely impaired T-cell dependent AChR-reactive B cell responses.

It has also been demonstrated that blockade of CD40L-CD40 signaling by anti-CD40L antibodies is capable of suppressing EAMG. Im et al., *J. Immunol.* 166: 6893-6898 (2001). Antibodies given to rats at the chronic stage of EAMG suppress the clinical progression of the autoimmune response and lead to a decrease in the AChR-specific humoral response and delayed-type hypersensitivity. The effect of anti-CD40L treatment during the chronic phase of EAMG is of particular relevance to human MG, which is a chronic disease. It suggests that antagonizing CD40L can be used for immunotherapy of MG and other antibody-mediated autoimmune diseases.

5. Thromboembolism

CD40-CD40L interactions on T and antigen presenting cells are important for adaptive immune responses, such as B-cell proliferation, immunoglobulin (Ig) production, upregulation of co-stimulatory activity (CD80, CD86), cytokine production, and Ig class-switching. The receptor and ligand are also expressed on platelets (off-target cell population), where CD40 is constitutively found on platelets, while CD40L is expressed on activated platelets and cleaved to sCD40L (>90% of circulating sCD40L is derived from platelets). Feroni et al., *Curr. Med. Chem.* 14: 2170-2180 (2007). At least three anti-CD40L monoclonal antibodies (mAb) caused TE in the clinic and/or nonclinical studies conducted in non-human primates (NHP). hu5c8 (BG9588) caused TE in multiple clinical trials (lupus and renal transplantation). Boumpas et al., *Arthritis & Rheumatism* 48: 719-727 (2003). IDEC131 caused TE in one patient in a Crohn's disease trial, leading to termination of ongoing trials at the time. Sidiropoulus & Boumpas, *Lupus* 13: 391-397 (2004). Both hu5c8 and ABI1793 (which binds CD40 at a different epitope from 5c8) caused TE/thrombosis in renal transplantation studies in cynomolgus or rhesus monkeys. Schuler et al., *Transplantation* 77: 717-726 (2004); Kanmaz et al., *Transplantation* 77: 914-920 (2004); Koyama et al., *Transplantation* 77: 460-461 (2004). In a non-published disclosure, Biogen reported a thrombosis incidence of 1/4 and 6/12 in rhesus monkeys given 5 and 20 mg/kg weekly, respectively, for 6-months, but not in cynomolgus monkeys given 50 mg/kg at the same frequency and duration. The basis for the species difference is not clear.

Figure 10:
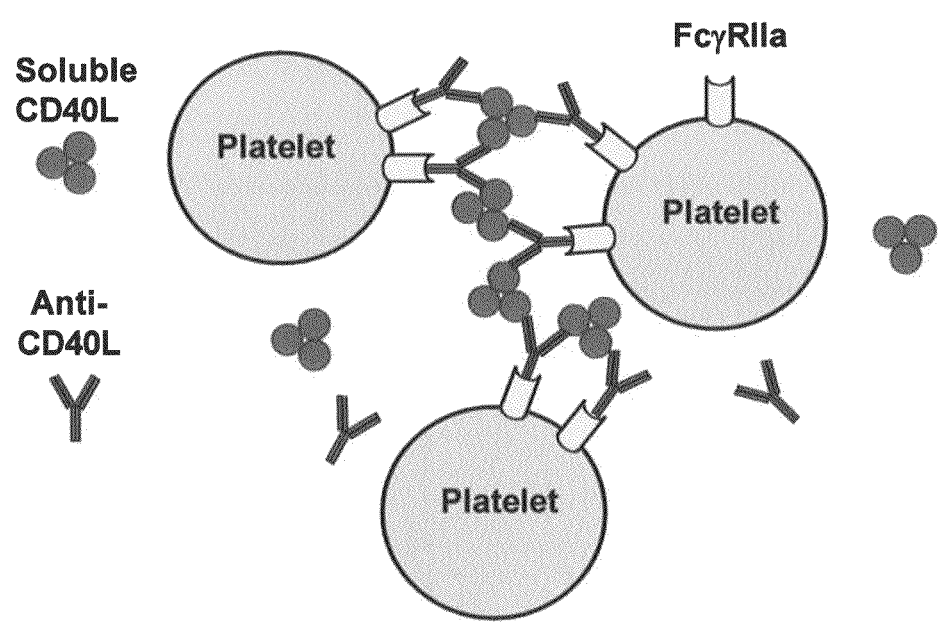
FIG. 10 provides a hypothetic model for anti-CD40 monoclonal antibody-mediated platelet aggregation.

One of the hypotheses is that the TE associated with administration of these antibodies is mediated by anti-CD40Lmab-CD40L immune complex (IC)-mediated cross linking of platelets, facilitated by IC binding to FcgRIIa, an IgG Fc receptor, causing activation and aggregation (FIG. 10). Blocking the interaction of Fc moiety of IgG with FcgRIIa is, therefore, expected to mitigate platelet cross linking and thrombosis. Approaches and methods developed to evaluate the risk for TE/thrombosis are described in Examples below.

EXAMPLES

TABLE 1 lists representative anti-human CD40L VH domain amino acid sequences useful for the disclosed antibody polypeptides. TABLE 2 discloses representative nucleic acids that encode the VH domain sequences listed in TABLE 1. TABLE 3 lists representative anti-human CD40L VK domain amino acid sequences useful for the antibody polypeptides of the present disclosure. TABLE 4 in turn discloses representative nucleic acids that encode the VK domain sequences listed in TABLE 3. As well known in the art, multiple codons can encode the same amino acid. Nucleic acids encoding a protein sequence thus include nucleic acids having codon degeneracy. The antibody polypeptides disclosed in TABLE 1 and TABLE 3 specifically bind CD40L. They were made using the reiterative initial/primary screening and affinity methodologies described in the examples that follow.

TABLE I

Anti-human CD40L VH Domain Amino Acid Sequences

```
BMS2h-10
                                                                    (SEQ ID NO: 15)
EVQLLESGGG LVQPGGSLRL SCAASGFTFI AYDMSWVRQA PGKGLEWVSW IDEWGLQTYY
ADSVKGRFTI SRDNSKNTLY LQMNSLRAED TAVYYCAKKT PEE------- FDYWGQGTLV TVSS

BMS2h-11
                                                                    (SEQ ID NO: 16)
EVQLLESGGG LVQPGGSLRL SCAASGFTFG DYEMSWVRQA PGKGLEVWSG IDGEGSDTYY
ADSVKGRFTI SRDNSKNTLY LQMNSLRAED TAVYYCAKPG RS-------- FDYWGQGTLV TVSS

BMS2h-111
                                                                    (SEQ ID NO: 17)
EVQLLESGGG LVQPGGSLRL SCAASGFTFE RYPMTWVRQA PGKGLEWVST IHGSGSATYY
ADSVKGRFTI SRDNSKNTLY LQMNSLRAED TAVYYGAKGP YTSRHNSLGH FDYWGQGTLV TVSS

BMS2h-112
                                                                    (SEQ ID NO: 18)
EVQLLESGGG LVQPGGSLRL SCAASGFTFM DYPMGWVRQA PGKGLEWVSS IGPVGMSTYY
ADSVKGRFTI SRDNSKNTLY LQMNSLRAED TAVYYCAKYG GTSGRHNTK- FDYWGQGTLV TVSS

BMS2h-113
                                                                    (SEQ ID NO: 19)
EVQLLESGGG LVQPGGSLRL SCAASGFTFT EYPMSWVRQA PGKGLEWVSV ISPLGFTTYY
ADSVKGRFTI SRDNSKNTLY LQMNSLRAED TAVYYCAKWT GGSGILNSS- FDYWGQGTLV TVSS

BMS2h-114
                                                                    (SEQ ID NO: 20)
EVQLLESGGG LVQPGGSLRL SCAASGFRVS NYDLTWVRQA PGKGLEWVST ISATNGSTYY
ADSVKGRFTI SRDNSKNTLY LQMNSLRAED TAVYYCAAVT WWLLRHNDN- LGFWGQGTLV TVSS

BMS2h-115
                                                                    (SEQ ID NO: 21)
EVQLLESGGG LVQPGGSLRL SCAASGFSIS YKNMAWVRQA PGKGLEWVSA IKAANGSTYY
ADSVKGRFTI SRDNSKNTLY LQMNSLRAED TAVYYCATGS QKKRTYT--- FDFWGQGTLV TVSS

BMS2h-12
                                                                    (SEQ ID NO: 22)
EVQLLESGGG LVQPGGSLRL SCAASGFTFR LYEMAWVRQA PGKGLEWVSG IDILGSRTYY
ADSVKGRFTI SRDNSKNTLY LQMNSLRAED TAVYYCAKDL SWQG------ FDYWGQGTLV TVSS

BMS2h-120
                                                                    (SEQ ID NO: 23)
EVQLLESGGG LVQPGGSLRL SCAASGFTFR SYTMGWVRQA PGKGLEWVSS INPMGYQTYY
ADSVKGRFTI SRDNSKNTLY LQMNSLRAED TAVYYCAKHG VGKGTKPHN  FDYWGQGTLV TVSS

BMS2h-121
                                                                    (SEQ ID NO: 24)
EVQLLESGGG LVQPGGSLRL SCAASGFTFE LYRMSWVRQA PGKGLEWVSE ISGSGFPTYY
ADSVKGRFTI SRDNSKNTLY LQMNSIRAED TAVYYCAKSL HDKTQHHQE  FDYWGQGTLV TVSS

BMS2h-123
                                                                    (SEQ ID NO: 25)
EVQLLESGGG LVQPGGSLRL SCAASGFTFI EYPMRWVRQA PGKGLEWVSL ISPSGVFTYY
ADSVKGRFTI SRDNSKNTLY LQMNSLRAED TAVYYCAKGD ESST FDYWGQGTLV TVSS
```

TABLE I-continued

Anti-human CD40L VH Domain Amino Acid Sequences

BMS2h-124
(SEQ ID NO: 26)
EVQLLESGGG LVQPGGSLRL SCAASGFTFK RYDMDWVRQA PGKGLEWVST IGSSGYPTYY
ADSVKGRFTI SRDNSKNTLY LQMNSLRAED TAVYYCAERM PGYFPGFARQ FDYWGQGTLV TVSS

BMS2h-125
(SEQ ID NO: 27)
EVQLLESGGG LVQPGGSLRL SCAASGFTFW RYAMGWVRQA PGKGLEWVST INDEGRETYY
ADSVKGRFTI SRDNSKNTLY LQMNSLRAED TAVYYCAKKR VSSSVNAPYE FDYWGQGTLV TVSS

BMS2h-126
(SEQ ID NO: 28)
EVQLLESGGG LVQPGGSLRL SCAASGFTFA NYSMSWVRQA PGKGLEWVSS IDRLGTHTYY
ADSVKGRFTI SRDNSKNTLY LQMNSLRAED TAVYYCAKVL ADLIAGHAE  FDYWGQGTLV TVSS

BMS2h-127
(SEQ ID NO: 29)
EVQLLESGGG LVQPGGSLRL SCAASGFTFP SYDMAWVRQA PGKGLEWVSG ISRSGSMTYY
ADSVKGRFTI SRDNSKNTLY LQMNSLRAED TAVYYCAKGV DAHVYYMEPF FDYWGQGTLV TVSS

BMS2h-128
(SEQ ID NO: 30)
EVQLLESGGG LVQPGGSLRL SCAASGFTFE RYQMAWVRQA PGKGLEWVST ISSDGGGTYY
ADSVKGRFTI SRDNSKNTLY LQMNSLRAED TAVYYCAKPG TV FDYWGQGTLV TVSS

BMS2h-129
(SEQ ID NO: 31)
EVQLLESGGG LVQPGGSLRL SCAASGFTFP KYEMAWVRQA PGKGLEWVSS IDGDGKSTYY
ADSVKGRFTI SRDNSKNTLY LQMNSLRAED TAVYYCAKPD QF FDYWGQGTLV TVSS

BMS2h-13
(SEQ ID NO: 32)
EVQLLESGGG LVQPGGSLRL SCAASGFTFS YYSMYWVRQA PGKGLEWVSS ISPFGWGTYY
ADSVKGRFTI SRDNSKDTLY LQMNSLRAED TAVYYCAKYG ETSGPISEN  FDYWGQGTLV TVSS

BMS2h-130
(SEQ ID NO: 33)
EVQLLESGGG LVQPGGSLRL SCTASGFTFA GYQMSWVRQA PGKGLEWVSS ITNEGVSTYY
ADSVKGRFTI SRDNSKNTLY LQMNSLRAED TAVYYCAKPG KY FDYWGQGTLV TVSS

BMS2h-131
(SEQ ID NO: 34)
EVQLLESGGG LVQPGGSLRL SCAASGFTFG EYEMVWVRQA PGKGLEWVSS ITSDGLSTYY
ADSVKGRFTI SRDNSKNTLY LQMNSLRAED TAVYYCAKPG IRFDYWGQGTLV TVSS

BMS2h-132
(SEQ ID NO: 35)
EVQLLESGGG LVQPGGSLRL SCAASGFTFA DYDMAWVRQA PGKGLEWVSG IVDDGLMTYY
ADSVKGRFTI SRDNSKNTLY LQMNSLRAED TAVYYCAKPD VAFDYWGQGTLVTVSN

BMS2h-133
(SEQ ID NO: 36)
EVQLLESGGG LVQPGGSLRL SCAASGFTFI GYAMAWVRQA PGKGLEWVSS IGPLGATTYY
ADSVKGRFTI SRDNSKNTLY LQMNSLRAED TAVYYCAKLP AGTSSHSVDFDYWGQGTLV TVSS

BMS2h-134
(SEQ ID NO: 37)
EVQLLESGGG LVQPGGSLRL SCAASGFTFA DYEMTWVRQA PGKGLEWVSS ITSDGLSTYY
ADSVKGRFTI SRDNSKNTLY LQMNSLRAED TAVYYCAKPS VQ FDYWGQGTLV TVSS

BMS2h-135
(SEQ ID NO: 38)
EVQLLESGGG LVQPGGSLRL SCAASGFTFR RYVMGWVRQA PGKGLEWVSW IEADGRTTYY
ADSVKGRFTI SRDNSKNTLY LQMNSLRAED TAVYYCAKGL TDQHVIE FDYWGQGTLV TVSS

BMS2h-136
(SEQ ID NO: 39)
EVQLLESGGG LVQPGGSLRL SCAASGFTFD GYRMGWVRQA PGKGLEWVSS IAPDGNYTYY
ADSVKGRFTI SRDNSKUTLY LQMNSLRAED TAVYYCAKFW GMQFDYWGQGTLV TVSS

BMS2h-137
(SEQ ID NO: 40)
EVQLLESGGG LVQPGGSLRL SCAASGFTFA SYPMGWVRQA PGKGLEWVSS IGPIGFTTYY
ADSVKGRFTI SRDNSKNTLY LQMNSLRAED TAVYYCAEMK SPYKPQ---- FDYWGQGTLV TVSS

TABLE I-continued

Anti-human CD40L VH Domain Amino Acid Sequences

BMS2h-138
(SEQ ID NO: 41)
EVQLLESGGG LVQPGGSLRL SCAASGFTFL AYWMWVRQA PGKGLEWVSS ISPSGTHTYY
ADSVKGRFTI SRDNSKNTLY LQMNSLRVED TAVYYCAKYT EPGLGS---- FDYWGQGTLV TVSS

BMS2h-139
(SEQ ID NO: 42)
EVQLLESGGG LVQPGGSLRL SCAASGFTFS NYEMGWVRQA PGKGLEWVSV ISEVGSLTYY
ADSVKGRFTI SRDNSKNTLY LQMNSLRAED TAVYYCAKPH DSSIG----- FDYWGQGTLV TVSS

BMS2h-14
(SEQ ID NO: 43)
EVQLLESGGG LVQPGGSLRL SCAASGFTFW SYDMTWVRQA PGKGLEWVSS IMASSDDTYY
ADSVKGRFTI SRDNSKNTLY LQMNSLRAED TAVYYCAKWD RD-------- FDYWGQGTLV TVSS

BMS2h-15
(SEQ ID NO: 44)
EVQLLESGGG LVQPGGSLRL SCAASGFTFE EYVMSWVRQA PGKGLEWVST ISPIGLTTYY
ADSVKGRFTI SRDNSKNTLY LQMNSLRAED TAVYYCAEFP LIILPD---- FDYWGQGTLV TVSS

BMS2h-16
(SEQ ID NO: 45)
EVQLLESGGG LVQPGGSLRL SCAASGFTFM EYAMIWVRQA PGKGLEWVSI ISPLGLSTYY
ADSVKGRFTI SRDNSKNTLY LQMNSLRAED TAVYYCAKYQ DSSDSQYTN- FDYWGQGTLV TVSS

BMS2h-17
(SEQ ID NO: 46)
EVQLLESGGG LVQPGGSLRL SCAASGFTFE DYGMGWARQA PGKGLEWVSS IGPLGLWIYY
ADSAKGRFTI SRDNSKNTLY LQMNSLRAED TAVYYCAKSP LEGLITN--- FDYWGQGTLV TVSS

BMS2h-176
(SEQ ID NO: 47)
EVQLLESGGG LVQPGGSLRL SCAASGFTFD AYEMGWVRQA PGKGLEWVSI IDWDGNSTYY
ADSVKGRFTI SRDNSKNTLY LQMNSLRAED TAVYYCAKPG DNVGI----- FDYWGQGTLV TVSS

BMS2h-177
(SEQ ID NO: 48)
EVQLLESGGG LVQPGGSLRL SCAASGFTFS NYYMVWVRQA PGKGLEWVSA IDEWGFATYY
ADSVKGRFTI SRDNSKNTLY LQMNSLRAED TAVYYCAKHW EFTSDTSR-- FDYWGQGTLV TVSS

BMS2h-178
(SEQ ID NO: 49)
EVQLLESGGG LVQPGGSLRL SCAASGFTFE DFDMAWVRQA PGKGLEWVSS INDQGSLTYY
ADSVKGRFTI SRDNSKNTLY LQMNSLRAED TAVYYCAKPD QF-------- FDYWGQGTLV TVSS

BMS2h-179
(SEQ ID NO: 50)
EVQLLESGGG LVQPGGSLRL SCAASGFTFS AYDMMWVRQA PGKGLEWVSR ISPQGRTYY
ADSVKGRFTI SRDNSKNTLY LQMNSLRAED TAVYYCAKIR GQSRIPMR-- FDYWGQGTLV TVSS

BMS2h-18
(SEQ ID NO: 51)
EVQLLESGGG LVQPGGSLRL SCAASGFTFP EYDMTWVRQA PGKGLEWVSY ISSDGYSTYY
ADSVKGRFTI SRDNSKNTLY LQMNSLRAED TAVYYCAKFH GSFRE----- FDYWGQGTLV TVSS

BMS2h-180
(SEQ ID NO: 52)
EVQLLESGGG LVQPGGSLRL SCAASGFTFT DYEMGWVRQA PGKGLEWVST ITSLGESTYY
ADSVKGRFTI SRDNSKNTLY LQMNSLRAED TAVYYCAKPG RI-------- FDYWGQGTLV TVSS

BMS2h-181
(SEQ ID NO: 53)
EVQLLESGGG LVQFGGSLRL SCAASGFTFA FYPMMWVRQA PGKGLEWVSW IDATGTRTYY
ADSVKGRFTI SRDNSKNTLY LQMNSLRAED TAVYYCAEGN YGSSYTMGV- FDYWGQGTLV TVSS

BMS2h-182
(SEQ ID NO: 54)
EVQLLESGGG LVQPGGSLRL SCAASGFTFD EYPMYWVRQA PGKGLEWVSS IGPSGPNTYY
ADSVKGRFTI SRDNSKNTLY LQMNSLRAED TAVYYCAKSP YFDVIPSY-- FDYWGQGTLV TVSS

BMS2h-153
(SEQ ID NO: 55)
EVQLLESGGG LVQPGGSLRL SCAASGFTFA DYGMGWVRQA PGKGLEWVSS IQSSGLRTYY
ADSVKGRFTI SRDNSKNTLY LQMNSLRAED TAVYYCAKRA NSRRG----- FDYWGQGTLV TVSS

TABLE I-continued

Anti-human CD40L VH Domain Amino Acid Sequences

BMS2h-184
(SEQ ID NO: 56)
EVQLLESGGG LVQPGGSLRL SCAASGFTFS DYEMMWVRQA PGKGLEWVSS ITSHGGSTYY
ADSVKGRFTI SRDNSKNTLY LQMNSLRAED TAVYYCAKPD KD-------- FDYWGQGTLV TVSS

BMS2h-185
(SEQ ID NO: 57)
EVQLLESGGG LVQPGGSLRL SCAASGFTFA HYPMSWVRQA PGKGLEWVSS IGRLGNRTYY
ADSVKGRFTI SRDNSKNTLY LQMNSLRAED TAVYYCAKRA TPVPIKGL-- FDYWGQGTLV TVSS

BMS2h-186
(SEQ ID NO: 58)
EVQLLESGGG LVQPGGSLRL SCAASGLTFG RYEMAWVRQA PGKGLEWVSS IDSDGWVTYY
ADSVKGRFTI SRDNSKNTLY LQMNSLRAED TAVYYCAQPD SL-------- FDYWGQGTLV TVSS

BMS2h-187
(SEQ ID NO: 59)
EVQLLESGGG LVQPGGSLRL SCAASGFIFS SYSMVWVRQA PGKGLEWVSG INRGGTRTYY
ADSVKGRFTI SRDNSKNTLY LQMNSLRAED TAVYYCAKGW RRG------- FDYWGQGTLV TVSS

BMS2h-188
(SEQ ID NO: 60)
EVQLLESGGG LVQPGGSLRL SCAASGFTFT RYRMSWVRQA PGKGLEWVSG ISRDGYRTYY
ADSVKGRFTI SRDNSKNTLY LQMNSLRAED TAVYYCAKGM TAS------- FDYWGQGTLV TVSS

BMS2h-189
(SEQ ID NO: 61)
EVQLLESGGG LVQPGGSLRL SCAASGFTFQ MYPMGWVRQA PGKGLEWVSM IEPAGDLTYY
ADSVKGRFTI SRDNSKNTLY LQMNSLRAED TAVYYCAKYQ EQFW------ FDYWGQGTLV TVSS

BMS2h-19
(SEQ ID NO: 62)
EVQLLESGGG LVQPGGSLRL SCAASGFPFP QYQMAWVRQA PGKGLEWVSM ITSDGLDTYY
ADSVKGRFTI SRDNSKNTLY LQMNSLRAED TAVYYCAKPE PL-------- FDYWGQGTLV TVSS

BMS2h-190
(SEQ ID NO: 63)
EVQLLESGGG LVQPGGSLRL SCAASGFTFS MYDMHWVRQA PGKGLEWVST ILSDGTDTYY
ADSVKGRFTI SRDNSKNTLY LQMNSLRAED TAVYYCAKYG AM-------- FDYWGQGTLV TVSS

BMS2h-191
(SEQ ID NO: 64)
EVQLLESGGG LVQPGGSLRL SCAASGFTFK LYPMTWVRQA PGKGLEWVSS IDAGGHETYY
ADSVKGRFTI SRDNSKNTLY LQMNSLRAED TAVYYCAKDW WDYL------ FDYWGQGTLV TVSS

BMS2h-192
(SEQ ID NO: 65)
EVQLLESGGG LVQPGGSLRL SCAASGFTFS RYPMSWVRQA PGKGLEWVSS INRSGMRTYY
ADSVKGRFTI SRDNSKNTLY LQMNSLRAED TAVYYCAEGH QAP------- FDYWGQGTLV TVSS

BMS2h-193
(SEQ ID NO: 66)
EVQLLESGGG LVQPGGSLRL SCAASGFTFT GYAMSWVRQA PGKGLEWVST INANGIRTYY
ADSVKGRFTI SRDNSKNTLY LQMNGLRAED TAVYYCAKGG VWRWGTGHK- FDYWGQGTLV TVSS

BMS2h-194
(SEQ ID NO: 67)
EVQLLESGGG LVQPGGSLRL SCAASGFTFK QYDMRWVRQA PGKGLEWVST ISONGTKTYY
ADSVKGRFTI SRDNSKNTLY LQMNSLRAED TAVYYCAKSR TGRY------ FDYWGQGTLV TVSS

BMS2h-195
(SEQ ID NO: 68)
EVQLLESGGG LVQPGGSLRL SCAASGFTFG TYDMGWVRQA PGKGLEWVSR INWQGDRTYY
ADSVKGRFTI SRDNSKNTLY LQMNSLRAED TAVYYCAKAG FGHYVDGLG- FDYWGQGTLV TVSS

BMS2h-196
(SEQ ID NO: 69)
EVQLLESGGG LVQPGGSLRL SCAASGFTFS GYEMAWVRQA PGKGLEWVSS ITDMGDSTYY
ADSVKGRFTI SRDNSKNTLY LQMNSLRAED TAVYYCAKPG TA-------- FDYWGPGTLV TVSS

BMS2h-197
(SEQ ID NO: 70)
EVQLLESGGG LVQPGGSLRL SCAASGFTFA KYKMWWVRQA PGKGLEWVSS ITPKGHSTYY
ADSVKGRFTI SRDNSKNTLY LQMNSLRAED TAVYYCAKRP MTP------- FDYWGQGTLV TVSS

TABLE I-continued

Anti-human CD40L VH Domain Amino Acid Sequences

BMS2h-198
(SEQ ID NO: 71)
EVQLLESGGG LVQPGGSLRL SCAASGFTFE RYNMSWVRQA PGKGLEWVSS IRPRGGKTYY
ADSVKGRFTI SRDNSKNTLY LQMNSLRAED TAVYYCAKWR REGYTGSK-- FDYWGQGTLV TVSS

BMS2h-199
(SEQ ID NO: 72)
EVQLLESGGG LVQPGGSLRL SCAASGFTFE RYGMTWVRQA PGKGLEWVSS IWPRGQKTYY
ADSVKGRFTI SRDNSKNTLY LQMNSLRAED TAVYYCAKGN SRYV------ FDYWGQGTLV TVSS

BMS2h-2
(SEQ ID NO: 73)
EVQLLESGGG LVQPGGSLRL SCAASGFTFS DYEMMWVRQA PGKGLEWVST ITSDGISTYY
ADSVKGRFTI FRDNSKNTLY LQMNSLRAED TAVYYCAKSG RF-------- FDYWGQGTLV TVSS

BMS2h-20
(SEQ ID NO: 74)
EVQLLESGGG LVQPGGSLRL SCAASGFTFS GYQMAWVRQA PGKGLEWVSG ISSEGLTTYY
ADSVKGRFTI SRDNSKNTLY LQMNSLRAED TAVYYCAKAG RR-------- FDYWGQGTLV TVSS

BMS2h-200
(SEQ ID NO: 75)
EVQLLESGGG LVQPGGSLRL SCAASGFTFT NYSMGWVRQA PGKGLEWVST IRPNGTKTYY
ADSVKGRFTI SRDNSKNTLY LQMNSLRAED TAVYYCAKRS SAHLQR---- FDYWGQGTLV TVSS

BMS2h-201
(SEQ ID NO: 76)
EVQLLESGGG LVQPGGSLRL SCAASGFITG NYSMGWVRQA PGKGLEWVSS IGRHGGRTYY
ADSVKGRFTI SRDNSKNTLY LQMNSLRAED TAVYYCAKKG STYPR----- FDYWGQGTLV TVSS

BMS2h-202
(SEQ ID NO: 77)
EVQLLESGGG LVQPGGSLRL SCTASGFTFS HYEMGWVRQA PGKGLEVWSS IEPFGGGTYY
ADSVKGRFTI SRDNSKNTLY LQMNSLRAED TAVYYCAKVY PQGS------ FDYWGQGTLV TVSS

BMS2h-203
(SEQ ID NO: 78)
EVQLLESGGG LVQPGGSLRL SCAASGFTFS NYTMGWVRQA PGKGLEWVSS IRPDGKITYY
ADSVKGRFTI SRDNSKNTLY LQMNSLRAED TAVYYCAEVY SSCAMCTPLL FDYWGQGTLV TVSS

BMS2h-204
(SEQ ID NO: 79)
EVQLLESGGG LVQPGGSLRL SCAASGFTFK RYSMAWVRQA PGKGLEVWSD IGPRGESTYY
ADSVKGRFTI SRDNSKNTLY LQMNSLRAED TAVYYCAKVG RGORDTSQP- FDYWGQGTLV TVSS

BMS2h-205
(SEQ ID NO: 80)
EVQLLESGGG LVQPGGSLRL SCAASGFTFA SYQMAWVRQA PGKGLEWVSG ITSGGLSTYY
ADSVKGRFTI SRDNSKNTLY LQMNSLRAED TAVYYCAKPG RG-------- FDYWGQGTLV TVSS

BMS2h-206
(SEQ ID NO: 81)
EVQLLESGGG LVQPGGSLRL SCAASGFTFA SYEMTWVRQA PGKGLEWVSG ISSDGLSTYY
ADSVKGRFTI SRDNSKNTLY LQMNSLRAED TAVYYCAKPG VL-------- FDYWGQGTLV TVSS

BMS2h-207
(SEQ ID NO: 82)
EVQLLESGGG LVQPGGSLRL SCAASGFTFD KYLMSWVRQA PGKGLEWVSG IEPLGDVTYY
ADSVKGRFTI SRDNSKNTLY LQMNSLRAED TAVYYCAKEA SGD------- FDYWGQGTLV TVSS

BMS2h-208
(SEQ ID NO: 83)
EVQLLESGGG LVQPGGSLRL SCAASGFTFT EYEMSWVRQA PGKGLEWVSS IDNVGSSTYY
ADSVKGRFTI SRDNSKNTLY LQMNSLRAED TAVYYCAKPG KL-------- FDYWGQGTLV TVSS

BMS2h-209
(SEQ ID NO: 84)
EVQLLESGGG LVQPGGSLRL SCAASGFTFA DYEMVWVRQA PGKGLEWVSA ISRQGFATYY
ADSVKGRFTI SRDNSKNTLY LQMNSLRAED TAVYYCAKDL ERDD------ FDYWGQGTLV TVSS

BMS2h-21
(SEQ ID NO: 85)
EVQLLESGGG LVQPGGSLRL SCAASGFTFA NYEMGWARQA PGKGLEWVSV ISEWGYSTYY
ADSAKGRFTI SRDNSKNTLY LQMNSLRAED TAVYYCAKLV GGTQYE---- FDYWGQGTLV TVSS

TABLE I-continued

Anti-human CD40L VH Domain Amino Acid Sequences

BMS2h-22
(SEQ ID NO: 86)
EVQLLESGGG LVQPGGSLRL SCAASGFTFH NYEMSWVRQA PGKGLEWVSS ISSGGSSTYY
ADSVKGRFTI SRDNSKNTLY LQMNSLRAED TAVYYCAKPG VK-------- FDYWGQGTLV TVSS

BMS2h-23
(SEQ ID NO: 87)
EVQLLESGGG LVQPGGSLRL SCAASGFTFG LYEMTWVRQA PGKGLEWVSS ITGDGISTYY
ADSVKGRFTI SRDNSRNTLY LQMNSLRAED TAVYYCAKAG RK-------- FDYWGQGTLV TVSS

BMS2h-24
(SEQ ID NO: 88)
EVQLLESGGG LVQPGGSLRL SCAASGFTES NYQMAWVRQA PGKGLEWVSS ITSEGGSTYY
ADSVKGRFTI SRDNSKNTLY LQMNSLRAED TAVYYCAKPG KN-------- FDYWGQGTLV TVSS

BMS2h-24-1
(SEQ ID NO: 89)
EVQLLESGGG LVQPGGSLRL SCAASGFTFS DYQMAWVRQA PGKGLEWVSS ITSEGGSTYY
ADSVKGRFTI SRDNSKNTVY LQMNSLRAED TAVYYCAKPG KN-------- FDYWGQGILV TVSS

BMS2h-25
(SEQ ID NO: 90)
EVQLLESGGG LVQPGGSLRL SCAASGFTFD NYEMTWVRQA PGKGLEWVST ITSQGISTYY
ADSVKGRFTI SRDNSKNTLY LQMNSLRAED TAVYYCAKPD RS-------- FDYWGQGTLV TVSS

BMS2h-26
(SEQ ID NO: 91)
EVQLLESGGG LVQPGGSLRL SCAASGFTFR SYEMTWVRQA PGKGLEWVSS ITSDGGTTYY
ADSVKGRFTI SRDNSKNTLY LQMNSLRAED TAVYYCAKPD KT-------- FDYWGQGTLV TVSS

BMS2h-27
(SEQ ID NO: 92)
EVQLLESGGG LVQPGGSLRL SCAASGFTFN LYEMTWVRQA PGKGLEWVSS ITSDGVSTYY
ADSVKGRFTI SRDNSKNTLY LQMNSLRAED TAVYYCAKPD SP-------- FDYWGQGTLV TVSS

BMS2h-28
(SEQ ID NO: 93)
EVQLLESGGG LVQPGGSLRL SCAASGFTFG HYDMAWVRQA PGKGLEWVST ISDNGNGTYY
ADSVKGRFTI SRDNSKNTLY LQMNSLRAED TAVYYCAKPG RD-------- FDYWGQGTLV TVSS

BMS2h-29
(SEQ ID NO: 94)
EVQLLESGGG LVQPGGSLRL SCAASGFTFG RYQMAWVRQA PGKGLEWVSS ISSDGGGTYY
ADSVKGRFTI SRDNSKNTLY LQMNSLRAED TAVYYCAKPG RA-------- FDYWGQGTLV TVSS

BMS2h-30
(SEQ ID NO: 95)
EVQLLESGGG LVQPGGSLRL SCAASGFTFA RYQMAWVRQA PGKGLEWVST ISDDGDSTYY
ADSVKGRFTI SRDNSKNTLY LQMNSLRAED TAVYYCAKLD KL-------- FDYWGQGTLV TVSS

BMS2h-300
(SEQ ID NO: 96)
EVQLLESGGG LVQPGGSLRL SCAASGFTFD NDEMTWVRQA PGKGLEWVSA IDTTGGQTYY
ADSVKGRFTI SRDNSKNTLY LQMNSLRAED TAVYYCAKPG KE-------- FDYWGQGTLV TVSS

BMS2h-301
(SEQ ID NO: 97)
EVQLLESGGG LVQPGGSLRL SCAASGFTFG ESEMSWVRQA PGKGLEVWSS ILDEGSGTYY
ADSVKGRFTI SRDNSKNTLY LQMNSLRAED TAVYYCAKPD KD-------- FDYWGQGTLV TVSS

BMS2h-302
(SEQ ID NO: 98)
EVQLLESGGG LVQPGGSLRL SCAASGFTFG EEEMSWVRQA PGKGLEWVSA ITDDGDDTYY
ADSVKGRFTI SRDNSKNTLY LQMNSLRAED TAVYYCAKFN AGA------- FDYWGQGTLV TVSS

BMS2h-303
(SEQ ID NO: 99)
EVQLLESGGG LVQPGGSLRL SCAASGFTFE VYDMAWVRQA PGKGLEWVSG IVNDGSSTYY
ADSVKGRFTI SRDNSKNTLY LQMNSLRAED TAVYYCAKPD KD-------- FDYWGQGTLV TVSS

BMS2h-304
(SEQ ID NO: 100)
EVQLLESGGG LVQPGGSLRL SCAASGFTFG NTEMTWVRQA PGKGLEWVSS IADDGSSTYY
ADSVKGRFTI SRDNSKNTLY LQMNSLRAED TAVYYCAKPG QA-------- FDYWGQGTLV TVSS

TABLE I-continued

Anti-human CD40L VH Domain Amino Acid Sequences

BMS2h-31
(SEQ ID NO: 101)
EVQLLESGGG LVQPGGSLRL SCAASGFTFE EYQMAWVRQA PGKGLEWVST ISDDGSSTYY
ADSVKGRFTI SRDNSKNTLY LQMNSLRAED TAVYYCAKPD LY-------- FDYWGQGTLV TVSS

BMS2h-32
(SEQ ID NO: 102)
EVQLLESGGG LVQPGGSLRL SCAASGFTFE VYQMGWVRQA PGKGLEWVSF IVPGGDLTYY
ADSVKGRFTI SRDNSKNTLY LQMNSLRAED TAVYYCAETW FE-------- FDYWGQGTLV TVSS

BMS2h-4
(SEQ ID NO: 103)
EVQLLESGGG LVQPGGSLRL SCAASGFTFD NYEMTVWRQA PGKGLEWVSS ITSDGTSTYY
ADSVKGRFTI SRDNSKNTLY LQMNSLRAED TAVYYCAKPN PP-------- FDYWGQGTLV TVSS

BMS2h-40
(SEQ ID NO: 104)
EVQLLESGGG LVQPGGSLRL SCAASGFTFK AYDMGWVRQA PGKGLEWVSQ IGRDGSFTYY
ADSVKGRFTI SRDNSKNTLY LQMNSLRAED TAVYYCAKPR RYAIF----- TFDRGQGTLV TVSS

BMS2h-400
(SEQ ID NO: 105)
EVQLLESGGG LVQPGGSLRL SCAASGFTFK QYPMVWRQA PGKGLEWVST ISTNGVRTYY
ADSVKGRFTI SRDNSKNTLY LQMNSLRAED TAVYYCAKWT DIISSSE--- FDYWGQGTLV TVSS

BMS2h-401
(SEQ ID NO: 106)
EVQLLESGGG LVQPGGSLRL SCAASGFTFF NYDMSWVRQA PGKGLEWVSA ISGSGGSTYY
ADSVKGRFTI SRDNSKNTLY LQMNSLRAED TAVYYCAKVF VWSADIDFD- FDYWGQGTLV TVSS

BMS2h-402
(SEQ ID NO: 107)
EVQLLESGGG LVQPGGSLRL SCAASGFTFS WYDMSWVRQA PGKGLEWVSH IASWGGKTYY
ADSVKGRFTI SRDNSKNTLY LQMNSLRAED TAVYYCAKVT VKDGGYLMD- FDYWGQGTLV TVSS

BMS2h-403
(SEQ ID NO: 108)
EVQLLESGGG LVQPGGSLRL SCAASGFTFA EYAMAWVRQA PGKGLEWVSS IGRDGAVTYY
ADSVKGRFTI SRDNSKNTLY LQMNSLRAED TAVYYCAKWK AAKERGSW-- FDYWGQGTLV TVSS

BMS2h-404
(SEQ ID NO: 109)
EVQLLESGGG LVQPGGSLRL SCAASGFTFQ AYQMQWVRQA PGKGLEWVST ISPNGLFTYY
ADSVKGRFTI SRDNSKNTLY LQMNSLRAED TAVYYCAKWL SS-------- FDYWGQGTLV TVSS

BMS2h-407
(SEQ ID NO: 110)
EVQLLESGGG LVQPGGSLRL SCAASGFTFA MYSMAWVRQA PGKGLEWVSG ISPRGVETYY
ADSVKGRFTI SRDNSKNTLY LQMNSLRAED TAVYYCAKTN WNGVDL---- FDYWGQGTLV TVSS

BMS2h-408
(SEQ ID NO: 111)
EVQLLESGGG LVQPGGSLRL SCAASGFTFP TYMMSWVRQA PGKGLEWVST INTNGRDTYY
ADSVKGRFTI SRDNSKNTLY LQMNSLRAED TAVYYCAKGD SNMSF----- FDYWGQGTLV TVSS

BMS2h-409
(SEQ ID NO: 112)
EVQLLESGGG LVQPGGSLRL SCAASGFTFE GYSMTWVRQA PGKGLEWVSS INASGTLTYY
ADSVKGRFTI SRDNSKNTLY LQMNSLRAED TAVYYCAKDG NRSEVF---- FDYWGQGTLV TVSS

BMS2h-41
(SEQ ID NO: 113)
EVQLLESGGG LVQPGGSLRL SCAASGFTFF EYEMTWVRQA PGKGLEWVSS IANDGSTTYY
ADSVKGRFTI SRDNSKNTLY LQMNSLRAED TAVYYCAKPD RQ-------- FDYWGQGILV TVSS

BMS2h-410
(SEQ ID NO: 114)
EVQLLESGGG LVQPGGSLRL SCAASGFTFQ DYLMAWVRQA PGKGLEWVSE INQDGTVTYY
ADSVKGRFTI SRDNSKNTLY LQMNSLRAED TAVYYCAESS PY-------- FDYWGQGTLV TVSS

BMS2h-411
(SEQ ID NO: 115)
EVQLLESGGG LVQPGGSLRL SCAASGFTFD NYAMSWVRQA PGKGLEWVSS ISRDGHVTYY
ADSVKGRFTI SRDNSKNTLY LQMNSLRAED TAVYYCAKLS SKGGTFASS- FDYWGQGTLV TVSS

TABLE I-continued

Anti-human CD40L VH Domain Amino Acid Sequences

BMS2h-412

(SEQ ID NO: 116)
EVQLLESGGG LVQPGGSLRL SCAASGFTFS AVPMTWVRQA PGKGLEWVSA ITDDGLRTYY
ADSVKGRFTI SRDNSKNTLY LQMNSLRAED TAVYYCAKGH IYGDY----- FDYWGQGTLV TVSS

BMS2h-413

(SEQ ID NO: 117)
EVQLLESGGG LVQPGGSLRL SCAASGFTFE LYRMMWVRQA PGKGLEWVSA ISSDGDTTYY
ADSVKGRFTI SRDNSKNTLY LQMNSLRAED TAVYYCAEHW LGTTLSLRD- FDYWGQGTLV TVSS

BMS2h-414

(SEQ ID NO: 118)
EVQLLESGGG LVQPGGSLRL SCAASGFTFY RYTMAWVRQA PGKGLEWVSQ ISPRGNITYY
ADSVKGRFTI SRDNSKNTLY LQMNSLRAED TAVYYCAKSG VAGAESPEY- FDYWGQGTLV TVSS

BMS2h-415

(SEQ ID NO: 119)
EVQLLESGGG LVQPGGSLRL SCAASGFTFL GYYMSWIRQA PGKGLEWVST IGPIGGGTYY
ADSVKGRFTI SRDNSKNTLY LQMNSLRAED TAVYYCAKSQ NIYGP----- FDYWGQGTLV TVSS

BMS2h-416

(SEQ ID NO: 120)
EVQLLESGGG LVQPGGSLRL SCAASGFTFE QYDMAWVRQA PGKGLEWVSE ISRDGGRTYY
ADSVKGRFTI SRDNSKNTLY LQMNSLRAED TAVYYCAEEY PY-------- FDYWGQGILV TVSS

BMS2h-417

(SEQ ID NO: 121)
EVQLLESGGG LVQPGGSLRL SCAASGFTFP QYSMVWVRQA PGKGLEWVST ISPLGSSTYY
ADSVKGRFTI SRDNSKNTLY LQMNSLRAED TAVYYCAKMS KLLLSRE--- FDYWGQGTLV TVSS

BMS2h-418

(SEQ ID NO: 122)
EVQLLESGGG LVQPGGSLRL SCAASGFTFA MYSMAWVRQA PGKGLEWVSG ISPRGVETYY
ADSVKGRFTI SRDNSKNTLY LQMNSLRAED TAVYYCAKTN WNGVDL---- FDYWGQGTLV TVSS

BMS2h-419

(SEQ ID NO: 123)
EVQLLESGGG LVQPGGSLRL SCAASGFTFT RHGMAWVRQA PGKGLEWVST ITPTGNTTYY
ADSVKGRFTI SRDNSKNTLY LQMNSLRAED TAVYYCAKDA HDEGY----- FDYWGQGTLV TVSS

BMS2h-42

(SEQ ID NO: 124)
EVQLLESGGG LVQPGGSLRL SCAASGFTFG PYEMTWVRQA PGKGLEWVSS IVGDGLDTYY
ADSVKGRFTI SRDNSKNTLY LQMNSLRAED TAVYYCAKPD RV-------- FDYWGQGTLV TVSS

BMS2h-420

(SEQ ID NO: 125)
EVQLLESGGG LVQPGGSLRL SCAASGFTFG STPMMWVRQA PGKGLEWVSE IRDTGLATYY
ADSVKGRFTI SRDNSKNTLY LQMNSLRAED TAVYYCASVS ---------- FDYWGQGTLV TVSS

BMS2h-421

(SEQ ID NO: 126)
EVQLLESGGG LVQPGGSLRL SCAASGFTFH LGDMHWVRQA PGKGLEWVSS ISGTGHTTYY
ADSVKGRFTI SRDNSKNTLY LQMNSLRAED TAVYYCAKPM NDQG------ FDYWGQGTLV TVSS

BMS2h-422

(SEQ ID NO: 127)
EVQLLESGGG LVQPGGSLRL SCAASGFTFM DEDMLWVRQA PGKGLEWVSR INSLGTHTYY
ADSVKGRFTI SRDNSKNTLY LQMNSLRAED TAVYYCAKSF MM-------- FDYWGQGTLV TVSS

BMS2h-423

(SEQ ID NO: 128)
EVQLLESGGG LVQPGGSLRL SCAASGFTFR NYQMHWVRQA PGKGLEWVSG IDATGRATYY
ADSVKGRFTI SRDNSKNTLY LQMNSLRAED TAVYYCARST RS-------- FDYWGQGTLV TVSS

BMS2h-424

(SEQ ID NO: 129)
EVQLLESGGG LVQPGGSLRL SCAASGFTFT NADMVWVRQA PGKGLEWVSS ISGSGGSTYY
ADSVKGRFTI SRDNSKNTLY LQMNSLRAED TAVYYCAKGY LTSH------ FDYWGQGTLV TVSS

BMS2h-425

(SEQ ID NO: 130)
EVQLLESGGG LVQPGGSLRL SCAASGFTFR DYSMAWVRQA PGKGLEWVST ITPSGLITYY
ADSVKGRFTI SRDNSKNTLY LQMNSLRAED TAVYYCAEWS QAVTRS---- FDYWGQGTLV TVSS

TABLE I-continued

Anti-human CD40L VH Domain Amino Acid Sequences

BMS2h-426
(SEQ ID NO: 131)
EVQLLESGGD LVQPGGSLRL SCAASGFTFS DEGMMWVRQA PGKGLEWVSE INQQGSATYY
ADSVKGRFTI SRDNSKNTLY LQMNSLRAED TAVYYCAKTI GM-------- FDYWGQGTLV TVSS

BMS2h-427
(SEQ ID NO: 132)
EVQLLESGGG LVQPGGSLRL SCAASGFTFT DQPMWVRQA PGKGLEWVSS IGARGGPTYY
ADSVKGRFTV SRDNSKNTLY LQMNSLRAED TAVYYCAKWF DIIAWDPFS- FDYWGQGTLV TVSS

BMS2h-428
(SEQ ID NO: 133)
EVQLLESGGG LVQPGGSLRL SCAASGFTFN QYPMMWVRQA PGKGLEWVSS ITPSGFLTYY
ADSVKGRFTI SRDNSKNTLY LQMNSLRAED TAVYYCAEWN PFITT----- FDYWGQGTLV TVSS

BMS2h-429
(SEQ ID NO: 134)
EVQLLESGGG LVQPGGSLRL SCAASGFTFG HQQMAWVRQA PGKGLEWVST ITPNGYYTYY
ADSVKGRFTI SRDNSKNTLY LQMNSLRAED TAVYYCAKFD YSLR------ FDYWGQGTLV TVSS

BMS2h-43
(SEQ ID NO: 135)
EVQLLESGGG LVQPGGSLRL SCAASGFTFA SYEMAWVRQA PGKGLEWVSS IGSDGGPTYY
ADSVKGRFTI SRDNSKNTLY LQMNSLRAED SAVYYCAKPD RA-------- FDYWGQGTLV TVSS

BMS2h-430
(SEQ ID NO: 136)
EVQLLESGGG LVQPGGSLRL SCAASGFTFS AEQMTWARQA PGKGLEWVST ITPHGDSTYY
ADSVKGRFTI SRDNSKNTLY LQMNSLRAED TAVYYCAKWR TLVDWPTSES FDYWGQGTLV TVSS

BMS2h-44
(SEQ ID NO: 137)
EVQLLESGGG LVQPGGSLRL SCAASGFTFT SYEMGWVRQA PGKGLEWVSS IEPTGITTYY
ADSVKGRFTI SRDNSKNTLY LQMNSLRAED TAVYYCAKPH FTELG----- FDYWGQGTLV TVSS

BMS2h-449
(SEQ ID NO: 138)
EVQLLESGGG LVQPGGSLRL SCAASGFTFE GEQMAWVRQA PGKGLEWVST ITLPGPYTFY
ADSVKGRFTI SRDNSKNTLY LQMNSLRAED TAVYYCAKGN GTF------- FDYWGQGTLV TVSS

BMS2h-45
(SEQ ID NO: 139)
EVQLLESGGG LVQPGGSLRL SCAASGFTFG NYAMAWVRQA PGKGLEWVSK IGAQGLHTYY
AGSVKGRFTI SRDNSKNTLY LQMNSLRAED TAVYYCAKQT TMDYER---- FDYWGQGTLV TVSS

BMS2h-450
(SEQ ID NO: 140)
EVQLLESGGG LVQPGGSLRL SCAASGFTFD EVDMSWVRQA PGKGLEWVSA IGNNGLKTYY
ADSVKGRFTI SRDNSKNTLY LQMNSLRAED TAVYYCAKSA LSYRPPV--- FDYWGQGTLV TVSS

BMS2h-451
(SEQ ID NO: 141)
EVQLLESGGG LVQPGGSLRL SCAASGFTFQ DDTMSWVRQA PGKGLEWVST ITLKGPSTYY
ADSVKGRFTI SRDNSKNTLY LQMNSLRAED TAVYYCAKSR DGLY------ FDYWGQGTLV TVSS

BMS2h-452
(SEQ ID NO: 142)
EVQLLESGGG LVQPGGSLRL SCAASGFTFA SSPMAWVRQA PGKGLEWVSS IGRDGSTTYY
ADSVKGRFTI SRDNSKNTLY LQMNSLRAED TAVYYCAKPS PYRR------ FDYWGQGTLV TVSS

BMS2h-453
(SEQ ID NO: 143)
EVQLLESGGG LVQPGGSLRL SCAASGFTFT DYSMVWVRQA PGKGLEWVST IVSHGGTTYY
ADSVKGRFTI SRDNSKNTLY LQMNSLRAED TAVYYCAKGK GYNAQY---- FDYWGQGTLV TVSS

BMS2h-454
(SEQ ID NO: 144)
EVQLLESGGG LVQPGGSLRL SCAASGFTFG HQQMAWVRQA PGKGLEWVST ITPNGYYTYY
ADSVKGRFTI SRDNSKNTLY LQMNSLRAED TAVYYCAKFD YSLR------ FDYWGQGTLV TVSS

BMS2h-455
(SEQ ID NO: 145)
EVQLLESGGG LVQPGGSLRL SCAASGFTFN DYDMIWVRQA PGKGLEWVST ISSHGDSTYY
ADSVKGRFTI SRDNSKNTLY LQMNSLRAED TAVYYCAKGD VF-------- FDYWGQGTLV TVSS

TABLE I-continued

Anti-human CD40L VH Domain Amino Acid Sequences

BMS2h-456
(SEQ ID NO: 146)
EVQLLESGGG LVQPGGSLRL SCAASGFTFG HQQMAWVRQA PGKGLEWVST ITPNGYYTYY
ADSVKGRFTI SRDNSKNTLY LQMNSLRAED TAVYYCAEWS DS-------- FDYRGQGTLV TVSS

BMS2h-457
(SEQ ID NO: 147)
EVQLLESGGG LVQPGGSLRL SCAASGFTFA DYEMAWVRQA PGKGLEWVSG IQSNGNITYY
ADSVKGRFTI SRDNSKNTLY LQMNSLRAED TAVYYCAKAN SQVEY----- FDYWGQGTLV TVSS

BMS2h-458
(SEQ ID NO: 148)
EVQLLESGGG LVQPGGSLRL SCAASGFTFG VEPMSWVRQA PGKGLEWVSN IGRDGSMTYY
ADSVKGRFTI SRDNSKNTLY LQMNSLRAED TAVYYCAKLG KHGT------ FDYWGQGTLV TVSS

BMS2h-459
(SEQ ID NO: 149)
EVQLLESGGG LVQPGGSLRL SCAASGFTFP EYRMMWVRQA FGKGLEWVSW IDERGSLTYY
ADSVKGRFTI SRDNSKNTLY LQMNSLRAED TAVYYCAKRR KGTKQ----- FDYWGQGTLV TVSS

BMS2h-46
(SEQ ID NO: 150)
EVQLLESGGG LVQPGGSLRL SCAASGFTFE LYAMAWVRQA PGKGLEWVSG IGAVGETTYY
ADSVKGRFTI SRDNSKNTLY LQMNSLRAED TAVYYCAKEA NNLSDNLV-- FDYWGQGTLV TVSS

BMS2h-460
(SEQ ID NO: 151)
EVQLLESGGG LVQPGGSLRL SCAASGFTFG HQQMAWVRQA PGKGLEWVST ITPNGYYTYY
ADSVKGRFTI SRDNSKNTLY LQMNSLRAED TAVYYCAKVVS VEIN------ FDYWGQGTLV TVSS

BMS2h-461
(SEQ ID NO: 152)
EVQLLESGGG LVQPGGSLRL SCAASGFTFN SYTMNWVRQA PGKGLEWVSS INPWGSRTYY
ADSVKGRFTI SRDNSKNTLY LQMNSLRAED TAVYYCAKGL VL-------- FDYWGQGTLV TVSS

BMS2h-462
(SEQ ID NO: 153)
EVQLLESGGG LVQPGGSLRL SCAASGFTFD GDMMSWVRQA PGKGLEWVSS ITQLGSRTYY
ADSVKGRFTI SRDNSKNTLY LQMNSLRAED TAVYYCAKQN WRTLT----- FDYWGQGTLV TVSS

BMS2h-463
(SEQ ID NO: 154)
EVQLLESGGG LVQPGGSLRL SCAASGFTFN AYGMMWVRQA PGKGLEWVSS ILSDGVITYY
ADSVKGRFTI SRDNSKNTLY LQMNSLRAED TAVYYCAKSA RGANF----- FDYWGQGTLV TVSS

BMS2h-464
(SEQ ID NO: 155)
EVQLLESGGG LVQPGGSLRL SCAASGFTFG HYMMVWVRQA PGKGLEWVSS ITPHGTSTYY
ADSVKGRFTI SRDNSKNTLY LQMNSLRAED TAVYYCAEFN AIFSEA---- FDYWGQGTLV TVSS

BMS2h-465
(SEQ ID NO: 156)
EVQLLESGGG LVQPGGSLRL SCAASGFTFR DYSMAWVRQA PGKGLEWVST ITPSGLTTYY
ADSVKGRFTI SRDNSKNTLY LQMNSLRAED TAVYYCAEWS QAVIRS---- FDYWGQGTLV TVSS

BMS2h-466
(SEQ ID NO: 157)
EVQLLESGGG LVQPGGSLRL SCAASGFTFD LYAMAWVRQA PGKGLEWVSM IGRDGRFTYY
ADSVKGRFTI SRDNSKNTLY LQMNSLRAED TAVYYCAKLA GSLRGR---- FDYWGQGTLV TVSS

BMS2h-467
(SEQ ID NO: 158)
EVQLLESGGG LVQPGGSLRL SCAASGFTFN KASMGWVRQA FGKGLEWVST ITPHGSSTYY
ADSVKGRFTI SRDNSKNTLY LQMNSLRAED TAVYYCAKQR WGVE------ FDYWGQGTLV TVSS

BMS2h-468
(SEQ ID NO: 159)
EVQLLESGGG LVQPGGSLRL SCAASGFTFQ GYSMGWVRQA PGKGLEWVSS IAGRGGVTYY
ADSVKGRFTI SRDNSKNTLY LQMNSLRAED TAVYYCAKGL YIYHSL---- FDYWGQGTLV TVSS

BMS2h-469
(SEQ ID NO: 160)
EVQLLESGGG LVQPGGSLRL SCAASGFTFP GMEMSWVRQA PGKGLEWVSA ITGTGSTTYY
ADSVKGRFTI SRDNSKNTLY LQMNSLRAED TAVYYCAKGY HP-------- FDYWGQGTLV TVSS

TABLE I-continued

Anti-human CD40L VH Domain Amino Acid Sequences

BMS2h-470
(SEQ ID NO: 161)
EVQLLESGGG LVQPGGSLRL SCAASGFTFP MVAMSWVRQA PGKGLEWVSS IARDGNVTYY
ADSVKGRFTI SRDNSKNTLY LQMNSLRAED AAVYYCAKVS PTG------- FDYWGQGTLV TVSS

BMS2h-471
(SEQ ID NO: 162)
EVQLLESGGG LVQPGGSLRL SCAASGFTFG HQDMSWVRQA PGKGLEWVSG ITDDGESTYY
ADSVKGRFTI SRDNSKNTLY LQMNSLRAED TAVYYCAKGD YD-------- FDYWGQGTLV TVSS

BMS2h-472
(SEQ ID NO: 163)
EVQLLESGGG LVQPGGSLRL SCAASGFTFG EYNMMWVRQA PGKGLEWVSQ ITRDGSRTYY
ADSVRGRFTI SRDNSRNTLY LQMNSLRAED SAVYYCAKLS MG-------- FDYWGQGTLV TVSS

BMS2h-473
(SEQ ID NO: 164)
EVQLLESGGG LVQPGGSLRL SCAASGFTFS DYSMIWARQA PGKGLEWVSS ITPYGSYTYY
ADSVKGRFTI SRDNSKNTLY LQMNSLRAED TAVYYCAKTD YL-------- FDYWGQGTLV TVSS

BMS2h-474
(SEQ ID NO: 165)
EVQLLESGGG LVQPGGSLRL SCAASGFTFD TYSMMWVRQA PGKGLEWVST ITPYGSSTYY
ADSVKGRFTI SRDNSKNTLY LQMNSLRAED TAVYYCAKWG LV-------- FDYWGQGTLV TVSS

BMS2h-475
(SEQ ID NO: 166)
EVQLLESGGG LVQPGGSLRL SCAASGFTFT TGPMMWVRQA PGKGLEWVSA IGIGGDTTYY
ADSVKGRFTI SRDNSKNTLY LQMNSLRAED TAVYYCAKLT PSNQ------ FDYWGQGTLV TVSS

BMS2h-476
(SEQ ID NO: 167)
EVQLLESGGG LVQPGGSLRL SCAASGFTFK QYQMMWVRQA PGKGLEWVSS ITPSGFLTYY
ADSVKGRFTI SRDNSKNTLY LQMNSLRAED TAVYYCAEWN PFIST----- FDYWGQGTLV TVSS

BMS2h-477
(SEQ ID NO: 168)
EVQLLESGGG LVQPGGSLRL SCAASGFTFP NYDMVWVRQA PGKGLEWVSS ISALGNVTYY
ADSVKGRFTI SRDNSKNTLY LQTNSLRAED TAVYYCAKWR SAITGN---- FDYWGQGTLV TVSS

BMS2h-478
(SEQ ID NO: 169)
EVQLLESGGG LVQPGGSLRL SCAASGFTFK EYQMSWVRQA PGKGLEWVST ISPSGMNTYY
ADSVKGRFTI SRDNSKNTLY LQMNSLRAED TAVYYCAEWR SWRPVVPGV- FDYWGQGTLV TVSS

BMS2h-479
(SEQ ID NO: 170)
EVQLLESGGG LVQPGGSLRL SCAASGFTFD DESMAWVRQA PGKGLEWVSS ITPHGTFTYY
ADSVKGRFTI SRDNSKNTLY LQMNSLRAED TAVYYCAKLH LKLYESH--- FDYWGQGTLV TVSS

BMS2h-480
(SEQ ID NO: 171)
EVQLLESGGG LVQPGGSLRL SCAASGFTFE GGEMGWVRQA PGKGLEWVSM IPMDGSATYY
ADSVKGRFTI SRDNSKNTLY LQMNSLRAED TAVYYCAKAG ST-------- FDYWGQGTLV TVSS

BMS2h-481
(SEQ ID NO: 172)
EVQLLESGGG LVQPGGSLRL SCAASGFTFD FMPMAWVRQA PGKGLEWVSS IGRDGAYTYY
ADSVKGRFTI SRDNSKNTLY LQMNSLRAED TAVYYCAKLA SPAQ------ FDYWGQGTLV TVSS

BMS2h-482
(SEQ ID NO: 173)
EVQLLESGGG LVQPGGSLRL SCAASGFTFG DEPMLWVRQA PGKGLEWVSS IGGTGTTTYY
ADSVKGRFTI SRDNSKNTLY LOMNSLRAED TAVYYCAKGN QGDFINR--- FHYWGQGTLV TVSS

BMS2h-483
(SEQ ID NO: 174)
EVQLLESGGG LVQPGGSLRL SCAASGFTFH AYNMAWVRQA PGKGLEWVST ISPRGSYTYY
ADSVKGRFTI SRDNSKNTLY LQMNSLRAED TAVYYCAKWP PPSSH----- FDYWGQGTLV TVSS

BMS2h-5
(SEQ ID NO: 175)
EVQLLESGGG LVQPGGSLRL SCAASGFTFD GYEMAWVRQA PGKGLEWVSS ITSDGTSTYY
ADSVKGRFTI SRDNSKNTLY LQMNSLRAED TAVYYCAKPG LR-------- FDYWGQGTLV TVSS

TABLE I-continued

Anti-human CD40L VH Domain Amino Acid Sequences

BMS2h-505
(SEQ ID NO: 176)
EVQLLESGGG LVQPGGSLRL SCAASGFTFE GYMMYWVHQA PGKGLEWVSS ISPQGHFTYY
ADSVKGRFTI SRDNSKNTLY LQMNSLRAED TAVYYCAELR ELPRL----- FDYWGQGTLV TVSS

BMS2h-506
(SEQ ID NO: 177)
EVQLLESGGG LVQPGGSLRL SCAASGFTFS SYAMGWVRQA PGKGLEWVSS IDASGGPTYY
ADSVKGRFTI SRDNSKNTLY LQMNSLRAED TAVYYCAKAN GKKFPFTKY- FDYWGQGTLV TVSS

BMS2h-507
(SEQ ID NO: 178)
EVQLLESGGG LVQPGGSLRL SCAASGFTFP SVHMAWVRQA PGKGLEWVSG INLTGVDTYY
ADSVKGRFTI SRDNSKNTLY LQMNSLRAED TAVYYCAKSA TTRQAHPLY- FDYWGQGTLV TVSS

BMS2h-515
(SEQ ID NO: 179)
EVQLLESGGG LVQPGGSLRL SCAASGFTFK EGEMYWVRQA PGKGLEWVST ISTNGLITYY
ADSVKGRFTI SRDNSKNTLY LQMNSLRAED TAVYYCAKST RDLG------ FAYWGQGTLV TVSS

BMS2h-516
(SEQ ID NO: 180)
EVQLLESGGG LVQPGGSLRL SCAASGFTFE EYEMAWARQA PGKGLEWVSF ISPRGHFTYY
ADSVKGRFTI SRDNSKNTLY LQMNSLRAED TAVYYCAKPA KT-------- FDYWGQGTLV TVSS

BMS2h-517
(SEQ ID NO: 181)
EVQLLESGGG LVQPGGSLRL SCAASGFTFD TYEMLWVRQA PGKGLEWVSR ISVDGSITYY
ADSVKGRFTI SRDNSKNTLY LQMNSLRAED TAVYYCAKTR MR-------- FDYWGQGTLV TVSS

BMS2h-518
(SEQ ID NO: 182)
EVQLLESGGG LVQPGGSLRL SCAASGFTFS SYAMSWVRQA PGKGLEWVSN ISRDGSKTYY
ADSVKGRFTI SRDNSKNTLY LQMNSLRAED TAVYYCAEAQ SGGLRSGLTT FDYWGQGTLV TVSS

BMS2h-519
(SEQ ID NO: 183)
EVQLLESGGG LVQPGGSLRL SCADSGFTFS SYAMSWVRQA PGKGLEWVSS IGRDGAYTYY
ADSVKGRFTI SRDNSKNTLY LQMNSLRAED TAVYYCAKAG PKGIA----- FDYWGQGTLV TVSS

BMS2h-520
(SEQ ID NO: 184)
EVQLLESGGG LVQPGGSLRL SCAASGFTFS PHAMAWVRQA PGKGLEWVSG IDGGGSMTYY
ADSVKGRFTI SRDNSKNTLY LQMNSLRAED TAVYYCAKSD PP-------- FDYWGQGTLV TVSS

BMS2h-521
(SEQ ID NO: 185)
EVQLLESGGG LVQPGGSLRL SCAASGFTFH AGEMHWVRQA PGKGLEWVSS ITLPGDMTYY
ADSVKGRFTI SRDNSKNTLY LQMNSLRAED TAVYYCAKPN TGYT------ FDYWGQGTLV TVSS

BMS2h-522
(SEQ ID NO: 186)
EVQLLESGGG LVQPGGSLRL SCAASGFTFG NYGMSWVRQA PGKGLEVWSS ISWDGSLTYY
ADSVKGRFTI SRDNSKNTLY LQMNSLRAED TAVYYCAQNT RL-------- FDYWGQGTLV TVSS

BMS2h-523
(SEQ ID NO: 187)
EVQLLESGGG LVQPGGSLRL SCAASGFTFH DADMLWVRQA PGKGLEWVSG ILSPGEDTYY
ADSVKGRFTI SRDNSKNTLY LQMNSLRAED TAVYYCAKFG LP-------- FDYWGQGTLV TVSS

BMS2h-524
(SEQ ID NO: 188)
EVQLLESGGG LVQPGGSLRL SCAASGFTFR TOQMNWVRQA PGKGLEWVSS ISPSGAYTYY
ADSVKGRFTI SRDNSKNTLY LQMNSLRAED TAVYYCAKGL GA-------- FDYWGQGTLV TVSS

BMS2h-525
(SEQ ID NO: 189)
EVQLLESGGG LVQPGGSLRL SCAASGFTFE QYQMWIVRQA PGKGLEWVSW ISPDGTHTYY
ADSVKGRFTI SRDNSKNTLY LQMNSLRAED TAVYYCAKFS LRKMEK---- FDYWGQGTLV TVSS

BMS2h-526
(SEQ ID NO: 190)
EVQLLESGGG LVQPGGSLRL SCAASGFTFQ DEQMAWVRQA PGKGLEWVSS IASDGMSTYY
ADSVKGRFTI SRDNSKNTLY LQMNSLRAED TAVYYCAQPG KN-------- FDHWGQGTLV TVSS

TABLE I-continued

Anti-human CD40L VH Domain Amino Acid Sequences

BMS2h-527
(SEQ ID NO: 191)
EVQLLESGGG LVQPGGSLRL SCAASGFTFS DYAMSWVRQA PGKGLEWVSS ITTGGERTYY
ADSVKGRFTI SRDNSKNTLY LQMNSLRAED TAVYYCAKRW NLYTES---- FDYWGQGTLV TVSS

BMS2h-528
(SEQ ID NO: 192)
EVQLLESGGG LVQPGGSLRL SCAASGFTFG GQPMDWVRQA PGKGLEWVSS IAPDGIHTYY
ADSVKGRFTI SRDNSKNTLY LQMNSLRAED TAVYYCAKNL GQG------- FDYWGQGTLV TVSS

BMS2h-529
(SEQ ID NO: 193)
EVQLLESGGG LVQPGGSLRL SCAASGFTFE RYQMTWVRQA PGKGLEWVSS ISPSGTFTYY
ADSVKGRFTI SRDNSKNTLY LQMNSLRAED TAVYYCAEWK AL-------- FDYWGQGTLV TVSS

BMS2h-530
(SEQ ID NO: 194)
EVQLLESGGG LVQPGGSLRL SCAASGFTFP HSTMYWVRQA PGKGLEVWSL ILPSGSRTYY
ADSVKGRFTI SRDNSKNTLY LQMNSLRAED TAVYYCAKFS DER------- FDYWGQGTLV TVSS

BMS2h-531
(SEQ ID NO: 195)
EVQLSESGGG LVQPGGSLRL SCAASGFTFG DGNMDWVRQA PGKGLEWVSG ISSDGVTTYY
ADSVKGRFTI SRDNSKNTLY LQMNSLRAED TAVYYCAKDR GQG------- FDYWGQGTLV TVSS

BMS2h-532
(SEQ ID NO: 196)
EVQLLESGGG LVQPGGSLRL SCAASGFTFD DYMMWWVRQA PGKGLEWVSS ISPHGVYTYY
ADSVKGRFTI SRDNSKNTLY LQMNSLRAED TAVYYCAKWL HT-------- FDYWGQGTLV TVSS

BMS2h-533
(SEQ ID NO: 197)
EVQLLESGGG LVQPGGSLRL SCAASGFTFS NYTMAWGRQA PGKGLEWVSF IAGPGNYTYY
ADSVKGRFTI SRDNSKNTLY LQMNSLRAED TAVYYCAKPG STATYNNGQ- FDYWGQGTLV TVSS

BMS2h-534
(SEQ ID NO: 198)
EVQLLESGGG LVQPGGSLRL SCAASGFTFT EYSMVWRQA PGKGLEWVSS ISGSGRVTYY
ADSVKGRFTI SRDNSKNTLY LQMNSLRAED TAVYYCAKWL KLVRAPNP-- FDYWGQGTLV TVSS

BMS2h-535
(SEQ ID NO: 199)
EVQLLESGGG LVQPGGSLRL SCAASGFTFS NYQMAWVRQA PGKGLEWVSG ISKTGHSTYY
ADSVKGRFTI SRDNSRNTLY LQMNSLRAED TAVYYCAKAS HSLGPL---- FDYWGQGTLV TVSS

BMS2h-54
(SEQ ID NO: 200)
EVQLLESGGG LVQPGGSLRL SCAASGFTFT AYRMAWVRQA PGKGLEWVSW ISPSGSGTYY
ADSVKGRFTI SRDNSKNTLY LQMNSLRAED TAVYYCAKTL TDSPSGHYE- FDYWGQGILV TVSS

BMS2h-55
(SEQ ID NO: 201)
EVQLLESGGG LVQPGGSLRL SCAASGFTFA RYEMGWVRQA PGKGLEWVSR ITAQGLGTYY
ADSVKGRFTI SRDNSKNTLY LQMNSLRAED TAVYYCAKYL TDFSSGHQE- FDYWGQGTLV TVSS

BMS2h-553
(SEQ ID NO: 202)
EVQLLESGGG LVQPGGSLRL SCAASGFTFD DYGMSWVRQV PGKGLEWVSG ISHNGMLTYY
ADSVKGRFTI SRDNSKNTLY LQMNSLRAED TAVYYCAKYW PSTSWETD-- FDYWGQGTLV TVSS

BMS2h-554
(SEQ ID NO: 203)
EVQLLESGGG SVQPGGSLRL SCAASGFTFG NEPMAWVRQA PGKGLEWVSS IEMQGKNTYY
ADSVKGRFTI SRDNSKNTLY LQMNSLRAED TAVYYCAKDR GQG------- FDYWGQGTLV TVSS

BMS2h-555
(SEQ ID NO: 204)
EVQLLESGGG LVQPGGSLRL SCAASGFTFG EEEMSWVRQA PGKGLEWVSC IDNLGSPTYY
ADSVKGRFTI SRDNSKNTLY LQMNSLRAED AAVYYCAKTI SHQYDR---- FDYWGQGTLV TVSS

BMS2h-556
(SEQ ID NO: 205)
EVQLLESGGG LVQPGGSLRL SCAASGFTFG EEEMSWVRQA PGKGLEWVSS IDEGGRWTYY
ADSVKGRFTI SRDNSKNTLY LQMNSLRAED TAVYYCAKWT PHKQLS---- FDYWGQGTLV TVSS

TABLE I-continued

Anti-human CD40L VH Domain Amino Acid Sequences

BMS2h-557
(SEQ ID NO: 206)
EVQLLESGGG LVQPGGSLRL SCAASGFSFA DEYMWVARQA PGKGLEWVSE IDPLGTGTYY
ADSVKGRFTI SRDNSKNTLY LQMNSLRAED TAVYYCAKYG TA-------- FDYWGQGTLV TVSS

BMS2h-558
(SEQ ID NO: 207)
EVQLLESGGG LVQPGGSLRL SCAASGFTFS THDMMWVRQA PGKGLEWVSS ISDDGISTYY
ADSVKGRFTI SRDNSKNTLY LQMNSLRAED TAVYYCAKPD MSLIE----- FDYWGQGTLV TVSS

BMS2h-559
(SEQ ID NO: 208)
EVQLLESGGG LVQPGGSLRL SCAASGFTFD GTPMWVRQA PGKGLEWVSG ISGDGRNTYY
ADSVKGRFTI SRDNSKNTLY LQMNSLRAED TAVYYCAEPY ALTSSKP--- FDYWGQGTLV TVSS

BMS2h-56
(SEQ ID NO: 209)
EVQLLESGGG LVQPGGSLRL SCAASGFTFN DYTMGWVRQA PGKGLEWVSW IHGTGGQTYY
ADSVKGRFTI SRDNSKNTLY LQMNSLRAED TAVYYCAKAL ADRSGGVVE- FDYWGQGTLV TVSS

BMS2h-560
(SEQ ID NO: 210)
EVQLLESGGG LVQPGGSLRL SCAASGFTFE AETMAWVRQA RGKGLEWVSC ISNDGNTTYY
ADSVKGRFTI SRDNSKNTLY LQMNSLRAED TAVYYCAKES LISPGL---- FDYWGQGTLV TVSS

BMS2h-561
(SEQ ID NO: 211)
EVQLLESGGG LVQPGGSLRL SCAASGFTFT GEYMNWVRQA PGKGLEWVST INETGYMTYY
ADSVKGRFTI SRDNSKNTLY LQMNSLRAED TAVYYCAKLS TRGVP----- FDYWGQGTLV TVSS

BMS2h-562
(SEQ ID NO: 212)
EVQLLESGGG LVQPGGSLRL SCAASGFTFR SYDMGWVRQA PGKGLEWVST ISPMGVFTYY
ADSVKGRFTI SRDNSKNTLY LQMNSLRAED TAVYYCAKSN QHAHDP---- FDYWGQGTLV TVSS

BMS2h-563
(SEQ ID NO: 213)
EVQLLESGGG LVQPGGSLRL SCAASGFTFS DYDMGWVRQA PGKGLEWVSS ISPMGTFTYY
ADSVKGRFTI SRDNSKNTLY LQMNSLRAED TAVYYCAKAA LTEPM----- FDYWGQGTLV TVSS

BMS2h-564
(SEQ ID NO: 214)
EVQLLESGGG LVQPGGSLRL SCAASGFTFR DYDMGWVRQA PGKGLEWVST ISPLGHFTYY
ADSVKGRSTI SRDNSKNTLY LQMNSLRAED TAVYYCAKAE EA-------- FDYWGQGTLV TVSS

BMS2h-565
(SEQ ID NO: 215)
EVQLLESGGG LVQPGGSLRL SCAASGFAFP RYGMTWVRQA PGKGLEWVSN IDQFGMKTYY
ADSVKGRFTI SRDNSKNTLY LQMNSLRAED TAVYYCAEEY AS-------- FDYWGQGTLV TVSS

BMS2h-566
(SEQ ID NO: 216)
EVQLLESGGG LVQPGGSLRL SCAASGFTFD KYDMGWVRQA PGKGLEWVST ISPMGVFTYY
ADSVKGRFTI SRDNSKNTLY LQMNSLRAED TAVYYCAKGR GNTSD----- FDYWGQGTLV TVSS

BMS2h-567
(SEQ ID NO: 217)
EVQLLESGGG LVQPGGSLRL SCAASGFTFS NYDMAWVRQA PGKGLEWVST ISGAGHFTYY
ADSVKGRFTI SRDNSKNTLY LQMNSLRAED TAVYYCAKSF PRDE------ FDYWGQGTLV TVSS

BMS2h-568
(SEQ ID NO: 218)
EVQLLESGGG LVQPGGSLRL SCAASGFTFP KYEMRWVRQA PGKGLEWVSE IGLDGSPTYY
ADSVKGRFTI SRDNSKNTLY LQMNSLRAED TAVYYCAKLG DPNG------ FDYWGQGTLV TVSS

BMS2h-569
(SEQ ID NO: 219)
EVQLLESGGG LVQPGGSLRL SCAASGFTFP TSEMDWVRQA PGKGLEWVSG IGPDGLTTYY
ADSVKGRFTI SRDNSKNTLY LQMNSLRAED TAVYYCAKHA DW-------- FDYWGQGTLV TVSS

BMS2h-57
(SEQ ID NO: 220)
EVQLLESGGG LVQPGGSLRL SCAASGFTFS EYDMYWVRQA PGKGLEWVSW IDTDGGDTYY
ADSVKGRFTI SRDNSKNTLY LQMNSLRAED TAVYYCAKPG LK-------- FDYWGQGTLV TVSS

TABLE I-continued

Anti-human CD40L VH Domain Amino Acid Sequences

BMS2h-570
(SEQ ID NO: 221)
EVQLLESGGG LVQPGGSLRL SCTASGFTFE NASMQWVRQA PGKGLEWVSS IEGQGNATYY
ADSVKGRFTI SRDNSKNTLY LQMNSLRAED TAVYYCAKSS SWS------ FDYWGQGTLV TVSS

BMS2h-571
(SEQ ID NO: 222)
EVQLLESGGG LVQPGGSLRL SCAASGFTFT RNEMGWVRQA PGKGLEWVST ITPTGTFTYY
ADSVKGRFTI SRDNSKNTLY LQMNSLRAED TAVYYCAKTD PGNRY----- FDYWGQGTLV TVSS

BMS2h-572
(SEQ ID NO: 223)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCAKVG KESN------ FDYRGQGTLV TVSS

BMS2h-572-1
(SEQ ID NO: 224)
EVQLLESGGG LVQPGGSLRL SCAASGFTFN WQLMGWFRQA PGKGLEWVSG IEGPGDVTYY
ADSVKGRFTI SRDNSKNTLY LQMNSLRAED TAVYYCAKVG KESN------ FDYRGQGTLV TVSS

BMS2h-572-10
(SEQ ID NO: 225)
EVQLLESGGG LVQPGGSLRL SCAASGFTFN WQLMGWVRQA PGKGLEWVSG IEGPGDVTYY
ADSVKGRFTV SRDNSKNTLY LQMNSLRAED TAVYYCAKVG KESN------ SDYRGQGTLV TVSS

BMS2h-572-11
(SEQ ID NO: 226)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG KESN------ SDYRGQGTQV TVSS

BMS2h-572-12
(SEQ ID NO: 227)
EVQLLESGGG LVQPGGSLRL SCAASGFTFN WQLMGWARQA PGKGLEWVSG IEGPGDVTYY
ADSVKGRFTI SRDNSKNTLY LQMNSLRAED TAVYYCAKVG KESN------ SDYRGQGTLV TVSS

BMS2h-572-13
(SEQ ID NO: 228)
EVQLLESGGG LVQPGGSLRL SCAASGFTFN WQLMGWARQA PGKGLEWVSG IEGPGDVTYY
ADSVKDRFTI SRDNSKNTLY LLMNSLRAED TAVYYCAKVG KESN------ FDYWGQGTLV TVSS

BMS2h-572-14
(SEQ ID NO: 229)
EVQLLESGGG LVQPGGSLRL SCAASGFTFN WQLMGWVRQA PGKGLEWVSG IEGPGDVTYY
ADSVKGRFTI SRDNTKNTLY LQMNSLRAED TAVYYCVKVG KESN------ SDYRGQGTLV TVSS

BMS2h-572-15
(SEQ ID NO: 230)
EVRLLESGGG LVQPGGSLRL SCAASGFNFN WQLMGWIRQA PGKGLEWVSG IEGPGDVTYY
ADSVKGRFTI SRDNSKNTLY LQMNSLRAED TAVYYCAKVG KESN------ SDYRGQGTLV TVSS

BMS2h-572-16
(SEQ ID NO: 231)
EVQLIESGGG LVRPGGSLRL SCVASGFTFN WQLMGWVRQA PGKGLEWVSG IEGPGDVTYY
ADSVKGRFTI SRDNSKNTLY LQMNSLRAED TAVYYCAKVG KESN------ FDYRGQGTLV TVSS

BMS2h-572-17
(SEQ ID NO: 232)
EVQILESGGG LVQTGGSLRL SCAASGFTYN WQLMGWVRQA PGKGLEWVSG IEGPGDVTYY
ADSVKGRFTI SRDNSKNTLY LQMNSLRADD TAVYYCVKVG KESN------ FDYRGHGTLV TVSS

BMS2h-572-18
(SEQ ID NO: 233)
EVQLLESGGG LVQPGGSLRL SCAASGFTFN WQLMGWVRKA PGKGLEWVSG IEGPGDVTYY
ADSVKGRFTI SRDNSKNTLY LQMNSLRAED TAVYYCAKVG KESN------ FDYRGQGTLV TVSS

BMS2h-572-19
(SEQ ID NO: 234)
EVQLLESGGG LVQPGGSLRL SCAASGFTFN WQLMGWVRQA PGKGLEWVSG IEGPGDVTYY
ADSVKGRFTI SRDNTKNTLY LQMNSLRAED TAVYYCAKVG KESN------ FDYRGQGTLV TVSS

BMS2h-572-2
(SEQ ID NO: 235)
EVQLLESGGG LVQPGGSLRL SCAASGFTEN WQLMGWVRQA PGKGLEWVSG IEGPGDVTYY
ADSVKGRFTI SRDNSKNTLY LQMNSLRAED TAVYYCAKVG KESK------ FDYLGQGTLV TVSS

TABLE I-continued

Anti-human CD40L VH Domain Amino Acid Sequences

BMS2h-572-21
(SEQ ID NO: 236)
EVQLLESGGG LVQPGGSLRL SCAASGFTFN WQLMGIWRQA PGKGLEWVSG IEGPGDVTYY
AESVKGRFTI SRDNSKNTLY LQMNSLRAED TAVYYCAKVG KESN------ LDYRGQGILV TVSS

BMS2h-572-22
(SEQ ID NO: 237)
EVQLFESGGG SVQPGGSLRL SCAASGFTFN WQLMGWVRQA PGKGLEWVSG IEGPGDVTYY
ADSVKGRFTI SRDNSKNTLY LQMNSLRAED TAVYYCAKVG KESN------ SDYRGQGTLV TVSS

BMS2h-572-23
(SEQ ID NO: 238)
EVQLLESGGG LVQPGGSLRL ICAASGFTEN WQLMGWVRQA PGKGLEWVSG IEGPGDVTYY
ADSVKGRFII SRDNSKNTLY LQMNSLRAED TAVYYCAKVG KESN------ SDYRGQGTLV TVSS

BMS2h-572-24
(SEQ ID NO: 239)
EVQLLESGGG LVQPGGSLRL SCAASGFTFN WQLMGWVRQA PGKGLEWVSG IEGPGDVTYY
ADSVKGRFTI SRDNSTNTLY LQMNSLRAED TAVYYCAKVG KESE------ FDYRGQGTLV TVSS

BMS2h-572-3
(SEQ ID NO: 240)
EVRLLESGGG LVQPGGSLRL SCAASGFTFN WQLMGWVRQA PGKGLEVWSG IEGPGDVTYY
ADSVKGRFTI TRDNSKNTLY LQMNSLRAED TAVYYCVKVG KESN------ LDYRGQGTLV TVSS

BMS2h-572-4
(SEQ ID NO: 241)
EVQLLVSGGG LVQPGGSLRL SCAASGFIFN WQLMGWVRQA PGKGLEVWSG IEGPGDVTYY
ADSVKGRFTI SRDNSKNTLY LQMNSLRAED TAVYYCAKVG KESN------ FDYRGQGTLV TVSS

BMS2h-572-5
(SEQ ID NO: 242)
EVQLLVSGGG LVQPGGSLRL SCAASGFTFN WQLMGWVRQA PGKGLEVWSG IEGPGDVTYY
ADSVKGRFTI SRDNSKNMLY LQMNGLRAED TAVYYCAKVG KESN------ FDYRGQGTLV TVSS

BMS2h-572-6
(SEQ ID NO: 243)
EVQLLESGGG LVQPGGSLRL SCAASGFTFN WQLMGWVRQA PGKGLEVWSG IEGPGDVTYY
ADSVKGRFTI SRDNSKNTLY LQMNSLRAED TAVYYCVKVG KESN------ SDYRGQGTLV TVSS

BMS2h-572-601
(SEQ ID NO: 244)
EVQLLESGGG LVQPGGSLRL SCAASGFTFK WQLMGWARQA PGKGLEWVSG IEGPGDVTYY
ADSVKGRFTI SRDNSKNTLY LQMNSLRAED TAVYYCVKVG KESN------ SDYRGQGTLV TVSS

BMS2h-572-602
(SEQ ID NO: 245)
EVQLLESGGG LVQPGGSLRL SCAASGFTFK WHLMGWVRQA PGKGLEWVSG IEGPGDVTYY
ADSVKGRFTI SRDNSKNTLY LQMNSLRAED TAVYYCVKVG KESS------ SDYRGQGTLV TVSS

BMS2h-572-603
(SEQ ID NO: 246)
EVQLLESGGG LVQPGGSLRL SCAASGFTFN WHLMAWARQA PGKGLEWVSG IEGPGDVTYY
ADSVKGRFTI SRDNSKNTLY LQMNSLRAED TAVYYCVKVG KESN------ SDYRGQGTLV TVSS

BMS2h-572-604
(SEQ ID NO: 247)
EVQLLESGGG LVQPGGSLRL SCAASGFTFK WQLMGWVRQA PGKGLEWVSG IEGPGDVTYY
ADSVKGRFTI SRDNSKNTLY LQMNSLRAED TAVYYCVKVG KESN------ SDYRGQGTLV TVSS

BMS2h-572-605
(SEQ ID NO: 248)
EVQLLESGGG LVQPGGSLRL SCAASGFTFK WQLMAWARQA PGKGLEWVSG IEGPGDITYY
ADSVKGRFTI SRDNSKNTLY LQMNSLRAED TAVYYCVKVG KESN------ SDYRGQGTLV TVSS

BMS2h-572-606
(SEQ ID NO: 249)
EVQLLESGGG LVQPGGSLRL SCAASGFTFN WHLMGWARQA PGKGLEWVSG IEGPGDVTYY
ADSVKGRFTI SRDNSKNTLY LQMNSLRAED TAVYYCVKVG KESN------ SDYRGQGTLV TVSS

BMS2h-572-607
(SEQ ID NO: 250)
EVQLLESGGG LVQPGGSLRL SCAASGFTFK WQLMGWARQA PGKGLEWVSG IEGPGDVTYY
ADSVKGRFTI SRDNSKNTLY LQMNSLRAED TAVYYCVKVG KESN------ SDYRGQGTLV TVSS

TABLE I-continued

Anti-human CD40L VH Domain Amino Acid Sequences

BMS2h-572-608
(SEQ ID NO: 251)
EVQLLESGGG LVQPGGSLRL SCAASGFTFN WELMGWARQA PGKGLEWVSG IEGPGDVTYY
ADSVKGRFTI SRDNSKNTLY LQMNSLRAED TAVYYCVKVG KESN------ SDYRGQGTLV TVSS

BMS2h-572-609
(SEQ ID NO: 252)
EVQLLESGGG LVQPGGSLRL SCAASGFTFN WQLMGWARQA PGKGLEWVSG IEGPGDVTYY
ADSVKGRFTI SRDNSKNTLY LQMNSLRAED TAVYYCVKVG KESN------ SDYRGQGTLV TVSS

BMS2h-572-610
(SEQ ID NO: 253)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG KDSK------ SDYRGQGTLV TVSS

BMS2h-572-611
(SEQ ID NO: 254)
EVQLLESGGG LVQPGGSLRL SCAASGFTFN WQLMGWVRRA PGKGLEWVSG IEGPGDVTYY
ADSVKGRFTI SRDNSKNTLY LQMNSLRAED TAVYYCVKVG KDSK------ SDYRGQGTLV TVSS

BMS2h-572-612
(SEQ ID NO: 255)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG KDSN------ SDYRGQGTLV TVSS

BMS2h-572-613
(SEQ ID NO: 258)
EVQLLESGGG LAQPGGSLRL SCAASGFTFN WQLMGWVRQA PGKGLEWVSG IEGPGDVTYY
ADSVKGRFTI SRDNSKNTLY LQMNSLRAED TAVYYCVKVG KDSK------ SDYRGQGTLV TVSS

BMS2h-572-614
(SEQ ID NO: 257)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG KDAK------ SDYRGQGTLV TVSS

BMS2h-572-615
(SEQ ID NO: 258)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG KDKN------ SDYRGQGTLV TVSS

BMS2h-572-616
(SEQ ID NO: 259)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG KESK------ SDYRGQGTLV TVSS

BMS2h-572-617
(SEQ ID NO: 260)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG RDSK------ SDYRGQGTLV TVSS

BMS2h-572-618
(SEQ ID NO: 261)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG KYSN------ SDYRGQGTLV TVSS

BMS2h-572-819
(SEQ ID NO: 262)
EVOLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG KDSR------ SDYRGQGTLV TVSS

BMS2h-572-620
(SEQ ID NO: 263)
EVQLLESGGG LVQPGGSLRL SCAASGFTFN WQLMGWVRQA PGKGLEWVSG IEGPGDVIYY
ADSVKGRFTI SRDNSKNTLY LQMNSLRAED TAVYYCVKVG KDDS------ SDYRGQGTLV TVSS

BMS2h-572-621
(SEQ ID NO: 264)
EVQLLEFGGG LVQPGGSLRF SCAASGFTFN WQLMGWFRQA PGKGLEANSG IEGPGDVTYY
ADSVKGRFTI SRDNSKNTLY LQMNSLRAED TAVYYCVKVG RDSN------ SDYRGQGTLV TVSS

BMS2h-572-822
(SEQ ID NO: 265)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG KDST------ SDYRGQGTLV TVSS

TABLE I-continued

Anti-human CD40L VH Domain Amino Acid Sequences

BMS2h-572-623
(SEQ ID NO: 266)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG KESS------ SDYRGQGTLV TVSS

BMS2h-572-624
(SEQ ID NO: 287)
EVQLLESGGG LVQPGGSLRL SCAASGFTFN WQLMGWVRQA PGKGLEWVSG IEGPGDVTYY
ADSVKGRFTI FRDNSKNTLY LQMNSLRAED TAVYYCVKVG KDSA------ SDYRGQGTLV TVSS

BMS2h-572-625
(SEQ ID NO: 268)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCVKVG NDSY------ SDYRGQGTLV TVSS

BMS2h-572-626
(SEQ ID NO: 269)
EVQLLESGGG LVQPGGSLRL SCAASGFTFN WQLMGWVRQA PGKGLEWVSG IEGPGDVTYY
ADSVKGRFTI SRDNSKNTLY LQMNGLRAED TAVYYCVKVG KDSS------ SDYRGQGTLV TVSS

BMS2h-572-627
(SEQ ID NO: 270)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAIYYCVKVG KDSA------ SDYRGQGTLV TVSS

BMS2h-572-630
(SEQ ID NO: 271)
EVQLLESGGG LVQPGGSLRL SCAASGFTFK WQLMGWVRQA PGKGLEWVSG IEGPGDVTYY
ADSVKGRFTI SRONSKNTLY LQMNSLRAED TAVYYCVKVG KDAK------ SDYRGQILV TVSS

BMS2h-572-631
(SEQ ID NO: 272)
EVQLLESGGG LVQPGGSLRL SCAASGFTFK WQLMGWVRQA PGKGLEWVSG IEGPGDVTYY
ADSVKGRFTI SRDNSKNTLY LQMNSLRAED TAVYYCVKVG KDSR------ SDYRGQGTLV TVSS

BMS2h-572-632
(SEQ ID NO: 273)
EVQLLESGGG LVQPGGSLRL SCAASGFTFK WQLMGWVRQA PGKGLEWVSG IEGPGDVTYY
ADSVKGRFTI SRDNSKNTLY LQMNSLRAED TAVYYCVKVG KDSK------ SDYRGQGTLV TVSS

BMS2h-572-633
(SEQ ID NO: 274)
EVQLLESGGG LVQPGGSLRL SCAASGFTFN WELMGWARQA PGKGLEWVSG IEGPGDVTYY
ADSVKGRFTI SRDNSKNTLY LQMNSLRAED TAVYYCVKVG KDAK------ SDYRGQGTLV TVSS

BMS2h-572-634
(SEQ ID NO: 275)
EVQLLESGGG LVQPGGSLRL SCAASGFTFN WELMGWARQA PGKGLEWVSG IEGPGDVTYY
ADSVKGRFTI SRDNSKNTLY LQMNSLRAED TAVYYCVKVG KDSR------ SDYRGQGTLV TVSS

BMS2h-572-635
(SEQ ID NO: 276)
EVQLLESGGG LVQPGGSLRL SCAASGFTFN WELMGWARQA PGKGLEWVSG IEGPGDVTYY
ADSVKGRFTI SRDNSKNTLY LQMNSLRAED TAVYYCVKVG KDSK------ SDYRGQGTLV TVSS

BMS2h-572-7
(SEQ ID NO: 277)
EVQLLESGGG LVQPGGSLRL SCAASGFTFN WQLMGWARQA PGKGLEWVSG IEGPGDVTYY
ADSVKGRFTI SRDNSKNTLY LQMNSLRAED SAVYYCAKVG KESN------ FDYLGQGTLV TVSS

BMS2h-572-8
(SEQ ID NO: 278)
EVQLLESGGG LVQPGGSLRL SCVASGFTFN WQLMGWVRQA PGKGLEWVSG IEGPGDVTYY
ADSVKGRFTI SRDNSKNTLY LQMNSLRAED TAVYYCAKVG KESN------ SDYRGQGTLV TVSS

BMS2h-572-9
(SEQ ID NO: 279)
EVQLLESGGG LVQPGGSLRL SCAASGFTFN WQLMGWVRQA PGKGLEWVSG IEGPGDVTYY
ADSVKGRFTI SRDNSKNTLY LQMNSLRAED TAVYYCAKVG KESN------ SDYRGQGTLV TVSS

BMS2h-573
(SEQ ID NO: 280)
EVQLLESGGG LVQPGGSLRL SCAASGFTFS GWEMGWVRQA PGKGLEWVSS IDESGLNTYY
ADSVKGRFTI SRDNSKNTLY LQMNSLRAED TAVYYCAEGA PQYQIT---- FDYWGQGTLV TVSS

TABLE I-continued

Anti-human CD40L VH Domain Amino Acid Sequences

BMS2h-574
(SEQ ID NO: 281)
EVQLLESGGG LVQPGGSLRL SCAASGFTFP NYGMYWVRQA PGKGLEWVSY ISRRGLLTYY
ADSVKGRFTI SRDNSKNTLY LQMNSLRAED TAVYYCAKTS HYMNNG---- FDYWGQGTLV TVSS

BMS2h-575
(SEQ ID NO: 282)
EVQLLESGGG LVQPGGSLRL SCAASGFTFV DYTMAWVRQA PGKGLEWVSS ISPIGTFTYY
ADSVKGRFTI SRDNSKNTLY LQMNSLRAED TAVYYCAKDP YGMEDGLTW- FDYWGQGTLV TVSS

BMS2h-576
(SEQ ID NO: 283)
EVQLLESGGG LVQPGGSLRL SCAASGFTFD AYDMQWVRQA PGKGLEWVST ITSEGLSTYY
ADSVKGRFTI SRDNSKNTLY LQMNSLRAED TAVYYCAKPS DL-------- FDYWGQGTLV TVSS

BMS2h-577
(SEQ ID NO: 284)
EVQLLESGGG LVQPGGSLRL SCAASGFTFD GYDMGWVRQA PGKGLEWVST ISRGGWFTYY
ADSVKGRFTI SRDNSKNTLY LQMNSLRAED TAVYYCAKGT SQSSTGS--- FDYWGQGTLV TVSS

BMS2h-578
(SEQ ID NO: 285)
EVQLLESGGG LVQPGGSLRL SCAASGFTFR RYDMLWARQA PGKGLEWVSE ISPTGALTYY
ADSVKGRFTI SRDNSKNTLY LQMNSLRAED TAVYYCAKLG ST-------- FDYWGQGTLV TVSS

BMS2h-579
(SEQ ID NO: 286)
EVQLLESGGG LVQPGGSLRL SCAASGFTFF PYYMSWVRQA PGKGLEWVSS ISGIGGLTYY
ADSVKGRFTI SRDNSKNTLY LQMNSLRAED TAVYYCAKTT QNATL----- FDYWGQGTLV TVSS

BMS2h-58
(SEQ ID NO: 287)
EVQLLESGGG LVQPGGSLRL SCAASGFTFE VYTMAWVRQA PGKGLEWVST IDESGRDTYY
ADSVKGRFTI SRDNSKNTLY LQMNSLRAED TAVYYCAKPG VW-------- FDYWGOGILV TVSS

BMS2h-580
(SEQ ID NO: 288)
EVQLLESGGG LVQPGGSLRL SCAASGFTFA FYKMGWVRQA PGKGLEWVST ITPKGHHTYY
ADSVKGRFTI SRDNSKNTLY LQMNSLRAED TAVYYCAKVF KGKGWTRPSG FDYWGQGTLV TVSS

BMS2h-581
(SEQ ID NO: 289)
EVQLLESGGG LVQPGGSLRL SCAASGFTFN EYSMMWVRQA PGKGLEWVSS IGRRGWLTYY
ADSVKGRFTI SRDNSKNTLY LQMNSLRAED TAVYYCAKAV LLDSTK---- FDYWGQGTLV TVSS

BMS2h-582
(SEQ ID NO: 290)
EVQLLESGGG LVQPGGSLRL SCAASGFTFD EYPMTWVRQA PGKGLEWVST ISARGPFTYY
ADSVKGRFTI SRDNSKNTLY LQMNSLRAED TAVYYCAKGR HWLRNGR--- FDYWGQGTLV TVSS

BMS2h-583
(SEQ ID NO: 291)
EVQLLESGGG LVQPGGSLRL SCAASGFTFG MQSMQWVROA PGKGLEWVSS ITDDGTSTYY
ADSVKGRFTI SRDNSKNTLY LQMNSLRAED TAVYYCAKPD RV-------- FDYWGQGTLV TVSS

BMS2h-584
(SEQ ID NO: 292)
EVQLLESGGG LVQPGGSLRL SCAASGFTFG AADMQWVRQA PGKGLEWVSL ITNDGISTYY
ADSVKGRFTI SRDNSKNTLY LQMNSLRAED TAVYYCAKAG DR-------- FDYWGQGTLV TVSS

BMS2h-586
(SEQ ID NO: 293)
EVQLLESGGG LVQPGGSLRL SCAASGFTFN KYRMQVWRQA PGKGLEWVSS IDSSGELTYY
ADSVKGRFTI SRDNSKNTLY LQMNSLRAED TAVYYCAEEV PMGNQTF--- FDYWGQGTLV TVSS

BMS2h-587
(SEQ ID NO: 294)
EVQLLESGGG LVQPGGSLRL SCAASGFTFT DYTMGWVROA PGKGLEWVSS ITSQGAFTYY
ADSVKGRFTI SRDNSKNTLY LQMNSLRAED TAVYYCAKAT GTDSS----- FDYWGQGTLV TVSS

BMS2h-588
(SEQ ID NO: 295)
EVQLLESGGG LVQPGGSLRL SCAASGFTFE DYEMSWVRQA PGKGLEWVSC IGPGGKPTYY
ADSVKGRFTI SRDNSKNTLY LQMNSLRAED TAVYYCAKVD GH-------- FDYWGQGTLV TVSS

TABLE I-continued

Anti-human CD40L VH Domain Amino Acid Sequences

BMS2h-589

(SEQ ID NO: 296)
EVQLLESGGG LVQPGGSLRL SCAASGFIFS QYDMGWVRQA PGKGLEWVST ISSRGWLTYY
ADSVKGRFTI SRDNSKNTLY LQMNSLRAED TAVYYCAKGP GGRRR----- FDYWGQGTLV TVSS

BMS2h-59

(SEQ ID NO: 297)
EVQLLESGGG LVQPGGSLRL SCAASGFTFL DYAMGWVRQA PGKGLDANST ISPMGMGTYY
ADSVKGRFTI SRDNSKNTLY LQMNSLRAED TAVYYCAKSS AISFTSDISN FDYWGQGTLV TVSS

BMS2h-590
(SEQ ID NO: 298)
EVQLLESGGG LVQPGGSLRL SCAASGFTFS DYPMSWVRQA PGKGLEVWSS ISWSGFQTYY
ADSVKGRFTI SRDNSKNTLY LQMNSLRAED TAVYYCAKPG VARMPTGIA- FDYWGQGTLV TVSS

BMS2h-591

(SEQ ID NO: 299)
EVQLLESGGG LVQPGGSLRL SCAASGFTFS AYEMQWVRQA PGKGLEWVSS IDSAGTFTYY
ADSVKGRFTI SRDNSKNTLY LQMNSLRAED TAVYYCAEPF GM------- FDYWGQGTLV TVSS

BMS2h-592

(SEQ ID NO: 300)
EVQLLESGGG LVQPGGSLRL SCAASGFTFS EYPMKWVRQA PGKGLEWVST IDRQGDRTYY
ADSVKGRFTI SRDNSKNTLY LQMNSLRAED TAVYYCAKTV RRGLPRPSRY FDYWGQGTLV TVSS

BMS2h-593

(SEQ ID NO: 301)
EVQLLESGGG LVQPGGSLRL SCAASGFTFS DYDMGWVRQA PGKGLEWVSS ISPMGTFTYY
ADSVKGRFTI SRDNSKNTLY LQMNSLRAED TAVYYCAKGL SVYSGLD--- FDYWGQGTLV TVSS

BMS2h-594

(SEQ ID NO: 302)
EVQLLESGGG LVQPGGSLRL SCAASGFTFS HYDMGWVRQA PGKGLEVWSD IDYIGKTTYY
ADSVKGRFTI SRDNSKNTLY LQMNSLRAED TAVYYCAKAS DEVGVNTSK- FDYWGQGTLV TVSS

BMS2h-595

(SEQ ID NO: 303)
EVQLLESGGG LVQPGGSLRL SCAASGFTFA RYDMGWVRQA PGKGLEWVST ISPTGVLTYY
ADSVKGRFTI SRDNSKNTLY LQMNSLRAED TAVYYCAKGF ED-------- FDYWGQGTLV TVSS

BMS2h-596

(SEQ ID NO: 304)
EVQLLESGGG LVQPGGSLRL SCAASGFTFE AYPMSVWRQA PGKGLEWVSL ISHTGHATYY
ADSVKGRFTI SRDNSKNTLY LQMNSLRAED TAVYYCAKGH WP-------- FDYRGQGTLI TVSS

BMS2h-597

(SEQ ID NO: 305)
EVQLLESGGG LVQPGGSLRL SCAASGFTFE DEWMSWVRQA PGKGLEWVSD ISPGGWTTYY
ADSVKGRFTI SRDNSKNTLY LQMNSLRAED TAVYYCAKGY RPFDE----- FDYWGQGTLV TVSS

BMS2h-598

(SEQ ID NO: 306)
EVQLLESGGG LVQPGGSLRL SCAASGVTFD AIEMSWVRQA PGKGLEWVSS ISRHGEYTYY
ADSVKGRFTI SRDNSKNTLY LQMNSLRAED TAVYYCAEDA WSRH------ FDYWGQGTLV TVSS

BMS2h-599

(SEQ ID NO: 307)
EVQLLESGGG LVQPGGSLRL SCAASGFTFD STDMSWVRQA PGKGLEWVSG ILDNGSNTYY
ADSVKGRFTI SRDNSKNMLY LQMNSLRAED TAVYYCAKGA RD-------- FDYWGQGTLV TVSS

BMS2h-600

(SEQ ID NO: 308)
EVQLLESGGG LVQPGGSLRL SCAASGFTFG RQSMQWVRQA PGKGLEWVSS IDDDGFSTYY
ADSVKGRFTI SRDNSKNTLY LQMNSLRAED TAVYYCAKGD PWG------- FDYWGQGTLV TVSS

BMS2h-601

(SEQ ID NO: 309)
EVQLLESGGG LVQPGGSLRL SCTASGFITS DTQMAWVRQA PGKGLEWVSG IDDGGVSTYY
ADSVKGRFTI SRDNSKNTLY LQMNSLRAED TAVYYCAKPD RH-------- FDYWGQGTLV TVSS

BMS2h-602

(SEQ ID NO: 310)
EVQLLESGGG LVQPGGSLRL SCAASGFTFG STIMGWVRQA PGKGLEVWSV ISDDGGFTYY
ADSVKGRFTI SRDNSRNTLY LQMNSLRAED TAVYYCAKVD GYGV------ FDYWGQGTLV TVSS

TABLE I-continued

Anti-human CD40L VH Domain Amino Acid Sequences

BMS2h-603
(SEQ ID NO: 311)
EVQLLESGGG LVQPGGSLRL SCAASGFTFR SGDMNWVRQA PGKGLEWVST ITNDGTSTYY
ADSVKGRFTI SRDNSKNTLY LQMNSLRAED TAVYYCAKSD SD-------- FDYWGQGTLV TVSS

BMS2h-61
(SEQ ID NO: 312)
EVQLLESGGG LVQPGGSLRL SCAASGFTFA AYAMTWVRQA PGKGLEWVSY ISPNGTATYY
ADSVKGRFTI SRDNSKNTLY LQMNSLRAED TAVYYCAEYV GMRWNS---- FDYWGQGTLV TVSS

BMS2h-62
(SEQ ID NO: 313)
EVQLLESGGG LVQPGGSLRL SCAASGFTFS SYEMAWVRQA PGKGLEWVSS ITSLGTSTYY
ADSVKGRFTI SRDNSKNTLY LQMNSLRAED TAVYYCAKPG RK-------- FDYWGQGTLV TVSS

BMS2h-65
(SEQ ID NO: 314)
EVQLLESGGG LVQPGGSLRL SCAASGFTFN EYEMTWVRQA PGKGLEWVST ITSEGSGTYY
ADSVKGRFTI SRDNSKNTLY LQMNSLRAED TAVYYCAKPN GK-------- FDYWGQGTLV TVSS

BMS2h-66
(SEQ ID NO: 315)
EVQLLESGGG LVQPGGSLRL SCAASGFTFS DYEMLWVRQA PGKGLEWVST ITSEGHSTYY
ADSVKGRFTI SRDNSKNTLY LQMNSLRAED TAVYYCAKPG TS-------- FDYWGQGTLV TVSS

BMS2h-67
(SEQ ID NO: 316)
EVQLLESGGG LVQPGGSLRL SCAASGFTFS DYEMSWVRQA PGKGLEWVST IDSDGSFTYY
ADSVKGRFTI SRDNSKNTLY LQMNSLRAED TAVYYCAKPG VK-------- FDYWGQGTLV TVSS

BMS2h-68
(SEQ ID NO: 317)
EVQLLESGGG LVQPGGSLRL SCAASGFTFK DYEMTWVRQA PGKGLEWVSS ISSTGQSTYY
ADSVKGRFTI SRDNSKNTLY LQMNSLRAED TAVYYCAKPG NK-------- FDYWGQGTLV TVSS

BMS2h-69
(SEQ ID NO: 318)
EVQLLESGGG LVQPGGSLRL SCAASGFTFL DYGMAWVRQA PGKGLEWVSA ISPLGLSTYY
ADSVKSRFTI SRDNSKNTLY LQMNSLRAED TAVYYCAKEV RVGRGVHPPK FDYWGQGTLV TVSS

BMS2h-7
(SEQ ID NO: 319)
EVQLLESGGG LVQPGGSLRL SCAASGFTFN LYEMTWVRQA PGKGLEWVSS ITSEGHSTYY
ADSVKGRFTI SRDNSKNTLY LQMNSLRAED TAVYYCAKAG VI-------- FDYWGQGTLV TVSS

BMS2h-70
(SEQ ID NO: 320)
EVQLLESGGG LVQPGGSLRL SCAASGFTFE NYAMSWVRQA PGKGLEWVST IAPLGVPTYY
ADSVKGRFTI SRDNSKNTLY LQMNSLRAED TAVYYCAKKK VGAWLQSRS- FDYWGQGTLV TVSS

BMS2h-701
(SEQ ID NO: 321)
EVQLLESGGG LVQPGGSLRL SCAASGFTFM DYEMHWVRQA PGKGLEWVST IGASGHYTYY
ADSVKGRFTI SRDNSKNTLY LQMNSLRAED TAVYYCAKYL DMLLFG---- FDYWGQGTLV TVSS

BMS2h-702
(SEQ ID NO: 322)
EVQLLESGGG LVQPGGSLRL SCAASGFTFA EYEMMWARQA PGKGLEWVSR IAGNGSRTYY
ADSVKGRFTI SRDNSKNTLY LQMNSLRAED TAVYYCAIML SH-------- FDYWGQGTLV TVSS

BMS2h-703
(SEQ ID NO: 323)
EVQLLESGGG LVQPGGSLRL SCAASGFTFY NYDMSWVRQA PGKGLEWVSG IDSMGLVTYY
ADSVKGRFTI SRDNSKNTLY LQMNSLRAED TAVYYCAKGS NASDWVV--- FDYWGQGTLV TVSS

BMS2h-704
(SEQ ID NO: 324)
EVQLLESGGG LVQPGGSLRL SCAASGFTFA SYHMTWVRQA PGKGLEWVSS IADTGDRTYY
ADSVKGRFTI SRDNSKNTLY LQMNSLRAED TAVYYCAKLR GMARWVG--- FDYWGQGTLV TVSS

BMS2h-705
(SEQ ID NO: 325)
EVQLLESGGG LVQPGGSLRL SCAASGFTFS YYDMMWVRQA PGKGLEWISS ISDRGLQTYY
ADSVKGRFTI SRDNSKNTLY LQMNSLRAED TAVYYCAKFT EIPLDWLEV- FDYWGQGTLV TVSS

TABLE I-continued

Anti-human CD40L VH Domain Amino Acid Sequences

BMS2h-706
(SEQ ID NO: 326)
EVQLLESGGG LVQPGGSLRL SCAASGFTFG SYKMLWVRQA PGKGLEWVSS ITNSGTETYY
ADSVKGRFTI SRDNSKNTLY LQMNSLRAED TAVYYCAKSM YPDLEIVH-- FDYWGQGTLV TVSS

BMS2h-707
(SEQ ID NO: 327)
EVQLLESGGG LVQPGGSLRL SCAASGFTFE TYRMSWVRQA PGKGLEWVSA IDQEGSATYY
ADSVKGRFTI SRDNSKNTLY LQMNSLRAED TAVYYCAKNS GIRPGLR--- FDYWGQGTLV TVSS

BMS2h-708
(SEQ ID NO: 328)
EVQLLESGGG LVQPGGSLRL SCAASGFTFS SYDMLWVRQA PGKGLEWVSR IDASGYFTYY
ADSVKGRFTI SRDNSKNTLY LQMNSLRAED TAVYYCAOLL KLSLNPN--- FDYWGQGTLV TVSS

BMS2h-709
(SEQ ID NO: 329)
EVQLLESGGG LVQPGGSLRL SCAASGFTFS SYAMSWVRQA PGKGLEWVSS IHNTGLSTYY
ADSVKGRFTI SRDNSKNTLY LQMNSLRAED TAVYYCAKGT QHRFVV---- FDYWGQGTLV TVSS

BMS2h-71
(SEQ ID NO: 330)
EVQLLESGGG LVQPGGSLRL SCAASGFTFE GYPMSWVRQA PGKGLEWVST ISPLGPDTYY
ADSVKGRFTI SRDNSKNTLY LQMNSLRAED TAVYYCAKLL MGEYLNSRT- FDYWGQGTLV TVSS

BMS2h-710
(SEQ ID NO: 331)
EVQLLESGGG LVQPGGSLRL SCAASGFTFN TYSMSWVRQA PGKGLEWVSW IDADGWVTYY
ADSVKGRFTI SRDNSKNTLY LQMNSLRAED TAVYYCAQTG HT-------- FDYWGQGTLV TVSS

BMS2h-711
(SEQ ID NO: 332)
EVQLLESGGG LVQPGGSLRL SCAASGFTFT DGEMGWARQA PGKGLEWVSR IVDPGDSTYY
ADSVKGRFTI SRDNSKNTLY LQMNSLRAED TAVYYCAKAG DQ-------- FDYWGQGTLV TVSS

BMS2h-712
(SEQ ID NO: 333)
EVQLLESGGG LVQPGGSLRL SCAASGFTFP EYEMKWVRQA PGKGLEWVST ITPSGGHTYY
ADSVKGRFTI SRDNSKNTLY LQMNSLRAED AAVYYCAIPL SS-------- FDYWGRGTLV TVSS

BMS2h-713
(SEQ ID NO: 334)
EVQLLESGGG LVQPGGSLRL SCAASGFTFS NYVMIWVRQA PGKGLEWVSL INGAGDMTYY
ADSVKGRFTI SRDNSKNTLY LQMNSLRAED TAVYYCAEGG ARSFGVPPN- FDYWGQGTLV TVSS

BMS2h-714
(SEQ ID NO: 335)
EVQLLESGGG LVQPGGSLRL SCAASGFTFT DGEMGWARQA PGKGLEWVSR IVDPGDSTYY
ADSVKGRFTI SRDNSKNTLY LQMNSLRAED TAVYYCAKAG DQ-------- FDYWGQGTLV TVSS

BMS2h-715
(SEQ ID NO: 336)
EVQLLESGGG LVQPGGSLRL SCVASGFTFT LYNMSWVRQA PGKGLEWVSV ISSKGDSTYY
ADSVKGRFTI SRDNSKNTLY LQMNSLRAED TAVYYCAQTS SV-------- FDYWGQGTLV TVSS

BMS2h-716
(SEQ ID NO: 337)
EVQLLESGGG LVQPGGSLRL SCAASGFTFE AYYMSWVRQA PGKGLEWVSG IVNNGLLTYY
ADSVKGRFTI SRDNSKNMLY LQMNSLRAED TAVYYCAKSA VHPSYRAEL- FDYWGQGTLV TVSS

BMS2h-717
(SEQ ID NO: 338)
EVQLLESGGG LVQPGGSLRL SCAASGFTFS SYEMAVWRQA PGKGLEWVSR IEPDGSNTYY
ADSVKGRFTI SRDNSKNTLY LQMNSLRAED TAVYYCAKGP DNFTM----- FDYWGQGTLV TVSS

BMS2h-718
(SEQ ID NO: 339)
EVQLLESGGG LVQPGGSLRL SCAASGFTFN KYMMGWVRQA PGKGLEWVSS IDSLGHYTYY
ADSVKGRFTI SRDNSKNTLY LQMNSLRAED TAVYYCAEAE FP-------- FDYWGQGTLV TVSS

BMS2h-719
(SEQ ID NO: 340)
EVQLLESGGG LVQPGGSLRL SCAASGFTFK RYEMTWVRQA PGKGLEWVSS ISSDGSFTYY
ADSVKGRFTI SRDNSKNTLY LQMNSLRAED TAVYYCAEPF TE-------- FDYWGQGTLV TVSS

TABLE I-continued

Anti-human CD40L VH Domain Amino Acid Sequences

BMS2h-719-1
(SEQ ID NO: 341)
EVQLLESGGG MVQPGGSLRL SCAASGFTFK RYEMMWVRQA PGKGLEWVSS ISSDGSFTYY
ADSVKGRFTI SRDNSKNTLY LQMNSLRAED TAVYYCAEPF TE-------- FDYWGQGTQV TVSS

BMS2h-719-10
(SEQ ID NO: 342)
EVQLLESGGG MVQPGGSLRL SCAASGFTFK RYEMMWVRQA PGKGLEWVSS ISSDGSFTYY
ADSVKGRFTI SRDNSKNTLY LQMNSLRAED TAVYYCAEPF TE-------- FDYWGQGTLV TVSS

BMS2h-719-11
(SEQ ID NO: 343)
EVQLLESGGG LVQPGGSLRL SCAASGFTFK RYEMMWVRKA PGKGLEWVSS ISSDGSFTYY
ADSVKGRFTI SRDNSENTLY LQMNSLRAED TAVYYCADPF TE-------- FDYWGQGTLV TVSS

BMS2h-719-12
(SEQ ID NO: 344)
EVQLLESGGG LVQPGGSLRL SCAASGFTFK RYEMMWVRQA PGKGLEWVSS ISSDGSFTYY
ADSVKGRFTV SRDNSKNTLY LQMNSLRAED TAVYYCADPF TE-------- FDYWGQGTLV TVSS

BMS2h-719-13
(SEQ ID NO: 345)
EVQLLESGGG LVQPGGSLRL SCAASGFTFK RYEMMWVRQA PGKGLEWVSS ISSDGSFTYY
ADSVKGRFTI SRDNTKNTLY LQMNSLRAED TAVYYCADPF TE-------- LDYWGHGTLV TVSS

BMS2h-719-14
(SEQ ID NO: 346)
EVQLLESGGG LVRPGGSLRL SCAASGFTFK RYEMMWVRQA PGKGLEWVSS ISSDGSFTYY
ADSVKGRFTI SRDNSKNTLY LQMNSLRAED TAVYFCADPF TE-------- FDYWGQGTLV TVSS

BMS2h-719-15
(SEQ ID NO: 347)
EVQLLESGGG LVQPGGSLRL SCAASGFTFK RYEMTWVRQA PGKGLEWVSS ISSDGSFTYY
ADSVKGRFTI SRDNSKNTLY LHMNSLRAED TAVYYCADPF TE-------- IDYWGQGTLV TVSS

BMS2h-719-16
(SEQ ID NO: 348)
EVQLLESGGG LVQPGGSLRL SCAASGFPFK RYEMTWVRQA PGKGLEWVSS ISSDGSFTYY
ADSVKGRFTI SRDNSKNTLY LQMNSLRAED TAVYYCAEPF TE-------- FDYRAQGTLV TVSS

BMS2h-719-17
(SEQ ID NO: 349)
EVQLLESGGG LVQPGGSLRL SCAASGFTFK RYEMSWVRQA PGKGLEWVSS ISSDGSFTYY
ADSVKGRFTI SRDNSKNTLY LQMNSLRAED TAVYYCADPF TE-------- IDWIGQGTQV TVSS

BMS2h-719-18
(SEQ ID NO: 350)
EVQLLESGGG LVHPGGSLRL SCAASGFTFK RYEMMWVRQA PGKGLEWVSS ISSDGSFTYY
ADSVKGRFTI SRDNSKNTLY LQMNSLRDED TAVYYCAEPF TE-------- FDYGGQGTLV TVSS

BMS2h-719-19
(SEQ ID NO: 351)
EVQLLESGGG WVQPGGSLRL SCAASGFTFK RYEMMWVRQA PGKGLEWVSS ISSDGSFTYY
ADSVKGRFTI SRDNSKNTLY LQMNSLRAED TAVYYCADPF TE-------- FDYWGQGTLV TVSS

BMS2h-719-2
(SEQ ID NO: 352)
EVQLLESGGG LVQPGGSLRL SCAASGFTFK RYEMMWVRQA PGKGLEWVSS ISSDGSFTYY
ADSVKGRFTI SRDNSKNTLY LQMNSLRAED TAVYYCAEPF TE-------- FDYWGHGTLV TVSS

BMS2h-719-20
(SEQ ID NO: 353)
EVQLLESGGG LVQPGGSLRL SCAASGFTFK RYEMPIWRQA PGKGLEWVSS ISSDGSFTYY
ADSVKGRFTI SRDNSKNTLY LQMNSLRAED TAVYYCAEPF TE-------- IDYRGQGTLV TVSS

BMS2h-719-202
(SEQ ID NO: 354)
EVQLLESGGG LVQPGGSLRL SCAASGFTFK KYEMMWVRQA PGKGLEWVSS ISSDGSFTYY
ADSVKGRFTI SRDNSKNTLY LQMNSLRAED TAVYYCAEPF TE-------- FDYWGQGTLV TVSS

BMS2h-719-203
(SEQ ID NO: 355)
EVQLLESGGG LVQPGGSLRL SCAASGFTFN SYEMMWVRQA PGKGLEWVSS ISSDGSFTYY
ADSVKGRFTI SRDNSKNTLY LQMNSLRAED TAVYYCAEPF TE-------- FDYWGHGTLV TVSS

TABLE I-continued

Anti-human CD40L VH Domain Amino Acid Sequences

BMS2h-719-21
(SEQ ID NO: 356)
EVQLLESGGG LVQPGGSLRL SCAASGFTFK RYEMMWVRQA PGKGLEWVSS ISSDGSFTYY
ADSVKGRFTI SRDNSKNTLY LQMNSLRAED TAVYYCADPF TE-------- FDYWGQGTLV TVSS

BMS2h-719-213
(SEQ ID NO: 357)
EVQLLESGGG LVQPGGSLRL SCAASGFTFK RYEMMWVRQA PGKGLEWVSS ISSDGSFTYY
ADSVKGRFTI SRDNSKNTLY LQMNSLRAED TAVYYCADPF TE-------- MDYWGHGTLV TVSS

BMS2h-719-214
(SEQ ID NO: 358)
EVQLLESGGG LVQPGGSLRL SCAASGFTFK RYEMMWVRQA PGKGLEWVSS ISSDGSFTYY
ADSVKGRFTI SRDNSKNTLY LQMNSLRAED TAVYYCADPF TE-------- FDYWGHGTLV TVSS

BMS2h-719-215
(SEQ ID NO: 359)
EVQLLESGGG LVQPGGSLRL SCAASGFTFK RYEMMWVRQA PGKGLEWVSS ISSDGSFTYY
ADSVKGRFTI SRDNSKNTLY LQMNSLRAED TAVYYCAEPF TE-------- LDYWGHGTLV TVSS

BMS2h-719-218
(SEQ ID NO: 360)
EVQLLESGGG LVQPGGSLRL SCAASGFTFK RYEMMWVRQA PGKGLEWVSS ISSDGSFTYY
AESVKGRPTI SRDNSKNTLY LQMNSLRAED TAVYYCAEPF TE-------- FDYWGQGTLV TVSS

BMS2h-719-225
(SEQ ID NO: 361)
EVQLLESGGG LVQPGGSLRL SCAASGFTFN TYEMQWVRQA PGKGLEWVSS ISSDGSFTYY
ADSVKGRFTI SRDNSKNTLY LQMNSLRAED TAVYYCAEPF TE-------- FDYWGHGTLV TVSS

BMS2h-719-226
(SEQ ID NO: 362)
EVQLLESGGG LVQPGGSLRL SCAASGFTFN KYEMMWARQA PGKGLEWVSS ISSDGSFTYY
ADSVKGRFTI SRDNSRNTLY LQMNSLRAED TAVYYCAEPF TE-------- FDYWGHGTLV TVSS

BMS2h-719-3
(SEQ ID NO: 363)
EVQLSESGGG LVQPGGSLRL SCAASGFTFK RYEMMWVRQA PGKGLEWVSS ISSDGSFTYY
ADSVKGRFTI SRDNSKNTLY LQMNSLRAED TAVYYCADPF TE-------- FDYWGQGTLV TVSS

BMS2h-719-4
(SEQ ID NO: 364)
EVQLLESGGG LVQPGGSLRL SCAASGFTFK RYEMMWVRQT PGKGLEWVSS ISSDGSFTYY
ADSVKGRFTI SRDNSKNTLY LQMNSLRAED TAVYYCAEPF TE-------- FDYWGQGTLV TVSS

BMS2h-719-5
(SEQ ID NO: 365)
EVQLLESGGG LVQPGGSLRL SCAASGFTFK RYEMMWVRQA PGKGLEWVSS ISSDGSFTYY
ADSVKGRFTI SRDNSKNTLY LEMNSMRAED TAVYYCAEPF TE-------- FDNWGQGTLV TVSS

BMS2h-719-6
(SEQ ID NO: 366)
EVQLLESGGG LVQPGGSLRL SCAASGFTFK RYEMMWVRQA PGKGLEWVSS ISSDGSFTYY
ADSVKGRFTI SRDNSKNTLY LQMNSLRAED TAVYYCAEPF TE-------- FDYWGQGTQV TVSS

BMS2h-719-7
(SEQ ID NO: 367)
EVQLLESGGG LVQPGGSLRL SCAASGFNFK RYEMTWVRQA PGKGLEWVSS ISSDGSFTYY
ADSVKGRFTI SRDNSKNTLY LQMNSLRAED TAVYYCADPF TE-------- FDYWGQGTLV TVSS

BMS2h-719-8
(SEQ ID NO: 368)
EVQLLESGGD LVQPGGSLRL SCAASGFTFK RYEMMWVRQA PGKGLEWVSS ISSDGSFTYY
ADSVKGRFTI SRDNSKNTLY LQMNSLRAED TAVYYCAEPF TE-------- FDYRGQGTLV TVSS

BMS2h-719-9
(SEQ ID NO: 369)
EVQLLESGGG LVQPGGSLRL SCAASGFTFK RYEMSWVRQA PGKGLEWVSS ISSDGSFTYY
ADSVKGRFTI SRDNSKNTLY LQMNSLRAED TAVYYCAEPF TE-------- FDYWGRGTLV TVSS

BMS2h-72
(SEQ ID NO: 370)
EVQLLESGGG LVQPGGSLRL SCAASGFTFE AYPMSWVRQA PGKGLEWVSS ISPLGLWTYY
ADSVKGRFTI SRDNSKNTLY LQMNSLRAED TAVYYCAKLS AGAETHVYRL FDYWGQGTLV TVSS

TABLE I-continued

Anti-human CD40L VH Domain Amino Acid Sequences

BMS2h-720
(SEQ ID NO: 371)
EVQLLESGGG LVQPGGSLRL SCAASGFTFG NYEMMWVRQA PGKGLEVWSS IGVLGHFTYY
ADSVKGRFTI SRDNSKNTLY LQMNSLRAED TAVYYCAKLM SLRTFENL-- FDYWGQGTLV TVSS

BMS2h-722
(SEQ ID NO: 372)
EVQLLESGGG LVQPGGSLRL SCAASGFTFT KYPMAWVRQA PGKGLEWVSG IDANGNRTYY
ADSVKGRFTI SRDNSKNTLY LQMNSLRAED TAVYYCAEGT WRRHFAI--- FDYWGQGTLV TVSS

BMS2h-723
(SEQ ID NO: 373)
EVQLLESGGG LVQPGGSLRL SCAASGFTFD LYDMMANRQA PGKGLEWVSS ISDLGTLTYY
ADSVKGRFTI SRDNSKNTLY LQMNSLRAED TAVYYCAKNG FRVTSNDRR- FDYWGQGTLV TVSS

BMS2h-724
(SEQ ID NO: 374)
EVQLLESGGG LVQPGGSLRL SCAASGFTFT GGDMWWVRQA PGKGLEWVSM IEGGGVITYY
ADSVKGRFTI SRDNSKNTLY LQMNSLRAED TAVYYCAELD LRTGQ----- FDYWGQGTLV TVSS

BMS2h-725
(SEQ ID NO: 375)
EVQLLESGGG LVQPGGSLRL SCAASGFTFS AYTMGWVRQA PGKGLEWVSL IGDRGSWTYY
ADSVKGRFTI SRDNSKNTLY LQMNSLRAED TAVYYCAEPS DPTK------ FDYWGQGTLV TVSS

BMS2h-725-1
(SEQ ID NO: 376)
EVQLLESGGG LVQPGGSLHL SCAASGFTFS AYTMGWVRQA PGKGLEWVSL IGDRGSWTYY
ADSVKGRFTI SRDNSKNTLY LQMNSLRAED TAVYFCADPS DPTK------ FDYWGQGTLV TVSS

BMS2h-725-10
(SEQ ID NO: 377)
EVQLLESGGG LVQPGGSLRL SCAASGFTFS AYTMGWVRQA PGKGLEWVSL IGDRGSWTYY
ADSVKGRFTI SRDNSKNTLY LQMNSLRAED TAVYYCADPS DPTK------ FDYWGQGTLV TVSS

BMS2h-725-11
(SEQ ID NO: 378)
EVQLLESGGG LVQPGGSLRL SCAASGFTFS AYTMGWVRQA PGKGLEWVSL IGDRGSWTYY
ADSVKGRFTI SRDNSKNTLY LQMSSLRAED TAVYYCADPS DPTK------ FDYWGQGTLV TVSS

BMS2h-725-12
(SEQ ID NO: 379)
EVQLLESGGG LVQPGGSLRL SCAASGFTFP AYTMGWVRQA PGKGLEWVSL IGDRGSWTYY
ADSVKGRFTI SRDDSKNTLY LQMNSLRVED TAVYYCAEPS DPTM------ FVYWGQGTLV TVSS

BMS2h-725-13
(SEQ ID NO: 380)
EVQLLESGGG LVQPGGSLRL SCAASGFTFS AYTMGWVRQA PGKGLEWVSL IGDRGSWTYY
ADSVKGRFTI SRDNSKNTLY LQMNSLRAED TAVYYCAEPS DPTM------ FVYWGQGTLV TVSS

BMS2h-725-14
(SEQ ID NO: 381)
EVQLLESGGG LVQPGGSLRL SCAASGFTFS AYTMGWVRQA PGKGLEWVSL IGDRGSWTYY
ADSVKGRFTI SRDNSKNTLY LQMNSLRAED TAVYYCADPS DPTM------ FDYWGQGTLV TVSS

BMS2h-725-15
(SEQ ID NO: 382)
EVQLLESGGG MVQPGGSLRL SCAASGFTFS AYTMGWVRQA PGKGLEWVSL IGQRGSWTYY
ADSVKGRFTI SRDNSKNTLY LQMNSMRAED TAVYYCADPS DPTK------ FDYWGQGTLV TVSS

BMS2h-725-16
(SEQ ID NO: 383)
EVQLLESGGG LVQPGGSLRL SCAASGFTFS AYTMGWVRQA PGKGLEWVTL IGDRGSWTYY
ADSVKGRFTI SRDNSKNTLY LQMNSLRAED TAVYYCAEPS DPTM------ FDYWGQGTLV TVSS

BMS2h-725-17
(SEQ ID NO: 384)
EVQLLESGGG LVQPGGSLRL SCAASGFTFT AYTMGWVRQA PGKGLEWVSL IGDRGSWTYY
ADSVKGRFTI SRDNSKNTLY LQMNSLRAED TAVYYCAEPS DPTK------ LDYWGQGTLV TVSS

BMS2h-725-18
(SEQ ID NO: 385)
EVQLSESGGG LVQPGGSLRL TCAASGFTFS AYTMGWVRQA PGKGLEWVSL IGDRGSWTYY
ADSVKGRFTI SRDNSKNTLY LQMNSLRAED TAVYYCADPS DPTK------ FVYWGQGTLV TVSS

TABLE I-continued

Anti-human CD40L VH Domain Amino Acid Sequences

BMS2h-725-19
(SEQ ID NO: 386)
EVQLLESGGG LVQPGGSLRL SCAASGFTFS AYTMGWVRQA PGKGLEWVSL IGDRGSWTYY
ADSVKGRFTI SRDNSKNTLY LQMNSLRAED TAVYYCADPS DPTK------ FVYWGQGTLV TVSS

BMS2h-725-2
(SEQ ID NO: 387)
EVQLLESGGG LVQPGGSLRL SCAASGFTFS AYTMGWVRQA PGKGLEWVSL IGDRGSWTYY
ADSVKGRFTI SRDNSKNTLY LQMNSLRAED TAVYYCAEPS DPTK------ FDYWGQGTLV TVSS

BMS2h-725-3
(SEQ ID NO: 388)
VQLLESGGG  LVQPGGSLRL SCAASGFTFS AYTMGWVRQA PGKGLEWVSL IGDRGSWTYY
ADSVKGRFTI SRDNSRNMLY LQMKSLRAED TAVYYCADPS DPTK------ FVYWGQGTQV TVSS

BMS2h-725-4
(SEQ ID NO: 389)
EVQLLESGGG LVQPGGSLRL SCAASGFTFS AYTMGWVRQA PGKGLEWVSL IGDRGSWTYY
ADSVKGRFTI FRDNSKNTLY LQMNSLRAED TAVYYCADPS DPTK------ FVYWGQGTLV TVSS

BMS2h-725-5
(SEQ ID NO: 390)
EVQLLESGGG LVQPGGSLRL SCAASGFTFS DYTMGWVRQA PGKGLEWVSL IGDRGSWTYY
ADSVKGRFTI SRDNSKNTLY LQMNSLRAED TAVYYCAEPS DPTK------ FDYWGRGTLV TVSS

BMS2h-725-6
(SEQ ID NO: 391)
EVQLLESGGG LVQPGGSLRL SCAASGFTFS AYTMGWVRQA PGKGLEWVSL IGDRGSWTYY
ADSVKGRFTI SRDNSKNTLY LQMNSLRAED TAVYYCAEPS DPTK------ FVYWGQGTLV TVSS

BMS2h-725-7
(SEQ ID NO: 392)
EVQLLESGGG LVQPGGSLRL SCAASGFTFS AYTMGWVRQA PGKGLEWVSL IGDRGTWTYY
ADSVKGRFTI SRDNSKNTLY LQMNSLRAED TAVYYCADPS DPTK------ FDYWGQGTLV TVSS

BMS2h-725-8
(SEQ ID NO: 393)
EVQLLESGGG LVQPGGSLRL SCAASGFTFS AYTMGWVRQA PGKGLEWVSL IGDRGSWTYY
ADSVKGRFTV SRDNSKNTLY LQMKSLRAED TAVYYCAEPS DPTK------ FDYWGQGTLV TVSS

BMS2h-725-9
(SEQ ID NO: 394)
EVQLLESGGG LVQPGGSLRL SCAASGFTFS AYTMGWVRQA PGMGLEWVSL IGDRGSWTYY
ADSVKGRFTI SRDNSKNTLY LQMNSLRAED TAVYYCAEPS DPTK------ FDYWGQGTLV TVSS

BMS2h-728
(SEQ ID NO: 395)
EVQLLESGGG LVQPGGSLRL SCAASGFTFD NYKMYWVRQA PGKGLEWVSS ISEIGNLTYY
ADSVKGRFTI SRDNSKNTLY LQMNSLRAED TAVYYCAIAL TR-------- FDYWGQGTLV TVSS

BMS2h-727
(SEQ ID NO: 396)
EVQLLESGGG LVQPGGSLRL SCAASGFTFA SYRMYWVRQA PGKGLEWVSY IDPPGSRTYY
ADSVKGRFTI SRDNSKNTLY LQMNSLRAED TAVYYCAKSL NLSFPYIN-- FDYWGQGTLV TVSS

BMS2h-726
(SEQ ID NO: 397)
EVQLLESGGG LVQPGGSLRL SCAASGFTFE RYEMDANRQA PGKGLEWVSR ISHSGRTTYY
ADSVKGRFTI SRDNSKNTLY LQMNSLRAED TAVYYCAQLD GP-------- FDYWGQGTLV TVSS

BMS2h-729
(SEQ ID NO: 398)
EVQLLESGGG LVQPGGSLRL SCAASGFTFK RYMDWVRQA PGKGLEVWSR INHNGSVTYY
ADSVKGRFTI SRDNSKNTLY LQMNSLRAED TAVYYCAKMP QGTSDVVYY- FDYWGQGTIV TVSS

BMS2h-73
(SEQ ID NO: 399)
EVQLLESGGG LVQPGGSLRL SCAASGFTFS KYDMSWVRQA PGKGLEWVST ILEDGLTTYY
ADSVKGRFTI SRDNSKNTLY LQMNSLRAED TAVYYCAKPG RL-------- FDYWGQGTLV TVSS

BMS2h-74
(SEQ ID NO: 400)
EVQLLESGGG LVQPGGSLRL SCAASGFTFS DYPMTWVRQA PGKGLEWVST ILSPGTETYY
ADSVKGRFTI SRDNSKNTLY LQMNSLRAED TAVYYCAKAE KD-------- FDYWGQGTLV TVSS

TABLE I-continued

Anti-human CD40L VH Domain Amino Acid Sequences

BMS2h-741
(SEQ ID NO: 401)
EVQLLESGGG LVQPGGSLRL SCAASGFTFE GGEMGWVRQA PGKGLEWVSM IPMDGSATYY
ADSVKGRFTI SRDNSKNTLY LQMNSLRAED TAVYYCAKAG EV-------- FDYWGQGTLV TVSS

BMS2h-742
(SEQ ID NO: 402)
EVQLLESGGG LVQPGGSLRL SCAASGFTFR EYHMKWARQA PGKGLEWVSG ISRDGMNTYY
ADSVKGRFTI SRDNSKNTLY LQMNSLRAED TAVYYCAIQL AL-------- FDYWGQGTLV TVSS

BMS2h-743
(SEQ ID NO: 403)
EVQLLESGGG LVQPGGSLRL SCAASGFTFR DYEMLWARQA PGKGLEWVSG ILPSGGATYY
ADSVKGRFTI SRDNSKNTLY LQMNSLRAED TAVYYCAKAG SGNGPIL--- FDYWGQGTLV TVSS

BMS2h-744
(SEQ ID NO: 404)
EVQLLESGGG LVQPGGSLRL SCAASGFTFK EHDMFWVRQA PGKGLEWVSG IGAEGVWTYY
ADSVKGRFTI SRDNSKNTLY LQMNSLRAED TAVYYCAEPT MSNGSQSR-- FDYWGQGTLV TVSS

BMS2h-745
(SEQ ID NO: 405)
EVQLLESGGG LVQPGGSLRL SCAASGFTFD NTEMAWVRQA PGKGLEWVSG IIEDGNRTYY
ADSVKGRFTI SRDNSKNTLY LQMNSLRAED TAVYYCAKIR NLHWDVGRQ- FDYWGQGTLV TVSS

BMS2h-745-1
(SEQ ID NO: 406)
EVQLLESGGG LVQPGGSLRL SCAASGFTFD NTEMAWVRQA PGKGLEWVSG ITEDGNRTYY
ADSVKGRFTI SRDNSKNTLY LQMNSLRAED TAVYYCAKIR NLHWDVGRQ- FDYWGQGTLV TVSS

BMS2h-745-10
(SEQ ID NO: 407)
EVQLLESGGG LVQPGGSLRL SCAASGFTFD NTEMAWVRQA PGKGLEWVSG ITEDGNRTYY
ADSVKGRFTI SRDNSKNTLY LOMNNLRAED TAVYYCAKIR NLHWDVGRQ- FDYWGQGTLV TVSS

BMS2h-745-11
(SEQ ID NO: 408)
EVQLLESGGG LVQPGGSLRL SCAASGFTFD NTEMAWIRQA PGKGLEWVSG ITEDGNRTYY
ADSVKGRFTI SRDNFKNTLY LQMNSLRAED TAVYYCAKIR NLHWDVGRQ- FDYWGQGTLV TVSS

BMS2h-745-12
(SEQ ID NO: 409)
EVQLLESGGG LVQPGGSLRL SCAASGFTFD NTEMAWVRQA PGKGLEWVSG ITEDGNRTYY
ADSVKGRFTI SRDNSMNTLY LQMNSLRAED TAVYYCAKIR NLHWDVGRQ- FVYWGQGTLV TVSS

BMS2h-745-13
(SEQ ID NO: 410)
EVQLLESGGG LVQPGGSLRL SCAASGFTFD NTEMAWIRQA PGKGLEVWSG IIEDGNRTYY
ADSVKGRFTI SRDNSKNTLY LQMNSLRAED TAVYYCAKIR NLHWDVGRQ- FDYWGQGTLV TVSS

BMS2h-745-14
(SEQ ID NO: 411)
EVQLLESGGG LVQPGGSLRL SCAASGFTFD NTEMAWIRQA PGKGLEWVSG ITEDGNRTYY
ADSVKGRFTI SRDNSKNTLY LQMNSLRAED TAVYYCAKIR NLHWDVGRQ- FDYWGQGTLV TVSS

BMS2h-745-15
(SEQ ID NO: 412)
EVQLLESGGG LVQPGGSLRL SCAASGFTFD NTEMAWIRQA PGKGLEWVSG ITEDGNRTYY
ADSVKGRFTI SRDNSKNALY LQMNSLRAED TAVYYCAKIR NLHWDVGRQ- FDYWGLGTLV TVSS

BMS2h-745-16
(SEQ ID NO: 413)
EVQLLESGGG LVQPGGSLRL SCAASGFTFD NTEMAWVRQA PGKGLEWVSG ITEDGNRTYY
ADSVKGRFTI SRDNTKNTLY LQMNSLRAED TAVYYCAKIR NLHWDVGRQ- FVYWGQGTLV TVSS

BMS2h-745-17
(SEQ ID NO: 414)
EVQLLESGGG LVQPGGSLRL SCAASGFTFD NTEMAWIRQA PGKGLEWVSG IIEDGNRTYY
ADSVKGRFTI SRDNSKNRLY LQMNSLRAED TAVYYCAKIR NLHWDVGRQ- FDYWGQGTLV TVSS

BMS2h-745-18
(SEQ ID NO: 415)
EVQLLESGGG LVQPGGSLRL SCAASGFTFD NTEMAWVRQA PGKGLEWVSG ITEDGNRTYY
ADSVKGRFTI SRDNSKNTLY LQMNSLRAED TAVYHCAKIR NLHWDVGRQ- FDYWGQGTLV TVSS

TABLE I-continued

Anti-human CD40L VH Domain Amino Acid Sequences

BMS2h-745-19
(SEQ ID NO: 416)
EVQLLESGGG LVQPEGSLRL SCAASGFTFD NTEMAWVRQA PGKGLEWVSG IIEDGNRTYY
ADSVKGRFTI SRDNSKNTLY LQMNSLRAED TAVYYCAKIR NLHWDVGRQ- FDYWGQGTLV TVSS

BMS2h-745-2
(SEQ ID NO: 417)
EVQLLESGGG LVQPGGSLRL SCAASGFTFD NTEMAWVRQA PGKGLEWVSG ISEDGNRTYY
ADSVKGRFTI SRDNSKNTLY LQMNSLRAED SAVYYCAKIR NLHWDVGRQ- FVYWGQGTLV TVSS

BMS2h-145-3
(SEQ ID NO: 418)
EVQLLESGGG LVEPGGSLRL SCAASGFTFD NTEMAWVRQA PGKGLEWVSG ITEDGNRTYY
ADSVKGRFTI SRDNSKNTLY LQMSSLRAED TAVYYCAKIR NLHWDVGRQ- FDYWGQGTLV TVSS

BMS2h-745-4
(SEQ ID NO: 419)
EVQLLESGGG LVQPGGSLRL SCAASGFTFD NTEMAWVRQA PGKGLEWVSG ISEDGNRTYY
ADSVKGRFTI SRDNSKNTLY LQMNSLRAED TAVYHCAKIR NLHWDVGRQ- FDYWGQGTLV TVSS

BMS2h-745-5
(SEQ ID NO: 420)
EVQLLESGGG LVQPGGSLRL SCAASGFTFD NTEMAWVRQA PGKGLEWVSG ITEDGNRTYY
ADSVKGRFII SRDNSKNTLN LQMNSLRAED TAVYYCAKIR NLHWDVGRQ- FDYWGQGTLV TVSS

BMS2h-745-6
(SEQ ID NO: 421)
EVQLLESGGG LVQPGGSLRL SCAASGFTFD NTEMAWIRQA PGRGLEWVSG VTEDGNRTYY
ADSVKGRFTI SRDNSKNTLY LQMNSLRAED TAVYYCAKIR NLHWDVGRQ- FDYWGQGTLV TVSS

BMS2h-745-7
(SEQ ID NO: 422)
EVQLLESGGG LVQPGGSLRL SCEASGFTFD NTEMAWIRQA PGKGLEWVSG IIEDGNRTYY
ADSVKGRFTI SRDNTKNTLY LQMNSLRAED TAVYYCAKIR NLHWDVGRQ- FDYWGQGTLV TVSS

BMS2h-745-8
(SEQ ID NO: 423)
EVQLLESGGG LVQPGGSLRL SCAASGFTFD NTEMAWIRQA PGKGLEWVSG ITEDGDRTYY
ADSVKGRFTI SRDNSKSSLY LQMNSLRAED TAVYYCAKIR NLHWDVGRQ- FDYWGQGTLV TVSS

BMS2h-745-9
(SEQ ID NO: 424)
EVQLLESGGG LVQPGGSLRL SCAASGFTFD NTEMAWVRQA PGKGLEWVSG ITEDGNRTYY
ADSVKGRFTI SRDNSKNTLY LQMNSLRAED TAVYYCAKIR NLHWDVGRQ- FVYWGQGTLV TVSS

BMS2h-746
(SEQ ID NO: 425)
EVQLLESGGG LVQPGGSLRL SCAASGFTFG SAEMGWVRQA PGKGLEWVSG ISRPGQVTYY
ADSVKGRFTI SRDNSKNTLY LQMNSLRAED TAVYYCAKIR NLHWDVGRQ- FDYWGQGTLV TVSS

BMS2h-747
(SEQ ID NO: 426)
EVQLLESGGG LVQPGGSLRL SCAASGFTFD DGTMGWARQA PGKGLEWVSL ILPSGSRTYY
ADSVKGRFTI SRDNSKNTLY LQMNSLRAED TAVYYCAKHS LTNRP----- FDYWGQGTLV TVSS

BMS2h-748
(SEQ ID NO: 427)
EVQLLESGGG LVQPGGSLRL SCAASGFTFS KYDMRWARQA PGKGLEWVSD IDAVGTRTYY
ADSVKGRFTI SRDNSKNTLY LQMNSLRAED TAVYYCAIPG GT-------- FDYWGQGTLV TVSS

BMS2h-749
(SEQ ID NO: 428)
EVQLLESGGG LVQPGGSLRL SCAASGFTFE MYGMMWARQA PGKGLEWVSS IEGAGHATYY
ADSVKGRFTI SRDNSKNTLY LQMNSLRAED TAVYYCAIVL GM-------- FDYWGQGTLV TVSS

BMS2h-75
(SEQ ID NO: 429)
EVQLLESGGG LVQPGGSLRL SCAASGFTFL QYPMGWVRQA PGKGLEWVST ISPVGLTTYY
ADSVKGRFTI SRDNSKNTLY LQMNSLRAED TAVYYCAKLF EGSRIQRDVG FDYWGQGTLV TVSS

BMS2h-750
(SEQ ID NO: 430)
EVQLLESGGG LVQPGGSLRL SCAASGFTFE KYQMGWARQA PGKGLEWVSS IRGSGLVTYY
ADSVKGRFTI SRDNSKNTLY LQMNSLRAED TAVYYCAKVH TTLHTEVIG- FDYWGQGTLV TVSS

TABLE I-continued

Anti-human CD40L VH Domain Amino Acid Sequences

BMS2h-751
(SEQ ID NO: 431)
EVQLLESGGG LVQPGGSLRL SCAASGFTFS QYTMYWARQA PGKGLEWVSE ISHSGSNTYY
ADSVKGRFTI SRDNSKNTLY LQMNSLRAED TAVYYCAISG LH-------- FDYWGQGTLV TVSS

BMS2h-752
(SEQ ID NO: 432)
EVQLLESGGG LVQPGGSLRL SCAASGFTFS DYAMAWVRQA PGKGLEWVSR IGVEGGDTYY
ADSVKGRFTI SRDNSKNTLY LQMNSLRAED TAVYYCAKLL RLYRLG---- FDYWGQGTLV TVSS

BMS2h-753
(SEQ ID NO: 433)
EVQLLESGGG LVQPGGSLRL SCAASGFTFA KYDMTWVRQA PGKGLEWVSK INSQGGLTYY
ADSVKGRFTI SRDNSKNTLY LQMNSLRAED TAVYYCAKGL HGRGFVI--- FDYWGQGTLV TVSS

BMS2h-754
(SEQ ID NO: 434)
EVQLLESGGG LVQPGGSLRL SCAASGFTFS RYDMVWVRQA PGKGLEWVSR INSMGLATYY
ADSVKGRFTI SRDNSKNTLY LQMNSLRAED TAVYYCAKDY SVAPHGYPLG FDYWGQGTLV TVSS

BMS2h-755
(SEQ ID NO: 435)
EVQLLESGGG LVQPGGSLRL SCAASGFTFK DYSMMWVRQA PGKGLEWVST ITDNGTSTYY
ADSVKGRFTI SRDNSKNTLY LQMNSLRAED TAVYYCAKHM SLATYLQF-- FDYWGQGTLV TVSS

BMS2h-756
(SEQ ID NO: 436)
EVQLLESGGG LVQPGGSLRL SCAASGFTFM EYDMLWVRQA PGKALEWVSR ISSDGLWTYY
ADSVKGRFTI SRDNSKNTLY LQMNSLRAED TAVYYCAKGV SALAPFDIG- FDYWGQGTLV TVSS

BMS2h-757
(SEQ ID NO: 437)
EVQLLESGGG LVQPGGSLRL SCAASGFTFK EYNMAWVRQA PGKGLEWVSS INFAGRTTYY
ADSVKGRFTI SRDNSKNTLY LQMNSLRAED TAVYYCAKLS LPLDIFS--- FDYWGQGTLV TVSS

BMS2h-758
(SEQ ID NO: 438)
EVQLLESGGG LVQPGGSLRL SCAASGFTFG DYGMNWVRQA PGKGLEWVSH ISSNGRFTYY
ADSVKGRFTI SRDNSKNTLY LQMNSLRAED TAVYYCAETS GY-------- FDYWGQGTLV TVSS

BMS2h-758-1
(SEQ ID NO: 439)
EVQLLESGGG LVQPGGSLRL SCAASGFTFG DYGMNWVRQA PGKGLEWVSH ISSNGRFTYY
ADSVKGRFTI SRDNSKNMLY LRMNSLRAED TAVYYCAETS GY-------- YEYWGQGTLV TVSS

BMS2h-758-2
(SEQ ID NO: 440)
EVQLLESGGG LVQPGGSLRL SCAASGFTFG DYGMNWVRQA PGKGLEWVSH ISSNGRFTYY
ADSVKGRFTI SRDNSKNTLY LQMNSLRAED TAVYYCAETS GY-------- FEYWGQGTLV TVSS

BMS2h-758-3
(SEQ ID NO: 441)
EVQLLESGGG LVQPGGSLRL SCAASGFTFG DYGMNWVRQA PGKGLEWVSH ISSNGRFTYY
ADSVKGRFTI SRDNSKNTLY LQMNSLRAED TAVYYCAETS SY-------- FEYWGQGTLV TVSS

BMS2h-758-4
(SEQ ID NO: 442)
EVQLLESGGG LVQPGGSLRL SCPASGFTFG DYGMNWVRQA PGKGLEWVSH ISSNGRFTYY
ADSVKGRFTI SRDNSKNTLF LQMNSLRAED TAVYYCAETS GY-------- YEYWGHGTLV TVSS

BMS2h-758-5
(SEQ ID NO: 443)
EVQLLESGGG LVQPGGSLRL SCAASGFAFG DYGMNWVRQA PGKGLEWVSH ISSNGRFTYY
ADSVKGRFTI SRDNSKNTLY LQMNSLRAED TAVYYCAETS GY-------- FEYWGQGTLV TVSS

BMS2h-758-6
(SEQ ID NO: 444)
EVQLLESGGG LVQPGGSLRL SCAASGFTFG DYGMNWVRQA PGKGLEWVSH ISSNGRFIYY
ADSVKGRFTI SRDNSKNTLY LQMNSLRAED TAVYYCAETS GY-------- FEYWGQGTLV TVSS

BMS2h-759
(SEQ ID NO: 445)
EVQLLESGGG LVQPGGSLRL SCAASGFTFR EYVMGWVRQA PGKGLEMST INGLGNVTYY
ADSVKGRFTI SRDNTKNTLY LQMNSLRAEE TAVYYCAIQL PN------- FDYWGQGTLV TVSS

TABLE I-continued

Anti-human CD40L VH Domain Amino Acid Sequences

BMS2h-760
(SEQ ID NO: 446)
EVQLLESGGG LVQPGGSLRL SCAASGFTFG NDGMWWVRQA PGKGLEWVSF INVDGRETYY
ADSVKGRFTI SRDNSKNTLY LQMNSLRAED TAVYYCAEWS PGRVQ----- FDYWGQGTLV TVSS

BMS2h-761
(SEQ ID NO: 447)
EVQLLESGGG LVQPGGSLRL SCAASGFTFG GWDMAWVRQA PGKGLEWVSS IAHEGGETYY
ADSVKGRFTI SRDNSKNTLY LQMNSLRAED TAVYYCAKYV PGSPL----- FDYWGQRTLV TVSS

BMS2h-762
(SEQ ID NO: 448)
EVQLLESGGG LVQPGGSLRL SCAASGFTFD QGWMYWVRQA PGKGLEWVSG IGSNGPRTSY
ADSVKGRFTI SRDNSKNTLY LQMNSLRAED TAVYYCAKSG EY-------- FDYWGQGTLV TVSS

BMS2h-763
(SEQ ID NO: 449)
EVQLLESGGG LVQPGGSLRL SCAASGFTFR QSDMWWVRQA PGKGLEWVSV IGNNGEFTYY
ADSVKGRFTI SRDNSKNTLY LQMNSLRAED TAVYYCAKDN WLL------- FDYWGQGTLV TVSS

BMS2h-764
(SEQ ID NO: 450)
EVQLLESGGG LVQPGGSLRL SCAASGFTFD LSTMYWVRQA PGKGLEWVST IGGDGSHTYY
ADSVKGRFTI SRDNSKNTLY LQMNSLRAED TAVYYCAEGT QY-------- FDYWGQGTLV TVSS

BMS2h-765
(SEQ ID NO: 451)
EVQLLESGGG LVQPGGSLRL SCAASGFITS AYTMEWVRQA PGKGLEWVSS IGVTGYDTYY
ADSVKGRFTI SRDNSKNTLY LQMNSLRAED TAVYYCAKGG QG-------- FDYWGQGTLV TVSS

BMS2h-766
(SEQ ID NO: 452)
EVQLLESGGG LVQPGGSLRL SCAASGFTFG DYGMSWVRQA PGKGLEWVSY IDPLGRLTYY
ADSVKGRFTI SRDNSKNTLY LQMNSLRAED TAVYYCAEDL SSLQYGVSPN FDYWGQGTLV TVSS

BMS2h-767
(SEQ ID NO: 453)
EVQLLESGGG LVQPGGSLRL SCAASGFTFF HYSMSWVRQA PGKGLEWVSS IGPVGRETYY
ADSVKGRFTI SRDNSKNTLY LQMNSLRAED TAVYYCAKMI QSPLFKD--- FDYWGQGTLV TVSS

BMS2h-768
(SEQ ID NO: 454)
EVQLLESGGG LVQPGGSLRL SCAASGFTFE WYDMYWVRQA PGKGLEWVSR IDSGGNQTYY
ADSVKGRFTI SRDNSKNTLY LQMNSLRAED TAVYYCAEAS LWKWRL---- FDYWGQGTLV TVSS

BMS2h-77
(SEQ ID NO: 455)
EVQLLESGGG LVQPGGSLRL SCAASGFTFE EYGMAWVRQA PGKGLEWVST ISPLGISTYY
ADSVKGRFTI SRDNSKNTLY LQMNSLRAED TAVYYCAKHA TSQESLRS-- FDYWGQGTLV TVSS

BMS2h-770
(SEQ ID NO: 456)
EVQLLESGGG LVQPGGSLRL SCAASGFTFS KYEMMVWRQA PGKGLEWVSA ISGSGGSTYY
ADSVKGRFTI SRDNSKNTLY LQMNSLRAED TAVYYCAKGP LPDAFWTRG- FDYWGQGTLV TVSS

BMS2h-771
(SEQ ID NO: 457)
EVQLLESGGG LVQPGGSLRL SCAASGFTFG TYSMAWVRQA PGKGLEWVST IDRHGLATYY
ADSVKGRFTI SRDNSKNTLY LQMNSLRAED TAVYYCAKTP GSSWQTV--- FGYWGQGTLV TVSS

BMS2h-772
(SEQ ID NO: 458)
EVQLLESGGG LVQPGGSLRL SCAASGFTFE SYPMGWVRQA PGKGLEWVSS IDHHGHSTYY
ADSAKGRFTI SRDNSKNTLY LQMNSLRAED TAVYYCAKLL RVSMIFG--- FDYWGQGTLV TVSS

BMS2h-773
(SEQ ID NO: 459)
EVQLLESGGG LVQPGGSLRL SCAASGFIFV QYGMSWVRQA PGKGLEWVSW ISSSGTYTYY
ADSVKGRFTI SRDNSKNTLY LQMNSLRAED TAVYYCAETS RM-------- FDYWGQGTLV TVSS

BMS2h-774
(SEQ ID NO: 460)
EVQLLESGGG LVQPGGSLRL SCAASGFTFR EYDMGWVRQA PGKGLEWVSL ISPPGRTTYY
ADSVKGRFTI SRDNSKNTLY LQMNSLRAED TAVYYCAKVV ILGYTNR--- FDYWGQGTLV TVSS

TABLE I-continued

Anti-human CD40L VH Domain Amino Acid Sequences

BMS2h-775
(SEQ ID NO: 461)
EVQLLESGGG LVQPGGSLRL SCAASGFTFP NYGMLWVRQA PGKGLEVWSS INSSGMETYY
ADSVKGRFTI SRDNSKNTLY LQMNSLRAED TAVYYCAKFF RLNDHNSVFG FDYWGQGTLV TVSS

BMS2h-776
(SEQ ID NO: 462)
EVQLLESGGG LVQPGGSLRL SCAASGFIFK DYKMMWIRQA PGKGLEWVSS IVGSGSMTYY
ADSVKGRFTI SRDNSKNTLY LQMNSLRAED TAVYYCAKGP GY-------- FDYWGQGTLV TVSS

BMS2h-777
(SEQ ID NO: 463)
EVQLLESGGG LVQPGGSLRL SCAASGFTFH NYAMGWVRRA PGKGLEWVSS IDEHGTITYY
ADSVKGRFTI SRDNSKNTLY LQMNSLRAED TAVYYCAKDS LDRWVI---- FDYWGQGTLV TVSS

BMS2h-778
(SEQ ID NO: 464)
EVQLLESGGG LVQPGGSLRL SCAASGFTFA DYPMTWVRQA PGKGLEWVSS IYSAGSPTYY
ADSVKGRFTI SRDNSKNTLY LQMNSLRAED TAVYYCAKLY HREPILFG-- FDYWGQGTLV TVSS

BMS2h-78
(SEQ ID NO: 465)
EVQLLESGGG LVQPGGSLRL SCAASGFTFE RYQMAWVRQA PGKGLEWVST ISSDGGGTYY
ADSVKGRFTI SRDNSKNTLY LQMNSLRAED TAVYYCAKPG HR-------- FDYWGQGTLV TVSS

BMS2h-780
(SEQ ID NO: 466)
EVQLLESGGG LVQPGGSLRL SCAASGFTFG SYTMMWVRQA PGKGLEWVSE IDRTGERTYY
ADSVKGRFTI SRDNSKNTLY LQMNSLRAED TAVYYCAEPG FASLP----- FDYWGQGTLV TVSS

BMS2h-781
(SEQ ID NO: 467)
EVQLLESGGG LVQPGGSLRL SCAASGFTFT DYTMYWVRQA PGKGLEWVSK ISPSGRSTYY
ADSVKGRFTI SRDNSKNTLY LQMNSLRAED TAVYYCAKDP FG-------- FDYWGQGTLV TVSS

BMS2h-782
(SEQ ID NO: 468)
EVQLLESGGG LVQPGGSLRL SCAASGFTED DAEMFWVRQA PGKGLEWVSS IDARGLTTYY
ADPVKGRFTI SRDNSKNTLY LQMNSLRAED TAVYYCAEAT SAMYP----- FDYWGQGTLV TVSS

BMS2h-783
(SEQ ID NO: 469)
EVQLLESGGG LVQPGGSLRL SCAASGFTER DYDMGWVRQA PGKGLEWVST ISPLGHFTYY
ADSVKGRFTI SRDNSKNTLY LQMNSLRAED TAVYYCAKSG FHEYTEG--- FDYWGQGTLV TVSS

BMS2h-784
(SEQ ID NO: 470)
EVQLLESGGG LVQPGGSLRL SCAASGFTFD RAGMGWVRQA PGKGLEWVSL IGRGGDITYY
ADSVKGRFTI SRDNSKNTLY LQMNSLRAED TAVYYCAKIR NLHWDVGRQ- FDYWGQGTLV TVSS

BMS2h-80
(SEQ ID NO: 471)
EVQLLESGGG LVQPGGSLRL SCAASGFTEG RYQMAWVRQA PGKGLEWVSS ISSDGGGTYY
ADSVKGRFTI SRDNSKNTLY LQMNSLRAED TAVYYCAKPS RR-------- FDYWGQGTLV TVSS

BMS2h-81
(SEQ ID NO: 472)
EVQLLESGGG LVQPGGFLRL SCAASGFTFE LYPMAWVRQA PGKGLEWVSS ISPVGFLTYY
ADSVKGRFTI SRDNSKNTLY LQMNSLRAED TAVYYCAKGH EGSYTPRSA- FDYWGQGTLV TVSS

BMS2h-82
(SEQ ID NO: 473)
EVQLLESGGG LVQPGGSLRL SCAASGFTFV AYPMAWVRQA PGKGLEWVST IAPLGGNTYY
ADSVKGRFTI SRDNSKNTLY LQMNSLRAED TAVYYCAKRP EGLQIDSQN- FDYWGQGTLV TVSS

BMS2h-33
(SEQ ID NO: 474)
EVQLLESGGG LVQPGGSLRL SCAASGFTFA LYQMAWNRQA PGKGLEWVSS IDSSGSDTYY
ADSVKGRFTI SRDNSKNTLY LQMNSLRAED TAVYYCAKPE RD-------- FDYWGQGTLV TVSS

BMS2h-84
(SEQ ID NO: 475)
EVQLLESGGG LVQPGGSLRL SCAASGFTFR QYQMAWARQA PGKGLEWVST IASDGVSTYY
ADSVKGRFTI SRDNSKNTLY LQMNSLRAED TAVYYCAKVG RD-------- FDYWGQGTLV TVSS

TABLE I-continued

Anti-human CD40L VH Domain Amino Acid Sequences

BMS2h-85
(SEQ ID NO: 476)
EVQLLESGGG LVQPGGSLRL SCAASGFTFE QYDMRWVRQA PGKGLEWVSW IDEAGHETYY
ADSVKGRFTI SRDNSRNTLY LQMNSLRAED TAVYYCAKGM DG-------- FDYWGQGTLV TVSS

BMS2h-92
(SEQ ID NO: 477)
EVQLLESGGG LVQPGGSLRL SCAASGFTFV DYPMGWVRQA PGKGLEWVST ISTGGFSTYY
ADSVKGRFTI SRDNSKNTLY LQMNSLRAED TAVYYCAKAR YYYLSQIKN- FDYWGQGTLV TVSS

BMS2h-93
(SEQ ID NO: 478)
EVQLLESGGG LVQPGGSLRL SCAASGFTFD IYGMTWVRQA PGKGLEWVSS ISPLGLVTYY
ADPVKGRFTI SRDNSKNTLY LQMNSLRAED TAVYYCAKLK EHGDVP---- FDYWGQGTLV TVSS

BMS2h-94
(SEQ ID NO: 479)
EVQLLESGGG LVQPGGSLRL SCAASGFTFE LYPMSWVRQA PGKGLEWVST ISPTGLLTYY
ADSVKGRFTI SRDNSKNTLY LQMNSLRAED TAVYYCAKFK RSGKTDDTN- FDYWGQGTLV TVSS

BMS2h-95
(SEQ ID NO: 480)
EVQLLESGGG LVQPGGSLRL SCAASGFTFR EYDMLWVRQA PGKGLEVWST IVGDGNGTYY
ADSVKGRFTI SRDNSKNTLY LQMNSLRAED TAVYYCAKQD RQ-------- FDYWGQGTLV TVSS

BMS2h-97
(SEQ ID NO: 481)
EVQLLESGGG LVQPGGSLRL SCAASGFTFE EYGMSWVRQA PGKGLEWVST ISPIGVITYY
ADSVKGRFTI SRDNSKNTLY LQMNSLRAED TAVYYCAKNA YDRKSN---- FDYWGQGTLV TVSS

BMS2h-98
(SEQ ID NO: 482)
EVQLLESGGG LVQPGGSLRL SCAASGFTFD RYVMVWVRQA PGKDLEVWSG ITPSGRRTYY
ADSVKGRFTI SRDNSKDTLY LQMNSLRAED TAVYYCAKVL GRHFDPLLPS FDYWGQGILV TVSS

BMS2h-99
(SEQ ID NO: 483)
EVQLLESGGG LVQPGGSLRL SCAASGFTFE DYAMSWVRQA PGKGLEWVST ITPGGFWTYY
ADSVKGRFTI SRDNSKNTLY LQMNSLRAED TAVYYCAKTS SGELQLVED- FDYWGQGTLV TVSS

TABLE 2

Human Anti-CD40L VH Domain Encoding Nucleotide Sequences

BMS2h-10
(SEQ ID NO: 484)
GAGGTGCAGCTGTTGGAGTCTGGGGGAGGCTTAGTACAGCCTGGGGGGTCCCTGCGTCTC

TCCTGTGCAGCCTCCGGATTCACCTTTATTGCTTATGATATGAGTTGGGTCCGCCAGGCT

CCAGGGAAGGGTCTGGAGTGGGTCTCATGGATTGATGAGTGGGGTCTGCAGACATACTAC

GCAGAGTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAAAGACG

CCTGAGGAGTTTGACTACTGGGGTCAGGGAACCCTGGTCACCGTCTCGAGC

BMS2h-11
(SEQ ID NO: 485)
GAGGTGCAGCTGTTGGAGTCTGGGGGAGGCTTGGTACAGCCTGGGGGGTCCCTGCGTCTC

TCCTGTGCAGCCTCCGGATTCACCTTTGGTGATTATGAGATGAGTTGGGTCCGCCAGGCT

CCAGGGAAGGGTCTAGAGTGGGTCTCAGGGATTGATGGTGAGGGTTCTGATACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAACCGGGG

AGGAGTTTTGACTACTGGGGTCAGGGAACCCTGGTCACCGTCTCGAGC

TABLE 2-continued

Human Anti-CD40L VH Domain Encoding Nucleotide Sequences

BMS2h-111
(SEQ ID NO: 486)
GAGGTGCAGCTGTTGGAGTCTGGGGGAGGCTTGGTACAGCCTGGGGGGTCCCTGCGTCTC

TCCTGTGCAGCCTCCGGATTCACCTTTGAGCGTTATCCTATGACGTGGGTCCGCCAGGCT

CCAGGGAAGGGTCTAGAGTGGGTCTCAACGATTCATGGTTCTGGTAGTGCTACATACTAC

GCAGACTCCGTGAAGGGCCGGTTCACCATCTCCCGCGACAATTCCAAGAACACGGTGTAT

CTGCAAATGAACAGCCTGCGTGCCGAGGACACCGCGGTATATTACTGTGCGAAAGGGCCG

TATACTAGTCGGCATAATAGTCTTGGGCATTTTGACTACTGGGGTCAGGGAACCCTGGTC

ACCGTCTCGAGC

BMS2h-112
(SEQ ID NO: 487)
GAGGTGCAGCTGTTGGAGTCTGGGGGAGGCTTGGTACAGCCTGGGGGGTCCCTGCGTCTC

TCCTGTGCAGCCTCCGGATTCACCTTTATGGATTATCCTATGGGGTGGGTCCGCCAGGCT

CCAGGGAAGGGTCTAGAGTGGGTCTCATCTATTGGGCCTGTTGGTATGAGTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAATATGGG

GGGACTAGTGGTAGGCATAATACTAAGTTTGACTACTGGGGTCAGGGAACCCTGGTCACC

GTCTCGAGC

BMS2h-113
(SEQ ID NO: 488)
GAGGTGCAGCTGTTGGAGTCTGGGGGAGGCTTGGTACAGCCTGGGGGGTCCCTGCGTCTC

TCCTGTGCAGCCTCCGGATTCACCTTTACTGAGTATCCTATGAGTTGGGTCCGCCAGGCT

CCAGGGAAGGGTCTAGAGTGGGTCTCAGTTATTTCTCCTCTTGGTTTTACGACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAATGGACT

GGTGGGAGTGGTATTTTGAATTCTTCTTTTGACTACTGGGGTCAGGGAACCCTGGTCACC

GTCTCGAGC

BMS2h-114
(SEQ ID NO: 489)
GAGGTGCAGCTGTTGGAGTCTGGGGGAGGCTTGGTACAGCCTGGGGGGTCCCTGCGTCTC

TCCTGTGCAGCCTCCGGATTTAGGGTTAGCAATTACGATTTGACCTGGGTCCGCCAGGCT

CCAGGGAAGGGTCTAGAGTGGGTATCAACCATTAGTGCCACAAACGGTAGCACATACTAC

GCAGACTCCGTGAAGGGCCGGTTCACCATCTCCCGTGACAATTCCAAGAACACGCTGTAT

CTGCAAATGAACAGCCTGCGTGCCGAGGACACCGCGGTATATTATTGCGCGGCAGTGACG

TGGTGGTTGTTGCGTCATAACGACAACTTGGGGTTTTGGGGTCAGGGAACCCTGGTCACC

GTCTCGAGC

BMS2h-115
(SEQ ID NO: 490)
GAGGTGCAGCTGTTGGAGTCTGGGGGAGGCTTGGTACAGCCTGGGGGGTCCCTGCGTCTC

TCCTGTGCAGCCTCCGGATTTAGCATTAGCTATAAGAATATGGCCTGGGTCCGCCAGGCT

CCAGGGAAGGGTCTAGAGTGGGTATCAGCCATTAAGGCGGCAAACGGTAGCACATACTAC

GCAGACTCCGTGAAGGGCCGGTTCACCATCTCCCGTGACAATTCCAAGAACACGCTGTAT

CTGCAAATGAACAGCCTGCGTGCCGAGGACACCGCGGTATATTATTGCGCGACAGGGAGT

TABLE 2-continued

Human Anti-CD40L VH Domain Encoding Nucleotide Sequences

CAGAAGAAGCGGACCTACACGTTCGACTTTTGGGGTCAGGGAACCCTGGTCACCGTCTCG

AGC

BMS2h-12
(SEQ ID NO: 491)
GAGGTGCAGCTGTTGGAGTCTGGGGGAGGCTTGGTACAGCCTGGGGGGTCCCTGCGTCTC

TCCTGTGCAGCCTCCGGATTCACCTTTAGGTTGTATGAGATGGCGTGGGTCCGCCAGGCT

CCAGGGAAGGGTCTAGAGTGGGTCTCAGGGATTGATATTTTGGGTTCGAGGACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAAGATCTG

TCGTGGCAGGGTTTTGACTACTGGGGTCAGGGAACCCTGGTCACCGTCTCGAGC

BMS2h-120
(SEQ ID NO: 492)
GAGGTGCAGCTGTTGGAGTCTGGGGGAGGCTTGGTACAGCCTGGGGGGTCCCTGCGTCTC

TCCTGTGCAGCCTCCGGATTCACCTTTAGGTCTTATACGATGGGTTGGGTCCGCCAGGCT

CCAGGGAAGGGTCTAGAGTGGGTCTCATCTATTAATCCTATGGGTTATCAGACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAACATGGG

GTGGGGAAGGGTACTAAGCCGCATAATTTTGACTACTGGGGTCAGGGAACCCTGGTCACC

GTCTCGAGC

BMS2h-121
(SEQ ID NO: 493)
GAGGTGCAGCTGTTGGAGTCTGGGGGAGGCTTGGTACAGCCTGGGGGGTCCCTGCGTCTC

TCCTGTGCAGCCTCCGGATTCACCTTTGAGCTGTATAGGATGTCTTGGGTCCGCCAGGCT

CCAGGGAAGGGTCTAGAGTGGGTCTCAGAGATTAGTGGTAGTGGTTTTCCTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAAGTCTG

CATGATAAGACTCAGCATCATCAGGAGTTTGACTACTGGGGTCAGGGAACCCTGGTCACC

GTCTCGAGC

BMS2h-123
(SEQ ID NO: 494)
GAGGTGCAGCTGTTGGAGTCTGGGGGAGGCTTGGTACAGCCTGGGGGGTCCCTGCGTCTC

TCCTGTGCAGCCTCCGGATTCACCTTTATTGAGTATCCTATGCGGTGGGTCCGCCAGGCT

CCAGGGAAGGGTCTAGAGTGGGTCTCACTTATTTCTCCGTCTGGTGTGTTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGGGGAT

GAGTCTAGTACTTTTGACTACTGGGGTCAGGGAACCCTGGTCACCGTCTCGAGC

BMS2h-124
(SEQ ID NO: 495)
GAGGTGCAGCTGTTGGAGTCTGGGGGAGGCTTGGTACAGCCTGGGGGGTCCCTGCGTCTC

TCCTGTGCAGCCTCCGGATTCACCTTTAAGCGGTATGATATGGATTGGGTCCGCCAGGCT

CCAGGGAAGGGTCTAGAGTGGGTCTCAACGATTGGGAGTTCGGGTTATCCGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGGAAAGGATG

TABLE 2-continued

Human Anti-CD40L VH Domain Encoding Nucleotide Sequences

CCTGGTTATTTTCCTGGGTTTGCTCGGCAGTTTGACTACTGGGGTCAGGGAACCCTGGTC

ACCGTCTCGAGC

BMS2h-125 (SEQ ID NO: 496)
GAGGTGCAGCTGTTGGAGTCTGGGGGAGGCTTGGTACAGCCTGGGGGGTCCCTGCGTCTC

TCCTGTGCAGCCTCCGGATTCACCTTTTGGCGGTATGCTATGGGGTGGGTCCGCCAGGCT

CCAGGGAAGGGTCTAGAGTGGGTCTCAACGATTAATGATGAGGGTCGGGAGACATACTAC

GCAGACTCCGTGAAGGGCCGGTTCACCATCTCCCGCGACAATTCCAAGAACACGCTGTAT

GTGCAAATGAACAGCCTGCGTGCCGAGGACACCGCGGTATATTACTGTGCGAAAAAGCGG

GTGTCTAGTTCTGTGAATGCTCCGTATGAGTTTGACTACTGGGGTCAGGGAACCCTGGTC

ACCGTCTCGAGC

BMS2h-126 (SEQ ID NO: 497)
GAGGTGCAGCTGTTGGAGTCTGGGGGAGGCTTGGTACAGCCTGGGGGGTCCCTGCGTCTC

TCCTGTGCAGCCTCCGGATTCACCTTTGCGAATTATAGTATGAGTTGGGTCCGCCAGGCC

CCAGGGAAGGGTCTAGAGTGGGTCTCATCGATTGATCGTCTTGGTACGCATACATACTAC

GCAGACTCCGTGAAGGGCCGGTTCACCATCTCCCGCGACAATTCCAAGAATACGCTGTAT

CTGCAAATGAACAGCCTGCGTGCCGAGGATACCGCGGTATATTACTGTGCGAAAGTGCTG

GCTGATCTTATTGCTGGGCATGCGGAGTTTGACTACTGGGGTCAGGGAACCCTGGTCACC

GTCTCGAGC

BMS2h-127 (SEQ ID NO: 498)
GAGGTGCAGCTGTTGGAGTCTGGGGGAGGCTTGGTACAGCCTGGGGGGTCCCTGCGTCTC

TCCTGTGCAGCCTCCGGATTCACCTTTCCGTCGTATGATATGGCGTGGGTCCGCCAGGCT

CCAGGGAAGGGTCTAGAGTGGGTCTCAGGGATTTCGAGGTCTGGTTCTATGACATACTAC

GCAGACTCCGTGAAGGGCCGGTTCACCATCTCCCGCGACAATTCCAAGAACACGCTGTAT

TTGCAAATGAACAGCCTGCGTGCCGAGGACACCGCGGTATATTACTGTGCGAAAGGTGTT

GATGCGCATGTTTATTATATGGAGCCTTTTTTTGACTACTGGGGTCAGGGAACCCTGGTC

ACCGTCTCGAGC

BMS2h-128 (SEQ ID NO: 499)
GAGGTGCAGCTGTTGGAGTCTGGGGGAGGCTTGGTACAGCCTGGGGGGTCCCTGCGTCTC

TCCTGTGCAGCCTCCGGATTCACCTTTGAGAGGTATCAGATGGCGTGGGTCCGCCAGGCT

CCAGGGAAGGGTCTAGAGTGGGTCTCAACGATTAGTTCTGATGGTGGGGGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCGGGT

ACTGTTTTTGACTACTGGGGTCAGGGAACCCTGGTCACCGTCTCGAGC

BMS2h-129 (SEQ ID NO: 500)
GAGGTGCAGCTGTTGGAGTCTGGGGGAGGCTTGGTACAGCCTGGGGGGTCCCTGCGTCTC

TCCTGTGCAGCCTCCGGATTCACATTTCCGAAGTATGAGATGGCGTGGGTCCGCCAGGCT

CCAGGGAAGGGTCTAGAGTGGGTCTCATCTATTGATGGTGATGGTAAGTCTACATACTAC

TABLE 2-continued

Human Anti-CD40L VH Domain Encoding Nucleotide Sequences

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAACCGGAT

CAGTTTTTTGACTACTGGGGTCAGGGAACCCTGGTCACCGTCTCGAGC

BMS2h-13
(SEQ ID NO: 501)
GAGGTGCAGCTGTTGGAGTCTGGGGGAGGCTTGGTACAGCCTGGGGGGTCCCTGCGTCTC

TCCTGTGCAGCCTCCGGATTCACCTTTTCTTATTATTCGATGTATTGGGTCCGCCAGGCT

CCAGGGAAGGGTCTAGAGTGGGTCTCATCGATTTCGCCTTTTGGTTGGGGTACATACTAC

GCAGACTCCGTGAAGGGCCGGTTCACCATCTCCCGCGACAATTCCAAGGACACGCTGTAT

CTGCAAATGAACAGCCTGCGTGCCGAGGACACCGCGGTATATTACTGTGCGAAATATGGG

GAGACGAGTGGTCCGATTTCTGAGAATTTTGACTACTGGGGTCAGGGAACCCTGGTCACC

GTCTCGAGC

BMS2h-130
(SEQ. ID NO: 502)
GAGGTGCAGCTGTTGGAGTCTGGGGGAGGCTTGGTACAGCCTGGGGGGTCCCTGCGTCTC

TCCTGTACAGCCTCCGGATTCACCTTTGCGGGTTATCAGATGTCGTGGGTCCGCCAGGCT

CCAGGGAAGGGTCTAGAGTGGGTCTCAAGTATTACTAATGAGGGTGTTTCTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCGGGG

AAGTATTTTGACTACTGGGGTCAGGGAACCCTGGTCACCGTCTCGAGC

BMS2h-131
(SEQ ID NO: 503)
GAGGTGCAGCTGTTGGAGTCTGGGGGAGGCTTGGTACAGCCTGGGGGGTCCCTGCGTCTC

TCCTGTGCAGCCTCCGGATTCACCTTTGGGGAGTATGAGATGGTGTGGGTCCGCCAGGCT

CCAGGGAAGGGTCTGGAGTGGGTCTCATCTATTACGTCGGATGGTCTGAGTACATACTAC

GCAGACTCCGTGAAGGGCCGGTTCACCATCTCCCGCGACAATTCCAAGAACACGCTGTAT

CTGCAAATGAACAGCCTGCGTGCTGAGGACACCGCGGTATATTACTGTGCGAAACCGGGT

ATTCGTTTTGACTACTGGGGTCAGGGAACCCTGGTCACCGTCTCGAGC

BMS2h-132
(SEQ ID NO: 504)
GAGGTGCAGCTGTTGGAGTCTGGGGGAGGCTTGGTACAGCCTGGGGGGTCCCTGCGTCTC

TCCTGTGCAGCCTCCGGATTCACCTTTGCTGATTATGATATGGCTTGGGTCCGCCAGGCT

CCAGGGAAGGGTCTAGAGTGGGTCTCAGGTATTGTTGATGATGGTCTTATGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCGGAT

GTTGCTTTTGACTACTGGGGTCAGGGGACCCTGGTCACCGTCTCGAAC

BMS2h-133
(SEQ ID NO: 505)
GAGGTGCAGCTGTTGGAGTCTGGGGGAGGCTTGGTACAGCCTGGGGGGTCCCTGCGTCTC

TCCTGTGCAGCCTCCGGATTCACCTTTATTGGTTATGCTATGGCGTGGGTCCGCCAGGCT

CCAGGGAAGGGTCTAGAGTGGGTCTCAAGTATTGGTCCTTTGGGTGCGACTACATACTAC

GCAGACTCCGTGAAGGGCCGGTTCACCATCTCCCGCGACAATTCCAAGAACACGCTGTAT

TABLE 2-continued

Human Anti-CD40L VH Domain Encoding Nucleotide Sequences

CTGCAAATGAACAGCCTGCGTGCCGAGGACACCGCGGTATATTACTGTGCGAAATTGCCT

GCTGGTACGAGTAGTCATAGTGTGGATTTTGACTACTGGGGTCAGGGAACCCTGGTCACC

GTCTCGAGC

BMS2h-134
(SEQ. ID NO: 506)
GAGGTGCAGCTGTTGGAGTCTGGGGGAGGCTTGGTACAGCCTGGGGGGTCCCTGCGTCTC

TCCTGTGCAGCCTCCGGATTCACCTTTGCGGATTATGAGATGACTTGGGTCCGCCAGGCT

CCAGGGAAGGGTCTAGAGTGGGTCTCATCTATTACTAGTGATGGTGTTTCTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCGTCG

GTTCAGTTTGACTACTGGGGTCAGGGAACCCTGGTCACCGTCTCGAGC

BMS2h-135
(SEQ ID NO: 507)
GAGGTGCAGCTGTTGGAGTCTGGGGGAGGCTTGGTACAGCCTGGGGGGTCCCTGCGTCTC

TCCTGTGCAGCCTCCGGATTCACCTTTCGTAGGTATGTTATGGGTGGGTCCGCCAGGCT

CCAGGGAAGGGTCTAGAGTGGGTCTCATGGATTGAGGCTGATGGTCGTACGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGGGCTT

ACGGATCAGCATGTTATTGAGTTTGACTACTGGGGTCAGGGAACCCTGGTCACCGTCTCG

AGC

BMS2h-136
(SEQ ID NO: 508)
GAGGTGCAGCTGTTGGAGTGTGGGGGAGGCTTGGTACAGCCTGGGGGGTCCCTGCGTCTC

TCCTGTGCAGCCTCCGGATTCACCTTTGATGGTTATCGTATGGGTGGGTCCGCCAGGCT

CCAGGGAAGGGTCTAGAGTGGGTCTCATCGATTGCTCCGGATGGTAATTATACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAATTTTGG

GGGATGCAGTTTGACTACTGGGGTCAGGGAACCCTGGTCACCGTCTCGAGC

BMS2h-137
(SEQ ID NO: 509)
GAGGTGCAGCTGTTGGAGTCTGGGGGAGGCTTGGTACAGCCTGGGGGGTCCCTGCGTCTC

TCCTGTGCAGCCTCCGGATTCACCTTTGCTTCGTATCCGATGGGTTGGGTCCGCCAGGCT

CCAGGGAAGGGTCTAGAGTGGGTCTCAAGTATTGGTCCTATTGGTTTTACTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGGAAATGAAG

TCGCCTTATAAGCCGCAGTTTGACTACTGGGGTCAGGGAACCCTGGTCACCGTCTCGAGC

BMS2h-138
(SEQ ID NO: 510)
GAGGTGCAGCTGTTGGAGTCTGGGGGAGGCTTGGTACAGCCTGGGGGGTCCCTGCGTCTC

TCCTGTGCAGCCTCCGGATTCACCTTTTTGGCTTATTGGATGGTTTGGGTCCGCCAGGCT

CCAGGGAAGGGTCTAGAGTGGGTCTCATCTATTTCTCCGTCGGGTACGCATACATACTAC

GCAGACTCCGTGAAGGGCCGGTTCACCATCTCCCGCGACAATTCCAAGAACACGCTGTAT

CTGCAAATGAACAGCCTGCGTGTCGAGGACACCGCGGTATATTACTGTGCGAAATATACT

GAGCCGGGGTTGGGTTCTTTTGACTACTGGGGTCAGGGAACCCTGGTCACCGTCTCGAGC

TABLE 2-continued

Human Anti-CD40L VH Domain Encoding Nucleotide Sequences

BMS2h-139
(SEQ ID NO: 511)
GAGGTGCAGCTGTTGGAGTCTGGGGGAGGCTTGGTACAGCCTGGGGGGTCCCTGCGTCTC
TCCTGTGCAGCCTCCGGATTCACCTTTTCGAATTATGAGATGGGGTGGGTCCGCCAGGCT
CCAGGGAAGGGTCTAGAGTGGGTCTCAGTGATTTCTGAGGTGGGTTCTCTGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCTCAT
GATAGTTCGATTGGGTTTGACTACTGGGGTCAGGGAACCCTGGTCACCGTCTCGAGC

BMS2h-14
(SEQ ID NO: 512)
GAGGTGCAGCTGTTGGAGTCTGGGGGAGGCTTGGTACAGCCTGGGGGGTCCCTGCGTCTC
TCCTGTGCAGCCTCCGGATTCACCTTTTGGTCTTATGATATGACGTGGGTCCGCCAGGCT
CCAGGGAAGGGTCTAGAGTGGGTCTCATCTATTATGGCTTCGGGTGATGATACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAATGGGAT
CGGGATTTTGACTACTGGGGTCAGGGAACCCTGGTCACCGTCTCGAGC

BMS2h-15
(SEQ ID NO: 513)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGGAGTATGTTATGTCGTGGGTCCGCCAGGCT
CCAGGGAAGGGTCTGGAGTGGGTCTCAACTATTTCTCCTATTGGTCTGACTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAATTTCCT
TTGATTATTCTTCCTGATTTTGACTACTGGGGTCAGGGAACCCTGGTCACCGTCTCGAGC

BMS2h-18
(SEQ ID NO: 514)
GAGGTGCAGCTGTTGGAGTCTGGGGGAGGCCTGGTACAGCCTGGGGGGTCCCTGCGTCTC
TCCTGTGCAGCCTCCGGATTCACCTTTATGGAGTATGCGATGATTTGGGTCCGCCAGGCT
CCAGGGAAGGGTCTAGAGTGGGTCTCAATTATTTCTCCGCTTGGTTTGTCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATATCAG
GATTCGTCTGATAGTCAGTATACGAATTTTGACTACTGGGGTCAGGGAACCCTGGTCACC
GTCTCGAGC

BMS2h-17
(SEQ ID NO: 515)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGGATTATGGGATGGGGTGGGCCCGCCAGGCT
CCAGGGAAGGGTCTAGAGTGGGTCTCAAGTATTGGTCCTCTGGGTCTTTGGACATACTAC
GCAGACTCCGCGAAGGGCCGGTTCACCATCTCCCGCGACAATTCCAAGAACACGCTGTAT
CTGCMATGAACAGCCTGCGTGCCGAGGACACCGCGGTATATTACTGTGCGAAATCTCCGC
TTGAGGGTTTGATTACGAATTTTGACTACTGGGGTCAGGGAACCCTGGTCACCGTCTCGA
GC

TABLE 2-continued

Human Anti-CD40L VH Domain Encoding Nucleotide Sequences

BMS2h-176
(SEQ ID NO: 516)
GAGGTGCAGCTGTTGGAGTCTGGGGGAGGCTTGGTACAGCCTGGGGGGTCCCTGCGTCTC

TCCTGTGCAGCCTCCGGATTCACCTTTGATGCGTATGAGATGGGGTGGGTCCGCCAGGCT

CCAGGGAAGGGTCTAGAGTGGGTCTCAATTATTGATTGGGATGGTAATTCTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAACCTGGG

GATAATGTTGGTATTTTTGACTACTGGGGTCAGGGAACCCTGGTCACCGTCTCGAGC

BMS2h-177
(SEQ ID NO: 517)
GAGGTGCAGCTGTTGGAGTCTGGGGGAGGCTTGGTACAGCCTGGGGGGTCCCTGCGTCTC

TCCTGTGCAGCCTCCGGATTCACCTTTAGTAATTATTATATGGTGTGGGTCCGCCAGGCT

CCAGGGAAGGGTCTAGAGTGGGTCTCAGCGATTGATGAGTGGGGTTTTGCGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACATTGG

GAGTTTACGTCTGATACGTCGCGTTTTGACTACTGGGGTCAGGGAACCCTGGTCACCGTC

TCGAGC

BMS2h-178
(SEQ ID NO: 518)
GAGGTGCAGCTGTTGGAGTCTGGGGGAGGCTTGGTACAGCCTGGGGGGTCCCTGCGTCTC

TCCTGTGCAGCCTCCGGATTCACCTTTGAGGATTTTGATATGGCTTGGGTCCGCCAGGCT

CCAGGGAAGGGTCTAGAGTGGGTCTCATCTATTAATGATCAGGGTTCTCTGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCGGAT

CAGTTTTTTGACTACTGGGGTCAGGGAACCCTGGTCACCGTCTCGAGC

BMS2h-179
(SEQ ID NO: 519)
GAGGTGCAGCTGTTGGAGTCTGGGGGAGGCTTGGTACAGCCTGGGGGGTCCCTGCGTCTC

TCCTGTGCAGCCTCCGGATTCACCTTTAGTGCTTATGATATGATGTGGGTCCGCCAGGCT

CCAGGGAAGGGTCTAGAGTGGGTCTCACGGATTAGTCCTCAGGGTCAGCGGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAATTCGT

GGGCAGTCGCGGATTCCTATGAGGTTTGACTACTGGGGTCAGGGAACCCTGGTCACCGTC

TCGAGC

BMS2h-18
(SEQ ID NO: 520)
GAGGTGCAGCTGTTGGAGTCTGGGGGAGGCTTGGTACAGCCTGGGGGGTCCCTGCGTCTC

TCCTGTGCAGCCTCCGGATTCACCTTTCCTGAGTATGATATGACGTGGGTCCGCCAGGCT

CCAGGGAAGGGTCTGGAGTGGGTCTCATATATTAGTTCTGATGGTTATTCTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCGCAT

GGGAGTCCGCGGGAGTTTGACTACTGGGGTCAGGGAACCCTGGTCACCGTCTCGAGC

TABLE 2-continued

Human Anti-CD40L VH Domain Encoding Nucleotide Sequences

BMS2h-180
(SEQ ID NO: 521)
GAGGTGCAGCTGTTGGAGTCTGGGGGAGGCTTGGTACAGCCTGGGGGGTCCCTGCGTCTC

TCCTGTGCAGCCTCCGGATTCACCTTTACGGATTATGAGATGGGGTGGGTCCGCCAGGCT

CCAGGGAAGGGTCTAGAGTGGGTCTCAACGATTACTAGTTTGGGTGAGAGTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCTGGT

CGTATTTTTGACTACTGGGGTCAGGGAACCCTGGTCACCGTCTCGAGC

BMS2h-181
(SEQ ID NO: 522)
GAGGTGCAGCTGTTGGAGTCTGGGGGAGGCTTGGTACAGCCTGGGGGGTCCCTGCGTCTC

TCCTGTGCAGCCTCCGGATTCACCTTTGCTTTTTATCCTATGATGTGGGTCCGCCAGGCT

CCAGGGAAGGGTCTAGAGTGGGTGTCATGGATTGATGCTACGGGTACGAGGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGGAAGGTAAT

TATGGGAGTTCGTATACTATGGGGGTTTTTGACTACTGGGGTCAGGGAACCCTGGTCACC

GTCTCGAGC

BMS2h-182
(SECS ID NO: 523)
GAGGTGCAGCTGTTGGAGTCTGGGGGAGGCTTGGTACAGCCTGGGGGGTCCCTGCGTCTC

TCCTGTGCAGCCTCCGGATTCACCTTTGATGAGTATCCGATGTATTGGGTCCGCCAGGCT

CCAGGGAAGGGTCTAGAGTGGGTCTCATCGATTGGTCCTTCTGGTCCGAATACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAATCTCCG

TATTTTGATGTTATTCCTAGTTATTTTGACTACTGGGGTCAGGGAACCCTGGTCACCGTC

TCGAGC

BMS2h-183
(SEQ ID NO: 524)
GAGGTGCAGCTGTTGGAGTCTGGGGGAGGCTTGGTACAGCCTGGGGGGTCCCTGCGTCTC

TCCTGTGCAGCCTCCGGATTCACCTTTGCGGATTACGGTATGGGTTGGGTCCGCCAGGCT

CCAGGGAAGGGTCTAGAGTGGGTCTCATCTATTCAGTCGTCGGGTTTGCGGACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAACGGGCT

AATTCTCGTAGGGGTTTTGACTACTGGGGTCAGGGAACCCTGGTCACCGTCTCGAGC

BMS2h-184
(SEQ ID NO: 525)
GAGGTGCAGCTGTTGGAGTCTGGGGGAGGCTTGGTACAGCCTGGGGGGTCCCTGCGTCTC

TCCTGTGCAGCCTCCGGATTCACCTTTTCTGATTATGAGATGATGTGGGTCCGCCAGGCT

CCAGGGAAGGGTCTAGAGTGGGTCTCATCTATTACTAGTCATGGTGGGTCTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAACCTGAT

AAGGATTTTGACTACTGGGGTCAGGGAACCCTGGTCACCGTCTCGAGC

TABLE 2-continued

Human Anti-CD40L VH Domain Encoding Nucleotide Sequences

BMS2h-185
(SEQ ID NO: 526)
GAGGTGCAGCTGTTGGAGTCTGGGGGAGGCTTGGTACAGCCTGGGGGGTCCCTGCGTCTC

TCCTGTGCAGCCTCCGGATTCACCTTTGCGCATTATCCGATGTCGTGGGTCCGCCAGGCT

CCAGGGAAGGGTCTAGAGTGGGTCTCATCGATTGGTAGGCTGGGTAATCGTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACGTGCT

ACGCCTGTGCCGATTAAGGGTTTGTTTGACTACTGGGGTCAGGGAACCCTGGTCACCGTC

TCGAGC

BMS2h-186
(SEQ ID NO: 527)
GAGGTGCAGCTGTTGGAGTCTGGGGGAGGCTTGGTACAGCCTGGGGGGTCCCTGCGTCTC

TCCTGTGCAGCCTCCGGACTCACCTTTGGGAGGTATGAGATGGCGTGGGTCCGCCAGGCT

CCAGGGAAGGGTCTAGAGTGGGTCTCAAGTATTGATTCGGATGGTTGGGTGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGCAACCGGAT

TCGTTGTTTGACTACTGGGGTCAGGGAACCCTGGTCACCGTCTCGAGC

BMS2h-187
(SEQ ID NO: 528)
GAGGTGCAGCTGTTGGAGTCTGGGGGAGGCTTGGTACAGCCTGGGGGGTCCCTGCGTCTC

TCCTGTGCAGCCTCCGGATTCACCTTTTCTAGTTATTCTATGGTGTGGGTCCGCCAGGCT

CCAGGGAAGGGTCTAGAGTGGGTCTCAGGTATTAATCGGGGTGGTACTCGTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGGTTGG

AGGAGGGGGTTTGACTACTGGGGTCAGGGAACCCTGGTCACCGTCTCGAGC

BMS2h-188
(SEQ ID NO: 529)
GAGGTGCAGCTGTTGGAGTCTGGGGGAGGCTTGGTACAGCCTGGGGGGTCCCTGCGTCTC

TCCTGTGCAGCCTCCGGATTCACCTTTACGCGTTATAGGATGTCTTGGGTCCGCCAGGCT

CCAGGGAAGGGTCTGGAGTGGGTCTCAGGGATTTCGAGGGATGGTTATCGGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGGTATG

ACTGCGTCGTTTGACTACTGGGGTCAGGGAACCCTGGTCACCGTCTCGAGC

BMS2h-189
(SEQ ID NO: 530)
GAGGTGCAGCTGTTGGAGTCTGGGGGAGGCTTGGTACAGCCTGGGGGGTCCCTGCGTCTC

TCCTGTGCAGCCTCCGGATTCACCTTTCAGATGTATCCGATGGGGTGGGTCCGCCAGGCT

CCAGGGAAGGGTCTAGAGTGGGTCTCAATGATTGAGCCGGCTGGTGATCTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAATATCAG

GAGCAGCCTTGGTTTGACTACTGGGGTCAGGGAACCCTGGTCACCGTCTCGAGC

BMS2h-19
(SEQ ID NO: 531)
GAGGTGCAGCTGTTGGAGTCTGGGGGAGGCTTGGTACAGCCTGGGGGGTCCCTGCGTCTC

TCCTGTGCAGCCTCCGGATTCCCCTTTCCGCAGTATCAGATGGCGTGGGTCCGCCAGGCT

TABLE 2-continued

Human Anti-CD40L VH Domain Encoding Nucleotide Sequences

CCAGGGAAGGGTCTAGAGTGGGTCTCAATGATTACTTCTGATGGTCTTGATACATATTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAACCTGAG

CCTCTTTTTGACTACTGGGGTCAGGGAACCCTGGTCACCGTCTCGAGC

BMS2h-190
(SEQ ID NO: 532)
GAGGTGCAGCTGTTGGAGTCTGGGGGAGGCTTGGTACAGCCTGGGGGGTCCCTGCGTCTC

TCCTGTGCAGCCTCCGGATTCACCTTTAGTATGTATGATATGCATTGGGTCCGCCAGGCT

CCAGGGAAGGGTCTAGAGTGGGTCTCAACGATTTTGTCTGATGGTACGGATACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAATATGGG

GCTATGTTTGACTACTGGGGTCAGGGAACCCTGGTCACCGTCTCGAGC

BMS2h-191
(SEQ ID NO: 533)
GAGGTGCAGCTGTTGGAGTCTGGGGGAGGCTTGGTACAGCCTGGGGGGTCCCTGCGTCTC

TCCTGTGCAGCCTCCGGATTCACCTTTAAGTTGTATCCGATGACGTGGGTCCGCCAGGCT

CCAGGGAAGGGTCTAGAGTGGGTCTCATCTATTGATGCGGGGGGTCATGAGACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAAGATTGG

TGGGATTATCTGTTTGACTACTGGGGTCAGGGPACCCTGGTCACCGTGTCGAGC

BMS2h-192
(SEQ ID NO: 534)
GAGGTGCAGCTGTTGGAGTCTGGGGGAGGCTTGGTACAGCCTGGGGGGTCCCTGCGTCTC

TCCTGTGCAGCCTCCGGATTCACCTTTTCGCGGTATCCGATGAGTTGGGTCCGCCAGGCT

CCAGGGAAGGGTCTAGAGTGGGTCTCATCTATTAATCGTTCGGGTATGCGGACATACTAC

GCAGACTCCGTGAAGGGCCGGTTCACCATCTCCCGCGACAATTCCAAGAACACGCTGTAT

CTGCNkATGAACAGCCTGCGTGCCGAGGACACCGCGGTATATTACTGTGCGGAAGGGCAT

CAGGCGCCGTTTGACTACTGGGGTCAGGGAACCCTGGTCACCGTCTCGAGC

BMS2h-193
(SEQ ID NO: 535)
GAGGTGCAGCTGTTGGAGTCTGGGGGAGGCTTGGTACAGCCTGGGGGGTCCCTGCGTCTC

TCCTGTGCAGCCTCCGGATTCACCTTTACGGGGTATGCTATGTCTTGGGTCCGCCAGGCT

CCAGGGAAGGGTCTAGAGTGGGTCTCAACTATTAATGCGAATGGTATTCGGACATACTAC

GCCGACTCCGTGAAGGGCCGGTTCACCATCTCCCGCGACAATTCCAAGAACACGCTGTAT

CTGCAAATGAACGGCCTGCGTGCCGAGGACACCGCGGTATATTACTGTGCGAAAGGGGGG

GTTTGGAGGTGGGGACTGGGCATAAGTTTGACTACTGGGGTCAGGGAACCCTGGTCACC

GTCTCGAGC

BMS2h-194
(SEQ ID NO: 536)
GAGGTGCAGCTGTTGGAGTCTGGGGGAGGCTTGGTACAGCCTGGGGGGTCCCTGCGTCTC

TCCTGTGCAGCCTCCGGATTCACCTTTAAGCAGTATGATATGCGGTGGGTCCGCCAGGCT

CCAGGGAAGGGTCTAGAGTGGGTCTCAACGATTTCGCAGAATGGTACTAAGACATACTAC

GCAGACTCCGTGAAGGGCCGGTTCACCATCTCCCGCGACAATTCCAAGAACACGCTGTAT

TABLE 2-continued

Human Anti-CD40L VH Domain Encoding Nucleotide Sequences

CTGCAAATGAACAGCCTGCGTGCCGAGGACACCGCGGTATATTACTGTGCGAAATCGAGG

ACTGGTAGGTATTTTGACTACTGGGGTCAGGGAACCCTGGTCACCGTCTCGAGC

BMS2h-195
(SEQ ID NO: 537)
GAGGTGCAGCTGTTGGAGTCTGGGGGAGGCTTGGTACAGCCTGGGGGGTCCCTGCGTCTC

TCCTGTGCAGCCTCCGGATTCACCTTTGGGACTTATGATATGGGGTGGGTCCGCCAGGCT

CCAGGGAAGGGTCTAGASTGGGTCTCAAGGATTAATTGGCAGGGTGATCGTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGCGGGG

TTTGGTCATTATGTTGATGGTCTTGGGTTTGACTACTGGGGTCAGGGAACCCTGGTCACC

GTCTCGAGC

BMS2h-196
(SEQ ID NO: 538)
GAGGTGCAGCTGTTGGAGTCTGGGGGAGGCTTGGTACAGCCTGGGGGGTCCCTGCGTCTC

TCCTGTGCAGCCTCCGGATTCACCTTTAGTGGGTATGAGATGGCGTGGGTCCGCCAGGCT

CCAGGGAAGGGTCTAGAGTGGGTCTCATCTATTACTGATATGGGTGATTCTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCTGGG

ACTGCGTTTGACTACTGGGGTCCGGGAACCCTGGTCACCGTCTCGAGC

BMS2h-197
(SEQ ID NO: 539)
GAGGTGCAGCTGTTGGAGTCTGGGGGAGGCTTGGTACAGCCTGGGGGGTCCCTGCGTCTC

TCCTGTGCAGCCTCCGGATTCACCTTTGCGAAGTATAAGATGTGGTGGGTCCGCCAGGCT

CCAGGGAAGGGTCTAGAGTGGGTCTCAAGTATTACTCCGAAGGGTCATTCTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAAAGGCCG

ATGACTCCGTTTGACTACTGGGGTCAGGGAACCCTGGTCACCGTCTCGAGC

BMS2h-198
(SEQ ID NO: 540)
GAGGTGCAGCTGTTGGAGTCTGGGGGAGGCTTGGTACAGCCTGGGGGGTCCCTGCGTCTC

TCCTGTGCAGCCTCCGGATTCACCTTTGAGCGGTATAATATGTCTTGGGTCCGCCAGGCT

CCAGGGAAGGGTCTAGAGTGGGTCTCATCTATTCGGCCGCGGGTGGGAAGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAATGGCGG

CGGGAGGGGTATACTGGTTCTAAGTTTGACTACTGGGGTCAGGGAACCCTGGTCACCGTC

TCGAGC

BMS2h-199
(SEQ ID NO: 541)
GAGGTGCAGCTGTTGGAGTCTGGGGGAGGCTTGGTACAGCCTGGGGGGTCCCTGCGTCTC

TCCTGTGCAGCCTCCGGATTCACCTTTGAGAGGTATGGTATGACTTGGGTCCGCCAGGCT

CCAGGGAAGGGTCTGGAGTGGGTCTCAAGTATTTGGCCGAGGGGTCAGAAGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGGGAAT

AGTCGGTATGTTTTTGACTACTGGGGTCAGGGAACCCTGGTCACCGTCTCGAGC

TABLE 2-continued

Human Anti-CD40L VH Domain Encoding Nucleotide Sequences

BMS2h-2
(SEQ ID NO: 542)
GAGGTGCAGCTGTTGGAGTCTGGGGGAGGCTTGGTACAGCCTGGGGGGTCCCTGCGTCTC
TCCTGTGCAGCCTCCGGATTCACCTTTTCTGATTATGAGATGATGTGGGTCCGCCAGGCT
CCAGGGAAGGGTCTAGAGTGGGTCTCAACTATTACTTCGGATGGTATTTCTACATACTAC
GCAGACTCCGTGAAGGGCCGGTTCACCATCTTCCGCGACAATTCCAAGAACACGCTGTAT
CTGCAAATGAACAGCCTGCGTGCCGAGGATACCGCGGTATATTACTGTGCGAAAAGTGGG
AGGTTTTTTGACTACTGGGGTCAGGGAACCCTGGTCACCGTCTCGAGC

BMS2h-20
(SEQ ID NO: 543)
GAGGTGCAGCTGTTGGAGTCTGGGGGAGGCTTGGTACAGCCTGGGGGGTCCCTGCGTCTC
TCCTGTGCAGCCTCCGGATTCACCTTTTCGGGTTATCAGATGGCTTGGGTCCGCCAGGCT
CCAGGGAAGGGTCTAGAGTGGGTCTCAGGTATTAGTTCGGAGGGTCTTACTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATTGGGG
CGTAGGTTTGACTACTGGGGTCAGGGAACCCTGGTCACCGTCTCGAGC

BMS2h-200
(SEQ ID NO: 544)
GAGGTGCAGCTGTTGGAGTCTGGGGGAGGCTTGGTACAGCCTGGGGGGTCCCTGCGTCTC
TCCTGTGCAGCCTCCGGATTCACCTTTACTAATTATAGTATGGGTTGGGTCCGCCAGGCT
CCAGGGAAGGGTCTAGAGTGGGTCTCAACTATTCGTCCTAATGGTACTAAGACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAACGGTCG
TCTGCGCATCTTCAGAGGTTTGACTACTGGGGTCAGGGAACCCTGGTCACCGTCTCGAGC

BMS2h-201
(SEQ ID NO: 545)
GAGGTGCAGCTGTTGGAGTCTGGGGGAGGCTTGGTACAGCCTGGGGGGTCCCTGCGTCTC
TCCTGTGCAGCCTCCGGATTCACCTTTGGTAATTATTCGATGGGTTGGGTCCGCCAGGCT
CCAGGGAAGGGTCTAGAGTGGGTCTCATCGATTGGTCGTCATGGTGGGCGTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAAAGGGG
AGTACTTATCCTAGGTTTGACTACTGGGGTCAGGGAACCCTGGTCACCGTCTCGAGC

BMS2h-202
(SEQ ID NO: 546)
GAGGTGCAGCTGTTGGAGTCTGGGGGAGGCTTGGTACAGCCTGGGGGGTCCCTGCGTCTC
TCCTGTACAGCCTCCGGATTCACCTTTTCGCATTATGAGATGGGGTGGGTCCGCCAGGCT
CCAGGGAAGGGTCTAGAGTGGGTCTCAAGTATTGAGCCTTTTGGTGGTGGGACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAAGTGTAT
CCTCAGGGTTCTTTTGACTACTGGGGTCAGGGAACCCTGGTCACCGTCTCGAGC

BMS2h-203
(SEQ ID NO: 547)
GAGGTGCAGCTGTTGGAGTCTGGGGGAGGCTTGGTACAGCCTGGGGGGTCCCTGCGTCTC
TCCTGTGCAGCCTCCGGATTCACCTTTAGTAATTATACTATGGGTGGGTCCGTCAGGCT
CCAGGGAAGGGTCTAGAGTGGGTCTCATCTATTCGGCCTGATGGTAAGATTACATACTAC

TABLE 2-continued

Human Anti-CD40L VH Domain Encoding Nucleotide Sequences

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGGAAGTTTAT

TCTTCGTGTGCGATGTGTACTCCGCTTTTGTTTGACTACTGGGGTCAGGGAACCCTGGTC

ACCGTCTCGAGC

BMS2h-204 (SEQ ID NO: 548)
GAGGTGCAGCTGTTGGAGTCTGGGGGGGGCTTGGTACAGCCTGGGGGGTCCCTGCGTCTC

TCCTGTGCAGCCTCCGGATTCACCTTTAAGCGGTATTCGATGGCGTGGGTCCGCCAGGCT

CCAGGGAAGGGTCTAGAGTGGGTCTCAGATATTGGGCCGAGGGGTTTTTCGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGTGGGT

CGTGGTCAGCGTGATACTAGTCAGCCGTTTGACTACTGGGGTCAGGGAACCCTGGTCACC

GTCTCGAGC

BMS2h-205 (SEQ ID NO: 549)
GAGGTGCAGCTGTTGGAGTCTGGGGGAGGCTTGGTACAGCCTGGGGGGTCCCTGCGTCTC

TCCTGTGCAGCCTCCGGATTCACCTTTGCTTCTTATCAGATGGCTTGGGTCCGCCAGGCT

CCAGGGAAGGGTCTAGAGTGGGTCTCAGGGATTACTTCGGGTGGTCTTAGTACGTACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCGGGG

AGGGGTTTTGACTACTGGGGTCAGGGAACCCTGGTCACCGTCTCGAGC

BMS2h-206 (SEQ ID NO: 550)
GAGGTGCAGCTGTTGGAGTCTGGGGGAGGCTTGGTACAGCCTGGTGGGTCCCTGCGTCTC

TCCTGTGCAGCCTCCGGATTCACCTTTGCTTCTTATGAGATGACTTGGGTCCGCCAGGCT

CCAGGGAAGGGTCTAGAGTGGGTCTCAGGGATTTCTTCTGATGGTCTGTCTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGCGGGG

GTGTTGTTTGACTACTGGGGTCAGGGAACCCTGGTCACCGTCTCGAGC

BMS2h-207 (SEQ ID NO: 551)
GAGGTGCAGCTGTTGGAGTCTGGGGGAGGCTTGGTACAGCCTGGGGGGTCCCTGCGTCTC

TCCTGTGCAGCCTCTGGATTCACCTTTGATAAGTATTTGATGTCGTGGGTCCGCCAGGCT

CCAGGGAAGGGTCTGGAGTGGGTCTCAGGTATTGAGCCTCTGGGTGATGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGAGGCT

TCGGGGGATTTTGACTACTGGGGTCAGGGAACCCTGGTCACCGTCTCGAGC

BMS2h-208 (SEQ ID NO: 552)
GAGGTGCAGCTGTTGGAGTCTGGGGGAGGCTTGGTACAGCCTGGGGGGTCCCTGCGTCTC

TCCTGTGCAGCCTCCGGGTTCACCTTTACTGAGTATGAGATGTCTTGGGTCCGCCAGGCT

CCAGGGAAGGGTCTAGAGTGGGTCTCAAGTATTGATAATGTGGGTAGTAGTACATACTAC

GCAGACTCCGTGAAGGGCCGGTTCACCATCTCCCGCGACAATTCCAAGAACACGCTGTAT

TABLE 2-continued

Human Anti-CD40L VH Domain Encoding Nucleotide Sequences

CTGCAAATGAACAGCCTGCGTGCCGAGGATACCGCGGTATATTACTGTGCGAAACCTGGG

AAGCTTTTTGACTACTGGGGTCAGGGAACCCTGGTCACCGTCTCGAGC

BMS2h-209
(SEQ ID NO: 553)
GAGGTGCAGCTGTTGGAGTCTGGGGGAGGCTTGGTACAGCCTGGGGGGTCCCTGCGTCTC

TCCTGTGCAGCCTCCGGATTCACCTTTGCTGATTATGAGATGTGGTGGGTCCGCCAGGCT

CCAGGGAAGGGTCTAGAGTGGGTCTCAGCGATTTCTAGGCAGGGTTTTGCTACATACTAC

GCAGACTCCGTGAAAGGCCGGTTCACCATCTCCCGCGACAATTCCAAGAACACGCTGTAT

CTGCAAATGAACAGCCTGCGTGCCGAGGACACCGCGGTATATTACTGTGCGAAAGATCTG

GAGCGGGATGATTTTGACTACTGGGGTCAGGGAACCCTGGTCACCGTCTCGAGC

BMS2h-21
(SEQ ID NO: 554)
GAGGTGCAGCTGTTGGAGTCTGGGGGAGGCTTGGTACAGCCTGGGGGGTCCCTGCGTCTC

TCCTGTGCAGCCTCCGGATTCACCTTTGCGAATTATGAGATGGGGTGGGCCCGCCAGGCT

CCAGGGAAGGGTCTAGAGTGGGTCTCAGTTATTTCTGAGTGGGGTTATTCTACATACTAC

GCAGACTCCGCGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACTTGTG

GGTGGGACTCAGTATGAGTTTGACTACTGGGGTCAGGGAACCCTGGTCACCGTCTCGAGC

BMS2h-22
(SEQ ID NO: 555)
GAGGTGCAGCTGTTGGAGTCTGGGGGAGGCTTGGTACAGCCTGGGGGGTCCCTGCGTCTC

TCCTGTGCAGCCTCCGGATTCACCTTTCATAATTATGAGATGTCGTGGGTCCGCCAGGCT

CCAGGGAAGGGTCTAGAGTGGGTCTCAAGTATTTCTTCGGGTGGTTCTTCTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCGGGG

GTTAAGTTTGACTACTGGGGTCAGGGAACCCTGGTCACCGTCTCGAGC

BMS2h-23
(SEQ ID NO: 556)
GAGGTGCAGCTGTTGGAGTCCGGGGGAGGCTTGGTACAGCCTGGGGGGTCCCTGCGTCTC

TCCTGTGCAGCCTCCGGATTCACCTTTGGGCTGTATGAGATGACGTGGGTCCGCCAGGCT

CCAGGGAAGGGTCTAGAGTGGGTCTCAAGTATTACGGGTGATGGTATTTCGACATACTAC

GCAGACTCCGTGAAGGGCCGGTTCACCATCTCCCGCGACAATTCCAGGAACACGCTGTAT

CTGCAAATGAACAGCCTGCGTGCCGAGGACACCGCGGTATATTACTGTGCGAAAGCTGGG

AGGAAGTTTGACTACTGGGGTCAGGGAACCCTGGTCACCGTCTCGAGC

BMS2h-24
(SEQ ID NO: 557)
GAGGTGCAGCTGTTGGAGTCTGGGGGAGGCTTGGTACAGCCTGGGGGGTCCCTGCGTCTC

TCCTGTGCAGCCTCCGGATTCACCTTTAGTAATTATCAGATGGCGTGGGTCCGCCAGGCT

CCAGGGAAGGGTCTAGAGTGGGTCTCAAGTATTACTAGTGAGGGTGGTTCGACATACTAC

GCAGACTCCGTGAAGGGCCGGTTCACCATCTCCCGCGACAATTCCAAGAACACACTGTAT

CTGCAAATGAACAGCCTGCGTGCCGAGGACACCGCGGTATATTACTGTGCGAAACCGGGT

AAGAATTTTGACTACTGGGGTCAGGGAACCCTGGTCACCGTCTCGAGC

TABLE 2-continued

Human Anti-CD40L VH Domain Encoding Nucleotide Sequences

BMS2h-24-1
(SEQ ID NO: 558)
GAGGTGCAGCTGTTGGAGTCTGGGGGAGGCTTGGTACAGCCTGGGGGGTCCCTGCGTCTC

TCCTGTGCAGCCTCCGGATTCACCTTTAGTGATTATCAGATGGCGTGGGTTCGCCAGGCT

CCAGGGAAGGGACTAGAGTGGGTCTCAAGTATTACTAGTGAGGGTGGTTCGACATACTAC

GCAGACTCCGTGAAGGGCCGGTTCACCATCTCCCGCGACAATTCCAAGAACACAGTGTAT

CTGCAAATGAACAGCCTGCGTGCCGAGGACACCGCGGTATATTACTGTGCGAAACCGGGT

AAGAATTTCGACTACTGGGGTCAGGGAACCCTGGTCACCGTCTCGAGC

BMS2h-25
(SEQ ID NO: 559)
GAGGTGCAGCTGTTGGAGTCTGGGGGAGGCTTGGTACAGCCTGGGGGGTCCCTGCGTCTC

TCCTGTGCAGCCTCCGGATTCACCTTTGATAATTATGAGATGACGTGGGTCCGCCAGGCT

CCAGGGAAGGGTCTAGAGTGGGTCTCAACTATTACGTCGCAGGGTACTAGTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCTGAT

CGTTCTTTTGACTACTGGGGTCAGGGAACCCTGGTCACCGTCTCGAGC

BMS2h-26
(SEQ ID NO: 560)
GAGGTGCAGCTGTTGGAGTCTGGGGGAGGCTTGGTACAGCCTGGGGGGTCCCTGCGTCTC

TCCTGTGCAGCCTCCGGATTCACCTTTCGTAGTTATGAGATGACTTGGGTCCGCCAGGCT

CCAGGGAAGGGTCTGGAGTGGGTCTCATCTATTACGTCGGATGGTGGTACTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCTGAT

AAGACGTTTGACTACTGGGGTCAGGGAACCCTGGTCACCGTCTCGAGC

BMS2h-27
(SEQ ID NO: 561)
GAGGTGCAGCTGTTGGAGTCTGGGGGAGGCTTGGTACAGCCTGGGGGGTCCCTGCGTCTC

TCCTGTGCAGCCTCCGGATTCACCTTTAATTTGTATGAGATGACTTGGGTCCGCCAGGCT

CCAGGGAAGGGTCTAGAGTGGGTCTCATCTATTACTAGTGATGGTGTTTCTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCGGAT

TCTCCGTTTGACTACTGGGGTCAGGGAACCCTGGTCACCGTCTCGAGC

BMS2h-28
(SEQ ID NO: 562)
GAGGTGCAGCTGTTGGAGTCTGGGGGAGGCTTGGTACAGCCTGGGGGGTCCCTGCGTCTC

TCCTGTGCAGCCTCCGGATTCACCTTTGGGCATTATGATATGGCTTGGGTCCGCCAGGCT

CCAGGGAAGGGTCTAGAGTGGGTCTCAACTATTAGTGATAATGGTAATGGGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGARACCGGGG

CGTGATTTTGACTACTGGGGTCAGGGAACCCTGGTCACCGTCTCGAGC

BMS2h-29
(SEQ ID NO: 563)
GAGGTGCAGCTGTTGGAGTCTGGGGGAGGCTTGGTACAGCCTGGGGGGTCCCTGCGTCTC

TCCTGTGCAGCCTCCGGATTCACCTTTGGTCGTTATCAGATGGCTTGGGTCCGCCAGGCT

CCAGGGAAGGGTCTAGAGTGGGTCTCATCTATTTCTTCTGATGGTGGGGGGACATACTAC

TABLE 2-continued

Human Anti-CD40L VH Domain Encoding Nucleotide Sequences

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAACCTGGG

CGGGCGTTTGACTACTGGGGTCAGGGAACCCTGGTCACCGTCTCGAGC

BMS2h-30
(SEQ ID NO: 564)
GAGGTGCAGCTGTTGGAGTCTGGGGGAGGCTTGGTACAGCCTGGGGGGTCCCTGCGTCTC

TCCTGTGCAGCCTCCGGATTCACCTTTGCGAGGTATCAGATGGCTTGGGTCCGCCAGGCT

CCAGGGAAGGGTCTGGAGTGGGTCTCAACTATTTCTGATGATGGTGATTCGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACTGGAT

AAGTTGTTTGACTACTGGGGTCAGGGAACCCTGGTCACCGTCTCGAGC

BMS2h-300
(SEQ ID NO: 565)
GAGGTGCAGCTGTTGGAGTCTGGGGGAGGCTTGGTACAGCCTGGGGGGTCCCTGCGTCTC

TCCTGTGCAGCCTCCGGATTCACCTTTGATAATGATGAGATGACGTGGGTCCGCCAGGCT

CCAGGGAAGGGTCTAGAGTGGGTCTCAGCTATTGATACGACGGGTGGGCAGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCTGGT

AAGGAGTTTGACTACTGGGGTCAGGGAACCCTGGTCACCGTCTCGAGC

BMS2h-301
(SEQ ID NO: 566)
GAGGTGCAGCTGTTGGAGTCTGGGGGAGGCTTGGTACAGCCTGGGGGGTCCCTGCGTCTC

TCCTGTGCAGCCTCCGGATTCACCTTTGGGGAGAGTGAGATGAGTTGGGTCCGCCAGGCT

CCAGGGAAGGGTCTAGAGTGGGTCTCAAGTATTCTTGATGAGGGTTCTGGGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCTGAT

AAGGATTTTGACTACTGGGGTCAGGGAACCCTGGTCACCGTCTCGAGC

BMS2h-302
(SEQ ID NO: 567)
GAGGTGCAGCTGTTGGAGTCTGGGGGAGGCTTGGTACAGCCTGGGGGGTCCCTGCGTCTC

TCCTGTGCAGCCTCCGGATTCACCTTTGGGGAGGAGGAGATGAGTTGGGTCCGCCAGGCT

CCAGGGAAGGGTCTAGAGTGGGTCTCAGCGATTACTGATGATGGTGATGATACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCTAAT

GCGGGTGCTTTTGACTACTGGGGTCAGGGAACCCTGGTCACCGTCTCGAGC

BMS2h-303
(SEQ ID NO: 568)
GAGGTGCAGCTGTTGGAGTCTGGGGGAGGCTTGGTACAGCCTGGGGGGTCCCTGCGTCTC

TCCTGTGCAGCCTCCGGATTCACCTTTGAGGTGTATGATATGGCTTGGGTCCGCCAGGCT

CCAGGGAAGGGTCTAGAGTGGGTCTCAGGGATTGTTAATGATGGTTCTTCTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCTGAT

AAGGATTTTGACTACTGGGGTCAGGGAACCCTGGTCACCGTCTCGAGC

TABLE 2-continued

Human Anti-CD40L VH Domain Encoding Nucleotide Sequences

BMS2h-304
(SEQ ID NO: 569)
GAGGTGCAGCTGTTGGAGTCTGGGGGAGGCTTGGTACAGCCTGGGGGGTCCCTGCGTCTC

TCCTGTGCAGCCTCCGGATTCACCTTTGGTAATACGGAGATGACTTGGGTCCGCCAGGCT

CCAGGGAAGGGTCTAGAGTGGGTCTCATCGATTGCGATGATGGTTCTAGTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCTGGT

CAGGCTTTTGACTACTGGGGTCAGGGAACCCTGGTCACCGTCTCGAGC

BMS2h-31
(SEQ ID NO: 570)
GAGGTGCAGCTGTTGGAGTCTGGGGGAGGCTTGGTACAGCCTGGGGGGTCCCTGCGTCTC

TCCTGTGCAGCCTCCGGATTCACCTTTGAGGAGTATCAGATGGCGTGGGTCCGCCAGGCT

CCAGGGAAGGGTCTAGAGTGGGTCTCAACGATTTCGGATGATGGTTCTTCGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCTGAT

CTTTATTTTGACTACTGGGGTCAGGGAACCCTGGTCACCGTCTCGAGC

BMS2h-32
(SEQ ID NO: 571)
GAGGTGCAGCTGTTGGAGTCTGGGGGAGGCTTGGTACAGCCTGGGGGGTCCCTGCGTCTC

TCCTGTGCAGCCTCCGGATTCACCTTTGAGGTGTATCAGATGGGTTGGGTCCGCCAGGCT

CCAGGGAAGGGTCTAGAGTGGGTCTCATTTATTGTGCCTGGGGGTGATTTGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGGAAACGTGG

CCGGAGTTTGACTACTGGGGTCAGGGAACCCTGGTCACCGTCTCGAGC

BMS2h-4
(SEQ ID NO: 572)
GAGGTGCAGCTGTTGGAGTCTGGGGGAGGCTTGGTACAGCCTGGGGGGTCCCTGCGTCTC

TCCTGTGCAGCCTCCGGATTCACCTTTGATAATTATGAGATGACGTGGGTCCGCCAGGCT

CCAGGGAAGGGTCTAGAGTGGGTCTCATCTATTACGAGTGATGGTACTTCGACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAACCTAAT

CCGCCGTTTGACTACTGGGGTCAGGGAACCCTGGTCACCGTCTCGAGC

BMS2h-40
(SEQ ID NO: 573)
GAGGTGCAGCTGTTGGAGTCTGGGGGAGGCTTGGTACAGCCTGGGGGGTCCCTGCGTCTC

TCCTGTGCAGCCTCCGGATTCACCTTTAAGGCGTATGATATGGGTTGGGTCCGCCAGGCT

CCAGGGAAGGGTCTAGAGTGGGTCTCACAGATTGGGAGGGATGGTTCTTTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCTCGT

CGGTATGCTATTTTTACTTTTGATCGGGGTCAGGGAACCCTGGTCACCGTCTCGAGC

BMS2h-400
(SEQ ID NO: 574)
GAGGTGCAGCTGTTGGAGTCTGGGGGAGGCTTGGTACAGCCTGGGGGGTCCCTGCGTCTC

TCCTGTGCAGCCTCCGGATTCACCTTTAAGCAGTATCCGATGGTGTGGGTCCGCCAGGCT

CCAGGGAAGGGTCTAGAGTGGGTCTCAACGATTTCTACTAATGGTGTGAGGACATACTAC

TABLE 2-continued

Human Anti-CD40L VH Domain Encoding Nucleotide Sequences

GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAATGGACG
GATATTATTTCGTCTTCGGAGTTTGACTACTGGGGTCAGGGAACCCTGGTCACCGTCTCG
AGC

BMS2h-401                                          (SEQ ID NO: 575)
GAGGTGCAGCTGTTGGAGTCTGGGGGAGGCTTGGTACAGCCTGGGGGGTCCCTGCGTCTC
TCCTGTGCAGCCTCCGGATTCACCTTTTTTAATTATGATATGTCTTGGGTCCGCCAGGCT
CCAGGGAAGGGTCTAGAGTGGGTCTCAGCTATTAGTGGTAGTGGTGGTAGCACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGTTTTT
GTGTGGTCGGCTGATATTGATTTTGATTTTGACTACTGGGGTCAGGGAACCCTGGTCACC
GTCTCGAGC

BMS2h-402                                          (SEQ ID NO: 576)
GAGGTGCAGCTGTTGGAGTCTGGGGGAGGCTTGGTACAGCCTGGGGGGTCCCTGCGTCTC
TCCTGTGCAGCCTCCGGATTCACCTTTTCGTGGTATGATATGAGTTGGGTCCGCCAGGCT
CCAGGGAAGGGTCTAGAGTGGGTCTCACATATTGCGAGTTGGGTGGTAAGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGTGACG
GTGAAGGATGGGGGGTATCTGATGGATTTTGACTACTGGGGTCAGGGAACCCTGGTCACC
GTCTCGAGC

BMS2h-403                                          (SEQ ID NO: 577)
GAGGTGCAGCTGTTGGAGTCTGGGGGAGGCTTGGTACAGCCTGGGGGGTCCCTGCGTCTC
TCCTGTGCAGCCTCCGGATTCACCTTTGCTGAGTATGCTATGGCGTGGGTCCGCCAGGCT
CCAGGGAAGGGTCTGGAGTGGGTCTCAAGTATTGGGCGGGATGGTGCGGTGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATGGAAG
GCGGCGAAGGAGCGGGGTTCTTGGTTTGACTACTGGGGTCAGGGAACCCTGGTCACCGTC
TCGAGC

BMS2h-404                                          (SEQ ID NO: 578)
GAGGTGCAGCTGTTGGAGTCTGGGGGAGGCTTGGTACAGCCTGGGGGGTCCCTGCGTCTC
TCCTGTGCAGCCTCCGGATTCACCTTTCAGGCTTATCAGATGCAGTGGGTCCGCCAGGCT
CCAGGGAAGGGTCTTGAGTGGGTCTCAACTATTAGTCCTAATGGTCTTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATGGTTG
AGTTCTTTTGACTACTGGGGTCAGGGAACCCTGGTCACCGTCTCGAGC

BMS2h-407                                          (SEQ ID NO: 579)
GAGGTGCAGCTGTTGGAGTCTGGGGGAGGCTTGGTACAGCCTGGGGGGTCCCTGCGTCTC
TCCTGTGCAGCCTCCGGATTCACCTTTGCTATGTATTCGATGGCTTGGGTCCGCCAGGCT
CCAGGGAAGGGTCTAGAGTGGGTCTCAGGTATTTCGCCTCGTGGTGTTGAGACATACTAC

TABLE 2-continued

Human Anti-CD40L VH Domain Encoding Nucleotide Sequences

GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAACTAAT
TGGAATGGTGTGGATCTGTTTGACTACTGGGGTCAGGGAACCCTGGTCACCGTCTCGAGC

BMS2h-408 (SEQ ID NO: 580)
GAGGTGCAGCTGTTGGAGTCTGGGGGAGGCTTGGTACAGCCTGGGGGGTCCCTGCGTCTC
TCCTGTGCAGCCTCCGGATTCACCTTTCCTACGTATATGATGAGTTGGGTCCGCCAGGCT
CCAGGGAAGGGTCTAGAGTGGGTCTCAACTATTAATACGAATGGTCGTGATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGGGAT
AGTAATATGTCGTTTTTTGACTACTGGGGTCAGGGAACCCTGGTCACCGTCTCGAGC

BMS2h-409 (SEQ ID NO: 581)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGGGTTATTCGATGACGTGGGTCCGCCAGGCT
CCAGGGAAGGGTCTAGAGTGGGTCTCATCTATTAATGCGTCGGGTACTCTGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGATGGT
AATAGGTCTGAGGTTTTTTTTGACTACTGGGGTCAGGGAACCCTGGTCACCGTCTCGAGC

BMS2h-41 (SEQ ID NO: 582)
GAGGTGCAGCTGTTGGAGTCTGGGGGAGGCTTGGTACAGCCTGGGGGGTCCCTGCGTCTC
TCCTGTGCAGCCTCCGGATTCACCTTTTTTGAGTATGAGATGACGTGGGTCCGCCAGGCT
CCAGGGAAGGGTCTAGAGTGGGTCTCATCTATTGCGAATGATGGTTCGACTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCTGAT
CGGCAGTTTGACTACTGGGGTCAGGGAACCCTGGTCACCGTCTCGAGC

BMS2h-410 (SEQ ID NO: 583)
GAGGTGCAGCTGTTGGAGTCTGGGGGAGGCTTGGTACAGCCTGGGGGGTCCCTGCGTCTC
TCCTGTGCAGCCTCCGGATTCACCTTTCAGGATTATTTGATGGCGTGGGTCCGCCAGGCT
CCAGGGAAGGGTCTAGAGTGGGTCTCAGAGATTAATCAGGATGGTACTGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAAAGTTCT
CCGTATTTTGACTACTGGGGTCAGGGAACCCTGGTCACCGTCTCGAGC

BMS2h-411 (SEQ ID NO: 584)
GAGGTGCAGCTGTTGGAGTCTGGGGGAGGCTTGGTACAGCCTGGGGGGTCCCTGCGTCTC
TCCTGTGCAGCCTCCGGATTCACCTTTGATAATTATGCGATGTCGTGGGTCCGCCAGGCT
CCAGGGAAGGGTCTAGAGTGGGTCTCATCTATTAGTCGGGATGGTCATGTGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACTTTCT
TCTAAGGGGGGACGTTTGCTAGTTCTTTTGACTACTGGGGTCAGGGAACCCTGGTCACC
GTCTCGAGC

TABLE 2-continued

Human Anti-CD40L VH Domain Encoding Nucleotide Sequences

BMS2h-412
(SEQ ID NO: 585)
GAGGTGCAGCTGTTGGAGTCTGGGGGAGGCTTGGTACAGCCTGGGGGGTCCCTGCGTCTC

TCCTGTGCAGCCTCCGGATTCACCTTTAGTGCTGTTCCGATGACGTGGGTCCGCCAGGCT

CCAGGGAAGGGTCTAGAGTGGGTCTCAGCGATTACGGATGATGGTCTTCGTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGANNGGTCAT

ATTTATGGGGATTATTTTGACTACTGGGGTCAGGGAACCCTGGTCACCGTCTCGAGC

BMS2h-413
(SEQ ID NO: 586)
GAGGTGCAGCTGTTGGAGTCTGGGGGAGGCTTGGTACAGCCTGGGGGGTCCCTGCGTCTC

TCCTGTGCAGCCTCCGGATTCACCTTTGAGCTTTATAGGATGATGTGGGTCCGCCAGGCT

CCAGGGAAGGGTCTAGAGTGGGTCTCAGCTATTAGTAGTGATGGTGATACTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGGAACATTGG

TTGGGTACTACGTTGTCTTTGAGGGATTTTGACTACTGGGGTCAGGGAACCCTGGTCACC

GTCTCGAGC

BMS2h-414
(SEQ ID NO: 587)
GAGGTGCAGCTGTTGGAGTCTGGGGGAGGCTTGGTACAGCCTGGGGGGTCCCTGCGTCTC

TCCTGTGCAGCCTCCGGATTCACCTTTTATCGTTATACGATGGCGTGGGTCCGCCAGGCT

CCAGGGAAGGGTCTAGAGTGGGTCTCACAGATTTCGCCTAGGGGTAATATTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAAGTGGT

GTGGCGGGGCGGAGTCGCCTGAGTATTTTGACTACTGGGGTCAGGGAACCGTGGTCACC

GTCTCGAGC

BMS2h-415
(SEQ ID NO: 588)
GAGGTGCAGCTGTTGGAGTCTGGGGGAGGTTTGGTGCAGCCTGGGGGGTCCCTGCGTCTC

TCCTGTGCAGCCTCCGGATTCACCTTTTTGGGTTATTATATGAGTTGGATCCGCCAGGCT

CCAGGGAAGGGTCTAGAGTGGGTCTCAACGATTGGGCCGATTGGTGGTGGGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAATCTCAG

AATATTTATGGTCCTTTTGACTACTGGGGTCAGGGAACCCTGGTCACCGTCTCGAGC

BMS2h-416
(SEQ ID NO: 539)
GAGGTGCAGCTGTTGGAGTCTGGGGGAGGCTTGGTACAGCCTGGGGGGTCCCTGCGTCTC

TCCTGTGCAGCCTCCGGATTCACCTTTGAGCAGTATGATATGGCTTGGGTCCGCCAGGCT

CCAGGGAAGGGTCTAGAGTGGGTCTCAGAGATTAGTCGTGATGGTGGGCGGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGGAAGAGTAT

CCTTATTTTGACTACTGGGGTCAGGGAACCCTGGTCACCGTCTCGAGC

TABLE 2-continued

Human Anti-CD40L VH Domain Encoding Nucleotide Sequences

BMS2h-417
(SEQ ID NO: 590)
GAGGTGCAGCTGTTGGAGTCTGGGGGAGGCTTGGTACAGCCTGGGGGGTCCCTGCGTCTC

TCCTGTGCAGCCTCCGGATTCACCTTTCCGCAGTATAGTATGGTGTGGGTCCGCCAGGCT

CCAGGGAAGGGTCTTGAGTGGGTCTCAACTATTTCGCCTCTGGGTTCTTCGACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAAATGAGT

AAGTTGTTGCTGTCGAGGGAGTTTGACTACTGGGGTCAGGGAACCCTGGTCACCGTCTCG

AGC

BMS2h-413
(SEQ ID NO: 591)
GAGGTGCAGCTGTTGGAGTCTGGGGGAGGCTTGGTACAGCCTGGGGGGTCCCTGCGTCTC

TCCTGTGCAGCCTCCGGATTCACCTTTGCTATGTATTCGATGGCTTGGGTCCGCCAGGCT

CCAGGGAAGGGTCTAGAGTGGGTCTCAGGTATTTCGCCTCGTGGTGTTGAGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAACTAAT

TGGAATGGTGTGGATCTGTTTGACTACTGGGGTCAGGGAACCCTGGTCACCGTCTCGAGC

BMS2h-419
(SEQ ID NO: 592)
GAGGTGCAGCTGTTGGAGTCTGGGGGAGGCTTGGTACAGCCTGGGGGGTCCCTGCGTCTC

TCCTGTGCAGCCTCCGGATTCACCTTTACGCGTCATGGTATGGCGTGGGTCCGCCAGGCT

CCAGGGAAGGGTCTAGAGTGGGTCTCAACGATTACGCCTACTGGTAATACTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGATGCT

CATGATGAGGGGTATTTTGACTACTGGGGTCAGGGAACCCTGGTCACCGTCTCGAGC

BMS2h-42
(SEQ ID NO: 593)
GAGGTGCAGCTGTTGGAGTCTGGGGGAGGCTTGGTACAGCCTGGGGGGTCCCTGCGTCTC

TCCTGTGCAGCCTCCGGATTCACCTTTGGTCCGTATGAGATGACTTGGGTCCGCCAGGCT

CCAGGGAAGGGTCTAGAGTGGGTCTCATCGATTGTTGGTGATGGTCTGGATACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCGGAT

CGGGTTTTTGACTACTGGGGTCAGGGAACCCTGGTCACCGTCTCGAGC

BMS2h-420
(SEQ ID NO: 594)
GAGGTGCAGCTGTTGGAGTCTGGGGGAGGCTTGGTACAGCCTGGGGGGTCCCTGCGTCTC

TCCTGTGCAGCCTCCGGATTCACCTTTGGTAGTACGCCTATGATGTGGGTCCGCCAGGCT

CCAGGGAAGGGTCTAGAGTGGGTCTCAGAGATTAGGGATACGGGTCTGGCTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAGTGTTTCG

TTTGACTACTGGGGTCAGGGAACCCTGGTCACCGTCTCGAGC

BMS2h-421
(SEQ ID NO: 595)
GAGGTGCAGCTGTTGGAGTCTGGGGGAGGCTTGGTACAGCCTGGGGGGTCCCTGCGTCTC

TCCTGTGCAGCCTCCGGATTCACCTTTCATCTGGGGGATATGCATTGGGTCCGCCAGGCT

TABLE 2-continued

Human Anti-CD40L VH Domain Encoding Nucleotide Sequences

CCAGGGAAGGGTCTAGAGTGGGTCTCATCGATTAGTGGGACGGGTCATACTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAACCTATG

AATGATCAGGGGTTTGACTACTGGGGTCAGGGAACCCTGGTCACCGTCTCGAGC

BMS2h-422 (SEQ ID NO: 596)
GAGGTGCAGCTGTTGGAGTCTGGGGGAGGCTTGGTACAGCCTGGGGGGTCCCTGCGTCTC

TCCTGTGCAGCCTCCGGATTCACCTTTATGGATGAGGATATGTTGTGGGTCCGCCAGGCT

CCAGGGAAGGGTCTAGAGTGGGTCTCAAGGATTAATTCGCTGGGTACTCATACATACTAC

GCAGACTCCGTGAAGGGCCGATTCACCATCTCCCGCGACAATTCCAAGAACACGCTGTAT

CTGCAAATGAACAGCCTGCGTGCCGAGGATACCGCGGTATATTACTGTGCGAAATCGTTT

ATGATGTTTGACTACTGGGGTCAGGGAACCCTGGTCACCGTCTCGAGC

BMS2h-423 (SEQ ID NO: 597)
GAGGTGCAGCTGTTGGAGTCTGGGGGAGGCTTGGTACAGCCTGGGGGGTCCCTGCGTCTC

TCCTGTGCAGCCTCCGGATTCACCTTTCGTAATTATCAGATGCATTGGGTCCGCCAGGCT

CCAGGGAAGGGTCTAGAGTGGGTCTCAGGTATTGATGCGACTGGTCGGGCGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAGATCTACT

AGGTCATTTGACTACTGGGGTCAGGGAACCCTGGTCACCGTCTCGAGC

BMS2h-424 (SEQ ID NO: 598)
GAGGTGCAGCTGTTGGAGTCTGGGGGAGGCTTGGTACAGCCTGGGGGGTCCCTGCGTCTC

TCCTGTGCAGCCTCCGGATTCACCTTTACGAATGCGGATATGGTGTGGGTCCGCCAGGCT

CCAGGGAAGGGTCTAGAGTGGGTCTCAAGTATTAGTGGTAGTGGTGGTAGCACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGGTTAT

TTGACTTCGCATTTTGACTACTGGGGTCAGGGAACCCTGGTCACCGTCTCGAGC

BMS2h-425 (SEQ ID NO: 599)
GAGGTGCAGCTGTTGGAGTCTGGGGGAGGCTTGGTACAGCCTGGGGGGTCCCTGCGTCTC

TCCTGTGCAGCCTCCGGATTCACCTTTAGGGATTATTCTATGGCTTGGGTCCGCCAGGCT

CCAGGGAAGGGTCTAGAGTGGGTCTCAACTATTACTCCGTCGGGTCTTACGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGGAATGGTCT

CAGGCGGTTACTCGGTCTTTTGACTACTGGGGTCAGGGAACCCTGGTCACCGTCTCGAGC

BMS2h-426 (SEQ ID NO: 600)
GAGGTGCAGCTGTTGGAGTCTGGGGGAGACTTGGTACAGCCTGGGGGGTCCCTGCGTCTC

TCCTGTGCAGCCTCCGGATTCACCTTTTCTGATGAGGGTATGATGTGGGTCCGCCAGGCT

CCAGGGAAGGGTCTAGAGTGGGTCTCAGAGATTAATCAGCAGGGTTCGGCGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAACGATT

GGGATGTTTGACTACTGGGGTCAGGGAACCCTGGTCACCGTCTCGAGC

TABLE 2-continued

Human Anti-CD40L VH Domain Encoding Nucleotide Sequences

BMS2h-427
(SEQ ID NO: 601)
GAGGTGCAGCTGTTGGAGTCTGGGGGAGGCTTGGTACAGCCTGGGGGGTCCCTGCGTCTC
TCCTGTGCAGCCTCCGGATTCACCTTTACTGATCAGCCGATGGTGTGGGTCCGCCAGGCT
CCAGGGAAGGGTCTAGAGTGGGTCTCATCGATTGGGGCGCGTGGTGGGCCTACATACTAC
GCAGACTCCGTGAAGGGCCGGTTCACCGTCTCCCGCGACAATTCCAAGAACACGCTGTAT
CTGCAAATGAACAGCCTGCGTGCCGAGGACACCGCGGTATATTACTGTGCGAAATGGTTT
GATATTATTGCTTGGGATCCTTTTAGTTTTGACTACTGGGGTCAGGGAACCCTGGTCACC
GTCTCGAGC

BMS2h-428
(SEQ ID NO: 602)
GAGGTGCAGCTGTTGGAGTCTGGGGGAGGCTTGGTACAGCCTGGGGGGTCCCTGCGTCTC
TCCTGTGCAGCCTCCGGATTCACCTTTAATCAGTATCCTATGATGTGGGTTCGCCAGGCT
CCAGGGAAGGGTCTAGAGTGGGTCTCAAGTATTACTCCTTCTGGTTTTTTGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAATGGAAT
CCTTTTATTACTACGTTTGACTACTGGGGTCAGGGAACCCTGGTGACCGTCTCGAGC

BMS2h-429
(SEQ ID NO: 603)
GAGGTGCAGCTGTTGGAGTCTGGGGGAGGCTTGGTACAGCCTGGGGGGTCCCTGCGTCTC
TCCTGTGCAGCCTCCGGATTCACCTTTGGGCATCAGCAGATGGCGTGGGTCCGCCAGGCT
CCAGGGAAGGGTCTAGAGTGGGTCTCAACTATTACTCCGAATGGTTATTATACATACTAC
GCAGACTCCGTGAAGGGCCGGTTCACCATCTCCCGCGACJMTTCCAAGAACACGCTGTAT
CTGCAAATGAACAGCCTGCGTGCCGAGGACACCGCGGTATATTACTGTGCGAAATTTGAT
TATTCGCTTCGTTTTGACTACTGGGGTCAGGGAACCCTGGTCACCGTCTCGAGC

BMS2h-43
(SEQ ID NO: 604)
GAGGTGCAGCTGTTGGAGTCTGGGGGAGGCTTGGTACAGCCTGGGGGGTCCCTGCGTCTC
TCCTGTGCAGCCTCCGGATTCACCTTTGCTTCTTATGAGATGGCGTGGGTCCGCCAGGCT
CCAGGGAAGGGTCTAGAGTGGGTCTCATCGATTGGTAGTGATGGTGGGCCGACATACTAC
GCAGACTCCGTGAAGGGCCGGTTCACCATCTCCCGCGACAATTCCAAGAACACGCTGTAT
CTGCAAATGAACAGCCTGCGTGCCGAGGACTCCGCGGTATATTACTGTGCGAAACCTGAT
AGGGCTTTTGACTACTGGGGTCAGGGAACCCTGGTCACCGTCTCGAGC

BMS2h-430
(SEQ ID NO: 605)
GAGGTGCAGCTGTTGGAGTCTGGGGGAGGCTTGGTACAGCCTGGGGGGTCCCTGCGTCTC
TCCTGTGCAGCCTCCGGATTCACCTTTTCTGCGGAGCAGATGACTTGGGCCCGCCAGGCT
CCAGGGAAGGGTCTAGAGTGGGTCTCAACTATTACTCCGCATGGTGATTCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATGGCGG
ACTTTGGTTGATTGGCTACGAGTGAGTCGTTTGACTACTGGGGTCAGGGAACCCTGGTC
ACCGTCTCGAGC

TABLE 2-continued

Human Anti-CD40L VH Domain Encoding Nucleotide Sequences

BMS2h-44
(SEQ ID NO: 606)
GAGGTGCAGCTGTTGGAGTCTGGGGGAGGCTTGGTACAGCCTGGGGGGTCCCTGCGTCTC

TCCTGTGCAGCCTCCGGATTCACCTTTACGTCTTATGAGATGGGGTGGGTCCGCCAGGCT

CCAGGGAAGGGTCTAGAGTGGGTCTCATCTATTGAGCCTACTGGTATTACGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCTCAT

TTTACTGAGCTTGGTTTTGACTACTGGGGTCAGGGAACCCTGGTCACCGTCTCGAGC

BMS2h-449
(SEQ ID NO: 607)
GAGGTGCAGCTGTTGGAGTCTGGGGGAGGCTTGGTACAGCCTGGGGGGTCCCTGCGTGTC

TCCTGTGCAGCCTCCGGATTCACCTTTGAGGGGGAGCAGATGGCTTGGGTCCGCCAGGCT

CCAGGGAAGGGTCTAGAGTGGGTCTCAACGATTACGCTGCCTGGTCCGTATACATTCTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGGGAAT

GGGACGTTTTTTGACTACTGGGGTCAGGGAACCGTGGTCACCGTCTCGAGC

BMS2h-45
(SEQ ID NO: 608)
GAGGTGCAGCTGTTGGAGTCTGGGGGAGGCTTGGTACAGCCTGGGGGGTCCCTGCGTCTC

TCCTGTGCAGCCTCCGGATTCACCTTTGGTAATTATGCGATGGCGTGGGTCCGCCAGGCT

CCAGGGAAGGGTCTAGAGTGGGTCTCAAAGATTGGGGCGCAGGGTCTTCATACATACTAC

GCAGGCTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACAGACG

ACGATGGATTATGAGAGGTTTGACTACTGGGGTCAGGGAACCCTGGTCACCGTCTCGAGC

BMS2h-450
(SEQ ID NO: 609)
GAGGTGCAGCTGTTGGAGTCTGGGGGAGGCTTGGTACAGCCTGGGGGGTCCCTGCGTCTC

TCCTGTGCAGCCTCCGGATTCACCTTTGATGAGGTTGATATGTCGTGGGTCCGCCAGGCT

CCAGGGAAGGGTCTGGAGTGGGTCTCAGCTATTGGTAATAATGGTCTTAAGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAATCGGCT

CTGTCGTATAGGCCTCCTGTTTTTGACTACTGGGGTCAGGGAACCCTGGTCACCGTCTCG

AGC

BMS2h-451
(SEQ ID NO: 610)
GAGGTGCAGCTGTTGGAGTCTGGGGGAGGCTTGGTACAGCCTGGGGGGTCCCTGCGTCTC

TCCTGTGCAGCCTCCGGATTCACCTTTCAGGATGATACTATGTCGTGGGTCCGCCAGGCT

CCAGGGAAGGGTCTAGAGTGGGTCTCAACGATTACGCTTAAGGGTCCGTCTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAATCGAGG

GATGGGTTGTATTTTGACTACTGGGGTCAGGGAACCCTGGTCACCGTCTCGAGC

BMS2h-452
(SEQ ID NO: 611)
GAGGTGCAGCTGTTGGAGTCTGGGGGAGGCTTGGTACAGCCTGGGGGGTCCCTGCGTCTC

TCCTGTGCAGCCTCCGGATTCACCTTTGCTTCGTCTCCGATGGCTTGGGTCCGCCAGGCT

TABLE 2-continued

Human Anti-CD40L VH Domain Encoding Nucleotide Sequences

CCAGGGAAGGGTCTAGAGTGGGTCTCAAGTATTGGTCGGGATGGTAGTACGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCTTCG

CCTTATCGGCGGTTTGACTACTGGGGTCAGGGAACCCTGGTCACCGTCTCGAGC

BMS2h-453
(SEQ ID NO: 612)
GAGGTGCAGCTGTTGGAGTCTGGGGGAGGCTTGGTACAGCCTGGGGGGTCCCTGCGTCTC

TCCTGTGCAGCCTCCGGATTCACCTTTACTGATTATTCGATGGTTTGGGTCCGCCAGGCT

CCAGGGAAGGGTCTAGAGTGGGTCTCAACTATTGTGAGTCATGGTGGTACTACATACTAC

GCAGACTCCGTGAAGGGCCGATTCACCATCTCCCGCGACAATTCCAAGAACACGCTGTAT

CTGCAAATGAACAGCCTGCGTGCCGAGGACACCGCGGTATATTACTGTGCGAAAGGTAAG

GGTTATAATGCGCAGTATTTTGACTAGTGGGGTCAGGGAACCCTGGTCACCGTCTCGAGC

BMS2h-454
(SEQ ID NO: 613)
GAGGTGCAGCTGTTGGAGTCTGGGGGAGGCTTGGTACAGCCTGGGGGGTCCCTGCGTCTC

TCCTGTGCAGCCTCCGGATTCACCTTTGGGCATCAGCAGATGGCGTGGGTCCGCCAGGCT

CCAGGGAAGGGTCTAGAGTGGGTCTCAACTATTACTCCGAATGGTTATTATACKFACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAATTTGAT

TATTCGCTTCGTTTTGACTACTGGGGTCAGGGAACCCTGGTCACCGTCTCGAGC

BMS2h-455
(SEQ ID NO: 614)
GAGGTGCAGCTGTTGGAGTCTGGGGGAGGCTTGGTACAGCCTGGGGGGTCCCTGCGTCTC

TCCTGTGCAGCCTCCGGATTCACCTTTAATGATTATGATATGATTTGGGTCCGCCAGGCT

CCAGGGAAGGGTCTAGAGTGGGTCTCAACTATTAGTTCGCATGGTGATAGTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGGTGAT

GTTTTTTTTGACTACTGGGGTCAGGGAACCCTGGTCACCGTCTCGAGC

BMS2h-456
(SEQ ID NO: 815)
GAGGTGCAGCTGTTGGAGTCTGGGGGAGGCTTGGTACAGCCTGGGGGGTCCCTGCGTCTC

TCCTGTGCAGCCTCCGGATTCACCTTTGGGCATCAGCAGATGGCGTGGGTCCGCCAGGCT

CCAGGGAAGGGTCTAGAGTGGGTCTCAACTATTACTCCGAATGGTTATTATACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGGAATGGTCG

GATTCTTTTGACTACAGGGGTCAGGGAACCCTGGTCACCGTCTCGAGC

BMS2h-457
(SEQ ID NO: 616)
GAGGTGCAGCTGTTGGAGTCTGGGGGAGGCTTGGTACAGCCTGGGGGGTCCCTGCGTCTC

TCCTGTGCAGCCTCCGGATTCACCTTTGCTGATTATGAGATGGCTTGGGTCCGCCAGGCT

CCAGGGAAGGGTCTAGAGTGGGTCTCAGGGATTCAGTCTAATGGTAATATTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGCTAAT

TCTCAGGTTGAGTATTTTGACTACTGGGGTCAGGGAACCCTGGTCACCGTCTCGAGC

TABLE 2-continued

Human Anti-CD40L VH Domain Encoding Nucleotide Sequences

BMS2h-458 (SEQ ID NO: 617)
GAGGTGCAGCTGTTGGAGTCTGGGGGAGGCTTGGTACAGCCTGGGGGGTCCCTGCGTCTC
TCCTGTGCAGCCTCCGGATTCACCTTTGGGGTGGAGCCTATGTCTTGGGTCCGCCAGGCT
CCAGGGAAGGGTCTAGAGTGGGTCTCAAATATTGGTCGTGATGGTTCGATGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATTGGGG
AAGCATGGTACTTTTGACTACTGGGGTCAGGGAACCCTGGTCACCGTCTCGAGC

BMS2h-459 (SEQ ID NO: 618)
GAGGTGCAGCTGTTGGAGTCTGGGGGAGGCTTGGTACAGCCTGGGGGGTCCCTGCGTCTC
TCCTGTGCAGCCTCCGGATTCACCTTTCCGGAGTATCGGATGATGTGGGTCCGCCAGGCT
CCAGGGAAGGGTCTGGAGTGGGTCTCATGGATTGATGAGCGGGGTTCGCTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAAGGCGG
AAGGGTACTAAGCAGTTTGACTACTGGGGTCAGGGAACCCTGGTCACCGTCTCGAGC

BMS2h-46 (SEQ ID NO: 619)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGTTGTATGCTATGGCGTGGGTCCGCCAGGCT
CCAGGGAAGGGTCTAGAGTGGGTCTCAGGTATTGGTGCTGTGGGTGAGACTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGAGGCT
AATAATCTTTCTGATAATCTTGTGTTTGACTACTGGGGTCAGGGAACCCTGGTCACCGTC
TCGAGC

BMS2h-460 (SEQ ID NO: 620)
GAGGTGCAGCTGTTGGAGTCTGGGGGAGGCTTGGTACAGCCTGGGGGGTCCCTGCGTCTC
TCCTGTGCAGCCTCCGGATTCACCTTTGGGCATCAGCAGATGGCGTGGGTCCGCCAGGCT
CCAGGGAAGGGTCTAGAGTGGGTCTCAACTATTACTCCGAATGGTTATTATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATGGTCG
GTTGAGTGGTTTGACTACTGGGGTCAGGGAACCCTGGTCACCGTCTCGAGC

BMS2h-461 (SEQ ID NO: 621)
GAGGTGCAGCTGTTGGAGTCTGGGGGAGGCTTGGTACAGCCTGGGGGGTCCCTGCGTCTC
TCCTGTGCAGCCTCCGGATTCACCTTTAATAGTTATACGATGAATTGGGTCCGCCAGGCT
CCAGGGAAGGGTCTAGAGTGGGTCTCAAGTATTAATCCTGGGGTAGTCGGACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAAGGTCTG
GTGCTGTTTGACTACTGGGGTCAGGGAACCCTGGTCACCGTCTCGAGC

BMS2h-462 0 (SEQ ID NO: 622)
GAGGTGCAGCTGTTGGAGTCTGGGGGAGGCTTGGTACAGCCTGGGGGGTCCCTGCGTCTC
TCCTGTGCAGCCTCCGGATTCACCTTTGATGGTGATATGATGTCTTGGGTCCGCCAGGCT

TABLE 2-continued

Human Anti-CD40L VH Domain Encoding Nucleotide Sequences

CCAGGGAAGGGTCTAGAGTGGGTCTCATCGATTACTCAGCTTGGTAGTAGGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACAGAAT

TGGCGGACTCTTACTTTTGACTACTGGGGTCAGGGAACCCTGGTCACCGTCTCGAGC

BMS2h-463
(SEQ ID NO: 623)
GAGGTGCAGCTGTTGGAGTCTGGGGGAGGCTTGGTACAGCCTGGGGGGTCCCTGCGTCTC

TCCTGCGCAGCCTCCGGATTCACCTTTAATGCTTATGGGATGATGTGGGTCCGCCAGGCT

CCAGGGAAGGGTCTAGAGTGGGTCTCATCTATTCTTTCTGATGGTGTTATTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAAGTGCT

CGGGGTGCGAATTTTTTGACTACTGGGGTCAGGGAACCCTGGTCACCGTCTCGAGC

BMS2h-464
(SEQ ID NO: 624)
GAGGTGCAGCTGTTGGAGTCTGGGGGAGGCTTGGTACAGCCTGGGGGGTCCCTGCGTCTC

TCCTGTGCAGCCTCCGGATTCACCTTTGGGCATTATATGATGGTGTGGGTCCGCCAGGCT

CCAGGGAAGGGTCTGGAGTGGGTCTCATCTATTACGCCTCATGGTACGAGTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGGAATTTAAT

GCTATTTTTAGTGAGGCGTTTGACTACTGGGGTCAGGGAACCCTGGTCACCGTCTCGAGC

BMS2h-465
(SEQ ID NO: 625)
GAGGTGCAGCTGTTGGAGTCTGGGGGAGGCTTGGTACAGCCTGGGGGGTCCCTGCGTCTC

TCCTGTGCAGCCTCCGGATTCACCTTTAGGGATTATTCTATGGCTTGGGTCCGCCAGGCT

CCAGGGAAGGGTCTAGAGTGGGTCTCAACTATTACTCCGTCGGGTCTTACGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGGAATGGTCT

CAGGCGGTTACTCGGTCTTTTGACTACTGGGGTCAGGGAACCCTGGTCACCGTCTCGAGC

BMS2h-466
(SEQ ID NO: 626)
GAGGTGCAGCTGTTGGAGTCTGGGGGAGGCTTGGTACAGCCTGGGGGGTCCCTGCGTCTC

TCCTGTGCAGCCTCCGGATTCACCTTTGATCTTTATGCGATGGCTTGGGTCCGCCAGGCT

CCAGGGAAGGGTCTAGAGTGGGTCTCAATGATTGGGAGGGATGGTCGTTTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACGGCGGTATATTACTGTGCGAAATTGGCT

GGTAAGCTGAGGGGTCGTTTTGACTACTGGGGTCAGGGAACCCTGGTCACCGTCTCGAGC

BMS2h-467
(SEQ ID NO: 627)
GAGGTGCAGCTGTTGGAGTCTGGGGGAGGCTTGGTACAGCCTGGGGGGTCCCTGCGTCTC

TCCTGTGCAGCCTCCGGATTCACCTTTAATAAGGCTAGTATGGGTTGGGTCCGCCAGGCT

CCAGGGAAGGGTCTAGAGTGGGTCTCAACTATTACGCCTCATGGTTCGTCTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACAGCGG

TGGGGTGTTGAGTTTGACTACTGGGGTCAGGGAACCCTGGTCACCGTCTCGAGC

TABLE 2-continued

Human Anti-CD40L VH Domain Encoding Nucleotide Sequences

BMS2h-468
(SEQ ID NO: 628)
GAGGTGCAGCTGTTGGAGTCTGGGGGAGGCTTGGTACAGCCTGGGGGGTCCCTGCGTCTC

TCCTGTGCAGCCTCCGGATTCACCTTTCAGGGGTATAGTATGGGTTGGGTCCGCCAGGCT

CCAGGGAAGGGTCTAGAGTGGGTCTCATCTATTGCTGGGCGTGGTGGTGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGGTTTG

TATATTTATCATAGTCTGTTTGACTACTGGGGTCAGGGAACCCTGGTCACCGTCTCGAGC

BMS2h-469
(SEQ ID NO: 629)
GAGGTGCAGCTGTTGGAGTCTGGGGGAGGCTTGGTACAGCCTGGGGGCTCCCTGCGTCTC

TCCTGTGCAGCCTCCGGATTCACCTTTCCTGGTATGGAGATGTCGTGGGTCCGCCAGGCT

CCAGGGAAGGGTCTAGAGTGGGTCTCAGCTATTACTGGGACTGGTAGTACGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGGTTAT

CATCCGTTTGACTACTGGGGTCAGGGAACCCTGGTCACCGTCTCGAGC

BMS2h-470
(SEQ ID NO: 630)
GAGGTGCAGCTGTTGGAGTCTGGGGGAGGCTTGGTACAGCCTGGGGGGTCCCTGCGTCTC

TCCTGTGCAGCCTCCGGATTCACCTTTCCGATGGTGGCTATGTCTTGGGTCCGCCAGGCT

CCAGGGAAGGGTCTAGAGTGGGTCTCATCTATTGCTCGGGATGGTAATGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACGCCGCGGTATATTACTGTGCGAAAGTTTCG

CCGACTGGTTTTGACTACTGGGGTCAGGGAACCCTGGTCACCGTCTCGAGC

BMS2h-471
(SEQ ID NO: 631)
GAGGTGCAGCTGTTGGAGTGTGGGGGAGGCTTGGTACAGCCTGGGGGGTCCCTGCGTCTC

TCCTGTGCAGCCTCCGGATTCACCTTTGGGCATCAGGATATGTCGTGGGTCCGCCAGGCT

CCAGGGAAGGGTCTAGAGTGGGTCTCAGGGATTACGGATGATGGTGAGAGTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGGTGAT

TATGATTTTGACTACTGGGGTCAGGGAACCCTGGTCACCGTCTCGAGC

BMS2h-472
(SEQ ID NO: 632)
GAGGTGCAGCTGTTGGAGTCTGGGGGAGGCTTGGTACAGCCTGGGGGGTCCCTGCGTCTC

TCCTGTGCAGCCTCCGGATTCACCTTTGGGGAGTATAATATGATGTGGGTCCGCCAGGCT

CCAGGGAAGGGTCTAGAGTGGGTCTCACAGATTACGAGGGATGGTTCTAGGACATACTAC

GCAGACTCCGTGAGGGCCGGTTCACCATCTCCCGCGACAATTCCAGGAACACGCTGTAT

CTGCAAATGAACAGCCTGCGTGCCGAGGACTCCGCGGTATATTACTGTGCGAAACTGTCG

AATATTGGGTTTGACTACTGGGGTCAGGGAACCCTGGTCACCGTCTCGAGC

BMS2h-473
(SEQ ID NO: 633)
GAGGTGCAGCTGTTGGAGTCTGGGGGAGGCTTGGTACAGCCTGGGGGGTCCCTGCGTCTC

TCCTGTGCAGCCTCCGGATTCACCTTTAGTGATTATTCTATGATTTGGGCCCGCCAGGCT

CCAGGGAAGGGTCTAGAGTGGGTCTCATCGATTACGCCGTATGGTTCTTATACATACTAC

TABLE 2-continued

Human Anti-CD40L VH Domain Encoding Nucleotide Sequences

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAAACTGAT

TATTTGTTTGACTACTGGGGTCAGGGAACCCTGGTCACCGTCTCGAGC

BMS2h-474
(SEQ ID NO: 634)
GAGGTGCAGCTGTTGGAGTCTGGGGGAGGCTTGGTACAGCCTGGGGGGTCCCTGCGTCTC

TCCTGTGCAGCCTCCGGATTCACCTTTGATACGTATAGTATGATGTGGGTCCGCCAGGCT

CCAGGGAAGGGTCTTGAGTGGGTCTCAACTATTACTCCTTATGGTAGTTCGACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAATGGGT

CTGGTGTTTGACTACTGGGGTCAGGGAACCCTGGTCACCGTCTCGAGC

BMS2h-475
(SEQ ID NO: 635)
GAGGTGCAGCTGTTGGAGTCTGGGGGAGGCTTGGTACAGCCTGGGGGGTCCCTGCGACTC

TCCTGTGCAGCCTCCGGATTCACCTTTACTACGGGTCCTATGATGTGGGTCCGCCAGGCT

CCAGGGAAGGGTCTAGAGTGGGTCTCAGCGATTGGTATTGGGGGTGATACGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTCTATTACTGTGCGAAATTGACT

CCGTCTAATCAGTTTGACTACTGGGGTCAGGGAACCCTGGTCACCGTCTCGAGC

BMS2h-476
(SEQ ID NO: 636)
GAGGTGCAGCTGTTGGAGTCTGGGGGAGGCTTGGTACAGCCTGGGGGGTCCCTGCGTCTC

TCCTGTGCAGCCTCCGGATTCACCTTTAAGCAGTATCAGATGATGTGGGTTCGCCAGGCT

CCAGGGAAGGGTCTAGAGTGGGTCTCAAGTATTACTCCTTCTGGTTTTTTGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGGAATGGAAT

CCTTTTATTAGTACGTTTGACTACTGGGGTCAGGGAACCCTGGTCACCGTCTCGAGC

BMS2h-477
(SEQ ID NO: 637)
GAGGTGCAGCTGTTGGAGTCTGGGGGAGGCTTGGTACAGCCTGGGGGGTCCCTGCGTCTC

TCCTGTGCAGCCTCCGGATTCACCTTTCCTAATTATGATATGGTTTGGGTCCGCCAGGCT

CCAGGGAAGGGTCTAGAGTGGGTCTCATCGATTTCTGCTTTGGGTAATGTTACATACTAC

GCAGACTCCGTGAAGGGCCGGTTCACCATCTCCCGCGACAATTCCAAGAACACGCTGTAT

CTGCAAACGAACAGCCTGCGTGCCGAGGACACTGCGGTATATTACTGTGCGAAATGGCGT

AGTGCTATTACTGGTAATTTTGACTACTGGGGTCAGGGAACCCTGGTCACCGTCTCGAGC

BMS2h-478
(SEQ ID NO: 638)
GAGGTGCAGCTGTTGGAGTCTGGGGGAGGCTTGGTACAGCCTGGGGGGTCCCTGCGTCTC

TCCTGTGCAGCCTCCGGATTCACCTTTAAGGAGTATCAGATGCTTGGGTCCGCCAGGCT

CCAGGGAAGGGTCTAGAGTGGGTCTCAACTATTTCGCCGTCGGGTATGAATACATACTAC

GCAGACTCCGTGAAGGGCCGGTTCACCATCTCCCGCGACMTTCCAAGTAACACGCTGTAT

CTGCAAATGAACAGCCTGCGTGCCGAGGACACCGCGGTATATTACTGTGCGGAATGGCGG

TCGGTTGTTCGTCCTTGGCCGGGTGTGTTTGACTACTGGGGTCAGGGAACCCTGGTCACC

GTCTCGAGC

TABLE 2-continued

Human Anti-CD40L VH Domain Encoding Nucleotide Sequences

BMS2h-479
(SEQ ID NO: 639)
GAGGTGCAGCTGTTGGAGTCTGGGGGAGGCTTGGTACAGCCTGGGGGGTCCCTGCGTCTC

TCCTGTGCAGCCTCCGGATTCACCTTTGATGATGAGAGTATGGCGTGGGTCCGCCAGGCT

CCAGGGAAGGGTCTAGAGTGGGTCTCATCGATTACTCCTCATGGTACTTTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACTTCAT

CTTAAGTTGTATGAGTCTCATTTTGACTACTGGGGTCAGGGAACCCTGGTCACCGTCTCG

AGC

BMS2h-480
(SEQ ID NO: 640)
GAGGTGCAGCTGTTGGAGTCTGGGGGAGGCTTGGTACAGCCTGGGGGGTCCCTGCGTCTC

TCCTGTGCAGCCTCCGGATTCACCTTTGAGGGTGGTGAGATGGGTTGGGTCCGCCAGGCT

CCAGGGAAGGGTCTAGAGTGGGTCTCAATGATTCCGATGGATGGTAGTGCGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGCGGGG

AGTACGTTTGACTACTGGGGTCAGGGAACCCTGGTCACCGTCTCGAGC

BMS2h-481
(SEQ ID NO: 641)
GAGGTGCAGCTGTTGGAGTCTGGGGGAGGCTTGGTACAGCCTGGGGGGTCCCTGCGTCTC

TCCTGTGCAGCCTCCGGATTCACCTTTGATTTTATGCCGATGGCGTGGGTCCGCCAGGCT

CCAGGGAAGGGTCTAGAGTGGGTCTCATCTATTGGGAGGGATGGTGCTTATACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACTTGCT

TCGCCGGCGCAGTTTGACTACTGGGGTCAGGGAACCCTGGTCACCGTCTCGAGC

BMS2h-482
(SEQ ID NO: 642)
GAGGTGCAGCTGTTGGAGTCTGGGGGAGGCTTGGTACAGCCTGGGGGGTCCCTGCGTCTC

TCCTGTGCAGCCTCCGGATTCACCTTTGGTGATGAGCCTATGCTGTGGGTCCGCCAGGCT

CCAGGGAAGGGTCTAGAGTGGGTCTCATCTATTGGGGGTACGGGTACGACGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGGTAAT

CAGGGTGATTTTATTAATCGGTTTCACTACTGGGGTCAGGGAACCCTGGTCACCGTCTCG

AGC

BMS2h-483
(SEQ ID NO: 643)
GAGGTGCAGCTGTTGGAGTCTGGGGGAGGCTTGGTACAGCCTGGGGGGTCCCTGCGTCTC

TCCTGTGCAGCCTCCGGATTCACCTTTCATGCGTATAATATGGCGTGGGTCCGCCAGGCT

CCAGGGAAGGGTCTAGAGTGGGTCTCAACGATTTCTCCGCGGGGTTCTTATACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAATGGCCG

CCGCCTTCGTCTCATTTTGACTACTGGGGTCAGGGAACCCTGGTCACCGTCTCGAGC

TABLE 2-continued

Human Anti-CD40L VH Domain Encoding Nucleotide Sequences

BMS2h-5
(SEQ ID NO: 644)
GAGGTGCAGCTGTTGGAGTCTGGGGGAGGCTTGGTACAGCCTGGGGGGTCCCTGCGTCTC
TCCTGTGCAGCCTCCGGATTCACCTTTGATGGGTATGAGATGGCGTGGGTCCGCCAGGCT
CCAGGGAAGGGTCTAGAGTGGGTCTCATCTATTACGAGTGATGGTACGAGTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCGGGG
CTGCGTTTTGACTACTGGGGTCAGGGAACCCTGGTCACCGTCTCGAGC

BMS2h-505
(SEQ ID NO: 645)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGGGTTATATGATGTATTGGGTCCACCAGGCT
CCGGGGAAGGGTCTAGAGTGGGTCTCATCTATTTCTCGTCAGGGTCATTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAACTTCGT
GAGCTTCCTCGTCTGTTTGACTACTGGGGTCAGGGAACCGTGGTCACCGTCTCGAGC

BMS2h-506
(SEQ ID NO: 646)
GAGGTGCAGCTGTTGGAGTCTGGGGGAGGCTTGGTACAGCCTGGGGGGTCCCTGCGTCTC
TCCTGTGCAGCCTCCGGATTCACCTTTAGTAGTTATGCTATGGGTTGGGTCCGCCAGGCT
CCAGGGAAGGGTCTAGAGTGGGTCTCATCGATTGATGCGAGTGGTGGTCCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGCGAAT
GGGAAGAAGTTTCCTTTTACTAAGTATTTTGACTACTGGGGTCAGGGAACCCTGGTCACC
GTCTCGAGC

BMS2h-507
(SEQ ID NO: 647)
GAGGTGCAGCTGTTGGAGTCTGGGGGAGGCTTGGTACAGCCTGGGGGGTCCCTGCGTCTC
TCCTGTGCAGCCTCCGGATTCACCTTTCCTAGTGTGCATATGGCGTGGGTCCGCCAGGCT
CCAGGGAAGGGTCTAGAGTGGGTCTCAGGGATTAATCTGACGGGTGTTGATACATACTAC
GCAGAGTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAAGTGCT
ACTACTAGGCAGGCGCATCCGTTGTATTTTGACTACTGGGGTCAGGGAACCCTGGTCACC
GTCTCGAGC

BMS2h-515
(SEC ID NO: 648)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGGAGGGTGAGATGTATTGGGTCCGCCAGGCT
CCAGGGAAGGGTCTAGAGTGGGTCTCAACGATTTCGACTAATGGTCTTACTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATCTACT
CGTGATCTGGGTTTTGCCTACTGGGGTCAGGGAACCCTGGTCACCGTCTCGAGC

TABLE 2-continued

Human Anti-CD40L VH Domain Encoding Nucleotide Sequences

BMS2h-516 (SEQ ID NO: 649)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGGAGTATGAGATGGCTTGGGCCCGCCAGGCT
CCAGGGAAGGGTCTAGAGTGGGTCTCATTTATTTCTCCTCGTGGTCATTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACCGGCT
AAGACTTTTGACTACTGGGGTCAGGGAACCCTGGTCACCGTCTCGAGC

BMS2h-517 (SEQ ID NO: 650)
GAGGTGCAGCTGTTGGAGTCTGGGGGAGGCTTGGTACAGCCTGGGGGGTCCCTGCGTCTC
TCCTGTGCAGCCTCCGGATTCACCTTTGATACGTATGAGATGCTTTGGGTCCGCCAGGCT
CCAGGGAAGGGTCTAGAGTGGGTCTCACGTATTTCTGTTGATGGTAGTATTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAAACGCGG
ATGCGTTTTGACTACTGGGGTCAGGGAACCCTGGTCACCGTCTCGAGC

BMS2h-518 (SEQ ID NO: 651)
GAGGTGCAGCTGTTGGAGTCTGGGGGAGGCTTGGTACAGCCTGGGGGGTCCCTGCGTCTC
TCCTGTGCAGCCTCCGGATTCACCTTTAGTTCGTATGCTATGTCGTGGGTCCGCCAGGCT
CCAGGGAAGGGTCTAGAGTGGGTCTCAAATATTTCTCGTGATGGTTCGAAGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAAGCGCAG
TCTGGGGGGCTTCGGTCGGGTTTGACTACGTTTGACTACTGGGGTCAGGGAACCCTGGTC
ACCGTCTCGAGC

BMS2h-519 (SEQ ID NO: 652)
GAGGTGCAGCTGTTGGAGTCTGGGGGAGGCTTGGTACAGCCTGGGGGGTCCCTGCGTCTC
TCCTGTGCAGACTCCGGATTCACCTTTAGCAGCTATGCCATGAGCTGGGTCCGCCAGGCT
CCAGGGAAGGGTCTAGAGTGGGTCTCATCTATTGGGAGGGATGGTGCTTATACATACTAC
GCAGACTCCGTGAAGGGCCGGTTCACCATCTCCCGCGACPATTCCAAGAACACGCTGTAT
CTGCAAATGAACAGCCTGCGTGCCGAGGACACCGCGGTATATTACTGTGCGAAAGCGGGG
CCGAAGGGTATTGCGTTTGACTACTGGGGTCAGGGAACCCTGGTCACCGTCTCGAGC

BMS2h-520 (SEQ ID NO: 653)
GAGGTGCAGCTGTTGGAGTCTGGGGGAGGCTTGGTACAGCCTGGGGGGTCCCTGCGTCTC
TCCTGTGCAGCCTCCGGATTCACCTTTAGTCCGCATGCTATGGCTTGGGTCCGCCAGGCT
CCAGGGAAGGGTCTGGAGTGGGTCTCAGGTATTGATGGGGGGGGTTCGATGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATCGGAT
CCTCCGTTTGACTACTGGGGTCAGGGAACCCTGGTCACCGTCTCGAGC

BMS2h-521 (SEQ ID NO: 654)
GAGGTGCAGCTGTTGGAGTCTGGGGGAGGCTTGGTACAGCCTGGGGGGTCCCTGCGTCTC
TCCTGCGCAGCCTCCGGATTCACCTTTCATGCGGGGGAGATGCATTGGGTCCGCCAGGCT

TABLE 2-continued

Human Anti-CD40L VH Domain Encoding Nucleotide Sequences

CCAGGGAAGGGTCTAGAGTGGGTCTCATCGATTACGCTGCCTGGTGATATGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCGAAT

ACTGGGTATACTTTTGACTACTGGGGTCAGGGAACCCTGGTCACCGTCTCGAGC

BMS2h-522
(SEQ ID NO: 655)
GAGGTGCAGCTGTTGGAGTCTGGGGGAGGCTTGGTACAGCCTGGGGGGTCCCTGCGTCTC

TCCTGTGCAGCCTCCGGATTCACCTTTGGGAATTATGGTATGTCGTGGGTCCGCCAGGCT

CCAGGGAAGGGTCTAGAGTGGGTCTCAAGTATTTCGTGGGATGGTTCTCTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGCAAAATACG

CGGCTTTTTGACTACTGGGGTCAGGGAACCCTGGTCACCGTCTCGAGC

BMS2h-523
(SEQ ID NO: 656)
GAGGTGCAGCTGTTGGAGTCTGGGGGAGGCTTGGTACAGCCTGGGGGGTCCCTGCGTCTC

TCCTGTGCAGCCTCCGGATTCACCTTTCATGATGCGGATATGCTGTGGGTCCGCCAGGCT

CCAGGGAAGGGTCTAGAGTGGGTCTCAGGTATTTTGTCTCCGGGTGAGGATACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAATTGGT

CTGCCGTTTGACTACTGGGGTCAGGGAACCCTGGTCACCGTCTCGAGC

BMS2h-524
(SEQ ID NO: 657)
GAGGTGCAGCTGTTGGAGTCTGGGGGAGGCTTGGTACAGCCTGGGGGGTCCCTGCGTCTC

TCCTGTGCAGCCTCCGGATTCACCTTTCGTACTGATCAGATGAATTGGGTCCGCCAGGCT

CCAGGGAAGGGTCTAGAGTGGGTCTCAAGTATTTCTCCTAGTGGTGCGTATACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAAGGTCTT

GGTGCTTTTGACTACTGGGGTCAGGGAACCCTGGTCACCGTCTCGAGC

BMS2h-525
(SEQ ID NO: 658)
GAGGTGCAGCTGTTGGAGTCTGGGGGAGGCTTGGTACAGCCTGGGGGGTCCCTGCGTCTC

TCCTGTGCAGCCTCCGGATTCATCTTTGAGCAGTATCAGATGGTTTGGGTCCGCCAGGCT

CCAGGGAAGGGTCTAGAGTGGGTCTCATGGATTTCGCCTGATGGTACGCATACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAATTTAGT

TTGCGTAAGATGGAGAAGTTTGACTACTGGGGTCAGGGAACCCTGGTCACCGTCTCGAGC

BMS2h-526
(SEQ ID NO: 659)
GAGGTGCAGCTGTTGGAATCTGGGGGAGGCTTGGTACAGCCTGGGGGGTCCCTGCGTCTC

TCCTGTGCAGCCTCCGGATTCACCTTTCAGGATGAGCAGATGGCGTGGGTCCGCCAGGCT

CCAGGGAAGGGTCTAGAGTGGGTCTCAAGTATTGCGTCTGATGGTATGTCTACATACTAC

GCAGACTCCGTGAAGGGCCGGTTCACCATCTCCCGCGACAATTCCAAGAACACGCTGTAT

CTGCAAATGAATAGCCTGCGTGCCGAGGACACCGCGGTATATTACTGTGCGCAACCTGGG

AAGAATTTTGACCACTGGGGTCAGGGAACCCTGGTCACCGTCTCGAGC

TABLE 2-continued

Human Anti-CD40L VH Domain Encoding Nucleotide Sequences

BMS2h-527 (SEQ ID NO: 660)
GAGGTGCAGCTGTTGGAGTCTGGGGGAGGCTTGGTACAGCCTGGGGGGTCCCTGCGTCTC
TCCTGTGCAGCCTCCGGATTCACCTTTAGTGATTATGCGATGAGTTGGGTCCGCCAGGCT
CCAGGGAAGGGTCTAGAGTGGGTCTCATCGATTACTACTGGGGGTGAGCGGACATACTAC
GCAGACTCCGTGAAGGGCCGGTTCACCATCTCCCGCGACAATTCCAAGAACACGCTGTAT
GTGCAAATGAACAGCCTGCGTGCCGAGGACACCGCGGTATATTACTGTGCGAAACGTTGG
AATCTGTATACGGAGTCTTTTGACTACTGGGGTCAGGGAACCCTGGTCACCGTCTCGAGC

BMS2h-528 (SEQ ID NO: 661)
GAGGTGCAGCTGTTGGAGTCTGGGGGAGGCTTGGTACAGCCTGGGGGGTCCCTGCGTCTC
TCCTGTGCAGCCTCCGGATTCACCTTTGGTGGTCAGCCGATGGATTGGGTCCGCCAGGCT
CCAGGGAAGGGTCTAGAGTGGGTCTCATCTATTGCTCCTGATGGTATTCATACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAAATTTG
GGTCAGGGTTTTGACTACTGGGGTCAGGGAACCCTGGTCACCGTCTCGAGC

BMS2h-529 (SEQ ID NO: 662)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGCGGTATCAGATGACGTGGGTCCGCCAGGCT
CCAGGGAAGGGTCTAGAGTGGGTCTCAAGTATTTCTCCTAGTGGTACGTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAATGGAAG
GCGCTTTTTGACTACTGGGGTCAGGGAACCCTGGTCACCGTCTCGAGC

BMS2h-530 (SEQ ID NO: 663)
GAGGTGCAGCTGTTGGAGTCTGGGGGAGGCTTGGTACAGCCTGGGGGGTCCCTGCGTCTC
TCCTGTGCAGCCTCCGGATTCACCTTTCCTCATTCGACTATGTATTGGGTCCGCCAGGCT
CCAGGGAAGGGTCTAGAGTGGGTCTCACTTATTTTGCCGTCGGGTAGTCGTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAATTTTCT
GATGAGCGTTTTGACTACTGGGGTCAGGGAACCCTGGTCACCGTCTCGAGC

BMS2h-531 (SEQ ID NO: 664)
GAGGTGCAGCTGTCGGAGTCTGGGGGAGGCTTGGTACAGCCTGGGGGGTCCCTGCGTCTC
TCCTGTGCAGCCTCCGGATTCACCTTTGGTGATGGGAATATGGATTGGGTCCGCCAGGCT
CCAGGGAAGGGTCTAGAGTGGGTCTCAGGTATTTCTAGTGATGGTGTGACGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGATAGG
GGTCAGGGGTTTGACTACTGGGGTCAGGGAACCCTGGTCACCGTCTCGAGC

BMS2h-532 (SEQ ID NO: 665)
GAGGTGCAGCTGTTGGAGTCTGGGGGAGGCTTGGTACAGCCTGGGGGGTCCCTGCGTCTC
TCCTGTGCAGCTTCCGGATTCACCTTTGATGATTATATGATGTGGTGGGTCCGCCAGGCT
CCAGGGAAGGGTCTAGAGTGGGTCTCATCTATTAGTCCGCATGGTGTTTATACATACTAC

TABLE 2-continued

Human Anti-CD40L VH Domain Encoding Nucleotide Sequences

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAATGGTTG

CATACGTTTGACTACTGGGGTCAGGGAACCCTGGTCACCGTCTCGAGC

BMS2h-533 (SEQ ID NO: 666)
GAGGTGCAGCTGTTGGAGTCTGGGGGAGGCTTGGTACAGCCTGGGGGGTCCCTGCGTCTC

TCCTGTGCAGCCTCCGGATTCACCTTTTCGAATTATACGATGGCGTGGGGCCGCCAGGCT

CCAGGGAAGGGTCTAGAGTGGGTCTCATTTATTGCTGGTCCGGGTAATTATACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCGGGG

AGTACTGCGACGTATAATAATGGTCAGTTTGACTACTGGGGTCAGGGAACCCTGGTCACC

GTCTCGAGC

BMS2h-534 (SEQ ID NO: 667)
GAGGTGCAGCTGTTGGAGTCTGGGGGAGGCTTGGTACAGCCTGGGGGGTCCCTGCGTCTC

TCCTGTGCAGCCTCCGGATTCACCTTTACGGAGTATAGTATGGTGTGGGTCCGCCAGGCT

CCAGGGAAGGGTCTGGAGTGGGTCTCATCTATTAGTGGGAGTGGTCGTGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAATGGCTT

AAGCTGGTTAGGGCTCCTAATCCGTTTGACTACTGGGGTCAGGGAACCCTGGTCACCGTC

TCGAGC

BMS2h-535 (SEQ ID NO: 668)
GAGGTGCAGCTGTTGGAGTCTGGGGGAGGCTTGGTACAGCCTGGGGGGTCCCTGCGTCTC

TCCTGTGCAGCCTCCGGATTCACCTTTAGTAATTATCAGATGGCGTGGGTCCGCCAGGCT

CCAGGGAAGGGTCTAGAGTGGGTCTCAGGTATTTCTAAGACTGGTCATTCTACATACTAC

GCAGACTCCGTGAAGGGCCGGTTCACCATCTCCCGCGACAATTCCAGGAACACGCTGTAT

CTGCAAATGAACAGCCTGCGTGCCGAGGACACCGCGGTATATTACTGTGCGAAAGCTTCG

GATTCGTTGGGGCCTCTTTTTGACTACTGGGGTCAGGGAACCCTGGTCACCGTCTCGAGC

BMS2h-54 (SEQ ID NO: 669)
GAGGTGCAGCTGTTGGAGTCTGGGGGAGGCTTGGTACAGCCTGGGGGGTCCCTGCGTCTC

TCCTGTGCAGCCTCCGGATTCACCTTTACGGCGTATAGGATGGCTTGGGTCCGCCAGGCT

CCAGGGAAGGGTCTAGAGTGGGTCTCATGGATTTCGCCTTCTGGTTCGGGGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAACTTTG

ACGGATTCGCCGTCGGGGCATTATGAGTTTGACTACTGGGGTCAGGGAACCCTGGTCACC

GTCTCGAGC

BMS2h-55 (SEQ ID NO: 670)
GAGGTGCAGCTGTTGGAGTCTGGGGGAGGCTTGGTACAGCCTGGGGGGTCCCTGCGTCTC

TCCTGTGCAGCCTCCGGATTCACCTTTGCGCGGTATGAGATGGGGTGGGTCCGCCAGGCT

CCAGGGAAGGGTCTAGAGTGGGTCTCACGGATTACTGCTCAGGGTCTTGGGACATACTAC

GCAGACTCCGTGAAGGGCCGGTTCACCATCTCCCGCGACAACTCCAAGAACACGCTGTAT

TABLE 2-continued

Human Anti-CD40L VH Domain Encoding Nucleotide Sequences

CTGCAAATGAACAGCCTGCGTGCCGAGGATACCGCGGTATATTACTGTGCGAAATATCTT

ACTGATTTTAGTAGTGGGCATCAGGAGTTTGACTACTGGGGTCAGGGAACCCTGGTCACC

GTCTCGAGC

BMS2h-553
(SEQ ID NO: 671)
GAGGTGCAGCTGTTGGAGTCTGGGGGAGGCTTGGTACAGCCTGGGGGGTCCCTGCGTCTC

TCCTGTGCAGCCTCCGGATTCACCTTTGATGATTATGGTATGTCGTGGGTCCGCCAGGTT

CCAGGGAAGGGTCTGGAGTGGGTCTCAGGTATTAGTCATAATGGTATGTTGACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAATATTGG

CCGTCTACTAGTTGGGAGACTGATTTTGACTACTGGGGTCAGGGAACCCTGGTCACCGTC

TCGAGC

BMS2h-554
(SEQ ID NO: 672)
GAGGTGCAGCTGTTGGAGTCTGGGGGAGGCTCGGTACAGCCTGGGGGGTCCCTGCGTCTC

TCCTGTGCAGCCTCCGGATTCACCTTTGGGAATGAGCCTATGGCTTGGGTCCGCCAGGCT

CCAGGGAAGGGTCTAGAGTGGGTCTCAAGTATTGAGATGCAGGGTAAGAATACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGATAGG

GGTCAGGGGTTTGACTACTGGGGTCAGGGAACCCTGGTCACCGTCTCGAGC

BMS2h-555 1
(SEQ ID NO: 673)
GAGGTGCAGCTGTTGGAGTCTGGGGGAGGCTTGGTACAGCCTGGGGGGTCCCTGCGTCTC

TCCTGTGCAGCCTCCGGATTCACCTTTGGGGAGGAGGAGATGAGTTGGGTCCGCCAGGCT

CCAGGGAAGGGTCTAGAGTGGGTCTCATGTATTGATAATCTGGGTAGTCCTACATACTAC

GCAGACTCCGTGAAGGGCCGGTTCACCATCTCCCGCGACAATTCCAAGAACACGCTGTAT

CTGCAAATGAACAGCCTGCGTGCCGAGGACGCCGCGGTATATTACTGTGCGAAAACGATT

TCTCATCAGTATGATAGGTTTGACTACTGGGGTCAGGGAACCCTGGTCACCGTCTCGAGC

BMS2h-556
(SEQ ID NO: 674)
GAGGTGCAGCTGTTGGAGTCTGGGGGAGGCTTGGTACAGCCTGGGGGGTCCCTGCGTCTC

TCCTGTGCAGCCTCCGGATTCACCTTTGGGGAGGAGGAGATGAGTTGGGTCCGCCAGGCT

CCAGGGAAGGGTCTAGAGTGGGTCTCATCGATTGATGAGGGGGTCGGTGGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAATGGACG

CCGCATAAGCAGTTGTCGTTTGACTACTGGGGTCAGGGAACCCTGGTCACCGTCTCGAGC

BMS2h-557
(SEQ ID NO: 675)
GAGGTGCAGCTGTTGGAGTCTGGGGGAGGCTTGGTACAGCCTGGGGGGTCCCTGCGTCTC

TCCTGTGCAGCCTCCGGATTCAGCTTTGCTGATGAGTATATGGTTTGGGCCCGCCAGGCT

CCAGGGAAGGGTCTAGAGTGGGTCTCAGAGATTGATCCGTTGGGTACTGGGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAATATGGG

ACGGCTTTTGACTACTGGGGTCAGGGAACCCTGGTCACCGTCTCGAGC

TABLE 2-continued

Human Anti-CD40L VH Domain Encoding Nucleotide Sequences

BMS2h-558
(SEQ ID NO: 676)
GAGGTGCAGCTGTTGGAGTCTGGGGGAGGCTTGGTACAGCCTGGGGGGTCCCTGCGCCTC

TCCTGTGCAGCCTCCGGATTCACCTTTTCTACGCATGATATGATGTGGGTCCGCCAGGCT

CCAGGGAAGGGTCTAGAGTGGGTCTCATCGATTTCTGATGATGGTATTAGTACATACTAC

GCAGACTCCGTGAAGGGCCGGTTCACCATTTCCCGCGACAATTCCAAGAACACGCTGTAT

CTGCAAATGAACAGCCTGCGTGCCGAGGATACCGCGGTATATTACTGTGCGAAACCTGAT

ATGTCTCTTATTGAGTTTGACTACTGGGGTCAGGGAACCCTGGTCACCGTCTCGAGC

BMS2h-559
(SEQ ID NO: 677)
GAGGTGCAGCTGTTGGAGTCTGGGGGAGGCTTGGTACAGCCTGGGGGGTCCCTGCGTCTC

TCCTGTGCAGCCTCCGGATTCACCTTTGATGGTACTCCGATGGTTTGGGTCCGCCAGGCT

CCAGGGAAGGGTCTAGAGTGGGTCTCAGGGATTAGTGGTGATGGTAGGAATACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGGAACCTTAT

GCGCTTACTTCGTCTAAGCCTTTTGACTACTGGGGTCAGGGAACCCTGGTCACCGTCTCG

AGC

BMS2h-56
(SEQ ID NO: 678)
GAGGTGCAGCTGTTGGAGTCTGGGGGAGGCTTGGTACAGCCTGGGGGGTCCCTGCGTCTC

TCCTGTGCAGCCTCCGGATTCACCTTTAATGATTATACTATGGGTTGGGTCCGCCAGGCT

CCAGGGAAGGGTCTAGAGTGGGTCTCATGGATTCATGGGACTGGTGGTCAGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGCTTTG

GCTGATAGGAGTGGGGGGGTTGTTGAGTTTGACTACTGGGGTCAGGGAACCCTGGTCACC

GTCTCGAGC

BMS2h-560
(SEQ ID NO: 679)
GAGGTGCAGCTGTTGGAGTCTGGGGGAGGCTTGGTACAGCCTGGGGGGTCCCTGCGTCTC

TCCTGTGCAGCCTCCGGATTCACCTTTGAGGCGGAGACGATGGCTTGGGTCCGCCAGGCT

CCAGGGAAGGGTCTAGAGTGGGTCTCATGTATTAGTAATGATGGTAATACGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGAGTCT

CTGATTAGTCCTGGTCTTTTTGACTACTGGGGTCAGGGAACCCTGGTCACCGTCTCGAGC

BMS2h-561
(SEQ ID NO: 680)
GAGGTGCAGCTGTTGGAGTCTGGGGGAGGCTTGGTACAGCCTGGGGGGTCCCTGCGTCTC

TCCTGTGCAGCCTCCGGATTCACCTTTACTGGTGAGTATATGAATTGGGTCCGCCAGGCT

CCAGGGAAGGGTCTAGAGTGGGTCTCAACTATTAATGAGACTGGTTATATGACATACTAC

GCAGACTCCGTGAAGGGCCGGTTCACCATCTCCCGCGACAATTCCAAGAACACGCTGTAT

CTGCAAATGAATAGCCTGCGTGCCGAGGACACCGCGGTATATTACTGTGCGAAACTTTCT

ACGAGGGGGGTGCCTTTTGACTACTGGGGTCAGGGAACCCTGGTCACCGTCTCGAGC

TABLE 2-continued

Human Anti-CD40L VH Domain Encoding Nucleotide Sequences

BMS2h-562
(SEQ ID NO: 681)
GAGGTGCAGCTGTTGGAGTCTGGGGGAGGCTTGGTACAGCCTGGGGGGTCCCTGCGTCTC

TCCTGTGCAGCCTCCGGATTCACCTTTAGGTCGTATGATATGGGTTGGGTCCGCCAGGCT

CCAGGGAAGGGTCTAGAGTGGGTCTCAACGATTTCGCCTATGGGTGTTTTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAATCTAAT

CAGCATGCTCATGATCCTTTTGACTACTGGGGTCAGGGAACCCTGGTCACCGTCTCGAGC

BMS2h-563
(SEQ ID NO: 682)
GAGGTGCAGCTGTTGGAGTCTGGGGGAGGCTTGGTACAGCCTGGGGGGTCCCTGCGTCTC

TCCTGTGCAGCCTCCGGATTCACCTTTAGTGATTATGATATGGGTTGGGTCCGCCAGGCT

CCAGGGAAGGGTCTGGAGTGGGTCTCAAGTATTTCGCCTATGGGTACGTTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGCTGCT

TTGACTGAGCCTATGTTTGACTACTGGGGTCAGGGAACCCTGGTCACCGTCTCGAGC

BMS2h-564
(SEQ ID NO: 683)
GAGGTGCAGCTGTTGGAGTCTGGGGGAGGCTTGGTACAGCCTGGGGGGTCCCTGCGTCTC

TCCTGTGCAGCCTCCGGATTCACCTTTCGTGATTATGATATGGGTTGGGTCCGCCAGGCT

CCAGGGAAGGGTCTAGAGTGGGTCTCAACTATTTCTCCTCTTGGTCATTTTACATACTAC

GCAGACTCCGTGAAGGGCCGGTCCACCATCTCCCGCGACAATTCCAAGAACACGCTGTAT

CTGCAAATGAACAGCCTGCGTGCCGAGGATACCGCGGTATATTACTGTGCGAAAGCTGAG

GAGGCTTTTGACTACTGGGGTCAGGGAACCCTGGTCACCGTCTCGAGC

BMS2h-565
(SEQ ID NO: 684)
GAGGTGCAGCTGTTGGAGTCTGGGGGAGGCTTGGTACAGCCTGGGGGGTCCCTGCGCCTC

TCCTGTGCAGCCTCCGGATTCGCCTTTCCTAGSTATGGTATGACGTGGGTCCGCCAGGCT

CCAGGGAAGGGTCTAGAGTGGGTCTCAAATATTGATCAGTTTGGTATGAAGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGGAAGAGTAT

GCTTCGTTTGACTACTGGGGTCAGGGAACCCTGGTCACCGTCTCGAGC

BMS2h-566
(SEQ ID NO: 685)
GAGGTGCAGCTGTTGGAGTCTGGGGGAGGCTTGGTACAGCCTGGGGGGTCCCTGCGTCTC

TCCTGTGCAGCCTCCGGATTCACCTTTGATAAGTATGATATGGGTTGGGTCCGCCAGGCT

CCAGGGAAGGGTCTAGAGTGGGTCTCAACGATTTCGCCTATGGGTGTTTTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGGGCGG

GGTAATACTTCGGATTTTGACTACTGGGGTCAGGGAACCCTGGTCACCGTCTCGAGC

BMS2h-567
(SEQ ID NO: 686)
GAGGTGCAGCTGTTGGAGTCTGGGGGAGGCTTGGTACAGCCTGGGGGGTCCCTGCGTCTC

TCCTGTGCAGCCTCCGGATTCACCTTTAGTAATTATGATATGGCGTGGGTCCGCCAGGCT

CCAGGGAAGGGTCTAGAGTGGGTCTCAACTATTTCTGGGGCGGGTCATTTTACATACTAC

TABLE 2-continued

Human Anti-CD40L VH Domain Encoding Nucleotide Sequences

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAAGTTTT

CCGCGTGATGAGTTTGACTACTGGGGTCAGGGAACCCTGGTCACCGTCTCGAGC

BMS2h-568 (SEQ ID NO: 687)
GAGGTGCAGCTGTTGGAGTCTGGGGGAGGCTTGGTACAGCCTGGGGGGTCCCTGCGTCTC

TCCTGTGCAGCCTCCGGATTCACCTTTCCGAAGTATGAGATGAGGTGGGTCCGCCAGGCT

CCAGGGAAGGGTCTAGAGTGGGTCTCAGAGATTGGTCTGGATGGTTCGCCTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAATGGGG

GATCCGAATGGTTTTGACTACTGGGGTCAGGGAACCCTGGTCACCGTCTCGAGC

BMS2h-569 (SEQ ID NO: 688)
GAGGTGCAGCTGTTGGAGTCTGGGGGAGGCTTGGTACAGCCTGGGGGGTCCCTGCGTCTC

TCCTGTGCAGCCTCCGGATTCACCTTTCCGACTAGTGAGATGGATTGGGTCCGCCAGGCT

CCAGGGAAGGGTCTGGAGTGGGTCTCAGGTATTGGGCCTGATGGTTTGACTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACATGCG

GATTGGTTTGACTACTGGGGTCAGGGAACCCTGGTCACCGTCTCGAGC

BMS2h-57 (SEQ ID NO: 689)
GAGGTGCAGCTGTTGGAGTCTGGGGGAGGCTTGGTACAGCCTGGGGGGTCCCTGCGTCTC

TCCTGTGCAGCCTCCGGATTCACCTTTTCTGAGTATGATATGTATTGGGTCCGCCAGGCT

CCAGGGAAGGGTCTAGAGTGGGTCTCATGGATTGATACTGATGGTGGGGATACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCTGGT

CTGAAGTTTGACTACTGGGGTCAGGGAACCCTGGTCACCGTCTCGAGC

BMS2h-570 (SEQ ID NO: 690)
GAGGTGCAGCTGTTGGAGTCTGGGGGAGGCCTGGTACAGCCTGGGGGGTCCCTGCGTCTC

TCCTGTACAGCCTCCGGATTCACCTTTGAGAATGCTTCTATGCAGTGGGTCCGCCAGGCT

CCAGGGAAGGGTCTAGAGTGGGTCTCATCTATTGAGGGGCAGGGTAATGCTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAAGTTCG

TCTTGGTCTTTTGACTACTGGGGTCAGGGAACCCTGGTCACCGTCTCGAGC

BMS2h-571 (SEQ ID NO: 691)
GAGGTGCAGCTGTTGGAGTCTGGGGGAGGCTTGGTACAGCCTGGGGGGTCCCTGCGTCTC

TCCTGTGCAGCCTCCGGATTCACCTTTACGCGTAATGAGATGGGGTGGGTCCGCCAGGCT

CCAGGGAAGGGTCTAGAGTGGGTCTCAACTATTACGCCGACTGGTACGTTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAACGGAT

CCTGGTAATAGGTATTTTGACTACTGGGGTCAGGGAACCCTGGTCACCGTCTCGAGC

TABLE 2-continued

Human Anti-CD40L VH Domain Encoding Nucleotide Sequences

BMS2h-572
(SEQ ID NO: 692)
GAGGTGCAGCTGTTGGAGTCTGGGGGAGGCTTGGTACAGCCTGGGGGGTCCCTGCGTCTC

TCCTGTGCAGCCTCCGGATTCACCTTTAATTGGCAGCTGATGGGTTGGGTCCGCCAGGCT

CCAGGGAAGGGTCTAGAGTGGGTCTCAGGTATTGAGGGTCCTGGTGATGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGTTGGG

AAGGAGAGTAATTTTGACTACCGGGGTCAGGGAACCGTGGTCACCGTCTCGAGC

BMS2h-572-1
(SEQ ID NO: 693)
GAGGTGCAGCTGTTGGAGTCTGGGGGAGGCTTGGTACAGCCTGGGGGGTCCCTGCGTCTC

TCCTGTGCAGCCTCCGGATTCACCTTTAATTGGCAGCTGATGGGTTGGTTCCGCCAGGCT

CCAGGGAAGGGTCTAGAGTGGGTCTCAGGTATTGAGGGTCCTGGTGATGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGTTGGG

AAGGAGAGTAATTTTGACTACCGGGGTCAGGGGACCCTGGTCACCGTCTCGAGC

BMS2h-572-10
(SEQ ID NO: 694)
GAGGTGCAGCTGTTGGAGTCTGGTGGAGGCTTGGTACAGCCTGGGGGGTCCCTGCGTCTC

TCCTGTGCAGCCTCCGGATTCACCTTTAATTGGCAGCTGATGGGTTGGGTCCGCCAGGCT

CCAGGGAAGGGTCTAGAGTGGGTCTCAGGTATTGAGGGTCCTGGTGATGTTACATACTAC

GCAGACTCCGTGAAGGGCCGGTTCACCGTCTCCCGCGACAATTCCAAGAACACGCTGTAT

CTGCAAATGAACAGCCTGCGTGCCGAGGACACCGCGGTATATTACTGTGCGAAAGTTGGG

AAGGAGAGTAATTCTGACTACCGGGGTCAGGGAACCCTGGTCACCGTCTCGAGC

BMS2h-572-11
(SEQ ID NO: 695)
GAGGTGCAGCTGTTGGAGTCTGGGGGAGGCTTGGTACAGCCTGGGGGGTCCCTGCGTCTC

TCCTGTGCAGCCTCAGGATTCACCTTTAATTGGCAGCTGATGGGTTGGGTCCGCCAGGCT

CCAGGGAAGGGTCTAGAGTGGGTCTCAGGTATTGAGGGTCCTGGTGATGTTACATACTAC

GCAGATTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGTGAAAGTTGGG

AAGGAGAGTAATTCTGACTACCGGGGTCAGGGAACCCAGGTCACCGTCTCGAGC

BMS2h-572-12
(SEQ ID NO: 696)
GAGGTGCAGCTGTTGGAGTCTGGGGGAGGCTTGGTACAGCCTGGGGGGTCCCTGCGTCTC

TCCTGTGCAGCCTCCGGATTCACCTTTAATTGGCAGCTGATGGGTTGGGCCCGCCAGGCT

CCAGGGAAGGGTCTAGAGTGGGTCTCAGGTATTGAGGGTCCTGGTGATGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGTTGGG

AAGGAGAGTAATTCTGACTACCGGGGTCAGGGAACCCTGGTCACCGTCTCGAGC

BMS2h-572-13
(SEQ ID NO: 697)
GAGGTGCAGTTGTTGGAGTCTGGGGGAGGCTTGGTACAGCCTGGGGGGTCCCTGCGTCTC

TCCTGTGCAGCCTCCGGATTCACCTTTAATTGGCAGCTGATGGGTTGGGCCCGCCAGGCT

CCAGGGAAGGGTCTAGAGTGGGTCTCAGGTATTGAGGGTCCTGGTGATGTTACATACTAC

TABLE 2-continued

Human Anti-CD40L VH Domain Encoding Nucleotide Sequences

GCAGACTCCGTGAAGGACCGGTTCACCATCTCCCGCGACAATTCCAAGAACACGCTGTAT

CTGCTAATGAACAGCCTGCGTGCCGAGGACACCGCGGTATATTACTGTGCGAAAGTAGGG

AAGGAGAGTAATTTTGACTACTGGGGTCAGGGAACCCTGGTCACCGTCTCGAGC

BMS2h-572-14
(SEQ ID NO: 696)
GAGGTGCAGCTGTTGGAGTCTGGGGGAGGCTTGGTACAGCCTGGGGGGTCCCTGCGTCTC

TCCTGTGCAGCCTCCGGATTCACCTTTAATTGGCAGCTGATGGGTTGGGTCCGCCAGGCT

CCAGGGAAGGGTCTAGAGTGGGTCTCAGGCATTGAGGGTCCTGGTGATGTTACATACTAC

GCAGACTCAGTGAAGGGCCGGTTCACCATCTCCCGCGACAATACCAAGAACACGCTGTAT

CTGCAAATGAACAGCCTGCGTGCCGAGGACACCGCGGTATATTACTGTGTGAAAGTTGGG

AAGGAGAGTAATTCTGACTACCGGGGTCAGGGAACCCTGGTCACCGTCTCGAGC

BMS2h-572-15
(SEQ ID NO: 699)
GAGGTGCGGCTATTGGAGTCTGGGGGAGGCTTGGTACAGCCTGGGGGGTCCCTGCGTCTC

TCCTGTGCAGCCTCCGGATTCAACTTTAATTGGCAGCTGATGGGTTGGATCCGCCAGGCT

CCAGGGAAGGGTCTAGAGTGGGTCTCAGGTATTGAGGGTCCTGGTGATGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCAGTATATTACTGTGCGAAAGTTGGG

AAGGAGAGTAATTCTGACTACCGGGGTCAGGGAACCCTGGTCACCGTCTCGAGC

BMS2h-572-16
(SEQ ID NO: 700)
GAGGTGCAGCTGTTGGAGTCTGGGGGAGGCTTGGTACGGCCTGGGGGGTCACTGCGTCTC

TCCTGTGTAGCCTCCGGATTCACCTTTAATTGGCAGCTGATGGGTTGGGTCCGCCAGGCT

CCAGGGAAGGGTCTAGAGTGGGTCTCAGGTATTGAGGGTCCTGGTGATGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGTTGGG

AAGGAGAGTAATTTTGACTACCGGGGTCAGGGAACCCTGGTCACCGTCTCGAGC

BMS2h-572-17
(SEQ ID NO: 701)
GAGGTGCAGCTGTTGGAGTCTGGGGGAGGCTTGGTACAGACTGGGGGGTCCCTGCGTCTC

TCCTGTGCAGCCTCCGGATTCACCTATAATTGGCAGCTGATGGGTTGGGTCCGCCAGGCT

CCAGGGAAGGGTCTAGAGTGGGTCTCAGGTATTGAGGGTCCTGGTGATGTTACATACTAC

GCAGACTCCGTGAAGGGCCGGTTCACCATCTCCCGCGACAATTCCAAGAACACGCTGTAT

CTGCAAATGAACAGCCTGCGTGCCGATGACACCGCGGTATATTACTGTGTGAAAGTTGGG

AAGGAGAGTAATTTTGACTACCGGGGTCACGGAACCCTGGTCACCGTCTCGAGC

BMS2h-572-18
(SEQ ID NO: 702)
GAGGTGCAGCTGTTGGAGTCTGGGGGAGGCTTGGTACAGCCTGGGGGGTCCCTGCGTCTC

TCCTGTGCAGCCTCCGGATTCACCTTTAATTGGCAGCTGATGGGTTGGGTCCGCAAGGCT

CCTGGGAAGGGTCTAGAGTGGGTCTCAGGTATTGAGGGTCCTGGTGATGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGTTGGG

AAGGAGAGTAATTTTGACTACCGGGGTCAGGGAACCCTGGTCACCGTCTCGAGC

TABLE 2-continued

Human Anti-CD40L VH Domain Encoding Nucleotide Sequences

BMS2h-572-19
(SEQ ID NO: 703)
GAGGTGCAGCTGTTGGAGTCTGGGGGAGGCTTGGTACAGCCTGGGGGGTCCCTGCGTCTC

TCCTGTGCAGCCTCCGGATTCACCTTTAATTGGCAGCTGATGGGTTGGGTCCGCCAGGCC

CCAGGGAAGGGTCTAGAGTGGGTCTCAGGTATTGAGGGTCCTGGTGATGTTACATACTAC

GCAGACTCCGTGAAGGGCCGGTTCACCATCTCCCGCGACAATACCAAGAACACGCTGTAT

CTGCAAATGAACAGCCTGCGTGCCGAGGACACCGCGGTATATTACTGTGCGAAAGTTGGG

AAGGAGAGTAATTTTGACTACCGGGGTCAGGGAACCCTGGTCACCGTCTCGAGC

BMS2h-572-2
(SEQ ID NO: 704)
GAGGTGCAGCTGTTGGAGTCTGGGGGAGGCTTGGTACAGCCTGGGGGGTCCCTGCGCCTC

TCCTGTGCAGCCTCCGGATTCACCTTTAATTGGCAGCTGATGGGTTGGGTCCGCCAGGCT

CCAGGGAAGGGTCTTGAGTGGGTCTCAGGTATTGAGGGTCCTGGTGATGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGTTGGG

AAGGAGAGTAAGTTTGACTACCTGGGTCAGGGAACCCTGGTCACCGTCTCGAGC

BMS2h-572-21
(SEQ ID NO: 705)
GAGGTGCAGCTGTTGGAGTCTGGGGGAGGCTTGGTACAGCCTGGGGGGTCCCTGCGTCTC

TCCTGTGCAGCCTCCGGATTCACCTTTAATTGGCAGCTGATGGGTTGGGTCCGCCAGGCT

CCAGGGAAGGGTCTAGAGTGGGTCTCAGGTATTGAGGGTCCTGGTGATGTTACATACTAC

GCAGAATCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGTTGGG

AAGGAGAGTAATCTTGACTACCGGGGTCAGGGAACCCTGGTCACCGTCTCGAGC

BMS2h-572-22
(SEQ ID NO: 706)
GAGGTGCAGCTGTTTGAGTCTGGGGGAGGCTCGGTACAGCCTGGGGGGTCCCTGCGTCTC

TCCTGTGCAGCCTCCGGATTCACCTTTAATTGGCAGCTGATGGGTTGGGTCCGCCAGGCT

CCAGGGAAGGGTCTAGAGTGGGTCTCAGGTATTGAGGGTCCTGGTGATGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGTTGGG

AAGGAGAGTAATTCTGACTACCGGGGTCAGGGGACCCTGGTCACCGTCTCGAGC

BMS2h-572-23
(SEQ ID NO: 707)
GAGGTGCAGCTGTTGGAGTCTGGGGGAGGCTTGGTACAGCCTGGGGGGTCCCTGCGTCTC

ACCTGTGCAGCCTCCGGATTCACCTTTAATTGGCAGCTGATGGGTTGGGTCCGCCAGGCT

CCAGGGAAGGGTCTAGAGTGGGTCTCGGGTATTGAGGGTCCTGGTGATGTTACATACTAC

GCAGACTCCGTGAAGGGCCGGTTCATCATCTCCCGCGACAATTCCAAGAACACGCTATAT

CTGCAAATGAACAGCCTGCGTGCCGAGGACACCGCGGTATATTACTGTGCGAAAGTTGGG

AAGGAGAGTAATTCTGACTACCGGGGTCAGGGAACCCTGGTCACCGTCTCGAGC

BMS2h-572-24
(SEQ ID NO: 708)
GAGGTGCAGCTGTTGGAGTCTGGGGGAGGCTTGGTACAGCCTGGGGGGTCCCTGCGTCTC

TCCTGTGCAGCCTCCGGATTCACCTTTAATTGGCAGCTGATGGGTTGGGTCCGCCAGGCT

CCAGGGAAGGGTCTAGAGTGGGTCTCAGGTATTGAGGGTCCTGGTGATGTTACATACTAC

TABLE 2-continued

Human Anti-CD40L VH Domain Encoding Nucleotide Sequences

GCGGACTCCGTGAAGGGCCGGTTCACCATCTCCCGCGACAATTCCACGAACACGCTGTAT
CTGCAAATGAACAGCCTGCGTGCCGAGGACACCGCGGTATATTACTGTGCGAAAGTTGGG
AAGGAGAGTGAATTTGACTACCGGGGTCAGGGAACCCTGGTCACCGTCTCGAGC

BMS2h-572-3
(SEQ ID NO: 709)
GAGGTGCGGCTGTTGGAGTCTGGGGGAGGCTTGGTACAGCCTGGGGGGTCCCTGCGTCTC
TCCTGTGCAGCCTCCGGATTCACCTTTAATTGGCAGCTGATGGGTTGGGTCCGCCAGGCT
CCAGGGAAGGGTCTAGAGTGGGTGTCAGGTATTGAGGGTCCTGGTGATGTTACATACTAC
GCAGACTCCGTGAAGGGCCGGTTCACCATCACCCGCGACAATTCCAAGAACACGCTGTAT
CTGCAAATGAACAGCCTGCGTGCCGAGGACACCGCGGTATATTACTGTGTGAAAGTTGGG
AAGGAGAGTAATCTTGACTACCGGGGTCAGGGAACCCTGGTCACCGTCTCGAGC

BMS2h-572-4
(SEQ ID NO: 710)
GAGGTGCAGCTGTTGGTGTCTGGGGGAGGCCTGGTACAGCCTGGGGGGTCCCTGCGTCTC
TCCTGTGCAGCCTCCGGATTCACCTTTAATTGGCAGCTGATGGGTTGGGTCCGCCAGGCT
CCAGGGAAGGGTCTAGAGTGGGTCTCAGGTATTGAGGGTCCTGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGTTGGG
AAGGAGAGTAATTTTGACTACCGGGGTCAGGGAACCCTGGTCACCGTCTCGAGC

BMS2h-572-5
(SEQ ID NO: 711)
GAGGTGCAGCTGTTGGTGTCTGGGGGAGGCTTGGTACAGCCTGGGGGGTCCCTGCGTCTC
TCCTGTGCAGCCTCCGGATTCACCTTTAATTGGCAGCTGATGGGTTGGGTCCGCCAGGCT
CCAGGGAAGGGTCTAGAGTGGGTCTCAGGTATTGAGGGTCCTGGTGATGTTACATACTAC
GCAGACTCCGTGAAGGGCCGGTTCACCATCTCCCGCGACAATTCCAAGAACATGCTGTAT
CTGCAAATGAACGGCCTGCGTGCCGAGGACACCGCGGTATATTACTGTGCGAAAGTTGGG
AAGGAGAGTAATTTTGACTACCGGGGTCAGGGAACCCTGGTCACCGTCTCGAGC

BMS2h-572-6
(SEQ ID NO: 712)
GAGGTGCAGCTGTTGGAGTCTGGGGGAGGCTTGGTACAGCCTGGGGGGTCCCTGCGTCTC
TCCTGTGCAGCCTCCGGATTCACCTTTAATTGGCAGCTGATGGGTTGGGTCCGGCAGGCT
CCAGGGAAGGGTCTAGAGTGGGTCTCAGGTATTGAGGGTCCAGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGTGAAAGTTGGG
AAGGAGAGTAATTCTGACTACCGGGGTCAGGGAACCCTGGTCACCGTATCGAGC

BMS2h-572-801
(SEQ ID NO: 713)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGTGGCAGCTCATGGGTGGGCCCGGCAGGCT
CCAGGGAAGGGTCTAGAGTGGGTCTCAGGTATTGAGGGTCCAGGTGATGTTACATACTAC
GCAGACCCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGTGAAAGTTGGG
AAGGAGAGTAATTCTGACTACCGGGGTCAGGGAACCCTGGTCACCGTATCGAGC

TABLE 2-continued

Human Anti-CD40L VH Domain Encoding Nucleotide Sequences

BMS2h-572-602
(SEQ ID NO: 714)
GAGGTGCAGCTGTTGGAGTCTGGGGGAGGCTTGGTACAGCCTGGGGGGTCCCTGCGTCTC

TCCTGTGCAGCCTCCGGATTCACCTTTAAGTGGCACCTGATGGGGTGGGTCCGGCAGGCT

CCAGGGAAGGGTCTAGAGTGGGTCTCAGGTATTGAGGGTCCAGGTGATGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGTGAAAGTTGGG

AAGGAGAGTAGTTCTGACTACCGGGGTCAGGGAACCCTGGTCACCGTATCGAGC

BMS2h-572-603
(SEQ ID NO: 715)
GAGGTGCAGCTGTTGGAGTCTGGGGGAGGCTTGGTACAGCCTGGGGGGTCCCTGCGTCTC

TCCTGTGCAGCCTCCGGATTCACCTTTAACTGGCACCTGATGGCCTGGGCCCGGCAGGCT

CCAGGGAAGGGTCTAGAGTGGGTGTCAGGTATTGAGGGTCCAGGTGATGTTACATACTAC

GCAGAGTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGTGAAAGTTGGG

AAGGAGAGTAATTCTGACTACCGGGGTCAGGGAACCCTGGTCACCGTATCGAGC

BMS2h-572-604
(SEQ ID NO: 716)
GAGGTGCAGCTGTTGGAGTCTGGGGGAGGCTTGGTACAGCCTGGGGGGTCCCTGCGTCTC

TCCTGTGCAGCCTCCGGATTCACCTTTAAGTGGCAGCTGATGGGCTGGGTCCGGCAGGCT

CCAGGGAAGGGTCTCGAGTGGGTGTCAGGTATTGAGGGTCCAGGTGATGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGTGAAAGTTGGG

AAGGAGAGTAATTCTGACTACCGGGGTCAGGGAACCCTGGTCACCGTATCGAGC

BMS2h-572-605
(SEQ ID NO: 717)
GAGGTGCAGCTGTTGGAGTCTGGGGGAGGCTTGGTGCAGCCTGGGGGGTCCCTGCGTCTC

TCCTGTGCAGCCTCCGGATTCACCTTTAAGTGGCAGCTGATGGCCTGGGCCCGGCAGGCT

CCAGGGAAGGGTCTAGAGTGGGTCTCAGGTATTGAGGGTCCAGGTGATATTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGTGAAAGTTGGG

AAGGAGAGTAATTCTGACTACCGGGGTCAGGGAACCCTGGTCACCGTATCGAGC

BMS2h-572-606
(SEQ ID NO: 718)
GAGGTGCAGCTGTTGGAGTCTGGGGGAGGCTTGGTACAGCCTGGGGGGTCCCTGCGTCTC

TCCTGTGCAGCCTCCGGATTCACCTTTAACTGGCACTTGATGGGCTGGGCCCGGCAGGCT

CCAGGGAAGGGTCTAGAGTGGGTCTCAGGTATTGAGGGTCCAGGTGATGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGTGAAAGTTGGG

AAGGAGAGTAATTCTGACTACCGGGGTCAGGGAACCCTGGTCACCGTATCGAGC

BMS2h-572-607
(SEQ ID NO: 719)
GAGGTGCAGCTGTTGGAGTCTGGGGGAGGCTTGGTACAGCCTGGGGGGTCCCTGCGTCTC

TCCTGTGCAGCCTCCGGATTCACCTTTAAGTGGCAGCTCATGGGTGGGCCCGGCAGGCT

CCAGGGAAGGGTCTAGAGTGGGTCTCAGGTATTGAGGGTCCAGGTGATGTTACATACTAC

TABLE 2-continued

Human Anti-CD40L VH Domain Encoding Nucleotide Sequences

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGTGAAAGTTGGG

AAGGAGAGTAATTCTGACTACCGGGGTCAGGGAACCCTGGTCACCGTATCGAGC

BMS2h-572-608
(SEQ ID NO: 720)
GAGGTGCAGCTGTTGGAGTCTGGGGGAGGCTTGGTACAGCCTGGGGGGTCCCTGCGTCTC

TCCTGTGCAGCCTCCGGATTCACCTTTAACTGGGAGCTGATGGGCTGGGCCCGGCAGGCT

CCAGGGAAGGGTCTAGAGTGGGTCTCAGGTATTGAGGGTCCAGGTGATGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGTGAAAGTTGGG

AAGGAGAGTAATTCTGACTACCGGGGTCAGGGAACCCTGGTCACCGTATCGAGC

BMS2h-572-609
(SEQ ID NO: 721)
GAGGTGCAGCTGTTGGAGTCTGGGGGAGGCTTGGTACAGCCTGGGGGGTCCCTGCGTCTC

TCCTGTGCAGCCTCCGGATTCACCTTTAACTGGCAGCTCATGGGCTGGGCCCGGCAGGCT

CCAGGGAAGGGTCTAGAGTGGGTCTCAGGTATTGAGGGTCCAGGTGATGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGTGAAAGTTGGG

AAGGAGAGTAATTCTGACTACCGGGGTCAGGGAACCCTGGTCACCGTATCGAGC

BMS2h-572-610
(SEQ ID NO: 722)
GAGGTGCAGCTGTTGGAGTCTGGGGGAGGCTTGGTACAGCCTGGGGGGTCCCTGCGTCTC

TCCTGTGCAGCCTCCGGATTCACCTTTAATTGGCAGCTGATGGGTTGGGTCCGGCAGGCT

CCAGGGAAGGGTCTAGAGTGGGTCTCAGGTATTGAGGGTCCAGGTGATGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGTGAAAGTGGGC

AAGGACAGCAAGTCCGACTACCGGGGTCAGGGAACCCTGGTCACCGTATCGAGC

BMS2h-572-611
(SEQ ID NO: 723)
GAGGTGCAGCTGTTGGAGTCTGGGGGAGGCTTGGTACAGCCTGGGGGGTCCCTGCGTCTC

TCCTGTGCAGCCTCCGGATTCACCTTTAATTGGCAGCTGATGGGTTGGGTCCGGCGGGCT

CCAGGGAAGGGTCTAGAGTGGGTCTCAGGTATTGAGGGTCCAGGTGATGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGTGAAAGTCGGG

AAGGACAGCAAGTCGGACTACCGGGGTCAGGGAACCCTGGTCACCGTATCGAGC

BMS2h-572-612
(SEQ ID NO: 724)
GAGGTGCAGCTGTTGGAGTCTGGGGGAGGCTTGGTACAGCCTGGGGGGTCCCTGCGTCTC

TCCTGTGCAGCCTCCGGATTCACCTTTAATTGGCAGCTGATGGGTTGGGTCCGGCAGGCT

CCAGGGAAGGGTCTAGAGTGGGTCTCAGGTATTGAGGGTCCAGGTGATGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGTGAAAGTCGGG

AAGGACAGCAACTCGGACTACCGGGGTCAGGGAACCCTGGTCACCGTATCGAGC

TABLE 2-continued

Human Anti-CD40L VH Domain Encoding Nucleotide Sequences

BMS2h-572-813
(SEQ ID NO: 725)
GAGGTGCAGCTGTTGGAGTCTGGGGGAGGCTTGGCACAGCCTGGGGGGTCCCTGCGTCTC

TCCTGTGCAGCCTCCGGATTCACCTTTAATTGGCAGCTGATGGGTTGGGTCCGGCAGGCT

CCAGGGAAGGGTCTAGAGTGGGTCTCAGGTATTGAGGGTCCAGGTGATGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGTGAAAGTGGGC

AAGGACAGCAAGTCCGACTACCGGGGTCAGGGAACCCTGGTCACCGTATCGAGC

BMS2h-572-614
(SEQ ID NO: 726)
GAGGTGCAGCTGTTGGAGTCTGGGGGAGGCTTGGTACAGCCTGGGGGGTCCCTGCGTCTC

TCCTGTGCAGCCTCCGGATTCACCTTTAATTGGCAGCTGATGGGTTGGGTCCGGCAGGCT

CCAGGGAAGGGTCTAGAGTGGGTCTCAGGTATTGAGGGTCCAGGTGATGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGTGAAAGTGGGG

AAGGACGCCAAGTCGGACTACCGGGGTCAGGGAACCCTGGTCACCGTATCGAGC

BMS2h-572-615
(SEQ ID NO: 727)
GAGGTGCAGCTGTTGGAGTCTGGGGGAGGCTTGGTACAGCCTGGGGGGTCCCTGCGTCTC

TCCTGTGCAGCCTCCGGATTCACCTTTAATTGGCAGCTGATGGGTTGGGTCCGGCAGGCT

CCAGGGAAGGGTCTAGAGTGGGTCTCAGGTATTGAGGGCCCAGGTGATGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGTGAAAGTGGGG

AAGGACAAGAACTCGGACTACCGGGGTCAGGGAACCCTGGTCACCGTATCGAGC

BMS2h-572-616
(SEQ ID NO: 728)
GAGGTGCAGCTGTTGGAGTCTGGGGGAGGCTTGGTACAGCCTGGGGGGTCCCTGCGTCTC

TCCTGTGCAGCCTCCGGATTCACCTTTAATTGGCAGCTGATGGGTTGGGTCCGGCAGGCT

CCAGGGAAGGGTCTAGAGTGGGTCTCAGGTATTGAGGGTCCAGGTGATGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGTGAAAGTGGGG

AAGGAGAGCAAGTCCGACTACCGGGGTCAGGGAACCCTGGTCACCGTATCGAGC

BMS2h-572-617
(SEQ ID NO: 729)
GAGGTGCAGCTGTTGGAGTCTGGGGGAGGCTTGGTACAGCCTGGGGGGTCCCTGCGTCTC

TCCTGTGCAGCCTCCGGATTCACCTTTAATTGGCAGCTGATGGGTTGGGTCCGGCAGGCT

CCAGGGAAGGGTCTAGAGTGGGTCTCAGGTATTGAGGGTCCAGGTGATGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGTGAAAGTGGGG

AGGGACAGCAAGTCGGACTACCGGGGTCAGGGAACCCTGGTCACCGTATCGAGC

BMS2h-572-618
(SEQ ID NO: 730)
GAGGTGCAGCTGTTGGAGTCTGGGGGAGGCTTGGTACAGCCTGGGGGGTCCCTGCGTCTC

TCCTGTGCAGCCTCCGGATTCACCTTTAATTGGCAGCTGATGGGTTGGGTCCGGCAGGCT

CCAGGGAAGGGTCTAGAGTGGGTCTCAGGTATTGAGGGTCCAGGTGATGTTACATACTAC

TABLE 2-continued

Human Anti-CD40L VH Domain Encoding Nucleotide Sequences

GCGGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGTGAAAGTCGGG

AAGTACAGCAACTCGGACTACCGGGGTCAGGGAACCCTGGTCACCGTATCGAGC

BMS2h-572-619
(SEQ ID NO: 731)
GAGGTGCAGCTGTTGGAGTCTGGGGGAGGCTTGGTACAGCCTGGGGGGTCCCTGCGTCTC

TCCTGTGCAGCCTCCGGATTCACCTTTAATTGGCAGCTGATGGGTTGGGTCCGGCAGGCT

CCAGGGAAGGGTCTAGAGTGGGTCTCAGGTATTGAGGGTCCAGGTGATGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGTGAAAGTGGGC

AAGGACAGCAGGTCGGACTACCGGGGTCAGGGAACCCTGGTCACCGTATCGAGC

BMS2h-572-620
(SEQ ID NO: 732)
GAGGTGCAGCTGTTGGAGTCTGGGGGAGGCTTGGTACAGCCTGGGGGGTCCCTGCGTCTC

TCCTGTGCAGCCTCCGGATTCACCTTTAATTGGCAGCTGATGGGTTGGGTCCGGCAGGCT

CCAGGGAAGGGTCTAGAGTGGGTCTCAGGTATTGAGGGTCCAGGTGATGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGTGAAAGTGGGG

AAGGACGACAGCTCGGACTACCGGGGTCAGGGAACCCTGGTCACCGTATCGAGC

BMS2h-572-621
(SEQ ID NO: 733)
GAGGTGCAGCTGTTGGAGTTTGGGGGAGGCTTGGTACAGCCTGGGGGGTCCTTGCGTTTT

TCCTGTGCAGCTTCCGGATTCACCTTTAATTGGCAGCTGATGGGTTGGTTCCGGCAGGCT

CCAGGGAAGGGTTTAGAGTGGGTTTCAGGTATTGAGGGTCCAGGTGATGTTACATATTAC

GCAGATTCCGTGAAGGGCCGGTTCACCATTTCCCGCGACAATTCCAAGAACACGCTGTAT

CTGCAAATGAACAGCTTGCGTGCCGAGGATACCGCGGTATATTACTGTGTGAAAGTGGGG

AGGGACAGCAATTCCGACTACCGGGGTCAGGGAACCCTGGTCACCGTATCGAGC

BMS2h-572-622
(SEQ ID NO: 734)
GAGGTGCAGCTGTTGGAGTCTGGGGGAGGCTTGGTACAGCCTGGGGGGTCCCTGCGTCTC

TCCTGTGCAGCCTCCGGATTCACCTTTAATTGGCAGCTGATGGTTGGGTCCGGCAGGCT

CCAGGGAAGGGTCTAGAGTGGGTCTCAGGTATTGAGGGTCCAGGTGATGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGTGAAAGTGGGG

AAGGACAGCACCTCGGACTACCGGGGTCAGGGAACCCTGGTCACCGTATCGAGC

BMS2h-572-623
(SEQ ID NO: 735)
GAGGTGCAGCTGTTGGAGTCTGGGGGAGGCTTGGTACAGCCTGGGGGGTCCCTGCGTCTC

TCCTGTGCAGCCTCCGGATTCACCTTTAATTGGCAGCTGATGGGTTGGGTCCGGCAGGCT

CCAGGGAAGGGTCTAGAGTGGGTCTCAGGTATTGAGGGTCCAGGTGATGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGTGAAAGTGGGG

AAGGAGAGCAGCTCGGACTACCGGGGTCAGGGAACCCTGGTCACCGTATCGAGC

TABLE 2-continued

Human Anti-CD40L VH Domain Encoding Nucleotide Sequences

BMS2h-572-624
(SEQ ID NO: 736)
GAGGTGCAGCTGTTGGAGTCTGGGGGAGGCTTGGTACAGCCTGGGGGGTCCCTGCGTCTC

TCCTGTGCAGCCTCCGGATTCACCTTTAATTGGCAGCTGATGGGTTGGGTCCGGCAGGCT

CCAGGGAAGGGTCTAGAGTGGGTCTCAGGTATTGAGGGTCCAGGTGATGTTACATACTAC

GCAGACTCCGTGAAOOOCCGGTTCACCATCTTCCGCGACAATTCCAAGAACACGCTGTAT

CTGCAAATGAACAGCCTGCGTGCCGAGGATACCGCGGTATATTACTGTGTGAAAGTGGGC

AAGGACAGCGCGTCCGACTACCGGGGTCAGGGAACCCTGGTCACCGTATCGAGC

BMS2h-572-625
(SEQ ID NO: 737)
GAGGTGCAGCTGTTGGAGTCTGGGGGAGGCTTGGTACAGCCTGGGGGGTCCCTGCGTCTC

TCCTGTGCAGCCTCCGGATTCACCTTTAATTGGCAGCTGATGGGTTGGGTCCGGCAGGCT

CCAGGGAAGGGTCTAGAGTGGGTCTCAGGTATTGAGGGTCCAGGTGATGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGTGAAAGTCGGC

AACGACAGCTACTCGGACTACCGGGGTCAGGGAACCCTGGTCACCGTATCGAGC

BMS2h-572-626
(SEQ ID NO: 738)
GAGGTGCAGCTGTTGGAGTCTGGGGGAGGCTTGGTACAGCCTGGGGGGTCCCTGCGTCTC

TCCTGTGCAGCCTCTGGATTCACCTTTAATTGGCAGCTGATGGGTTGGGTCCGGCAGGCT

CCAGGGAAGGGTCTAGAGTGGGTCTCAGGTATTGAGGGTCCAGGTGATGTTACATACTAC

GCAGACTCCGTGAAGGGCCGGTTCACCATCTCCCGCGACAATTCCAAGAACACGCTGTAT

CTGCAAATGAACGGCCTGCGTGCCGAGGACACCGCGGTATATTACTGTGTGAAAGTGGGG

AAGGACAGCAGCTCGGACTACCGGGGTCAGGGAACCCTGGTCACCGTATCGAGC

BMS2h-572-627
(SEQ ID NO: 739)
GAGGTGCAGCTGTTGGAGTCTGGGGGAGGCTTGGTACAGCCTGGGGGGTCCCTGCGTCTC

TCCTGTGCAGCCTCCGGATTCACCTTTAATTGGCAGCTGATGGGTTGGGTCCGGCAGGCT

CCAGGGAAGGGTCTAGAGTGGGTCTCAGGTATTGAGGGTCCAGGTGATGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGATATATTACTGTGTGAAAGTGGGC

AAGGACAGCGCGTCGGACTACCGGGGTCAGGGAACCCTGGTCACCGTATCGAGC

BMS2h-572-630
(SEQ ID NO: 740)
GAGGTGCAGCTGTTGGAGTCTGGGGGAGGCTTGGTACAGCCTGGGGGGTCCCTGCGTCTC

TCCTGTGCAGCCTCCGGATTCACCTTTAAGTGGCAGCTGATGGGCTGGGTCCGGCAGGCT

CCAGGGAAGGGTCTAGAGTGGGTCTCAGGTATTGAGGGTCCAGGTGATGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGTGAAAGTGGGG

AAGGACGCCAAGTCGGACTACCGGGGTCAGGGAACCCTGGTCACCGTATCGAGC

BMS2h-572-631
(SEQ ID NO: 741)
GAGGTGCAGCTGTTGGAGTCTGGGGGAGGCTTGGTACAGCCTGGGGGGTCCCTGCGTCTC

TCCTGTGCAGCCTCCGGATTCACCTTTAAGTGGCAGCTGATGGGCTGGGTCCGGCAGGCT

CCAGGGAAGGGTCTAGAGTGGGTCTCAGGTATTGAGGGTCCAGGTGATGTTACATACTAC

TABLE 2-continued

Human Anti-CD40L VH Domain Encoding Nucleotide Sequences

GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGTGAAAGTGGGC
AAGGACAGCAGGTCGGACTACCGGGGTCAGGGAACCCTGGTCACCGTATCGAGC

BMS2h-572-632

(SEQ ID NO: 742)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGTGGCAGCTGATGGGCTGGGTCCGGCAGGCT
CCAGGGAAGGGTCTAGAGTGGGTCTCAGGTATTGAGGGTCCAGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGTGAAAGTGGGC
AAGGACAGCAAGTCCGACTACCGGGGTCAGGGAACCCTGGTCACCGTATCGAGC

BMS2h-572-633

(SEQ ID NO: 743)
GAGGTGCAGCTGTTGGAGTCTGGGGGAGGCTTGGTACAGCCTGGGGGGTCCCTGCGTCTC
TCCTGTGGAGCCTCCGGATTCACCTTTAACTGGGAGCTGATGGGCTGGGCCCGGCAGGCT
CCAGGGAAGGGTCTAGAGTGGGTCTCAGGTATTGAGGGTCCAGGTGATGTTACATACTAC
GCAGACTCCGTGAAGGGCCGGTTCACCATCTCCCGCGACAATTCCAAGPACACGCTGTAT
CTGCAAATGAACAGCCTGCGTGCCGAGGATACCGCGGTATATTACTGTGTGAAAGTGGGG
AAGGACGCCAAGTCGGACTACCGGGGTCAGGGAACCCTGGTCACCGTATGGAGG

BMS2h-572-634

(SEQ ID NO: 744)
GAGGTGCAGCTGTTGGAGTCTGGGGGAGGCTTGGTACAGCCTGGGGGGTCCGTGCGTCTC
TCCTGTGCAGCCTCCGGATTCACCTTTAACTGGGAGCTGATGGGCTGGGCCCGGCAGGCT
CCAGGGAAGGGTCTAGAGTGGGTCTCAGGTATTGAGGGTCCAGGTGATGTTACATACTAC
GCAGAGTCCGTGAAGGGCCGGTTCACCATCTCCCGCGACAATTCCAAGAACACGCTGTAT
CTGCAAATGAACAGCCTGCGTGCCGAGGAGACCGCGGTATATTACTGTGTGAAAGTGGGC
AAGGACAGGAGGTCGGACTACCGGGGTCAGGGAACCCTGGTCACCGTATCGAGC

BMS2h-572-635

(SEQ ID NO: 745)
GAGGTGCAGCTGTTGGAGTCTGGGGGAGGCTTGGTACAGCCTGGGGGGTCCCTGCGTCTC
TCCTGTGCAGCCTCCGGATTCACCTTTAACTGGGAGCTGATGGGCTGGGCGCGGCAGGCT
CCAGGGAAGGGTCTAGAGTGGGTCTCAGGTATTGAGGGTCCAGGTGATGTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGTGAAAGTGGGC
AAGGACAGCAAGTCCGACTACCGGGGTCAGGGAACCCTGGTCACCGTATCGAGC

BMS2h-572-7

(SEQ ID NO: 746)
GAGGTGCAGCTGTTGGAGTCTGGGGGAGGCTTGGTACAGCCTGGGGGGTCCCTGCGTCTC
TCCTGTGCAGCCTCCGGATTCACCTTTAATTGGCAGCTGATGGGATGGGCCCGCCAGGCT
CCAGGGAAGGGTCTAGAGTGGGTCTCAGGTATTGAGGGTCCTGGTGATGTTACATACTAC
GCAGACTCCGTGAAGGGTCGGTTCACCATCTCGCGCGACAATTCCAAGAACACGCTGTAT
CTACAAATGAACAGCCTGCGTGCCGAGGACTGCGCGGTATATTACTGTGCGAAAGTTGGG
AAGGAGAGTAATTTTGACTACCTGGGTCAGGGAACCCTGGTCACCGTCTCGAGC

TABLE 2-continued

Human Anti-CD40L VH Domain Encoding Nucleotide Sequences

BMS2h-572-8
(SEQ ID NO: 747)
GAGGTGCAGCTGTTGGAGTCTGGGGGAGGCTTGGTACAGCCTGGGGGGTCCCTGCGTCTC

TCCTGTGTAGCCTCCGGATTCACCTTTAATTGGCAGCTGATGGGTTGGGTCCGCCAGGCG

CCAGGGAAGGGTCTAGAGTGGGTCTCAGGTATTGAGGGTCGTGGTGATGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGTCGGG

AAGGAGAGTAATTGTGACTACCGGGGTCAGGGAACCCTGGTCACCGTTTCGAGC

BMS2h-572-9
(SEQ ID NO: 748)
GAGGTGCAGCTGTTGGAGTCTGGGGGAGGCTTGGTACAGCCTGGGGGTGGCTGCGTCTC

TCCTGTGCAGCCTCCGGATTCACCTTTAATTGGCAGCTGATGGGTTGGGTCCGCCAGGCT

CCAGGGAAGGGTCTAGAGTGGGTCTCAGGTATTGAGGGTCCTGGTGATGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGTTGGG

AAGGAGAGTAATTCTGACTACCGGGGTCAGGGAACCCTGGTCACCGTCTCGAGC

BMS2h-573
(SEQ ID NO: 749)
GAGGTGCAGCTGTTGGAGTCTGGGGGAGGCTTGGTACAGCCTGGGGGGTCCCTGCGTCTC

TCCTGTGCAGCGTCCGGATTCACCTTTAGTGGGTGGGAGATGGGTTGGGTCCGCCAGGCT

CCAGGGAAGGGTCTAGAGTGGGTCTCATCTATTGATGAGTCTGGTCTTAATACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGGAAGGTGCG

CCGCAGTATCAGATTACATTTGACTACTGGGGTCAGGGAACCCTGGTCACCGTCTCGAGC

BMS2h-574
(SEQ ID NO: 750)
GAGGTGCAGCTGTTGGAGTCTGGGGGAGGCTTGGTACAGCCTGGGGGGTCCCTGCGTCTC

TCCTGTGCAGCCTCCGGATTCACCTTTCCTAATTATGGGATGTATTGGGTCCGCCAGGCT

CCAGGGAAGGGTCTAGAGTGGGTCTCATATATTTCGCGGAGGGGTTTGTTGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAACGTCG

CATTATATGAATAATGGGTTTGACTACTGGGGTCAGGGAACCCTGGTCACCGTCTCGAGC

BMS2h-575
(SEQ ID NO: 751)
GAGGTGCAGCTGTTGGAGTCTGGGGGAGGCTTGGTACAGCCTGGGGGGTCCCTGCGTCTC

TCCTGTGCAGCCTCCGGATTCACCTTTGTGGATTATACGATGGCTTGGGTCCGCCAGGCT

CCAGGGAAGGGTCTGGAGTGGGTCTCATCTATTAGTCCGATTGGTACTTTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGATCCT

TATGGGATGGAGGATGGTCTGACGTGGTTTGACTACTGGGGTCAGGGAACCCTGGTCACC

GTCTCGAGC

BMS2h-578
(SEQ ID NO: 752)
GAGGTGCAGCTGTTGGAGTCTGGGGGAGGCTTGGTACAGCCTGGGGGGTCCCTGCGTCTC

TCCTGTGCAGCCTCCGGATTCACCTTTGATGCGTATGATATGCAGTGGGTCCGCCAGGCT

TABLE 2-continued

Human Anti-CD40L VH Domain Encoding Nucleotide Sequences

CCAGGGAAGGGTCTGGAGTGGGTCTCAACGATTACGTCGGAGGGTCTTTCTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAACCTAGT

GATTTGTTTGACTACTGGGGTCAGGGAACCCTGGTCACCGTCTCGAGC

BMS2h-577 (SEQ ID NO: 753)
GAGGTGCAGCTGTTGGAGTCTGGGGGAGGCTTGGTACAGCCTGGGGGGTCCCTGCGTCTC

TCCTGTGCAGCCTCCGGATTCACCTTTGATGGGTATGATATGGGTTGGGTCCGCCAGGCT

CCAGGGAAGGGTCTAGAGTGGGTCTCAACTATTTCTCGTGGGGGTTGGTTCACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGGGACG

AGTCAGTCGTCTACGGGGAGTTTTGACTACTGGGGTCAGGGAACCCTGGTCACCGTCTCG

AGC

BMS2h-578 (SEQ ID NO: 754)
GAGGTGCAGCTGTTGGAGTCTGGGGGAGGCTTGGTACAGCCTGGGGGGTCCCTGCGTCTC

TCCTGTGCAGCCTCCGGATTCACCTTTCGTCGGTATGATATGCTTTGGGCCCGCCAGGCT

CCAGGGAAGGGTCTAGAGTGGGTCTCAGAGATTTCGCCTACGGGTGCTCTTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAACTTGGT

TCGACTTTTGACTACTGGGGTCAGGGAACCCTGGTCACCGTCTCGAGC

BMS2h-579 (SEQ ID NO: 755)
GAGGTGCAGCTGTTGGAGTCTGGGGGAGGCTTGGTACAGCCTGGGGGGTCCCTGCGTCTC

TCCTGTGCAGCCTCCGGATTCACCTTTTTTCCGTATTATATGAGTTGGGTCCGCCAGGCT

CCAGGGAAGGGTCTAGAGTGGGTCTCATCTATTTCGGGTACGGGTGGGCTTACATACTAC

GCAGACTCCGTGAAGGGCCGGTTCACCATCTCCCGCGACAATTCCAAGAALACGCTGTAT

CTGCAAATGAACAGCCTGCGTGCCGAGGACACCGCGGTATATTACTGTGCGAAAACGACG

CAGAATGCGACGCTTTTTGACTACTGGGGTCAGGGAACCCTGGTCACCGTCTCGAGC

BMS2h-58 (SEQ ID NO: 756)
GAGGTGCAGCTGTTGGAGTCTGGGGGAGGCTTGGTACAGCCTGGGGGGTCCCTGCGTCTC

TCCTGTGCAGCCTCCGGATTCACCTTTGAGGTTTATACTATGGCGTGGGTCCGCCAGGCT

CCAGGGAAGGGTCTGGAGTGGGTCTCAACGATTGATGAGTCTGGTCGTGATACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCTGGT

GTTTGGTTTGACTACTGGGGTCAGGGAACCCTGGTCACCGTCTCGAGC

BMS2h-580 (SEQ ID NO: 757)
GAGGTGCAGCTGTTGGAGTCTGGGGGAGGCTTGGTACAGCCTGGGGGGTCCCTGCGTCTC

TCCTGTGCAGCCTCCGGATTCACCTTTGCGTTTTATAAGATGGGGTGGGTCCGCCAGGCT

CCAGGGAAGGGTCTAGAGTGGGTCTCAACGATTACTCGTAAGGGTCATCATACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGTTTTT

TABLE 2-continued

Human Anti-CD40L VH Domain Encoding Nucleotide Sequences

AAGGGTAAGGGTTGGACTCGTCCGAGTGGGTTTGACTACTGGGGTCAGGGAACCCTGGTC

ACCGTCTCGAGC

BMS2h-581                                                        (SEQ ID NO: 758)
GAGGTGCAGCTGTTGGAGTCTGGGGGAGGCTTGGTACAGCCTGGGGGGTCCGTGCGTCTC

TCCTGTGCAGCCTCCGGATTCACCTTTAATGAGTATAGTATGATGTGGGTCCGCCAGGCT

CCAGGGAAGGGTCTAGAGTGGGTCTGATCTATTGGGAGGCGTGGTTGGCTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGCTGTG

CTGCTGGATTCTACTAAGTTTGACTACTGGGGTCAGGGAACCCTGGTCACCGTCTCGAGC

BMS2h-582                                                        (SEQ ID NO: 759)
GAGGTGCAGCTGTTGGAGTCTGGGGGAGGCTTGGTACAGCCTGGGGGGTCCCTGCGTCTC

TCCTGTGCAGCCTCCGGATTCACCTTTGATGAGTATCCGATGACTTGGGTCCGCCAGGCT

CCAGGGAAGGGTCTAGAGTGGGTCTCAACTATTTCTGCGCGTGGTCCTTTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGGTAGG

CATTGGCTTCGTAATGGTCGTTTTGACTACTGGGGTCAGGGAACCCTGGTCACCGTCTCG

AGC

BMS2h-583                                                        (SEQ ID NO: 760)
GAGGTGCAGCTGTTGGAGTCTGGGGGAGGCTTGGTACAGCCTGGGGGGTCCCTGCGTCTC

TCCTGTGCAGCCTCCGGATTCACCTTTGGTATGCAGTCGATGCAGTGGGTCCGCCAGGCT

CCAGGGAAGGGTCTAGAGTGGGTCTCAAGTATTACTGATGATGGTACTAGTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCTGAT

CGGGTTTTTGACTACTGGGGTCAGGGAACCCTGGTCACCGTCTCGAGC

BMS2h-584                                                        (SEQ ID NO: 761)
GAGGTGCAGCTGTTGGAGTCTGGGGGAGGCTTGGTACAGCGTGGGGGGTCGCTGCGTCTC

TCCTGTGCAGCCTCGGATTCACCTTTGGGCGGCTGATATGCAGTGGGTCCGCCAGGCT

CCAGGGAAGGGTCTAGAGTGGGTCTCACTGATTACTAATGATGGTATTTCTACATACTAC

GCAGACTCCGTGAAGGGCCGGTFCACCATCTCCCGCGACAATTCCAAGAACACGCTGTAT

CTGCAAATGAACAGCCTGCGTGCCGAGGACACCGCGGTATATTACTGTGCGAAAGCGGGT

GATCGTTTTGACTACTGGGGTCAGGGAACCCTGGTCACCGTCTCGAGC

BMS2h-586                                                        (SEQ ID NO: 762)
GAGGTGCAGCTGTTGGAGTCTGGGGGAGGCTTGGTACAGCCTGGGGGGTCCCTGCGTCTC

TCCTGTGCAGCCTCCGGATTCACCTTTAATAAGTATAGGATGCAGTGGGTCCGCCAGGCT

CCAGGGAAGGGTCTAGAGTGGGTCTCAAGTATTGATAGTTCTGGTGAGCTGACATACTAC

GCAGACTCCGTGAAGGGCCGGTTCACCATCTCCCGCGACAATTCGAAGAACACGCTGTAT

CTGCAAATGAACAGCCTGCGTGCCGAGGACACCGCGGTATATTACTGTGCGGAAGAGGTT

CCGATGGGGAATCAGACTTTTTTTGACTACTGGGGTCAGGGAACCCTGGTCACCGTCTCG

AGC

TABLE 2-continued

Human Anti-CD40L VH Domain Encoding Nucleotide Sequences

BMS2h-587
(SEQ ID NO: 763)
GAGGTGCAGCTGTTGGAGTCTGGGGGAGGCTTGGTACAGCCTGGGGGGTCCCTGCGTCTC

TCCTGTGCAGCCTCCGGATTCACCTTTACTGATTATACTATGGGGTGGGTCCGCCAGGCT

CCAGGGAAGGGTCTAGAGTGGGTCTCATCGATTACGTCTCAGGGTGCTTTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGCTACG

GGTACGGATTCGTCGTTTGACTACTGGGGTCAGGGAACCCTGGTCACCGTCTCGAGC

BMS2h-588
(SEQ ID NO: 764)
GAGGTGCAGCTGTTGGAGTCTGGGGGAGGCTTGGTACAGCCTGGGGGGTCCCTGCGTCTC

TCCTGTGCAGCCTCCGGATTCACCTTTGAGGATTATGAGATGTCTTGGGTCCGCCAGGCT

CCAGGGAAGGGTCTGGAGTGGGTCTCATGTATTGGGCCGGGGGTAAGCCTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGTGGAT

GGGCATTTTGACTACTGGGGTCAGGGAACCCTGGTCACCGTCTCGAGC

BMS2h-589
(SEQ ID NO: 765)
GAGGTGCAGCTGTTGGAGTCTGGGGGAGGCTTGGTACAGCCTGGGGGGTCCCTGCGTCTC

TCCTGTGCAGCCTCCGGATTCACCTTTAGTCAGTATGATATGGGGTGGGTCCGCCAGGCT

CCAGGGAAGGGTCTAGAGTGGGTCTCAACGATTTCTTCGAGGGGTTGGCTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGGTCCG

GGGGGTCGTCGGCGGTTTGACTACTGGGGTCAGGGAACCCTGGTCACCGTCTCGAGC

BMS2h-59
(SEQ ID NO: 766)
GAGGTGCAGCTGTTGGAGTCTGGGGGAGGCTTGGTACAGCCTGGGGGGTCCCTGCGTCTC

TCCTGTGCAGCCTCCGGATTCACCTTTCTGGATTATGCGATGGGTTGGGTCCGCCAGGCT

CCAGGGAAGGGTCTGGAGTGGGTCTCAACTATTTCTCCGATGGGTATGGGTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAATCGAGT

GCTATTTCGTTTACTTCTGATATTTCTAATTTTGACTACTGGGGTCAGGGAACCCTGGTC

ACCGTCTCGAGC

BMS2h-590
(SEQ ID NO: 767)
GAGGTGCAGCTGTTGGAGTCTGGGGGAGGCTTGGTACAGCCTGGGGGGTCCCTGCGTCTC

TCCTGTGCAGCCTCCGGATTCACCTTTAGTGATTATCCGATGTCTTGGGTCCGCCAGGCT

CCAGGGAAGGGTCTAGAGTGGGTCTCAAGTATTTCTTGGTCTGGTTTTCAGACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAACCTGGT

GTTGCGAGGATGCCTACTGGGATTGCTTTTGACTACTGGGGTCAGGGAACCCTGGTCACC

GTCTCGAGC

TABLE 2-continued

Human Anti-CD40L VH Domain Encoding Nucleotide Sequences

BMS2h-591 (SEQ ID NO: 768)
GAGGTGCAGCTGTTGGAGTCTGGGGGAGGCTTGGTACAGCCTGGGGGGTCCCTGCGTCTC
TCCTGTGCAGCCTCCGGATTCACCTTTAGTGCTTATGAGATGCAGTGGGTCCGCCAGGCT
CCAGGGAAGGGTCTAGAGTGGGTCTCATCTATTGATAGTGCTGGTACTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTCTATTACTGTGCGGAACCTTTT
GGGATGTTTGACTACTGGGGTCAGGGAACCCTGGTCACCGTCTCGAGC

BMS2h-592 (SEQ ID NO: 769)
GAGGTGCAGCTGTTGGAGTCTGGGGGAGGCTTGGTACAGCCTGGGGGGTCCCTGCGTCTC
TCCTGTGCAGCCTCCGGATTCACCTTTTCGGAGTATCCGATGAAGTGGGTCCGCCAGGCT
CCAGGGAAGGGTCTAGAGTGGGTCTCAACGATTGATCGGCAGGGTGATCGGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAACGGTG
CGGAGGGGTCTTCCTCGTCCGAGTCGTTATTTTGACTACTGGGGTCAGGGAACCCTGGTC
ACCGTCTCGAGC

BMS2h-593 (SEQ ID NO: 770)
GAGGTGCAGCTGTTGGAGTCTGGGGGAGGCTTGGTACAGCCTGGGGGGTCCCTGCGTCTC
TCCTGTGCAGCCTCCGGATTCACCTTTAGTGATTATGATATGGGTTGGGTCCGCCAGGCT
CCAGGGAAGGGTCTGGAGTGGGTCTCAAGTATTTCGCCTATGGGTACGTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGTCTG
AGTGTGTATTCGGGTCTTGATTTTGACTACTGGGGTCAGGGAACCCTGGTCACCGTCTCG
AGC

BMS2h-594 (SEQ ID NO: 771)
GAGGTGCAGCTGTTGGAGTCTGGGGGAGGCCTGGTACAGCCTGGGGGGTCCCTGCGTCTC
TCCTGCGCAGCCTCCGGATTCACCTTTTCTCATTATGATATGGGTTGGGTCCGCCAGGCT
CCAGGGAAGGGTCTGGAGTGGGTCTCAGATATTGATTATATTGGTAAGACTACATACTAC
GCAGACTCCGTGAAGGGCCGGTTCACCATCTCTCGCGACAATTCCAAGAACACGCTGTAT
CTGCAPATGAACAGCCTGCGTGCCGAGGACACCGCGGTATATTACTGTGCGAAAGCTTCG
GATGAGGTGGGTGTTAATACTTCCAAGTTTGACTACTGGGGTCAGGGAACCCTGGTCACC
GTCTCGAGC

BMS2h-595 (SEQ ID NO: 772)
GAGGTGCAGCTGTTGGAGTCTGGGGGAGGCTTGGTACAGCCTGGGGGGTCCCTGCGTCTC
TCCTGTGCAGCCTCCGGATTCACCTTTGCGCGGTATGATATGGGGTGGGTCCGCCAGGCT
CCAGGGAAGGGTCTAGAGTGGGTCTCAACTATTTCTCCTACTGGTGTGTTGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAaaGGTTTT
GAGGATTTTGACTACTGGGGTCAGGGAACCCTGGTCACCGTCTCGAGC

TABLE 2-continued

Human Anti-CD40L VH Domain Encoding Nucleotide Sequences

BMS2h-596
(SEQ ID NO: 773)
GAGGTGCAGCTGTTGGAGTCTGGGGGAGGCTTGGTACAGCCTGGGGGGTCCCTGCGTCTC

TCCTGTGCAGCCTCCGGATTCACCTTTGAGGCTTATCCGATGAGTTGGGTCCGCCAGGCT

CCAGGGAAGGGTCTAGAGTGGGTCTCACTGATTTCTCATACGGGTCATGCTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGGGCAT

TGGCCTTTTGACTACCGGGGTCAGGGAACCCTGATCACCGTCTCGAGC

BMS2h-597 0
(SEQ ID NO: 774)
GAGGTGCAGCTGTTGGAGTCTGGGGGAGGCTTGGTACAGCCAGGGGGGTCCCTGCGCCTC

TCCTGTGCAGCCTCCGGATTCACCTTTGAGGATGAGTGGATGAGTTGGGTCCGCCAGGCT

CCAGGGAAGGGTCTAGAGTGGGTCTCAGATATTAGCCCGGGTGGTTGGACTACATACTAC

GCCGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGGTTAT

CGTCCGTTTGATGAGTTTGACTACTGGGGTCAGGGAACCCTGGTCACCGTCTCGAGC

BMS2h-598
(SEQ ID NO: 775)
GAGGTGCAGCTGTTGGAGTCTGGGGGAGGCTTGGTACAGCCTGGGGGGTCCCTGCGTCTC

TCCTGTGCAGCCTCCGGAGTCACCTTTGATGCTATTGAGATGTCTTGGGTCCGCCAGGCT

CCAGGGAAGGGTCTGGAGTGGGTCTCATCGATTTCGCGTCATGGTGAGTATACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGGAAGATGCT

TGGTCTCGGCATTTTGACTACTGGGGTCAGGGAACCCTGGTCACCGTCTCGAGC

BMS2h-599
(SEQ ID NO: 776)
GAGGTGCAGCTGTTGGAGTCTGGGGGAGGCTTGGTACAGCCTGGGGGGTCCCTGCGTCTC

TCCTGTGCAGCCTCCGGATTCACCTTTGATAGTACGGATATGAGTTGGGTCCGCCAGGCT

CCAGGGAAGGGTCTAGAGTGGGTCTCAGGTATTTTGGATAATGGTAGTAATACATACTAC

GCAGACTCCGTGAAGGGCCGGTTCACCATCTCCCGCGACAATTCCAAGAACATGCTGTAT

CTGCAAATGAATAGCCTGCGTGCCGAGGATACCGCGGTATATTACTGTGCGAAAGGGGCG

AGGGATTTTGACTACTGGGGTCAGGGAACCCTGGTCACCGTCTCGAGC

BMS2h-600
(SEQ ID NO: 777)
GAGGTGCAGCTGTTGGAGTCTGGGGGAGGCTTGGTACAGCCTGGGGGGTCCCTGCGTCTC

TCCTGTGCAGCTTCCGGATTCACCTTTGGTAGGCAGAGTATGCAGTGGGTCCGCCAGGCT

CCAGGGAAGGGTCTAGAGTGGGTCTCAAGTATTGATGATGATGGTTTTTCGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGGGGAT

CCGTGGGGTTTTGACTACTGGGGTCAGGGAACCCTGGTCACCGTCTCGAGC

BMS2h-601
(SEQ ID NO: 778)
GAGGTGCAGCTGTTGGAGTCTGGGGGAGGCTTGGTACAGCCTGGGGGGTCCCTGCGTCTC

TCCTGTACAGCCTCCGGATTCACCTTTAGTGATACGCAGATGGCGTGGGTCCGCCAGGCT

CCAGGGAAGGGTCTAGAGTGGGTCTCAGGTATTGATGATGGGGGTGTGAGTACATACTAC

TABLE 2-continued

Human Anti-CD40L VH Domain Encoding Nucleotide Sequences

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCGGAT

CGTCATTTTGACTACTGGGGTCAGGGAACCCTGGTCACCGTCTCGAGC

BMS2h-602
(SEQ ID NO: 779)
GAGGTGCAGCTGTTGGAGTCTGGGGGAGGCTTGGTACAGCCTGGGGGGTCCCTGCGTCTC

TCCTGTGCAGCCTCCGGATTCACCTTTGGGAGTACGACGATGGGGTGGGTCCGCCAGGCT

CCAGGGAAGGGTCTGGAGTGGGTCTCAGTGATTTCGGATGATGGTGGTTTTACATACTAC

GCAGACTCCGTGAAGGGCCGGTTCACCATCTCCCGCGACAATTCCAGGAACACGCTGTAT

CTGCAAATGAACAGCCTGCGTGCCGAGGACACCGCGGTATATTACTGTGCGAAAGTTGAT

GGTTATGGTGTTTTTGACTACTGGGGTCAGGGAACCCTGGTCACCGTCTCGAGC

BMS2h-603
(SEQ ID NO: 780)
GAGGTGCAGCTGTTGGAGTCTGGGGGAGGCTTGGTACAGCCTGGGGGGTCCCTGCGTCTC

TCCTGTGCAGCCTCCGGATTCACCTTTCGGAGTGGGGATATGAATTGGGTCCGCCAGGCT

CCAGGGAAGGGTCTAGAGTGGGTCTCAACTATTACGAATGATGGTACGTCTACATACTAC

GCAGACTCCGTGAAGGGCCGGTTCACCATCTCCCGCGACAATTCCAAGAATACGCTGTAT

CTGCAAATGAACAGCGTGCGTGCCGAGGACACCGCGGTATATTACTGTGCGAAATCTGAT

TCTGATTTTGACTACTGGGGTCAGGGAACCCTGGTCACCGTCTCGAGC

BMS2h-61
(SEQ ID NO: 781)
GAGGTGCAGCTGTTGGAGTCTGGGGGAGGCTTGGTACAGCCTGGGGGGTCCCTGCGTCTC

TCCTGTGCAGCCTCCGGATTCACCTTTGCTGCTTATGCTATGACGTGGGTCCGCCAGGCT

CCAGGGAAGGGTCTAGAGTGGGTCTCATATATTAGTCCGAATGGTACGGCGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGGAATATGTG

GGGATGCGTTGGAATTCTTTTGACTACTGGGGTCAGGGAACCCTGGTCACCGTCTCGAGC

BMS2h-62
(SEQ ID NO: 782)
GAGGTGCAGCTGTTGGAGTCTGGGGGAGGCTTGGTACAGCCTGGGGGGTCCCTGCGTCTC

TCCTGTGCAGCCTCCGGATTCACCTTTTCGAGTTATGAGATGGCTTGGGTCCGCCAGGCT

CCAGGGAAGGGTCTAGAGTGGGTCTCATCTATTACGAGTCTTGGTACTTCTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCGGGT

AGGAAGTTTGACTACTGGGGTCAGGGAACCCTGGTCACCGTCTCGAGC

BMS2h-65
(SEQ ID NO: 783)
GAGGTGCAGCTGTTGGAGTCTGGGGGAGGCTTGGTACAGCCTGGGGGGTCCCTGCGTCTC

TCCTGTGCAGCCTCCGGATTCACCTTTAATGAGTATGAGATGACGTGGGTCCGCCAGGCT

CCAGGGAAGGGTCTAGAGTGGGTCTCAACGATTACTAGTGAGGGTAGTGGGACATACTAC

GCAGACTCCGTAAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCTAAT

GGTAAGTTTGACTACTGGGGTCAGGGAACCCTGGTCACCGTCTCGAGC

TABLE 2-continued

Human Anti-CD40L VH Domain Encoding Nucleotide Sequences

BMS2h-66
(SEQ ID NO: 784)
GAGGTGCAGCTGTTGGAGTCTGGGGGAGGCTTGGTACAGCCTGGGGGGTCCCTGCGTCTC

TCCTGTGCAGCCTCCGGATTCACCTTTTCTGATTATGAGATGTTGTGGGTCCGCCAGGCT

CCAGGGAAGGGTCTGGAGTGGGTCTCAACTATTACTAGTGAGGGTCATTCTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCTGGG

ACTTCGTTTGACTACTGGGGTCAGGGAACCCTGGTCACCGTCTCGAGC

BMS2h-67
(SEQ ID NO: 785)
GAGGTGCAGCTGTTGGAGTCTGGGGGAGGCTTGGTACAGCCTGGGGGGTCCCTGCGTCTC

TCCTGTGCAGCCTCCGGATTCACCTTTAGTGATTATGAGATGAGTTGGGTCCGCCAGGCT

CCAGGGAAGGGTCTAGAGTGGGTCTCAACGATTGATTCTGATGGTAGTTTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCGGGT

GTGAAGTTTGACTACTGGGGTCAGGGAACCCTGGTCACCGTCTCGAGC

BMS2h-68
(SEQ ID NO: 786)
GAGGTGCAGCTGTTGGAGTCTGGGGGAGGCTTGGTACAGCCTGGGGGGTCCCTGCGTCTC

TCCTGTGCAGCCTCCGGATTCACCTTTAAGGATTATGAGATGACTTGGGTCCGCCAGGCT

CCAGGGAAGGGTCTAGAGTGGGTCTCATCTATTTCTTCTACTGGTCAGTCTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCGGGT

AATAAGTTTGACTACTGGGGTCAGGGAACCCTGGTCACCGTCTCGAGC

BMS2h-69
(SEQ ID NO: 787)
GAGGTGCAGCTGTTGGAGTCTGGGGGAGGCTTGGTACAGCCTGGGGGGTCCCTGCGTCTC

TCCTGTGCAGCCTCCGGATTCACCTTTCTTGATTATGGTATGGCTTGGGTCCGCCAGGCT

CCAGGGAAGGGTCTAGAGTGGGTCTCAGCTATTTCGCCTCTTGGTCTTAGTACATACTAC

GCAGACTCCGTGAAGAGCCGGTTCACCATCTCCCGCGACAATTCCAAGAACACGCTGTAT

CTGCAAATGAACAGCCTGCGTGCCGAGGATACCGCGGTATATTACTGTGCGAAAGAGGTG

AGGGTGGGTAGGGGTGTTCATCCTCCGAAGTTTGACTACTGGGGTCAGGGAACCCTGGTC

ACCGTCTCGAGC

BMS2h-7
(SEQ ID NO: 788)
GAGGTGCAGCTGTTGGAGTCTGGGGGAGGCTTGGTACAGCCTGGGGGGTCCCTGCGTCTC

TCCTGTGCAGCCTCCGGATTCACCTTTAATTTGTATGAGATGACTTGGGTCCGCCAGGCT

CCAGGGAAGGGTCTAGAGTGGGTCTCATCTATTACTAGTGATGGTGTTTCTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGCTGGG

GTGATTTTTGACTACTGGGGTCAGGGAACCCTGGTCACCGTCTCGAGC

BMS2h-70
(SEQ ID NO: 789)
GAGGTGCAGCTGTTGGAGTCTGGGGGAGGCTTGGTACAGCCTGGGGGGTCCCTGCGTCTC

TCCTGTGCAGCCTCCGGATTCACCTTTGAGAATTATGCTATGTCGTGGGTCCGCCAGGCT

TABLE 2-continued

Human Anti-CD40L VH Domain Encoding Nucleotide Sequences

CCAGGGAAGGGTCTAGAGTGGGTCTCAACGATTGCTCCGCTGGGTGTTCCGACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAAAAGAAG

GTTGGGGCGTGGCTGCAGTCGCGGAGTTTTGACTACTGGGGTCAGGGAACCCTGGTCACC

GTCTCGAGC

BMS2h-701 (SEQ ID NO: 790)
GAGGTGCAGCTGTTGGAGTCTGGGGGAGGCTTGGTACAGCCTGGGGGGTCCCTGCGTCTC

TCCTGTGCAGCCTCCGGATTCACCTTTATGGATTATGAGATGCATTGGGTCCGCCAGGCT

CCAGGGAAGGGTCTAGAGTGGGTCTCAACGATTGGTGCTTCTGGTCATTATACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAATATCTT

GATATGCTGCTGTTTGGGTTTGACTACTGGGGTCAGGGAACCCTGGTCACCGTCTCGAGC

BMS2h-702 (SEQ ID NO: 791)
GAGGTGCAGCTGTTGGAGTCTGGGGGAGGCTTGGTACAGCCTGGGGGGTCCCTGCGTCTC

TCCTGTGCAGCCTCCGGATTCACCTTTGCTGAGTATGAGATGATGTGGGCCCGCCAGGCT

CCAGGGAAGGGTCTAGAGTGGGTCTCACGTATTGCTGGTAATGGTTCTCGTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGATAATGCTT

TCTCATTTTGACTAGTGGGGTCAGGGAACCCTGGTCACCGTCTCGAGC

BMS2h-703 (SEQ ID NO: 792)
GAGGTGCAGCTGTTGGAGTCTGGGGGAGGCTTGGTACAGCCTGGGGGGTCCCTGCGTCTC

TCCTGTGCAGCCTCCGGATTCACCTTTTATAATTATGATATGAGTTGGGTCCGCCAGGCT

CCAGGGAAGGGTCTAGAGTGGGTCTCAGGTATTGATTCGATGGGTCTTGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAAGGGTCT

AATGCGAGTGATTGGGTTGTTTTTGACTACTGGGGTCAGGGAACCCTGGTCACCGTCTCG

AGC

BMS2h-704 (SEQ ID NO: 793)
GAGGTGCAGCTGTTGGAGTCTGGGGGAGGCTTGGTACAGCCTGGGGGGTCCCTGCGTCTC

TCCTGTGCAGCCTCCGGATTCACCTTTGCGTCGTATCATATGACTTGGGTCCGCCAGGCT

CCAGGGAAGGGTCTAGAGTGGGTCTCATCGATTGCGGATACGGGTGATCGTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACTGCGGTATATTACTGTGCGAAATTGCGT

GGGATGGCTCGGGTTTGGGGGTTTGACTACTGGGGTCAGGGAACCCTGGTCACCGTCTCG

AGC

BMS2h-705 (SEQ ID NO: 794)
GAGGTGCAGCTGTTGGAGTCTGGGGGAGGCTTGGTACAGCCTGGGGGGTCCCTGCGTCTC

TCCTGTGCAGCCTCCGGATTCACCTTTAGTTATTATGATATGATGTGGGTCCGCCAGGCT

CCAGGGAAGGGTCTAGAGTGGATCTCATCTATTTCGGATCGTGGTCTTCAGACATACTAC

TABLE 2-continued

Human Anti-CD40L VH Domain Encoding Nucleotide Sequences

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAATTTACG

GAGATTCCGTTGGATTGGTTGGAGGTGrfTGACTACTGGGGTCAGGGAACCCTGGTCACC

GTCTCGAGC

BMS2h-706
(SEQ ID NO: 795)
GAGGTGCAGCTGTTGGAGTCTGGGGGAGGCTTGGTACAGCCTGGGGGGTCCCTGCGTCTC

TCCTGTGCAGCCTCCGGATTCACCTTTGGGAGTTATAAGATGTTGTGGGTCCGCCAGGCT

CCAGGGAAGGGTCTAGAGTGGGTCTCATCGATTACTAATTCTGGTACTGAGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAATCGATG

TATCCGGATTTGGAGATTGTGCATTTTGACTACTGGGGTCAGGGAACCCTGGTCACCGTC

TCGAGC

BMS2h-707
(SEQ ID NO: 796)
GAGGTGCAGCTGTTGGAGTCTGGGGGAGGCTTGGTACAGCCTGGGGGGTCCCTGCGTCTC

TCCTGTGCAGCCTCCGGATTCACCTTTGAGACTTATCGTATGAGTTGGGTCCGCCAGGCT

CCAGGGAAGGGTCTAGAGTGGGTCTCAGCTATTGATCAGGAGGGTTCTGCTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAAAATAGT

GGGACGAGGCCGGGGCTTCGGTTTGACTACTGGGGTCAGGGAACCCTGGTCACCGTCTCG

AGC

BMS2h-708
(SEQ ID NO: 797)
GAGGTGCAGCTGTTGGAGTCTGGGGGAGGCTTGGTACAGCCTGGGGGGTCCCTGCGCCTC

TCCTGTGCAGCCTCCGGATTCACCTTTAGTAGTTATGATATGCTTTGGGTCCGCCAGGCT

CCAGGGAAGGGTCTAGAGTGGGTCTCACGGATTGATGCGAGTGGTTATTTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGCAATTGTTG

AAGCTGTCGTTGAATCCTAATTTTGACTACTGGGGTCAGGGAACCCTGGTCACCGTCTCG

AGC

BMS2h-709 1
(SEQ ID NO: 798)
GAGGTGCAGCTGTTGGAGTCTGGGGGAGGCTTGGTACAGCCTGGGGGGTCCCTGCGTCTC

TCCTGTGCAGCCTCCGGATTCACCTTTAGCAGCTATGCCATGAGCTGGGTCCGCCAGGCT

CCAGGGAAGGGTCTAGAGTGGGTCTCATCGATTCATAATACTGGTTTGTCTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGGGACT

CAGCATCGTTTTGTTGTTTTTGACTACTGGGGTCAGGGAACCCTGGTCACCGTCTCGAGC

BMS2h-71
(SEQ ID NO: 799)
GAGGTGCAGCTGTTGGAGTCTGGGGGAGGCTTGGTACAGCCTGGGGGGTCCCTGCGTCTC

TCCTGTGCAGCCTCCGGATTCACCTTTGAGGGTTATCCTATGTCGTGGGTCCGCCAGGCT

CCAGGGAAGGGTCTAGAGTGGGTCTCAACTATTAGTCCTTTGGGTCCTGATACATACTAC

TABLE 2-continued

Human Anti-CD40L VH Domain Encoding Nucleotide Sequences

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAACTGTTG

ATGGGGGAGTATTTGAATTCTAGGACGTTTGACTACTGGGGTCAGGGAACCCTGGTCACC

GTCTCGAGC

BMS2h-710
(SEQ ID NO: 800)
GAGGTGCAGCTGTTGGAGTCTGGGGGAGGCTTGGTACAGCCTGGGGGGTCCCTGCGTCTC

TCCTGTGCAGCCTCCGGATTCACCTTTAATACGTATAGTATGTCTTGGGTCCGCCAGGCT

CCAGGGAAGGGTCTGGAGTGGGTCTCATGGATTGATGCTGATGGTTGGGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGCAAACTGGG

CATACGTTTGACTACTGGGGTCAGGGAACCCTGGTCACCGTCTCGAGC

BMS2h-711
(SEQ ID NO: 801)
GAGGTGCAGCTGTTGGAGTCTGGGGGAGGCTTGGTACAGCCTGGGGGGTCCCTGCGTCTC

TCCTGTGCAGCCTCCGGATTCACCTTTACGGATGGGGAGATGGGTTGGGCCCGCCAGGCT

CCAGGGAAGGGTCTAGAGTGGGTCTCAAGGATTGTGGATCCTGGTGATTCTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGCGGGT

GATCAGTTTGACTACTGGGGTCAGGGAACCCTGGTCACCGTCTCGAGC

BMS2h-712
(SEQ ID NO: 802)
GAGGTGCAGCTGTTGGAGTCTGGGGGAGGCTTGGTACAGCCTGGGGGGTCCCTGCGTCTC

TCCTGTGCAGCCTCCGGATTCACCTTTCCTGAGTATGAGATGAAGTGGGTCCGCCAGGCT

CCAGGGAAGGGTCTAGAGTGGGTCTCAACTATTACTCCGTCGGGTGGTCATACATACTAC

GCAGACTCCGTGAAGGGCCGGTTCACCATCTCCCGCGACAATTCCAAGAACACGCTGTAT

CTGCAAATGAACAGCCTGCGTGCCGAGGACGCCGCGGTATATTACTGTGCGATACCTCTT

TCTAGTTTTGACTACTGGGGTCGGGGAACCCTGGTCACCGTCTCGAGC

BMS2h-713
(SEQ ID NO: 803)
GAGGTGCAGCTGTTGGAGTCTGGGGGAGGCTTGGTACAGCCTGGGGGGTCCCTGCGTCTC

TCCTGTGCAGCCTCCGGATTCACCTTTTCTAATTATGTGATGATTTGGGTCCGCCAGGCT

CCAGGGAAGGGTCTAGAGTGGGTCTCACTTATTAATGGTGCTGGTGATATGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGGAAGGGGGT

GCGCGTTCGTTTGGGGTTCCGCCTAATTTTGACTACTGGGGTCAGGGAACCCTGGTCACC

GTCTCGAGC

BMS2h-714
(SEQ ID NO: 804)
GAGGTGCAGCTGTTGGAGTCTGGGGGAGGCTTGGTACAGCCTGGGGGGTCCCTGCGTCTC

TCCTGTGCAGCCTCCGGATTCACCTTTACGGATGGGGAGATGGGTTGGGCCCGCCAGGCT

CCAGGGAAGGGTCTAGAGTGGGTCTCAAGGATTGTGGATCCTGGTGATTCTACATACTAC

GCAGACTCCGTGAAGGGCCGGTTCACCATCTCCCGCGACAATTCCAAGAACACGCTGTAT

TABLE 2-continued

Human Anti-CD40L VH Domain Encoding Nucleotide Sequences

CTGCAAATGAACAGCCTGCGTGCCGAGGACACCGCGGTATATTACTGTGCGAAAGCGGGT

GATCAGTTTGACTACTGGGGTCAGGGAACCCTGGTCACCGTCTCGAGC

BMS2h-715
(SEQ ID NO: 805)
GAGGTGCAGCTGTTGGAGTCTGGGGGAGGCTTGGTACAGCCTGGGGGGTCCCTGCGTCTC

TCCTGTGTAGCCTCCGGATTCACCTTTACGCTGTATAATATGTCTTGGGTCCGCCAGGCT

CCAGGGAAGGGTCTGGAGTGGGTCTCAGTTATTTCTAGTAAGGGTGATAGTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGCAAACGAGT

AGTGTTTTTGACTACTGGGGTCAGGGAACCCTGGTCACCGTCTCGAGC

BMS2h-716
(SEQ ID NO: 806)
GAGGTGCAGCTGTTGGAGTCTGGGGGAGGCTTGGTACAGCCTGGGGGGTCCCTGCGTCTC

TCCTGTGCAGCCTCCGGATTCACCTTTGAGGCGTATTATATGAGTTGGGTCCGCCAGGCT

CCAGGGAAGGGTCTAGAGTGGGTCTCAGGTATTGTTAATAATGGTTTGTTGACATACTAC

GCAGACTCCGTGAAGGGCCGGTTCACCATCTCCCGCGACAATTCCAAGAACATGCTGTAT

CTGCAAATGAACAGCCTGCGTGCCGAGGACACCGCGGTATATTACTGTGCGAAATCGGCT

GTTCATCCTTCGTATAGGGCGGAGTTGTTCGACTACTGGGGTCAGGGAACCCTGGTCACC

GTCTCGAGC

BMS2h-717
(SEQ ID NO: 807)
GAGGTGCAGCTGTTGGAGTCTGGGGGAGGCTTGGTACAGCCTGGGGGGTCCCTGCGTCTC

TCCTGTGCAGCCTCCGGATTCACCTTTAGTTCGTATGAGATGGCGTGGGTCCGCCAGGCT

CCAGGGAAGGGTCTAGAGTGGGTCTCACGTATTGAGCCTGATGGTAGTAATACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGGTCCG

GATAATTTTACTATGTTTGACTACTGGGGTCAGGGAACCCTGGTCACCGTCTCGAGC

BMS2h-718
(SEQ ID NO: 808)
GAGGTGCAGCTGTTGGAGTCTGGGGGAGGCTTGGTACAGCCTGGGGGGTCCCTGCGTCTC

TCCTGTGCAGCCTCCGGATTCACCTTTAATAAGTATATGATGGGGTGGGTCCGCCAGGCT

CCAGGGAAGGGTCTAGAGTGGGTCTCATCTATTGATAGTCTTGGTCATTATACATACTAC

GCAGACTCTGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGGAAGCGGAG

TTTCCGTTTGACTACTGGGGTCAGGGAACCCTGGTCACCGTCTCGAGC

BMS2h-719
(SEQ ID NO: 809)
GAGGTGCAGCTGTTGGAGTCTGGGGGAGGCTTGGTACAGCCTGGGGGGTCCCTGCGTCTC

TCCTGTGCAGCCTCCGGATTCACCTTTAAGAGGTATGAGATGACGTGGGTCCGCCAGGCT

CCAGGGAAGGGTCTGGAGTGGGTCTCATCTATTTCGTCGGATGGTTCTTTTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGGAACCGTTT

ACTGAGTTTGACTACTGGGGTCAGGGAACCCTGGTCACCGTCTCGAGC

TABLE 2-continued

Human Anti-CD40L VH Domain Encoding Nucleotide Sequences

BMS2h-719-1
(SEQ ID NO: 810)
GAGGTGCAGCTGTTGGAGTCTGGGGGAGGCATGGTACAGCCTGGGGGGTCCCTGCGTCTC

TCCTGTGCAGCCTCCGGATTCACCTTTAAGAGGTATGAGATGATGTGGGTCCGCCAGGCT

CCAGGGAAGGGTCTGGAGTGGGTCTCATCTATTTCGTCGGATGGTTCTTTTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGGAACCGTTT

ACTGAGTTTGACTACTGGGGTCAGGGAACCCAGGTCACCGTCTCGAGC

BMS2h-719-10
(SEQ ID NO: 811)
GAGGTGCAGCTGTTGGAGTCTGGGGGAGGCATGGTGCAGCCTGGGGGGTCCCTGCGTCTC

TCCTGTGCAGCCTCCGGATTCACCTTTAAGAGGTATGAGATGATGTGGGTCCGCCAGGCT

CCAGGGAAGGGTCTGGAGTGGGTCTCATCTATTTCGTCGGATGGTTCTTTTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGGAACCGTTT

ACTGAGTTTGACTACTGGGGTCAGGGAACCCTGGTCACCGTCTCGAGC

BMS2h-719-11
(SEQ ID NO: 812)
GAGGTGCAGCTGTTGGAGTCTGGGGGAGGCTTGGTACAGCCTGGGGGGTCCCTGCGTCTC

TCCTGTGCAGCCTCCGGATTCACCTTTAAGAGGTATGAGATGATGTGGGTCCGCAAGGCT

CCAGGGAAGGGTCTGGAGTGGGTCTCATCTATTTCGTCGGATGGTTCTTTTACATACTAC

GCAGACTCCGTGAAGGGCCGGTTCACCATCTCCCGCGACAATTCCGAGAACACGCTGTAT

CTGCAAATGAACAGCCTGCGTGCCGAGGATACCGCGGTATATTACTGTGCGGATCCGTTT

ACTGAGTTTGACTATTGGGGTCAGGGTACCCTGGTCACCGTCTCGAGC

BMS2h-719-12
(SEQ ID NO: 813)
GAGGTGCAGCTGTTGGAGTCTGGGGGAGGCTTGGTACAGCCTGGGGGGTCCCTGCGTCTC

TCCTGTGCAGCCTCCGGATTCACCTTTAAGAGGTATGAGATGATGTGGGTCCGCCAGGCT

CCAGGGAAGGGTCTGGAGTGGGTCTCATCTATTTCGTCGGATGGTTCTTTTACATACTAC

GCAGACTCCGTGAAGGGCCGGTTCACCGTCTCCCGCGACAATTCCAAGAACACGCTGTAT

CTGCAAATGAACAGCCTGCGTGCCGAGGATACCGCGGTATATTACTGTGCGGACCCGTTT

ACTGAGTTTGACTACTGGGGTCAGGGAACCCTGGTCACCGTCTCGAGC

BMS2h-719-13
(SEQ ID NO: 814)
GAGGTGCAGCTGTTGGAGTCGGGGGGAGGCTTGGTACAGCCTGGGGGGTCCCTGCGTCTC

TCGTGTGCAGCCTCCGGATTCACCTTTAAGAGGTATGAGATGATGTGGGTCCGCCAGGCT

CCAGGGAAGGGTCTGGAGTGGGTCTCATCTATTTCGTCGGATGGTTCTTTTACATACTAC

GCAGACTCCGTGAAGGGCCGGTTCACCATCTCCCGCGACAATACCAAGAACACGCTGTAT

CTACAGATGAACAGCCTGCGTGCCGAGGATACCGCGGTATATTACTGTGCGGACCCGTTT

ACTGAGCTTGACTACTGGGGTCATGGAACCCTGGTCACCGTCTCGAGC

BMS2h-719-14
(SEQ ID NO: 815)
GAGGTGCAGCTGTTGGAGTCTGGGGGAGGCTTGGTACGGCCTGGGGGGTCCCTGCGTCTC

TCCTGTGCAGCCTCCGGATTCACCTFTAAGAGGTATGAGATGATGTGGGTCCGCCAGGCT

CCAGGGAAGGGTCTGGAGTGGGTCTCATCTATTTCGTCGGATGGTTCTTTTACATACTAC

TABLE 2-continued

Human Anti-CD40L VH Domain Encoding Nucleotide Sequences

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTTCTGTGCAGATCCGTTT

ACTGAGTTTGACTACTGGGGTCAGGGAACCCTGGTCACCGTCTCGAGC

BMS2h-719-15
(SEQ ID NO: 816)
GAGGTGCAGCTGTTGGAGTCTGGGGGAGGCTTGGTACAGCCTGGGGGGTCCCTGCGTCTC

TCCTGTGCAGCCTCCGGATTCGCCTTTAAGAGGTATGAGATGACATGGGTCCGCCAGGCT

CCAGGGAAGGGTCTGGAGTGGGTCTCATCTATTFCGTCGGATGGTTCTTTTACATACTAC

GCAGACTCCGTGAAGGGCCGGTTCACCATCTCCCGCGACAATTCCAAGAACACGCTGTAT

CTGCATATGAACAGCCTGCGTGCCGAGGATACCGCGGTATATTACTGTGCGGATCCGTTT

ACTGAGATTGACTACTGGGGTCAGGGAACCCTGGTCACCGTCTCGAGC

BMS2h-719-16
(SEQ ID NO: 817)
GAGGTGCAGCTGTTGGAGTCTGGGGGAGGCTTGGTACAGCCTGGGGGGTCCCTGCGTCTC

TCCTGTGCAGCCTCCGGATTCCCCTTTAAGAGGTATGAGATGACGTGGGTCCGCCAGGCT

CCAGGGAAGGGTCTGGAGTGGGTCTCATCTATTTCGTCGGATGGTTCTTTTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGGAACCGTTT

ACTGAGTTTGACTACCGGGCTCAGGGAACCCTGGTCACCGTCTCGAGC

BMS2h-719-17
(SEQ ID NO: 818)
GAGGTGCAGCTGTTGGAGTCTGGGGGAGGCTTGGTACAGCCTGGGGGGTCCCTGCGTCTC

TCCTGTGCAGCCTCCGGATTCACCTTTAAGAGGTATGAGATGTCGTGGGTCCGCCAGGCT

CCAGGGAAGGGTCTGGAGTGGGTCTCTTCTATTTCGTCGGATGGTTCTTTTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGGATCCGTTT

ACTGAGATTGACTACTGGGGTCAGGGAACCCAGGTCACCGTCTCGAGC

BMS2h-719-18
(SEQ ID NO: 819)
GAGGTGCAGCTGTTGGAGTCTGGGGGAGGCTTGGTACATCCTGGGGGGTCCCTGCGTCTC

TCCTGTGCAGCTTCCGGATTCACCTTTAAGAGGTATGAGATGATGTGGGTCCGCCAGGCT

CCAGGGAAGGGTCTGGAGTGGGTCTCATCTATTTCGTCGGATGGTTCTTTTACATACTAC

GCAGACTCCGTGAAGGGCCGGTTCACCATCTCCCGCGACAATTCCAAGAACACGCTGTAT

CTGCAAATGAACAGCCTGCGTGACGAGGATACCGCGGTATATTACTGTGCGGAACCGTTT

ACTGAGTTTGACTACGGGGGTCAGGGAACCCTGGTCACCGTCTCGAGC

BMS2h-719-19
(SEQ ID NO: 820)
GAGGTGCAGCTGTTGGAGTCTGGGGGAGGCTGGGTACAGCCTGGGGGGTCCCTGCGTCTC

TCCTGTGCAGCCTCAGGATTCACCTTTAAGAGGTATGAGATGATGTGGGTCCGCCAGGCT

CCAGGGAAGGGTCTGGAGTGGGTCTCATCTATTTCGTCGGATGGTTCTTTTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGGATCCGTTT

ACTGAGTTTGACTACTGGGGTCAGGGAACCCTGGTCACCGTCTCGAGC

TABLE 2-continued

Human Anti-CD40L VH Domain Encoding Nucleotide Sequences

BMS2h-719-2
(SEQ ID NO: 821)
GAGGTGCAGCTGTTGGAGTCTGGGGGAGGCTTGGTACAGCCTGGGGGGTCCCTGCGTCTC

TCCTGTGCAGCCTCCGGATTCACCTTTAAGAGGTATGAGATGATGTGGGTCCGCCAGGCT

CCAGGGAAGGGTCTGGAGTGGGTCTCATCTATTTCGTCGGATGGTTCTTTTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGGAACCGTTT

ACTGAGTTTGACTACTGGGGTCATGGAACCCTGGTCACCGTCTCGAGC

BMS2h-719-20
(SEQ ID NO: 822)
GAGGTGCAGCTGTTGGAGTCTGGGGGAGGCTTGGTACAGCCTGGGGGGTCCCTGCGTCTC

TCCTGTGCAGCCTCCGGATTCACCTTTAAGAGGTATGAGATGACGTGGGTCCGCCAGGCT

CCAGGGAAGGGTCTGGAGTGGGTCTCATCTATTTCGTCGGATGGTTCTTTTACATACTAC

GCAGACTCCGTGAAGGGCCGGTTCACCATCTCCCGCGACAATTCCAAGAACACTCTGTAT

CTGCAAATGAACAGCCTGCGTGCCGAGGATACCGCGGTATATTACTGTGCGGAACCGTTT

ACTGAGATTGACTACCGGGGTCAGGGAACCCTGGTCACCGTCTCGAGC

BMS2h-719-202
(SEQ ID NO: 823)
GAGGTGCAGCTGTTGGAGTCTGGGGGAGGCTTGGTACAGCCTGGGGGGTCCCTGCGTCTC

TCCTGTGCAGCCTCCGGATTCACCTTTAAGAAGTATGAGATGATGTGGGTCCGCCAGGCT

CCAGGGAAGGGTCTGGAGTGGGTCTCATCTATTTCGTCGGATGGTTCTTTTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGGAACCGTTT

ACTGAGTTTGACTACTGGGGTCATGGAACCCTGGTCACCGTCTCGAGC

BMS2h-719-203
(SEQ ID NO: 824)
GAGGTGCAGCTGTTGGAGTCTGGGGGAGGCTTGGTACAGCCTGGGGGGTCCCTGCGTCTC

TCCTGTGCAGCCTCCGGATTCACCTTTAACAGCTATGAGATGATGTGGGTCCGCCAGGCT

CCAGGGAAGGGTCTAGAGTGGGTCTCATCTATTTCGTCGGATGGTTCTTTTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGGAACCGTTT

ACTGAGTTTGACTACTGGGGTCATGGAACCCTGGTCACCGTCTCGAGC

BMS2h-719-21
(SEQ ID NO: 825)
GAGGTGCAGCTGTTGGAGTCTGGGGGAGGCTTGGTACAGCCTGGGGGGTCCCTGCGTCTC

TCCTGTGCAGCCTCCGGATTCACCTTTAAGAGGTATGAGATGATGTGGGTCCGCCAGGCT

CCAGGGAAGGGTCTGGAGTGGGTCTCATCTATTTCGTCGGATGGTTCTTTTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGGATCCATTT

ACTGAGTTTGACTACTGGGGTCAGGGAACCCTGGTCACCGTCTCGAGC

BMS2h-719-213
(SEQ ID NO: 826)
GAGGTGCAGCTGTTGGAGTCTGGGGGAGGCTTGGTACAGCCTGGGGGGTCCCTGCGTCTC

TCCTGTGCAGCCTCCGGATTCACCTTTAAGAGGTATGAGATGATGTGGGTCCGCCAGGCT

CCAGGGAAGGGTCTGGAGTGGGTCTCATCTATTTCGTCGGATGGTTCTTTTACATACTAC

TABLE 2-continued

Human Anti-CD40L VH Domain Encoding Nucleotide Sequences

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGGACCCGTTC

ACGGAGATGGACTACTGGGGTCATGGAACCCTGGTCACCGTCTCGAGC

BMS2h-719-214  
(SEQ ID NO: 827)  
GAGGTGCAGCTGTTGGAGTCTGGGGGAGGCTTGGTACAGCCTGGGGGGTCCCTGCGTCTC

TCCTGTGCAGCCTCCGGATTCACCTTTAAGAGGTATGAGATGATGTGGGTCCGCCAGGCT

CCAGGGAAGGGTCTGGAGTGGGTCTCATCTATTTCGTCGGATGGTTCTTTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGGACCCGTTC

ACGGAGTTCGACTACTGGGGTCATGGAACCCTGGTCACCGTCTCGAGC

BMS2h-719-215  
(SEQ ID NO: 828)  
GAGGTGCAGCTGTTGGAGTCTGGGGGAGGCTTGGTACAGCCTGGGGGGTCCCTGCGTCTA

TCCTGTGCAGCCTCCGGATTCACCTTTAAGAGGTATGAGATGATGTGGGTCCGCCAGGCT

CCAGGGAAGGGTCTGGAGTGGGTCTCATCTATTTCGTCGGATGGTTCTTTTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGGAGCCGTTC

ACGGAGTTGGACTACTGGGGTCATGGAACCCTGGTCACCGTCTCGAGC

BMS2h-719-218  
(SEQ ID NO: 829)  
GAGGTGCAGCTGTTGGAGTCTGGGGGAGGCTTGGTACAGCCTGGGGGGTCCCTGCGTCTC

TCCTGTGCAGCCTCCGGATTCACCTTTAAGAGGTATGAGATGATGTGGGTCCGCCAGGCC

CCAGGGAAGGGTCTGGAGTGGGTCTCATCGATTTCGTCCGACGGTTCCTTCACGTACTAC

GCCGAGTCGGTCAAGGGCCGGTTCACCATCTCCCGCGACAATTCCAAGAACACGCTGTAT

CTGCAAATGAACAGCCTGCGTGCCGAGGATACCGCGGTATATTACTGTGCGGAACCGTTT

ACTGAGTTTGACTACTGGGGTCATGGAACCCTGGTCACCGTCTCGAGC

BMS2h-719-225  
(SEQ ID NO: 830)  
GAGGTGCAGCTGTTGGAGTCTGGGGGAGGCTTGGTACAGCCTGGGGGGTCCCTGCGTCTC

TCCTGTGCAGCCTCCGGATTCACCTTTAACACGTATGAGATGCAGTGGGTCCGCCAGGCT

CCAGGGAAGGGTCTGGAGTGGGTCTCATCTATTTCGTCGGATGGTTCTTTTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGGAACCGTTT

ACTGAGTTTGACTACTGGGGTCATGGAACCCTGGTCACCGTCTCGAGC

BMS2h-719-226  
(SEQ ID NO: 831)  
GAGGTGCAGCTGTTGGAGTCTGGGGGAGGCTTGGTACAGCCTGGGGGGTCCCTGCGTCTC

TCCTGTGCAGCCTCCGGATTCACCTTTAACAAGTATGAGATGATGTGGGCCCGCCAGGCT

CCAGGGAAGGGTCTGGAGTGGGTCTCATCTATTTCGTCGGATGGTTCTTTTACATACTAC

GCAGACTCCGTGAAGGGCCGGTTCACCATCTCCCGCGACAATTCCAGGAACACGCTGTAT

CTGCAAATGAACAGCCTGCGTGCCGAGGATACCGCGGTATATTACTGTGCGGAACCGTTT

ACTGAGTTTGACTACTGGGGTCATGGAACCCTGGTCACCGTCTCGAGC

TABLE 2-continued

Human Anti-CD40L VH Domain Encoding Nucleotide Sequences

BMS2h-719-3
(SEQ ID NO: 832)
GAGGTGCAGGTGTCGGAGTGTGGGGGAGGCTTGGTACAGCCTGGGGGGTCCGTGCGTCTC

TCCTGTGCAGCCTCCGGATTCACCTTTAAGAGGTATGAGATGATGTGGGTCCGCCAGGCT

CCAGGGAAGGGTCTGGAGTGGGTCTCATCTATTTCGTCGGATGGTTCTTTTACATACTAC

GCAGACTCCGTGAAGGGCCGGTTCACCATCTCCCGCGACAATTCCAAGAATACGCTGTAT

CTGCAAATGAACAGCCTGCGTGCCGAGGATACCGCGGTATATTACTGTGCGGATCCGTTT

ACTGAGTTTGACTACTGGGGTCAGGGAACCCTGGTCACCGTCTCGAGC

BMS2h-719-4
(SEQ ID NO: 833)
GAGGTGCAGCTGTTGGAGTCTGGGGGAGGCTTGGTACAGCCTGGGGGGTCCCTGCGTCTC

TCCTGTGCAGCCTCCGGATTCACCTTTAAGAGGTATGAGATGATGTGGGTCCGCCAGACT

CCAGGGAAGGGTCTGGAGTGGGTCTCATCTATTTCGTCGGATGGTTCTTTTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCAGTATATTACTGTGCGGAACCGTTT

ACTGAGTTTGACTACTGGGGTCAGGGAACCCTGGTCACCGTCTCAAGC

BMS2h-719-5
(SEQ ID NO: 834)
GAGGTGCAGGTGTTGGAGTCTGGGGGAGGCTTGGTACAGCCTGGGGGGTCCCTGCGTCTC

TCCTGTGCAGCCTCCGGATTCACCTTTAAGAGGTATGAGATGATGTGGGTCCGCCAGGCT

CCAGGGAAGGGTCTGGAGTGGGTCTCATCTATTTCGTCGGATGGTTCTTTTACATACTAC

GCAGACTCCGTGAAGGGCCGGTTCACCATCTCCCGCGACAATTCCAAGAACACGCTGTAT

CTGGAAATGAACAGCATGCGTGCCGAGGATACCGCGGTATATTACTGTGCGGAACCGTTT

ACTGAGTTTGACAACTGGGGTCAGGGAACCCTCGTCACCGTCTCGAGC

BMS2h-719-6
(SEQ ID NO: 835)
GAGGTGCAGCTGTTGGAGTCTGGGGGAGGCTTGGTACAGCCTGGGGGGTCCCTGCGTCTC

TCCTGTGCAGCCTCCGGATTCACCTTTAAGAGGTATGAGATGATGTGGGTCCGCCAGGCT

CCAGGGAAGGGTCTGGAGTGGGTCTCATCTATTTCGTCGGATGGTTCTTTTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCAGAACCGTTT

ACTGAGTTTGACTACTGGGGTCAGGGAACCCAGGTCACCGTCTCGAGC

BMS2h-719-7
(SEQ ID NO: 836)
GAGGTGCAGCTGTTGGAGTCTGGGGGAGGCTTGGTACAGCCTGGGGGGTCCCTGCGTCTC

TCCTGTGCAGCCTCCGGATTCAACTTTAAGAGGTATGAGATGACGTGGGTCCGCCAGGCT

CCAGGGAAGGGTCTGGAGTGGGTCTCATCTATTTCGTCGGATGGTTCTTTTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCAGACCCGTTT

ACTGAGTTTGACTACTGGGGTCAGGGAACCCTGGTCACCGTCTCGAGC

BMS2h-719-8
(SEQ ID NO: 837)
GAGGTGCAGCTGTTGGAGTCTGGGGGAGACTTGGTACAGCCTGGGGGGTCCCTGCGTCTC

TCCTGTGCAGCCTCCGGATTCACCTTTAAGAGGTATGAGATGATGTGGGTCCGCCAGGCT

CCAGGGAAGGGTCTGGAGTGGGTCTCATCTATTTCGTCGGATGGTTCTTTTACATACTAC

TABLE 2-continued

Human Anti-CD40L VH Domain Encoding Nucleotide Sequences

GCAGACTCCGTGAAGGGCCGGTTCACCATCTCACGCGACAATTCCAAGAACACGCTGTAT

CTGCAAATGAACAGCCTGCGTGCCGAGGATACCGCGGTATATTACTGTGCGGAACCGTTT

ACTGAGTTTGACTACAGGGGTCAGGGAACCCTGGTCACCGTCTCGAGC

BMS2h-719-9
(SEQ ID NO: 838)
GAGGTGCAGCTGTTGGAGTCTGGGGGAGGCTTGGTACAGCCTGGGGGGTCCCTGCGTCTC

TCCTGTGCAGCCTCCGGATTCACCTTTAAGAGGTATGAGATGTCGTGGGTCCGCCAGGCT

CCAGGGAAGGGTCTGGAGTGGGTCTCATCTATTTCGTCGGATGGTTCTTTTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGGAACCGTTT

ACTGAGTTTGACTACTGGGGTCGGGGAACCCTGGTCACCGTCTCGAGC

BMS2h-72
(SEQ ID NO: 839)
GAGGTGCAGCTGTTGGAGTCTGGGGGAGGCTTGGTACAGCCTGGGGGGTCCCTGCGTCTC

TCCTGTGCAGCCTCCGGATTCACCTTTGAGGCGTATCCTATGTCGTGGGTCCGCCAGGCT

CCAGGGAAGGGTCTAGAGTGGGTCTCAAGTATTTCCCCTCTTGGTTTGTGGACATACTAC

GCAGACTCCGTGAAGGGCCGGTTCACCATCTCCCGCGACAATTCCAAGAACACGGTGTAT

CTGCAAATGAACAGCCTGCGTGCCGAGGACACCGCGGTATATTACTGTGCGAAACTTAGT

GCTGGGCGGAGACTCATGTTTATCGGCTTTTTGACTACTGGGGTCAGGGAACCCTGGTC

ACCGTCTCGAGC

BMS2h-720
(SEQ ID NO: 840)
GAGGTGCAGCTGTTGGAGTCTGGGGGAGGCTTGGTACAGCCTGGGGGGTCCCTGCGTCTC

TCCTGTGCAGCCTCCGGATTCACCTTTGGTAATTATGAGATGATGTGGGTCCGCCAGGCT

CCAGGGAAGGGTCTAGAGTGGGTCTCATCTATTGGGGTGTTGGGTCATACGACATACTAC

GCAGACTCCGTGAAGGGCCGGTTCACCATCTCCCGCGACAATTCCPAGAACACGCTGTAT

CTGCAAATGAACAGCCTGCGTGCCGAGGATACCGCGGTATATTACTGTGCGAAACTTATG

TCGTTGAGGACGTTTGAGAATCTTTTTGACTACTGGGGTCAGGGAACCCTGGTCACCGTC

TCGAGC

BMS2h-722
(SEQ ID NO: 841)
GAGGTGCAGCTGTTGGAGTCTGGGGGAGGCTTGGTACAGCCTGGGGGGTCCCTGCGTCTC

TCCTGTGCAGCCTCCGGATTCACCTTTACGAAGTATCCTATGGCTTGGGTCCGCCAGGCT

CCAGGGAAGGGTCTAGAGTGGGTCTCAGGTATTGATGurAATGGTAATAGGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGGAAGGGACT

TGGCGTAGGCATTTTGCGATTTTTGACTACTGGGGTCAGGGAACCCTGGTCACCGTCTCG

AGC

BMS2h-723
(SEQ ID NO: 842)
GAGGTGCAGGTGTTGGAGTCTGGGGGAGGCTTGGTACAGCCTGGGGSGTCCCTGCGTCTC

TCCTGTGCAGCCTCCGGATTCACCTTTGATCTGTATGATATGATGTGGGTCCGCCAGGCT

CCAGGGAAGGGTCTAGAGTGGGTCTCATCTATTTCTGATCTGGGTACGCTTACATACTAC

GCAGACTCCGTGAAGGGCCGGTTCACCATCTCCCGCGACAATTCCAAGAACACGCTGTAT

TABLE 2-continued

Human Anti-CD40L VH Domain Encoding Nucleotide Sequences

CTGCAAATGAACAGCCTGCGTGCCGAGGACACCGCGGTATATTACTGTGCGAAAAATGGT

TTTAGGGTTACGAGTAATGATCGTAGGTTTGACTACTGGGGTCAGGGAACCCTGGTCACC

GTCTCGAGC

BMS2h-724
(SEQ ID NO: 843)
GAGGTGCAGCTGTTGGAGTCTGGGGGAGGCTTGGTACAGCCTGGGGGGTCCCTGCGTCTC

TCCTGTGCAGCCTCCGGATTCACCTTTACTGGTGGGGATATGTGGTGGGTCCGCCAGGCT

CCAGGGAAGGGTCTAGAGTGGGTCTCAATGATTGAGGGTGGTGGTGTGACTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGGAACTTGAT

CTTCGGACGGGTCAGTTTGACTACTGGGGTCAGGGAACCCTGGTCACCGTCTCGAGC

BMS2h-725
(SEQ ID NO: 844)
GAGGTGCAGCTGTTGGAGTCTGGGGGAGGCTTGGTACAGCCTGGGGGGTCCCTGCGTCTC

TCCTGTGCAGCCTCCGGATTCACCTTTTCGGCTTATACTATGGGTTGGGTCCGCCAGGCT

CCAGGGAAGGGTCTGGAGTGGGTCTCACTTATTGGGGATCGTGGTTCTTGGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGGAACCGTCG

GATCCTACTAAGTTTGACTACTGGGGTCAGGGAACCCTGGTCACCGTCTCGAGC

BMS2h-725-1
(SEQ ID NO: 845)
GAGGTGCAGCTGTTGGAGTCTGGGGGAGGCTTGGTACAGCCTGGGGGGTCCCTGCATCTC

TCCTGTGCAGCCTCCGGATTCACCTTTTCGGCTTATACTATGGGTTGGGTCCGCCAGGCT

CCAGGGAAGGGTCTGGAGTGGGTCTCACTTATTGGGGATCGTGGTTCTTGGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTTCTGTGCGGATCCGTCG

GATCCTACTAAGTTTGACTACTGGGGTCAGGGAACCCTGGTCACCGTCTCGAGC

BMS2h-725-10
(SEQ ID NO: 846)
GAGGTGCAGCTGTTGGAGTCTGGGGGAGGCTTGGTACAGCCTGGGGGGTCCCTGCGTCTC

TCCTGTGCAGCCTCCGGATTCACCTTTTCGGCTTATACTATGGGTTGGGTCCGCCAGGCT

CCAGGGAAGGGTCTGGAGTGGGTCTCACTTATTGGGGATCGTGGTTCTTGGACATACTAC

GCAGACTCCGTGAAGGGCCGGTTCACCATCTCCCGTGACAATTCCAAGAACACGCTGTAT

CTGCAAATGAACAGCCTGCGTGCCGAGGACACCGCGGTATATTACTGTGCGGATCCGTCG

GATCCTACTAAGTTTGACTACTGGGGTCAGGGAACCCTGGTCACCGTCTCGAGC

BMS2h-725-11
(SEQ ID NO: 847)
GAGGTGCAGCTGTTGGAGTCTGGGGGAGGCTTGGTACAGCCTGGGGGGTCCCTGCGTCTC

TCCTGTGCAGCCTCCGGATTCACCTTTTCGGCTTATACTATGGGTTGGGTCCGCCAGGCT

CCAGGGAAGGGTCTGGAGTGGGTCTCACTTATTGGGGATCGTGGTTCTTGGACATACTAC

GCAGACTCCGTGAAGGGCCGGTTCACCATCTCCCGCGACAATTCCAAGAACACGCTGTAT

CTGCAAATGAGCAGCCTGCGTGCCGAGGACACCGCGGTATATTACTGTGCGGATCCGTCG

GATCCTACTAAGTTTGACTACTGGGGTCAGGGAACCCTGGTCACCGTCTCGAGC

TABLE 2-continued

Human Anti-CD40L VH Domain Encoding Nucleotide Sequences

BMS2h-725-12
(SEQ ID NO: 848)
GAGGTGCAGCTGTTGGAGTCTGGGGGTGGCTTGGTACAGCCTGGGGGGTCCCTGCGTCTC

TCCTGTGCAGCCTCCGGATTCACCTTCCCGGCTTATACTATGGGTTGGGTCCGCCAGGCT

CCAGGGAAGGGTCTGGAGTGGGTCTCACTTATTGGGGATCGTGGTTCTTGGACATACTAC

GCAGACTCCGTGAAGGGCCGGTTCACCATCTCCCGCGACGATTCCAAGAACACGCTGTAT

CTGCAAATGAACAGCCTGCGTGTCGAGGACACCGCGGTATATTACTGTGCGGAACCGTCG

GATCCTACTATGTTTGTCTACTGGGGTCAGGGAACCCTTGTCACCGTCTCGAGC

BMS2h-725-13
(SEQ ID NO: 849)
GAGGTGCAGCTGTTGGAGTCTGGGGGAGGCTTGGTACAGCCTGGGGGTCCCTGCGTCTC

TCCTGTGCAGCCTCCGGATTCACCTTTTCGGCTTATACTATGGGCTGGGTCCGCCAGGCT

CCAGGGAAGGGTCTGGAGTGGGTCTCTCTTATTGGGGATCGTGGTTCTTGGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGGAACCGTCG

GATCCTACTATGTTTGTCTACTGGGGTCAGGGAACCCTGGTCACCGTCTCGAGC

BMS2h-725-14
(SEQ ID NO: 850)
GAGGTGCAGCTGTTGGAGTCTGGGGGAGGCTTGGTACAGCCTGGGGGGTCCCTGCGTCTC

TCCTGTGCAGCATCCGGATTCACCTTTTCGGCTTATACTATGGGTTGGGTCCGCCAGGCT

CCAGGGAAGGGTCTGGAGTGGGTCTCACTTATTGGGGATCGTGGTTCTTGGACATACTAC

GCAGACTCCGTGAAGGGCCGGTTCACCATCTCCCGTGACAATTCCAAGAACACGCTGTAT

CTGCAAATGAACAGCCTGCGTGCCGAGGACACCGCGGTATATTACTGTGCGGATCCGTCA

GATCCTACTATGTTTGACTACTGGGGTCAGGGAACCCTGGTCACCGTCTCGAGC

BMS2h-725-15
(SEG ID NO: 851)
GAGGTGCAGCTGTTGGAGTCTGGGGGGGGCATGGTACAGCCTGGGGGGTCCCTGCGTCTC

TCCTGTGCAGCCTCCGGATTCACCTTTTCGGCTTATACTATGGGTTGGGTCCGCCAGGCT

CCAGGGAAGGGTCTGGAGTGGGTCTCACTTATTGGGGATCGTGGTTCTTGGACATACTAC

GCAGACTCCGTGAAGGGCCGGTTCACCATCTCCCGCGACAATTCCAAGAACACGCTGTAT

CTGCAAATGAACAGCATGCGTGCCGAGGACACCGCGGTATATTACTGTGCGGATCCGTCG

GATCCTACTAAGTTTGACTACTGGGGTCAGGGAACCCTGGTCACCGTCTCGAGC

BMS2h-725-16
(SEQ ID NO: 852)
GAGGTGCAGCTGTTGGAGTCTGGGGGAGGCTTGGTACAGCCTGGGGGGTCCCTGCGTGTC

TCCTGTGCAGCCTCCGGATTCACCTTTTCGGCTTATACTATGGGTTGGGTCCGCCAGGCT

CCAGGGAAGGGTCTGGAGTGGGTCACACTTATTGGGGATCGTGGTTCTTGGACATACTAC

GCAGACTCCGTGAAGGGCCGGTTCACCATCTCCCGCGACAATTCCAAGAACACGCTGTAT

CTSCAAATGAACAGCCTGCGTGCCGAGGACACCGCGGTATATTACTGTGCGGAACCGTCG

GATCCTACTATGTTTGACTACTGGGGTCAGGGAACCCTGGTCACCGTCTCGAGC

BMS2h-725-17
(SEQ ID NO: 853)
GAGGTGCAGCTGTTGGAGTCTGGGGGAGGCTTGGTGCAGCCTGGGGGGTCCCTGCGTCTC

TCCTGTGCAGCCTCCGGATTCACCTTTACGGCTTATACTATGGGTTGGGTCCGCCAGGCT

CCAGGGAAGGGTCTGGAGTGGGTCTCACTTATTGGGGATCGTGGTTCTTGGACATACTAC

TABLE 2-continued

Human Anti-CD40L VH Domain Encoding Nucleotide Sequences

GCAGACTCCGTGAAGGGCCGGTTCACCATCTCCCGCGACAATTCCAAGAACACACTGTAT
CTGCAAATGAACAGCCTGCGTGCCGAGGACACCGCGGTATATTACTGCGCGGAACCGTCG
GATCCTACTAAGTTAGACTACTGGGGTCAGGGAACCCTGGTCACCGTCTCGAGC

BMS2h-725-18 (SEQ ID NO: 854)
GAGGTGCAGCTGTCGGAGTCTGGGGGAGGCTTGGTACAGCCTGGGGGGTCCCTGCGTCTC
ACCTGTGCAGCCTCCGGATTCACCTTTTCGGCTTATACTATGGGTTGGGTCCGCCAGGCT
CCAGGGAAGGGTCTGGAGTGGGTCTCACTTATTGGGGATCGTGGTTCTTGGACATACTAC
GCAGACTCCGTGAAGGGCCGGYTCACCATCTCCCGCGACAATTCCAAGAACACGCTGTAT
CTGCAAATGAACAGCCTGCGTGCCGAGGACACCGCGGTATATTACTGTGCGGATCCGTCG
GATCCTACTAAGTTTGTCTACTGGGGTCAGGGAACCCTGGTCACCGTCTCGAGC

BMS2h-725-19 (SEQ ID NO: 855)
GAGGTGCAGCTGTTGGAGTCTGGGGGAGGCTTGGTACAGCCTGGGGGGTCCCTGCGTCTC
TCCTGTGCAGCCTCCGGATTCACCTTTTCGGCTTATACTATGGGTTGGGTCCGCCAGGCT
CCAGGGAAGGGTCTGGAGTGGGTCTCACTTATTGGGGATCGTGGTTCTTGGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCAGATCCGTCG
GATCCTACTAAGTTTGTCTACTGGGGTCAGGGAACCCTGGTCACCGTCTCGAGC

BMS2h-725-2 (SEQ ID NO: 856)
GAGGTGCAGCTGTTGGAGTCTGGGGGAGGCTTGGTACAGCCTGGGGGGTCCCTGCGTCTC
TCCTGTGCAGCCTCCGGATTCACCTTTTCGGCTTATACTATGGGTTGGGTCCGCCAGGCT
CCAGGGAAGGGTCTGGAGTGGGTCTCACTTATTGGGGATCGTGGTTCTTGGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGCGCGGAACCGTCG
GATCCTACTAAGTTTGTCTACTGGGGTCAGGGAACCCCGGTCACCGTCTCGAGC

BMS2h-725-3 (SEQ ID NO: 857)
GAGGTGCAGCTGTTGGAGTCTGGGGGAGGCTTGGTACAGCCTGGGGGGTCCCTGCGTCTC
TCCTGTGCAGCCTCCGGATTCACCTTTTCGGCTTATACTATGGGTTGGGTCCGCCAGGCT
CCAGGGAAGGGTCTGGAGTGGGTCTCGCTTATTGGGGATCGTGGTTCTTGGACATACTAC
GCAGACTCCGTGAAGGGCCGGTTCACCATCTCCCGCGACAATTCCAGGAACATGCTGTAT
CTGCAAATGAAAAGCCTGCGTGCCGAGGACACCGCGGTATATTACTGCGCGGATCCGTCG
GATCCTACTAAGTTTGTCTACTGGGGTCAAGGAACCCAGGTCACCGTCTCGAGC

BMS2h-725-4 (SEQ ID NO: 858)
GAGGTGCAGCTGTTGGAGTCTGGGGGAGGCTTGGTACAGCCTGGGGGGTCCCTGCGTCTC
TCCTGTGCAGCCTCCGGATTCACCTTTTCGGCTTATACTATGGGTTGGGTCCGCCAGGCT
CCAGGGAAGGGTCTGGAGTGGGTCTCACTTATTGGGGATCGTGGTTCTTGGACATACTAC
GCAGACTCCGTGAAGGGCCGGTTCACCATCTTCCGCGACAATTCCAAGAACACGCTGTAT
CTGCAAATGAACAGCCTGCGTGCCGAGGACACCGCGGTATATTACTGTGCGGATCCGTCG
GATCCTACTAAGTTTGTCTACTGGGGTCAGGGAACCCTGGTCACCGTCTCGAGC

TABLE 2-continued

Human Anti-CD40L VH Domain Encoding Nucleotide Sequences

BMS2h-725-5
(SEQ ID NO: 859)
GAGGTGCAGCTGTTGGAGTCTGGGGGAGGCTTGTTACAGCCTGGGGGGTCCCTGCGTCTC

TCCTGTGCAGCCTCCGGATTCACCTTTTCGGATTATACTATGGGTTGGGTCCGCCAGGCT

CCAGGGAAGGGTCTGGAGTGGGTCTCACTTATTGGGGATCGTGGTTCTTGGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGGAACCGTCG

GATCCTACTAAGTTCGACTACTGGGGTCGGGGAACCCTGGTCACCGTCTCGAGC

BMS2h-725-6
(SEQ ID NO: 860)
GAGGTGCAGCTGTTGGAGTCTGGGGGAGGCTTGGTACAGCCTGGGGGGTCCCTGCGTCTC

TCCTGTGCAGCCTCCGGATTCACCTTTTCGGCTTATACTATGGGTTGGGTCCGCCAGGCT

CCAGGGAAGGGTCTGGAGTGGGTCTCACTTATTGGGGATCGTGGTTCTTGGACATACTAC

GCAGACTCCGTGAAGGGCCGGTTCACCATCTCACGCGACAATTCCAAGAACACGCTGTAT

CTGCAAATGAACAGCCTGCGTGCCGAGGACACCGCGGTATATTACTGTGCGGAACCGTCC

GATCCTACTAAGTTTGTCTACTGGGGTCAGGGAACCCTGGTCACCGTCTCGAGC

BMS2h-725-7
(SEQ ID NO: 861)
GAGGTGCAGCTGTTGGAGTCTGGGGGAGGCTTGGTACAGCCTGGGGGGTCCCTGCGTCTC

TCCTGTGCAGCCTCCGGATTCACCTTTTCGGCTTATACTATGGGTTGGGTCCGCCAGGCT

GCAGGGAAGGGTCTGGAGTGGGTCTCACTTATTGGGGATCGTGGTACTTGGACATATTAC

GCAGACCCCGTGAAGGGCCGGTTCACCATCTCCCGCGACAATTCCAAGAACACACTGTAT

CTGCAAATGAACAGCCTGCGTGCCGAGGACACTGCGGTATATTATTGTGCGGATCCGTCG

GATCCTACTAAGTTTGACTACTGGGGTCAGGGAACCCTGGTCACCGTCTCGAGC

BMS2h-725-8
(SEQ ID NO: 862)
GAGGTGCAGCTGTTGGAGTCTGGGGGAGGCTTGGTACAGCCTGGGGGGTCCCTGCGTCTC

TCCTGTGCAGCCTCCGGATTCACCTTTTCGGCTTATACTATGGGTTGGGTCCGCCAGGCT

CCAGGGAAGGGTCTGGAGTGGGTCTCACTTATTGGGGATCGTGGTTCTTGGACATACTAC

GCAGACTCCGTGAAGGGCCGGTTCACCGTCTCCCGCGACAATTCCAAGAACACGCTGTAT

CTGCAAATGAACAGCCTGCGTGCCGAGGACACCGCGGTATATTACTGTGCGGAACCGTCG

GATCCTACTAAGTTTGACTACTGGGGTCAGGGAACCCTGGTCACCGTCTCGAGC

BMS2h-725-9
(SEQ ID NO: 863)
GAGGTGCAGCTGTTGGAGTCTGGGGGAGGCTTGGTACAGCCTGGGGGGTCCCTGCGTCTC

TCCTGTGCAGCCTCCGGATTCACCTTTTCGGCTTATACTATGGGTTGGGTCCGCCAGGCT

CCAGGGATGGGTCTGGAGTGGGTCTCACTTATTGGGGATCGTGGTTCTTGGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGGAACCGTCG

GATCCTACTAAGTTTGACTACTGGGGTCAGGGAACCCTGGTCACCGTCTCGAGC

BMS2h-726
(SEQ ID NO: 864)
GAGGTGCAGCTGTTGGAGTCTGGGGGAGGCTTGGTACAGCCCGGGGGGTCCCTGCGTCTC

TCCTGTGCAGCCTCCGGATTCACCTTTGATAATTATAAGATGTATTGGGTCCGCCAGGCT

CCAGGGAAGGGTCTGGAGTGGGTCTCAAGTATTTCGGAGATAGGTAATCTGACATACTAC

TABLE 2-continued

Human Anti-CD40L VH Domain Encoding Nucleotide Sequences

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGATAGCTCTG

ACGCGTTTTGACTACTGGGGTCAGGGAACCCTGGTCACCGTCTCGAGC

BMS2h-727
(SEQ ID NO: 865)
GAGGTGCAGCTGTTGGAGTCTGGGGGAGGCTTGGTACAGCCTGGGGGGTCCCTGCGTCTC

TCCTGTGCAGCCTCCGGATTCACCTTTGCGAGTTATCGTATGTATTGGGTCCGCCAGGCT

CCAGGGAAGGGTCTGGAGTGGGTCTCATATATTGATCCGCCGGGTAGTCGTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAAGTTTG

AATTTGTCGTTTCCTTATATTAATTTTGACTACTGGGGTCAGGGAACCCTGGTCACCGTC

TCGAGC

BMS2h-728
(SEQ ID NO: 866)
GAGGTGCAGCTGTTGGAGTCTGGGGGAGGCTTGGTACAGCCTGGGGGGTCCCTGCGTCTC

TCCTGTGCAGCCTCCGGATTCACCTTTGAGCGGTATGAGATGCTGTGGGTCCGCCAGGCT

CCAGGGAAGGGTCTAGAGTGGGTCTCACGTATTTCTCATTCGGGTCGGACGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGCAATTGGAT

GGTCCGTTTGACTACTGGGGTCAGGGAACCCTGGTCACCGTCTCGAGC

BMS2h-729
(SEQ ID NO: 867)
GAGGTGCAGCTGTTGGAGTCTGGGGGAGGCTTGGTACAGCCTGGGGGGTCCCTGCGTCTC

TCCTGTGCAGCCTCCGGATTCACCTTTAAGAGGTATTATATGGATTGGGTCCGCCAGGCT

CCAGGGAAGGGTCTAGAGTGGGTCTCAAGGATTAATCATAATGGTTCTGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAAATGCCG

CAGGGTACTTCTGATTGGTATTATTTTGACTACTGGGGTCAGGGAACCCTGGTCACCGTC

TCGAGC

BMS2h-73
(SEQ ID NO: 868)
GAGGTGCAGCTGTTGGAGTCTGGGGGAGGCTTGGTACAGCCTGGGGGGTCCCTGCGTCTC

TCCTGTGCAGCCTCCGGATTCACCTTTTCTAAGTATGATATGTCTTGGGTCCGCCAGGCT

CCAGGGAAGGGTCTAGAGTGGGTCTCAACTATTCTGGAGGATGGTCTGACTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCGGGG

CGTTTGTTTGACTACTGGGGTCAGGGAACCCTGGTCACCGTCTCGAGC

BMS2h-74
(SEQ ID NO: 869)
GAGGTGCAGCTGTTGGAGTCTGGGGGAGGCTTGGTACAGCCTGGGGGGTCCCTGCGTCTC

TCCTGTGCAGCCTCCGGATTCACCTTTTCGGATTATCCTATGACGTGGGTCCGCCAGGCT

CCAGGGAAGGGTCTGGAGTGGGTCTCAACTATTCTGTCTCCGGGTACGGAGACATACTAC

GCAGACTCCGTGAAGGGCCGGTTCACCATGTCCCGCGACAATTCCAAGAACACGCTGTAT

TABLE 2-continued

Human Anti-CD40L VH Domain Encoding Nucleotide Sequences

CTGCAAATGAACAGCCTGCGTGCCGAGGACACCGCGGTATATTACTGTGCGAAAGCTGAG

AAGGATTTTGACTACTGGGGTCAGGGAACCCTGGTCACCGTCTCGAGC

BMS2h-741
(SEQ ID NO: 870)
GAGGTGCAGCTGTTGGAGTCTGGGGGAGGCTTGGTACAGCCTGGGGGGTCCCTGCGTCTC

TCCTGTGCAGCCTCCGGATTCACCTTTGAGGGTGGTGAGATGGGTTGGGTCCGCCAGGCT

CCAGGGAAGGGTCTAGAGTGGGTCTCAATGATTCCGATGGATGGTAGTGCGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGCGGGT

GAGGTGTTTGACTACTGGGGTCAGGGAACCCTGGTCACCGTCTCGAGC

BMS2h-742
(SEQ ID NO: 871)
GAGGTGCAGCTGTTGGAGTCTGGGGGAGGCTTGGTACAGCCTGGGGGGTCCCTGCGTCTC

TCCTGTGCAGCCTCCGGATTCACCTTTAGGGAGTATCATATGAAGTGGGCCCGCCAGGCT

CCAGGGAAGGGTCTAGAGTGGGTCTCAGGGATTAGTAGGGATGGTATGAATACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGATACAGCTT

GCTTTGTTTGACTACTGGGGTCAGGGAACCCTGGTCACCGTCTCGAGC

BMS2h-743
(SEQ ID NO: 872)
GAGGTGCAGCTGTTGGAGTCTGGGGGAGGCTTGGTACAGCCTGGGGGGTCCCTGCGCCTC

TCCTGTGCAGCCTCCGGATTCACCTTTCGTGATTATGAGATGCTTTGGGCCCGCCAGGCT

CCAGGGAAGGGTCTAGAGTGGGTCTCAGGTATTCTTCCGTCGGGTGGGGCTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGCTGGT

TCGGGGAATGGGCCTATTCTTTTTGACTACTGGGGTCAGGGAACCCTGGTCACCGTCTCG

AGC

BMS2h-744
(SEQ ID NO: 873)
GAGGTGCAGCTGTTGGAGTCTGGGGGAGGCTTGGTACAGCCTGGGGGGTCCCTGCGTCTC

TCCTGTGCAGCCTCCGGATTCACCTTTAAGGAGCATGATATGTTTTGGGTCCGCCAGGCT

CCAGGGAAGGGTCTAGAGTGGGTCTCAGGGATTGGGCTGAGGGTGTTTGGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGGAACCGACG

ATGTCTAATGGTTCTCAGTCGCGTTTTGACTACTGGGGTCAGGGAGACCTGGTCACCGTC

TCGAGC

BMS2h-745
(SEQ ID NO: 874)
GAGGTGCAGCTGTTGGAGTGTGGGGGAGGCTTGGTACAGCCTGGGGGGTCCCTGCGTCTC

TCCTGTGCAGCCTCCGGATTCACCTTTGATAATACTGAGATGGCTTGGGTCCGCCAGGCT

CCAGGGAAGGGTCTAGAGTGGGTCTCAGGTATTATTGAGGATGGTAATCGTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAATTCGT

TABLE 2-continued

Human Anti-CD40L VH Domain Encoding Nucleotide Sequences

AATCTGCATTGGGATGTGGGGAGGCAGTTTGACTACTGGGGTCAGGGAACCCTGGTCACC

GTCTCGAGC

BMS2h-745-1

(SEQ ID NO: 875)
GAGGTGCAGCTGTTGGAGTCTGGGGGAGGCTTGGTACAGCCTGGGGGGTCCCTGCGTCTC

TCCTGTGCAGCCTCCGGATTCACCTTTGATAATACTGAGATGGCTTGGGTCCGCCAGGCT

CCAGGGAAGGGTCTAGAGTGGGTTTCAGGTATTACTGAGGATGGTAATCGTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAATTCGT

AATCTGCATTGGGATGTGGGGAGGCAGTTTGACTACTGGGGTCAGGGAACCCTGGTCACC

GTCTCGAGC

BMS2h-745-10

(SEQ ID NO: 876)
GAGGTGCAGCTGTTGGAGTCTGGGGGAGGCTTGGTACAGCCTGGGGGGTCCCTTCGTCTC

TCCTGTGCAGCCTCCGGATTCACCTTTGATAATACTGAGATGGCTTGGGTCCGCCAGGCT

CCAGGGAAGGGTCTAGAGTGGGTCTCAGGTATTACTGAGGATGGTAATCGTACATACTAC

GCAGACTCCGTGAAGGGCCGGTTCACCATCTCCCGCGACAATTCCAAGAACACGCTGTAT

CTGCAAATGAACAACCTGCGTGCCGAAGACACCGCGGTATATTACTGTGCGAAAATTCGT

AATCTGCATTGGGATGTGGGGAGGCAGTTTGACTACTGGGGTCAGGGAACCCTGGTCACC

GTCTCGAGC

BMS2h-745-11

(SEQ ID NO: 877)
GAGGTGCAGCTGTTGGAGTCTGGGGGAGGCTTGGTACAGCCTGGGGGGTCCCTGCGTCTC

TCCTGTGCAGCCTCCGGATTCACCTTTGATAATACTGAGATGGCTTGGATCCGCCAGGCT

CCAGGGAAGGGTCTAGAGTGGGTCTCAGGTATTACTGAGGATGGTAATCGTACATACTAC

GCAGAGTCCGTGAAGGGCCGGTTCACCATCTCCCGCGACAATTTCAAGAACACGCTGTAT

CTGCAGATGAACAGCCTGCGTGCCGAGGACACCGCGGTATATTACTGTGCGAAAATTCGT

AATCTGCATTGGGATGTGGGGAGGCAGTTTGACTACTGGGGTCAGGGAACCCTGGTCACC

GTCTCGAGC

BMS2h-745-12

(SEQ ID NO: 878)
GAGGTGCAGCTGTTGGAGTCTGGGGGAGGCTTGGTACAGCCTGGGGGGTCCCTGCGTCTC

TCCTGTGCAGCCTCCGGATTCACCTTTGATAATACTGAGATGGCTTGGGTCCGCCAGGCT

CCAGGGAAGGGTCTAGAGTGGGTCTCAGGTATTACTGAGGATGGTAATCGTACATACTAC

GCAGATTCCGTGAAGGGCCGGTTCACCATCTCCCGCGACAATTCCATGAACACGCTGTAT

CTGCAAATGAACAGCCTGCGTGCCGAGGACACCGCGGTATATTACTGTGCGAAAATTCGT

AATCTGCATTGGGATGTGGGGAGGCAGTTTGTCTACTGGGGTCAGGGAACCCTGGTCACC

GTCTCGAGC

BMS2h-745-13

(SEQ ID NO: 879)
GAGGTGCAGCTGTTGGAGTCTGGGGGAGGCTTGGTACAGCCTGGGGGGTCCTTGCGTCTC

TCCTGTGCAGCCTCCGGATTCACCTTTGATAACACTGAGATGGCTTGGATCCGCCAGGCT

CCAGGGAAGGGTCTAGAGTGGGTCTCAGGTATTATTGAGGATGGTAATCGTACATACTAC

GCAGACTCCGTGAAGGGCCGGTTCACCATCTCCCGCGACAATTCCAAGAACACGCTGTAT

TABLE 2-continued

Human Anti-CD40L VH Domain Encoding Nucleotide Sequences

CTGCAAATGAACAGCCTGCGTGCCGAGGACACCGCGGTATATTACTGTGCGAAAATTCGT

AATCTGCATTGGGATGTGGGGAGGCAGTTTGACTACTGGGGTCAGGGAACCCTGGTCACC

GTCTCGAGC

BMS2h-745-14 (SEQ ID NO: 880)
GAGGTGCAGCTGTTGGAGTCTGGGGGAGGCTTGGTACAGCCTGGGGGGTCCCTGCGTCTC

TCCTGTGCAGCCTCCGGGTTCACCTTTGATAATACTGAGATGGCTTGGATCCGCCAGGCT

CCAGGGAAGGGTCTAGAGTGGGTCTCAGGTATTACTGAGGATGGTAATCGTACATACTAC

GCAGACTCCGTGAAGGGCCGGTTCACCATCTCCCGCGACAATTCCAAGAACACGCTGTAT

CTGCAAATGAACAGCCTGCGTGCTGAGGACACCGCGGTATATTACTGTGCGAAAATTCGT

AATCTGCATTGGGATGTGGGGAGGCAGTTTGACTACTGGGGTCAGGGAACCCTGGTCACC

GTCTCGAGC

BMS2h-745-15 (SEQ ID NO: 881)
GAGGTGCAGCTGTTGGAGTCTGGGGGAGGCTTGGTACAGCCAGGGGGGTCCCTGCGTCTC

TCCTGTGCAGCCTTTGGATTCACCTTTGATAATACTGAGATGGCTTGGATCCGCCAGGCT

CCAGGGAAGGGTCTAGAGTGGGTCTCAGGTATTACTGAGGATGGTAATCGTACATACTAC

GCAGACTCCGTGAAGGGCCGGTTCACCATCTCCCGCGACAATTCCAAGAACGCGCTGTAT

CTGCAAATGAACAGCCTGCGTGCCGAGGACACCGCGGTATATTACTGTGCGAAAATTCGT

AATCTGCATTGGGATGTGGGGAGGCAGTTTGACTACTGGGGTCTGGGAACCCTGGTCACC

GTCTCGAGC

BMS2h-745-16 (SEQ ID NO: 882)
GAGGTGCAGCTGTTGGAGTCTGGGGGAGGCTTGGTACAGCCTGGGGGGTCCCTGCGTCTC

TCCTGTGCAGCCTCCGGATTCACCTTTGATAATACTGAGATGGCTTGGGTCCGCCAGGCT

CCAGGGAAGGGTCTAGAGTGGGTCTCAGGTATTACTGAGGATGGTAATCGTACATACTAC

GCAGACTCCGTGAAGGGCCGGTTCACCATCTCCCGCGACAATACCAAGAACACGCTGTAT

CTGCAAATGAACAGCCTGCGTGCCGAGGACACCGCGGTATATTACTGTGCGAAAATTCGT

AATCTGCATTGGGATGTGGGGAGGCAGTTTGTCTACTGGGGTCAGGGAACCCTGGTCACC

GTCTCGAGC

BMS2h-745-17 (SEQ ID NO: 883)
GAGGTGCAGCTGTTGGAGTCTGGGGGAGGCTTGGTACAGCCTGGGGGGTCCCTGCGTCTC

TCCTGTGCAGCCTCCGGATTCACCTTTGATAATACTGAGATGGCCTGGATCCGCCAGGCT

CCAGGGAAGGGTCTAGAGTGGGTCTCAGGTATTATTGAGGATGGTAATCGTACATACTAC

GCAGACTCCGTGAAGGGCCGGTTCACCATCTCCCGCGACAATTCCAAGAACAGGCTGTAT

CTGCAAATGAACAGCCTGCGTGCCGAGGACACCGCGGTATATTACTGTGCGAAAATTCGT

AATCTGCATTGGGATGTGGGGAGGCAGTTTGACTACTGGGGTCAGGGCACCCTGGTCACC

GTTTCGAGC

BMS2h-745-18 (SEQ ID NO: 884)
GAGGTGCAGCTGTTGGAGTCTGGGGGAGGCTTGGTACAGCCTGGGGGGTCCCTGCGTCTC

TCCTGTGCAGCCTCCGGATTCACCTTTGATAATACTGAGATGGCTTGGGTCCGCCAGGCT

CCAGGGAAGGGTCTAGAGTGGGTCTCAGGTATTACTGAGGATGGTAATCGTACATACTAC

TABLE 2-continued

Human Anti-CD40L VH Domain Encoding Nucleotide Sequences

GCAGACTCCGTGNNGGGCCGGTTCACCATCTCCCGCGACAATTCCAAGAACACGCTGTAT
CTGCAAATGAACAGCCTGCGTGCCGAGGACACCGCGGTATATCACTGTGCGAAAATTCGT
AATCTGCATTGGGATGTGGGGAGGCAGTTTGACTACTGGGGTCAGGGAACCCTCGTCACC
GTCTCGAGC

BMS2h-745-19
(SEQ ID NO: 885)
GAGGTGCAGCTGTTGGAGTCTGGGGGAGGCTTGGTACAGCCTGAGGGGTCCCTGCGTCTC
TCCTGTGCAGCCTCCGGATTCACCTTTGATAATACTGAGATGGCTTGGGTCCGCCAGGCT
CCAGGGAAGGGTCTAGAGTGGGTCTCAGGTATTATTGAGGATGGTAATCGTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAATTCGT
AATCTGCATTGGGATGTGGGGAGGCAGTTTGACTACTGGGGTCAGGGAACCCTGGTCACC
GTCTCGAGC

BMS2h-745-2
(SEQ ID NO: 886)
GAGGTGCAGCTGTTGGAGTCTGGGGGAGGCTTGGTACAGCCTGGGGGGTCCCTGCGTCTC
TCCTGTGCAGCCTCCGGATTCACCTTTGATAATACTGAGATGGCTTGGGTCCGCCAGGCT
CCAGGGAAGGGTCTAGAGTGGGTCTCAGGTATTAGTGAGGATGGTAATCGTACATACTAC
GCAGACTCCGTGAAGGGCCGGTTCACCATCTCCCGCGACAATTCCAAGAACACGCTGTAT
CTGCAAATGAACAGCCTGCGTGCAGAGGACTCCGCGGTATATTACTGTGCGAAAATTCGT
AATCTGCATTGGGATGTGGGGAGGCAGTTTGTCTACTGGGGTCAGGGAACCCTGGTCACC
GTCTCGAGC

BMS2h-745-3
(SEQ ID NO: 887)
GAGGTGCAGCTGTTGGAGTCTGGGGGAGGCTTGGTAGAGCCTGGGGGGTCCCTGCGTCTC
TCCTGTGCAGCCTCCGGATTCACCTTTGATAATACTGAGATGGCTTGGGTCCGCCAGGCT
CCTGGGAAGGGTCTCGAGTGGGTCTCAGGTATTACTGAGGATGGTAATCGTACATACTAC
GCAGACTCCGTGAAGGGCCGGTTCACCATCTCCCGCGACAATTCCAAGAACACGCTGTAT
CTGCAAATGAGCAGCCTGCGTGCCGAGGACACCGCGGTATATTACTGTGCGAAAATTCGT
AATCTGCATTGGGATGTGGGGAGGCAGTTTGACTACTGGGGTCAGGGAACCCTGGTCACC
GTCTCGAGC

BMS2h-745-4
(SEQ ID NO: 888)
GAGGTGCAGCTGTTGGAGTCTGGGGGAGGCCTGGTACAGCCTGGGGGGTCCCTGCGTCTC
TCCTGTGCAGCCTCCGGATTCACCTTTGATAATACTGAGATGGCTTGGGTCCGCCAGGCT
CCAGGGAAGGGTCTAGAGTGGGTCTCAGGTATTAGTGAGGATGGTAATCGTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATCACTGTGCGAAAATTCGT
AATCTGCATTGGGATGTGGGGAGGCAGTTTGACTACTGGGGTCAGGGAACCCTGGTCACC
GTCTCGAGC

BMS2h-745-5
(SEQ ID NO: 889)
GAGGTGCAGCTGTTGGAGTCTGGGGGAGGCTTGGTACAGCCTGGGGGGTCCCTGCGTCTC
TCCTGTGCAGCCTCCGGATTCACCTTTGATAATACTGAGATGGCTTGGGTCCGCCAGGCT

TABLE 2-continued

Human Anti-CD40L VH Domain Encoding Nucleotide Sequences

CCAGGGAAGGGTCTAGAGTGGGTCTCAGGTATTACTGAGGATGGTAATCGTACATACTAC

GCTGACTCCGTGAAGGGCCGGTTCATCATCTCCCGCGACAATTCCAAGAACACGCTGAAT

CTGCAAATGAACAGCCTGCGTGCCGAGGACACCGCGGTATATTACTGTGCGAAAATTCGT

AATCTGCATTGGGATGTGGGGAGGCAGTTTGACTACTGGGGTCAGGGAACCCTGGTCACC

GTCTCGAGC

BMS2h-745-6
(SEQ ID NO: 890)
GAGGTGCAGCTGTTGGAGTCTGGGGGAGGCTTGGTACAGCCTGGGGGGTCCCTGCGTCTC

TCCTGTGCAGCCTCCGGATTCACCTTTGATAATACTGAGATGGCTTGGATCCGCCAGGCT

CCAGGGAGGGGTCTAGAGTGGGTCTCAGGTGTTACTGAGGATGGTAATCGTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAATTCGT

AATCTGCATTGGGATGTGGGGAGGCAATTTGACTACTGGGGTCAGGGAACCCTGGTCACC

GTCTCGAGC

BMS2h-745-7
(SEQ ID NO: 891)
GAGGTGCAGCTGTTGGAGTCAGGGGGAGGCTTGGTACAGCCTGGGGGGTCCCTGCGTCTC

TCCTGTGAAGCCTCCGGATTCACCTTTGATAATACTGAGATGGCTTGGATCCGCCAGGCT

CCAGGGAAGGGTCTAGAGTGGGTCTCAGGTATTATTGAGGATGGTAATCGTACATACTAC

GCAGACTCCGTGAAGGGCCGGTTCACCATCTCCCGCGACAATACCAAGAACACGCTGTAT

CTGCAAATGAACAGCCTGCGTGCCGAGGACACCGCGGTATATTATTGTGCGAAAATTCGT

AATCTGCATTGGGATGTGGGGAGGCAGTTTGACTACTGGGGTCAGGGAACCCTGGTCACC

GTCTCGAGT

BMS2h-745-8
(SEQ ID NO: 892)
GAGGTGCAGCTGTTGGAGTCTGGGGGAGGCTTGGTACAGCCTGGGGGGTCCCTGCGTCTC

TCCTGTGCAGCCTCCGGATTCACCTTTGATAATACTGAGATGGCTTGGATCCGCCAGGCT

CCAGGGAAGGGTCTAGAGTGGGTCTCAGGTATTACTGAGGATGGTGATCGTACATACTAC

GCAGACTCCGTGAAGGGCCGGTTCACCATCTCCCGCGACAATTCCAAGAGCTCGCTGTAT

CTGCAAATGAACAGCCTGCGTGCCGAGGACACCGCGGTATATTACTGTGCGAAAATTCGT

AATCTGCATTGGGATGTGGGGAGGCAGTTTGACTACTGGGGTCAGGGAACCCTGGTCACC

GTCTCCAGC

BMS2h-745-9
(SEQ ID NO: 893)
GAGGTGCAGCTGTTGGAGTCTGGGGGAGGCTCGGTACAGCCTGGGGGGTCCCTGCGTCTC

TCCTGTGCAGCCTCCGGATTCACCTTTGATAATACTGAGATGGCTTGGGTCCGCCAGGCT

CCAGGGAAGGGTCTAGAGTGGGTCTCAGGTATTACTGAGGATGGTAATCGTACATACTAC

GCAGACTCCGTGAAGGGCCGGTTCACCATCTCCCGCGACAATTCCAAGAACACTCTGTAT

CTGCAAATGAACAGCCTGCGTGCCGAGGACACCGCGGTATATTACTGTGCGAAAATTCGT

AATCTGCATTGGGATGTGGGGAGGCAGTTGTCTACTGGGGTCAGGGAACCCTGGTCACC

GTCTCGAGC

TABLE 2-continued

Human Anti-CD40L VH Domain Encoding Nucleotide Sequences

BMS2h-746
(SEQ ID NO: 894)
GAGGTGCAGCTGTTGGAGTCTGGGGGAGGCTTGGTACAGCCTGGGGGGTCCCTGCGTCTC

TCCTGTGCAGCCTCCGGATTCACCTTTGGGTCGGCTGAGATGGGGTGGGTCCGCCAGGCT

CCAGGGAAGGGTCTAGAGTGGGTCTCAGGTATTTCGAGGCCTGGTCAGGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAtATTCGT

AATCTGCATTGGGATGTGGGGAGGCAGTTTGACTACTGGGGTCAGGGAACCCTGGTCACC

GTCTCGAGC

BMS2h-747
(SEQ ID NO: 895)
GAGGTGCAGCTGTTGGAGTCTGGGGGAGGCTTGGTACAGCCTGGGGGGTCCCTGCGTCTC

TCCTGTGCAGCCTCCGGATTCACCTTTGATGATGGTACTATGGGGTGGGCCCGCCAGGCT

CCAGGGAAGGGTCTAGAGTGGGTCTCACTTATTTTGCCGTCGGGTAGTCGTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACATTCG

CTGACTAATCGTCCGTTTGACTACTGGGGTCAGGGAACCCTGGTCACCGTCTCGAGC

BMS2h-748
(SEQ ID NO: 896)
GAGGTGCAGCTGTTGGAGTCTGGGGGAGGCTTGGTACAGCCTGGGGGGTCCCTGCGTCTC

TCCTGTGCAGCCTCCGGATTCACCTTTAGTAAGTATGATATGCGGTGGGCCCGCCAGGCT

CCAGGGAAGGGTCTAGAGTGGGTCTCAGATATTGATGCTGTTGGTACTCGGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGATACCGGGG

GGGACGTTTGACTACTGGGGTCAGGGAACCCTGGTCACCGTCTCGAGC

BMS2h-749
(SEQ ID NO: 897)
GAGGTGCAGCTGTTGGAGTCTGGGGGAGGCTTGGTACAGCCTGGGGGGTCCCTGCGTCTC

TCCTGTGCAGCCTCCGGATTCACCTTTGAGATGTATGGTATGATGTGGGCCCGCCAGGCT

CCAGGGAAGGGTCTAGAGTGGGTCTCATCTATTGAGGGTGCGGGTCATGCGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACTGCGGTATATTACTGTGCGATAGTGCTT

GGTATGTTTGACTACTGGGGTCAGGGAACCCTGGTCACCGTCTCGAGC

BMS2h-75
(SEQ ID NO: 898)
GAGGTGCAGCTGTTGGAGTCTGGGGGAGGCTTGGTACAGCCTGGGGGGTCCCTGCGTCTC

TCCTGTGCAGCCTCGGGATTCACCTTTTTGCAGTATCCGATGGGTTGGGTCCGCCAGGCT

CCAGGGAAGGGTCTAGAGTGGGTCTCAACTATTTCTCCTGTTGGTTTGACTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAATTGTTT

GAGGGGTCGAGGATTCAGCGTGATGTGGGTTTTGACTACTGGGGTCAGGGAACCCTGGTC

ACCGTCTCGAGC

TABLE 2-continued

Human Anti-CD40L VH Domain Encoding Nucleotide Sequences

BMS2h-750
(SEQ ID NO: 899)
GAGGTGCAGCTGTTGGAGTCTGGGGGAGGCTTGGTACAGCCTGGGGGGTCCCTGCGTCTC

TCCTGTGCAGCCTCCGGATTCACCTTTGAGAAGTATCAGATGGGTTGGGCCCGCCAGGCT

CCAGGGAAGGGTCTAGAGTGGGTCTCATCGATTCGGGGTCTGGTCTTGTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGTGCAT

ACTACGCTGCATACGGAGGTGATTGGGTTTGACTACTGGGGTCAGGGAACCCTGGTCACC

GTCTCGAGC

BMS2h-751
(SEQ ID NO: 900)
GAGGTGCAGCTGTTGGAGTCTGGGGGAGGCTTGGTACAGCCGGGGGGGTCCCTGCGTCTC

TCCTGTGCAGCCTCCGGATTCACCTTTAGTCAGTATACGATGTATTGGGCCCGCCAGGCT

CCAGGGPAGGGTCTAGAGTGGGTCTCAGAGATTTCTCATAGTGGTTCTAATACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGATATCGGGG

CTGCATTTTGACTACTGGGGTCAGGGAACCCTGGTCACCGTCTCGAGC

BMS2h-752
(SEQ ID NO: 901)
GAGGTGCAGCTGTTGGAGTCTGGGGGAGGCTTGGTACAGCCTGGGGGGTCCCTGCGTCTC

TCCTGTGCAGCCTCCGGATTCACCTTTTCGGATTATGCGATGGCTTGGGTCCGCCAGGCT

CCAGGGAAGGGTCTGGAGTGGGTCTCACGTATTGGTGTGGAGGGTGGGGATACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAATTGTTG

CGGCTTTATCGTCTGGGGTTTGACTACTGGGGTCAGGGAACCCTGGTCACCGTCTCGAGC

BMS2h-753
(SEQ ID NO: 902)
GAGGTGCAGCTGTTGGAGTCTGGGGGAGGCTTGGTACAGCCTGGGGGGTCCCTGCGTCTC

TCCTGTGCAGCCTCCGGATTCACCTTTGCTAAGTATGATATGACGTGGGTCCGCCAGGCT

CCAGGGAAGGGTCTAGAGTGGGTCTCAAAGATTAATTCTGATGGTGGTCTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGGGTTG

CATGGTAGGGGTTTGTTATTTTTGACTACTGGGGTCAGGGAACCCTGGTCACCGTCTCG

AGC

BMS2h-754
(SEQ ID NO: 903)
GAGGTGCAGCTGTTGGAGTCTGGGGGAGGCTTGGTACAGCCTGGGGGGTCCCTGCGTCTC

TCCTGTGCAGCCTCCGGATTCACCTTTTCGCGGTATGATATGGTGTGGGTCCGCCAGGCT

CCAGGGAAGGGTCTAGAGTGGGTCTCACGGATTAATTCTATGGGTCTGGCTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAAGATTAT

TCGGTTGCGCCGCATGGGTATCCTTTGGGTTTTGACTACTGGGGTCAGGGAACCCTGGTC

ACCGTCTCGAGC

TABLE 2-continued

Human Anti-CD40L VH Domain Encoding Nucleotide Sequences

BMS2h-755
(SEQ ID NO: 904)
GAGGTGCAGCTGTTGGAGTCTGGGGGAGGCTTGGTACAGCCTGGGGGGTCCCTGCGTCTC
TCCTGTGCAGCCTCCGGATTCACCTTTAAGGATTATTCGATGATGTGGGTCCGCCAGGCT
CCAGGGAAGGGTCTAGAGTGGGTCTCAACGATTACTGATAATGGTACGTCTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACATATG
TCGCTTGCTACTTATCTGCAGTTTTTTGACTACTGGGGTCAGGGAACCCTGGTCACCGTC
TCGAGC

BMS2h-756
(SEQ ID NO: 905)
GAGGTGCAGCTGTTGGAGTCTGGGGGAGGCTTGGTACAGCCTGGGGGGTCCCTGCGTCTC
TCCTGTGCAGCCTCCGGATTCACCTTTATGGAGTATGATATGCTTTGGGTCCGCCAGGCT
CCAGGGAAGGCTCTAGAGTGGGTCTCACGTATTTCGTCGGATGGTTTTTGGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAAGGGGTG
AGTGCGCTTGCTCCTTTTGATATTGGTTTTGACTACTGGGGTCAGGGAACCCTGGTCACC
GTCTCGAGC

BMS2h-757
(SEQ ID NO: 906)
GAGGTGCAGCTGTTGGAGTCTGGGGGAGGCTTGGTACAGCCTGGGGGGTCCCTGCGTCTC
TCCTGTGCAGCCTCCGGATTCACCTTTAVGGAGTATAATATGGCTTGGGTCCGCCAGGCT
CCAGGGAAGGGTCTGGAGTGGGTCTCAAGTATTAATTTTGCTGGTCGGACGACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGAAACTGTCT
CTTCCTTTGGATATTTTTTCTTTTGACTACTGGGGTCAGGGAACCCTGGTCACCGTCTCG
AGC

BMS2h-758
(SEQ ID NO: 907)
GAGGTGCAGCTGTTGGAGTCTGGGGGAGGCTTGGTACAGCCTGGGGGGTCCCTGCGTCTC
TCCTGTGCAGCCTCCGGATTCACCTTTGGTGATTATGGTATGAATTGGGTCCGCCAGGCT
CCAGGGAAGGGTCTGGAGTGGGTCTCACATATTTCTTCTAATGGTCGTTTTACATACTAC
GCAGACTCCGTGAAGGGCCGGTTCACCATCTCCCGCGACAATTCCAAGAACACGCTGTAT
CTGCAAATGAACAGCCTGCGTGCCGAGGACACCGCGGTATATTACTGTGCGGAAACTAGT
GGTTATTTTGACTACTGGGGTCAGGGAACCCTGGTCACCGTCTCGAGC

BMS2h-758-1
(SEQ ID NO: 908)
GAGGTGCAGCTGTTGGAGTCTGGGGGAGGCTTGGTACAGCCTGGGGGGTCCCTGCGTCTC
TCCTGTGCAGCCTCCGGATTCACCTTTGGTGATTATGGTATGAATTGGGTCCGCCAGGCT
CCAGGGAAGGGTCTGGAGTGGGTCTCACATATTTCTTCTAATGGTCGTTTTACATACTAC
GCAGACTCCGTGAAGGGCCGGTTCACCATCTCCCGCGACAATTCCAAGAACATGCTGTAT
CTGCGAATGAACAGCCTGCGTGCCGAGGACACCGCGGTATATTACTGTGCGGAAACTAGT
GGTTATTATGAATACTGGGTCAGGGAACCCTGGTCACCGTCTCGAGC

TABLE 2-continued

Human Anti-CD40L VH Domain Encoding Nucleotide Sequences

BMS2h-758-2
(SEQ ID NO: 909)
GAGGTGCAGCTGTTGGAGTCTGGGGGAGGCTTGGTACAGCCTGGGGGGTCCCTGCGCCTC

TCCTGTGCAGCCTCCGGATTCACCTTTGGTGATTATGGTATGAATTGGGTCCGCCAGGCT

CCAGGGAAGGGTCTGGAGTGGGTCTCACATATTTCTTCTAATGGTCGTTTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGGAAACTAGT

GGTTATTTTGAATACTGGGGTCAGGGAACCCTGGTCACCGTCTCGAGC

BMS2h-758-3
(SEQ ID NO: 910)
GAGGTGCAGCTGTTGGAGTCTGGGGGAGGCTTGGTACAGCCTGGGGGGTCCCTGCGTCTC

TCCTGTGCAGCCTCCGGATTCACCTTTGGTGATTATGGTATGAATTGGGTCCGCCAGGCC

CCAGGGAAGGGTCTGGAGTGGGTCTCACATATTTCTTCTAATGGTCGTTTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGGAAACTAGT

AGTTATTTTGAATACTGGGGTCAGGGAACCCTGGTCACCGTCTCGAGC

BMS2h-758-4
(SEQ ID NO: 911)
GAGGTGCAGCTGTTGGAGTCTGGGGGAGGCTTGGTACAGCCTGGGGGGTCCCTGCGTCTC

TCCTGTGCAGCCTCCGGGTTCACCTTTGGTGATTATGGTATGAATTGGGTCCGCCAGGCT

CCAGGGAAGGGTCTGGAGTGGGTCTCACATATTTCTTCTAATGGTCGTTTTACATACTAC

GCAGACTCCGTGAAGGGCCGGTTCACCATCTCCCGCGACAATTCCAAGAACACGCTGTTT

CTGCAAATGAACAGCCTGCGTGCCGAGGACACCGCGGTATATTACTGTGCGGAAACTAGT

GGTTATTATGAGTACTGGGGTCATGGAACCCTGGTCACCGTCTCGAGC

BMS2h-758-5
(SEQ ID NO: 912)
GAGGTGCAGCTGTTGGAGTCTGGGGGAGGCTTGGTCCAGCCTGGGGGGTCCCTGCGTCTC

TCCTGTGCTGCCTCCGGATTCGCCTTTGGTGATTATGGTATGAATTGGGTCCGCCAGGCT

CCAGGGAAGGGTCTGGAGTGGGTCTCACATATTTCTTCTAATGGTCGTTTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGGAAACTAGT

GGTTATTTTGAATACTGGGGTCAGGGAACCCTGGTCACCGTCTCGAGC

BMS2h-758-6
(SEQ ID NO: 913)
GAGGTGCAGCTGTTGGAGTCTGGGGGAGGCTTGGTACAGCCTGGGGGGTCCCTGCGTCTC

TCCTGTGCAGCCTCCGGATTCACCTTTGGTGATTATGGTATGAATTGGGTCCGCCAGGCT

CCAGGGAAGGGTCTGGAGTGGGTCTCACATATTTCTTCTAATGGTCGTTTTATATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGGAAACTAGT

GGTTACTTTGAATACTGGGGTCAGGGAACCCTGGTCACCGTCTCGAGC

BMS2h-759
(SEQ ID NO: 914)
GAGGTGCAGCTGTTGGAGTCTGGGGGAGGCTTGGTACAGCCTGGGGGGTCCCTGCGTCTC

TCCTGTGCAGCCTCCGGATTCACCTTTAGGGAGTATGTTATGGGGTGGGTCCGCCAGGCT

CCAGGGAAGGGTCTAGAGTGGGTCTCAACTATTAATGGTTTGGGTAATGTTACATACTAC

TABLE 2-continued

Human Anti-CD40L VH Domain Encoding Nucleotide Sequences

GCAGACTCCGTGAAGGGCCGGTTCACCATCTCCCGCGACAATACCAAGAACACGCTGTAT

CTGCAAATGAACAGCCTGCGTGCCGAGGAGACCGCGGTATATTACTGTGCGATACAGCTG

CCTAATTTTGACTACTGGGGTCAGGGAACCCTGGTCACCGTCTCGAGC

BMS2h-760
(SEQ ID NO: 915)
GAGGTGCAGCTGTTGGAGTCTGGGGGAGGCTTGGTACAGCCTGGGGGGTCCCTGCGTCTC

TCCTGTGCAGCCTCCGGATTCACCTTTGGTAATGATGGGATGTGGTGGGTCCGCCAGGCT

CCAGGGAAGGGTCTAGAGTGGGTCTCATTTATTAATGTTGATGGTAGGGAGACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGGAATGGTCT

CCTGGGCGGGTTCAGTTTGACTACTGGGGTCAGGGAACCCTGGTCACCGTCTCGAGC

BMS2h-761
(SEQ ID NO: 916)
GAGGTGCAGCTGTTGGAGTCTGGGGGAGGCTTGGTACAGCCTGGGGGGTCCCTGCGTCTC

TCCTGTGCAGCCTCCGGATTCACCTTTGGTGGTTGGGATATGGCGTGGGTCCGCCAGGCT

CCAGGGAAGGGTCTAGAGTGGGTCTCAAGTATTGCTCATGAGGGTGGTGAGACATACTAC

GCAGACTCCGTGAAGGGCCGGTTCACCATCTCCGCGACAATTCCAAGAACACGCTGTAT

CTGCAAATGAACAGCCTGCGTGCCGAGGACACCGCGGTATATTACTGTGCGAAATATGTT

CCTGGGTCTCCTCTGTTTGACTACTGGGGTCAGAGAACCCTGGTCACCGTCTCGAGC

BMS2h-762
(SEQ ID NO: 917)
GAGGTGCAGCTGTTGGAGTCTGGGGGAGGCTTGGTACAGCCTGGGGGGTCCCTGCGTCTC

TCCTGTGCAGCCTCCGGATTCACCTTTGATCAGGGTTGGATGTATTGGGTCCGCCAGGCT

CCAGGGAAGGGTCTAGAGTGGGTCTCAGGGATTGGTTCGAATGGTCCTCGGACATCCTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAATCGGGG

GAGTATTTTGACTACTGGGGTCAGGGAACCCTGGTCACCGTCTCGAGC

BMS2h-763
(SEQ ID NO: 918)
GAGGTGCAGCTGTTGGAGTCTGGGGGAGGCTTGGTACAGCCTGGGGGGTCCCTGCGTCTC

TCCTGTGCAGCCTCCGGATTCACCTTTAGGCAGAGTGATATGTGGTGGGTCCGCCAGGCT

CCAGGGAAGGGTCTAGAGTGGGTCTCAGTTATTGGTAATAATGGTGAGTTTACATACTAC

GCAGACTCGGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGATAAT

TGGCTGTTGTTTGACTACTGGGGTCAGGGAACCCTGGTCACCGTCTCGAGC

BMS2h-764
(SEQ ID NO: 919)
GAGGTGCAGCTGTTGGAGTCTGGGGGAGGCTTGGTACAGCCTGGGGGGTCCCTGCGTCTC

TCCTGTGCAGCCTCCGGATTCACCTTTGATCTTAGTACTATGTATTGGGTCCGCCAGGCT

CCAGGGAAGGGTCTAGAGTGGGTCTCAACTATTGGTGGGATGGTAGTCATACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGGAAGGTACG

CAGTATTTTGACTACTGGGGTCAGGGAACCCTGGTCACCGTCTCGAGC

TABLE 2-continued

Human Anti-CD40L VH Domain Encoding Nucleotide Sequences

BMS2h-765
(SEQ ID NO: 920)
GAGGTGCAGCTGTTGGAGTCTGGGGGAGGCTTGGTACAGCCTGGGGGGTCCCTGCGTCTC

TCCTGTGCAGCCTCCGGATTCACCTTTTCGGCGTATACGATGGAGTGGGTCCGCCAGGCT

CCAGGGAAGGGTCTAGAGTGGGTCTCAAGTATTGGGGTTACGGGTTATGATACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGGTGGT

CAGGGTTTTGACTACTGGGGTCAGGGAACCCTGGTCACCGTCTCGAGC

BMS2h-766
(SEQ ID NO: 921)
GAGGTGCAGCTGTTGGAGTCTGGGGGAGGCTTGGTACAGCCTGGGGGGTCCCTGCGTCTC

TCCTGTGCAGCCTCCGGATTCACCTTTGGGGATTATGGGATGTCTTGGGTCCGCCAGGCT

CCAGGGAAGGGTCTAGAGTGGGTCTCATATATTGATCCTCTGGGTCGTCTTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGGAAGATTTG

TCGTCGCTGCAGTATGGGGTGTCGCCTAATTTTGACTACTGGGGTCAGGGAACCCTGGTC

ACCGTCTCGAGC

BMS2h-767
(SEQ ID NO: 922)
GAGGTGCAGCTGTTGGAGTCTGGGGGAGGCTTGGTACAGCCTGGGGGGTCCCTGCGTCTC

TCCTGTGCAGCCTCCGGATTCACCTTTTTTCATTATTCTATGAGTTGGGTCCGCCAGGCT

CCAGGGAAGGGTCTAGAGTGGGTCTCATCTATTGGTCCGGTTGGTCGGGAGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAATGATT

CAGTCGCCGTTGTTTAAGGATTTTGACTACTGGGGTCAGGGAACCCTGGTCACCGTCTCG

AGC

BMS2h-768
(SEQ ID NO: 923)
GAGGTGCAGCTGTTGGAGTCTGGGGGAGGCTTGGTACAGCCTGGGGGGTCCCTGCGTCTC

TCCTGTGCAGCCTCCGGATTCACCTTTGAGTGGTATGATATGTATTGGGTCCGCCAGGCT

CCAGGGAAGGGTCTAGAGTGGGTCTCACGTATTGATAGTGGGGGTAATCAGACATACTAC

GCAGACTCCGTGAAGGGCCGGTTCACCATCTCCCGCGACAATTCCAAGAACACGCTGTAT

CTGCAAATGAATAGCCTGCGTGCCGAGGACACCGCGGTATATTACTGTGCGGAAGCGTCG

CTTTGGAAGTGGAGGTTGTTTGACTACTGGGGTCAGGGAACCCTGGTCACCGTCTCGAGC

BMS2h-77
(SEQ ID NO: 924)
GAGGTGCAGCTGTTGGAGTCTGGGGGAGGCTTGGTACAGCCTGGGGGGTCCCTGCGTCTC

TCCTGTGCAGCCTCCGGATTCACCTTTGAGGAGTATGGTATGGCGTGGGTCCGCCAGGCT

CCAGGGAAGGGTCTAGAGTGGGTCTCAACTATTTCTCCGCTGGGTATTTCGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACATGCT

TABLE 2-continued

Human Anti-CD40L VH Domain Encoding Nucleotide Sequences

ACGTCTCAGGAGTCTTTGCGGTCTTTTGACTACTGGGGTCAGGGAACCCTGGTCACCGTC

TCGAGC

BMS2h-770 (SEQ ID NO: 925)
GAGGTGCAGCTGTTGGAGTCTGGGGGAGGCTTGGTACAGCCTGGGGGGTCCCTGGGTCTC

TCCTGTGCAGCCTCCGGATTCACCTTTAGTAAGTATGAGATGATGTGGGTCCGCCAGGCT

CCAGGGAAGGGTCTAGAGTGGGTGTCAGCTATTAGTGGTAGTGGTGGTAGCACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGGTCCT

CTGCCTGATGCGTTTTGGACTAGGGGTTTTGACTACTGGGGTCAGGGAACCCTGGTCACC

GTCTCGAGC

BMS2h-771 (SEQ ID NO: 926)
GAGGTGCAGCTGTTGGAGTCTGGGGGAGGCTTGGTACAGCCTGGGGGGTCCCTGCGTCTC

TCCTGTGCAGCCTCCGGATTCACCTTTGGTACTTATTCTATGGCGTGGGTCCGCCAGGCT

CCAGGGAAGGGTCTAGAGTGGGTCTCAACTATTGATCGGCATGGTTTGGCTACATACTAC

GCAGACTCCGTGAAGGGCCGGTTCACCATCTGCCGCGACAATTCCAAGAACACGCTGTAT

CTGCAAATGAACAGCCTGCGTGCCGAGGACACCGCGGTATATTACTGTGCGAAAACTCCT

GGTTGTTCTTGGCAGACTGTTTTTGGCTACTGGGGTCAGGGAACCCTGGTCACCGTCTCG

AGC

BMS2h-772 (SEQ ID NO: 927)
GAGGTGCAGCTGTTGGAGTCTGGGGGAGGCTTGGTACAGCCTGGGGGGTCCCTGCGTCTC

TCCTGTGCAGCCTCCGGATTCACCTTTGAGTCGTATCCTATGGGTTGGGTCCGCCAGGCT

CCAGGGAAGGGTCTAGAGTGGGTCTCAAGTATTGATCATCATGGTCATTCGACATACTAC

GCAGACTCCGCGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAATTGCTT

AGGGTTTCGATGATTTTTGGTTTTGACTACTGGGGTCAGGGAACCCTGGTCACCGTCTCG

AGC

BMS2h-773 (SEQ ID NO: 928)
GAGGTGCAGCTGTTGGAGTCTGGGGGAGGCTTGGTACAGCCTGGGGGGTCCCTGCGTCTC

TCCTGTGGAGCCTCCGGATTCACCTTTGTGCAGTATGGGATGAGTTGGGTCCGCCAGGCT

CCAGGGAAGGGTCTAGAGTGGGTCTCATGGATTAGTAGTAGTGGTACGTATACATACTAC

GCAGACTCCGTGAAGGGCCGGTTCACCATCTCGCGCGACAATTGCAAGAACACGCTGTAT

CTGCAAATGAACAGCCTACGTGCCGAGGACACCGCGGTATATTACTGTGCGGAAACGTCT

AGGATGTTTGACTACTGGGGTCAGGGAACCCTGGTCACCGTCTCGAGC

BMS2h-774 (SEQ ID NO: 929)
GAGGTGCAGCTGTTGGAGTCTGGGGGAGGCTTGGTACAGGCTGGGGGGTCCCTGCGTGTC

TCCTGTGCGGCCTCCGGATTCACCTTTCGGGAGTATGATATGGGTTGGGTCCGCCAGGCT

CCAGGGAAGGGTCTAGAGTGGGTCTCACTTATTTCGCCTCCTGGTCGTACTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAAGTTGTG

TABLE 2-continued

Human Anti-CD40L VH Domain Encoding Nucleotide Sequences

ATTCTGGGTTATACGAATAGGTTTGACTACTGGGGTCAGGGAACCCTGGTCACCGTCTCG

AGC

BMS2h-775
(SEQ ID NO: 930)
GAGGTGCAGCTGTTGGAGTCTGGGGGAGGCTTGGTACAGCCTGGGGGGTCCGTGCGTCTC

TCCTGTGCAGCCTCCGGATTCACCTTTCCTAATTACGGGATGTTGTGGGTCCGCCAGGCT

CCAGGGAAGGGTCTAGAGTGGGTCTCATCGATTAATTCTTCGGGTATGGAGACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAATTTTTT

CGTCTGAATGATCATAATTCTGTGTTTGGTTTTGAGTACTGGGGTCAGGGAACCCTGGTC

ACCGTCTCGAGC

BMS2h-776
(SEQ ID NO: 931)
GAGGTGCAGCTGTTGGAGTCTGGGGGAGGCTTGGTACAGCCTGGGGGGTCCCTGCGTCTC

TCCTGTGCAGCCTCCGGATTCACCTTTAAGGATTATAAGATGATGTGGATCCGCCAGGCT

CCAGGGAAGGGTCTAGAGTGGGTCTCATCGATTGTTGGGTCTGGTTCGATGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGNTAGGGCCT

GGTTATTTTGACTACTGGGGTCAGGGAACCCTGGTCACCGTCTCGAGC

BMS2h-777
(SEQ ID NO: 932)
GAGGTGCAGCTGTFGGAGTCTGGGGGAGGCTTGGTACAGCCTGGGGGGTCCCTGCGTCTC

TCCTGTGCAGCCTCCGGATTCACCTTTCATAATTATGCTATGGGTGGGTCCGCCGGGCT

CCAGGGAAGGGTCTAGAGTGGGTCTCAAGTATTGATGAGCATGGTACTATTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGATAGT

CTGGATCGGGTTTGGATTTTTGACTACTGGGGTCAGGGAACCCTGGTCACCGTCTCGAGC

BMS2h-778
(SEQ ID NO: 933)
GAGGTGCAGCTGTTGGAGTCTGGGGGGGGCTTGGTACAGCCTGGGGGGTCCCTGCGTCTC

TCCTGTGCAGCCTCCGGATTCACCTTTGCTGATTATCCGATGACTTGGGTCCGCCAGGCT

CCAGGGAAGGGTCTAGAGTGGGTCTCAAGTATTTATTCTGCGGGTTCTCCTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAACTTTAT

CATCGGGAGCCGATTCTTTTTGGGTTTGACTACTGGGGTCAGGGAACCCTGGTCACCGTC

TCGAGC

BMS2h-78
(SEQ ID NO: 934)
GAGGTGCAGCTGTTGGAGTCTGGGGGAGGCTTGGTACAGCCTGGGGGGTCCCTGCGTCTC

TCCTGTGCAGCCTCCGGATTCACCTTTGAGAGGTATCAGATGGCGTGGGTCCGCCAGGCT

CCGGGGAAGGGTCTAGAGTGGGTCTCAACGATTAGTTCTGATGGTGGGGGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCTGGT

CATCGGTTTGACTACTGGGGTCAGGGAACCCTGGTCACCGTCTCGAGC

TABLE 2-continued

Human Anti-CD40L VH Domain Encoding Nucleotide Sequences

BMS2h-780
(SEQ ID NO: 935)
GAGGTGCAGCTGTTGGAGTCTGGGGGAGGCTTGGTACAGCCTGGGGGGTCCCTGCGTCTC

TCCTGTGCAGCCTCCGGATTCACCTTTGGTTCTTATACTATGATGTGGGTCCGCCAGGCT

CCAGGGAAGGGTCTAGAGTGGGTCTCAGAGATTGATCGGACGGGTGAGCGTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGGAACCTGGG

TTTGCTTCTCTTCCTTTTGACTACTGGGGTCAGGGAACCCTGGTCACCGTCTCGAGC

BMS2h-781
(SEQ ID NO: 936)
GAGGTGCAGCTGTTGGAGTCTGGGGGAGGCTTGGTACAGCCTGGGGGGTCCCTGCGTCTC

TCCTGTGCAGCCTCCGGATTCACCTTTACGGATTATACTATGTATTGGGTCCGCCAGGCT

CCAGGGAAGGGTCTAGAGTGGGTCTCAAAGATTTCTCCGAGTGGTCGTTCTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAAGATCCG

TTTGGGTTTGACTACTGGGGTCAGGGAACCCTGGTCACCGTCTCGAGC

BMS2h-782
(SEQ ID NO: 937)
GAGGTGCAGCTGTTGGAGTCTGGGGGAGGCTTGGTACAGCCTGGGGGGTCCCTGCGTCTC

TCCTGTGCAGCCTCCGGATTCACCTTTGATGATGCGGAGATGTTTTGGGTCCGCCAGGCT

CCAGGGAAGGGTCTAGAGTGGGTCTCATCTATTGATGCTCGTGGTTTGACGACATACTAC

GCAGACCCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGGAAGCGACG

TCGGCTATGTATCCTTTTGACTACTGGGGTCAGGGAACCTTTGGCACCGTCTCGAGC

BMS2h-783
(SEQ ID NO: 938)
GAGGTGCAGCTGTTGGAGTCTGGGGGAGGCTTGGTACAGCCTGGGGGGTCCCTGCGTCTC

TCCTGTGCAGCCTCCGGATTCACCTTTCGTGATTATGATATGGGTTGGGTCCGCCAGGCT

CCAGGGAAGGGTCTAGAGTGGGTCTCAACTATTTCTCCTCTTGGTCATTTTACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAATCTGGG

TTTCATGAGTATACTGAGGGGTTTGACTACTGGGGTCAGGGAACCCTGGTCACCGTCTCG

AGC

BMS2h-784
(SEQ ID NO: 939)
GAGGTGCAGCTGTTGGAGTCTGGGGGAGGCTTGGTACAGCCTGGGGGGTCCCTGCGTCTC

TCCTGTGCAGCCTCCGGATTCACCTTTGATCGTGCGGGTATGGGTGGGTCCGCCAGGCT

CCAGGGAAGGGTCTAGAGTGGGTCTCACTGATTGGGCGTGGTGGTGATATTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAATTCGT

AATCTGCATTGGGATGTGGGGAGGCAGTTTGACTACTGGGGTCAGGGAACCCTGGTCACC

GTCTCGAGC

TABLE 2-continued

Human Anti-CD40L VH Domain Encoding Nucleotide Sequences

BMS2h-80
(SEQ ID NO: 940)
GAGGTGCAGCTGTTGGAGTCTGGGGGAGGCTTGGTACAGCCTGGGGGGTCCCTGCGTCTC

TCCTGTGCAGCCTCCGGATTCACCTTTGGTCGTTATCAGATGGCTTGGGTCCGCCAGGCT

CCAGGGAAGGGTCTAGAGTGGGTCTCATCTATTTCTTCTGATGGTGGGGGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCGTCT

CGTCGGTTTGACTACTGGGGTCAGGGAACCCTGGTCACCGTCTCGAGC

BMS2h-81
(SEQ ID NO: 941)
GAGGTGCAGCTGTTGGAGTCTGGGGGAGGCTTGGTACAGCCTGGGGGGTTCCTGCGTCTC

TCCTGTGCAGCCTCCGGATTCACCTTTGAGTTGTATCCGATGGCGTGGGTCCGCCAGGCT

CCAGGGAAGGGTCTGGAGTGGGTCTCATCGATTTCTCCGGTTGGTTTTCTGACATACTAC

GCAGACTCCGTGAAGGGCCGGTTCACCATCTCCCGCGACAATTCCAAGAACACGCTGTAT

CTGCAAATGAACAGCCTGCGTGCCGAGGATACCGCGGTATATTACTGTGCGAAAGGGCAT

GAGGGGTCGTATACTCCGCGGTCGGCTTTTGACTACTGGGGTCAGGGAACCCTGGTCACC

GTCTCGAGC

BMS2h-82
(SEQ ID NO: 942)
GAGGTGCAGCTGTTGGAGTCTGGGGGAGGCTTGGTACAGCCTGGGGGGTCCCTGCGTCTC

TCCTGTGCAGCCTCCGGATTCACCTTTGTGGCGTATCCTATGGCGTGGGTCCGCCAGGCT

CCAGGGAAGGGTCTGGAGTGGGTCTCAACTATTGCGCCTCTGGGTGGTAATACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACGGCCG

GAGGGGCTGCAGATTGATTCTCAGAATTTTGACTACTGGGGTCAGGGAACCCTGGTCACC

GTCTCGAGC

BMS2h-83
(SEQ ID NO: 943)
GAGGTGCAGCTGTTGGAGTCTGGGGGAGGCTTGGTACAGCCTGGGGGGTCCCTGCGTCTC

TCCTGTGCAGCCTCCGGATTCACCTTTGCGTTGTATCAGATGGCTTGGGTCCGCCAGGCT

CCAGGGAAGGGTCTAGAGTGGGTCTCATCGATTGATTCTTCTGGTAGTGATACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACCTGAG

CGTGATTTTGACTACTGGGGTCAGGGAACCCTGGTCACCGTCTCGAGC

BMS2h-84
(SEQ ID NO: 944)
GAGGTGCAGCTGTTGGAGTCTGGGGGAGGCTTGGTACAGCCTGGGGGGTCCCTGCGTCTC

TCGTGTGCAGCCTCCGGATTCACCTTTAGGCAGTACCAGATGGCTTGGGCCCGCCAGGCT

CCAGGGAAGGGTCTAGAGTGGGTCTCAACGATTGCGTCGGATGGTGTTTCTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGTTGGT

CGTGATTTTGACTACTGGGGTCAGGGAACCCTGGTCACCGTCTCGAGC

TABLE 2-continued

Human Anti-CD40L VH Domain Encoding Nucleotide Sequences

BMS2h-85
(SEQ ID NO: 945)
GAGGTGCAGCTGTTGGAGTCTGGGGGAGGCTTGGTACAGCCTGGGGGGTCCCTGCGTCTC

TCCTGTGCAGCCTCCGGATTCACCTTTGAGCAGTATGATATGAGGTGGGTCCGCCAGGCT

CCAGGGAAGGGTCTAGAGTGGGTCTCATGGATTGATGAGGCGGGTCATGAGACATACTAT

GCAGACTCCGTGAAGGGCCGGTTCACCATCTCCCGCGACAATTCCAGGAACACGGTGTAT

CTGCAAATGAACAGCCTGCGTGCCGAGGACACCGCGGTATATTACTGTGCGAAAGGGATG

GATGGGTTTGACTACTGGGGTCAGGGAACCCTGGTCACCGTCTCGAGC

BMS2h-92
(SEQ ID NO: 946)
GAGGTGCAGCTGTTGGAGTCTGGGGGAGGCTTGGTACAGCCTGGGGGGTCCCTGCGTCTC

TCCTGTGCAGCCTCCGGATTCACCTTTGTTGATTATCCGATGGGTTGGGTCCGCCAGGCT

CCAGGGAAGGGTCTAGAGTGGGTCTCAACGATTTCTACGGGGGTTTTTCGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAAGCGCGG

TATTATTATCTTAGTCAGATTAAGAATTTTGACTACTGGGGTCAGGGAACCCTGGTCACC

GTCTCGAGC

BMS2h-93
(SEQ ID NO: 947)
GAGGTGCAGCTGTTGGAGTCTGGGGGAGGCTTGGTACAGCCTGGGGGGTCCCTGCGTCTC

TCCTGTGCAGCCTCCGGATTCACCTTTGATATTTATGGGATGACTTGGGTCCGCCAGGCT

CCAGGGAAGGGTCTGGAGTGGGTCTCAAGTATTTCGCCTCTTGGTCTTGTTACATACTAC

GCAGACCCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACTGAAG

GAGCATGGGGATGTTCCTTTTGACTACTGGGGTCAGGGAACCCTGGTCACCGTCTCGAGC

BMS2h-94
(SEQ ID NO: 948)
GAGGTGCAGCTGTTGGAGTCTGGGGGAGGCTTGGTACAGCCTGGGGGGTCCCTGCGTCTC

TCCTGTGCAGCCTCCGGATTCACCTTTGAGCTTTATCCGATGAGTTGGGTCCGCCAGGCT

CCAGGGAAGGGTCTAGAGTGGGTCTCAACTATTTCTCCTACGGGTTTGTTGACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAATTTAAG

AGGAGTGGGAAGACTGATGATACTAATTTTGACTACTGGGGTCAGGGAACCCTGGTCACC

GTCTCGAGC

BMS2h-95
(SEQ ID NO: 949)
GAGGTGCAGCTGTTGGAGTCTGGGGGAGGCTTGGTACAGCCTGGGGGGTCCCTGCGTCTC

TCCTGTGCAGCCTCCGGATTCACCTTTCGGGAGTATGATATGCTGTGGGTCCGCCAGGCT

CCAGGGAAGGGTCTAGAGTGGGTCTCAACGATTGTGGGGATGGTAATGGTACATACTAC

GCAGACTCCGTGAAGGGCCGGTTCACCATCTCCCGCGACAATTCCAAGAACACGCTGTAT

CTGCAAATGAACAGCCTGCGTGCCGAGGACACCGCGGTATATTACTGTGCGAAACAGGAT

CGTCAGTTTGACTACTGGGGTCAGGGAACCCTGGTCACCGTCTCGAGC

TABLE 2-continued

Human Anti-CD40L VH Domain Encoding Nucleotide Sequences

BMS2h-97 (SEQ ID NO: 950)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGGAGTATGGTATGAGTTGGGTCCGCCAGGCT
CCAGGGAAGGGTCTAGAGTGGGTCTCAACGATTTCGCCTATTGGTGTTACTACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAAAATGCT
TATGATCGGAAGTCTAATTTTGACTACTGGGGTCAGGGAACCCTGGTCACCGTCTCGAGC

BMS2h-98 (SEQ ID NO: 951)
GAGGTGCAGCTGTTGGAGTCTGGGGGAGGCTTGGTACAGCCTGGGGGGTCCCTGCGTCTC
TCCTGTGCAGCCTCCGGATTCACCTTTGATCGGTATGTGATGGTGTGGGTCCGCCAGGCT
CCAGGGAAGGATCTAGAGTGGGTCTCAGGTATTACTCCGAGTGGTAGGAGGACATACTAC
GCAGACTCCGTGAAGGGCCGGTTCACCATCTCCCGCGACAATTCCAAGGACACGCTGTAT
CTGCAAATGAACAGCCTGCGTGCCGAGGACACCGCGGTATATTACTGTGCGAAAGTGTTG
GGGCGTCATTTTGATCCTCTTCTGCCTTCGTTTGACTACTGGGGTCAGGGAACCCTGGTC
ACCGTCTCGAGC

BMS2h-99 (SEQ ID NO: 952)
GAGGTGCAGCTGTTGGAGTCTGGGGGAGGCTTGGTACAGCCTGGGGGGTCCCTGCGTCTC
TCCTGTGCAGCCTCCGGATTCACCTTTGAGGATTATGCTATGAGTTGGGTCCGCCAGGCT
CCAGGGAAGGGTCTAGAGTGGGTCTCAACTATTACTCCGGGTGGTTTTTGGACATACTAC
GCAGACTCCGTGAAGGGCCGGTTCACCATCTCCCGCGACAATTCCAAGAACACGCTGTAT
CTGCAAATGAACAGCCTGCGTGCCGAGGATACCGCGGTATATTACTGTGCGAAAACGTCT
AGTGGGGAGTTGCAGTTGGTTGAGGATTTTGACTACTGGGGTCAGGGAACCCTGGTCACC
GTCTCGAGC

TABLE 3

Anti-human CD40L VK Domain Amino Acid Sequences

BMS2h-100 (SEQ ID NO: 953)
DIQMTQSPSS LSASVGDRVT ITCRASONIK HSLRWYQQKP GKAPRLLIYH RSQLQSGVPS
RFSGSGSGTD FTLTISSLQP EDFATYYCQQ VRHRPYTFGQ GTKVEIKR

BMS2h-101 (SEQ ID NO: 954)
DIQMTQSPSS LSASVGDRVT ITCRASQAIG HRLRWYQQKP GKAPKLLIYH RSKLQSGVPS
RFSGSGSGTD FTLTISSLQP EDFATYYCQQ VALFPYTFGQ GTKVEIKR

BMS2h-102 (SEQ ID NO: 955)
DIQMTQSPSS LSASVGDRVT ITCRASQHIG HHLRWYOOKP GKAPKLLIYH RSHLQSGVPS
RFSGSGSGTD FTLTISSLOP EDSATYYCQQ WDRPPYTFGQ GTKVEIKR

BMS2h-103 (SEQ ID NO: 956)
DIQMTQSPSS LSASVGDRVT ITCRASOAIG HRLRWYQQKP GKAPKLLIYH
RSKLQSGVPS RFSGSGSGTD FTLTIssLop EDFATYYCQQ VRAVPYTFGQ GTKVEIKR

BMS2h-104 (SEQ ID NO: 957)
DIQMTQSPSS LSASVGDRVT ITCRASQAIG HRLRWYQQKP GKAPKLLIYH RSKLQSGVPS
RFSGSGSGTD FTLTISSLQP EDFATYYCQQ VRFSPYTFGQ GTKVEIKR

TABLE 3-continued

Anti-human CD40L VK Domain Amino Acid Sequences

BMS2h-105
(SEQ ID NO: 958)
DIQMTOSPSS LSASVGDRVT ITCRASQAIG HRLRWYQQKP GKAPKLLIYH RSKLQSGVPS
RFSGSGSGTD FTLTISSLQP EDFATYYCQQ SYARPVTFGQ GTKVEIKR

BMS2h-106
(SEQ ID NO: 959)
DIQMTQSPSS LSASVGDRVT ITCRASQSIN HRLYWYQQKP GKAPKLLIYH RSRLQSGVPS
RFSGSGSGTD FTLTISSLQP EDFATYYCQQ YKVRPNTFGQ GTKVEIKR

BMS2h-107
(SEQ ID NO: 960)
DIQMTQSPSS LSASVGDRVT ITCRASQAIG HRLRWYQQKP GKAPKLLIYH RSKLQSGVPS
RFSGSGSGTD FTLTISSLOR EDFATYYCQQ TYSSPHTFGQ GTKVEIKR

BMS2h-108
(SEQ ID NO: 961)
DIQMTQSPSS LSASVGDRVT ITCRASQAIG HRLRWYQQKP GKAPKLLIYH RSKLQSGVPS
RFSGSGSGTD FILTISSLQF EDFATYYCQQ RAVRPFTFGQ GTKVEIKR

BMS2h-109
(SEQ ID NO: 962)
DIQMTQSPSS LSASVGDRVT ITCRASQAIG HRLRWYQQKP GKAPKLLIYH RSKLQSGVPS
RFSGSGSGTD FTLTISSLQP EDFATYYCQQ TYYRPLTFGQ GTKVEIKR

BMS2h-110
(SEQ ID NO: 963)
DIQMTQSPAS LSASVGDRVT ITCRASQDID PMLRWYQQKP GKAPKLLIYA GSILQSGVPS
RFSGSGSGTD FTLTISSLQP EDFATYYCQQ TSIRPYTFGQ GTKVEIKR

BMS2h-116
(SEQ ID NO: 964)
DIQMTOSPSS LSASVGDRVT ITCRASQPIG PDLLWYQQKP GKAPKLLIYQ TSILQSGVPS
RFSGSGSGTD FTLTISSLQP EDFATYYCQQ YWAFPVTFGQ GTKVEIKR

BMS2h-116-1
(SEQ ID NO: 965)
DIQMTQSPSS LSASVGDRVT ITCRASQPIG PDILWYQQKP GKAPKLLIYQ TSILQSGVPS
RFSGSESGTD FTLTISSLQP EDFATYYCQQ YWAFPVTFGQ GTKVEIKR

BMS2h-116-10
(SEQ ID NO: 966)
DIQITQSPSS LSASVGDRVT ITCRASOPIG PDLLWYQQKP GKAPKLLIYQ TSILRSGVPS
RFSGSGSGTD FTLTISSLQP EDLATYYCQQ YWAFPVTFGQ GTKVEIKR

BMS2h-116-11
(SEQ ID NO: 967)
DIQMTQSPSS LSASVGDRVF ITCRASQPIG PDLLWYQQKP GKAPKLLIYQ TSILRSGVPS
RFSGRGSGTD FTLTISSLQP EDFATYYCQQ YWAFPVTFGQ GTKVEIKR

BMS2h-116-12
(SEQ ID NO: 968)
DIQMTQSPSS LSASVGDRVT ITCRASQPIG PDLLWYQQKP GKAPKLLIYQ TSILRSGVPS
RFSGSGSGTD FTLTISSLQP EDFATYYCQQ YWTFPVTFGQ GTKVEIKR

BMS2h-116-13
(SEQ ID NO: 969)
DIQMTQSPSS LSASVGDRVT ITCRASOPIG PDLLWYQQKP GKAPKLLIYQ TSILRSGVPS
RFSGSGSETD FTLTISNLQP EDFATYYCQQ WVAFPVTFGQ GTKVVIKR

BMS2h-116-1312
(SEQ ID NO: 970)
DIQMTQSPSS LSASVGDRVT ITCRASQPIG PDLLWYQQKP GKAPKLLIYQ TSILRSGVPS
RFSGSGSETD FTLTISNLQP EDLATYYCQQ YWAFPVTFGK GTKVVIKR

BMS2h-116-1313
(SEQ ID NO: 971)
DIQMTQSPSS LSASVGDRVT ITCRASQPIG PDLLWYQQKP GKAPKLLIYQ TSILRSGVPS
RFSGSGSETD FTLTISNLQP EDFATYYCQQ YWAFPVTFGR GTKVVIKR

BMS2h-116-1314
(SEQ ID NO: 972)
DIQMTQSPSS LSASVGDRVT ITCRASQPIG PDLLWYRQKP GKAPKLLIYQ TSILRSGVPS
RFSGSGSETD FTLTISNLQP EDFATYYCQQ YWAFPVTFGQ GTKVVIKR

TABLE 3-continued

Anti-human CD40L VK Domain Amino Acid Sequences

BMS2h-116-1319
(SEQ ID NO: 973)
DIQMTQSFSS LSASVGDRVT ITCRASQPIG PDLLWYQQKP GKAPKLLIYQ TSIMRSGVPS
RFSGSGSETD FTLTISNLQP EDFATYYCQQ YWTFPVTFGQ GTKVEIKR

BMS2h-116-1320
(SEQ ID NO: 974)
DIQMTQSPSS LSAYVGDRVT ITCRASQPIG PDLLWYQQKP GKAPKLLIYQ TSILRSGVPS
RFSGSGSETD FTLTISNLQP EDFAKYYCQO YWAFPVTFGQ GTKVVIKR

BMS2h-116-138
(SEQ ID NO: 975)
DIQMTQSPSS LSASVGDRVT ITCRASQPIG PDLLWYQQKP GKAPKLLIYQ TSILRSGVPS
RFSGSGSETD FTLIISNLQP VDFATYYCQQ YWAFPVTFGQ GTKVVIKR

BMS2h-116-14
(SEQ ID NO: 976)
DIQMTQSPSS LSASVGDRVT ITCRASQPIG PDLLWFQQKP GKAPKLLIYQ TSILQSGVPS
RFSGSESGTD FTLTISSLQP EDFATYYCQQ YWAFPVTFGQ GTKVEIKR

BMS2h-116-15
(SEQ ID NO: 977)
DIQMTQSPSS LSASVGDRVT ITCRASQPIG PDLLWYRQKP GKAPKLLIYQ TSILQSGVPS
RFSGSGSGTD FTLTISSLQP EDFATYYCQQ YWTFPVITGQ GTKVEIKR

BMS2h-116-16
(SEQ ID NO: 978)
DIQMTQSPSS LSASVGDRVT ITCRASQPID PDLLWYQQKP GKAPKLLIYQ TSILQSGVPS
RFSGSGSGTV FTLTISSLQP EDFATYYCQQ YWAFPVTFGQ GTKVEIKR

BMS2h-116-17
(SEQ ID NO: 979)
DIQMTQSPSS LSASVGDRVT ITCRASQPIG PDLLWYQQKP GKAPKLLIYQ TSILRSGVPS
RFSGSGSGTD FTLTISSLQP EDFATYYCQQ YWAFPVTFGQ GTKVEIKR

BMS2h-116-2
(SEQ ID NO: 980)
DIQMTQSPSS LSASVGDRVT ITCRASQPIE PDLLWYQQKP GKAPKLLIYQ TSILQSGVPS
RFSGSGSGTD FTLTISSLQP EDFATYYCQQ YWASPVTFGQ GTKVEIKR

BMS2h-116-3
(SEQ ID NO: 981)
DIQMTQSPSS LSASVGDRVT ITCRASQPIG PDLLWYQQKP GKAPKLLIYQ TSILQSGVPS
RFSGSESGTD FTLTISSLQP EDIATYYCQQ YWAFPVTFGQ GTRVEIKR

BMS2h-116-4
(SEQ ID NO: 982)
DIQMTQSPSS LSASVGDRVT ITCRASQPIG PDLLWYQQKP GKAPKLLIYQ TSILQSGVPS
RFSGSESGTD FTLTISSLQP EDFATYYCQQ YWAFPVTFGQ GTKVEIKR

BMS2h-116-5
(SEQ ID NO: 983)
DIQMTQSPSS LSASVGDRVA ITCRASQPIG PDILWYQQKP GKAPKLLIYQ TSILRSGVPS
RFSGSGSGTD FTLTISSLQP EDSATYYCQQ YWAFPVTFGQ GTKVEIKR

BMS2h-116-6
(SEQ ID NO: 984)
DIQMTQSPSS LSASVGDRVT ITCRASQPIG PDLLWYQQKP GKAPKLLIYQ TSILRSGVPS
RFSGSGSVTD FTLTISSLQP EDFATYYCQQ YWAFPVTFGQ GTKVEIKR

BMS211-116-7
(SEQ ID NO: 985)
DIQMTQSPSS LSASVGDRVT ITCRASQPID PDLLWYQQKP GKAPKLLIYQ TSILQSGVPS
RFSGSGSRTD FTLTISSLQP EDFATYYCQQ YWAFPVTFGQ GTKVEIKR

BMS2h-116-8
(SEQ ID NO: 986)
DIQMTQSPSS LSASVGDRVT ITCRASQPIG PDLLWYQQKP GKAPKLLIYQ TSILQSGVPS
RFSGSGSGTD FTLTISGLQP EDFATYYCQQ YWAFPVTFGQ GTKVEIKR

BMS2h-116-9
(SEQ ID NO: 987)
DIQMTQSPSS LSASVGDRVT ITCRASMPIG PDLLWYQQKP GKAPKLLIYQ TSILRSGVPS
RFSGSESGTD FTLTISSLQP EDFATYYCQQ YWAFPVTFGQ GTKVEIKR

TABLE 3-continued

Anti-human CD40L VK Domain Amino Acid Sequences

BMS2h-141
(SEQ ID NO: 988)
DIQMTQSPSS LSASVGDRVT ITCRASQWIG DILIWYQQKL GKAPKLLIYG GSELQSGVPP
RFSGSGSGTD FTLTISSLQP EDFATYYCQQ CISSPCTFGQ GTKVEIKR

BMS2h-142
(SEQ ID NO: 989)
DIQMTQSPSS LSASVGDRVT ITCRASQFIG DSLSWYQQKP GKAPKLLIYF SSILQSGVPS
RFSGSGSGTD FTLTISSLQP EDFATYYCQQ YHTSPTTFGR GTKVKIKR

BMS2l1-143
(SEQ ID NO: 990)
DIQMTQSPSS LSASVGDRVT ITCRASQTIE TNLEWYQQKP GKAPKLLIYD SSQLQSGVPS
RFSGSGSGTD FTLTISSLQP EDLATYYCQQ YHGYPTTFGQ GTKVEIKR

BMS2h-144
(SEQ ID NO: 991)
DIQMTQSPSS LSASVGDRVT ITCRASQMID QDLEWYQQKP GKAPKLLIYN ASWLQSGVPS
RFSGSGSGTD FTLTISSLQP EDFATYYCQQ YHGYPITEGQ GTKVEIKR

BMS2h-145
(SEQ ID NO: 992)
DIQMTQSPSS LSASVGDRVT ITCRASQTIY TSLSWYQQKP GKAPKLLIHY GSVLQSGVPS
RFSGSGSGTD FTLTISSLQP EDSATYYCQQ VHQAPTTFGQ GTKVEIKR

BMS2h-146
(SEQ ID NO: 993)
DIRMTQSPSS LSASVGDRVT ITCRASQWIG DSLAWYQQKP GKAPKLLIYG ISELQSGVPS
RFSGSGSGTD FTLTISSLQP EDSATYYCQL SSSMPHTFGQ GTKVEIKR

BMS2h-147
(SEQ ID NO: 994)
DIQMTQSPSS LSASVGDRVT ITCRASQEIE TNLEWYQQKP GKAPKLLIYD SSHLQSGVPS
RFSGSGSGTD FTLTISSLQP EDFATYYCQQ YHQNPPTFGQ GTKVEIKR

BMS2h-149
(SEQ ID NO: 995)
DIQMTQSPSS LSASVGDRVT ITCRASQWIG RQLVWYQQKP GKAPKLLIYG ATELQSGVPS
RFSGSGSGTD FTLTISSLQP EDFATYYCQQ QSKGPLTFGH GTKVEIKR

BMS2h-150
(SEQ ID NO: 996)
DIQMTQSPSS LSASVGDRVT ITCRASQGIG TDLNWYQQKP GKAPKLLIYM GSYLQSGVPS
RFSGSGSGTD FTLTISSLQP EDFATYYCQQ IYSFPITFGQ GTKVEIKR

BMS2h-154
(SEQ ID NO: 997)
DIQMTQSPSS LSASVGDRVT ITCRASQEIE EMLHWYQQKP GKAPKLLIYF GSLLQSGVPS
RFSGSRSGTD FTLTISSLQP EDFATYYCQQ HHTRPYTFGQ GTKVEIKR

BMS2h-155
(SEQ ID NO: 998)
DIQMTQSPSS LSASVGDRVT ITCRASQDIG MDLEWYQQIP GKVPKLLIYD ASYLQSGVPS
RFSGSGSGTD FTLTISSLQP EDFATYYCQQ YHKLPATFGQ GTKVEIKR

BMS2h-156
(SEQ ID NO: 999)
DIQMTQSPSS LSASVGDRVT ITCRASQDIM DNLEWYQQKP GKAPKLLIYA ASWLQSGVPS
RFSGSGSGTD FTLTISSLQP EDFATYYCQQ YHKLPVTFGQ GTKVEIKR

BMS2h-I57
(SEQ ID NO: 1000)
DIQMTQSPSS LSASVGDRVT ITCRASQNIG EDLEWYQQKP GNAPKLLIYS ASHLQSGVPS
RFSGSGSGTD FTLTISSLQP EDFATYYCQQ YSSYPVTFGQ GTKVEIKR

BMS2h-158
(SEQ ID NO: 1001)
DIQMTQSPSS LSASVGDRVT ITCRASQPID EDLEWYQQKP GNAPKLLIYS ASYLQSGVPS
RFSGSGSGTD FTLTISRLQP EDFATYYCQQ YHLLPATFGQ GTKVEIKR

BMS2h-159
(SEQ ID NO: 1002)
DIQMIQSPSS LSASVGDRVT ITCRASQDIN EDLEWYQQKP GKAPKLLIYN ASMLQSGVPS
RFSGSGSGTD FTLTISSLQP KDFATYYCQQ YHTNPTTFGQ GTKVEIKR

TABLE 3-continued

Anti-human CD40L VK Domain Amino Acid Sequences

BMS2h-160
(SEQ ID NO: 1003)
DIQMTQSPSS LSASVGDRVT ITCRASQDIE ADLEWYQQKP GKAPKLLIYH SSELQSGVPS
RFSGSGSGTD FTLTISSLQP EDFATYYCQQ YHMSPVTFGQ GTKVEIKR

BMS2h-161
(SEQ ID NO: 1004)
DIQMTQSPSS LSASVGDRVT ITCRASQDID SDLEWYQQKP GKAPMLLIYS SSDLQSGVPS
RFSGSGSGTD FTLTISSLQP EDFATYYCQQ YHSLPVTFGQ GTKVEIKR

BMS211-162
(SEQ ID NO: 1005)
DIQMTQSPSS LSASVGDRVT ITCRASQDIS DDLEWYQQKP GKAPKLLIYN SSFLQSGVPS
RFSGSGSGAD FTLTISSLQP EDFATYYCQQ YHSLPVTFGQ GTKVEIKR

BMS2h-163
(SEQ ID NO: 1006)
DIQMTQSPSS LSASVGDRVT ITCRASQDIE GNLEWYQQKP GKAPKLLIYD SSQLQSGVPS
RFSGSGSGTD FTLTISSLQP EDFATYYCQQ YHHLPTTFGQ GTKVEIKR

BMS2h-164
(SEQ ID NO: 1007)
DIQMTQSPSS LSASVGDRVT ITCRASQSID TDLEWYQQKP GKAPKLLIYD GSWLQSGVPS
RFSGSGSGTD FTLTISSLQP EDFATYYCQQ YRWIPVTFGQ GTKVEIKR

BMS2h-165
(SEQ ID NO: 1008)
DIQMTQSPSS LSASVGDRVT ITCRASQSIS TDLEWYQQKL GKAPKLLIYD ASLLQSGVPS
RFSGSGSGTD FTLTISSLQP EDFATYYCQQ YSSLPVTFGQ GTKVEIKR

BMS2h-166
(SEQ ID NO: 1009)
DIQMTQSPSS LSASVGDRVT ITCRASQPIT TSLEWYQQKP GKAPKLLIYD ASMLQSGVPS
RFSGSGSGTD FTLTISSLQP EDFATYYCQQ YWVIPVTFGQ GTKVEIKR

BMS2h-167
(SEQ ID NO: 1010)
DIQMTQSPSS LSASVGDRVT ITCRASQNIH TNLEWYQQKP GKAPKLLIYD GSMLQSGVPS
RFSGSGSGTD FTLTISSLQP EDFATYYCQQ YSANPVTFGQ GTKVGIKR

BMS2h-168
(SEQ ID NO: 1011)
DIQMTQSPSS LSASVGDRVT ITCRASQWIH TDLEWYQQKP GKAPKLLIYD GSMLQSGVPS
RFSGSGSGTD FTLTISSLQP EDFATYYCQQ YSVSPVTFGQ GTKVEIKR

BMS2h-169
(SEQ ID NO: 1012)
DIQMTQSPSS LSASVGDRVT ITCRASQSID NNLEWYQQKP GEAPKLLIYD GSLLQSGVPS
RFSGSGSGTD FTLTISSLQP EDFATYYCQQ YHLHPVTFGQ GTKVEIKR

BMS2h-170
(SEQ ID NO: 1013)
DIQMTQSPSS LSASVGDRVT ITCRASQDID TNLEWYQQKP GEAPKLLIYD RSTLQSGVPS
RFSGSGSGTD FTLTISSLQP EDFATYYCQQ YDSYPVTFGQ GTKVEIKR

BMS2h-171
(SEQ ID NO: 1014)
DIQMTOSPSS LSASVGDRVT ITCRASQSIE SNLEWYQQKP GKAPKLLIYN ASELQSGVPS
RFSGSGSGTD FTLTISSLRP EDFATYYCQQ YDQWPITFGQ GTKVEIKR

BMS211-172
(SEQ ID NO: 1015)
DIQMTQSPSS LSASVGDRVT ITCRASQAIG NTLRWYQQKP GKAPKLLIYL SSRLQSGVPS
RFSGSGSGTD FTLTISSLQP EDFATYYCQQ LKKPPYTFGQ GTKVEIKR

BMS2h-173
(SEQ ID NO: 1016)
DIQMTQSPSS LSASVGDRVT ITCRASQKIK NRLAWYQQKP GKAPKLLIYE VSHLQSGVPS
RFSGSGSGTD FTLTIGSLQP EDFATYYCQQ RRQSPYTFGQ GTKVEIKR

BMS2h-174
(SEQ ID NO: 1017)
DIQMTQSPSS LSASVGDRVT ITCRASEDIG EELFWYQQKP GKAPKLLIYS ASTLQSEVFS
RFSGSGSGTD FTLTISSLQH EDFATYYCQQ WEVVPYITGQ GTKVEIKR

TABLE 3-continued

Anti-human CD40L VK Domain Amino Acid Sequences

BMS2h-175
(SEQ ID NO: 1018)
DIQMTQSPSS LSASVGDRVT ITCRASQPIS GGLRWYQQKP GKAPKLLIYS TSMLQSGVPS
RFSGSGSGTD FTLTISSLQP EDFATYYCQQ LYSAPYTTGQ GTKVEIKR

BMS2h-305
(SEQ ID NO: 1019)
DIQMTQSFSS LSASVGDRVT ITCRASQDID QDLEWYQQKP GKAPKLLIYN VSLLQSGVPS
RFSGSGSGTD FTLTISSLQP EDFATYYCQQ YSMNPVITGQ GTKVEIKR

BMS2h-306
(SEQ ID NO: 1020)
DIQMTQSPSS LSASVGDRVT ITCRASQDIG NQLKWYQQKP GKAPKLLIYQ ASGLQSGVPS
RFSGSGSGTD FTLTISSLQF EDFATYYCQQ YDLRPQTFGQ GTKVEIKR

BMS2h-307
(SEQ ID NO: 1021)
DIQMTQSPSF LSASVGDRVT ITCRASQKIS TSLEWYQQKP GKAPRLLIYD SSWLQSGVPS
RFSGSGSGTD FTLTISSLQP EDFATYYCQQ YEYNPITFGQ GTKVEIKR

BMS2h-33
(SEQ ID NO: 1022)
DIMITQSPSS LSASVGDRVT ITCRASQTIG ESLHWYQQKP GKAPRLLIYF ASLLQSGVPS
RFSGSGSGTD FTLTISSLQP EDFATYYCQQ HHMLPSTFGQ GTKVEIKR

BMS2h-35
(SEQ ID NO: 1023)
DIQMTQSPSS LSASVGDRVT ITCRASQFIG DSLSWYQQKP GKAPKLLIYF SSILQSGVPS
RFSGSGSGTD FILTISSLQP EDFATYYCQQ YMDIPITFGQ GTKVEIKR

BMS2h-36
(SEQ ID NO: 1024)
DIQMTQSPSS LSASVGDRVT ITCRASQDID HNLEWYQQKP GKAPKLLIYD SSMLQSGVPS
RFSGSGSGTD FTLTISSLQP EDFATYYCQQ YHSIPVTFGQ GTKVEIKR

BMS2h-37
(SEQ ID NO: 1025)
DIQMTQSPSS LSASVGDRVT ITCRASQQIE TNLEWYQQKP GKAPKLLIYD GSWLQSGVPS
RFSGSGSGTD FTLTISSLQP EDFATYYCQQ YHSLPATFGQ GTKVEIKR

BMS2h-38
(SEQ ID NO: 1028)
DIQMTQSPSS LSASVGDRVT ITCRASQDIG NNLEWYQQKP GKAPRLLIYH GSWLQSGVPS
RFSGSGSGTD FTLTISSLQP EOFATYYCQQ YDENPITFGQ GTKVEIKR

BMS2h-39
(SEQ ID NO: 1027)
DIQMTQSPSS LSASVGDCVT ITCRASQNID GLLWWYQQKP GKAPKLLIYA GSGLQSGVPS
RFSGSGSGTD FTLTISSLQP EDFATYYCQQ KAFEPFTFGQ GTKVEIKR

BMS2h-405
(SEQ ID NO: 1028)
DIQMTQTPSS LSASVGDRVT ITCRASQSIG HDLEWYQQKP GKAPKLLIYN VSWLQSGVPS
RFSGSGSGTD FTLTISSLQP EDFATYYCQQ YSHNPPTFGQ GTKVEIKR

BMS2h-406
(SEQ ID NO: 1029)
DIQMTQSPSS LSASVGDRVT ITCRASQHIE NDLEWYQQKP GKAPKLLIYS ASHLQSGVPS
RFSGSGSGTD FTLTISSLQP EDFATYYCQQ YHLQPTIFGP GTKVEIKR

BMS2h-431
(SEQ ID NO: 1030)
DIQMTQSPSS LSASVGDRVT ITCRASQVIE GSLNWYQQKP GKAPKLLIYH RSILQSGVPS
RFSGRGSGTD FTLTISSLQP EDFATYYCQQ TYQLPLTFGQ GTKVEIKR

BMS2h-432
(SEQ ID NO: 1031)
DIQMTQSPSS LSASVGDRVT ITCRASRPIN GKLFWYQQKP GKAPKLLIAF ASALQSGVPS
RFSGSGSGTD FTLTISSLQP EDFATYYCVQ QAVYFITFGQ GTKVEIKR

BMS2h-433
(SEQ ID NO: 1032)
DIQMTQSPSS LSASVGDRVT ITCRASQAIE TNLEWYQQKP GKAPKLLIYD GSLLQSGVPS
RFSGRGSGTD FTLTISSLQP EDFATYYCQQ YHYQPATFGQ GTKVEIKR

TABLE 3-continued

Anti-human CD40L VK Domain Amino Acid Sequences

BMS2h-434
(SEQ ID NO: 1033)
DIQMTQSPSS LSASVGDRVT ITCRASQDIE HDLEWYQQKP GKAPKLLIYS ASQLQSGVPS
RFSGSGSGTD FTLTISSLQP EDFATYYCQQ YQQQPTTFGQ GTKVEIKR

BMS2h-435
(SEQ ID NO: 1034)
DIQMTQSPSS LSASVGDRVT ITCRASSQIE ESLWWYQQKP GKAPKLLIAD VSLLQSGVPS
RFSGSGSGTD FTLTISSLQP EDFATYYCAQ GVVEPRTFGQ GTKVEIKR

BMS2h-436
(SEQ ID NO: 1035)
DIQMTQSPSS LSASVGDRVT ITCRASQYIG LDLEWYQQKP GKAPKLLIYA ASWLQSGVPS
RFSGSGSGTD FTLTISSLQP EDFATYYCQQ YFRQPITFGQ GTKVEIKR

BMS2h-437
(SEQ ID NO: 1036)
DIQMTQSPSS LSASVGDRVT ITCRASTPIG TMLDWYQQKP GKAPKLLIGH SSWLQSGVPS
RFSGSGSGTD FTLTISSLQP EDFATYYCGQ HVRPPATFGQ GTKVEIKR

BMS2h-437-1
(SEQ ID NO: 1037)
DIQLTQSPTS LSATVGDRVT ITCRASTFIG TMLDWYQQKP GKAPKLLIGH SSWLQSGVPS
RFSGSGSGTD FTLTISSLQP EDFATYYCGQ HVRHPATFGQ GTKVEIKR

BMS2h-437-2
(SEQ ID NO: 1038)
DIQMTQSPSS LSASVGDRVT ITCRASTPIG TMLDWYQQKP GKAPKLLIGH SSWLQSGVPS
RFSGSGSGTD FTLTISSLQP EDFATYYCGQ HVRPPATFGQ GTKVGIKR

BMS2h-437-3
(SEQ ID NO: 1039)
DIQMTQSPSS LSASVGDRVT ITCRVSTPIG TMLDWYQQKP GKAPKLLIGH SSWLQSGVPP
RFSGSGSGTD FTLTISSLQP EDFATYYCGQ HVRPPATFGQ GTKVEIKR

BMS2h-437-4
(SEQ ID NO: 1040)
DIQMTQSPSS LSASVGDRVT ITCRASTFIG TMLDWYQQKP GKAPKLLIGH SSWLQSGVPS
RFSGCGSGTD FTLTISSLQP EDFATYYCGQ HVRPPATFGQ GTKVEIKR

BMS2h-437-5
(SEQ ID NO: 1041)
DIQMTQSPSS LSASVGDRVT ITCRASTPIG TMIDWYQQKP GKAPKLLIGH SSWLQSGVPS
RFSGSGSGTD FTLTISSLQP EDFATYYCGQ HVRPPATFGK GTKVEIKR

BMS2h-438
(SEQ ID NO: 1042)
DIQMTQSPSS LSASVGDRVT ITCRASQYID TNLEWYQQKP GKAPRLLIYD GSQLQSGVPS
RFSGSGSGTD FTLTISSLQP EDFATYYCQQ YQVVPVTFGQ GTKVEIKR

BMS2h-439
(SEQ ID NO: 1043)
DIQMTQSPSS LSASVGDRVT ITCRASQSIS SYLNWYQQKP GKAPRLLIVD SSGLQSGVPS
RFSGSGSGTD FTLTISSLQP EDFATYYCGQ DRWSPATFGQ GTKVEIKR

BMS2h-440
(SEQ ID NO: 1044)
DIQMTQSPSS LSASVGDRVT ITCRASSRIQ HMLSWYQQKP GKAPKLLIGG HSGLQSGVPS
RFSGSGSGTD FTLTISSLQP EDFATYYCAQ SCAWPLTFGQ GTKVEIKR

BMS2h-441
(SEQ ID NO: 1045)
DIQMTQSPSS LSASVGDRVT ITCRASRGID GDLWWYQQKP GKAPKLLIAD SSLLQSGVPS
RFSGSGSGTD FTLTISSLQP EDFATYYCGQ GAVRPMTFGQ GTKVEIKR

BMS2h-442
(SEQ ID NO: 1046)
DIQMTQSPSS LSASVGDRVT ITCRASRGID IDLWWYQQKP GKAPKLLIAD SSLLQSGVPS
RFSGSGSGTD FTLTISSLQP EDFATYYCGQ GAVRPMTFGQ GTKVEIKR

BMS2h-443
(SEQ ID NO: 1047)
DIQMTQSPSS LSASVGDRVT ITCRASYTIP VALDWYQQKP GKAPKLLIAD ASLLQSGVPS
RFSGSGSGTD FTLTISSLQP EDFATYYCAQ GWPGPMTFGQ GTKVEIKR

TABLE 3-continued

Anti-human CD40L VK Domain Amino Acid Sequences

BMS2h-444
(SEQ ID NO: 1048)
DIQMTQSPSS LSASVGDRVT ITCRASQSIA TDLEWNQQKP GKAPKLLIYD TSMLQSGVPS
RFSGSGSGTD FTLTISSLQP EDFATYYCQQ YSYNPSTFGQ GTKVEIKR

BMS2h-445
(SEQ ID NO: 1049)
DIQMTQSPSS LSASVGDRVT ITCRASVPIT EGLSWYQQKP GKAPKLLIQA NSWLQSGVPS
RFSGSGSGTD FTLTISSLQP EDFATYYCGQ WEHVPATFGQ GTKVEIKR

BMS2h-446
(SEQ ID NO: 1050)
DIQMTQSPSS LSASVGDRVT ITCRASSMIL YGLDWYQQKP GKAPKLLIGG TSALQSGVPS
RFSGSGSGTD FTLTISSLQP EDFATYYCGQ WETVPATFGQ GTKVEIKR

BMS2h-447
(SEQ ID NO: 1051)
DIQMTQSPSS LSASVGDRVT ITCRASQPIN GLLIWYQQKP GKAPKLLIYA MSSLQSGVPS
RFSGSGSGTD FTLTISSLQP EDFATYYCQQ LARIPFTFGQ GTKVGIKR

BMS2h-448
(SEQ ID NO: 1052)
DIQMTQSPSS LSASVGDRVT ITCRASQLIR TYLAWYQQKP GKAPKLLIYQ SSQLQSGVPS
RFSGSGSGTD FTLTISSLQP EDFATYYCQQ YNSYPDTFGQ GTKVEIKR

BMS2h-47
(SEQ ID NO: 1053)
DIQMTQSPSS LSASVGDRVT ITCRASQWIG DSLSWYQQKP GKAPKLLIYF GSYLQSGVPS
RFSGSGSGTD FTLTISSLQP EDFATYYCQQ YLHTPSTFGQ GTKVEIKR

BMS2h-484
(SEQ ID NO: 1054)
DIQMTQSPSS LSASVGDRVT ITCRASQDIE ADLEWYQQKP GKAPKLLIYH SSELQSGVPS
RFSGSGSGTD FTLTISSLQP EDFATYYCQQ YGFNPPTFGQ GTKVEIKR

BMS2h-485
(SEQ ID NO: 1055)
DIQMTQSPSS LSASVGDRVT ITCRASSPIE YGLDWYQQKP GKAPKLLIGG GSALQSGVPS
RFSGSGSGTD FTLTISSLQP EDFATYYCGQ WEVQPATFGQ GTKVEIKR

BMS2h-486
(SEQ ID NO: 1056)
DIQMTQSPSS LSASVGDRVT ITCRASQRID TDLEWYQQKP GKAPKLLIYD SSQLQSGVPS
RFSGSGSGTD FTLTISSLQP EDFATYYCQQ YHSAPATFGQ GTKVEIKR

BMS2h-487
(SEQ ID NO: 1057)
DIQMTQSPSS LSASVGDRVT ITCRASGWIG MSLEWHQQKP GKAPKLLIRG ASSLQSGVPS
RFSGSGSGTD FTLTISSLQP EDFATYYCSQ SRWPPVTFGQ GTKVEIKR

BMS2h-488
(SEQ ID NO: 1058)
DIQMTQSPSS LSASVGDRVT ITCRASRNIS NALSWYQQKP GKAPKLLILG ASWLQSGVPS
RFSGSGSGTD FTLTISSLQP EDFATYYCTQ VWDRPFTFGQ GTKVEIKR

BMS2h-489
(SEQ ID NO: 1059)
DIQMTQSPSS LSASVGDRVT ITCRASQDIM SALSWYQQKP GKAPKIIIYS TSILQSGVPS
RFSGSGSGTD FTLTISSLQP EDFATYYCQQ VYLLPVTFGQ GTKVEIKR

BMS2h-490
(SEQ ID NO: 1060)
DIQMTQSPSS LSASVGDRVT ITCRASQEIG IDLEWYQQKP GKAPKLLIYA ASYLQSGVPS
RFSSSGSGTD FILTISSLQP EDFATYYCQQ YASNPPIFGR GTKVEIKR

BMS2h-491
(SEQ ID NO: 1061)
DIQMTQSPSS LSASVGDRVT ITCRASQMIG DWLNWYQQKP GKAPKLLIYR SSELQSGVPS
RFSGSGSGTD FTLTISSLQP EDFATYYCQQ LYFWPRTFGQ GTKVEIKR

BMS2h-492
(SEQ ID NO: 1062)
DIQMTQSPSS LSASVGDRVT ITCRASQAIE LNLEWYQQKP GKAPKLLIYD ASMLQSGVPS
RFSGSGSGTD FTLTISSLQP EDFATYYCQQ YDVYPPTPGQ GTKVEIKR

TABLE 3-continued

Anti-human CD40L VK Domain Amino Acid Sequences

BMS2h-492-1
(SEQ ID NO: 1063)
DIQMTQSPSS LSASVGDRVT ITCRASQAIE HNLEWYQQKP GKAPKLLIYD ASMLQSGVPS
RFSGSGSGTD FTLTISSLQP EDLATYYCQQ YDAYPPTYGQ GTKVEIKR

BMS2h-492-2
(SEQ ID NO: 1064)
DIQMTQSPSS LSASVGDRVT ITCRASRAIE TNLEWYQQKP GKAPKLLFYD ASMLQSGVPS
RFGGSGSGTD FTLTISSLQP EDFATYYCLQ YDVYPPTFGQ GTKVEIKR

BMS2h-492-3
(SEQ ID NO: 1065)
DIQMTQSPSS LSATVGDRVT ITCRASQAIE TNLEWYQQKP GKAPKLLIYD ASMLQSGVPS
RFSGSGSGTD FTLTISSLQP EDFATYYCQQ YDAYPPTFGQ GTKVEIKR

BMS2h-492-4
(SEQ ID NO: 1066)
DIQMTQSPSS LSASVGDRVT ITCRASQAIE HNLEWYQQKP GKAPKLLIYD ASMLQSGVPS
RFSGRGSGTD FTLTISSLQP EDFATYYCQQ YDAYPPTFGQ GTKVEIKR

BMS2h-492-5
(SEQ ID NO: 1067)
DIQMNQSPSS LSASVGDRVS ITCRASQAIE HNLEWYQQKP GKAPKLLIYD ASMLQSGVPS
RFSGSGSGTD FTLTISSLQP EDFATYYCQQ YDAYPPTFGQ GTKVEIKR

BMS2h-492-6
(SEQ ID NO: 1068)
DIQMTQSPSS LSASVGDRVT ITCRASQAIE SNLEWYQQKP GKAPKLLIYD ASMLQSGVPS
RFSGSGSGTD FILTISSLQP EDFATYYCQQ YDVYPPTFGQ GTKVEIKR

BMS2h-492-7
(SEQ ID NO: 1069)
DIQMTQSPSS LSASVGDRVT ITCRASQAIE HNLEWYQQKP GKAPKLLIYD ASMLQSGVPS
RFSGSGSGTD FTLTISSLQP EDFATYYCQQ YDAYPPTFGQ GTKVEIKR

BMS2h-493
(SEQ ID NO: 1070)
DIQMTQSPSS LSASVGDRVT ITCRASQGID EDLEWYQQKP GKAPRLLIYS SSWLQSGVPS
RFSGSGSGTD FTLTISSLQP EDFATYYCQQ YFQYPPTFGQ GTKVEIKR

BMS2h-494
(SEQ ID NO: 1071)
DIQMTQSPSS LSASVGDRVT ITCRASQSID EDLEWYQQKP GKAPRLLIYS SSWLQSGVPS
RFSGSGSGTD FTLTISSLQP EDFATYYCQQ YFQYPPIFGQ GTKVEIKR

BMS2h-494-1
(SEQ ID NO: 1072)
DIQMTQSPSS LSASVGDRVT ITCRASQSID EDLEWYQQKP GKAPRLLIYS SSWLQSGVPS
RFSGSGSGTD FTLTISSLQP EDFATYYCQQ YSQYPPTFGQ GTKVEIKR

BMS2h-494-2
(SEQ ID NO: 1073)
DIQMTQSPSS LSASVGDRVT ITCRASQSIE EDLEWYQQKP GKAPRLLIYS SSWLQSGVPS
RFSGSGSGTD FTLTISSLQP EDFATYYCQQ YFQYPPTFGH GTKVEIKR

BMS2h-494-3
(SEQ ID NO: 1074)
DIQMTQSPSS LSASVGDRVT ITCRASQSID EDLEWYQQKP GKAPRLLIYS SSWLQSGVPS
RFSGSGSGTD FTLTISSLQP EDFATYFCQQ YFQYPPTFGQ GTKVEIKR

BMS2h-494-4
(SEQ ID NO: 1075)
EIQMTQSPSS LSASVGDRVT MTCRASQSID KDLEWYQQKP GKAPRLLIYS SSWLQRGVPS
RFSGSGSGTD FTLTISSLQP EDFATYYCQQ YFQYPPTLGQ GTKVEIKR

BMS2h-494-5
(SEQ ID NO: 1076)
DIQMTQSPSS LSASVGDRVT ITCRASQSID EDLEWYQQKP GKAPRLLIYS SSWLQSGVPS
RFSGSGSGTD FTLTISGLQP EDIATYYCKQ YSQYPPTFGQ GTKVEIKR

BMS2h-494-6
(SEQ ID NO: 1077)
DIQMTQSPPS LSASVGDRVT ITCRASQSID KDLEWYQQKP GKAPRLLIYS SSWLQRGVPS
RFSGSGSGTD FTLTISSLQP EDFATYYCQQ YFQYPPTFGQ GTKVEIKR

TABLE 3-continued

Anti-human CD40L VK Domain Amino Acid Sequences

BMS2h-495
(SEQ ID NO: 1078)
DIQMTQSPSS LSASVGDRVT ITCRASEYIN AELAWYQQKP GKAPKLLIYG SSGLQSGVPS
RFSGSGSGTD FTLTISSLQP EDFATYYCQQ NAMWPITFGQ GTKVEIKR

BMS2h-496
(SEQ ID NO: 1079)
DIQMTQSPSS LSASVGDRVT ITCRASLDIN NGLIWYQQKP GKAPRLLILG ASGLQSGVPS
RFSGSGSGTD FTLTISSLQP EDFATYYCSQ VRSRPFTFGQ GTKVEIKR

BMS2h-497
(SEQ ID NO: 1080)
DIQMTQSPSS LSASVGDRVT ITCRASQDIL SALAWYQQKP GKAPKLLIYG SSVLQSGVPS
RFSGSGSGTD FTLTISSLQP EDFATYYCQQ NYSLPITFGQ GTKVEIKR

BMS2h-498
(SEQ ID NO: 1081)
DIQMTQSPSS LSASVGDRVT ITCRASSPIE SYLRWYQQKP GKAPKLLIRY VSVLQSGVPS
RFSGSGSGTD FTLTISSLQP EDFATYYCGQ WFRAPVTFGQ GTKVEIKR

BMS2h-499
(SEQ ID NO: 1082)
DIQMTQSPSS LSASVGDRVT ITCRVSESIN AELHWYQQKP GKAPKLLISG FSGLQSGVPS
RFSGSGSGTD FTLTISSLQP EDFATYYCVQ FAMWPFTFGQ GTKVEIKR

BMS2h-500
(SEQ ID NO: 1083)
DIQMTQSPSS LSASVGDRVT ITCRASMMIR FGLDWYQQKP GKAPKLLIGG GSSLQSGVPS
RFSGSGSGTD FTLTISSLQP EDFATYYCGQ HERWPATFGQ GTKVEIKR

BMS2h-501
(SEQ ID NO: 1084)
DIQMTQSPSS LSASVGDRVT ITCRASQSIG TLLRWYQQKP GKAPKLLIYL TSVLQSGVPS
RFSGSGSGTD FTLTISSLQP EDFATYYCQQ MVYRPYTFGQ GTKVEIKR

BMS2h-502
(SEQ ID NO: 1085)
DIQMTQSPSS LSASVGDRVT ITCRASQTIE TNLEWYQQKP GKAPKLLIYD SSQLQSGVPS
RFSGSGSGTD FTLTISSLQP EDFATYYCQQ YDKVPATFGQ GTKVEIKR

BMS2h-503
(SEQ ID NO: 1086)
DIQMTQSPSS LSASVGDRVT ITCRASHHIQ RYLSWYQQKP GKAPKLLILW GSQLQSGVPS
RFSGSGSGTD FTLTISSLQP EDFATYYCGQ WWAPPPTFGQ GTKVEIKR

BMS2h-503-1
(SEQ ID NO: 1087)
DIQMTQSPSS LSASVGDRVT ITCRASHHIQ RYLSWYQQKP GKAPKLLILW GSQLQSGVPS
RFSGSGSGTD FTLTISSLQP EDFATYYCGQ WWAPPQTFGQ GTKVEIKR

BMS2h-503-2
(SEQ ID NO: 1088)
DIQMTQSPSS LSASVGDRVT ITCRASHDIQ RYLSWYQQKP GKAPKLLILW GSQLQSGVPS
RFSGSGSGTD FTLTISSLQP EDFATYYCGQ WWAPPQTFGQ GTKVEIKR

BMS2h-504
(SEQ ID NO: 1089)
DIQMTQSPSS LSASVGDRVT ITCRASQYID TNLEWYQQKP GKAPKLLIYD GSLLQSGVPS
RFSGSGSGTD FTLTISSLQP EDFATYYCGQ GAVVPVTFGQ GTKVEIKR

BMS2h-508
(SEQ ID NO: 1090)
DIQMTQSPSS LSASVGDRVT ITCRASQDIA FDLEWYQQKP GKAPKLLIYS ASMLQSGVPS
RFSGSGSGSD FTLTISSLQP EDFATYYCQQ YNLQPPTFGQ GTKVEIKR

BMS2h-509
(SEQ ID NO: 1091)
DIQMTQSPSS LSASVGDRVT ITCRASQNIA TLLRWYQQKP GKAPKLLIYA GSMLQSGVPS
RFSGSGSGTD FTLTISSLQP EDFATYYCQQ MWQRPYTFGQ GTKVEIKR

BMS2h--51
(SEQ ID NO: 1092)
DIQMTQSPSS LSASVGDRVT ITCRASQPIV DELDWYQQKP GKAPKLLIYA ASILQSGVPS
RFSGSGSGTD FTLTISSLQP EDFATYYCHQ WSTYPTTFGQ GTKVEIKR

TABLE 3-continued

Anti-human CD40L VK Domain Amino Acid Sequences

BMS2h-510
(SEQ ID NO: 1093)
DIQMTQSPSS LSASVGDRVT ITCRASQSIS SYLNWYQQKP GKAPKLLIDG VSGLQSGVPS
RFSGSGSGTD FTLTISSLQP EDFATYYCGQ DWDWPRTFGQ GTKVEIKR

BMS2h-511
(SEQ ID NO: 1094)
DIQMTQSPSS LSASVGDRVT ITCRASRNIR DWLRWYQQKP GKAPKLLIQW GSVLQSGVPS
RFSGSGSGTD FTLTISSLQP EDFATYYCAQ TWDDPLTFGQ GTKVEIKR

BMS2h-511-1
(SEQ ID NO: 1095)
DIQMTQSPSS LSAFVGDRVT ITCRASRNIR DWLRWYQQKP GKAPKLLIDW GSELQSGVPS
RFSGSGSGTD FTLTISSLQP EDFATYYCQQ TWYDPLTFGH GTKVEIKR

BMS2h-512
(SEQ ID NO: 1096)
DIQMTQSPSS LSASVGDRVT ITCRASIDIH GGLTWYQQKP GKAPKLLIVG VSGLQSGVPS
RFSGSGSGTD FTLTISNLQP EDFATYYCAQ VWRRPFTFGQ GTKVEIKR

BMS2h-513
(SEQ ID NO: 1097)
DIQMTQSPSS LSASVGDRVT ITCRASQDIG SSLSWYQQKP GKAPKLLIYA SSLLQSGVPS
RFSGSGSGTD FTLTISSLQP EDFATYYCQQ TYALPVTFGQ GTKVEIKR

BMS2h-514
(SEQ ID NO: 1098)
DIQMTQSPSS LSASVGDRVT ITCRASQQIE TNLEWYQQKP GKAPKLLIYD GSWLQSGVPS
RFSGSGSGTD FTLTISSLQP EDFATYYCQQ YKYLPVTFGQ GTKVEIKR

BMS2h-52
(SEQ ID NO: 1099)
DIQMTQSPSS LSASVGDRVT ITCRASQDIG SALRWYQQKP GKAPKLLIYL GSDLQSGVPS
RFSGSGSGTD FTLTISSLQP EDFATYYCQQ TQYFPTTFGQ GTKVEIKR

BMS211-53
(SEQ ID NO: 1100)
DIQMTQSPSS LSASVGDRVT ITCRASQAIY GGLRWYQQKP GKAPKLLIYG ESMLQSGVPS
RFSGSGSGTD FTLTISSLHP EDFATYYCQQ VYHKPFTFGQ GTKVEIKR

BMS2h--536
(SEQ ID NO: 1101)
DIQMTQSPSS LSASVGDRVT ITCRASQRIG VWLDWYQQKP GKAPKLLIYD GSFLQSGVPS
RFSGSGSGTD FTLTISSLQP EDFATYYCQQ TFSSPSTFGQ GTKVEIKR

BMS2h-537
(SEQ ID NO: 1102)
DIQMTQSPSS LSASVGDRVP ITCRASQWIG DELYWYQQKP GKAPKLLIYS SSTLQSGVPS
RFSGSGSGTD FTLTISSLQP EDFATYYCQQ SFQFPYTFGQ GTKVEIKR

BMS2h-538
(SEQ ID NO: 1103)
DIQMTQSPSS LSASVGDRVT ITCRASSNIT GPLEWYQQKP GKAPKLLIPG WSTLQSGVPS
RFSGSGSGTD FTLTISSLQP EDFATYYCGQ VWGEPVTFGQ GTKVEIKR

BMS2h-539
(SEQ ID NO: 1104)
DIQMTQSPSS LSASIGDRVT ITCRASQRIA YGLHWYQQKP GKAPRLLIGG RSGLQSGVPS
RFSGSGSGTD FTLTISSLQP EDFATYYCVQ PGMPPDTFGQ GTKVEIKR

BMS2h-540
(SEQ ID NO: 1105)
DIQMTQSPSS LSASVGDRVT ITCRASKQIV GGLSWYQQKP GKAPKLLIGR HSGLQSGVPS
RFSGSGSGTD FTLTISSLQP EDFATYYCVQ GVWAPGTFGQ GTKVEIKR

BMS2h-541
(SEQ ID NO: 1106)
DIQMTQSPSS LSASVGDRVT ITCRASPAIA AKLDWYQQKP GKAPKLLIGA DSGLQSGVPS
RFSGSGSGTD FTLTISSLQP EDFATYYCGQ LWAGPPTFGQ GTKVEIKR

BMS2h-542
(SEQ ID NO: 1107)
DIQMTQSPSS LSASVGDRVT ITCRASRTIA DGLDWYQQKP GKAPKLLIGA YSGLQSGVPS
RFSGSGSGTD FTLTISSLQP EDFATYYCGQ LWEGPPTFGQ GTKVEIKR

TABLE 3-continued

Anti-human CD40L VK Domain Amino Acid Sequences

BMS2h-543
(SEQ ID NO: 1108)
DIQMTQSPSS LSASVGDRVT ITCRASQRIY GFLDWYQQKP GKAPKLLIYG VSSLQSGVPS
RFSGSGSGTD FTLTISSLQP EDFATYYCQQ TLAWPFTFGQ GTKVEIKR

BMS2h-544
(SEQ ID NO: 1109)
DIQMTQSPSS LSASVGDRVT ITCRASQDIR DWLMWYQQKP GKAPKLLIYW GSFLQSGVPS
RFSGSGSGTD FTLTISSLQP EDFATYYCQQ LYDTPYTFGQ GTKVEIKR

BMS2h-545
(SEQ ID NO: 1110)
DIQMTQSPSS LSASVGDRVT ITCRASQNIN TGLDWYQQKP GKAPKLLIYD SSALQSGVPS
RFSGSGSGTD FTLTISSLQP EDFATYYCQQ TSYYPYTFGQ GTKVEIKR

BMS2h-546
(SEQ ID NO: 1111)
DIQMTQSPSS LSASVGDRVT ITCRASQKIF GWLDWYQQKP GKAPKLLIYG TSKLQSGVPS
RFSGSGSGTD FTLTISSLQP EDFATYYCQQ VYSLPYTFGQ GTKVEIKR

BMS2h-547
(SEQ ID NO: 1112)
DIQMTQSPSS LSASVGDRVT ITCRASSNIG ADLDWYQQKP GKAPKLLIGG ASGEQSGVPS
RFSGSGSGTD FTLTISSLQP EDFATYYCGQ LWNGPPTFGQ GTKVEIKR

BMS2h-548
(SEQ ID NO: 1113)
DIQMTQSPSS LSASVGDRVT ITCRASSPIY DGLDWYQQKP GKAPKLLISG ASWLQSGVPS
RFSGSGSGTD FTLTISSLQP EDFATYYCGQ LWLGPPTFGQ GTKVEIKQ

BMS2h-549
(SEQ ID NO: 1114)
DIQMTQSPSS LSASVGDRVT ITCRASSRIY NGLHWYQQKP GKAPKLLIGG RSGLQSGVPS
RFSGSGSGTD FTLTISSLQP EDFATYYCAQ VGEAPSTFGQ GTKVEIKR

BMS2h-550
(SEQ ID NO: 1115)
DIQMTQSPSS LSASVGDRVT ITCRASRFIN EELDWYQQKP GKAPKLLISW SSWLQSGVPS
RFSGSGSGTD FTLTISSLQP EDFATYYCVQ PGGGPGTFGQ GTKVEIKR

BMS2h-551
(SEQ ID NO: 1116)
DIQMTQSPSS LSASVGDRVT ITCRASRDIL DELDWYQQKP GKAPRLLIGG GSGLQSGVPS
RFSGSGSGTD FTLTISSLQP EDFATYYCGQ LWHGPPIFGQ GTKVEIKR

BMS2h-552
(SEQ ID NO: 1117)
DIQMTQSPSS LSASVGDRVT ITCRASSPIY TGLHWYQQKP GKAPKLLIGG RSGLQSGVPS
RFSGSGSGTD FTLTISSLQP EDFATYYCMQ VGTAPATFGQ GTKVEIKR

BMS2h-535
(SEQ ID NO: 1118)
DIRMTQSPSS LSASVGDRVT ITCRASQNIS RRLLWYQQKP GKAPKLLIYS SSRLQSGVPS
RFGGSGSGTD FTLTISSLQP EDFATYYCQQ TYSYPHTFGQ GTKVEIKR

BMS2h-804
(SEQ ID NO: 1119)
DIQMTQSPSS LSASVGDRVT ITCRASSPIP QDLYWYQQKP GKAPKLLIVG ISOLGSGVPS
RFSGSGSGTD FTLTISSLQP EDFATYYCGQ LWSAPATFGQ GTKVEIKR

BMS2h-605
(SEQ ID NO: 1120)
DIQMTQSPSS LSASVGDRVT ITCRASKSID GMLDWYQQKP GKAPKLLIPG FSGLQSGVPS
RFSGSGSGTD FTLTISSLQP EDFATYYCGQ SVEAPWTFGQ GTKVEIKR

BMS2h-606
(SEQ ID NO: 1121)
DIQMTQSPSS LSASVGDRVT ITCRASRYIA HPLDWYQQKP GKAPKLLIPG SSVLQSGVPS
RFSGSGSGTD FTLTISSLQP EDFATYYCGQ SVVVPWTFGQ GTKVEIKR

BMS2h-807
(SEQ ID NO: 1122)
DIQMTQSPSS LSASVGDRVT ITCRASRTIE GGLDWYQQKP GKAPKLLIMG GSGLQSGVPS
RFSGSGSGTD FTLTISSLQP EDFATYYCGQ LWVGPPTFGQ GTKVEIKR

TABLE 3-continued

Anti-human CD40L VK Domain Amino Acid Sequences

BMS2h-608
(SEQ ID NO: 1123)
DIQMTQSPSS LSASVGDRVT ITCRASKFIR DELYWYQQKP GKAPRLLIGG SSLLQSGVPS
RFSGSGSGTD FTLTISSLQP EDFATYYCGQ LWRAPATFGQ GTKVEIKR

BMS2h-609
(SEQ ID NO: 1124)
DIQMTQSPSS LSASVGDRVT ITCRASKPIY GGLEWYQQKP GKAPRLLIGG GSVLQSGVPS
RFSGSGSGTD FTLTISSLQP EDFATYYCGQ VWGGPVTFGQ GTKVEIKR

BMS2h-810
(SEQ ID NO: 1125)
DIRMTQSPSS LSASVGDRVT ITCRASRPIS GCLDWYQQKP GKAPKLLIDG ASGLQSGVPS
RFSGSGSGTD FTLTISSLQP EDFATYYCGQ WWEYPPTFGQ GTKVEIKR

BMS2h-611
(SEQ ID NO: 1126)
DIQMTOSPSS LSASVGDRVT ITCRASKPIV RDLEWYQQKP GKAPKLLIHG VSTLQSGVPS
RFSGSGSGTD FTLTISSLQP EDFATYYCGQ LEAAPATFGQ GTKVEIKR

BMS2h-612
(SEQ ID NO: 1127)
DIQMTQSPSS LSASVGDRVT ITCRASRDIG DWLYWYQQKP GKAPRLLIVW ASVLQSGVPS
RFSGSGSGTD FTLTISSLQP EDFATYYCAQ WGTPPTFGQ GTKVEIKR

BMS2h-613
(SEQ ID NO: 1128)
DIQMTQSPSS LSASVGDRVT ITCRASNRIE YGLDWYQQKP GKAPKLLISG SSRLQSGVPS
RFSSSGSGTD FTLTISSLOP EDFATYYCGQ LEAAPATFGQ GTKVEIKR

BMS2h-614
(SEQ ID NO: 1129)
DIQMTQSPSS LSASVGDRVT ITCRASRNIG HFLDWYQQKP GKAPKLLILG GSSLQSGVPS
RFSGSGSGTD FTLTISSLQP EDFATYYCGQ LVEPPATFGQ GTKVEIKR

BMS2h-615
(SEQ ID NO: 1130)
DIQMTQSPSS LSASVGDRVT ITCRASSSIY SDLYWYQQKP GKAPKLLIDG WSGLQSGVPS
RFSGSGSGTD FTLTISSLQP EDFATYYCGQ LHRAPATFGQ GTKVEIKR

BMS2h-616
(SEQ ID NO: 1131)
DIQMTOSPSS LSASVGDRVT ITCRASRFIT DRLDWYQQKP GKAPKLLIGG VSGLQSGVPS
RFSGSGSGTD FTLTISSLQP EDFATYYCGQ SSELPWTFGQ GTKVEIKR

BMS2h-617
(SEQ ID NO: 1132)
DIQMTQSPSS LSASVGDRVT ITCRASRKIG SELYWYQQKP GKAPKLLIGG RSRLQSGVPS
RFSGSGSGTD FTLTISSLQP EDFATYYCGQ LWEPPATFGQ GTKVEIKR

BMS2h-613
(SEQ ID NO: 1133)
DIQMTQSPSS LSASVGDRVT ITCRASRNIG NGLDWYQQKP GKAPKLLIGE GSRLQSGVPS
RFSGSGSGTD FTLTISSLQP EDFATYYCGQ LWHTPPTFGQ GTKVEIKR

BMS2h-619
(SEQ ID NO: 1134)
DIQMTQSPSS LSASVGDRVT ITCRASRNIY GWLSWYQQKP GKAPRLLIGG WSGLQSGVPS
RFSGSGSGTD FTLTISSLQP EDFATYYCAQ DYTLPGTFGQ GTKVEIKR

BMS2h-730
(SEQ ID NO: 1135)
DIQMTQSPSS LSASVGDRVT ITCRASQDIK DWLHWYQQKP GKAPKLLIYF ASGLQSGVPS
RFSGSGSGTD FTLTISSLQP EDSATYYCQQ HYSTPYTSGQ GTKVEIKR

BMS2h-731
(SEQ ID NO: 1136)
DIQMTQSPPS LSASVGDRVT ITCRASQLIS SHLDWYQQKP GKAPKLLVYD ASELQSGVPS
RFSGSGSGTD FTLTISSLQP EDFATYYCQQ HRSLPFTFGQ GTKVEIKR

BMS2h-732
(SEQ ID NO: 1137)
DIQMTQSPSS LSASVGDRVI ITCRASQWIG GALAWYQQKP GKAPRLLIYQ ISVLQSGIPS
RFSGSGSGTD FTLTISSLQP EDFATYYCQQ YIRSPFTFGQ GTKVEIKR

TABLE 3-continued

Anti-human CD40L VK Domain Amino Acid Sequences

BMS2h-733
(SEQ ID NO: 1138)
DIQMTQSPSS LSASVGDRVT ITCRASQSIG AALNWYQQKP GKAPKLLIYG LSSLQSGVPS
RFSGSGSGTD FTLTISSLQP EDFATYYCQQ LFRLPLTFGQ GTKVEIKR

BMS2h-734
(SEQ ID NO: 1139)
DIQMTQSPSS LSASVGDRVT ITCRASQPIG GRLVWYQQKP GKAPKLLIYG SSILQSGVPS
RFSGSGSGTD FTLTISSLQP EDFATYYCQQ YAEAPITFGQ GTKVEIKR

BMS2h-735
(SEQ ID NO: 1140)
DIQMTQSPSS LSASVGDRVT ITCRASQNIG SSLIWYQQKP GKAPTLLIYY SSKLQSGVPS
RFSGSGSGTD FTLTISSLQP EDFATYYCQQ SLSSPYTVGQ GTKVEIKR

BMS2h-736
(SEQ ID NO: 1141)
DIQMTQSPSS LSASVGDRVT ITCRASQWIG SELAWYQQKP GKAPKLLIYW TSNLQSGVPS
RFSGSGSGTD FTLTISNLQP EDFATYYCQQ ILETPLTFGQ GTKVEIKR

BMS2h-737
(SEQ ID NO: 1142)
DIQMTQSPSS LSASVGDRVT ITCRASQKIW DALYWYQQKP GKAPKLLIYR GSILQSGVPS
RFSGSGSGTD FTLTISSLQP EDFATYYCQQ FYRWPHTFGQ GTKVEIKR

BMS2h-738
(SEQ ID NO: 1143)
DIQMTQSPSS LSASVGDRVT ITCRASQHIE DSLRWYQQKP GKAPKLLIYY GSVLQSGVPS
RFSGSGSGTD FTLTISSLQP EDFATYYCQQ MYKFPITFGQ GTKVEIKR

BMS2h-739
(SEQ ID NO: 1144)
DIQMTQSPSS LSASVGDRVI ITCRASQRIN SSLLWYQQKP GKAPKLLIYD TSTLQSGVPS
RFSGSRSGTD FTLTISSLQP EDFATYYCQQ IWGSPPTFGQ GTKVEIKR

BMS2h-740
(SEQ ID NO: 1145)
DIQMTQSPSS LSASVGDRVT ITCRASQSIP VGLNWYQQKP GKAPRLLIYS GSTLQSGVPS
RFSGSGSGTD FTLTISSLQP EDFATYYCQQ DWYYPNTFGQ GTKVEIKR

BMS2h-785
(SEQ ID NO: 1146)
DIQMTQSPSS LSASVGDRVT ITCRASQPIY GWLNWYQQKP GKAPKLLIYL TSGLQSGVPS
RFSGSGSGTD FTLTISSLQP EDFATYYCQQ IHSSPFTFGQ GTKVEIKR

BMS2h-8
(SEQ ID NO: 1147)
DIQMTQSPSS LSASVGDRVT ITCRASQFID TSLEWYQQKP GKAPKLLIYD GSHLQSGVPS
RFSGSGSGTD FTLTISSLQP EDLATYYCQQ YWVLPLTFGQ GTKVEIKR

BMS2h-86
(SEQ ID NO: 1148)
DIQMTQSPSS LSASVGDRVT ITCRASQDIG DALFWYQQKP GKAPKLLIYY SSMLQSGVPS
RFSGGGSGTD FTLTISSLQP EDFATYYCQQ RHSTPATFGQ GTKVEIKR

BMS2h-87
(SEQ ID NO: 1149)
DIQMTQSPSS LSASVGDRVT ITCRASQDID ESLMWYQQKP GKAPRLLIYG VSYLQSGVPS
RFSGSGSGTD FTLTISSLQP EDFATYYCQQ RWKAPFTFGQ GTKVEIKR

BMS2h-88
(SEQ ID NO: 1150)
DIQMTQSPSS LSASVGDRVT ITCRASQEIV EDLYWYQQKP GKAAKLLIYG ASWLQSGVPS
RFSGSGSGTD FTLTISSLQP EDFATYYCQQ TRRRPYTFGQ GTKVEIKR

BMS2h-89
(SEQ ID NO: 1151)
DIQMTQSPAS LSASVGDRVT ITCRASQDID PMLRWYQQKP GKAPKLLIYA GSILQSGVPS
RFSGSGSGTD FILTISSLQP EDFATYYCQQ TLVITYTFGQ GTKVEIKR

BMS2h-90
(SEQ ID NO: 1152)
DIQMTQSPSS LSASVGDRVT ITCRASQSIS DALFWYQQKP GKAPRLLIYY GSVLQSGVPS
RFSGSGSGTD FTLTISSLQP EDFATYYCQQ RFQEPVTFGQ GTKVEIKR

TABLE 3-continued

Anti-human CD40L VK Domain Amino Acid Sequences

BMS2h-91
(SEQ ID NO: 1153)
DIQMTQSPSS LSASVGDRVT ITCRASQQIS DELNWYQQKP GKAPKLLIYA VSILQSGVPS
RFSGSGSGTD FTLTISSLQP EDFATYYCQQ WLSFPSTFGQ GTKVEIKR

TABLE 4

Human Anti-CD40L VK Domain Encoding Nucleotide Sequences

BMS2h-100
(SEQ ID NO: 1154)
GACATCCAGATGACCCAGTCTCCATCCTCCCTGTCTGCATCTGTAGGAGACCGTGTCACC
ATCACTTGCCGAGCAAGTCAGAATATTAAGCATTCGTTACGGTGGTACCAGCAGAAACCA
GGGAAAGCCCCTAGGCTCCTGATCTATCATCGTTCCCAGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGTTAGGCATCGTCCTTATACGTTCGGCCAA
GGGACCAAGGTGGAAATCAAACGG

BMS2h-101
(SEQ ID NO: 1155)
GACATCCAGATGACCCAGTCTCCATCCTCTCTGTCTGCATCTGTAGGAGACCGTGTCACC
ATCACTTGCCGGGCAAGTCAGGCTATTGGGCATCGGTTACGTTGGTATCAGCAGAAACCA
GGGAAAGCCCCTAAGCTCCTGATCTATCATCGGTCCAAGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGTTGCTTTGTTTCCCTATACGTTCGGCCAA
GGGACCAAGGTGGAAATCAAACGG

BMS2h-102
(SEQ ID NO: 1156)
GACATCCAGATGACCCAGTCTCCATCCTCCCTGTCTGCATCTGTAGGAGACCGTGTCACC
ATCACTTGCCGGGCAAGTCAGCATATTGGTCATCATTTAAGGTGGTACCAGCAGAAACCA
GGGAAAGCCCCCAAGCTCCTGATCTATCATAGGTCCCATTTGCAAAGTGGGGTCCCATCA
CGTTTCAGTGGCAGTGGATCTGGGACAGATTTCACTCTCACCATCAGCAGTCTGCAACCT
GAAGATTCTGCTACGTACTACTGTCAACAGTGGGATAGGCCGCCTTATACGTTCGGCCAA
GGGACCAAGGTGGAAATCAAACGG

BMS2h-103
(SEQ ID NO: 1157)
GACATCCAGATGACCCAGTCCCCATCCTCCCTGTCTGCATCTGTAGGAGACCGTGTCACC
ATCACTTGCCGGGCAAGTCAGGCTATTGGGCATCGGTTACGTTGGTATCAGCAGAAACCA
GGGAAAGCCCCTAAGCTCCTGATCTATCATCGGTCCAAGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGGTGCGGGCTGTGCCTTATACGTTTGGCCAA
GGGACCAAGGTGGAAATTAAACGG

BMS2h-104
(SEQ ID NO: 1156)
GACATCCAGATGACCCAGTCTCCATCCTCCCTGTCTGCATCTGTAGGAGACCGTGTCACC
ATCACTTGCCGGGCAAGTCAGGCTATTGGGCATCGGTTACGTTGGTATCAGCAGAAACCA
GGGAAAGCCCCTAAGCTCCTGATCTATCATCGGTCCAAGTTGCAAAGTGGGGTCCCATCA
CGTTTCAGTGGCAGTGGATCTGGGACAGATTTCACTCTCACCATCAGCAGTCTGCAACCT

TABLE 4-continued

Human Anti-CD40L VK Domain Encoding Nucleotide Sequences

GAAGATTTTGCTACGTACTACTGTCAACAGGTTCGTTTTTCTCCTTATACGTTCGGCCAA

GGGACCAAGGTGGAAATCAAACGG

BMS2h-105
(SEQ ID NO: 1159)
GACATCCAGATGACCCAGTCTCCATCCTCCCTGTCTGCATCTGTAGGAGACCGTGTCACC

ATCACTTGCCGGGCAAGTCAGGCTATTGGGCATCGGTTACGTTGGTATCAGCAGAAACCA

GGGAAAGCCCCTAAGCTCCTGATCTATCATCGGTCCAAGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGTCTTATGCTAGGCCTGTGACGTTCGGCCAA

GGGACCAAGGTGGAAATCAAACGG

BMS2h-106
(SEQ ID NO: 1160)
GACATCCAGATGACCCAGTCTCCATCCTCCCTGTCTGCATCTGTAGGAGACCGTGTCACC

ATCACTTGCCGGGCAAGTCAAAGTATTAATCATAGGTTATATTGGTACCAGCAGAAACCA

GGGAAAGCCCCTAAGCTCCTGATCTATCATCGGTCCAGGTTGCAAAGTGGGGTCCCATCA

CGTTTCAGTGGCAGTGGATCTGGGACAGATTTCACTCTCACCATCAGCAGTCTGCAACCT

GAGGATTTTGCTACGTACTACTGTCAACAGTATAAGGTTAGGCCTAATACGTTCGGCCAA

GGGACCAAGGTGGAAATCAAACGG

BMS2h-107
(SEQ ID NO: 1161)
GACATCCAGATGACCCAGTCTCCATCCTCCCTGTCTGCATCTGTAGGAGACCGTGTCACC

ATCACTTGCCGGGCAAGTCAGGCTATTGGGCATCGGTTACGTTGGTATCAGCAGAAACCA

GGGAAAGCCCCTAAGCTCCTGATTTATCATCGGTCCAAGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGACTTATTCGTCCTCATACGTTCGGCCAA

GGGACCAAGGTGGAAATCAAACGG

BMS2h-108
(SEQ ID NO: 1162)
GACATCCAGATGACCCAGTCTCCATCCTCCCTGTCTGCATCTGTAGGAGACCGTGTCACC

ATCACTTGCCGGGCAAGTCAGGCTATTGGGCATCGGTTACGTTGGTATCAGCAGAAACCA

GGGAAAGCCCCTAAGCTCCTGATCTATCATCGGTCCAAGTTGCAAAGTGGGGTCCCATCA

CGTTTCAGTGGCAGTGGATCTGGGACAGATTTCACTCTCACCATCAGCAGTCTACAACCT

GAAGATTTGCTACGTACTACTGTCAACAGAGGGCGGTGAGGCCTTTTACGTTCGGCCAA

GGGACCAAAGTGGAAATCAAACGG

BMS2h-109
(SEQ ID NO: 1163)
GACATCCAGATGACCCAGTCTCCATCCTCCCTGTCTGCATCTGTAGGAGACCGTGTCACC

ATCACTTGCCGGGCAAGTCAGGCTATTGGGCATCGGTTACGTTGGTATCAGCAGAAACCA

GGGAAAGCCCCTAAGGTCCTGATCTATCATCGGTCCAAGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGACTTATTATCGTCCTCTTACGTTCGGCCAA

GGGACCAAGGTGGAAATCAAACGG

TABLE 4-continued

Human Anti-CD40L VK Domain Encoding Nucleotide Sequences

BMS2h-110
(SEQ ID NO: 1164)
GACATCCAGATGACCCAGTCTCCAGCCTCCCTGTCTGCATCTGTAGGAGACCGTGTCACC

ATCACTTGCCGGGCAAGTCAGGATATTGATCCTATGTTAAGGTGGTACCAGCAGAAACCA

GGGAAAGCCCCTAAGCTCCTGATCTATGCGGGTTCCATTTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGACTAGTATTAGGCCTTATACGTTCGGCCAA

GGGACCAAGGTGGAAATCAAACGG

BMS2h-116
(SEQ ID NO: 1165)
GACATCCAGATGACCCAGTCTCCATCCTCCCTGTCTGCATCTGTAGGAGACCGTGTCACC

ATCACTTGCCGGGCAAGTCAGCCTATTGGTCCTGATTTACTGTGGTACCAGCAGAAACCA

GGGAAAGCCCCTAAGCTCCTGATCTATCAGACGTCCATTTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGTATTGGGCTTTTCCTGTGACGTTCGGCCAA

GGGACCAAGGTGGAAATCAAACGG

BMS2h-116-1
(SEQ ID NO: 1166)
GACATCCAGATGACCCAGTCTCCATCCTCCCTGTCTGCATCTGTAGGAGACCGTGTCACC

ATCACTTGCCGGGCAAGTCAGCCTATTGGTCCTGATATACTGTGGTACCAGCAGAAACCA

GGGAAAGCCCCTAAGCTCCTGATCTATCAGACGTCCATCTTGCAAAGTGGGGTCCCATCA

CGTTTCAGTGGCAGTGAATCTGGGACAGATTTCACTCTCACCATCAGCAGTCTGCAACCT

GAAGATTTTGCTACGTACTACTGTCAACAGTATTGGGCTTTTCCTGTGACGTTCGGCCAA

GGGACCAAGGTGGAAATCAAACGG

BMS2h-116-10
(SEQ ID NO: 1167)
GACATCCAGATAACCCAGTCTCCATCCTCCCTGTCTGCATCTGTAGGAGACCGTGTCACC

ATCACTTGCCGGGCAAGTCAGCCTATTGGTCCTGATTTACTGTGGTACCAGCAGAAACCA

GGGAAAGCCCCTAAGCTCCTGATCTATCAGACGTCCATATTGCGAAGTGGAGTCCCATCA

CGTTTCAGTGGCAGTGGGTCTGGGACAGATTTCACTCTCACCATCAGCAGTCTGCAACCT

GAAGATCTTGCTACGTACTACTGTCAACAGTATTGGGCTTTTCCTGTGACGTTCGGCCAA

GGGACCAAGGTGGAAATCAAACGG

BMS2h-116-11
(SEQ ID NO: 1168)
GACATCCAGATGACCCAGTCTCCATCCTCCCTGTCTGCATCTGTAGGAGACCGTGTCACC

ATCACTTGCCGGGCAAGTCAGCCTATTGGTCCTGATTTACTGTGGTACCAGCAGAAACCA

GGGAAAGCCCCTAAGCTTCTGATCTATCAGACGTCCATTTTGCGAAGTGGGGTCCCATCA

CGTTTCAGTGGCAGAGGATCTGGGACAGATTTCACTCTCACCATCAGCAGTCTGCAACCT

GAAGATTTTGCTACGTACTACTGTCAACAGTATTGGGCTTTTCCTGTGACGTTCGGCCAA

GGGACCAAGGTGGAAATCAAACGG

BMS2h-116-12
(SEQ ID NO: 1169)
GACATCCAGATGACCCAGTCTCCATCCTCCCTGTCTGCATCTGTAGGAGACCGTGTCACC

ATCACTTGCCGGGCAAGTCAACCTATTGGTCCTGATTTACTGTGGTACCAGCAGAAACCA

GGGAAAGCCCCTAAGCTCTTGATCTATCAGACGTCCATTTTGCGAAGTGGGGTCCCATCA

TABLE 4-continued

Human Anti-CD40L VK Domain Encoding Nucleotide Sequences

CGTTTCAGTGGCAGCGGATCTGGGACTGATTTCACTCTCACCATCAGCAGTCTGCAACCT

GAAGATTTTGCTACGTACTACTGTCAACAGTATTGGACTTTTCCTGTGACGTTCGGCCAA

GGGACCAAGGTGGAAATCAAACGG

BMS2h-116-13
(SEQ ID NO: 1170)
GACATCCAGATGACCCAGTCTCCATCCTCCCTGTCTGCATCTGTAGGAGACCGTGTCACC

ATCACTTGCCGGGCAAGTCAGCCTATTGGTCCTGATTTACTGTGGTACCAGCAGAAACCA

GGGAAAGCCCCTAAGCTCCTGATCTATCAGACGTCCATTTTGCGAAGTGGGGTCCCATCA

CGTTTCAGTGGCAGTGGATCTGAGACAGATTTCACTCTCACCATCAGCAATCTGCAACCT

GAAGATTTTGCTACGTACTACTGTCAACAGTATTGGCTTTTCCTGTGACGTTCGGCCAA

GGGACCAAGGTGGTAATCAAACGG

BMS2h-116-1312
(SEQ ID NO: 1171)
GACATCCAGATGACCCAGTCTCCATCCTCCCTGTCTGCATCTGTAGGAGACCGTGTCACC

ATCACTTGCCGGGCAAGTCAGCCTATTGGTCCTGATTTACTGTGGTACCAGCAGAAACCA

GGGAAAGCCCCTAAGCTCCTGATCTATCAGACGTCCATTTTGCGAAGTGGGGTCCCATCA

CGTTTCAGTGGCAGTGGATCTGAGACAGATTTCACTCTCACCATCAGCAATCTGCAACCT

GAAGATCTTGCTACGTACTACTGTCAACAGTATTGGCTTTTCCTGTGACGTTCGGCAAA

GGGACCAAGGTGGTAATCAAACGG

BMS2h-116-1313
(SEQ ID NO: 1172)
GACATCCAGATGACCCAGTCTCCATCCTCCCTGTCTGCATCTGTAGGAGACCGTGTCACC

ATCACTTGCCGGGCAAGTCAGCCTATTGGTCCTGATTTACTGTGGTACCAGCAGAAACCA

GGGAAAGCCCCTAAGCTCCTGATCTATCAGACGTCCATTTTGCGAAGTGGGGTCCCATCA

CGTTTCAGTGGCAGTGGATCTGAGACAGATTTCACTCTCACCATCAGCAATCTGCAACCT

GAAGATTTTGCTACGTACTACTGTCAACAGTATTGGCTTTTCCTGTGACGTTCGGCCGA

GGGACCAAGGTGGTAATCAAACGG

BMS2h-116-1314
(SEQ ID NO: 1173)
GACATCCAGATGACCCAGTCTCCATCCTCCCTGTCTGCATCTGTAGGAGACCGTGTCACC

ATCACTTGCCGAGCAAGTCAGCCTATTGGTCCTGATTTACTGTGGTACCGGCAGAAACCA

GGGAAAGCCCCTAAGCTCCTGATCTATCAGACGTCCATTTTGCGAAGTGGTGTCCCATCA

CGTTTCAGTGGCAGTGGATCTGAGACAGATTTCACTCTCACCATCAGCAATCTGCAACCT

GAAGATTTGCTACGTACTACTGTCAACAGTATTGGCTTTTCCTGTGACGTTCGGCCAA

GGGACCAAGGTGGTAATCAAACGG

BMS2h-116-1319
(SEQ ID NO: 1174)
GACATCCAGATGACCCAGTCTCCATCCTCCCTGTCTGCATCTGTAGGAGACCGTGTCACC

ATCACTTGCCGGGCAAGTCAGCCTATTGGTCCTGATTTACTGTGGTACCAGCAGAAACCA

GGGAAAGCCCCTAAGCTCCTGATCTATCAGACGTCCATTATGCGAAGTGGGGTCCCATCA

CGTTTCAGTGGCAGTGGATCTGAGACAGATTTCACTCTCACCATCAGCAATCTGCAACCT

GAAGATTTTGCTACGTACTACTGTCAACAGTATTGGACTTTTCCTGTGACGTTCGGCCAA

GGGACCAAGGTGGAAATCAAACGG

TABLE 4-continued

Human Anti-CD40L VK Domain Encoding Nucleotide Sequences

BMS2h-116-1320
(SEQ ID NO: 1175)
GACATCCAGATGACCCAGTCTCCATCCTCCCTGTCTGCATATGTAGGAGACCGTGTCACC

ATCACTTGCCGGGCAAGTCAGCCTATTGGTCCTGATTTACTTTGGTACCAGCAGAAACCA

GGGAAAGCCCCTAAGCTCCTGATCTATCAGACGTCCATTTTGCGAAGTGGGGTCCCATCA

CGTTTCAGTGGCAGTGGATCTGAGACAGATTTCACCCTCACCATCAGCAATCTGCAACCT

GAAGATTTTGCTAAGTACTACTGTCAACAGTATTGGGCTTTTCCTGTGACGTTCGGCCAA

GGGACCAAGGTGGAAATCAAACGG

BMS2h-116-138
(SEQ ID NO: 1176)
GACATCCAGATGACCCAGTCTCCATCCTCCCTGTCTGCATCTGTAGGAGACCGTGTCACC

ATCACTTGCCGGGCAAGTCAGCCTATTGGTCCTGATTTACTGTGGTACCAGCAGAAACCA

GGGAAAGCCCCTAAGCTCCTGATCTATCAGACGTCCATTTTGCGAAGTGGGGTCCCATCA

CGTTTCAGTGGCAGTGGATCTGAGACAGATTTCACTCTCACCATCAGCAATCTGCAACCT

GTAGATTTTGCTACGTACTACTGTCAACAGTATTGGGCTTTTCCTGTGACGTTCGGCCAA

GGGACCAAGGTGGAAATCAAACGG

BMS2h-116-14
(SEQ ID NO: 1177)
GACATCCAGATGACCCAGTCTCCATCCTCCCTGTCTGCATCTGTAGGAGACCGTGTCACC

ATCACTTGCCGGGCAAGTCAGCCTATTGGTCCTGATTTACTGTGGTTCCAGCAGAAACCA

GGGAAAGCCCCTAAGCTCCTGATCTATCAGACGTCCATTTTGCAAAGTGGGGTCCCATCA

CGTTTCAGTGGCAGTGAATCTGGGACAGATTTCACTCTCACCATCAGCAGTCTGCAACCT

GAAGATTTTGCTACGTACTACTGTCAACAGTATTGGGCTTTTCCTGTGACGTTCGGCCAA

GGGACCAAGGTGGAAATCAAACGG

BMS2h-116-15
(SEQ ID NO: 1178)
GACATCCAGATGACCCAGTCTCCATCCTCCCTGTCTGCATCTGTAGGAGACCGTGTCACC

ATCACTTGCCGGGCAAGTCAGCCTATCGGTCCTGATTTACTGTGGTACCGGCAGAAACCA

GGGAAAGCCCCTAAGCTCCTGATCTATCAGACGTCCATTTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGTATTGGACTTTTCCTGTGACGTTCGGCCAA

GGGACCAAGGTGGAAATCAAACGG

BMS2h-116-16
(SEQ ID NO: 1179)
GACATCCAGATGACCCAGTCTCCATCCTCCCTGTCTGCATCTGTAGGAGACCGTGTCACC

ATCACTTGCCGGGCAAGTCAGCCTATTGATCCTGACTTACTGTGGTACCAGCAGAAACCA

GGTAAAGCCCCTAAGCTCCTGATCTATCAGACGTCCATTTTGCAAAGTGGGGTCCCATCA

CGTTTCAGTGGCAGTGGATCTGGGACAGTTTTCACTCTCACCATCAGCAGTCTGCAACCT

GAAGATTTTGCTACGTACTACTGTCAACAGTATTGGGCATTTCCTGTGACGTTCGGCCAA

GGGACCAAGGTGGAAATCAAACGG

BMS2h-116-17
(SEQ ID NO: 1180)
GACATCCAGATGACCCAGTCTCCATCCTCCCTGTCTGCATCAGTAGGAGACCGTGTCACC

ATCACTTGCCGGGCAAGTCAGCCTATTGGTCCTGATTTACTGTGGTACCAGCAGAAGCCA

GGGAAAGCCCCTAAGCTCCTGATCTATCAGACGTCCATTTTGCGAAGTGGGGTCCCATCA

TABLE 4-continued

Human Anti-CD40L VK Domain Encoding Nucleotide Sequences

CGTTTCAGTGGCAGTGGATCTGGGACAGATTTCACTCTCACCATCAGCAGTCTGCAACCT

GAAGATTTTGCTACGTACTACTGTCAACAGTATTGGGCTTTTCCTGTGACGTTCGGCCAA

GGGACCAAGGTGGAAATCAAACGG

BMS2h-116-2
(SEQ ID NO: 1181)
GACATCCAGATGACCCAGTCTCCATCATCCCTGTCTGCATCTGTAGGAGACCGTGTCACC

ATCACTTGCCGGGCAAGTCAGCCTATTGAACCTGATTTACTGTGGTACCAGCAGAAACCA

GGGAAAGCCCCTAAGCTCCTGATCTATCAGACGTCCATTTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGTATTGGGCTTCTCCTGTGACGTTCGGCCAA

GGGACCAAGGTGGAAATCAAACGG

BMS2h-116-3
(SEQ ID NO: 1182)
GACATCCAGATGACCCAGTCACCATCCTCCCTGTCTGCATCTGTAGGAGACCGTGTCACC

ATCACTTGCCGGGCTAGTCAGCCTATTGGTCCTGATTTACTGTGGTACCAGCAGAAACCA

GGGAAAGCCCCTAAGCTCCTGATCTATCAGACGTCCATTTTGCAAAGTGGGGTCCCATCA

CGTTTCAGCGGCAGTGAATCCGGGACAGATTTCACTCTCACCATCAGCAGTCTGCAACCT

GAAGATATTGCAACGTACTACTGTCAACAGTATTGGGCTTTTCCTGTGACGTTCGGCCAA

GGGACCAGGGTGGAAATCAAACGG

BMS2h-116-4
(SEQ ID NO: 1183)
GACATCCAGATGACCCAGTCTCCATCCTCCCTGTCTGCATCTGTAGGAGACCGTGTCACC

ATCACTTGCCGGGCAAGTCAGCCTATTGGTCCTGATTTACTGTGGTACCAGCAGAAACCA

GGGAAAGCCCCTAAGCTCCTGATCTATCAGACGTCCATTTTGCAAAGTGGGGTCCCTTCA

CGTTTCAGTGGCAGTGAATCTGGGACAGATTTCACTCTCACCATCAGCAGTCTGCAACCT

GAAGATTTTGCTACGTACTACTGTCAACAGTATTGGGCTTTTCCTGTGACGTTCGGCCAA

GGGACCAAGGTGGAAATCAAACGG

BMS2h-116-5
(SEQ ID NO: 1184)
GACATCCAGATGACCCAGTCTCCATCCTCCCTGTCTGCATCTGTAGGAGACCGTGTCGCC

ATCACTTGCCGGGCAAGTCAGCCTATTGGTCCTGATATACTGTGGTACCAGCAGAAACCA

GGGAAAGCCCCTAAGCTCCTGATCTATCAGACGTCCATTTTGCGAAGTGGGGTCCCATCA

CGTTTCAGTGGCAGTGGATCTGGGACAGATTTCACTCTCACCATCAGCAGTCTGCAACCT

GAAGATTCTGCTACGTACTACTGTCAACAGTATTGGGCTTTTCCTGTGACGTTCGGTCAA

GGGACCAAGGTGGAAATCAAACGG

BMS2h-116-6
(SEQ ID NO: 1185)
GACATCCAGATGACCCAGTCTCCATCCTCCCTGTCTGCATCTGTAGGAGACCGTGTCACC

ATCACTTGCCGGGCAAGTCAGCCTATTGGTCCTGATTTACTGTGGTACCAGCAGAAACCA

GGGAAAGCCCCTAAGCTCCTGATCTATCAGACGTCCATTTTGCGAAGTGGGGTCCCGTCA

CGTTTCAGTGGCAGTGGATCTGTGACAGATTTCACTCTCACCATCAGCAGTCTGCAACCT

GAAGATTTTGCTACGTACTACTGTCAACAGTATTGGGCTTTTCCTGTGACGTTCGGCCAA

GGGACCAAGGTGGGAATCAAGCGG

TABLE 4-continued

Human Anti-CD40L VK Domain Encoding Nucleotide Sequences

BMS2h-116-7
(SEQ ID NO: 1136)
GACATCCAGATGACCCAGTCTCCATCCTCCCTGTCTGCATCTGTAGGAGACCGTGTCACC

ATCACTTGCCGGGCAAGTCAGCCTATTGATCCTGATTTACTGTGGTACCAGCAGAAACCA

GGGAAAGCCCCTAAGCTCCTGATCTATCAGACGTCCATTTTGCAAAGTGGGGTCCCATCA

CGTTTCAGTGGCAGTGGATCTAGGACAGATTTCACTCTCACCATCAGCAGTCTGCAACCT

GAAGATTTTGCTACGTACTACTGTCAACAGTATTGGGCTTTTCCTGTGACGTTCGGCCAA

GGGACCAAGGTGGAAATCAAACGG

BMS2h-116-8
(SEQ ID NO: 1187)
GACATCCAGATGACCCAGTCTCCATCCTCCCTGTCTGCATCTGTAGGAGACCGTGTCACC

ATCACTTGCCGGGCAAGTCAGCCTATTGGTCCTGATTTACTGTGGTACCAGCAGAAACCA

GGGAAAGCCCCTAAGCTCCTGATCTATCAGACGTCCATTTTGCAAAGTGGGGTCCCATCA

CGTTTCAGTGGCAGTGGATCTGGGACAGATTTCACTCTCACCATCAGCGGTCTGCAACCT

GAAGATTTTGCTACGTACTACTGTCAGCAGTATTGGGCTTTTCCTGTGACGTTCGGCCAA

GGGACCAAGGTGGAAATCAAACGG

BMS2h-116-9
(SEQ ID NO: 1188)
GACATCCAGATGACCCAGTCTCCATCCTCCCTGTCTGCATCTGTAGGAGACCGTGTCACC

ATCACTTGCCGGGCAAGTATGCCTATTGGTCCTGATTTACTGTGGTACCAGCAGAAACCA

GGGAAGGCCCCTAAGCTCCTGATCTATCAGACGTCCATTTTGCGAAGTGGGGTCCCATCA

CGTTTCAGTGGCAGTGAATCTGGGACAGATTTCACTCTCACCATCAGCAGTCTGCAACCT

GAAGATTTTGCTACGTACTACTGTCAACAGTATTGGGCTTTTCCTGTGACGTTCGGCCAA

GGGACCAAGGTGGAAATCAAACGG

BMS2h-141
(SEQ ID NO: 1189)
GACATCCAGATGACCCAGTCTCCATCCTCCCTGTCTGCATCTGTAGGAGACCGTGTCACC

ATCACTTGCCGGGCAAGTCAGTGGATTGGGGATACGTTAACGTGGTACCAGCAGAAACTA

GGGAAAGCCCCTAAGCTCCTGATCTATGGTGGTTCCGAGTTGCAAAGTGGGGTCCCACCA

CGTTTCAGTGGCAGTGGATCTGGGACAGATTTCACTCTCACCATCAGCAGTCTGCAACCT

GAAGATTTTGCTACGTACTACTGTCAACAGTGTATTAGTAGTCCTTGTACGTTCGGCCAA

GGGACCAAGGTGGTAAATCAAACGG

BMS2h-142
(SEQ ID NO: 1190)
GACATCCAGATGACCCAGTCTCCATCCTCCCTGTCTGCATCTGTAGGAGACCGTGTCACC

ATCACTTGCCGGGCAAGTCAGTTTATTGGTGATTCTTTATCTTGGTACCAGCAGAAACCA

GGGAAAGCCCCTAAGCTCCTGATCTATTTTTCTTCCATTTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGTATCATACTTCGCCTACTACGTTCGGCCGA

GGGACCAAGGTGAAAATCAAACGG

BMS2h-143
(SEQ ID NO: 1191)
GACATCCAGATGACCCAGTCTCCATCCTCCCTGTCCGCATCTGTAGGAGACCGTGTCACC

ATCACTTGCCGGGCAAGTCAGACTATTGAGACTAATTTAGAGTGGTACCAGCAGAAACCA

GGGAAAGCCCCTAAGCTCCTGATCTATGATTCTTCCCAGTTGCAAAGTGGGGTCCCATCA

TABLE 4-continued

Human Anti-CD40L VK Domain Encoding Nucleotide Sequences

CGTTTCAGTGGCAGTGGATCTGGGACAGATTTTACTCTCACCATCAGCAGTCTGCAACCT

GAAGATTTAGCTACGTACTACTGTCAACAGTATCATGGGTATCCTACGACGTTCGGCCAA

GGGACCAAGGTGGAAATCAAACGG

BMS2h-144 (SEQ ID NO: 1192)
GACATCCAGATGACCCAGTCTCCATCCTCCCTGTCTGCATCTGTAGGAGACCGTGTCACC

ATCACTTGCCGGGCAAGTCAGATGATTGATCAGGATTTAGAGTGGTACCAGCAGAAACCA

GGGAAAGCCCCTAAGCTCCTGATCTATAATGCGTCCTGGTTGCAAAGTGGGGTCCCATCA

CGTTTCAGCGGCAGTGGATCTGGGACAGATTTCACTCTCACCATCAGCAGTCTGCAACCT

GAAGATTTTGCTACGTACTACTGTCAACAGTATCATGGTTATCCTATTACGTTCGGCCAA

GGGACCAAGGTGGAAATCAAACGG

BMS2h-145 (SEQ ID NO: 1193)
GACATCCAGATGACCCAGTCTCCATCCTCCCTGTCTGCATCTGTAGGAGACCGTGTCACC

ATCACTTGCCGGGCAAGTCAGACGATTTATACTTCGTTAAGTTGGTATCAGCAGAAACCA

GGGAAAGCCCCTAAGCTCCTGATCCATTATGGTTCCGTGTTGCAAAGTGGGGTCCCATCA

CGTTTCAGTGGCAGTGGATCTGGGACAGATTTCACTCTCACCATCAGCAGTCTGCAACCT

GAAGATTCTGCTACGTACTACTGTCAACAGGTTCATCAGGCTCCTACGACGTTCGGCCAA

GGGACCAAGGTGGAAATCAAACGG

BMS2h-146 (SEQ ID NO: 1194)
GACATCCGGATGACCCAGTCTCCATCCTCCCTGTCTGCATCTGTAGGAGACCGTGTCACC

ATCACTTGCCGGGCAAGTCAGTGGATTGGGGATTCTTTAGCGTGGTACCAGCAGAAGCCA

GGGAAAGCCCCTAAGCTCCTGATCTATGGTATTTCCGAGTTGCAAAGTGGGGTCCCATCA

CGTTTCAGTGGCAGTGGATCTGGGACAGATTTCACTCTCACCATCAGCAGTCTGCAACCT

GAAGATTCTGCTACGTACTACTGTCAACTGTCTAGTAGTATGCCTCATACGTTCGGCCAA

GGGACCAAGGTGGAAATCAAACGG

BMS2h-147 (SEQ ID NO: 1195)
GACATCCAGATGACCCAGTCTCCATCCTCCCTGTCTGCATCTGTAGGAGACCGTGTCACC

ATCACTTGCCGGGCAAGTCAGGAGATTGAGACGAATTTAGAGTGGTACCAGCAGAAACCA

GGGAAAGCCCCTAAGCTCCTGATCTATGATTCGTCCCATTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGTATCATCAGAATCCTCCGACGTTCGGCCAA

GGAACCAAGGTGGAAATCAAACGG

BMS2h-149 (SEQ ID NO: 1196)
GACATCCAGATGACCCAGTCTCCATCCTCCCTGTCTGCATCTGTAGGAGACCGTGTCACC

ATCACTTGCCGGGCAAGTCAGTGGATTGGGAGGCAGTTAGTTTGGTACCAGCAGAAACCA

GGGAAAGCCCCTAAGCTCCTGATCTATGGGCGACCGAGTTGCAAAGTGGGGTCCCATCA

CGTTTTAGTGGCAGTGGATCTGGGACAGATTTCACTCTCACCATCAGCAGTCTGCAACCT

GAAGATTTTGCTACGTACTACTGTCAACAGCAGTCGAAGGGTCCTCTTACGTTCGGCCAT

GGGACCAAGGTGGAAATCAAACGG

TABLE 4-continued

Human Anti-CD40L VK Domain Encoding Nucleotide Sequences

BMS2h-150
(SEQ ID NO: 1197)
GACATCCAGATGACCCAGTCTCCATCCTCCCTGTCTGCATCTGTAGGAGACCGTGTCACC

ATCACTTGCCGGGCAAGTCAGGGGATTGGTACTGATTTAAATTGGTATCAGCAGAAACCA

GGGAAAGCCCCTAAGCTCCTGATCTATATGGGTTCCTATTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGATTTATTCTTTTCCTATTACGTTCGGCCAA

GGGACCAAGGTGGAAATCAAACGG

BMS2h-154
(SEQ ID NO: 1198)
GACATCCAGATGACCCAGTCTCCATCCTCCCTGTCTGCATCTGTAGGAGACCGTGTCACC

ATCACTTGCCGGGCAAGTCAGGATATTGAGGAGATGTTACATTGGTATCAGCAGAAACCA

GGGAAAGCCCCTAAGCTCCTGATCTATTTTGGTTCCCTGTTGCAAAGTGGGGTCCCATCA

CGTTTCAGTGGCAGTAGATCTGGGACAGATTTCACTCTCACCATCAGCAGTCTGCAACCT

GAAGATTTTGCTACGTACTACTGTCAACAGCATCATACTCGTCCTTATACGTTCGGCCAA

GGGACCAAGGTGGAAATCAAACGG

BMS2h-155
(SEQ ID NO: 1199)
GACATCCAGATGACCCAGTCTCCATCCTCCCTGTCTGCATCTGTAGGAGACCGTGTCACC

ATCACTTGCCGGGCAAGTCAGGATATTGGGATGGATTTAGAGTGGTACCAGCAGATACCA

GGGAAAGTCCCTAAGCTCCTGATCTATGATGCGTCCTATTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGTATCATAAGCTTCCTGCGACGTTTGGCCAA

GGGACCAAGGTGGAAATCAAACGG

BMS2h-156
(SEQ ID NO: 1200)
GACATCCAGATGACCCAGTCTCCATCCTCCCTGTCTGCATCTGTAGGAGACCGTGTCACC

ATCACTTGCCGGGCAAGTCAGGATATTATGGATAATTTAGAGTGGTATCAGCAGAAACCA

GGGAAAGCCCCTAAGCTCCTGATCTATGCGGCGTCCTGGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGTATCATAAGTTGCCTGTGACGTTCGGCCAA

GGGACCAAGGTGGAAATCAAACGG

BMS2h-157
(SEQ ID NO: 1201)
GACATCCAGATGACCCAGTCTCCATCCTCCCTGTCTGCATCTGTAGGAGACCGTGTCACC

ATCACTTGCCGAGCAAGTCAGAATATTGGGGAGGATTTAGAGTGGTACCAGCAGAAACCA

GGGAATGCCCCTAAGCTCCTGATCTATAGTGCGTCCCATTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGTATTCTAGTTATCCTGTTACGTTCGGCCAA

GGGACCAAGGTGGAAATCAAACGG

BMS2h-158
(SEQ ID NO: 1202)
GACATCCAGATGACCCAGTCTCCATCCTCCCTGTCTGCATCCGTAGGAGACCGTGTCACC

ATCACTTGCCGGGCAAGTCAGCCGATTGATGAGGATTTAGAGTGGTACCAGCAGAAACCA

GGGAATGCCCCTAAGCTCCTGATCTATAGTGCGTCCTATTTGCAAAGTGGGGTCCCATCA

TABLE 4-continued

Human Anti-CD40L VK Domain Encoding Nucleotide Sequences

CGTTTCAGTGGCAGTGGATCTGGGACAGATTTCACTCTCACCATCAGCAGACTGCAACCT

GAAGATTTTGCTACGTACTACTGTCAACAGTATCATCTTCTGCCTGCTACGTTCGGCCAA

GGGACCAAGGTGGAAATCAAACGG

BMS2h-159 (SEQ ID NO: 1203)
GACATCCAGATGATCCAGTCTCCATCCTCCCTGTCTGCATCTGTAGGAGACCGTGTCACC

ATCACTTGCCGGGCAAGTCAGGATATTAATGAGGATTTAGAGTGGTATCAGCAGAAACCA

GGGAAAGCCCTAAGCTCCTGATCTATAATGCTTCCATGTTGCAAAGCGGGGTCCCATCA

CGTTTCAGTGGCAGTGGATCTGGGACAGATTTCACTCTCACCATCAGCAGTCTGCAACCT

AAAGATTTTGCTACGTACTACTGTCAACAGTATCATACTAATCCTACTACGTTCGGCCAA

GGGACCAAGGTGGAAATCAAACGG

BMS2h-160 (SEQ ID NO: 1204)
GACATCCAGATGACCCAGTCTCCATCCTCCCTGTCTGCATCTGTAGGAGACCGTGTCACC

ATCACTTGCCGGGCAAGTCAGGATATTGAGGCGGATTTAGAGTGGTACCAGCAGAAACCA

GGGAAAGCCCCTAAGCTCCTGATCTATCATTCTTCCGAGTTGCAAAGTGGGGTCCCATCA

CGTTTCAGTGGAAGTGGATCTGGGACAGATTTCACTCTCACCATCAGCAGTCTGCAACCT

GAAGATTTTGCTACGTACTACTGTCAACAGTATCATATGTCGCCTGTGACGTTCGGCCAA

GGGACCAAGGTGGAAATCAAACGG

BMS2h-161 (SEQ ID NO: 1205)
GACATCCAGATGACCCAGTCTCCATCCTCCCTGTCTGCATCTGTAGGAGACCGTGTCACC

ATCACTTGCCGGGCAAGTCAGGATATTGATAGTGATTTAGAGTGGTACCAGCAGAAACCA

GGGAAAGCCCCTATGCTCCTGATCTATTCTTCGTCCGATTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGTATCATAGTCTGCCTGTTACGTTCGGCCAA

GGGACCAAGGTGGAAATCAAACGG

BMS2h-162 (SEQ ID NO: 1206)
GACATCCAGATGACCCAGTCTCCATCCTCCCTGTCTGCATCTGTAGGAGACCGTGTCACC

ATCACTTGCCGGGCAAGTCAGGATATTTCGGATGATTTAGAGTGGTACCAGCAGAAACCA

GGGAAAGCCCCTAAGCTCCTGATCTATAATTCGTCCTTTTTGCAAAGTGGGGTCCCATCA

CGTTTCAGTGGCAGTGGATCTGGGGCAGATTTCACTCTCACCATCAGCAGTCTGCAACCT

GAAGATTTTGCTACGTACTACTGTCAACAGTATCATAGTTTGCCTGTTACGTTCGGCCAA

GGGACCAAGGTGGAAATCAAACGG

BMS2h-163 (SEQ ID NO: 1207)
GACATCCAGATGACCCAGTCTCCATCCTCCCTGTCTGCATCTGTAGGAGACCGTGTCACC

ATCACTTGCCGGGCAAGTCAGGATATTGAGGGTAATTTAGAGTGGTACCAGCAGAAACCA

GGGAAAGCCCCTAAGCTCCTGATCTATGATTCGTCCCAGTTGCAAAGTGGGGTCCCATCA

CGTTTCAGTGGCAGTGGGTCTGGGACAGATTTCACTCTCACCATCAGCAGTCTGCAACCT

GAAGATTTTGCTACGTACTACTGTCAACAGTATCATCATCTTCCTACGACGTTCGGCCAA

GGGACCAAGGTGGAAATCAAACGG

TABLE 4-continued

Human Anti-CD40L VK Domain Encoding Nucleotide Sequences

BMS2h-164
(SEQ ID NO: 1208)
GACATCCAGATGACCCAGTCTCCATCCTCCCTGTCTGCATCTGTAGGAGACCGTGTCACC

ATCACTTGCCGGGCAAGTCAGAGTATTGATACGGATTTAGAGTGGTATCAGCAGAAACCA

GGGAAAGCCCCTAAGCTCCTGATCTATGATGGGTCCTGGTTGCAAAGTGGGGTCCCATCA

CGTTTCAGTGGCAGTGGATCTGGGACAGATTTTACTCTCACCATCAGCAGTCTGCAACCT

GAAGATTTTGCTACGTACTACTGTCAACAGTATCGGTGGATTCCTGTTACGTTCGGCCAA

GGGACCAAGGTGGAAATCAAACGG

BMS2h-165
(SEQ ID NO: 1209)
GACATCCAGATGACCCAGTCTCCATCCTCCCTGTCTGCATCTGTAGGAGACCGTGTCACC

ATCACTTGCCGGGCAAGTCAGAGTATTAGTACTGATTTAGAGTGGTACCAGCAGAAACTA

GGGAAAGCCCCTAAGCTCCTGATCTATGATGCTTCCCTTTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGTATTCGAGTCTGCCTGTTACGTTCGGCCAA

GGGACCAAGGTGGAAATCAAACGG

BMS2h-166
(SEQ ID NO: 1210)
GACATCCAGATGACCCAGTCTCCATCCTCCCTGTCTGCATCTGTAGGAGACCGTGTCACC

ATCACTTGCCGGGCAAGTCAGCCTATTACGACGTCTTTAGAGTGGTACCAGCAGAAACCA

GGGAAAGCCCCTAAGCTCCTGATCTATGATGCGTCCATGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGTATTGGGTTACGCCTGTTACGTTCGGCCAA

GGGACCAAGGTGGAAATCAAACGG

BMS2h-167
(SEQ ID NO: 1211)
GACATCCAGATGACCCAGTCTCCATCCTCCCTGTCTGCATCTGTAGGAGACCGTGTCACC

ATCACCTGCCGGGCAAGTCAGAATATTCATACGAATTTAGAGTGGTATCAGCAGAAACCA

GGGAAAGCCCCTAAGCTCCTGATCTATGATGGTTCCATGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGTATTCGGCTAATCCTGTTACGTTCGGCCAA

GGGACCAAGGTGGGAATCAAACGG

BMS2h-168
(SEQ ID NO: 1212)
GACATCCAGATGACCCAGTCTCCATCCTCCCTGTCTGCATCTGTAGGAGACCGTGTCACC

ATCACTTGCCGGGCAAGTCAGTGGATTCATACGGATTTAGAGTGGTATCAGCAGAAACCA

GGGAAAGCCCCTAAGCTCCTGATCTATGATGGTTCCATGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGTATAGTGTCGCCTGTTACGTTCGGCCAA

GGGACCAAGGTGGAAATCAAACGG

BMS2h-169
(SEQ ID NO: 1213)
GACATCCAGATGACCCAGTCTCCATCCTCCCTGTCTGCATCTGTAGGAGACCGTGTCACC

ATCACTTGCCGGGCAAGTCAGAGTATTGATAATAATTTAGAGTGGTACCAGCAGAAACCA

GGGGAAGCCCCTAAGCTCCTGATCTATGATGGGTCCCTTTTGCAAAGTGGGGTCCCATCA

TABLE 4-continued

Human Anti-CD40L VK Domain Encoding Nucleotide Sequences

CGTTTCAGTGGCAGTGGATCTGGGACAGATTTCACTCTTACCATCAGCAGTCTGCAACCT

GAAGATTTTGCTACGTACTACTGTCAACAGTATCATCTTCATCCTGTTACGTTCGGCCAA

GGGACCAAGGTGGAAATCAAACGG

BMS2h-170
(SEQ ID NO: 1214)
GACATCCAGATGACCCAGTCTCCATCCTCCCTGTCTGCATCTGTAGGAGACCGTGTCACC

ATCACTTGCCGGGCAAGTCAGGATATTGATACGAATTTAGAGTGGTATCAGCAGAAACCA

GGGGAAGCCCCTAAGCTCCTGATCTATGATCGTTCCACGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGTATGATTCTTATCCTGTGACGTTCGGCCAA

GGGACCAAGGTGGAAATCAAACGG

BMS2h-171
(SEQ ID NO: 1215)
GACATCCAGATGACCCAGTCTCCATCCTCCCTGTCTGCATCTGTAGGAGACCGTGTCACC

ATCACTTGCCGGGCAAGTCAGTCTATTGAGTCTAATTTAGAGTGGTACCAGCAGAAACCA

GGGAAAGCCCCTAAGCTCCTGATCTATAATGCGTCCGAGTTGCAAAGTGGGGTCCCATCA

CGTTTCAGTGGCAGTGGATCTGGGACAGATTTCACTCTCACCATCAGCAGTCTGCGACCT

GAAGATTTTGCTACGTACTACTGTCAACAGTATGATCAGTGGCCTACGACGTTCGGCCAA

GGGACCAAGGTGGAAATCAAACGG

BMS2h-172
(SEQ ID NO: 1216)
GACATCCAGATGACCCAGTCTCCATCCTCCCTGTCTGCATCTGTAGGAGACCGTGTCACT

ATCACTTGCCGGGCAAGTCAGGCTATTGGTAATACTTTACGGTGGTACCAGCAGAAACCA

GGGAAAGCCCCTAAGCTCCTGATCTATCTTAGTTCCAGGTTGCAAAGTGGGGTCCCATCA

CGTTTCAGTGGCAGTGGATCTGGGACAGATTTTACTCTCACCATCAGCAGTCTGCAACCT

GAAGATTTTGCTACGTACTACTGTCAACAGCTGAAGAAGCCTCCTTATACGTTCGGCCAA

GGGACCAAGGTGGAAATCAAACGG

BMS2h-173
(SEQ ID NO: 1217)
GACATCCAGATGACCCAGTCTCCATCCTCCCTGTCTGCATCTGTAGGAGACCGTGTCACC

ATCACTTGCCGGGCAAGTCAGAAGATTAAGAATCGGTTAGCGTGGTACCAGCAGAAACCA

GGGAAAGCCCCTAAGCTCCTGATCTATGAGGTTTCCCATTTGCAAAGTGGGGTCCCATCA

CGTTTCAGTGGCAGTGGATCTGGGACAGATTTCACTCTCACCATCGGCAGTCTGCAACCT

GAAGATTTTGCTACGTACTACTGTCAACAGAGGAGGCAGTCGCCTTATACGTTCGGCCAA

GGGACCAAGGTGGAAATCAAACGG

BMS2h-174
(SEQ ID NO: 1218)
GACATCCAGATGACCCAGTCTCCATCCTCCCTGTCTGCATCTGTAGGAGACCGTGTCACC

ATCACTTGCCGGGCAAGTGAGGATATTGGGGAGGAGTTATTTTGGTATCAGCAGAAACCA

GGGAAAGCCCCTAAGCTCCTGATCTATTCGGCGTCCACGTTGCAAAGTGAGGTCCCATCA

CGTTTCAGTGGCAGTGGATCTGGGACAGATTTCACTCTCACCATCAGCAGTCTGCAACAT

TABLE 4-continued

Human Anti-CD40L VK Domain Encoding Nucleotide Sequences

GAAGATTTTGCTACGTACTACTGTCAACAGGTTTATGAGTGGCCTTATACGTTCGGCCAA

GGGACCAAGGTGGAAATCAAACGG

BMS2h-175
(SEQ ID NO: 1219)
GACATCCAGATGACCCAGTCTCCATCCTCCCTGTCTGCATCTGTAGGAGACCGTGTCACC

ATCACTTGCCGGGCAAGTCAGCCTATTTCTGGGGGTTTAAGGTGGTACCAGCAGAAACCA

GGGAAAGCCCCTAAGCTCCTGATCTATTCTACTTCCATGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGCTTTATTCTGCTCCTTATACGTTCGGCCAA

GGGACCAAGGTGGAAATCAAACGG

BMS2h-305
(SEQ ID NO: 1220)
GACATCCAGATGACCCAGTCTCCATCCTCCCTGTCTGCATCTGTAGGAGACCGTGTCACC

ATCACTTGCCGGGCAAGTCAGGATATTGATCAGGATTTAGAGTGGTACCAGCAGAAACCA

GGGAAAGCCCCTAAGCTCCTGATCTATAATGTTTCCCTGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGTATTCTATGAATCCTGTTACGTTCGGCCAA

GGGACCAAGGTGGAAATCAAACGG

BMS2h-306
(SEQ ID NO: 1221)
GACATCCAGATGACCCAGTCTCCATCCTCCCTGTCTGCATCTGTAGGAGACCGTGTCACC

ATCACTTGCCGGGCAAGTCAGGATATTGGGAATCAGTTAAAGTGGTACCAGCAGAAACCA

GGGAAAGCCCCTAAGCTCCTGATCTATCAGGCTTCCGGGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGTATGATTTGAGGCCTCAGACGTTCGGCCAA

GGGACCAAGGTGGAAATCAAACGG

BMS2h-307
(SEQ ID NO: 1222)
GACATCCAGATGACCCAGTCTCCATCCTTCCTGTGTGCATCTGTAGGTGACCGTGTCACC

ATCACTTGCCGGGCGAGTCAGAAGATTTCTACGTCTTTAGAGTGGTATCAGCAGAAACCA

GGGAAAGCCCCTAGGCTCCTGATCTATGATTCTTCCTGGTTGCAAAGTGGGGTCCCATCA

CGTTTCAGTGGCAGTGGATCTGGGACAGATTTCACTCTCACCATTAGCAGTCTGCAACCT

GAAGATTTGCTACGTACTACTGTCAACAGTATGAGTATAATCCTATTACGTTCGGCCAA

GGGACCAAGGTGGAAATCAAACGG

BMS2h-33
(SEQ ID NO: 1223)
GACATCCAGATGACCCAGTCTCCATCCTCCCTGTCTGCATCTGTAGGAGACCGTGTCACC

ATCACTTGCCGGGCAAGTCAGACGATTGGGGAGAGTTTACATTGGTACCAGCAGAAACCA

GGGAAAGCCCCTAGGCTCCTGATCTATTTTGCTTCCCTGTTGCAAAGTGGGGTCCCATCG

CGTTTCAGTGGCAGTGGATCTGGGACAGATTTTACTCTCACCATCAGCAGTCTGCAACCT

GAAGATTTTGCTACGTACTACTGTCAACAGCATCATATGCTTCCTTCTACGTTCGGCCAA

GGGACCAAGGTGGAAATCAAACGG

TABLE 4-continued

Human Anti-CD40L VK Domain Encoding Nucleotide Sequences

BMS2h-35
(SEQ ID NO: 1224)
GACATCCAAATGACCCAGTCTCCATCCTCCCTGTCTGCATCTGTAGGAGACCGTGTCACC

ATCACTTGCCGGGCAAGTCAGTTTATTGGTGATTCTTTATCTTGGTACCAGCAGAAACCA

GGGAAAGCCCCTAAGCTCCTGATCTATTTTTCTTCCATTTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGTATATGGATATTCCTATTACGTTCGGCCAA

GGGACCAAGGTGGAAATCAAACGG

BMS2h-36
(SEQ ID NO: 1225)
GACATCCAGATGACCCAGTCTCCATCCTCCCTGTCTGCATCTGTAGGAGACCGTGTCACC

ATCACTTGCCGGGCAAGTCAGGATATTGATCATAATTTAGAGTGGTATCAGCAGAAACCA

GGGAAAGCCCCTAAGCTCCTGATCTATGATAGTTCCATGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGTATCATTCTATTCCTGTTACGTTCGGCCAA

GGGACCAAGGTGGAAATCAAACGG

BMS2h-37
(SEQ ID NO: 1226)
GACATCCAGATGACCCAGTCTCCATCCTCCCTGTCTGCATCTGTAGGAGACCGTGTCACC

ATCACTTGCCGGGCAAGTCAGCAGATTGAGACGAATTTAGAGTGGTATCAGCAGAAACCA

GGGAAAGCCCCTAAGCTCCTGATCTATGATGGTTCGTGGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGTATCATAGTTTGCCTGCTACGTTCGGCCAA

GGGACCAAGGTGGAAATCAAACGG

BMS2h-38
(SEQ ID NO: 1227)
GACATCCAGATGACCCAGTCTCCATCCTCCCTGTCTSCATCTGTAGGAGACCGTGTCACC

ATCACTTGCCGGGCAAGTCAGGATATTGGTAATAATTTAGAGTGGTACCAGCAGAAACCA

GGGAAAGCCCCTAGGCTCCTGATCTATCATGGGTCCTGGTTGCAAAGTGGGGTCCCATCG

CGTTTCAGTGGCAGTGGATCTGGGACAGATTTCACTCTTACCATCAGCAGTCTGCAACCT

GAAGATTTTGCTACGTACTACTGTCAACAGTATGATTTTAATCCTACTACGTTCGGCCAA

GGGACCAAGGTGGAAATCAAACGG

BMS2h-39
(SEQ ID NO: 1228)
GACATCCAGATGACCCAGTCTCCATCCTCCCTGTCTGCATCTGTAGGAGACTGTGTCACC

ATCACTTGCCGGGCAAGTCAGAATATTGATGGTCTGTTATGGTGGTATCAGCAGAAACCA

GGGAAAGCCCCTAAGCTCCTGATCTATGCGGGGTCCGGGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGAAGGCTTTTGAGCCTTTTACGTTCGGCCAA

GGGACCAAGGTGGAAATCAAACGG

BMS2h-405
(SEQ ID NO: 1229)
GACATCCAGATGACCCAGACTCCATCCTCCCTGTCTGCATCTGTAGGAGACCGTGTCACC

ATCACTTGCCGGGCAAGTCAGAGTATTGGTCATGATTTAGAGTGGTACCAGCAGAAACCA

GGGAAAGCCCCTAAGCTCCTGATCTATAATGTGTCCTGGTTGCAAAGTGGGGTCCCATCA

TABLE 4-continued

Human Anti-CD40L VK Domain Encoding Nucleotide Sequences

CGTTTCAGTGGCAGTGGATCTGGGACAGATTTTACTCTCACCATCAGCAGTCTGCAACCT

GAAGATTTTGCTACGTACTACTGTCAACAGTATAGTCATAATCCTCCTACGTTCGGCCAA

GGGACCAAGGTGGAAATCAAACGG

BMS2h-406 (SEQ ID NO: 1230)
GACATCCAGATGACCCAGTCTCCATCCTCCCTGTCTGCATCTGTAGGAGACCGTGTCACT

ATCACTTGCCGGGCAAGTCAGCATATTGAGAATGATTTAGAGTGGTACCAGCAGAAACCA

GGGAAAGCCCCTAAGCTCCTGATCTATTCTGCTTCCCATTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGTATCATCTTCAGCCTACGACGTTCGGCCCA

GGGACCAAGGTGGAAATCAAACGG

BMS2h-431 (SEQ ID NO: 1231)
GACATCCAGATGACCCAGTCTCCATCCTCCCTGTCTGCATCTGTAGGAGACCGTGTCACT

ATCACTTGCCGGGCAAGTCAGGTTATTGAGGGTAGTTTAAATTGGTACCAGCAGAAACCA

GGGAAAGCCCCTAAGCTCCTGATCTATCATAGGTCCATTTTGCAAAGTGGGGTCCCATCA

CGTTTCAGTGGCCGTGGATCTGGGACAGATTTCACTCTCACCATCAGCAGTCTGCAACCT

GAAGATTTTGCTACGTACTACTGTCAACAGACTTATCAGCTTCCTTTGACGTTCGGCCAA

GGGACCAAGGTGGAAATCAAACGG

BMS2h-432 (SEQ ID NO: 1232)
GACATCCAGATGACCCAGTCTCCATCCTCCCTGTCTGCATCTGTAGGAGACCGTGTCACC

ATCACTTGCCGGGCAAGTCGTCCTATTAATGGTAAGTTATTTTGGTACCAGCAGAAACCA

GGCAAAGCCCCTAAGCTCCTGATCGCGTTTGCTTCCGCTTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGTGCAGCAGGCTGTGTATCCTATTACGTTCGGCCAA

GGGACCAAGGTGGAAATCAAACGG

BMS2h-433 (SEQ ID NO: 1233)
GACATCCAGATGACCCAGTCTCCATCCTCCCTGTCTGCATCTGTAGGAGACCGTGTCACC

ATCACTTGCCGGGCAAGTCAGGCTATTGAGACGAATTTAGAGTGGTATCAGCAGAAACCA

GGGAAAGCCCCTAAGCTCCTGATCTATGATGGGTCCCTTTTGCAAAGTGGGGTCCCATCA

CGTTTCAGTGGCAGAGGATCTGGGACAGATTTCACTCTCACCATCAGCAGTCTGCAACCT

GAAGATTTTGCTACGTACTACTGTCAACAGTATCATTATCAGCCTGCGACGTTCGGCCPA

GGGACCAAGGTGGAAATCAAACGG

BMS2h-434 (SEQ ID NO: 1234)
GACATCCAGATGACCCAGTCTCCATCCTCCCTGTCTGCATCTGTAGGAGACCGTGTCACC

ATCACTTGCCGGGCAAGTCAGGATATTGAGCATGATTTAGAGTGGTACCAGCAGAAACCA

GGGAAAGCCCCTAAGCTCCTGATCTATCGGCGTCCCAGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGTATCAGCAGCAGCCTACTACGTTCGGCCAA

GGGACCAAGGTGGAAATCAAACGG

TABLE 4-continued

Human Anti-CD40L VK Domain Encoding Nucleotide Sequences

BMS2h-435 (SEQ ID NO: 1235)
GACATCCAGATGACCCAGTCTCCATCCTCCCTGTCTGCATCTGTAGGAGACCGTGTCACC
ATCACTTGCCGGGCAAGTTCGCAGATTGAGGAGTCTTTATGGTGGTACCAGCAGAAACCA
GGGAAAGCCCCTAAGCTCCTGATCGCGGATGTTTCCCTGTTGCAAAGTGGAGTCCCATCA
CGTTTCAGTGGCAGTGGATCTGGGACAGATTTCACTCTCACCATCAGCAGTCTGCAACCT
GAAGATTTTGCTACGTACTACTGTGCTCAGGGTGTGGTGGAGCCTCGTACGTTCGGCCAA
GGGACCAAGGTGGAAATCAAACGG

BMS2h-436 (SEQ ID NO: 1236)
GACATCCAGATGACCCAGTCTCCATCCTCCCTGTCTGCATCTGTAGGAGACCGTGTCACC
ATCACTTGCCGGGCAAGTCAGTATATTGGTCTGGATTTAGAGTGGTATCAGCAGAAACCA
GGGAAAGCCCCTAAGCTCCTGATCTATGCTGCTTCCTGGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTCAACAGTATTTTCGGCAGCCTATTACGTTCGGCCAA
GGGACCAAGGTGGAAATCAAACGG

BMS2h-437 (SEQ ID NO: 1237)
GACATCCAGATGACCCAGTCTCCATCCTCCCTGTCTGCATCTGTAGGAGACCGTGTCACC
ATCACTTGCCGGGCAAGTACGCCGATTGGTACTATGTTAGATTGGTACCAGCAGAAACCA
GGGAAAGCCCCTAAGCTCCTGATCGGGCATTCGTCCTGGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGGCAGCATGTGCGTCCTCCTGCGACGTTCGGCCAA
GGGACCAAGGTGGAAATCAAACGG

BMS2h-437-1 (SEQ ID NO: 1238)
GACATCCAGTTGACCCAGTCTCCAACCTCCCTGTCTGCAACTGTAGGAGACCGTGTCACC
ATCACTTGCCGGGCAAGTACGCCGATTGGTACTATGTTAGATTGGTACCAGCAGAAACCT
GGGAAAGCCCCTAAGCTCCTGATCGGGCATTCGTCCTGGTTGCAAAGTGGGGTCCCATCA
CGTTTCAGTGGCAGTGGATCTGGGACTGATTTCACTCTCACCATCAGCAGTCTGCAACCT
GAAGATTTTGCTACGTACTACTGTGGGCAGCATGTGCGTCATCCTGCGACGTTCGGCCAA
GGGACCAAGGTGGAAATCAAGCGG

BMS2h-437-2 (SEQ ID NO: 1239)
GACATCCAGATGACCCAGTCTCCATCCTCCCTGTCTGCATCTGTAGGAGACCGTGTCACC
ATCACTTGCCGGGCAAGTACGCCGATTGGTACTATGTTAGATTGGTACCAGCAGAAACCA
GGGAAAGCCCCTAAGCTCCTGATCGGGCATTCGTCCTGGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGGACAGCATGTGCGTCCTCCTGCGACGTTCGGCCAA
GGGACCAAGGTGGGAATCAAACGG

BMS2h-437-3 (SEQ ID NO: 1240)
GACATCCAGATGACCCAGTCTCCGTCCTCCCTGTCTGCATCTGTAGGAGACCGTGTCACC
ATCACTTGCCGGGTAAGTACGCCGATTGGTACTATGTTAGATTGGTACCAGCAGAAACCA
GGGAAAGCCCCTAAGCTCCTGATCGGGCATTCGTCCTGGTTGCAAAGTGGGGTCCCACCA

TABLE 4-continued

Human Anti-CD40L VK Domain Encoding Nucleotide Sequences

CGTTTCAGTGGCAGCGGATCTGGGACAGATTTCACTCTCACCATCAGCAGTCTGCAACCT

GAAGATTTTGCTACGTACTACTGTGGGCAGCATGTGCGTCCTCCTGCGACGTTCGGCCAA

GGGACCAAGGTGGAAATCAAACGG

BMS2h-437-4
(SEQ ID NO: 1241)
GACATCCAGATGACCCAGTCTCCATCCTCCCTGTCTGCATCTGTAGGAGACCGTGTCACC

ATCACTTGCCGGGCAAGTACGCCGATTGGTACTATGTTAGATTGGTACCAGCAGAAACCA

GGGAAAGCCCCTAAGCTCCTGATCGGGCATTCGTCCTGGTTGCAAAGTGGGGTCCCATCA

CGTTTCAGTGGCTGTGGATCTGGGACAGATTTCACTCTCACCATCAGCAGTCTGCAACCT

GAAGATTTTGCTACGTACTACTGTGGGCAGCATGTGCGTCCTCCTGCGACGTTCGGCCAA

GGGACCAAGGTGGAAATCAAACGG

BMS2h-437-5
(SEQ ID NO: 1242)
GACATCCAGATGACCCAGTCTCCATCCTCCCTGTCTGCATCTGTAGGAGACCGTGTCACC

ATCACTTGCCGGGCAAGTACGCCGATTGGTACTATGATAGATTGGTACCAGCAGAAACCA

GGGAAAGCCCCTAAGCTCCTGATCGGGCATTCGTCCTGGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGGGCAGCATGTGCGTCCTCCTGCGACGTTCGGCAAA

GGGACCAAGGTGGAAATCAAACGG

BMS2h-438
(SEQ ID NO: 1243)
GACATCCAGATGACCCAGTCTCCATCCTCCCTGTCTGCATCTGTAGGAGACCGTGTCACC

ATCACATGCCGGGCAAGTCAGTATATTGATACTAATTTAGAGTGGTACCAGCAGAAACCA

GGGAAAGCCCCTAGGCTCCTGATCTATGATGGTTCCCAGTTGCAAAGTGGGGTCCCATCA

CGTTTCAGTGGCAGTGGATCTGGGACAGATTTCACTCTCATCATCAGCAGTCTGCAACCT

GAAGATTTTGCTACGTACTACTGTCAACAGTATCAGGTTGTGCCTGTTACGTTCGGCCAA

GGGACCAAGGTGGAAATCAAACGG

BMS2h-439
(SEQ ID NO: 1244)
GACATCCAGATGACCCAGTCTCCATCCTCCCTGTCTGCATCTGTAGGAGACCGTGTCACC

ATCACTTGCCGGGCAAGTCAGAGCATTAGCAGCTATTTAAATTGGTACCAGCAGAAACCA

GGGAAAGCCCCTAGGCTCCTGATCGTGGATTCTTCCGGGTTGCAAAGTGGGGTCCCATCA

CGTTTCAGTGGCAGTGGATCTGGGACAGATTTCACTCTCACCATCAGCAGTCTGCAACCT

GAAGATTTGCTACGTACTACTGTGGTCAGGATCGTTGGTCTCCTGCTACGTTCGGCCAA

GGGACCAAGGTGGAAATCAAACGG

BMS2h-440
(SEQ ID NO: 1245)
GACATCCAGATGACCCAGTCTCCATCCTCCCTGTCTGCATCTGTAGGAGACCGTGTCACC

ATCACTTGCCGGGCAAGTTCGCGGATTCAGCATATGTTATCTTGGTACCAGCAGAAACCA

GGGAAAGCCCCTAAGCTCCTGATCGGTGGGCATTCCGGGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGCGCAATCGTGTGCGTGGCCTCTGACGTTCGGCCAA

GGGACCAAGGTGGAAATCAAACGG

TABLE 4-continued

Human Anti-CD40L VK Domain Encoding Nucleotide Sequences

BMS2h-441
(SEQ ID NO: 1246)
GACATCCAGATGACCCAGTCTCCATCCTCCCTGTCTGCATCTGTAGGAGACCGTGTCACC

ATCACTTGCCGGGCAAGTAGGGGTATTGATGGTGATTTATGGTGGTACCAGCAGAAACCA

GGGAAAGCCCCTAAGCTCCTGATCGCGGATTCTTCCCTGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGGGCAGGGGCTGTTCGGCCTATGACGTTCGGCCAA

GGGACCAAGGTGGAAATCAAACGG

BMS2h-442
(SEQ ID NO: 1247)
GACATCCAGATGACCCAGTCTCCATCCTCCCTGTCTGCATCTGTAGGAGACCGTGTCACC

ATCACTTGCCGGGCAAGTAGGGGTATTGATACTGATTTATGGTGGTACCAGCAGAAACCA

GGGAAAGCCCCTAAGCTCCTGATCGCGGATTCTTCCCTGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGGGCAGGGGCTGTTCGGCCTATGACGTTCGGCCAA

GGGACCAAGGTGGAAATCAAACGG

BMS2h-443
(SEQ ID NO: 1248)
GACATCCAGATGACCCAGTCTCCATCCTCCCTGTCTGCATCTGTAGGAGACCGTGTCACC

ATCACTTGCCGGGCAAGTTATACTATTCCGGTTGCTTTAGATTGGTACCAGCAGAAACCA

GGGAAAGCCCCTAAGCTCCTGATCGCTGATGCGTCCTTGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGCGCAGGGTTGGCCGGGGCCTCAGACGTTCGGCCAA

GGGACCAAGGTGGAAATCAAACGG

BMS2h-444
(SEQ ID NO: 1249)
GACATCCAGATGACCCAGTCTCCATCCTCCCTGTCTGCATCTGTAGGAGACCGTGTCACC

ATCACTTGCCGGGCAAGTCAGAGTATTGCGACGGACTTAGAGTGGTATCAGCAGAAACCA

GGGAAAGCCCCTAAGCTCCTGATCTATGATACTTCCATGTTGCAAAGCGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGTATAGTTATAATCCTTCGACGTTCGGCCAA

GGGACCAAGGTGGAAATCAAACGG

BMS2h-445
(SEQ ID NO: 1250)
GACATCCAGATGACCCAGTCTCCATCCTCCCTGTCTGCATCTGTAGGAGACCGTGTCACC

ATCACTTGCCGGGCAAGTGTGCCTATTACTGAGGGTTTATCGTGGTACCAGCAGAAACCA

GGGAAAGCCCCTAAGCTCCTGATCCAGGCTAATTCCTGGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGGGCAGTGGGAGCATGTTCCTGCGACGTTCGGCCAA

GGGACCAAGGTGGAAATCAAACGG

BMS2h-446
(SEQ ID NO: 1251)
GACATCCAGATGACCCAGTCTCCATCCTCCCTGTCTGCATCTGTAGGAGACCGTGTCACC

ATCACTTGCCGGGCAAGTAGTATGATTCTTTATGGTTTAGATTGGTACCAGCAGAAACCA

GGGAAAGCCCCTAAGCTCCTGATCGGTGGTACTTCCGCGTTGCAAAGTGGGGTCCCATCA

TABLE 4-continued

Human Anti-CD40L VK Domain Encoding Nucleotide Sequences

CGTTTCAGTGGCAGTGGATCTGGGACAGATTTCACTCTCACCATCAGCAGTCTGCAACCT

GAAGATTTTGCTACGTACTACTGTGGGCAGTGGGAGACGGTTCCTGCTACGTTCGGCCAA

GGGACCAAGGTGGAAATCAAACGG

BMS2h-447 (SEQ ID NO: 1252)
GACATCCAGATGACCCAGTCTCCATCCTCCCTGTCTGCATCTGTAGGAGACCGTGTCACC

ATCACTTGCCGGGCAAGTCAGCCTATTAATGGGCTTTTAATTTGGTATCAGCAGAAACCA

GGGAAAGCCCCTAAGCTCCTGATCTATGCGATGTCCAGTTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGTTGGCTCGGATTCCTTTTACGTTCGGCCAA

GGGACCAAGGTGGAATCAAACGG

BMS2h-448 (SEQ ID NO: 1253)
GACATCCAGATGACCCAGTCTCCATCCTCCCTGTCTGCATCTGTAGGAGACCGTGTCACC

ATCACTTGCCGAGCAAGTCAGCTGATTCGGACTTATTTAGCGTGGTACCAGCAGAAACCA

GGGAAAGCCCCTAAGCTCCTGATCTATCAGTCTTCTCAGTTGCAAAGTGGTGTCCCATCA

CGTTTCAGTGGCAGTGGATCTGGGACAGATTTCACTCTCACCATCAGCAGTCTGCAACCT

GAAGATTTTGCTACGTACTACTGTCAACAGTATAATTCTTATCCTGATACGTTCGGCCAA

GGGACCAAGGTGGAAATCAAACGG

BMS2h-47 (SEQ ID NO: 1254)
GACATCCAGATGACCCAGTCTCCATCCTCCCTGTCTGCATCTGTAGGAGACCGTGTCACC

ATCACTTGCCGGGCAAGTCAGTGGATTGGGGATTCGTTAAGTTGGTACCAGCAGAAACCA

GGGAAAGCCCCTAAGCTCCTGATCTATTTTGGTTCCTATTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGTATTTGCATACTCCTTCGACGTTCGGCCAA

GGGACCAAGGTGGAAATCAAACGG

BMS2h-484 (SEQ ID NO: 1255)
GACATCCAGATGACCCAGTCTCCATCCTCCCTGTCTGCATCTGTAGGAGACCGTGTCACC

ATCACTTGCCGGGCAAGTCAGGATATTGAGGCGGATTTAGAGTGGTACCAGCAGAAACCA

GGGAAAGCCCCTAAGCTCCTGATCTATCATTCTTCCGAGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGTATGGTTTTAATCCTCCTACGTTCGGCCAA

GGGACCAAGGTGGAAATCAAACGG

BMS2h-485 (SEQ ID NO: 1256)
GACATCCAGATGACCCAGTCTCCATCCTCCCTGTCTGCATCTGTAGGAGACCGTGTCACC

ATCACTTGCCGGGCAAGTTCTCCTATTGAGTATGGTTTAGATTGGTACCAGCAGAAACCA

GGGAAAGCCCCTAAGCTCCTGATCGGGGGGGGTCCGCGTTGCAAAGTGGGGTCCCATCA

CGTTTCAGTGGCAGTGGATCTGGGACAGATTTCACTCTCACCATCAGCAGTCTGCAACCT

GAAGATTTAACTACGTACTACTGTGGGCAGTGGGAGGTTCAGCCTGCTACGTTCGGCCAA

GGGACCAAGGTGGAAATCAAACGG

TABLE 4-continued

Human Anti-CD40L VK Domain Encoding Nucleotide Sequences

BMS2h-486
(SEQ ID NO: 1257)
GACATCCAGATGACCCAGTCTCCATCCTCCCTGTCTGCATCTGTAGGAGACCGTGTCACC

ATCACTTGCCGGGCAAGTCAGCGGATTGATACTGATTTAGAGTGGTACCAGCAGAAACCA

GGGAAAGCCCCTAAGCTCCTGATCTATGATAGTTCACAGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGTATCATAGTGCGCCTGCGACGTTCGGCCAA

GGGACCAAGGTGGAAATCAAACGG

BMS2h-457
(SEQ ID NO: 1258)
GACATCCAGATGACCCAGTCTCCATCCTCCCTGTCTGCATCTGTAGGAGACCGTGTCACC

ATCACTTGCCGGGCAAGTGGGTGGATTGGTATGTCTTTAGAGTGGCACCAGGAGAAACCA

GGGAAAGCCCCTAAGCTCCTGATCCGTGGGGCTTCCTCTTTGCAAAGTGGGGTCCCATCA

CGTTTCAGTGGCAGTGGATCTGGGACAGATTTCACTCTCACCATCAGCAGTCTGCCACCT

GAAGATTTTGCTACGTACTACTGTAGTCAGTCTCGGTGGCCGCCTGTGACGTTCGGCCAA

GGGACCAAGGTGGAAATCAAACGG

BMS2h-488
(SEQ ID NO: 1259)
GACATCCAGATGACCCAGTCTCCATCCTCCCTGTCTGCATCTGTAGGAGACCGTGTCACC

ATCACTTGCCGGGCAAGTCGTAATATTTCGAATGOTTTATCGTGGTACCAGCAGAAACCA

GGGAAAGCCCCTAAGCTCCTGATCCTTGGGGCTTCCTGGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTACTCAGGTGTGGGATAGGCCTTTTACGTTCGGCCAA

GGGACCAAGGTGGAAATCAAACGG

BMS2h-489
(SEQ ID NO: 1260)
GACATCCAGATGACCCAGTCTCCATCCTCCCTGTCTGCATCTGTAGGAGACCGTGTCACC

ATCACTTGCCGGGCAAGTCAGGATATTATGTCGGCTTTATCTTGGTATCAGCAGAAACCA

GGGAAAGCCCCTAAGCTCCTGATCTATTCTACTTCCATTTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGGTTTATTTGCTGCCTGTTACGTTCGGCCAA

GGGACCAAGGTGGAAATCAAACGG

BMS2h-490
(SEQ ID NO: 1261)
GACATCCAGATGACCCAGTCTCCATCCTCCCTGTCTGCATCTGTAGGAGACCGTGTCACC

ATCACTTGCCGGGCAAGTCAGGAGATTGGGATTGATTTAGAGTGGTATCAGCAGAAACCA

GGGAAAGCCCCTAAGCTCCTGATCTATGCTGCTTCTTATTTGCAAAGTGGGGTCCCATCA

CGTTTCAGTAGCAGTGGATCTGGGACAGATTTCACTCTCACCATCAGCAGTCTGCAACCT

GAAGATTTTGCTACGTACTACTGTCAACAGTATGCTTCTAATCCTCCTACGTTCGGCCGA

GGGACCAAGGTGGAAATCAAACGG

BMS2h-491
(SEQ ID NO: 1262)
GACATCCAGATGACCCAGTCTCCATCCTCCCTGTCTGCATCTGTAGGAGACCGTGTCACC

ATCACTTGCCGGGCAAGTCAGATGATTGGGGATTGGTTAAATTGGTACCAGCAGAAACCA

GGGAAAGCCCCTAAACTCCTGATCTATCGTAGTTCCGAGTTGCAAAGTGGGGTCCCATCA

TABLE 4-continued

Human Anti-CD40L VK Domain Encoding Nucleotide Sequences

CGTTTCAGTGGCAGTGGATCTGGGACAGATTTCACTCTCACCATCAGCAGTCTGCAACCT

GAAGATTTTGCTACGTACTACTGTCAACAGTTGTATTTTTGGCCTCGTACGTTCGGCCAA

GGGACCAAGGTGGAAATCAAACGG

BMS2h-492 (SEQ ID NO: 1263)
GACATCCAGATGACCCAGTCTCCATCCTCCCTGTCTGCATCTGTAGGAGACCGTGTCACC

ATCACTTGCCGGGCAAGTCAGGCGATTGAGCTTAATTTAGAGTGGTACCAGCAGAAACCA

GGGAAGGCCCCTAAGCTCCTGATCTATGATGCTTCCATGTTGCAAAGCGGGGTCCCATCA

CGTTTCAGTGGCAGTGGATCTGGGACAGATTTCACTCTCACCATTAGCAGTCTGCAACCT

GAAGATTTTGCTACGTACTACTGTCAACAGTATGATGTTTATCCTCCTACGTTCGGCCAA

GGGACCAAGGTGGAAATCAAACGG

BMS2h-492-1 (SEQ ID NO: 1264)
GACATCCAGATGACCCAGTCTCCATCCTCCCTGTCTGCATCTGTAGGAGACCGTGTCACC

ATCACTTGCCGGGCCAGTCAGGCGATTGAGCATAATTTAGAGTGGTACCAGCAGAAGCCA

GGGAAGGCCCCTAAGCTCCTGATCTATGATGCTTCCATGTTGCAAAGCGGGGTCCCATCA

CGTTTCAGTGGCAGTGGATCTGGGACAGATTTCACTCTCACCATTAGCAGTCTCCAACCT

GAAGATTTAGCTACGTACTACTGTCAACAGTATGATGCTTATCCTCCTACGTACGGCCAA

GGGACCAAGGTGGAAATCAAACGG

BMS2h-492-2 (SEQ ID NO: 1265)
GACATCCAGATGACACAGTCTCCATCCTCCCTGTCCGCATCTGTAGGAGACCGTGTCACC

ATCACTTGCCGGGCAAGTCGGGCGATAGAGACTAATTTAGAGTGGTACCAGCAGAAACCA

GGGAAGGCCCCTAAGCTCCTGTTCTATGATGCTTCCATGTTGCAAAGCGGGGTCCCATCA

CGTTTCGGTGGCAGTGGATCTGGGACAGATTTCACTCTCACCATTAGCAGTCTGCAACCT

GAAGATTTTGCTACGTACTACTGTCTACAGTATGATGTTTATCCTCCTACGTTCGGCCAA

GGGACCAAGGTGGAAATCAAACGG

BMS2h-492-3 (SEQ ID NO: 1266)
GACATCCAGATGACCCAGTCTCCATCCTCCCTGTCTGCAACTGTAGGAGACCGTGTCACC

ATCACTTGTCGTGCAAGTCAGGCGATTGAGACTAATTTAGAGTGGTACCAGCAGAAACCA

GGGAAGGCCCCTAAGCTCCTGATCTATGATGCTTCCATGTTGCAAAGCGGGGTCCCATCA

CGTTTCAGTGGCAGTGGATCTGGGACAGACTTCACTCTCACCATTAGCAGTCTGCAACCT

GAAGATTTTGCTACGTACTACTGTCAACAGTATGATGCTTATCCTCCTACGTTCGGCCAA

GGGACCAAGGTGGAAATCAAACGG

BMS2h-492-4 (SEQ ID NO: 1267)
GACATCCAGATGACCCAGTCTCCATCCTCCCTGTCTGCATCTGTAGGAGACCGTGTCACC

ATCACTTGCCGGGCAAGTCAGGCGATTGAGCATAACTTAGAGTGGTACCAGCAGAAACCA

GGGAAGGCCCCTAAGCTCCTGATCTATGATGCTTCCATGTTGCAAAGCGGGGTCCCATCA

CGTTTCAGTGGCAGAGGATCTGGGACAGATTTCACTCTCACCATTAGCAGTCTGCAACCT

GAAGATTTTGCTACGTACTACTGTCAACAGTATGATGCTTATCCTCCTACGTTCGGCCAA

GGGACCAAGGTGGAAATCAAACGG

TABLE 4-continued

Human Anti-CD40L VK Domain Encoding Nucleotide Sequences

BMS2h-4925
(SEQ ID NO: 1268)
GACATCCAGATGAACCAGTCTCCATCCTCCCTGTCTGCATCTGTAGGAGACCGTGTCTCC

ATCACTTGCAGGGCAAGTCAGGCTATTGAGCATAATTTAGAGTGGTACCAGCAGAAACCA

GGGAAGGCCCCTAAGCTCCTGATCTATGATGCTTCCATGTTGCAAAGCGGGGTCCCATCA

CGCTTCAGTGGCAGTGGATCTGGGACAGATTTCACTCTCACCATTAGCAGTCTGCAACCT

GAAGATTTTGCTACGTACTACTGTCAACAGTATGATGCTTATCCTCCTACGTTCGGCCAA

GGGACCAAGGTGGAAATCAAACGG

BMS2h-492-6
(SEQ ID NO: 1269)
GACATCCAGATGACCCAGTCTCCATCCTCCCTGTCTGCATCTGTAGGAGACCGTGTCACC

ATCACTTGCCGGGCAAGTCAGGCGATTGAGTCTAATTTAGAGTGGTACCAGCAAAAACCA

GGGAAGGCCCCTAAGCTCCTGATCTATGATGCTTCCATGTTGCAAAGCGGGGTCCCATCA

CGTTTCAGTGGCAGTGGATCTGGGACAGATTTCACTCTCACCATTAGCAGTCTGCAACCT

GAAGATTTTGCTACGTACTACTGTCAACAGTATGATGTTTATCCTCCTACGTTCGGCCAA

GGGACCAAGGTGGAAATCAAACGG

BMS2h-492-7
(SEQ ID NO: 1270)
GACATCCAGATGACCCAGTCTCCATCCTCCCTGTCTGCATCTGTAGGAGACCGTGTCACC

ATCACTTGCCGTGCAAGTCAGGCGATTGAGCATAATTTAGAGTGGTACCAGCAGAAACCA

GGGAAGGCCCCTAAGCTCCTGATCTATGATGCTTCCATGTTGCAAAGCGGGGTCCCATCA

CGTTTCAGTGGCAGTGGATCTGGGACAGATTTCACTCTCACCATTAGCAGTCTGCAACCT

GAAGATTTTGCTACGTACTACTGTCAACAGTATGATGCTTATCCTCCTACGTTCGGCCAA

GGGACCAAGGTGGAAATCAAACGG

BMS2h-493
(SEQ ID NO: 1271)
GACATCCAGATGACCCAGTCTCCATCCTCCCTGTCTGCATCTGTAGGAGACCGTGTCACC

ATCACTTGCCGGGCAAGTCAGGGTATTGATGAGGATTTAGAGTGGTACCAGCAGAAACCA

GGGAAAGCCCCTAGGCTCCTGATCTATTCTAGTTCCTGGTTGCAAAGTGGGGTCCCATCA

CGTTTCAGTGGGAGTGGATCTGGGACAGATTTCACTCTCACCATCAGCAGTCTGCAACCT

GAAGATTTTGCTACGTACTACTGTCAACAGTATTTTCAGTATCCTCCGACGTTCGGCCAA

GGGACCAAGGTGGAAATCAAACGG

BMS2h-494
(SEQ ID NO: 1272)
GACATCCAGATGACCCAGTCTCCATCCTCCCTGTCTGCATCTGTAGGAGACCGTGTCACC

ATCACTTGCCGGGCAAGTCAGAGTATTGATGAGGATTTAGAGTGGTACCAGCAGAAACCA

GGGAAAGCCCGTAGGCTCCTGATCTATTCTAGTTCCTGGTTGCAAAGTGGGGTCCCATCA

CGTTTCAGTGGGAGTGGATCTGGGACAGATTTCACTCTCACCATCAGCAGTCTGCAACCT

GAAGATTTTGCTACTACTACTGTCAACAGTATTTTCAGTATCCTCCGACGTTCGGCCAA

GGGACCAAGGTGGAAATCAAACGG

BMS2h-494-1
(SEQ ID NO: 1273)
GACATCCAGATGACCCAGTCTCCATCCTCCCTGTCCGCATCTGTAGGAGACCGTGTCACC

ATCACTTGCAGGGCAAGTCAGAGTATTGATGAGGATTTAGAGTGGTACCAGCAGAAACCA

GGGAAAGCCCCTAGGCTCCTGATCTATTCTAGTTCCTGGTTGCAAAGTGGGGTCCCATCA

TABLE 4-continued

Human Anti-CD40L VK Domain Encoding Nucleotide Sequences

CGTTTCAGTGGGAGTGGATCTGGGACAGATTTCACTCTCACCATCAGCAGTCTGCAACCT

GAAGATTTTGCTACGTACTACTGTCAACAGTATTCTCAGTATCCTCCGACGTTCGGCCAA

GGGACCAAGGTGGAAATCAAACGG

BMS2h-494-2
(SEQ ID NO: 1274)
GACATCCAGATGACCCAGTCTCCATCCTCCCTGTCTGCATCTGTAGGAGACCGTGTCACC

ATCACTTGCCGGGCAAGTCAGAGTATTGAAGAGGATTTAGAGTGGTACCAGCAGAAACCA

GGGAAAGCCCCTAGGCTCCTGATCTATTCTAGTTCCTGGTTGCAAAGCGGGGTCCCATCA

CGTTTCAGTGGGAGTGGCTCTGGGACAGATTTCACTCTCACCATCAGCAGTCTGCAACCT

GAAGATTTTGCTACGTACTACTGTCAACAGTATTTTCAGTATCCTCCGACGTTCGGCCAT

GGGACCAAGGTGGAAATCAAACGG

BMS2h-494-3
(SEQ ID NO: 1275)
GACATCCAGATGACCCAGTCTCCATCCTCCCTGTCTGCATCTGTAGGAGACCGTGTCACC

ATCACTTGCCGGGCAAGTCAGAGTATTGATGAGGATTTAGAGTGGTACCAGCAGAAACCA

GGGAAAGCCCCTAGGCTCCTGATCTATTCTAGTTCCTGGTTGCAAAGTGGGGTCCCATCA

CGTTTCAGTGGGAGTGGATCTGGGACAGATTTCACTCTCACCATCAGCAGTCTGCAACCT

GAAGATTTTGCTACGTACTTCTGTCAACAGTATTTTCAGTATCCTCCGACGTTCGGCCAA

GGGACCAAGGTGGAAATCAAACGG

BMS2h-494-4
(SEQ ID NO: 1276)
GAGATCCAGATGACCCAGTCTCCATCCTCCCTGTCTGCATCTGTAGGAGACCGTGTCACC

ATGACTTGCCGGGCAAGTCAGAGTATTGATAAGGATTTAGAGTGGTACCAGCAGAAACCA

GGGAAAGCCCCTAGGCTCCTGATCTATTCTAGTTCCTGGTTGCAAAGAGGGGTCCCATCA

CGTTTCAGTGGGAGTGGATCTGGGACAGATTTCACTCTCACCATCAGCAGTCTGCGACCT

GAAGATTTTGCTACGTACTACTGTCAACAGTATTTTCAGTATCCTCCGACGTTGGGCCAA

GGGACCAAGGTGGAAATCAAACGG

BMS2h-494-5
(SEQ ID NO: 1277)
GACATCCAGATGACCCAGTCTCCATCCTCCCTGTCTGCATCTGTAGGAGACCGAGTCACC

ATCACTTGCCGGGCAAGTCAGAGTATTGATGAGGATTTAGAGTGGTACCAGCAGAAACCA

GGGAAAGCCCCTAGGCTCCTGATCTATTCTAGTTCCTGGTTGCAAAGTGGGGTCCCATCA

CGTTTCAGTGGGAGTGGATCTGGGACAGATTTCACTCTCACCATCAGCGGTCTGCAACCT

GAAGATATCGCTACGTACTACTGTAAACAGTATTCTCAGTATCCTCCGACGTTCGGCCAA

GGGACCAAGGTGGAAATCAAACGG

BMS2h-494-6
(SEQ ID NO: 1278)
GACATCCAGATGACCCAGTCCCCACCCTCCCTGTCTGCATCTGTAGGAGACCGTGTCACC

ATCACTTGCCGGGCAAGTCAGAGTATTGATAAGGATTTAGAGTGGTACCAGCAGAAACCA

GGGAAAGCCCCTAGGCTCCTGATCTATTCTAGTTCCTGGTTGCAAAGAGGGGTCCCATCA

CGTTTCAGTGGGAGTGGATCTGGGACAGATTTCACTCTCACCATCAGCAGTCTGCAACCT

GAAGATTTTGCTACGTACCACTGTCAACAGTATTTTCAGTATCCTCCGACGTTCGGCCAA

GGGACCAAGGTGGAAATCAAACGG

TABLE 4-continued

Human Anti-CD40L VK Domain Encoding Nucleotide Sequences

BMS2h-495
(SEQ ID NO: 1279)
GACATCCAGATGACCCAGTCTCCATCCTCCCTGTCTGCATCTGTAGGAGACCGTGTCACC

ATCACTTGCCGGGCAAGTGAGTATATTAATGCTGAGTTAGCTTGGTATCAGCAGAAACCA

GGGAAAGCCCCTAAGCTCCTGATCTATGGGAGTTCCGGGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTAGTGTCTGCAGAATGCGATGTGGCCTATTACGTTCGGCCAA

GGGACCAAGGTGGAAATCAAACGG

BMS2h-496
(SEQ ID NO: 1280)
GACATCCAGATGACCCAGTCTCCATCCTCCCTGTCTGCATCTGTAGGAGACCGTGTCACC

ATCACTTGCCGGGCAAGTCTGGATATTAATAATGGTTTAATTTGGTACCAGCAGAAACCA

GGGAAAGCCCCTAGGCTCCTGATCTTGGGTGCGTCCGGTTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTTCGCAGGTGCGTTCTCGGCCTTTTACGTTCGGCCAA

GGGACCAAGGTGGAAATCAAACGG

BMS2h-497
(SEQ ID NO: 1281)
GACATCCAGATGACCCAGTCTCCATCCTCCCTGTCTGCATCTGTAGGAGACCGTGTCACC

ATCACTTGCCGGGCAAGTCAGGATATTCTGAGTGCGTTAGCTTGGTATCAGCAGAAACCA

GGGAAAGCCCCTAAGCTCCTGATCTATGGGAGTTCCGTTTTGCAAAGTGGGGTCCCATCA

CGTTTCAGTGGCAGTGGATCAGGGACAGATTTCACTCTCACCATCAGCAGTCTGCAACCT

GAAGATTTTGCTACGTACTACTGTCAACAGAATTATAGTCTTCCTATTACGTTCGGCCAA

GGGACCAAGGTGGAAATCAAACGG

BMS2h-498
(SEQ ID NO: 1282)
GACATCCAGATGACCCAGTCTCCATCCTCCCTGTCTGCATCTGTAGGAGACCGTGTCACC

ATCACTTGCCGGGCAAGTTCTCCTATTGAGTCGTATTTAAGGTGGTACCAGCAGAAACCA

GGGAAAGCCCCTAAGCTCCTGATCAGGTATGTGTCCGTGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGGGCAGTGGTTTCGGGCGCCTGTTACGTTCGGCCAA

GGGACCAAGGTGGAAATCAAACGG

BMS2h-499
(SEQ ID NO: 1283)
GACATCCAGATGACCCAGTCTCCATCCTCCCTGTCTGCATCTGTAGGAGACCGTGTCACC

ATCACTTGCCGGGTAAGTGAGTCTATTAATGCTGAGTTACATTGGTACCAGCAGAAACCA

GGGAAAGCCCCTAAGCTCCTGATCTCTGGGTTTTCCGGGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGTGCAGTTTGCGATGTGGCCTTTTACGTTCGGCCAA

GGGACCAAGGTGGAAATCAAACGG

BMS2h-500
(SEQ ID NO: 1284)
GACATCCAGATGACCCAGTCTCCATCCTCCCTGTCTGCATCTGTAGGAGACCGTGTCACC

ATCACTTGCCGGGCAAGTATGATGATTAGGTTTGGGTTAGATTGGTACCAGCAGAAACCA

GGGAAAGCCCCTAAGCTCCTGATCGGTGGTGGGTCCTCTTTGCAAAGTGGGGTCCCATCA

TABLE 4-continued

Human Anti-CD40L VK Domain Encoding Nucleotide Sequences

CGTTTCAGTGGCAGTGGATCTGGGACAGATTTCACTCTCACCATCAGCAGTCTGCAACCT

GAAGATTTTGCTACGTACTACTGTGGGCAGCATGAGCGGTGGCCTGCTACGTTCGGCCAA

GGGACCAAGGTGGAAATCAAACGG

BMS2h-501
(SEQ ID NO: 1285)
GACATCCAGATGACCCAGTCTCCATCCTCCCTGTCTGCATCTGTAGGAGACCGTGTCACC

ATCACTTGCCGGGCAAGTCAGAGTATTGGTACTCTTTTACGTTGGTATCAGCAGAAACCA

GGGAAAGCCCCTAAGCTCCTGATCTATCTTACTTCCGTTTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGATGGTTTATCGTCCTTATACGTTCGGCCAA

GGGACCAAGGTGGAAATCAAACGG

BMS2h-502
(SEQ ID NO: 1286)
GACATCCAGATGACCCAGTCTCCATCCTCCCTGTCTGCATCTGTAGGAGACCGTGTCACC

ATCACTTGCCGGGCAAGTCAGACTATTGAGACTAATTTAGAGTGGTACCAGCAGAAACCA

GGGAAAGCCCCTAAGCTCCTGATCTATGATTCTTCCCAGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGTATGATAAGGTTCCTGCGACGTTCGGCCAA

GGGACCAAGGTGGAAATCAAACGG

BMS2h-503
(SEQ ID NO: 1287)
GACATCCAGATGACCCAGTCTCCATCCTCCCTGTCTGCATCTGTAGGAGACCGTGTCACC

ATCACTTGCCGGGCAAGTCATCATATTCAGAGGTATTTATCGTGGTACCAGCAGAAACCA

GGGAAAGCCCCTAAGCTCCTGATCCTTTGGGGTTCCCAGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGGGCAGTGGTGGGCTCCTCCTCCGACGTTCGGCCAA

GGGACCAAGGTGGAAATCAAACGG

BMS2h-503-1
(SEQ ID NO: 1288)
GACATCCAGATGACCCAGTCTCCATCCTCCCTGTCTGCATCTGTAGGAGACCGTGTCACC

ATCACTTGCCGGGCAAGTCATCATATTCAGAGGTATTTATCGTGGTACCAGCAGATACCA

GGGAAAGCCCCTAAGCTCCTGATCCTTTGGGGTTCCCAGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGGGCAGTGGTGGGCTCCTCCTCAGACGTTCGGCCAA

GGGACCAAGGTGGAAATCAAACGG

BMS2h-503-2
(SEQ ID NO: 1289)
GACATCCAGATGACCCAGTCTCCATCCTCCCTGTCTGCATCTGTAGGAGACCGTGTCACC

ATCACTTGCCGGGCAAGTCATGATATTCAGAGGTATTTATCGTGGTACCAGCAGAAACCA

GGGAAAGCCCCTAAGCTCCTGATCCTTTGGGGTTCCCAGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGGGCAGTGGTGGGCTCCTCCTCAGACGTTCGGCCAA

GGGACCAAGGTGGAAATCAAACGG

TABLE 4-continued

Human Anti-CD40L VK Domain Encoding Nucleotide Sequences

BMS2h-504
(SEQ ID NO: 1290)
GACATCCAGATGACCCAGTCTCCATCCTCCCTGTCTGCATCTGTAGGAGACCGTGTCACC

ATCACATGCCGGGCAAGTCAGTATATTGATACTAATTTAGAGTGGTACCAGCAGAAACCA

GGGAAAGCCCCTAAGCTCCTGATCTATGATGGTTCCCTGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGGGCAGGGGCTGTTGTGCCTGTTACGTTCGGCCAA

GGGACCAAGGTGGAAATCAAACGG

BMS2h-508
(SEQ ID NO: 1291)
GACATCCAGATGACCCAGTCTCCATCCTCCCTGTCTGCATCTGTAGGAGACCGTGTCACC

ATCACTTGCCGGGCAAGTCAGGATATTGCTTTTGATTTAGAGTGGTATCAGCAGAAACCA

GGGAAAGCCCCTAAGCTCCTGATCTATTCGGCGTCCATGTTGCAAAGTGGGGTCCCATCA

CGTTTCAGTGGCAGTGGATCTGGGTCAGATTTCACTCTCACCATCAGCAGTCTGCAACCT

GAAGATTTTGCTACGTACTACTGTCAACAGTATAATCTTCAGCCTCCTACGTTCGGCCAA

GGGACCAAGGTGGAAATCAAACGG

BMS2h-509
(SEQ ID NO: 1292)
GACATCCAGATGACCCAGTCTCCATCCTCCCTGTCTGCATCTGTAGGAGACCGTGTCACC

ATCACTTGCCGGGCAAGTCAGAATATTGCTACGCTGTTACGTTGGTACCAGCAGAAACCA

GGGAAAGCCCCTAAGCTCCTGATCTATGCTGGTTCCATGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGATGTGGCAGCGTCCTTATACGTTCGGCCAA

GGGACCAAGGTGGAAATCAAACGG

BMS2h-51
(SEQ ID NO: 1293)
GACATCCAGATGACCCAGTCTCCATCCTCCCTGTCTGCATCTGTAGGAGACCGTGTCACC

ATCACTTGCCGGGCAAGTCAGCCTATTGTTGATGAGTTAGATTGGTACCAGCAGAAACCA

GGGAAAGCCCCTAAGCTCCTGATCTATGCTGCGTCCATTTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCATCAGTGGTCTACTTATCCTACGACGTTCGGCCAA

GGGACCAAGGTGGAAATTAAACGG

BMS2h-510
(SEQ ID NO: 1294)
GACATCCAGATGACCCAATCTCCATCCTCCCTGTCTGCATCTGTAGGAGACCGTGTCACC

ATCACTTGCCGGGCAAGTCAGAGCATTAGCAGCTATTTAAATTGGTACCAGCAGAAACCA

GGGAAAGCCCCTAAGCTCCTAATCGATGGTGTTTCCGGTTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGGGCAGGATTGGGATTGGCCTCGTACGTTCGGCCAA

GGGACCAAGGTGGAAATCAAACGG

BMS2h-511
(SEQ ID NO: 1295)
GACATCCAGATGACCCAGTCTCCATCCTCCCTGTCTGCATCTGTAGGAGACCGTGTCACC

ATCACTTGCCGGGCAAGTAGGAATATTCGTGATTGGTTACGGTGGTACCAGCAGAAACCA

GGGAAAGCCCCTAAGCTCCTGATCGATTGGGGGTCCGTGTTGCAAAGTGGGGTCCCATCA

TABLE 4-continued

Human Anti-CD40L VK Domain Encoding Nucleotide Sequences

CGTTTCAGTGGCAGTGGATCTGGGACAGATTTCACTCTCACCATCAGCAGTCTGCAACCT

GAAGATTTTGCTACGTACTACTGTGCTCAGACGTGGGATGATCCTCTGACGTTCGGCCAA

GGGACCAAGGTGGAAATCAAACGG

BMS2h-511-1 (SEQ ID NO: 1296)
GACATCCAGATGACCCAGTCTCCATCCTCCCTGTCTGCATTTGTAGGAGACCGTGTCACC

ATCACTTGCCGGGCAAGTAGGAATATTCGTGATTGGTTACGGTGGTACCAACAGAAACCA

GGGAAAGCCCCTAAGCTCCTGATCGATTGGGGGTCCGAGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGCTCAGACGTGGTATGATCCTCTGACGTTCGGCCAC

GGGACCAAGGTGGAAATCAAACGG

BMS2h-512 (SEQ ID NO: 1297)
GACATCCAGATGACCCAGTCTCCATCCTCCCTGTCTGCATCTGTAGGAGACCGTGTCACC

ATCACTTGCCGGGCAAGTATTGATATTCATGGTGGTTTAACTTGGTACCAGCAGAAACCA

GGGAAAGCCCCTAAGCTCCTGATCGTGGGGGTTTCCGGTTTGCAAAGTGGGGTCCCATCA

CGTTTCAGTGGCAGTGGATCTGGGACAGATTTCACTCTCACCATCAGCAATCTGCAACCT

GAAGATTTTGCTACGTACTACTGTGCGCAGGTGTGGCGTAGGCCTTTTACGTTCGGCCAA

GGGACCAAGGTGGAAATCAAACGG

BMS2h-513 (SEQ ID NO: 1298)
GACATCCAGATGACCCAGTCTCCATCCTCCCTGTCTGCATCTGTAGGAGACCGTGTCACC

ATCACTTGCCGGGCAAGTCAGGATATTGGGAGTTCGTTATCTTGGTATCAGCAGAAACCA

GGGAAAGCCCCTAAGCTCCTGATCTATGCTTCTTCCCTGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGACTTATGCTCTTCCTGTTACGTTCGGCCAA

GGGACCAAGGTGGAAATCAAACGG

BMS2h-514 (SEQ ID NO: 1299)
GACATCCAGATGACCCAGTCTCCATCCTCCCTGTCTGCATCTGTAGGAGACCGTGTCACC

ATCACTTGCCGGGCAAGTCAGCAGATTGAGACGAATTTAGAGTGGTATCAGCAGAAACCA

GGGAAAGCCCCTAAGCTCCTGATCTATGATGGTTCCTGGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGTATAAGTATCTGCCTGTGACGTTCGGCCAA

GGGACCAAGGTGGAAATCAAACGG

BMS2h-52 (SEQ ID NO: 1300)
GACATCCAGATGACCCAGTCTCCATCCTCCCTGTCTGCATCTGTAGGTGACCGTGTCACC

ATCACTTGCCGGGCAAGTCAGGATATTGGTCTGCGTTAAGGTGGTATCAGCAGAAACCA

GGGAAAGCCCCTAAGGTCCTGATCTATTTGGGTTCCGATTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGACGCAGTATTTTCCTACGACGTTCGGCCAA

GGGACCAAGGTGGAAATCAAACGG

TABLE 4-continued

Human Anti-CD40L VK Domain Encoding Nucleotide Sequences

BMS2h-53
(SEQ ID NO: 1301)
GACATCCAGATGACCCAGTCTCCATCCTCCCTGTCTGCATCTSTAGGAGACCGTGTCACC

ATCACTTGCCGGGCAAGTCAGGCGATTTATGGGGGGTTACGGTGGTACCAGCAGAAACCA

GGGAAAGCCCCTAAGCTCCTGATCTATGGGGAGTCCATGTTGCAAAGTGGGGTCCCATCA

CGTTTCAGTGGCAGTGGATCTGGGACAGATTTCACTCTCACCATCAGCAGTCTGCATCCT

GAAGATTTTGCTACGTACTACTGTCAACAGGTTTATCATAAGCCTTTTACGTTCGGCCAA

GGGACCAAGGTGGAAATCAAACGG

BMS2h-536
(SEQ ID NO: 1302)
GACATCCAGATGACCCAGTCTCCATCCTCCCTGTCTGCATCTGTAGGAGACCGTGTCACC

ATCACGTGCCGGGCAAGTCAGCGTATTGGGGTGTGGTTAGATTGGTATCAGCAGAAACCA

GGGAAAGCCCCTAAGCTCCTGATCTATGATGGTTCCTTTTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGACTTTTTCGAGTCCTTCTACGTTCGGCCAA

GGGACCAAGGTGGAAATCAAACGG

BMS2h-537
(SEQ ID NO: 1303)
GACATCCAGATGACCCAGTCTCCATCCTCCCTGTCTGCATCTGTAGGAGACCGTGTCCCC

ATCACTTGCCGGGCAAGTCAGTGGATTGGGGATGAGTTATATTGGTATCAGCAGAAACCA

GGGAAAGCCCCTAAGCTCCTGATCTATAGTTCTTCCACTTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGTCGTTTCAGTTTCCTTATACGTTCGGCCAA

GGGACCAAGGTGGAAATCAAACGG

BMS2h-538
(SEQ ID NO: 1304)
GACATCCAGATGACCCAGTCTCCATCCTCCCTSTCTGCATCTGTAGGAGACCGTGTCACC

ATCACTTGCCGGGCAAGTAGTAATATTACGGGGCCGTTAGAGTGGTACCAGCAGAAACCA

GGGAAAGCCCCTAAGCTCCTGATCCCTGGTTGGTCCACTTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGGTCAGGTGTGGGGGAGCCTGTTACGTTCGGCCAA

GGGACCAAGGTGGAAATCAAACGG

BMS2h-539
(SEQ ID NO: 1305)
GACATCCAGATGACCCAGTCTCCATCCTCCCTGTCTGCGTCTATAGGAGACCGTGTCACC

ATCACTTGCCGGGCAAGTCAGCGTATTGCTTATGGTTTACATTGGTACCAGCAGAAACCA

GGGAAAGCCCCTAGGCTCCTGATCGGGGGCGGTCCGGTTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGTGCAGCCTGGGATGCCGCCTGATACGTTCGGCCAA

GGGACCAAGGTGGAAATCAAACGG

BMS2h-540
(SEQ ID NO: 1306)
GACATCCAGATGACCCAGTCTCCATCCTCCCTGTCTGCATCTGTAGGAGACCGTGTCACC

ATCACTTGCCGGGCAAGTAAGCAGATTGTTGGTGGTTTATCTTGGTACCAGCAGAAACCA

GGGAAAGCCCCTAAGCTCCTGATCGGGCGTCATTCTGGGTTGCAAAGTGGGGTCCCATCA

TABLE 4-continued

Human Anti-CD40L VK Domain Encoding Nucleotide Sequences

CGTTTCAGTGGCAGTGGATCTGGGACAGATTTCACTCTCACCATCAGCAGTCTGCAACCT

GAAGATTTTGCTACGTACTACTGTGTGCAGGGGTTTGGGCTCCTGGGACGTTCGGCCAA

GGGACCAAGGTGGAAATCAAACGG

BMS2h-541 (SEQ ID NO: 1307)
GACATCCAGATGACCCAGTCTCCATCCTCCCTGTCTGCATCTGTAGGAGACCGTGTCACC

ATCACTTGCCGGGCAAGTCCTGCTATTGCTGCTAAGTTAGATTGGTACCAGCAGAAACCA

GGGAAAGCCCCTAAGCTCCTGATCGGTGCGGATTCCGGGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGGTCAGCTGTGGGCGGGGCCTCCGACGTTCGGCCAA

GGGACCAAGGTGGAAATCAAACGG

BMS2h-842 (SEQ ID NO: 1308)
GACATCCAGATGACCCAGTCTCCATCCTCCCTGTCTGCATCTGTAGGAGACCGTGTCACC

ATCACTTGCCGGGCAAGTCGTACTATTGCTGATGGGTTAGATTGGTACCAGCAGAAACCA

GGGAAAGCCCCTAAGCTCCTGATCGGGGCGTATTCCGGTTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGGTCAGCTTTGGGAGGGTCCTCCGACGTTCGGCCAA

GGGACCAAGGTGGAAATCAAACGG

BMS2h-543 (SEQ ID NO: 1309)
GACATCCAGATGACCCAGTCTCCATCCTCCCTGTCTGCATCTGTAGGAGACCGTGTCACC

ATCACTTGCCGGGCAAGTCAGAGGATTTATGGGTTTTTAGATTGGTATCAGCAGAAACCA

GGGAAAGCCCCTAAGCTCCTGATCTATGGGGTGTCCTCGTTGCAAAGTGGGGTCCCATCA

CGTTTTAGTGGCAGCGGATCTGGGACAGATTTCACTCTCACCATCAGCAGTCTGCAACCT

GAAGATTTTGCTACGTACTACTGTCAACAGACTTTGGCGTGGCCTTTTACGTTCGGCCAA

GGGACCAAGGTGGAAATCAAACGG

BMS2h-544 (SEQ ID NO: 1310)
GACATCCAGATGACCCAGTCTCCATCCTCCCTGTCTGCATCTGTAGGAGACCGTGTCACC

ATCACTTGCCGGGCAAGTCAGGATATTCGGGATTGGTTAATGTGGTACCAGCAGAAACCA

GGGAAAGCCCCTAAGCTCCTGATCTATTGGGGTTCCTTTTTGCAAAGTGGGGTCCCATCA

CGTTTCAGTGGCAGTGGATCTGGGACAGATTTCACTCTCACCATCAGCAGTCTGCAACCT

GAAGATTTGCTACGTACTACTGTCAACAGCTGTATGATACTCCTTATACGTTCGGCCAA

GGGACCAAGGTGGAAATCAAACGG

BMS2h-545 (SEQ ID NO: 1311)
GACATCCAGATGACCCAGTCTCCATCCTCCCTGTCTGCATCTGTAGGAGACCGTGTCACC

ATCACTTGCCGGGCAAGTCAGAATATTAATACGGGTTTAGATTGGTATCAGCAGAAACCA

GGGAAAGCCCCTAAGCTCCTGATCTATGATAGTTCCGCTTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGACGTCGTATTATCCTTATACGTTCGGCCAA

GGGACCAAGGTGGAAATCAAACGG

TABLE 4-continued

Human Anti-CD40L VK Domain Encoding Nucleotide Sequences

BMS2h-546
(SEQ ID NO: 1312)
GACATCCAGATGACCCAGTCTCCATCCTCCCTGTCTGCATCTGTAGGAGACCGTGTCACC

ATCACTTGCCGGGCAAGTCAGAAGATTTTTGGTTGGTTAGATTGGTACCAGCAGAAACCA

GGGAAAGCCCCTAAGCTCCTGATCTATGGGACTTCCAAGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGGTTTATTCGCTTCCTTATACGTTCGGCCAA

GGGACCAAGGTGGAAATCAAACGG

BMS2h-547
(SEQ ID NO: 1313)
GACATCCAGATGACCCAGTCTCCATCCTCCCTGTCTGCATCTGTAGGAGACCGTGTCACC

ATCACTTGCCGGGCAAGTTCGAATATTGGGGCGGATTTAGATTGGTACCAGCAGAAACCA

GGGAAAGCCCCTAAGCTCCTGATCGGGGGGCGTCCGGGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGGGCAGCTGTGGAATGGGCCTCCTACGTTCGGCCAA

GGGACCAAGGTGGAAATCAAACGG

BMS2h-548
(SEQ ID NO: 1314)
GACATCCAGATGACCCAGTCTCCATCCTCCCTGTCTGCATCTGTAGGAGACCGTGTCACC

ATCACTTGCCGGGCAAGTAGTCCGATTTATGATGGTTTAGATTGGTACCAGCAGAAACCA

GGGAAAGCCCCTAAGCTCCTGATCTCTGGTGCTTCCTGGTTGCAAAGTGGGGTCCCATCA

CGCTTCAGTGGCAGTGGATCTGGGACAGATTTCACTCTCACCATCAGCAGTCTGCAACCT

GAAGATTTTGCTACGTACTACTGTGGTCAGTTGTGGTTGGGTCCTCCGACGTTCGGCCAA

GGGACCAAGGTGGAAATCAAACAG

BMS2h-549
(SEQ ID NO: 1315)
GACATCCAGATGACCCAGTCTCCATCCTCCCTGTCTGCATCTGTAGGAGACCGTGTCACC

ATCACTTGCCGGGCAAGTTCGCGTATTTATAATGGTTTACATTGGTACCAGCAGAAACCA

GGGAAAGCCCCTAAGCTCCTGATCGGTGGTCGGTCCGGGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGCTCAGGTGGGGGAGGCTCCTTCTACGTTCGGCCAA

GGGACCAAGGTGGAAATCAAACGG

BMS2h-550
(SEQ ID NO: 1316)
GACATCCAGATGACCCAGTCTCCATCCTCCCTGTCTGCATCTGTAGGAGACCGTGTCACC

ATCACTTGCCGGGCAAGTAGGTTTATTAATGAGGAGTTAGATTGGTACCAGCAGAAACCA

GGGAAAGCCCCTAAGCTCCTGATCTCGTGGTCTTCCTGGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGTGCAGCCGGGGGTGGTCCTGGGACGTTCGGCCAA

GGGACCAAGGTGGAAATCAAACGG

BMS2h-551
(SEQ ID NO: 1317)
GACATCCAGATGACCCAGTCTCCATCCTCCCTGTCTGCATCTGTAGGAGACCGTGTCACC

ATCACTTGCCGGGCAAGTAGGGATATTCTGGATGAGTTAGATTGGTACCAGCAGAAACCA

GGGAAAGCCCCTAGGCTCCTGATCGGTGGGGGGTCCGGGTTGCAAAGTGGGGTCCCATCA

TABLE 4-continued

Human Anti-CD40L VK Domain Encoding Nucleotide Sequences

CGTTTCAGTGGCAGTGGATCTGGGACAGATTTCACTCTCACCATCAGCAGTCTGCAACCT

GAAGATTTTGCTACGTACTACTGTGGTCAGCTGTGGCATGGGCCTCCGACGTTCGGCCAA

GGGACCAAGGTGGAAATCAAACGG

BMS2h-552
(SEQ ID NO: 1318)
GACATCCAGATGACCCAGTCTCCATCCTCCCTGTCTGCATCTGTAGGAGACCGTGTCACC

ATCACTTGCCGGOCAAGTAGTCCTATTTATACGGTTTACATTGGTACCAGCAGAAACCA

GGGAAAGCCCCTAAGCTCCTGATCGGTGGGCGGTCCGGGTTGCAAAGTGGGGTCCCATCA

CGTTTCAGTCGCAGTGGATCTGGGACAGATTTCAGTCTCACCATCAGCAGTCTGCAACCT

GAAGATTTTGCTACGTACTACTGTATGCAGGTTGGGACGGCTCCTGCTACGTTCGGCCAA

GGGACCAAGGTGGAAATCAAACGG

BMS2h-585
(SEQ ID NO: 1319)
GACATCCGGATGACCCAGTCTCCATCCTCCCTGTCTGCATCTGTAGGAGACCGTGTCACC

ATCACTTGCCGGGCAAGTCAGAATATTTCTAGGCGGTTACTGTGGTACCAGCAGAAACCA

GGGAAAGCCCCTAAGCTCCTGATCTATTCTTCTTCCCGGTTGCAAAGTGGGGTCCCATCA

CGTTTCGGTGGCAGTGGATCTGGGACAGATTTCACTCTCACCATCAGCAGTCTOCAACCT

GAAGATTTTGCTACGTACTACTGTCAACAGACGTATAGCTATCCTCATACGTTCGGCCAA

GGGACCAAGGTGGAAATCAAACGG

BMS2h-604
(SEQ ID NO: 1320)
GACATCCAGATGACCCAGTOTCCATCCTCCCTGTCTGCATCTGTAGGAGACCGTGTCACC

ATCACTTGCCGGGCAAGTAGTCCGATTCCGCAGGATTTATATTGGTACCAGCAGAAACCA

GGGAAAGCCCCTAAGCTCCTGATCGTTGGGATTTCCCAGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGGGCAGTTGTGGAGTGCGCCTGCTACGTTCGGCCAA

GGGACCAAGGTGGAAATCAAACGG

BMS2h-605
(SEQ ID NO: 1321)
GACATCCAGATGACCCAGTCTCCATCCTCCCTGTCTGCATCTGTAGGAGACCGTGTCACC

ATCACTTGCCGGGCAAGTAAGTCTATTGATGGGATGTTAGATTGGTACCAGCAGAAACCA

GGGAAAGCCCCTAAGCTCCTGATCCCTGGTTTTTCCGGTTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGGGCAGTCGGTTGAGGCGCCTTGGACGTTCGGCCAA

GGGACCAAGGTGGAAATCAAACGG

BMS2h-606
(SEQ ID NO: 1322)
GACATCCAGATGACCCAGTCTCCATCCTCCCTGTCTGCATCTGTAGGAGACCGTGTCACC

ATCACTTGCCGGGCAAGTCGGTATATTGCTCATCCTTTAGATTGGTACCAGCAGAAACCA

GGGAAAGCCCCTAAGCTCCTGATCCCGGGTTCGTCCGTTTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGGTCAGTCGGTTGTGGTGCCTTGGACGTTCGGCCAA

GGGACCAAGGTGGAAATCAAACGG

TABLE 4-continued

Human Anti-CD40L VK Domain Encoding Nucleotide Sequences

BMS2h-607
(SEQ ID NO: 1323)
GACATCCAGATGACCCAGTCTCCATCCTCCCTGTCTGCATCTGTAGGAGACCGTGTCACC

ATCACTTGCCGGGCAAGTCGGACGATTGAGGGTGGTTTAGATTGGTACCAGCAGAAACCA

GGGAAAGCCCCTAAGCTCCTGATCATGGGGGGTTCCGGYTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGGGCAGTTGTGGGTGGGTCCTCCTACGTTCGGCCAA

GGGACCAAGGTGGAAATCAAACGG

BMS2h-608
(SEQ ID NO: 1324)
GACATCCAGATGACCCAGTCTCCATCCTCCCTGTCTGCATCTGTAGGAGACCGTGTCACC

ATCACTTGCCGGGCAAGTAAGTTTATTAGGGATGAGTTATATTGGTACCAGCAGAAACCA

GGGAAAGCCCCTAGGCTCCTGATCGGTGGTTCGTCCTTGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGGGCAGCTGTGGCGGGCGCCTGCGACGTTCGGCCAA

GGGACCAAGGTGGAAATCAAACGG

BMS2h-609
(SEQ ID NO: 1325)
GACATCCAGATGACCCAGTCTCCATCCTCCCTGTCTGCATCTGTAGGAGACCGTGTCACC

ATCACTTGCCGGGCAAGTAAGCCGATTTATGGTGGTTTAGAGTGGTACCAGCAGAAACCA

GGGAAAGCCCCTAGGCTCCTGATCGGGGGGGGTTCCGTGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGGGCAGGTGTGGGGGGTCCTGTTACGTTCGGCCAA

GGGACCAAGGTGGAAATCAAACGG

BMS2h-610
(SEQ ID NO: 1326)
GACATCCGGATGACCCAGTCTCCATCCTCCCTGTCTGCATCTGTAGGAGACCGTGTCACC

ATCACTTGCCGGGCAAGTCGGCCGATTAGTGGTTGTTTAGATTGGTACCAGCAGAAACCA

GGGAAAGCCCCTAAGCTCCTGATCGATGGGGCTTCCGGGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGGGCAGTGGTGGGAGTATCCTCCTACGTTCGGCCAA

GGGACCAAGGTGGAAATCAAACGG

BMS2h-611
(SEQ ID NO: 1327)
GACATCCAGATGACCCAGTCTCCATCCTCCCTGTCTGCATCTGTAGGAGACCGTGTCACC

ATCACTTGCCGGGCAAGTAAGCCTATTGTGAGGGATTTAGAGTGGTACCAGCAGAAACCA

GGGAAAGCCCCTAAGCTCCTGATCCATGGTGTGTCCACGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGGGCAGCTTGAGGCGGCGCCTGCGACGTTCGGCCAA

GGGACCAAGGTGGAAATCAAACGG

BMS2h-612
(SEQ ID NO: 1328)
GACATCCAGATGACCCAGTCTCCATCCTCCCTGTCTGCATCTGTAGGAGACCGTGTCACC

ATCACTTGCCGGGCAAGTCGGGATATTGGTGATTGGTTATATTGGTACCAGCAGAAACCA

GGGAAAGCCCCTAGGCTCCTGATCGTTTGGGCGTCCGTGTTGCAAAGTGGGGTCCCATCA

TABLE 4-continued

Human Anti-CD40L VK Domain Encoding Nucleotide Sequences

CGTTTCAGTGGCAGTGGATCTGGGACAGATTTCACTCTCACCATCAGCAGTCTGCAACCT

GAAGATTTTGCTACGTACTACTGTGCGCAGTGGGGGACTCCTCCTACGACGTTCGGCCAA

GGGACCAAGGTGGAAATCAAACGG

BMS2h-613
(SEQ ID NO: 1329)
GACATCCAGATGACCCAGTCTCCATCCTCCCTGTCTGCATCTGTAGGAGACCGTGTCACC

ATCACTTGCCGGGCAAGTAATCGTATTGAGTATGGTTTAGATTGGTACCAGCAGAAACCA

GGGAAAGCCCCTAAGCTCCTGATCTCGGGGTCTTCCCGTTTGCAAAGTGGGGTCCCATCA

CGTTTCAGTAGCAGTGGATCTGGGACAGATTTCACTCTCACCATCAGCAGTCTGCAACCT

GAAGATTTTGCTACGTACTACTGTGGGCAGCTTGAGGCGGCGCCTGCGACGTTCGGCCAA

GGGACCAAGGTGGAAATCAAACGG

BMS2h-614
(SEQ ID NO: 1330)
GACATCCAGATGACCCAGTCTCCATCCTCCCTGTCTGCATCTGTAGGAGACCGTGTCACC

ATCACTTGCCGGGCAAGTCGGAATATTGGGCATTTTTAGATTGGTACCAGCAGAAACCA

GGGAAAGCCCCTAAGCTCCTGATCTTGGGGGGGTCGTCGTTGCAAAGTGGGGTCCCATCA

CGTTTCAGTGGCAGCGGGTCTGGGACAGATTTCACTCTCACCATCAGCAGTCTGCAACCT

GAAGATTTTGCTACGTACTACTGTGGGCAGTTGGTGGAGCCTCCTGCGACGTTCGGCCAA

GGGACCAAGGTGGAAATCAAACGG

BMS2h-615
(SEQ ID NO: 1331)
GACATCCAGATGACCCAGTCTCCATCCTCCCTGTCTGCATCTGTAGGAGACCGTGTCACC

ATCACTTGCCGGGCAAGTTCGAGTATTTATAGTGATTTATATTGGTACCAGCAGAAACCA

GGGAAAGCCCCTAAGCTCCTGATCGATGGGTGGTCCGGGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGGGCAGCTGCATCGTGCTCCTGCGACGTTCGGCCAA

GGGACCAAGGTGGAAATCAAACGG

BMS2h-616
(SEQ ID NO: 1332)
GACATCCAGATGACCCAGTCTCCATCCTCCCTGTCTGCATCTGTAGGAGACCGTGTCACC

ATCACTTGCCGGGCAAGTAGGTTTATTACTGATCGTTTAGATTGGTACCAGCAGAAACCA

GGGAAAGCCCCTAAGCTCCTGATCGGTGGTGTTTCCGGGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGGGCAGAGTTCGGAGTTGCCTTGGACGTTCGGCCAA

GGGACCAAGGTGGAAATCAAACGG

BMS2h-617
(SEQ ID NO: 1333)
GACATCCAGATGACCCAGTCTCCATCCTCCCTGTCTGCATCTGTAGGAGACCGTGTCACC

ATCACTTGCCGGGCAAGTCGTAAGATTGGTAGTGAGTTATATTGGTACCAGCAGAAACCA

GGGAAAGCCCCTAAGCTCCTGATCGGTGGTAGGTCCCGGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGGGCAGTTGTGGGAGCCTCCTGCGACGTTCGGCCAA

GGGACCAAGGTGGAAATCAAACGG

TABLE 4-continued

Human Anti-CD40L VK Domain Encoding Nucleotide Sequences

BMS2h-618
(SEQ ID NO: 1334)
GACATCCAGATGACCCAGTCTCCATCCTCCCTGTCTGCATCTGTAGGAGACCGTGTCACC

ATCACTTGCCGGGCAAGTAGGAATATTGGTAATGGTTTAGATTGGTACCAGCAGAAACCA

GGGAAAGCCCCTAAGCTCCTGATCGGGGAGGGGTCCCGTTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGGGCAGCTTTGGCATACTCCTCCTACGTTCGGCCAA

GGGACCAAGGTGGAAATCAAACGG

BMS2h-619
(SEQ ID NO: 1335)
GACATCCAGATGACCCAGTCTCCATCCTCCCTGTCTGCATCTGTAGGAGACCGTGTCACC

ATCACTTGCCGGGCAAGTCGGAATATTTATGGTTGGTTATCGTGGTACCAGCAGAAACCA

GGGAAAGCCCCTAGGCTCCTGATCGGTGGGTGGTCCGGTTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTGCGCAGGATTATACGTTGCCTGGTACGTTCGGCCAA

GGGACCAAGGTGGAAATCAAACGG

BMS2h-730
(SEQ ID NO: 1336)
GACATCCAGATGACCCAGTCTCCATCCTCCCTGTCTGCATCTGTAGGAGACCGTGTCACC

ATCACTTGCCGGGCAAGTCAGGATATTAAGGATTGGTTACATTGGTACCAGCAGAAACCA

GGGAAAGCCCCTAAGCTCCTGATCTATTTTGCGTCCGGTTTGCAAAGTGGGGTCCCATCA

CGTTTCAGTGGCAGTGGATCTGGGACAGATTTCACTCTCACCATCAGCAGTCTGCAACCT

GAAGATTCTGCTACGTACTACTGTCAACAGCATTATAGTACGCCTTATACGTCCGGCCAA

GGGACCAAGGTGGAAATCAAACGG

BMS2h-731
(SEQ ID NO: 1337)
GACATCCAGATGACCCAGTCTCCACCCTCCCTGTCTGCATCTGTAGGAGACCGTGTCACC

ATCACTTGCCGGGCAAGTCAGTTGATTTCTTCTCATTTAGATTGGTACCAGCAGAAACCA

GGGAAAGCCCCTAAGCTCCTGGTCTATGATGCTTCCGAGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGCATCGCAGTCTGCCTTTTACGTTCGGCCAA

GGGACCAAGGTAGAAATCAAACGG

BMS2h-732
(SEQ ID NO: 1338)
GACATCCAGATGACCCAGTCTCCATCCTCCCTGTCTGCATCTGTAGGAGACCGTGTCACC

ATCACTTGCCGGGCAAGTCAGTGGATTGGTGGGGCGTTAGCGTGGTACCAGCAGAAACCA

GGGAAAGCCCCTAGGCTCCTTATCTATCAGATTTCCGTTTTGCAAAGTGGGATCCCATCA

CGTTTCAGTGGCAGTGGATCTGGGACAGATTTCACTCTCACCATCAGCAGTCTGCAACCT

GAAGATTTTGCTACGTACTACTGTCAACAGTATATTCGGTCTCCTTTTACGTTCGGCCAA

GGGACCAAGGTGGAAATCAAACGG

BMS2h-733
(SEQ ID NO: 1339)
GACATCCAGATGACCCAGTCTCCATCCTCCCTGTCTGCATCTGTAGGAGACCGTGTCACC

ATCACTTGCCGGGCAAGTCAGAGTATTGGGGCGGCGTTAAATTGGTATCAGCAGAAACCA

GGGAAAGCCCCTAAGCTCCTGATCTATGGTCTGTCCTCTTTGCAAAGTGGGGTCCCATCA

TABLE 4-continued

Human Anti-CD40L VK Domain Encoding Nucleotide Sequences

CGTTTCAGTGGCAGTGGATCTGGGACAGATTTCACTCTCACCATCAGCAGTCTGCAACCT

GAAGATTTTGCTACGTACTACTGTCAACAGCTGTTTAGGCTTCCTTTGACGTTCGGCCAA

GGGACCAAGGTGGAAATCAAACGG

BMS2h-734
(SEQ ID NO: 1340)
GACATCCAGATGACCCAGTCTCCATCCTCCCTGTCTGCATCTGTAGGAGACCGTGTCACC

ATCACTTGCCGGGCAAGTCAGCCTATTGGGGGTCGTTTAGTGTGGTACCAGCAGAAACCA

GGGAAAGCCCCTAAGCTCCTGATCTATGGGTCTTCCATTTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGTATGCTGAGGCTCCTATTACGTTCGGCCAA

GGGACCAAGGTGGAAATCAAACGG

BMS2h-735
(SEQ ID NO: 1341)
GACATCCAGATGACCCAGTCTCCATCCTCCCTGTCTGCATCTGTAGGAGACCGTGTCACC

ATCACTTGCCGGGCAAGTCAGAATATTGGGTCTAGTTTAATTTGGTACCAGCAGAAACCA

GGGAAAGCCCCTACGCTCCTGATCTATTATTCGTCCAAGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGTCTTTGTCGAGTCCTTATACGGTCGGCCAA

GGGACCAAGGTGGAAATCAAACGG

BMS2h-736
(SEQ ID NO: 1342)
GACATCCAGATGACCCAGTCTCCATCCTCCCTGTCTGCATCTGTAGGAGACCGTGTCACC

ATCACTTGCCGGGCAAGTCAGTGGATTGGGAGTGAGTTAGCGTGGTATCAGCAGAAACCA

GGGAAAGCCCCTAAGCTCCTGATCTATTGGACGTCCAATTTGCAAAGTGGGGTCCCATCA

CGTTTCAGTGGCAGTGGATCTGGGACAGATTTCACTCTCACCATCAGCAATCTGCAACCT

GAAGATTTTGCTACGTACTACTGTCAACAGATTCTGGAGACTCCTTTGACGTTTGGCCAA

GGGACCAAGGTGGAAATCAAACGG

BMS2h-737
(SEQ ID NO: 1343)
GACATCCAGATGACCCAGTCTCCATCCTCCCTGTCTGCATCTGTAGGAGACCGTGTCACC

ATCACTTGCCGGGCAAGTCAGAAGATTGGGATGCTTTATATTGGTATCAGCAGAAACCA

GGGAAAGCCCCTAAGCTCCTGATCTATCGTGGGTCCATTTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGTTTTATCGGTGGCCTCATACGTTCGGCCAA

GGGACCAAGGTGGAAATCAAACGG

BMS2h-738
(SEQ ID NO: 1344)
GACATCCAGATGACCCAGTCTCCATCCTCCCTGTCTGCATCTGTAGGAGACCGTGTCACC

ATCACTTGCCGGGCAAGTCAGCATATTGAGGATTCTTTACGGTGGTACCAGCAGAAACCA

GGGAAAGCCCCTAAGCTCCTGATCTATTATGGTTCCGTGTTGCAAAGTGGGGTCCCATCA

CGTTTCAGTGGCAGTGGATCTGGGACAGATTTCACTCTCACCATCAGCAGTCTGCAACCT

TABLE 4-continued

Human Anti-CD40L VK Domain Encoding Nucleotide Sequences

GAAGATTTTGCTACGTACTACTGTCAACAGATGTATAAGTTTCCTATTACGTTCGGCCAA

GGGACCAAGGTGGAAATCAAACGG

BMS2h-739
(SEQ ID NO: 1345)
GACATCCAGACGACCCAGTCTCCATCCTCCCTGTCTGCATCTGTAGGAGACCGTGTCACC

ATCACTTGCCGGGCAAGTCAGCGGATTAATTCTTCTTTACTGTGGTACCAGCAGAAACCA

GGGAAAGCCCCTAAGCTCCTGATCTATGATACTTCCACTTTGCAAAGTGGGGTCCCATCA

CGTTTCAGTGGCAGTAGATCTGGGACAGATTTCACTCTCACCATCAGCAGTCTGCAACCT

GAAGATTTCGCTACGTACTACTGTCAACAGATTTGGGGTTCGCCTCCTACGTTCGGCCAG

GGGACCAAGGTGGAAATCAAACGG

BMS2h-740
(SEQ ID NO: 1346)
GACATCCAGATGACCCAGTCTCCATCCTCCCTGTCTGCATCTGTAGGAGACCGTGTCACC

ATCACTTGCCGGGCAAGTCAGTCGATTCCTGTTGGTTTAAATTGGTACCAGCAGAAACCA

GGGAAAGCCCCTAGGCTCCTGATCTATTCTGGGTCCACTTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGGATTGGTATTATCCTAATACGTTCGGCCAA

GGGACCAAGGTGGAAATCAAACGG

BMS2h-785
(SEQ ID NO: 1347)
GACATCCAGATGACCCAGTCTCCATCCTCCCTGTCTGCATCTGTAGGAGACCGTGTCACC

ATCACTTGCCGGGCAAGTCAGCCTATTTATGGTTGGTTAAATTGGTATCAGCAGAAACCA

GGGAAAGCCCCTAAGCTCCTGATCTATTTGACGTCCGGGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGATTCATAGTTCTCCTTTTACGTTCGGCCAA

GGGACCAAGGTGGAAATCAAACGG

BMS2h-8
(SEQ ID NO: 1348)
GACATCCAGATGACCCAGTCTCCATCCTCCCTGTCTGCATCTGTAGGAGACCGTGTCACC

ATCACTTGCCGGGCAAGTCAGTTTATTGATACGTCGTTAGAGTGGTATCAGCAGAAACCA

GGGAAAGCCCCTAAGCTCCTGATCTATGATGGGTCCCATTTGCAAAGTGGGGTCCCATCA

CGTTTCAGTGGCAGTGGATCTGGGACAGATTTCACTCTCACCATCAGCAGTCTGCAACCT

GAAGATTTAGCTACGTACTACTGTCAACAGTATTGGGTTCTTCCTCTGACGTTCGGCCAA

GGGACCAAGGTGGAAATCAAACGG

BMS2h-86
(SEQ ID NO: 1349)
GACATCCAGATGACCCAGTCTCCATCCTCCCTGTCTGCATCTGTAGGAGACCGTGTCACC

ATCACTTGCCGGGCAAGTCAGGATATTGGGATGCTTTATTTTGGTACCAGCAGAAACCA

GGGAAAGCCCCTAAGGTCCTGATCTATTATTCTTCCATGTTGCAAAGTGGGGTCCCATCA

CGTTTCAGTGGCGGTGGATCTGGGACAGATTTCACTCTCACCATCAGCAGTCTGCAACCT

GAAGATTTTGCTACGTACTACTGTCAACAGCGGCATAGTACTCCTGCTACGTTCGGCCAA

GGGACCAAGGTGGAAATCAAACGG

TABLE 4-continued

Human Anti-CD40L VK Domain Encoding Nucleotide Sequences

BMS2h-87
(SEQ ID NO: 1350)
GACATCCAGATGACCCAGTCTCCATCCTCCCTGTCTGCATCTGTAGGAGACCGTGTCACC

ATCACTTGCCGGGCAAGTCAGGATATTGATGAGTCTTTAATGTGGTACCAGCAGAAACCA

GGGAAAGCCCCTAGGCTCCTGATCTATGGGGTGTCCTATTTGCAAAGTGGGGTCCCATCA

CGTTTCAGTGGCAGTGGATCTGGGACAGATTTCACTCTCACCATCAGCAGTCTGCAACCT

GAAGATTTCGCTACGTACTACTGTCAACAGCGGTGGAAGGCTCCTTTTACGTTCGGCCAA

GGGACCAAGGTGGAAATCAAACGG

BMS2h-88
(SEQ ID NO: 1351)
GACATCCAGATGACCCAGTCTCCATCCTCCCTGTCTGCATCTGTAGGAGACCGTGTTACC

ATCACTTGCCGGGCAAGTCAGGAGATTGTGGAGGATTTATATTGGTATCAGCAGAAACCA

GGGAAAGCCGCTAAGCTCCTGATCTATGGTGCGTCCTGGTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGACGCGTAGGCGTCCTTATACGTTCGGCCAA

GGGACCAAGGTGGAAATCAAACGG

BMS2h-89
(SEQ ID NO: 1352)
GACATCCAGATGACCCAGTCTCCAGCCTCCCTGTCTGCATCTGTAGGAGACCGTGTCACC

ATCACTTGCCGGGCAAGTCAGGATATTGATCCTATGTTAAGGTGGTACCAGCAGAAACCA

GGGAAAGCCCCTAAGCTCCTGATCTATGCGGGTTCCATTTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGACGCTGGTGACTCCTTATACGTTCGGCCAA

GGGACCAAGGTGGAAATCAAACGG

BMS2h-90
(SEQ ID NO: 1353)
GACATCCAGATGACCCAGTCTCCATCCTCCCTGTCTGCATCTGTAGGAGACCGTGTCACC

ATCACTTGCCGGGCAAGTCAGTCGATTTCGGATGCGTTATTTTGGTACCAGCAGAAACCA

GGGAAAGCCCCTAGGCTCCTGATCTATTATGGTTCCGTTTTGCAAAGTGGGGTCCCATCA

CGTTTCAGTGGCAGTGGATCTGGGACAGATTTCACTCTCACCATCAGCAGTCTGCAACCT

GAAGATTTTGCTACGTACTACTGTCAACAGCGTTTTCAGGAGCCTGTGACGTTCGGCCAA

GGGACCAAGGTGGAAATCAAACGG

BMS2h-91
(SEQ ID NO: 1354)
GACATCCAGATGACCCAGTCTCCATCCTCCCTGTCCGCATCTGTAGGAGACCGTGTCACC

ATCACTTGCCGGGCAAGTCAGCAGATTAGTGATGAGTTAAATTGGTATCAGCAGAAACCA

GGGAAAGCCCCTAAGCTCCTGATCTATGCTGTGTCCATTTTGCAAAGTGGGGTCCCATCA

CGTTTCAGTGGCAGTGGATGTGGGACAGATTTCACTCTCACCATCAGCAGTCTGCAACCT

GAAGATTTTGCTACGTACTACTGTCAACAGTGGTTGAGTTTTCCTTCGACGTTTGGCCAA

GGGACCAAGGTGGAAATCAAACGG

Example 1

Generation of Human Anti-CD40L Variable Domains BMS2h-2 through BMS2h-785

The following example describes the generation of the 2h lineage of anti-human CD40L variable domains, designated BMS2h-2 through BMS2h-785. Following recombinant expression of a repertoire of single immunoglobulin variable domains on the surface of phage, selection is performed by contacting the phage repertoire with immobilized target antigen, washing to remove unbound phage, and propagating the bound phage. This process is frequently referred to as "panning." It is applicable to the screening of single immunoglobulin variable domains, as well as other antibody fragments that can be expressed on a display library, e.g., scFv, Fab, and Fab'. Alternatively, phage may be pre-selected for the expression of properly folded member variants by panning against an immobilized generic ligand (e.g., protein A or protein L) that is only bound by folded members. This has the advantage of reducing the proportion of non-functional members, thereby increasing the proportion of members likely to bind a target antigen. Pre-selection with generic ligands is taught in WO 99/20749, for example. The screening of phage antibody libraries is generally described, for example, by Harrison et al., *Meth. Enzymol.* 267: 83-109 (1996).

Screening is commonly performed using purified antigen immobilized on a solid support, for example, plastic tubes or wells, or on a chromatography matrix, for example Sepharose™ (Pharmacia). Screening or selection can also be performed on complex antigens, such as the surface of cells (Marks et al., *BioTechnology* 11: 1145 (1993); de Kruif et al., *Proc. Natl. Acad. Sci. USA* 92: 3938 (1995)). Another alternative involves selection by binding biotinylated antigen in solution, followed by capture on streptavidin-coated beads. dAb Selection for Clone BMS2h-719 and BMS2h-7xx Series:

Three rounds of selection using decreasing concentrations of antigen (500 nM at round 1; 50 nM at round 2; 50 nM or 5 nM at round 3 depending on the library output used) were performed in parallel against biotinylated (1.2 moles biotin/ mole CD40L) human CD40L monomer triple mutant (T211 E, S222Y, H224K, [108-261] Construct #7) provided by Bristol-Myers Squibb. Phage from the naïve 4G and 6G Domantis dAb libraries were combined into the pools a) to g) indicated below before initiating selections:

a) 4G VH CDR3 lengths between 7-10 amino acids.
b) 4G VH CDR3 lengths between 11-15 amino acids.
c) 4G VH CDR3 lengths between 7-15 amino acids.
d) 4G VK
e) 6G VH CDR3 lengths between 7-9
f) 6G VH CDR3 lengths between 10-15
g) 6G VK Each round of selection involved adding the desired concentration of biotinylated CD40L to a mixture of 200 µl of phage (from one of the naïve library pools indicated above, or subsequent selection output phage) and 1000 µl of 2% MPBS (Phosphate Buffered Saline) containing 2% (w/v) Marvel [Premier Foods, UK]) and incubating at room temperature for 1 hour by mixing end-over-end. The biotinylated antigen phage complex was then captured by adding 100 µl of resuspended Dynabeads M-280 Streptavidin [Invitrogen, UK] and incubated for 5 minutes with mixing end-over-end at room temperature. The Dynabeads were then recovered using a KingFisher magnetic separator [Thermo Fisher Scientific, UK] and washed 7×1 ml PBST (PBS containing 0.1% (v/v) polyoxyethylenesorbitan 20 monolaurate [Sigma-Aldrich, UK]) followed by 1×1 ml PBS. Bound phage retained on the washed Dynabeads were eluted by incubation with 500 µl of trypsin-PBS (50 µl of 10 mg/ml trypsin [Sigma-Aldrich, UK] dissolved in 50 mM Tris-HCl pH 7.4, 1 mM CaCl$_2$ added to 450 µl PBS). The phage-containing solution was recovered and 250 µl used to infect 1.75 ml of logarithmic growth phase *E. coli* TG1 (at an OD$_{600}$ of 0.4) for 30 minutes at 37° C. The *E. coli* TG1 phage infected culture was centrifuged at 11,600 g in a micro centrifuge for 1 minute and the resulting cell pellet resuspended in 1 ml 2×TY (16 g Tryptone, 10 g Yeast Extract and 5 g NaCl in 1 liter, autoclaved for 15 minutes at 121° C.) and plated onto a 9 cm Petri dish containing TYE media supplemented with 15 µg/ml tetracycline. The plates were incubated overnight at 37° C. then 2 ml of 2×TY supplemented with 15% glycerol was added to each plate and cells loosened with a glass spreader and mixed thoroughly. Fifty microliters of the scraped bacteria was used to inoculate 50 ml of 2×TY supplemented with 15 µg/ml tetracycline and grown overnight at 37° C. with shaking at 250 rpm. The overnight culture was centrifuged at 3,300 g for 15 min to pellet the bacteria. To precipitate phage, 10 ml PEG/NaCl (20% Polyethylene glycol 8000, 2.5 M NaCl) was added to 40 ml supernatant. The phage/PEG solution was mixed and left on ice for 1 h, then spun at 3,300 g for 30 min at 4° C. and the supernatant discarded. The pellet was resuspended in 2 ml PBS and spun at 11,600 g for 10 min in a micro centrifuge to remove the remaining bacterial debris. The resultant supernatant containing phage was then used for the next round of selection against the appropriate concentration of biotinylated CD40L monomer triple mutant antigen.

Phage ELISA

Monoclonal phage ELISAs were carried out following selection rounds 2 and 3. All washes were performed using 3 washes of 250 µl PBST followed by 3 washes of 250 µl PBS. The plates were coated overnight at 4° C. with 50 µl/well of 1 µg/ml NeutrAvidin [Thermo Scientific, UK] in 0.2M carbonate-bicarbonate buffer, pH 9.4. The plates were washed and then blocked with 2% MPBS for 1 hour at room temperature. The plates were then washed and incubated with 50 µl/well of ~1.0 µg/ml biotinylated human CD40L monomer triple mutant in 2% MPBS. The plates were washed and 25 µl/well phage supernatants added to an equal volume of 2% MPBS and incubated for 1 hour at room temperature. The plates were washed and bound phage detected with 50 µl/well anti-M13-HRP conjugate [GE Healthcare, UK] diluted 1:5000 in 2% MPBS and incubated for 1 hour at room temperature. The plates were washed and the ELISA developed using 50 µl/well SureBlue 1-Component TMB MicroWell Peroxidase solution [KPL Inc, USA]. The colorimetric reaction was stopped by the addition of an equal volume of 1 M HCl and the ELISA plate read at 450 nm. Specific phage were identified by comparison to wells coated with NeutrAvidin but without biotinylated CD40L monomer triple mutant.

Recovery of dAb Genes from MidiPrep pDOM4 Plasmid

The dAb V-genes from the following round 3 outputs were recovered by DNA restriction enzyme digestion of the phage vector pDOM4:

a) 4G VH CDR3 lengths between 7-10 amino acids (50 nM antigen concentration).
b) 4G VH CDR3 lengths between 11-15 amino acids (50 nM antigen concentration).

c) 4G VH CDR3 lengths between 11-15 amino acids (5 nM antigen concentration).

d) 4G VH CDR3 lengths between 7-15 amino acids (50 nM antigen concentration).

e) 4G VK (50 nM antigen concentration).

f) 4G VK (5 nM antigen concentration).

g) 6G VH CDR3 lengths between 7-9 (50 nM antigen concentration).

h) 6G VH CDR3 lengths between 10-15 (5 nM antigen concentration).

Approximately 20 μg of MidiPrep [Qiagen, UK] DNA was digested with SalI and NotI as follows: 20 μl DNA (~1 μg/μl) was mixed with 1.5 μl SalI (20 U/μl) [NEB, UK] and 3 μl NotI (10 U/μl) [NEB, UK], 4 μl Buffer 3 [NEB, UK], 0.4 μl BSA (10 mg/ml) [NEB, UK] and tissue culture grade water [Sigma, UK] added to 40 μl. Samples were incubated for 5 hours at 37° C. in an air incubator following which the digested dAb genes were isolated by running the digestion mix on a 2% agarose gel [E-gel, Invitrogen, UK], the appropriate DNA bands excised and cleaned using a PCR purification kit [Qiagen, UK]. The purified V-genes were ligated into a SalI and NotI double digested pDOM5 expression vector.

Soluble dAb ELISA

Binding dAbs were identified as follows. Ninety-six individual colonies containing dAb V-genes cloned into the soluble dAb expression vector pDOM5 were picked from each output into 200 μl Terrific Broth containing OnEx Autoinduction media [Novagen, UK] and incubated overnight at 37° C. with shaking at 250 rpm in Costar 96 Well Cell Culture Clusters [Corning Incorporated, USA] sealed with a gas permeable adhesive plastic strip. The cultures were centrifuged to pellet the cells and the supernatants assayed by antigen binding ELISA for dAbs that bound to CD40L monomer triple mutant and IZ-CD40L mutant (CD40L containing an isoleucine zipper trimerization domain, supplied by Bristol-Myers Squibb). MaxiSorp 96 well immunoplates [Nunc, USA] were coated overnight at 4° C. with 50 μl/well of 1 μg/ml NeutrAvidin in 0.2 M carbonate-bicarbonate buffer, pH 9.4. All washes were as described for the phage ELISA. The plates were blocked for 1 hour at room temperature with 200 μl of PBS containing 1% Tween 20. The plate was then washed and incubated for 1 hour at room temperature with 50 μl/well of 1 μg/ml biotinylated human CD40L monomer triple mutant in PBST or 1 μg/ml biotinylated human IZ-CD40L mutant in PBST (both antigens supplied by Bristol-Myers Squibb). The ELISA plate was washed and dAb-containing culture supernatant clarified by centrifugation at 1,800 g for 10 min at 4° C., then added to the ELISA plate (30 μl/well) to which was added an equal volume of PBST. The plates were incubated for 1 hour at room temperature and then washed. Bound dAb was detected by adding 50 μl/well 9E10 [anti-myc IgG, Sigma-Aldrich, UK] diluted 1:2000 in PBST and incubating for 1 hour at room temperature; the ELISA plate was then washed and 50 μl/well anti-mouse Fc-HRP [Sigma-Aldrich, UK] diluted 1:2000 in PBST added and incubated for 1 hour at room temperature. The plates were washed and the ELISA developed by adding 50 μl/well Sure-Blue 1-Component TMB MicroWell Peroxidase solution [KPL Inc, USA] and the colour allowed to develop. The colourimetric reaction was stopped by the addition of an equal volume of 1 M HCl and the ELISA plate read at 450 nm. Antigen binding dAbs were identified by comparison of the signal intensity from human CD40L monomer triple mutant and human IZ-CD40L mutant wells with control wells not containing antigen.

Expression & Purification of dAb at 50 ml Scale

Unique dAbs were identified by DNA sequencing ELISA positive clones. The unique dAbs identified were expressed as follows in 250 ml baffled flasks, to which was added:
  a) 50 ml of Terrific Broth [Sigma-Aldrich, UK].
  b) 100 μg/ml carbenicillin [Sigma-Aldrich, UK].
  c) 1 drop of antifoam A204 [Sigma-Aldrich, UK].
  d) Novagen Overnight Express Autoinduction Kit [Novagen, UK].

A bacterial scrape from a fresh confluent 9 cm diameter agar plate or from a glycerol stock of the desired dAb clone was used to inoculate the Terrific Broth, then the flask sealed with Milliwrap PTFE membrane [Millipore, UK], and incubated for 48 hrs, 250 rpm shaking at 30° C. The bacterial overnight culture was clarified by centrifugation and the VH or VK dAb purified using Streamline Protein A [GE Healthcare, UK] or Protein L agarose [generated in-house] respectively. The resulting purified proteins were assayed by RBA to determine which clones could inhibit the binding of CD40L for CD40.

CD40L Bead Receptor Binding Assay

Inhibitory dAbs were initially identified by screening purified dAb in a CD40L bead receptor binding assay (RBA). Sphero streptavidin polystyrene beads (0.5% w/v, 6.7 μm diameter) [Saxon, Europe] were prepared and washed according to the manufacturer's instructions. The beads were then pelleted at 11,600 g for 1 minute, the supernatant discarded and the beads resuspended in 1 ml PBS by vortexing. The washing step was repeated twice more, the supernatant discarded and the beads resuspended in 1 ml (0.5 mg/ml) of biotinylated human IZ-CD40L in PBS and incubated overnight at room temperature with end-over-end rotation. Following incubation, the beads were pelleted and washed three times with 1 ml PBS as before and then resuspended in 0.5 ml PBS containing 0.1% bovine serum albumin (BSA). The antigen coated beads were then diluted 1:10 in PBS containing 0.1% BSA prior to use. The reagents for the RBA assay were added as follows to duplicate wells in a 384-well black sided clear bottomed FMAT plate [Applied Biosystems, UK]:
  a) 12.5 μl dAb protein or buffer control. The dAb titration starting concentration was typically 10 μM (final concentration) which was diluted 1:3.3 (i.e., 30 μl sample added to 70 μl PBS containing 0.1% BSA) to produce an 8-point titration effect curve.
  b) 12.5 μl CD40-Fc [supplied by Bristol-Myers Squibb, USA; lot CY24Feb06-1] at 0.2 μg/ml (for a final concentration of 0.05 μg/ml) diluted in PBS containing 0.1% BSA.
  c) 12.5 μl Mixture of mouse anti-human Fc [Sigma-Aldrich, UK] at 2 μg/ml (for a final concentration of 0.5 μg/ml) and goat anti-mouse Alexa Fluor 647 [Invitrogen, UK] at 1 μg/ml (for a final concentration of 0.25 μg/ml) diluted in PBS containing 0.1% BSA.
  d) 12.5 μl IZ-CD40L coated beads described above were added to the centre of the well so they did not disperse to the edge of the well.

Following addition of the reagents to the 384 well plate, it was incubated at room temperature for 6 hours in the dark and then read in an AB8200 FMAT system [Applied Biosystems, UK].

Example 2 dAb Selection for Clone BMS2h-572

Three rounds of selection using decreasing concentrations of antigen (300 nM at round 1; 30 nM at round 2; 3 nM at round 3) were performed in parallel against biotinylated (1.42 moles biotin/mole trimer) human isoleucine zipper-CD40L (IZ-hCD40L) provided by Bristol-Myers Squibb. Phage from the naïve 4G and 6G Domantis dAb libraries were combined into the pools a) to h) indicated below before initiating selections:
- a) 4G VH CDR3 lengths between 7-9 amino acids.
- b) 4G VH CDR3 lengths between 10-12 amino acids.
- c) 4G VH CDR3 lengths between 13-15 amino acids.
- d) 4G VK
- e) 6G VH CDR3 lengths between 7-9
- f) 6G VH CDR3 lengths between 10-12
- g) 6G VH CDR3 lengths between 13-15
- h) 6G VK Each round of selection involved adding the desired concentration of biotinylated CD40L to a mixture of phage (from one of the naïve library pools indicated above, or subsequent selection output phage) in 1000 µl of 2% MPBS (Phosphate Buffered Saline containing 2% (w/v) Marvel [Premier Foods, UK]) and incubating at room temperature for 1 hour by mixing end-over-end. The biotinylated antigen phage complex was then captured by adding 100 µl of resuspended Dynabeads M-280 Streptavidin [Invitrogen, UK](rounds 1 and 3) or 50 µl of M-280 tosyl activated Dynabeads (Invitrogen) that had been coupled with NeutrAvidin [Thermo Fisher Scientific, UK](round 2) and incubated for 5 minutes with mixing end-over-end at room temperature. The Dynabeads were then recovered using a KingFisher magnetic separator [Thermo Fisher Scientific, UK] and washed 7×1 ml PBST (PBS containing 0.1% (v/v) polyoxyethylenesorbitan 20 monolaurate [Sigma-Aldrich, UK]) followed by 1×1 ml PBS. Bound phage retained on the washed Dynabeads were eluted by incubation with 500 µl of trypsin-PBS (50 µl of 10 mg/ml trypsin [Sigma-Aldrich, UK] dissolved in 50 mM Tris-HCl pH 7.4, 1 mM $CaCl_2$ added to 450 µl PBS). The phage-containing solution was recovered and 250 µl used to infect 1.75 ml of logarithmic growth phase E. coli TG (at an $OD_{600}$ of 0.4) for 30 minutes at 37° C. The E. coli TG1 phage infected culture was centrifuged at 11,600 g in a micro centrifuge for 1 minute and the resulting cell pellet resuspended in 1 ml 2×TY (16 g Tryptone, 10 g Yeast Extract and 5 g NaCl in 1 liter, autoclaved for 15 minutes at 121° C.) and plated onto a 9 cm Petri dish containing TYE media supplemented with 15 µg/ml tetracycline. The plates were incubated overnight at 37° C. then 2 ml of 2×TY supplemented with 15% glycerol was added to each plate and cells loosened with a glass spreader and mixed thoroughly. Fifty microliters of the scraped bacteria was used to inoculate 50 ml of 2×TY supplemented with 15 µg/ml tetracycline and grown overnight at 37° C. with shaking at 250 rpm. The overnight culture was centrifuged at 3,300 g for 15 min to pellet the bacteria. To precipitate phage, 10 ml PEG/NaCl (20% Polyethylene glycol 8000, 2.5 M NaCl) was added to 40 ml supernatant. The phage/PEG solution was mixed and left on ice for 1 h, then spun at 3,300 g for 30 min at 4° C. and the supernatant discarded. The pellet was resuspended in 2 ml PBS and spun at 11,600 g for 10 min in a micro centrifuge to remove the remaining bacterial debris. The resultant supernatant containing phage was then used for the next round of selection against the appropriate concentration of biotinylated IZ-hCD40L.

Phage ELISA

Monoclonal phage ELISAs were carried out following selection rounds 2 and 3. All washes were performed using 3 washes of 250 µl PBST followed by 3 washes of 250 µl PBS. The plates were coated overnight at 4° C. with 50 µl/well of 1 µg/ml IZ-hCD40L in PBS. The plates were washed and then blocked with 2% MPBS for 1 hour at room temperature. The plates were washed and 25 µl/well phage supernatants added to an equal volume of 2% MPBS and incubated for 1 hour at room temperature. The plates were washed and bound phage detected with 50 µl/well anti-M13-HRP conjugate [GE Healthcare, UK] diluted 1:5000 in 2% MPBS and incubated for 1 hour at room temperature. The plates were washed and the ELISA developed using 50 µl/well SureBlue 1-Component TMB MicroWell Peroxidase solution [KPL Inc, USA]. The colorimetric reaction was stopped by the addition of an equal volume of 1 M HCl and the ELISA plate read at 450 nm. Specific phage were identified by comparison to wells that were not coated with antigen but otherwise identically treated.

Recovery of dAb Genes from pDOM4 Plasmid

The dAb V-genes from round 2 and 3 outputs were recovered by SalI and NotI restriction enzyme digestion of the phage vector pDOM4 and ligated into a SalI and NotI double digested pDOM5 expression vector.

Soluble dAb ELISA

Binding dAbs were identified as follows. Ninety-six individual colonies containing dAb V-genes cloned into the soluble dAb expression vector pDOM5 were picked from each output into 200 µl Terrific Broth containing OnEx Autoinduction media [Novagen, UK] and incubated overnight at 37° C. with shaking at 250 rpm in Costar 96 Well Cell Culture Clusters [Corning Incorporated, USA] sealed with a gas permeable adhesive plastic strip. The cultures were centrifuged to pellet the cells and the supernatants assayed by antigen binding ELISA for dAbs that bound to IZ-hCD40L. MaxiSorp 96 well immunoplates [Nunc, USA] were coated overnight at 4° C. with 50 µl/well of 1 µg/ml IZ-hCD40L in PBS. All washes were as described for the phage ELISA. The plates were blocked for 1 hour at room temperature with 200 µl of PBS containing 1% Tween 20. The ELISA plate was washed and dAb-containing culture supernatant clarified by centrifugation at 1,800 g for 10 min at 4° C., then added to the ELISA plate (30 µl/well) to which was added an equal volume of PBST. The plates were incubated for 1 hour at room temperature and then washed. Bound dAb was detected by adding 50 µl/well 9E10 [anti-myc IgG, Sigma-Aldrich, UK] diluted 1:2000 in PBST and incubating for 1 hour at room temperature; the ELISA plate was then washed and 50 µl/well anti-mouse Fc-HRP [Sigma-Aldrich, UK] diluted 1:2000 in PBST added and incubated for 1 hour at room temperature. The plates were washed and the ELISA developed by adding 50 µl/well SureBlue 1-Component TMB MicroWell Peroxidase solution [KPL Inc, USA] and the colour allowed to develop. The colorimetric reaction was stopped by the addition of an equal volume of 1 M HCl and the ELISA plate read at 450 nm. Antigen binding dAbs were identified by comparison of the signal intensity from IZ-hCD40L wells with control wells not containing antigen.

Example 3

Identification of Clones BMS2h-503-1, BMS2h-719-2, and BMS2h-572-6

BMS2h-503, BMS2h-719 and BMS2h-572 dAbs were subjected to error-prone affinity maturation to generate BMS2h-503, BMS2h-719 and BMS2h-572 lineages, respectively. This was performed using random mutagenesis where on average 3.6 amino acid changes were introduced per dAb. Phage libraries (average size $6 \times 10^8$) were selected using biotinylated monomeric and trimeric human CD40L with alternating streptavidin/neutravidin bead capture of the antigen (as described). Three rounds of selections using decreasing concentrations of antigen (100 nM at round 1; 10 nM at round 2; 1 nM at round 3) were performed. Sequencing was used to monitor diversity following each selection round. Selection outputs (round 2 selected on CD40L trimer for BMS2h-572; round 3 selected on CD40L trimer for BMS2h-503 and round 3 selected on CD40L monomer for BMS2h-719) were sub-cloned into soluble expression vector pDOM13 (no C terminal tag) (as described) and screened as monoclonal bacterial micro-culture supernatants by BIAcore for improved off-rates compared to parental clones on both monomeric and trimeric CD40L. Identified improved variants were DNA sequenced and unique dAbs expressed, purified and then assayed using the BMS2h bead RBA as well as cellular CD40L driven assays (as described). As a result, BMS2h-503-1 (sequence listed in TABLE 3), BMS2h-719-2 and BMS2h-572-6 dAbs (sequences listed in TABLE 1) were identified. Activities of these dAbs are listed in TABLE 5 below.

Formatting BMS2h-503-1, BMS2h-719-2 and BMS2h-572-6 as Fc Fusions

BMS2h-572-6, BMS2h-503-1 and BMS2h-719-2 dAbs were cloned into pDOM38 vector containing Fc tail derived from human IgG1 to create DMS0502, DMS0500 and DMS0501, respectively. BMS2h-572-6, BMS2h-503-1 and BMS2h-719-2 dAbs were also cloned into pDOM38 vector containing Fc tail derived from human IgG4 to create DMS0505, DMS0506 and DMS0504, respectively. The constructs were transiently expressed in HEK293 cells and the proteins were purified using Protein A. Purified Fc fusions were analysed by Biacore for binding to monomeric and trimeric CD40L as well as in various cell assays (as described).

Identification of Clones BMS2h-572-608, BMS2h-572-614 and BMS2h-572-619

BMS2h-572-6 dAb was subjected to affinity maturation using doped oligo approach. Four doped libraries were constructed for this dAb:
Library 1—5 residues in CDR1 diversified
Library 2—6 residues in CDR2 diversified
Library 3—13 residues in CDR2 diversified
Library 4—7 residues in CDR3 diversified
In each library, diversification was performed using nnS codons where n retained a large fraction of the parent base (85%) and split the rest between the equimolar amounts of the remaining three bases (5% each) and S stood for G or C. Phage libraries (average size $8 \times 10^8$) were selected using biotinylated monomeric and trimeric human CD40L with alternating streptavidin/neutravidin bead capture of the antigen (as described). Libraries 2 and 3 were pulled together during the selection process. Three rounds of selections using decreasing concentrations of antigen (50 nM at round 1; 5 nM at round 2; 1 nM at round 3 with 200 fold excess of competitor—non biotinylated CD40L trimer) were performed. Sequencing was used to monitor diversity following each selection round. Selection outputs (rounds 2 and 3) were sub-cloned into soluble expression vector pDOM13 (no C terminal tag) (as described) and screened as monoclonal bacterial micro-culture supernatants by BIAcore for improved off-rates compared to parental clones on both monomeric and trimeric CD40L. Identified improved variants were DNA sequenced and unique dAbs expressed, purified and then assayed using the BMS2h bead RBA as well as cellular CD40L driven assays (as described). As a result, BMS2h-572-608, BMS2h-572-614 and BMS2h-572-619 dAbs were identified.

Construction of clone BMS2h-572-633

Sequence analysis revealed that all of the amino acid differences between BMS2h-572-608 and the parental dAb BMS2h-572-6 were located in CDR1 and the differences between BMS2h-572-614 and parental dAb BMS2h-572-6 were located in CDR3. Both matured dAbs shared CDR2 with the parental dAb BMS2h-572-6. This created an opportunity to construct a combination mutant which had CDR1 of BMS2h-572-608 and CDR3 of BMS2h-572-614. Firstly, CDR1 region of BMS2h-572-608 was PCR amplified. Secondly, CDR2+CDR3 fragment of BMS2h-572-614 was PCR amplified. This was followed by SOE PCR assembly of the two fragments to create a combination mutant BMS2h-572-633. The assembled dAb PCR product was cloned into soluble expression vector pDOM13 (no C terminal tag), sequence verified, expressed, purified and then assayed using the BMS2h bead RBA as well as cellular CD40L driven assays (as described).

Formatting BMS2h-572-633 as Fc Fusion

BMS2h-572-633 dAb was cloned into pDOM38 vector containing Fc tail derived from human IgG1 to create DMS0507. The construct was transiently expressed in HEK293 cells and the protein was purified using Protein A. Purified Fc fusion was analysed by Biacore for binding to monomeric and trimeric CD40L as well as in various cell assays (as described).

Example 4

CD40L Activity Cell Assays

Anti-human CD40L dAbs were assayed functionally for their ability to antagonize CD40L activities. The CD40L activities tested were B cell proliferation and cytokine production by hCD40L-driven activation of primary monocytes-derived dendritic cells (DCs). Unless otherwise noted, all assays were performed in RPMI media supplemented with 10% fetal calf serum (FCS). The results of various assays, described in detail below, are shown in TABLE 5 and TABLE 6.
Soluble IZ-hCD40L-Driven Primary Human B Cell Proliferation:
$1 \times 10^5$ tonsillar human B cells were incubated with 0.6 µg/ml of IZ-hCD40L along with varying titration of dAb or mAb in a final volume of 200 µl/well in a 96-well round bottom plate. The plates were incubated at 37° C. for 72 hours following which thymidine ($^3$H, 0.5 µci/well) was added for 6 hours. B cell proliferation was quantified based on thymidine incorporation. All assays, unless otherwise noted, were performed in RPMI media supplemented with 10% fetal calf serum (FCS).
CHO-hCD40L-Driven Primary Human B Cell Proliferation:
CHO cells were transfected with human CD40L to generate a stable cell line expressing high levels of CD40L on the cell surface. CHO-CD40L cells were irradiated at 10,000 Rads before incubation with human B cells. 1×10⁵ tonsillar human B cells were incubated with 1×10³ CHO-CD40L cells (1:100 ratio of CHO-CD40L: human B cells) along with varying titration of dAb or mAb in a final volume of 200 µl/well in a 96-well round bottom plate. The plates were incubated at 37° C. for 72 hours following which thymidine (³H; 0.5 µci/well) was added for 6 hours. B cell proliferation was quantified based on thymidine incorporation. All assays, unless otherwise noted, were performed in RPMI media supplemented with 10% fetal calf serum (FCS).

Primary T Cell-Driven Human B Cell Proliferation:

T cells were isolated from human peripheral blood mononuclear cells (PBMCs) and enriched using via sheep red blood cell (SRBC) affinity. Enriched human T cells were cultured with PM-LCLs (EBV-transformed B cell line; irradiated at 10,000 Rads) at a 5:1 ratio (T:LCL) for 6 days at 37° C. to generate a population of allogeneic T cells. At day 6, the expanded T cells were isolated and irradiated at 3000 Rads, and then cultured (5×10⁴ T cells/well) with primary human tonsillar B cells (1×10⁵ B cells/well) at a 1:2 ratio in 96-well flat bottom plated coated with anti-CD3 mAb (OKT3). Varying titrations of dAbs/mAbs were added to each well; the final volume in each well was 200 µl. Test plates were incubated at 37° C. for 3 days. Human B cell proliferation was determined via the addition of thymidine (³H, 0.5 µci/well) to the cultures for the last 18 hours. All assays, unless otherwise noted, were performed in RPMI media supplemented with 10% fetal calf serum (FCS). In some instances, the supernatant was harvested and measured for the presence of IL-6.

CHO-hCD40L-Driven Activation of Primary Human Monocytes-Derived Dendritic Cells (DCs):

Human PBMCs were enriched for monocytes by depleting T cells via SRBC resetting. The monocyte-enriched PBMCs were cultured with 10 ng/ml GM-CSF and 5 ng/ml IL-4 in 6-well plates for six days at 37° C. The cultured plates were replenished with fresh media (with GM-CSF and IL-4) on days 2 and 5. The immature DCs were used in cell assays on day 6. 8×10⁴ immature DCs were cultured with 4×10³ CHO-hCD40L cells (irradiated at 10,000 Rads) along with varying titrations of dAbs/mAbs in a 96-well flat bottom plate. After 24 hours, supernatants were harvested and tested for the presence of various cytokines (IL-12, TNF, IL-23). DC activation was determined by the levels of cytokine production. All assays, unless otherwise noted, were performed in RPMI media supplemented with 10%0/fetal calf serum (FCS).

TABLE 5

Potency of Monomeric dAb Molecules in Various Primary Cell Assays

| Clone | hIZCD40L-driven Human B Cell Proliferation EC50 (nM) | CHO-hCD40L-driven Human B Cell Proliferation EC50 (nM) | T-B cell MLR EC50 (nM) | CHO-hCD40L-driven DC Activation IL-12 EC50 (nM) |
|---|---|---|---|---|
| 2h116-13 | 130.0 ± 40.0 | 1300.0, 700.0 | | 888.0, >2000.0, 1000.0 |
| 2h116-1312 | 23.0 ± 3.0 | 530.0 ± 300.0 | 234 ± 46 | 112.0 ± 47.0 |
| 2h116-1313 | 29.0 ± 4.0 | 211.0, 334.0 | 258 ± 79 | 136.0 ± 51.0 |
| 2h116-1314 | 41.0 ± 10.0 | 1300.0, 4400.0 | 1687 ± 1150 | 664.0 ± 353.0 |
| 2h116-1319 | 180.0 ± 57.0 | >7000.0 | | |
| 2h116-1320 | 20.0 ± 7.0 | 138.0 ± 60.0 | 191 ± 72 | 32.0 ± 10.0 |
| 2h437 | 5700.0 ± 1800 | | | |
| 2h437-4 | 203.0 ± 90.0 | >7000.0 | | 1329.0 ± 412.0 |
| 2h492 | >7000.0 | | | |
| 2h492-3 | 1100.0 ± 400.0 | >7000.0 | | |
| 2h492-4 | 1700.0 ± 900.0 | >7000.0 | | |
| 2h492-5 | 2300.0 ± 700.0 | | | |
| 2h492-6 | 6300.0 ± 1400.0 | | | |
| 2h492-7 | 1900.0 ± 600.0 | | | |
| 2h494 | 6100.0 ± 1200.0 | | | |
| 2h494-2 | 4800.0 ± 2300.0 | | | |
| 2h494-3 | >7000.0 | | | |
| 2h494-4 | 590.0 ± 250.0 | >7000.0 | | |
| 2h494-6 | 2000.0 ± 2100.0 | >7000.0 | | |
| 2h503 | 4200.0 ± 316.0 | >7000.0 | | |
| 2h503-1 | 24.0 ± 2.0 | 2300.0 ± 700.0 | | 756.0 ± 333.0 |
| 2h503-104 | 16.0, 19.0 | | | |
| 2h503-2 | 44.0 ± 6.0 | 3000.0 ± 1000.0 | | 1562.0 ± 96.0 |
| 2h572 | >7000.0 | | | |
| 2h572-6 | 208.0 ± 73.0 | >7000.0 | >7000.0 | >2000.0, 608.0 ± 260.0 |
| 2h572-604 | 254.0, 354.0 | >700.0 | | 387.0 |
| 2h572-608 | 96.0 ± 19.0 | | >7000.0 | 152.0 ± 61.0 |
| 2h572-610 | 109.0 ± 34.0 | | >7000.0 | 207.0 ± 87.0 |
| 2h572-614 | 93.0 ± 53.0 | | >7000.0 | 135.0 ± 54.0 |
| 2h572-616 | 204.0, 340.0 | | >7000.0 | 608.0 ± 136.0 |
| 2h572-617 | 157.0, 189.0 | | >7000.0 | 338.0 ± 101.0 |
| 2h572-619 | 90.0 ± 62.0 | 421.0, 1496.0 | >7000.0 | 188.0 ± 41.0 |
| 2h572-622 | 301.0, 293.0 | | >7000.0 | 281.0 ± 127.0 |
| 2h572-623 | 181.0, 261.0 | | >7000.0 | 280.0 ± 73.0 |
| 2h572-630 | 103.0 ± 71.0 | | | 246.0 ± 240.0 |
| 2h572-631 | 108.0 ± 77.0 | | | 230.0 ± 200.0 |
| 2h572-632 | 117.0 ± 91.0 | | | 241.0 ± 190.0 |
| 2h572-633 | 20.0 ± 15.0 | | | 53.0 ± 60.0 |
| 2h572-634 | 31.0 ± 18.0 | | | 77.0 ± 67.0 |
| 2h572-635 | 29.0 ± 19.0 | | | 52.0 ± 26.0 |
| 2h572-9 | 324.0, 243.0 | | | >2000.0 |

TABLE 5-continued

Potency of Monomeric dAb Molecules in Various Primary Cell Assays

| Clone | hIZCD40L-driven Human B Cell Proliferation EC50 (nM) | CHO-hCD40L-driven Human B Cell Proliferation EC50 (nM) | T-B cell MLR EC50 (nM) | CHO-hCD40L-driven DC Activation IL-12 EC50 (nM) |
|---|---|---|---|---|
| 2h572-11 | 140.0 ± 33.0 | >7000.0 | | 671.0 ± 165.0 |
| 2h572-12 | 79.0, 76.0 | | | 225.0, >2000.0 |
| 2h572-14 | 134.0 ± 12.0 | >7000.0 | | 882.0 ± 310.0 |
| 2h572-15 | 168.0 ± 67.0 | >7000.0 | | 876.0 ± 391.0 |
| 2h572-22 | 357.0, 305.05 | | | |
| 2h702 | >7000.0 | | | |
| 2h703 | >7000.0 | | | |
| 2h706 | >7000.0 | | | |
| 2h707 | >7000.0 | | | |
| 2h710 | >7000.0 | | | |
| 2h712 | >7000.0 | | | |
| 2h717 | >7000.0 | | | |
| 2h719 | 600.0 ± 640.0 | | | 134.0, 646.0 |
| 2h719-2 | 82.0 ± 39.0 | >7000.0 | | 196.0 ± 150.0 |
| 2h719-202 | 29.0 ± 12.0 | | | 79.0 ± 29.0 |
| 2h719-203 | 81.0, 96.0 | | | |
| 2h719-213 | 62.0, 98.0 | | | |
| 2h719-214 | 66.0, 89.0 | | | |
| 2h719-215 | 92.0, 91.0 | | | |
| 2h719-218 | 57.0, 60.0 | | | |
| 2h719-225 | 253.0, 198.0 | | | 176.0 ± 84.0 |
| 2h719-226 | 164.0, 247.0 | | | 812.0 ± 53.0 |
| 2h719-12 | 358.0 ± 159.0 | | | 266.0 ± 66.0 |
| 2h719-13 | 50.0 ± 8.0 | 659.0, 683.0, 4450.0, 1750.0 | | 219.0 ± 88.0 |
| 2h719-17 | 132.0 ± 50.0 | 236.0, 268.0 | | 113.0 ± 49.0 |
| 2h719-19 | 138.0 ± 31.0 | 202.0, >7000.0, >7000.0, 3800.0, 5400.0 | | 184.0 ± 99.0 |
| 2h722 | >7000.0 | | | |
| 2h723 | >7000.0 | | | |
| 2h725 | 6400.0 ± 1200.0 | | | |
| 2h725-2 | >7000.0 | | | |
| 2h725-9 | >7000.0 | | | |
| 2h725-19 | >7000.0 | | | |
| 2h726 | >7000.0 | | | |
| 2h730 | >7000.0 | | | |
| 2h731 | 5800.0 ± 2500.0 | | | |
| 2h744 | >7000.0 | | | |
| 2h745 | 6400.0, 3500.0, >7000.0 | | | |
| 2h745-1 | >7000.0 | | | |
| 2h745-2 | >7000.0 | | | |
| 2h745-9 | >7000.0 | | | |
| 2h745-13 | >7000.0 | | | |
| 2h745-14 | >7000.0 | | | |
| 2h746 | >7000.0 | | | |
| 2h747 | >7000.0 | | | |
| 2h752 | >7000.0 | | | |
| 2h754 | 6600.0 ± 900.0 | | | |
| 2h757 | 6400.0 ± 800.0 | | | |
| 2h758 | 5900.0 ± 1500.0 | | | |
| 2h758-1 | >7000.0 | | | |
| 2h758-2 | >7000.0 | | | |
| 2h758-3 | >7000.0 | | | |
| 2h758-4 | >7000.0 | | | |
| 2h758-5 | >7000.0 | | | |
| 2h765 | >7000.0 | | | |
| 2h766 | >7000.0 | | | |
| 2h774 | >7000.0 | | | |
| 2h775 | >7000.0 | | | |
| 2h780 | >7000.0 | | | |
| 2h781 | >7000.0 | | | |
| 2h782 | >7000.0 | | | |
| 2h783 | >2000.0 | | | |
| 2h784 | >4700.0 | | | |
| 2h785 | 3700.0, >7000.0 | | | |

TABLE 6

Potency of Fc*-formatted Molecules in Various Primary Cell Assays

| Clone | hIZCD40L-driven Human B Cell Proliferation EC50 (nM) | CHO-hCD40L-driven Human B Cell Proliferation EC50 (nM) | T-B cell MLR EC50 (nM) | T-B cell MLR IL-6 EC50 (nM) | CHO-hCD40L-driven DC Activation IL-12 EC50 (nM) | CHO-hCD40L-driven DC Activation IL-6 EC50 (nM) | CHO-hCD40L-driven DC Activation IL-23 EC50 (nM) | CHO-hCD40L-driven DC Activation TNF EC50 (nM) |
|---|---|---|---|---|---|---|---|---|
| 2h116-1320-Fc | 13.0 ± 2.0 | >130.0 | 244.0 ± 112.0 | | 14.0 ± 11.0 | | | |
| 2h503-1 Fc | 4.0 ± 0.5 | 60.0 ± 20.0 | 45 ± 6 | | 2.8 ± 2.0 | | | |
| 2h503-1 IgG1 | 4.5 ± 1.0 | 67.0 ± 40.0 | 39.5 ± 12.04 | | 1.4 ± 0.7 | | | |
| 2h503-1 IgG4 | 2.5 ± 1.0 | 69.0 ± 50.0 | 48.3 ± 8.8 | | 18.1 ± 6.4 | | | |
| 2h572-6 Fc | 0.6 ± 0.4 | 3.0 ± 1.0 | 1.9 ± 0.7 | | 0.22 ± 0.18 | | | |
| 2h572-6 IgG1 | 1.0 ± 0.4 | 10.0 ± 5.0 | 3.1 ± 1.4 | 2.9 ± 1.7 | 0.58 ± 0.36 | | | |
| 2h572-6 IgG4 | 0.9 ± 0.2 | 11.0 ± 5.0 | 3.2 ± 1.5 | 1.3 ± 0.5 | 1.1 ± 0.5 | | | |
| 2h572-6-CT Long Fc | 1.0 ± 0.5 | 6.0 ± 6.0 | 13.6 ± 9.2 | 8.1 ± 3.1 | 3.0 ± 1.9 | | | |
| 2h572-633 Fc | 3.5 ± 0.6 | 3.0 ± 3.0 | 0.15 ± 0.02 | 0.11 ± 0.02 | 0.34 ± 0.17 | | | |
| 2h572-634 Fc | 3.0 ± 0.0 | 3.5 ± 3.0 | 0.23 ± 0.08 | 0.19 ± 0.03 | 0.42 ± 0.05 | | | |
| 2h572-635 Fc | 2.0 ± 0.8 | 2.5 ± 1.0 | 0.16 ± 0.09 | 0.11 ± 0.02 | 0.445 ± 0.14 | | | |
| 2h572-619-Ctshort Fc | 1.5 ± 0.6 | 2.0 | 0.40 ± 0.1 | 0.3 ± 0.07 | 1.8 ± 1.3 | | | |
| 2h572-619-Ctlong Fc | 1.6 ± 0.5 | 2.0 ± 1.0 | 0.72 ± 0.45 | 0.43 ± 0.12 | 1.4 ± 0.6 | 1.5 ± 0.36 | 1.5 ± 0.46 | 2.0 ± 0.7 |
| 2h572-619-N297Qshort Fc | 0.9 ± 0 | 1.0 ± 0.6 | 0.226, 0.216 | 0.1, 0.1 | 1.2 ± 0.6 | | | |
| 2h572-619-N297Qlong Fc | 0.98 ± 0.05 | 2.0 ± 0.0 | 0.480, 0.474 | 0.22, 0.11 | 1.1 ± 0.23 | | | |
| 2h572-608-N297Qshort Fc | 1.0 ± 0.05 | 2.0 ± 0.0 | | | 0.93 ± 0.4 | | | |
| 2h572-608-CT Long Fc | 2.0 ± 1.0 | 2.0 ± 1.0 | 0.468 ± 0.156 | 0.38 ± 0.06 | 1.6 ± 0.74 | | | |
| 2h572-614-CT Long Fc | 2.0 ± 1.0 | 2.0 ± 0.5 | 0.283 ± 0.038 | 0.25 ± 0.02 | 1.4 ± 0.68 | | | |
| 2h572-633-CT Long Fc | 3.0 ± 0.7 | 1.0 ± 1.0 | 0.174 ± 0.077 | 0.13 ± 0.07 | 1.9 ± 1.3 | 1.3 ± 0.3 | 1.2 ± 0.3 | 1.7 ± 0.43 |
| 2h572-633-CT-Fc SP5 | 5.0 ± 0.5 | 1.0 ± 0.5 | 0.161 ± 0.053 | 0.13 ± 0.04 | 2.3 ± 1.5 | 1.5 ± 0.7 | | 2.9 ± 1.3 |
| 2h572-634-CT Long Fc | 2.0 ± 1.0 | 1.0 ± 0.6 | 0.162 ± 0.029 | 0.13 ± 0.02 | 1.5 ± 0.91 | | | |
| 2h572-635-CT Long Fc | 3.0 ± 1.0 | 2.0 ± 0.6 | 0.149 ± 0.014 | 0.13 ± 0.01 | 1.6 ± 0.93 | | | |
| 2h719-2 Fc | 1.0 ± 0 | 0.7 ± 0.4 | 6 ± 1.4 | | 0.13 ± 0.08 | | | |
| 2h719-2 IgG1 | 1.0 ± 0.5 | 6.0 ± 0.3 | 13.8 ± 10.6 | 2.2 ± 1.3 | 0.35 ± 0.23 | | | |
| 2h719-2 IgG4 | 1.5 ± 0.6 | 16.0 ± 13.0 | 15.9 ± 10.9 | 2.1 ± 0.7 | 1.1 ± 0.48 | | | |
| 2h719-202-N297Qshort Fc | 1.8 ± 0.5 | 1.7 ± 0.7 | | | 0.66 ± 0.26 | | | |
| 2h719-202-CT Long Fc | 3.0 ± 1.0 | 2.5 ± 0.6 | 1.7 ± 0.7 | 1.3 ± 0.3 | 3.1 ± 2.0 | | | |

*FIG. 3 provides sequences of various Fc domains. FIG. 4 shows examples of vaious Fc-formatted dAbs.

Example 5

Binding Kinetics and CD40L Affinity of Various Antibodies

BMS-986004 is a dimeric fusion protein, composed of a modified Fc fragment of IgG1 linked to the C-terminus of the dAb BMS2h-572-633. Surface plasmon resonance (SPR) was used to characterize the kinetics and affinity of BMS-986004 or the monovalent component domain antibody BMS2h-572-633 binding to CD40L. The BMS-986004 values were compared to those for the benchmark antibodies 5c8-IgG1 and 5c8-CT and the monovalent component 5c8 FAB fragment. The SPR experiments utilized a hCD40L construct containing an N-terminal isoleucine zipper motif (IZ-hCD40L) which facilitates the specific assembly of the CD40L molecule into the native trimeric form. A biotinylated version of IZ-hCD40L (biot-IZ-hCD40L) with equivalent binding activity was also utilized for some SPR experiments.

The monovalent BMS2h-572-633 domain antibody binds biot-IZ-hCD40L with a Kd of 7.8 nM, compared to an affinity of 5.4 nM for the monovalent 5c8 FAB fragment, TABLE 7.

Because BMS-986004 is bivalent, and the IZ-hCD40L target is trivalent, the SPR binding data are influenced by avidity regardless of whether CD40L target is on the chip surface or in solution. To estimate the avidity-influenced binding affinity, the SPR data for BMS-986004 binding to a biot-IZ-hCD40L surface was fitted to a 1:1 Langmuir model, suggesting a dissociation constant of less than 1 nM, TABLE 7. Similar results were obtained for 5c8-IgG1 and 5c8-CT.

TABLE 7

IZ-hCD40L kinetic and affinity values as determined using SPR (Biacore)

| Anti-CD40L Ab | Temperature (° C.) | Model | ka (M-1s-1) | kd (s-1) | Kd (nM) |
|---|---|---|---|---|---|
| BMS-986004 | 25 | 1:1 Langmuir | 2.3E+06* | 2.6E-04* | 0.11* |
| 2h572-633 | 25 | 1:1 Langmuir | 1.0E+06 | 8.1E-03 | 7.8 |
| 5c8-IgG1 | 25 | 1:1 Langmuir | 5.4E+05* | 2.3E-04* | 0.42* |
| 5c8-CT | 25 | 1:1 Langmuir | 5.8E+05* | 1.3E-04* | 0.22* |

TABLE 7-continued

IZ-hCD40L kinetic and affinity values as determined using SPR (Biacore)

| Anti-CD40L Ab | Temperature (° C.) | Model | ka (M−1s−1) | kd (s−1) | Kd (nM) |
|---|---|---|---|---|---|
| 5c8 FAB fragment | 25 | 1:1 Langmuir | 1.4E+05 | 7.6E−04 | 5.4 |

*Value is influenced by avidity due to analyte bivalency.

Figure 5:
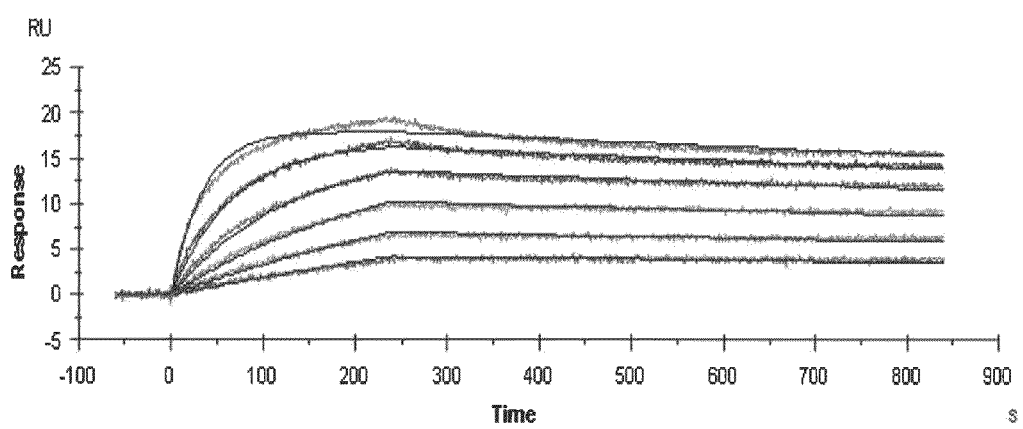
FIG. 5 depicts SPR sensorgram data for the binding of 12.5-0.39 nM BMS-986004 (2:1 dilution series) to biot-IZ-hCD40L captured on a streptavidin SPR sensor chip at 25° C. Colored lines show the double-referenced sensorgram data, and black lines show the 1:1 Langmuir fit to the data, with an avidity-influenced apparent Kd value of 0.11 nM.

FIG. 5 shows SPR sensorgram data for the binding of 12.5-0.39 nM BMS-986004 (2:1 dilution series) to biot-IZ-hCD40L captured on a streptavidin SPR sensor chip at 25° C. Colored lines show the double-referenced sensorgram data, and black lines show the 1:1 Langmuir fit to the data, with an avidity-influenced apparent Kd value of 0.11 nM.

Figure 6:
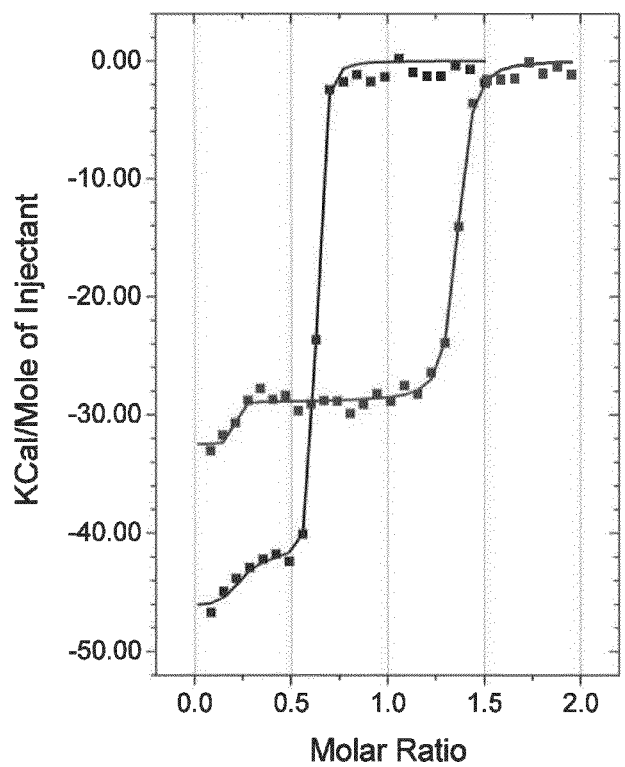
FIG. 6 shows ITC data for titrations of 19 µM IZ-hCD40L into 2 µM BMS-986004 (black) or 18 µM BMS-986004 into 2 µM IZ-hCD40L (blue). The molar ratio (apparent stoichiometry) is defined per mole of IZ-hCD40L trimer and per mole of bivalent BMS-986004 Fc-dimer. Molar ratio values obtained as the equivalence points on the abscissa suggest more than one mole of BMS-986004 can bind per mole of IZ-hCD40L trimer; however, an exact structural model for the complex cannot be determined from the ITC data alone. Squares represent the integrated heat of binding data and solid lines represent the best fit to a "2 sets of sites model."

The affinity and thermodynamics of BMS-986004 binding to CD40L were also characterized in solution using isothermal titration calorimetry (ITC) at temperatures ranging from 15-37° C. These data suggested the presence of multiple thermodynamically distinct binding modes (FIG. 6) with Kd values for the different modes beyond the high-affinity limit of detection (Kd<2 nM) (TABLE 8), consistent with the SPR data. The affinity of the monovalent 5c8 FAB fragment for IZ-hCD40L as determined by ITC (3.5 nM) was also consistent with the value determined by SPR.

TABLE 8

IZ-hCD40L affinity as determined using ITC

| Molecule in the ITC syringe | Molecule in the ITC cell | Kd (nM) |
|---|---|---|
| BMS-986004 | IZ-hCD40L | <2 |
| 5c8-CT | IZ-hCD40L | <2 |
| IZ-hCD40L | BMS-986004 | <2 |
| IZ-hCD40L | 5c8-CT | <2 |
| IZ-hCD40L | 5c8 FAB fragment | 3.5 |

Example 6

Fc receptor Affinity of Various Antibodies

The Fc-domain of BMS-986004 (termed "CT") was engineered from a wild type IgG1 Fc domain to retain the ability to bind FcRn, but to disrupt the binding to Fcγ receptors. To confirm that the engineered molecule has the desired Fc receptor binding profile, the binding affinities of BMS-986004 for human FcRn, and the human Fcγ receptors CD64 (FcγRI), CD32a (FcγRIIa), CD32b/c (FcγRIIb/c); CD16a (FcγRIIIa), CD16b (FcγRIIIb) were measured using SPR, in comparison to 5c8-IgG1 and 5c8-CT. For these experiments, BMS-986004 was captured via the domain antibody domains on a biot-IZ-hCD40L sensor surface, and the soluble Fc receptor proteins were tested for binding to the exposed Fc domain. Likewise, 5c8-IgG1 and 5c8-CT were captured on a biot-IZ-hCD40L surface via the FAB domains, with soluble FcR binding.

BMS-986004 bound FcRn with Kd of 670 nM at pH 6.0 which is the relevant pH for binding within the endosome, TABLE 9. However, binding was significantly reduced (Kd>5000 nM) at neutral pH suggesting efficient release of from FcRn under these conditions. BMS-986004 bound CD64 with a Kd of 0.6 nM, and had a statistically weak affinity for CD32a, CD32b/c, CD16a and CD16b (Kd>3000 nM). Both 5c8-IgG1 and 5c8-CT had a similar FcRn affinity as BMS-986004. 5c8-CT, which has the identical "CT" Fc region as BMS-986004, also had a similar FcγR binding properties as BMS-986004, whereas 5c8-IgG1, which has a wild type IgG1 Fc domain, bound more strongly to FcγRs, TABLE 9.

TABLE 9

Fc receptor affinity as determined using SPR (Biacore).

| Sample | pH | BMS-986004 Kd (nM) | 5c8-IgG1 Kd (nM) | 5c8-CT Kd (nM) |
|---|---|---|---|---|
| hFcRn | 6 | 670 | 590 | 720 |
| hFcRn | 7.1 | >5000 | >5000 | >5000 |
| CD64 | 7.1 | 0.6 | <0.05 | 0.9 ± 0.4 |
| CD32a | 7.1 | >3000 | ~$10^{-7}$M* | >3000 |
| CD32b/c | 7.1 | >3000 | >3000 | >3000 |
| CD16a | 7.1 | >3000 | 240 ± 40 | >3000 |
| CD16b | 7.1 | >3000 | >3000 | >3000 |

*CD32a binding to 5c8-IgG1 was biphasic. Kd was estimated as ~$10^{-7}$M based on steady state fit to dominant binding even. This Kd is in range of literature reported KD for CD32a binding to IgG1.

Example 7

In-Vitro Cell-Based Assays

The potency of BMS-986004 was evaluated in various primary immune cell assays to ensure robust potency across different cell types. The primary human B cell proliferation assays were conducted two ways, as described in detail above in Example 4: (1) recombinant CD40L trimer was used to drive B cell proliferation; and (2) CHO cells expressing CD40L on the membrane (CHO-CD40L) were utilized to induce B cell proliferation. The utility of CHO-CD40L cells was particularly important to ensure that signals from membrane-bound CD40L were inhibited equally well when compared to the soluble CD40L trimer. The CHO-CD40L cells were also used to drive the activation of primary human DCs differentiated from culturing PBMC-derived monocytes in presence of GM-CSF and IL-4. Similarly, the T-B MLR assay measured B cell activation driven by CD40L present on activated T cells. In all of the above described primary assays, BMS-986004 was equipotent to the benchmark 5c8 mAb: potencies ranged from signal-digit nM to sub-nM, depending on the assay (TABLE 10).

TABLE 10

Potency of BMS-986004 in Various Primary Cell Assays

| mAb/dAb-Fc | Trimer B cell Assay EC50 (nM) | CHO-CD40L B Cell Assay EC50 (nM) | T-B MLR EC50 (nM) | T-B MLR IL-6 EC50 (nM) | CHO-CD40L DC Assay IL-12 EC50 (nM) | CHO-CD40L DC Assay IL-6 EC50 (nM) | CHO-CD40L DC Assay TNF-a EC50 (nM) |
|---|---|---|---|---|---|---|---|
| 5c8 | 8.0 ± 3.0 | 2.0 ± 2.0 | 0.54 ± 0.37 | 0.23 ± 0.09 | 2.0 ± 1.5 | | |
| 5c8-IgG1 | 5.0 ± 1.0 | 2.0 ± 2.0 | 0.34 ± 0.13 | 0.21 ± 0.06 | 0.92 ± 0.94 | 0.73 ± 0.5 | 2.3 ± 1.3 |
| BMS-986004 | 5.0 ± 0.5 | 1.0 ± 0.5 | 0.16 ± 0.05 | 0.13 ± 0.04 | 3.1 ± 1.6 | 1.9 ± 0.6 | 3.6 ± 1.1 |

Example 8

Assessment of Whole Blood Receptor Occupancy (RO)

A receptor occupancy method was developed to measure CD40L target engagement by BMS-986003 in cynomolgus whole blood samples and, subsequently, in BMS-986004 in human whole blood samples. BMS-986003 is a dAb which shares the same amino acid sequence as BMS-986004, except for a non-native glycine residue at its amino-terminus.

Occupancy is measured on CD4+ T cells by flow cytometry using an anti-CD40L mAb that competes for binding to CD40L with BMS-986003/BMS-986004, and is cross-reactive with human and cynomolgus CD40L. In the presence of bound dAb, the anti-CD40L detection mAb is blocked from binding to CD40L in a concentration-dependent manner, providing a measure of target occupancy. Given that basal CD40L is expressed at low levels on resting T cells in peripheral blood, RO was assessed in both unstimulated blood samples and in samples where phytohemagglutinin (PHA) was used to induce up-regulation of CD40L on the T cell surface. Binding potency curves were generated following ex vivo whole blood treatment with BMS-986003 and BMS-986004. The average $EC_{50}$ and $EC_{90}$ values obtained are shown in TABLE 11.

TABLE 11

Binding Potency of BMS-986003 and BMS-986004 on CD4+ T-cells in ex vivo Whole Blood Receptor Occupancy Assay

|  | n | Average $EC_{50}$, nM | Average $EC_{90}$, nM |
|---|---|---|---|
| BMS-986003 |  |  |  |
| Human (basal) | 1 | 0.9 | 3 |
| Human (PHA-induced) | 6 | 0.8 | 9 |
| Cyno (basal) | 3 | 0.6 | 3 |
| Cyno (PHA-induced) | 3 | 0.4 | 2 |
| BMS-986004 |  |  |  |
| Human (basal) | 3 | 0.4 | 3 |
| Human (PHA-induced) | 3 | 0.7 | 5 |

The target binding potency in whole blood for BMS-986003 and BMS-986004 closely correlates between human and cynomolgus monkey. The $EC_{50}$ values for BMS-986003 and BMS-986004 are also similar when bound to basal and PHA-induced CD40L. Additionally, these values are comparable to those obtained in human in vitro cell based assays (see TABLE 10). Based on the measured $EC_{90}$ values, full target saturation in peripheral blood should be achieved at concentrations ≤10 nM.

To support the preclinical PK/PD profile of BMS-986003 and BMS-986004, RO was assessed in both the cynomolgus KLH study (immunization with keyhole limpet hemocyanin) with BMS-986003 and the IV bridging study with BMS-986004. Further details of these findings can be found in Examples below.

Example 9

In Vivo Pharmacology

To show efficacy of a CD40L dAb in mouse disease models, a mouse CD40L dAb 2m126-24 was formatted with mouse IgG1 Fc with D265A point mutation to further tower the Fc effector function. This mouse surrogate dAb 2m126-24-Fc shows potency comparable to BMS-986004 and MR-1, a hamster anti-mouse CD40L antibody (TABLE 12).

TABLE 12

In vitro Potency Comparison

|  | mAb/dAb-Fc | Trimer B cell Assay $EC50$ (nM) | CHO-CD40L B cell Assay $EC50$ (nM) | CHO-CD40L DC Assay IL-6 $EC50$ (nM) |
|---|---|---|---|---|
| Human | 5cB | 8.0 ± 3.0 | 2.0 ± 2.0 |  |
|  | BMS-986004 | 5.0 ± 0.5 | 1.0 ± 0.5 | 1.9 ± 0.6 |
| Mouse | 2m126-24-Fc | 4.7 ± 0.9 | 0.4 ± 0.06 | 0.5 ± 0.2 |
|  | MR-1 (mAb) | 1.7 ± 0.4 | 0.6 ± 0.2 | 0.6 ± 0.3 |

Inhibition of KLH Induced Antibody Response by the Mouse CD40L dAb

Figure 7:
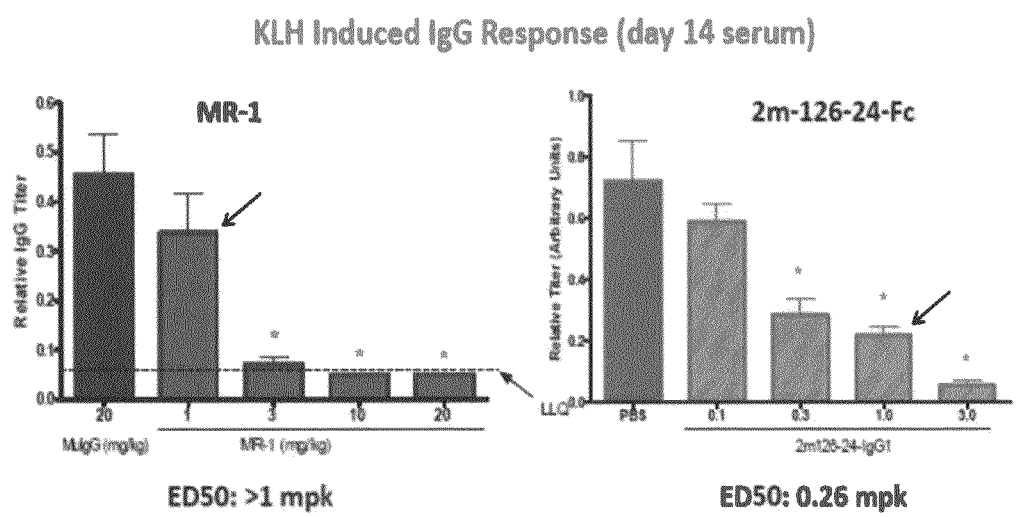
FIG. 7 shows in vivo efficacy of mouse CD40L surrogate dAb-Fc (KLH-induced antibody response.

Female BALB/c mice were injected intraperitoneally (i.p.) with 250 μg KLH on day 0. Mice were dosed subcutaneously (s.c.) with MR-1 or BMS-2m-126-24-Fc at indicated doses on day −1 and day 6. Blood was collected and the serum was analyzed for anti-KLH IgM on day 7 and IgG on day 14 by ELISA. Serum from BALB/c mice collected on day 14 after immunization with KLH was pooled and used as a positive comparator, and the data is expressed as a ratio of the titre of the test serum to the titre of the pooled BALB/c serum. As shown in FIG. 7, BMS-2m-126-24-Fc demonstrated a dose dependent suppression of IgG titers with maximal effect shown at 3 mg/kg, with ED50 calculated to be 0.26 mg/kg. Both the CD40L dAb and the antibody were tested at 1 mg/kg, showing 70% vs. 30% reduction in IgG response, respectively. Similar exposure of the dAb and the antibody were observed at 1 mg/kg, suggesting that the dAb is slightly more potent than the antibody at suppressing KLH-induced IgG response. In conclusion, the CD40L dAb has demonstrated at least the same level of efficacy as the anti-CD40L antibody at inhibiting a T cell dependent antibody response.

Inhibition of TNBS-induced Colitis by the Mouse CD40L dAb

Figure 8:
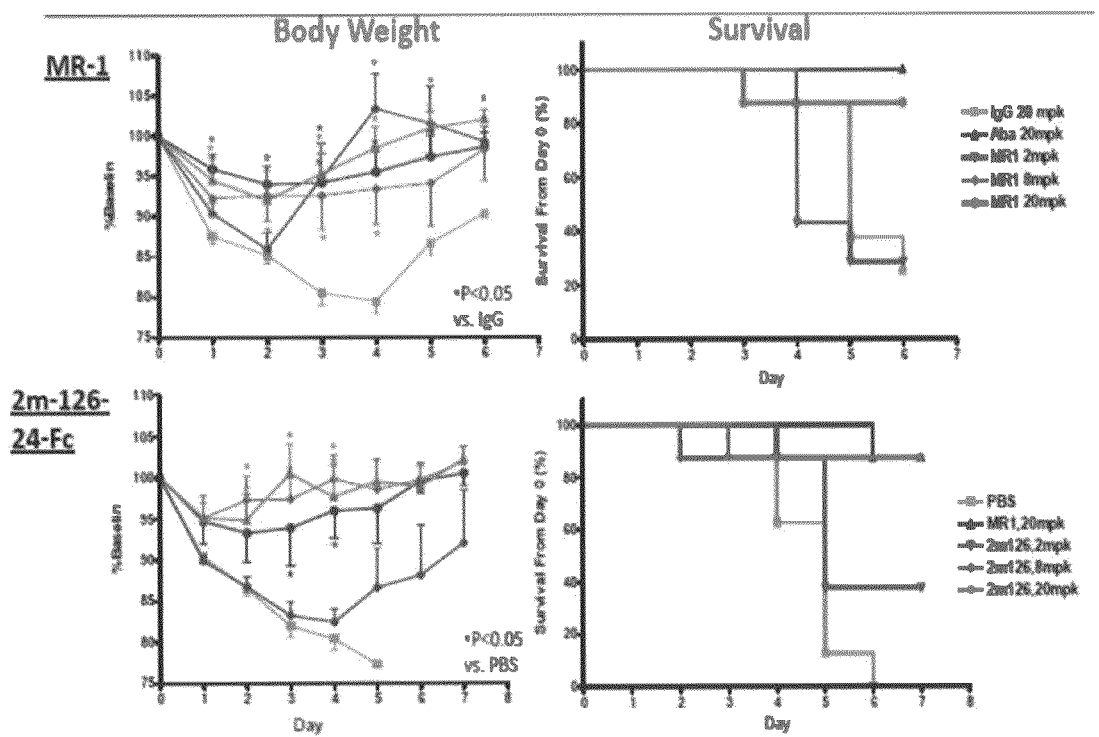
FIG. 8 demonstrates that mouse dAb BMS-2m-126-24-Fc and antibody MR-1 inhibit TNBS-induced colitis in mice.

Male SJL/J mice were intrarectally administered with 2.5 mg Trinitrobenzene sulfonic acid (TNBS) in 50% EtOH via a catheter inserted 4 cm distal to the anus. Mice were dosed once s.c. with MR-1 or BMS-2m-126-24-Fc at indicated doses 4 hours prior to TNBS injection. FIG. 8 presents the changes in the mean body weight and the percent survival of groups of mice treated with PBS/IgG or varying dose levels of MR-1 or the dAb. Abatacept was used as a positive control (20 mg/kg, i.p. every other day). A typical profile of TNBS-induced colitis was shown in the IgG control group: loss of body weight, peaking at day 3-4; colitis-related death occurring at day 3 and beyond; and the survived mice showing signs of recovery after day 4. Treatment with the CD40L dAb or the antibody (both tested at 2, 8 and 20 mg/kg) caused a dose-dependent inhibition of the body-weight loss and the increase in survival rate; both compounds at 8 mg/kg yielded a degree of efficacy that is comparable to that of Abatacept at 20 mg/kg. In conclusion, the mouse CD40L dAb BMS-2m-126-24-Fc has demonstrated comparable efficacy to the anti-CD40L antibody MR-1 in an acute TNBS-induced colitis model.

Figure 9:
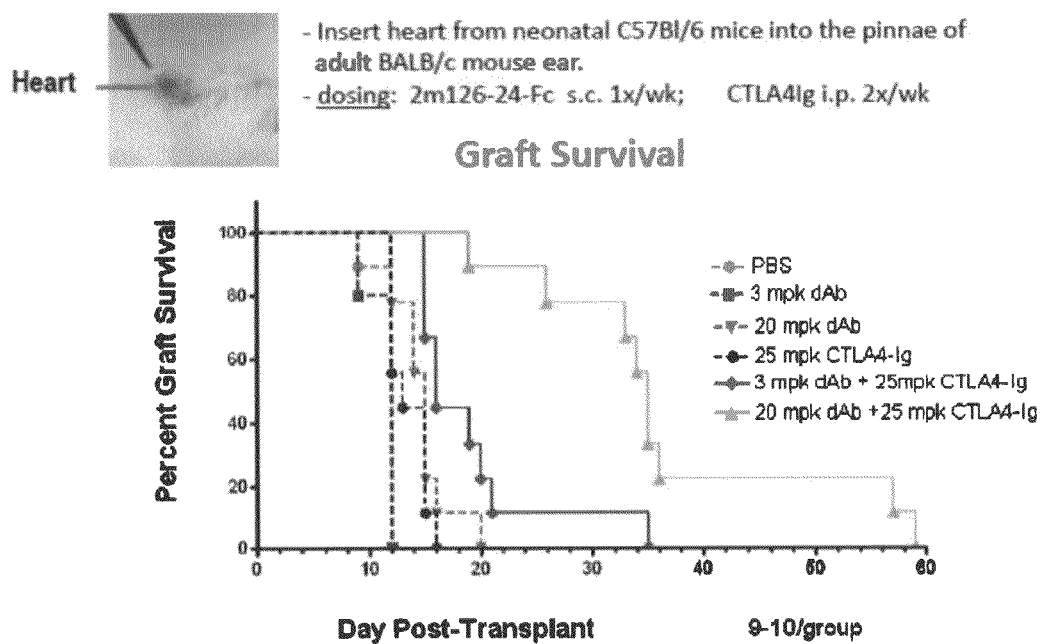
FIG. 9 shows that BMS-2m-126-24-Fc and CTLA4-Ig work synergistically to prolong the survival of cardiac allografts.

Synergistic Effect Between CTLA4 Ig and the Mouse CD40L dAb in a Mouse "Heart-to-Ear" Transplant Model Heart grafts from neonatal (48-72 hrs) C57B1/6 mice were implanted into a subcutaneous pocket created in the ear pinnae of BALB/c mice. Mice were treated with CTLA4-Ig (i.p. 2×/wk), BMS-2m126-24-Fc (s.c. 1×/wk), or combination of both at indicated doses, with first dosing initiated the day prior to transplantation. Time to rejection was defined by the absence of cardiac contractility for three consecutive days as assessed daily by the electrocardiogram (ECG) device of allograft. As expected, without any treatment, C57BL/6 mice that received the neonatal BALB/c heart rejected the graft shortly thereafter, with median survival time (MST) of 12 days. The monotherapy with 3, 20 mg/kg of the dAb or 25 mg/kg of CTLA4-Ig had no or little impact on prolonging the survival of the allograft (MST: 12, 15 and 13 days respectively). However, in the groups treated with combination of 20 mg/kg of the dAb and 25 mg/kg of CTLA4-Ig, the graft survival was significantly prolonged showing MST of 35 days (FIG. 9). This data has provided rationale for combining CD40L dAb with belatacept in human renal transplant patients. Future transplant studies in non-human primates will further define the dose level and assess the potential effect on tolerance induction with CD40L, dAb BMS-986004.

Example 10

In Vivo Nonclinical Pharmacokinetics (PK) and Pharmcodynamics (PD)

Various in vivo studies were conducted to characterize the PK and PD of BMS-986004, BMS-986003, and a mouse CD40L dAb-Fc surrogate BMS-2m-126-24-CT, in the nonclinical setting. The key findings are summarized below.

ELISA to Measure BMS-986004 dAb

Enzyme-linked immunosorbency assay (ELISA)-based bioanalytical methods were developed to support the PK studies, acute and chronic efficacy studies in mice, and exploratory PK/PD studies employing cynomolgus monkeys. In all cases, whole blood was obtained and plasma prepared in the presence of EDTA, the samples were then subjected to ELISA analysis.

Plasma concentrations of BMS-986004 were measured with an ELISA assay that utilized human CD40L antigen to capture the analyte from test samples. Test samples were thawed at 4° C., mixed well and diluted 1:100 in assay diluent composed of 1×PBS, 0.05% Tween-20, and 1% BSA (PTB). Subsequent dilutions of the sample were made using 1% normal monkey plasma/PTB as diluent. This allowed the test analyte to be assayed at several dilutions ($10^2$-$10^5$) while keeping the sample matrix at 1%.

Recombinant trimeric human CD40L was obtained from Protein Structure and Science (PSS), LVL and was bound to 96 well plates at a final concentration of 2 µg/mL. Test samples, quality control (QC) samples and the standards were detected with affinity-purified rabbit anti-heavy chain (Vh) domain framework polyclonal antibody (Covance Research Products, Denver, Pa.) diluted to a concentration of 0.25 µg/ml in PTB, followed by horseradish peroxidase-labeled donkey anti-rabbit polyclonal secondary antibody (Jackson Immunoresearch, West Grove, Pa.) with substrate (TMB— tetramethylbenzidine) added, and the enzymatic reaction stopped with 1 M phosphoric acid. Absorbance was measured at a wavelength of 450 nm. The analysis of BMS-986004 in test samples was conducted using a standard curve. Standard curve calibrators prepared on the day of each run in 1% monkey plasma were used to define the dynamic range of the bioanalytical method. The range of resulting standard curve in 100% plasma was 10-1200 ng/mL. The reference standard for BMS-986004 was obtained from Biologics Process and Product Development (BPPD), HPW. The reference standard material was representative of the manufacturing batch and was used in the study protocol. Standard curves and QCs were evaluated using criteria for accuracy and precision of ≤20% which was considered to be acceptable for assay performance. Test samples were quantified using a 4-parameter logistic fit regression model weighted by reciprocal concentration (1/x) derived from the calibrators.

Performance of the QC samples, measured by the deviation of the calculated concentration from its nominal value indicated the reference material was stable in neat monkey plasma at concentrations of 30-1000 ng/ml when stored at −70° C. for over 2 months.

ELISA to Measure a Mouse Surrogate dAb

Mouse CD40L-specific dAb BMS-2m-126-24-CT was measured in mouse plasma samples to provide exposure data in support of several acute and chronic efficacy studies as well as PK assessment.

While the assay format for mouse dAbs was quite similar to that for human dAbs in monkey samples, there were a few differences. The mouse plasma matrix was diluted to 1:10 (10%) in assay diluent, and all subsequent dilutions of test samples were made using 10% mouse matrix. Likewise, all standards and QCs were also incubated on ELISA plates in 10% mouse plasma. The concentration of BMS-2m-126-24-CT in test samples was measured using mouse CD40L to capture the analyte. As the mouse dAb has Vk framework, all test samples, QCs, and the standards were detected with affinity purified rabbit anti-kappa (Vk) domain polyclonal antibody (Covance Research Products, Denver, Pa.) diluted to a concentration of 0.5 µg/mL in PTB. The rest of the assay and analysis procedure was similar to the procedure for the analysis of human CD40L dAbs. Acceptance criteria for back-calculated concentrations of standards and QCs were also similar to those for human CD40L dAbs. The quantitative range of BMS-2m-126-24-CT as determined from the standard curve was 12.5 to 600 ng/mL in neat sample matrix.

Nonclinical Pharmacokinetics

TABLE 13 summarizes the PK parameters for BMS-986004, BMS-986003, and BMS-2m-126-24-CT in nonclinical animal species.

Figure 12:
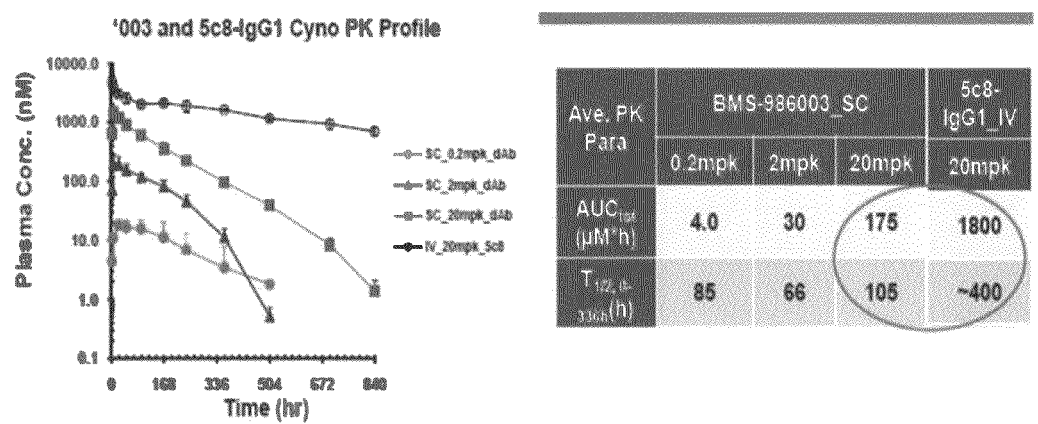
FIG. 12 presents plasma concentrations vs. time profiles of BMS-986003 (after SC dosing at 0.2, 2 and 20 mg/kg in monkeys) and of 5c8 IgG1 (after IV dosing at 20 mg/kg in monkeys).

The monkeys were administered with BMS-986003 as single subcutaneous doses of 0 (vehicle control), 0.2, 2 and 20 mg/kg, at 24 h prior to the immunization with keyhole limpet hemocyanin (KLH), a T cell-dependent antigen. After dosing, BMS-986003 was slowly absorbed, with a Tmax ranging from 6-96 h (FIG. 12). The exposure of BMS-986003 appeared to be less than dose-proportional across all dose levels. With a dose ratio of 1:10:100, the average Cmax and AUC0-inf ratios were 1:12:80 and 1:7:44, respectively. With

TABLE 13

Single-dose PK Parameters (mean ± SD) from Two Nonclinical Animal Species

| Species | dAb | Route | Dose (mg/kg) | Cmax (μM) | Tmax (h) | AUC0-inf (μM · h) | T½ (h) | CLTp (mL/h/kg) | Vss (L/kg) | F (%) |
|---|---|---|---|---|---|---|---|---|---|---|
| Mouse | BMS-2m-126-24-CT | IV | 1 (N = 3) | — | — | 6.9 | 101 | 1.85 | 0.26 | — |
|  |  | SC | 1 (N = 3) | 0.063 | 24 | 10 | 100 | — | — | 100 |
|  |  |  | 10 (N = 3) | 0.68 | 24 | 114 | 120 | — | — | 100 |
| Monkey | BMS-986003 | IV | 2 (N = 2) | — | — | 40 | 106 | 0.67 | 0.067 | — |
|  |  | SC | 0.2 (N = 4) | 0.019 ± 0.004 | 60 ± 72 | 4.0 ± 2.7 | 85 ± 29 | — | — | 88 |
|  |  |  | 2 (N = 4) | 0.22 ± 0.075 | 33 ± 43 | 29.7 ± 4.9 | 68 ± 11 | — | — | 74 |
|  |  |  | 20 (N = 4) | 1.48 ± 0.34 | 11 ± 9 | 175 ± 27 | 105 ± 18 | — | — | 44 |
|  | BMS-986004 | IV | 11 (N = 4) | — | — | 241 ± 18 | 124 ± 12 | 0.59 ± 0.04 | 0.098 ± 0.01 | — |
|  | 5c8-IgG1 | IV | 20 (N = 4) | — | — | 1800 ± 74 | 400 | 0.074 | 0.042 |  |

Figure 11A:
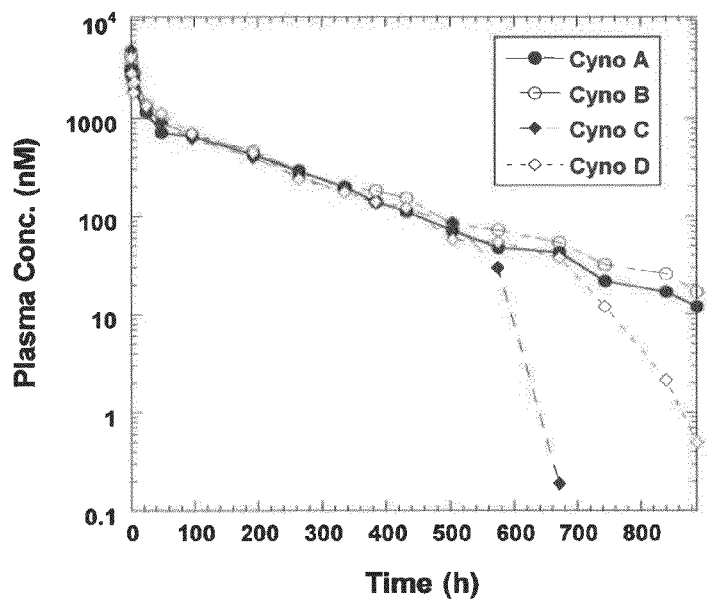
FIG. 11A shows plasma concentration vs. time profile of BMS-986004 after IV dosing of 11 mg/kg in monkeys.
Figure 11B:
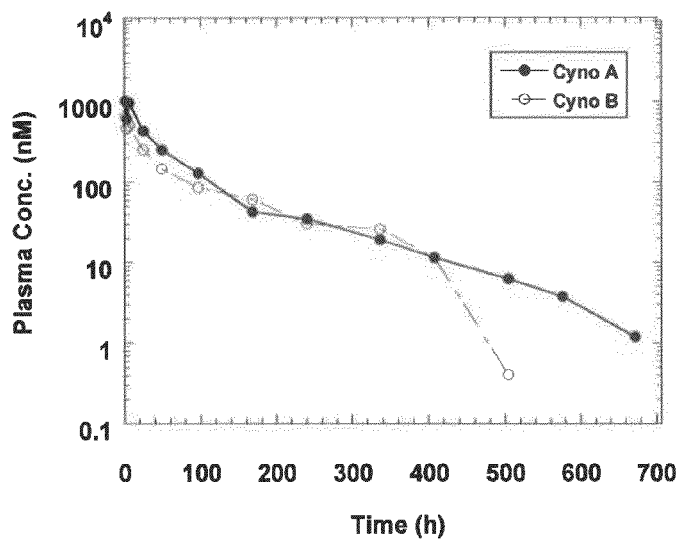
FIG. 11B demonstrates plasma concentration vs. time profiles of BMS-986003 after IV dosing of 2 mg/kg in monkeys.

BMS-986004 and BMS-986003 exhibited comparable PK profiles in monkeys (FIG. 11A and FIG. 11B). After IV administration, the plasma concentrations of BMS-986004 and BMS-986003 exhibited a bi-exponential decline up to 504 and 408 h, respectively. Accelerated clearance was observed afterward in 50% of monkeys enrolled in both studies. Immunogenicity testing of the plasma samples collected at 38 d after BMS-986004 treatment suggested that all monkeys developed anti-drug antibody (ADA); and that the monkeys with higher ADA levels showed faster clearance. Although no immunogenicity test was conducted for the IV PK study with BMS-986003, a similar level of immunogenicity was observed in monkeys after subcutaneous dosing with BMS-986003 in the PK/PD study, suggesting both proteins were immunogenic in monkeys. The terminal half-life (T½) of 124 and 106 h for BMS-986004 and BMS-986003 was, therefore, determined using the exposures collected up to two weeks (336 h) only. The steady-state volume of distribution (Vss) of BMS-986004 and BMS-986003 was 0.098 and 0.074 L/kg, respectively. The values are greater than the plasma volume (0.06 L/kg) but less than the volume of extracellular fluid (0.2 L/kg), suggesting that the proteins largely reside in the extracellular space. The total body plasma clearance (CLTp) of BMS-986004 and BMS-986003 was 0.59 and 0.65 mL/h/kg, respectively.

The PK parameters of BMS-986004 in monkeys were compared to those of abatacept, a similar size protein (78.5 vs 78-kDa BMS-986004, based on amino acid sequence), with the same modified human IgG1 Fc format. As expected, the parameters of BMS-986004 were nearly identical with those of abatacept (CLTp of 0.6 mL/h/kg, Vss of 0.087 L/kg, T1/2 of 5 d), suggesting the humans PK of BMS-986004 and abatacept is likely to be similar.

The absorption of BMS-986003 after subcutaneous (SC) administration was evaluated in the monkey PK/PD study. The exposure following the IV dose (2 mg/kg) as reference, and assuming linear PK after IV dosing, the SC bioavailability of BMS-986003 was 88%, 74%, and 44% at 0.2, 2, and 20 mg/kg, respectively. The terminal T½ was confounded by the immunogenicity observed with most of the monkeys at 2 to 5 weeks after dosing. Therefore, the T½ was estimated to be 85, 66, and 105 h at 0.2, 2 and 20 mg/kg, respectively.

The PK of 5c8-IgG1, an anti-human CD40L monoclonal antibody used as a positive control in the PK/PD study, was evaluated after IV administration at 20 mg/kg (FIG. 12). 5c8-IgG1 exhibited 10-fold higher plasma exposures and 4-fold longer T1/2 when compared to BMS-986003 given SC at the same dose (TABLE 13).

Figure 13:
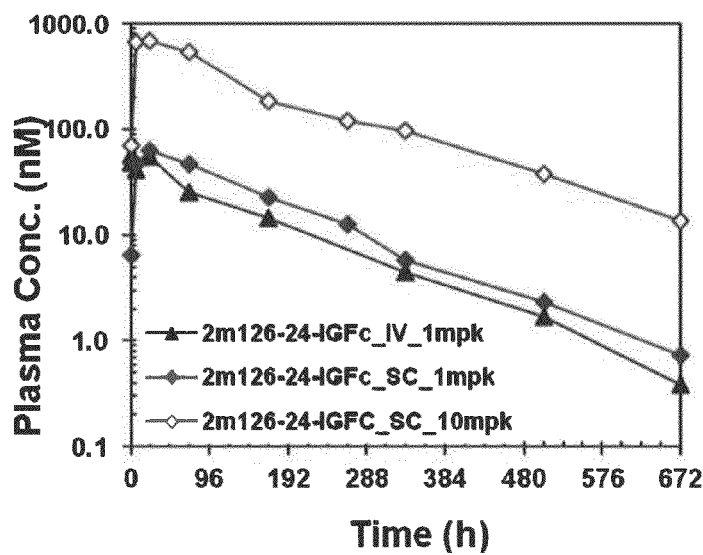
FIG. 13 shows plasma concentrations vs. time profiles of BMS-2m-126-24-CT after 1 mg/kg IV and SC dosing, and 10 mg/kg SC dosing to mice.

The PK of the mouse surrogate dAb-Fc fusion protein, BMS-2m-126-24-CT, was evaluated in mice following single IV and SC administration (TABLE 13). After a single IV (1 mg/kg), the plasma concentrations followed a mono-exponential decline with a terminal T½ of 101 h (FIG. 13). The CLTp was 1.85 mL/h/kg; and the Vss was at 0.26 L/kg, indicating extracellular distribution. After single SC doses of 1 and 10 mg/kg, BMS-2m-126-24-CT was slowly absorbed with a Tmax of 24 h. The systemic exposures increased in a dose-proportional manner. With a dose ratio of 1:10, the Cmax and AUC0-inf increased in the proportion of 1:11. The terminal T½ was 100 and 120 h at 1 and 10 mg/kg, respectively. The ratio of the dose-adjusted exposure (AUC0-inf) after SC and IV administration was greater than 1, suggesting complete absorption after SC administration.

Pharmacokinetic/Pharmacodynamic Modeling

The PD of BMS-986003 was measured as the suppression of anti-KLH antibody response in the PK/PD study. BMS-986003 suppressed 70% the antibody response to KLH $$\left(\% \text{ response suppressed} = \left(1 - \frac{AUEC_{0-1008h\ IgG\ titers}\ \text{treated group}}{AUEC_{0-1008h\ IgG\ titers}\ \text{vehicle group}}\right) * 100\right)$$

at the highest dose of 20 mg/kg. Marginal (15%) and no suppression of the antibody response occurred at 2 and 0.2 mg/kg. In comparison, 5c8-IgG1 exhibited 10-fold higher plasma exposures and 4-fold longer T½ than BMS-986003 at the same dose level (20 mg/kg). As a result, 5c8-IgG1 suppressed 97% anti-KLH antibody response. In order to compare the in vivo potency between BMS-986003 and 5c8-IgG1, PK/PD modeling was performed using SAAM II (version 1.2.1, Seattle, Wash.). The plasma concentrations of BMS-986003 following SC administration were described using a first-order absorption kinetics coupled with a 2-compartment model, where the elimination occurred in both central and peripheral compartments. Because of complications from immunogenicity and possible nonlinear absorption, the PK data were fitted individually at each dose.

For 5c8-IgG1, a two-compartment model with central elimination was used. The anti-KLH antibody response, expressed as the average value of IgG titers, was modeled using a 6-compartment signal transduction model. The kinetics of KLH in the body was assumed to be a 1-compartment model. The inhibition of the IgG production by BMS-986003 and 5c8-IgG1 was described using an Imax model, with a maximum inhibition equal to 100%. As shown in FIG. 14, the model-fitted curves were able to describe both the PK and PD profile. The plasma IC50 of BMS-986003 and 5c8-IgG1 for the suppression of KLH-induced IgG production was estimated to be 74±14 and 60±18 nM, respectively. These results demonstrated that the potency of these two molecules was comparable in vivo.

The CD40L receptor occupancy (RO) of BMS-986004 was measured in the IV PK study. Following IV administration of 11 mg/kg, the RO of BMS-986004 on the peripheral-blood mononuclear cells (PBMC) was time- and concentration-dependent. PK/PD modeling was performed to estimated an RO EC50. The plasma concentrations were modeled using a modified two-compartment model with an additional ADA-mediated first order elimination constant introduced at 504 h after dosing; and the RO was modeled using an Emax model $$\left(RO\ \% = \frac{Emax * Cp^\gamma}{EC50^\gamma + Cp^\gamma}\right).$$

Figure 15:
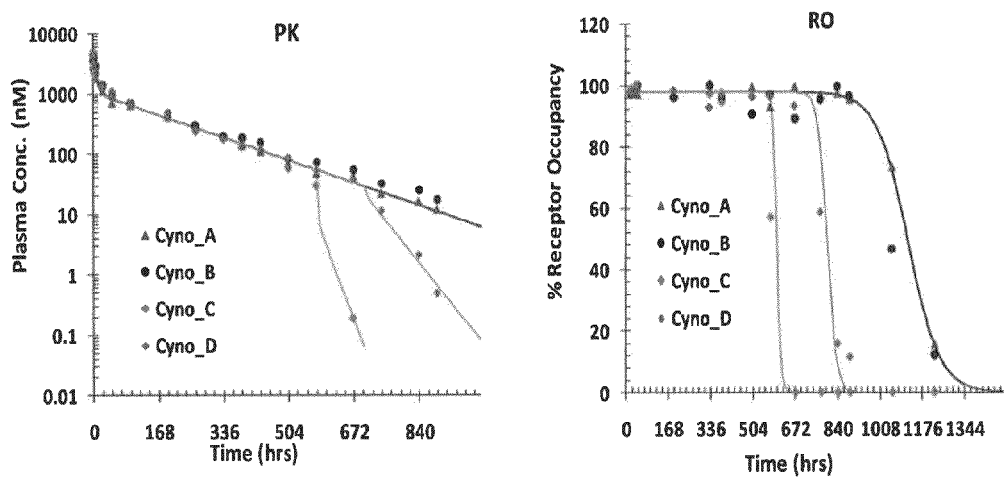
FIG. 15 shows PK/PD modeling of BMS-986004 plasma exposures and ex vivo RO on peripheral blood mononuclear cells (PBMC).

As shown in FIG. 15, the fitted curves were able to describe both exposure and RO, with an estimated RO EC50 of 3.4±0.3 nM and the γ (hill factor) of 3.1±0.1. In comparison, the RO EC50 was ~22-fold lower than the anti-KLH antibody response IC50 of 74±14 nM, suggesting that >95% RO is required in order to achieve appreciable (>50%) anti-KLH antibody suppression.

Example 11

Nonclinical Toxicology Single-Dose PK/PD Study

The objectives of this study were to I determine the tolerability of BMS-986003, including its potential immunogenicity, when given subcutaneously as a single dose to monkeys; 2) evaluate its PD e.g., inhibition of the antibody response to T-cell-dependent antigen) and PK profiles; 3) evaluate the receptor occupancy of BMS-986003 and peripheral T-cell counts following subcutaneous dosing; and 4) aid dose selection for renal transplant studies and first-in-human dosing.

BMS-986003 was administered s.c. in the posterior thorax as single doses of 0 (vehicle control), 0.2, 2, or 20 mg/kg to groups of 2 cynomolgus monkeys per sex. An additional two monkeys/sex received a single intravenous dose of 20 mg/kg 5c8-IgG1, a monoclonal antibody to human CD40L that was used as a positive control in this study. All doses were administered at 2 mL/kg in the vehicle (PBS; pH 7.2). To assess the effects on the T-cell dependent antibody response, animals were immunized at approximately 24 hours after dosing with test article or immediately after dosing the positive control with 10 mg of KLH by intramuscular injection (posterior quadriceps or caudal thigh). Criteria for evaluation included survival, PK, immunogenicity, PD (inhibition of the antibody response to the T-cell-dependent antigen, KLH), clinical signs, body weights, food consumption, peripheral-blood immunophenotyping, receptor occupancy, and clinical-pathology evaluations (hematology, serum chemistry, and coagulation). Animals were returned to stock following a 6-week post-dose observation period.

At doses ≤20 mg/kg, BMS-986003 was slowly absorbed (Tmax=6-96 h) and Cmax and AUCtot values increased in a less than dose-proportional manner across all dose groups and there were no apparent gender differences. The T½ values estimated ranged from 69-104 h across all doses. BMS-986003 was substantially immunogenic; all monkeys developed a positive anti-drug antibody (ADA) response during the 6-week post-dose period. At 0.2 and 2 mg/kg, the mean group total ADA response peaked at Day 22 at mean group end point titers (EPT) of 4203 and 6469, respectively. At 20 mg/kg, the ADA response, while positive, was somewhat delayed and partially suppressed, consistent with target pharmacology, peaking at Day 36 at a mean group EPT of 1828. Further characterization of the antibodies demonstrated the majority of binding to the dAb (non-Fc) portion of the molecule and these antibodies were shown to block the binding of BMS-986003 to CD40L in 2 different immunoassay formats suggesting that the ADA were neutralizing. In addition, the formation of ADA appeared to accelerate the elimination of BMS-986003 in several monkeys.

Mean PK parameters for BMS-986003 are presented in TABLE 14.

TABLE 14

Pharmacokinetic Summary

| Mean Parameter Gender | BMS-986003 SC | | | 5C8-IgG1 IV |
|---|---|---|---|---|
| | 0.2 mg/kg (N = 4) Male/Female | 2 mg/kg (N = 4) Male/Female | 20 mg/kg (N = 4) Male/Female | 20 mg/kg (N = 4) Male/Female |
| AUC (0-inf) μg · h/mL | 219/407 | 2165/2477 | 14195/13114 | 267750/272250 |
| CLTp mL/h/kg | Not applicable | Not applicable | Not applicable | ND/0.074 |
| T½ h | 69/101 | 68/69 | 107/104 | ND/400 |
| Cmax μg/mL | 69/101 | 45/49 | 88/91 | Not applicable |
| Tmax h | 24/96 | 51/15 | 6/15 | Not applicable |

Molecular weight used for conversion was 78104 Da for BMS-986003, 150000 Da for 5c8-IgG1 mAb.
ND = not determined;
AUC extra for males was above 20%, therefore the T½ was not reported.

There were no BMS-986003- or 5c8-IgG1-related clinical observations or effects on body weights or clinical pathology parameters except 1 male treated with 5c8-IgG1 had decreased red blood cells (0.74× control), hemoglobin (0.73× predose), and hematocrit (0.75× predose) on Day 8, and 3 of 4 monkeys receiving 5c8-IgG had decreased lymphocytes (0.53× to 0.65× predose) on Day 8, suggestive of lymphocyte depletion.

CD40L receptor occupancy was generally time- and dose-dependent and more sustained following administration of 20 mg/kg BMS-986003, consistent with higher and more sustained exposures at this dose and PD activity. For BMS-986003, mean peak receptor occupancy on peripheral-blood mononuclear cells (PBMC) was achieved at 24 hrs (97%), 6 hrs (99%) or 48 hrs (99%) post-dose, decreasing to <90% occupancy at 240, 360, or 696 hrs and to <50% occupancy at 360, 696, or 1032 hrs, at 0.2, 2, or 20 mg/kg, respectively. In comparison, for 5c8-IgG1 at 20 mg/kg, mean peak receptor occupancy on PBMC was achieved at 48 hours (≥100%), and was sustained at ≥97% for the entire study (1032 hr or through Day 44).

BMS-986003 suppressed the antibody response to KLH only at the high dose of 20 mg/kg. On Days 8-30 at 20 mg/kg, there was a 69 to 83% suppression of the geometric group mean antibody response to KLH, relative to the control group, with a peak suppression of 83% occurring on Day 16. No suppression of the antibody response occurred at 0.2 or 2 mg/kg BMS-986003. These data demonstrate that BMS-986003 at a sustained receptor occupancy of >90% for at least 1 month and at sustained plasma concentrations above ~10 µg/mL through Day 11 is able to inhibit a T-cell dependent antibody response in cynomolgus monkeys. For the positive control antibody, 5c8-IgG1, suppression of 74-97% of the geometric group mean antibody response to KLH occurred on Days 8-30, with peak suppression of 97% by Day 16 which was generally sustained through Day 30.

No biologically relevant BMS-986003 related changes in absolute numbers of B cells (CD45+, CD20+, CD3−), total T (CD45+, CD3+) cells, helper T (CD45+, CD3+, CD4+, CD8−) cells, cytotoxic T (CD45+, CD3+, CD4−, CD8+) cells, or natural killer (CD45+, CD3−, CD16+) cells occurred during the study, which confirmed lack of any Fc effector function. However, on Day 8, 3 of 4 monkeys treated with 20 mg/kg 5c8-IgG1 had decreased T-lymphocytes (0.53×-0.66× predose), both helper T-cell (0.64× to 0.77× predose) and cytotoxic (0.40× to 0.61× predose) T-cell populations, suggestive of depletion.

In conclusion, BMS-986003 administered as single SC doses of 0.2, 2, or 20 mg/kg (AUC≤14195 µg*hr/mL) was well tolerated in cynomolgus monkeys with no adverse drug-related effects. The positive control, 5c8-IgG1, at a dose of 20 mg/kg, resulted in complete, sustained inhibition of the antibody response to KLH and sustained receptor occupancy of nearly 100% through 30 days post-dose. Mild depletion of T-cells was also noted by Day 8 in monkeys receiving 5c8-IgG1 (0.40× to 0.77× predose), which was not observed with BMS-986003. BMS-986003 was able to suppress an antibody response to KLH at 20 mg/kg (peak suppression of 83%) following KLH immunization on Day I and had sustained receptor occupancy of ≥90% through Day 22 and ≥50% through Day 29. Similar dampening of the immunogenicity to BMS-986003 occurred at 20 mg/kg. However, lower BMS-986003 doses of 0.2 and 2 mg/kg did not suppress the antibody response to KLH or the anti-drug antibody response. The lack of pharmacology at the lower doses also correlated with decreasing receptor occupancy (i.e., <90% by Day 11 [0.2 mg/kg] or 16 [2 mg/kg]; <50% by Day 16 [0.2 mg/kg] or 30 [2 mg/kg]) and accelerated clearance, presumably due to the formation of ADA. The inhibition of TDAR is consistent with the mechanism of action of this compound and was not considered adverse.

Example 12

Evaluation of the Risk for TE/Thrombosis

It has been hypothesized that the TE associated with administration of the anti-CD40L monoclonal antibodies is mediated by anti-CD40L mAb-CD40L immune complex On-mediated cross linking of platelets, facilitated by IC binding to FcgRIIa, an IgG Fc receptor, causing activation and aggregation (FIG. 10). Blocking the interaction of Fc moiety of IgG with FcgRIIa is, therefore, expected to mitigate platelet cross linking and thrombosis. The following methods and approaches were designed to evaluate the risk of TE and/or thrombosis.

In Vitro Platelet Activation Assays

Several in vitro assays were conducted to test the hypothesis that platelets are activated by CD40L mab/sCD40L IC in a FcgRIIa-dependent manner. The positive control 5c8-IgG1 was used to validate the assays prior to testing BMS-986003 and BMS-986004. Blood from human donors or mice expressing hFcgRIIa receptor on platelets were used for these studies. Platelet activation was detected by flow cytometry using antibodies against the well-validated platelet activation markers P-selectin (CD62P) and PAC-1 (activated GPIIb/IIIa). Briefly, blood was diluted 1:25 in modified Tyrodes-HEPES containing 1 mM CaCl2 to which detection antibodies and test reagents was added, incubated, and analyzed for platelet activation. Initial experiments determined that sCD40L or 5c8IgG1 alone did not activate platelets, but different immune complex ratios of 1:1 to 1:8 of 5c8:sCD40L significantly activated platelets. Subsequent experiments used 5c8-IgG1 or 5c8-mIgG2a IC, mostly at a 1:3 molar ratio of 5c8:sCD40L.

Platelet Activation by 5c8/sCD40L IC can be Blocked by Anti-FcgRIIa Antibody

Figure 16:
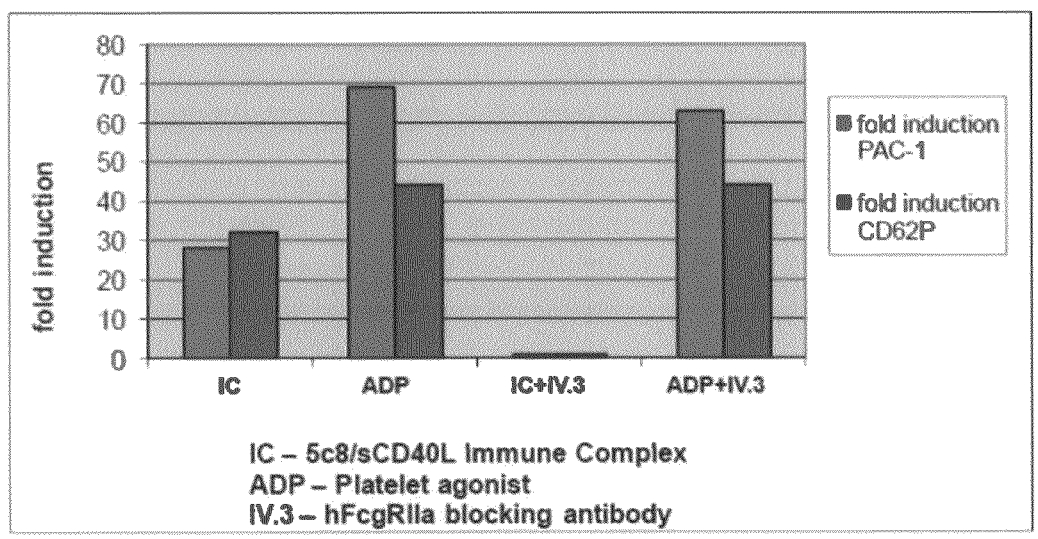
FIG. 16 demonstrates that IV.3 blocks 5c8/sCD40L. IC-mediated activation of platelets in human blood.

Studies were conducted with the FcgRIIa blocking antibody IV.3 to test whether activation of platelets by 5c8/sCD40L IC was indeed FcgRIIA-mediated. Blood from human donors was pre-incubated with 0.5 µg/µl of the FcgRIIa blocking antibody IV.3 prior to dilution and incubation with detection antibodies as described above. Adenosine diphosphate (ADP), a platelet activator via a different mechanism, was used as a positive control. As illustrated in FIG. 16, platelet activation by 5c8/sCD40 IC was completely blocked by IV.3, while activation by ADP was not inhibited by the blocking antibody, indicating that activation by the IC is FcgRIIa-mediated.

Selection of Inert Fc Tails

Figure 17:
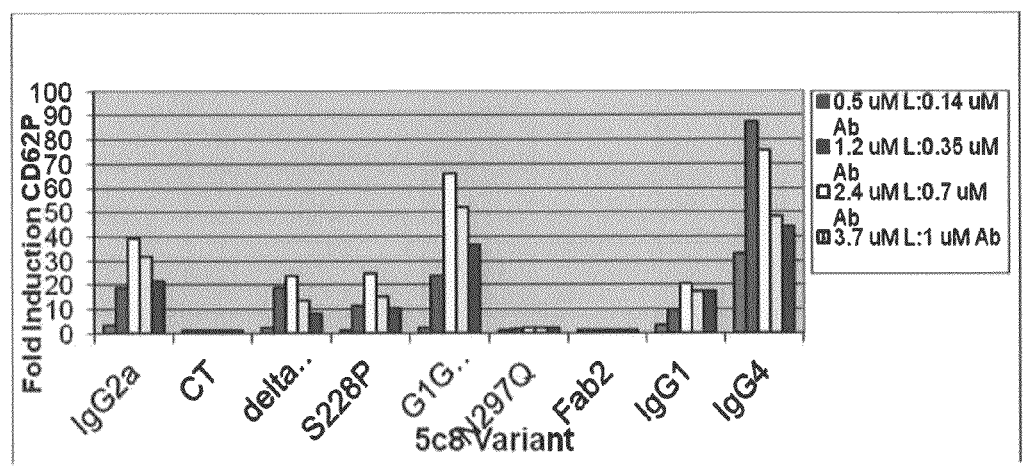
FIG. 17 shows the effect of Fc variants on platelet activation in human blood.

A requirement for potential candidate molecules was absence of binding to FcgRIIa to prevent potential platelet activation. Several 5c8 constructs containing different mutations derived from IgG1 (e.g 5c8-CT and N297Q) or IgG4 (e.g., 5c8-S228P) were expressed and screened for Fc tails that did not activate platelets using different molar ratios of sCD40L to mAbs. Wild-type and most mutated constructs activated platelets except for 5c8-CT and 5c8-N297Q (FIG. 17). Absence of Fc (5c8-Fab2) also did not activate platelets further confirming that IC-platelet activation is Fc-mediated. The CT tail was chosen to format the dAb candidates BMS-986003 and BMS-986004.

Effect of FcgRIIa Polymorphism on Platelet Activation

Figure 18:
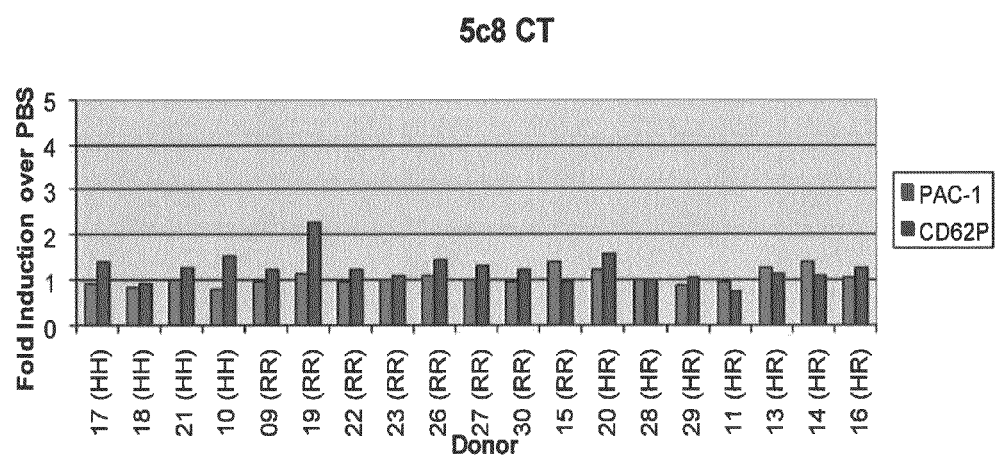
FIG. 18 demonstrates activation of platelets with 5c8-CT/sCD40L IC in blood from human donors genotyped for FcgRIIa polymorphism.

The gene for FcgRIIa is variable at codon 131, resulting in His-Arg (C<u>A</u>T/C<u>G</u>T) polymorphism. The genotype distribution in approximately 100 individuals with about equal distribution of Caucasians and African Americans was A/A (His homozygous; 14%), A/G (His/Arg heterozygous; 60%), and G/G (Arginine homozygous; 26%) for Caucasian Americans and A/A (30%), A/G (51%), and G/G (19%) for African-Americans. Reilly et al., *Clin. Diagn. Lab. Immunol.* 1: 640-644 (1994). Fc-dependent platelet aggregation was noted in samples from R131 individuals when treated with anti-CD9 in mIgG2 or mIgG1 Fc format, while platelets from H131 individuals aggregated only with anti-CD9 as mIgG2 format; this suggests that Fc-dependent aggregation with an IgG1 mAb could potentially segregate a patient population into low and high responders, which has previously been reported with this polymorphism. Tomiyama et al., *Blood* 80: 2261-2268 (1992). To address any potential differences in platelet activation with the IgG1 and CT Fc tail, 19 donors were genotyped for hFcgRIIa polymorphism and samples tested for platelet activation. The donor pool polymorphism (RR; 42%, HH; 21%, HR; 37%) was sufficient to evaluate any potential differences in platelet activation to the IgG1 format. Representative of literature reports, platelet activation with 5c8-IgG1/sCD40L IC was similar across all genotyped individuals. No activation was found with 5c8-CT/sCD40L IC (FIG. 18), suggesting no or minimal risk of increased TE in a patient population with an antibody formatted with the CT tail.

BMS-986004: Platelet Activation in Human Blood Donors

Figure 19:
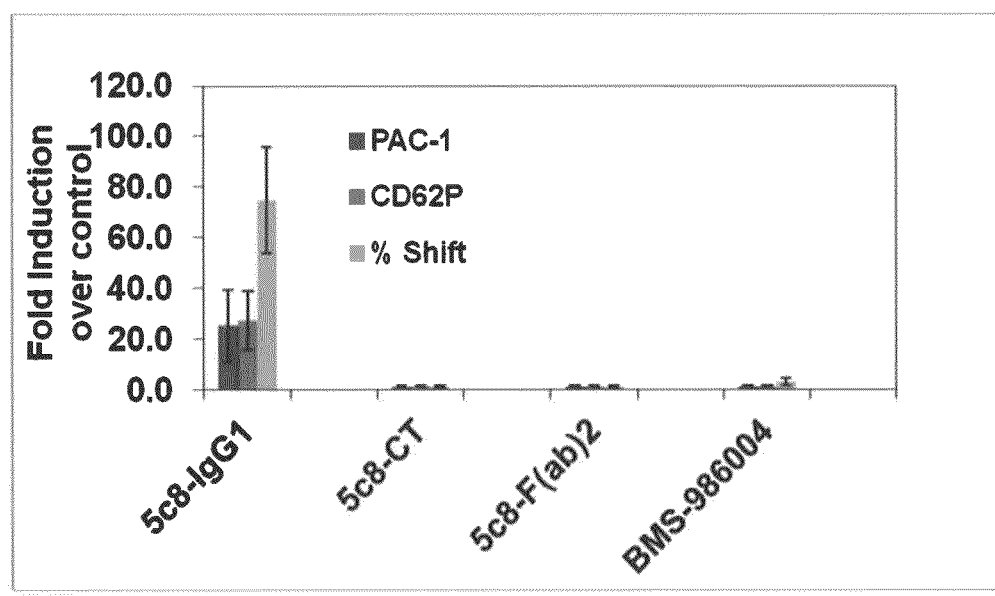
FIG. 19 diagrams platelet activation by various antibodies in blood from human donors.

The experiments described above using 5c8, supported selection of the CT-tail as the best format for BMS-986004 (also called BMS2h-572-633-CT-L2). Blood obtained from 6 donors was treated with 5c8-IgG1, 5c8-CT, F(ab)₂, and BMS-986004. Platelets were activated by 5c8-IgG1 but not by any of the other constructs, including BMS-986004 (FIG. 19), suggesting that this dAb has no or low risk for causing platelet activation and TE in clinical studies.

BMS-986003: Platelet Activation in Blood from Mice Expressing hFcgRIIa

Figure 20:
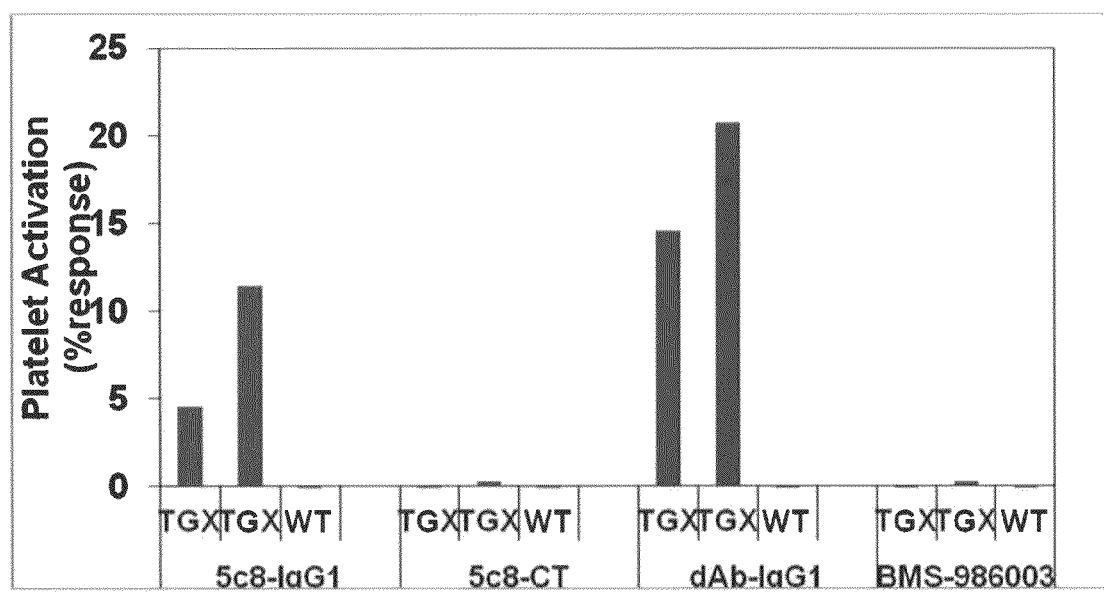
FIG. 20 shows levels of platelet activation by various antibodies, including BMS-986003, in hFcgRIIa-expressing transgenic mice.

To further confirm that activation of platelets by anti-CD40L antibodies was mediated by FcgRIIa receptor, blood from transgenic mice expressing the human receptor (R131 genotype) was treated with 5c8-IgG1, 5c8-IgG2a, dAb-IgG1, 5c8-CT, and BMS-986003 (also called BMS-2h572-633-CT). Platelets were specifically activated by 5c8-IgG1, 5c8-IgG2a, and dAb-IgG1/sCD40L IC in blood from mice expressing hFcgRIIa, but not wild-type littermates. 5c8-CT and BMS-986003 did not activate platelets, further confirming a low risk for TE with the presently disclosed antibodies (FIG. 20).

Example 13

Epitope Binding Experiments

Figure 25:
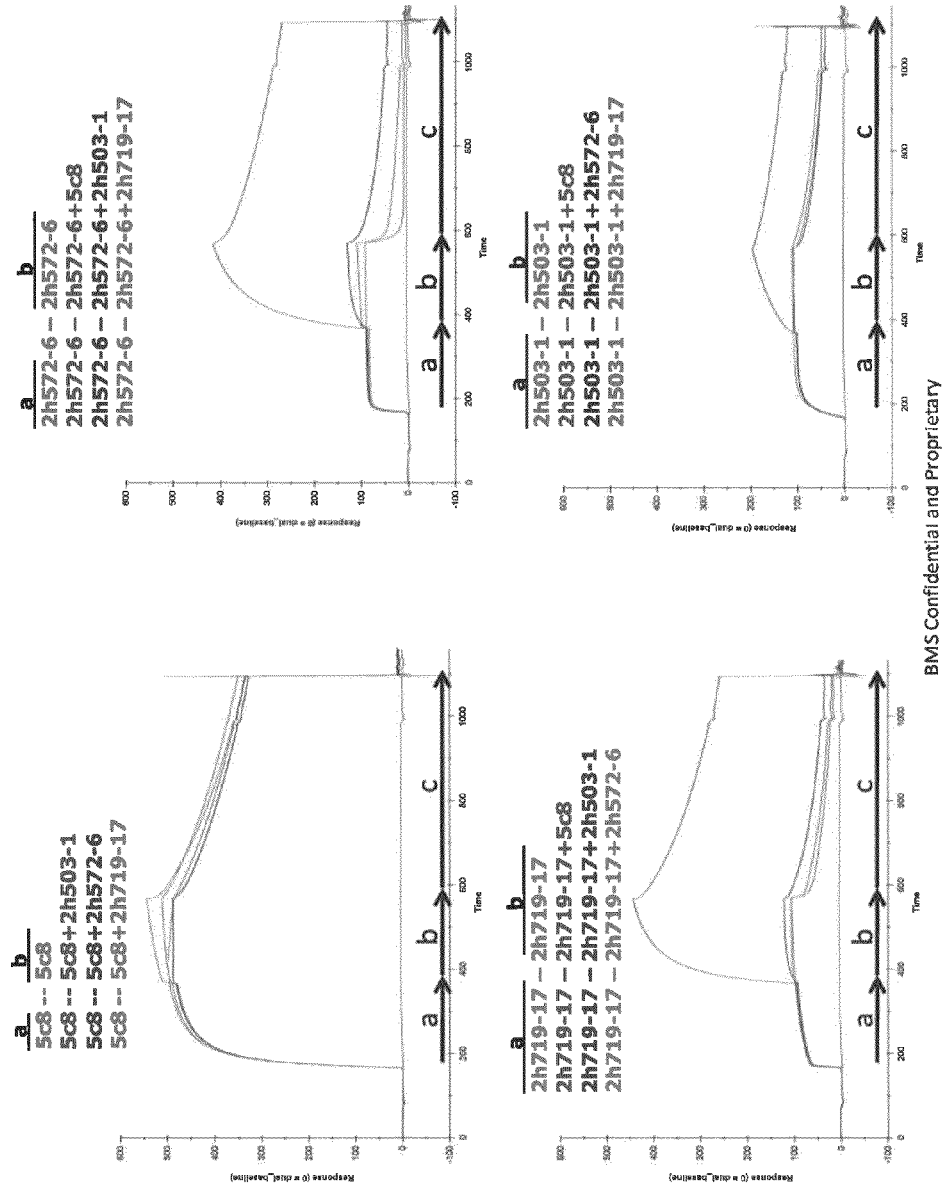
FIG. 25 shows SPR sensorgram data for binding experiments using monovalent dAbs BMS2h-503-1, BMS2h-572-6, BMS2h-719-17, and monovalent Fab fragment of 5c8, where the indicated molecules compete with each other for binding to CD40L. (biotinylated IZ-hCD40L).

FIG. 25 shows SPR sensorgram data for experiments designed to test whether or not monovalent dAb molecules BMS2h-5031, BMS2h-572-6, BMS2h-719-17, and the monovalent anti-CD40L 5c8 Fab fragment compete with each other for binding to CD40L. Experiments were performed using biotinylated CD40L (biot-IZ-hCD40L) that was captured on a streptavidin sensor chip surface. The tests involved the sequential injection of a specified molecule (phase "a"), immediately followed by injection of the same molecule in the presence of a second specified molecule (phase "b"), followed by dissociation (phase "c"), Competition for binding is identified as a reduction (blocking) of the binding signal for the second molecule in the presence of the first, with the level of blocking being governed by the association and dissociation kinetics of each molecule. For each pair of molecules tested, the binding of the second molecule was shown to be reduced when the first molecule was present. These results suggest that BMS2h-503-1, BMS2h-572-6, BMS2h-719-17, and 5c8 Fab compete with each other for binding to biot-IZ-hCD40L.

Figure 26:
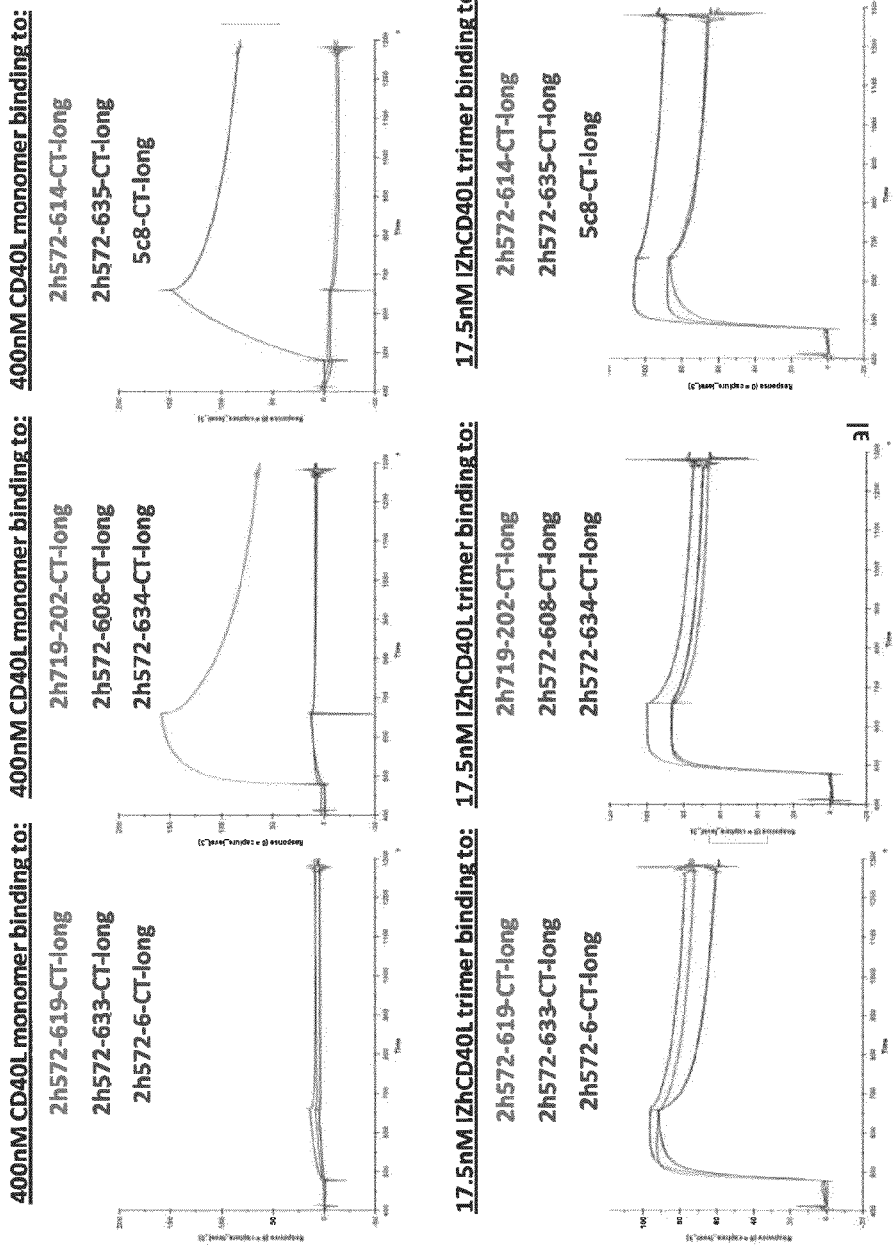
FIG. 26 shows SPR sensorgram data for experiments testing the binding of BMS2h-572-619-CT-long, BMS2h-572-633-CT-long, BMS2h-572-6-CT-long, BMS2h-719-202-CT-long, BMS2h-572-608-CT-long, BMS2h-572-634-CT-long, BMS2h-572-614-CT-long, BMS2h-572-635-CT-long, and 5c8-CT-long molecules to either CD40L monomer (upper 3 panels) or CD40L trimer (lower 3 panels).

FIG. 26 shows SPR sensorgram data for binding of the indicated dAb-CT-long and the 5c8-CT-long molecules to either human CD40L monomer (triple CD40L mutant (T211E, S222Y, H224K, [108-261])) or to CD40L trimer (IZ-hCD40L). The dAb-CT-long and the 5c8-CT-long molecules were captured via their "CT-long" Fc-domain on an immobilized anti-human IgG Fc (Biacore, GE Healthcare) antibody sensor chip surface. The data in the top 3 panels show that human CD40L monomer binds specifically to BMS2h-719-202-CT-long and 5c8-CT-long, but does not bind to any of the indicated dAb-CT-long molecules that contain dAbs from the BMS2h-572-6 lineage. In contrast, the bottom 3 panels show that CD40L trimer (IZ-hCD40L) binds strongly to all the tested dAb-CT-long molecules from the BMS2h-572-6 lineage, as well as to BMS2h-719-202-CT-long and 5c8-CT-long. These results suggest that the molecules from the BMS2h-572-6xx-CT-long lineage are specific for an epitope that is only present on the CD40L trimer and not present on monomeric human CD40L, whereas BMS2h-719-202-CT-long and 5c8-CT-long bind to an epitope that is present on both the CD40L monomer and trimer.

Although the present embodiments have been described in detail with reference to examples above, it is understood that various modifications can be made without departing from the spirit of these embodiments, and would be readily known to the skilled artisan.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09228018B2). An electronic copy of the "Sequence Listing" will also be available from the USPTO upon request and payment of the fee set forth in 37 CFR 1.19(b)(3).

What is claimed is:

1. An isolated antibody polypeptide comprising a first variable domain that specifically binds human CD40L comprising the amino acid sequence of SEQ ID NO:1, wherein the amino acid sequence of the first variable domain is at least 95% identical to the amino acid sequence of BMS2h-572-633 (SEQ ID NO: 274).

2. The antibody polypeptide of claim 1, wherein the antibody polypeptide is a domain antibody (dAb).

3. The antibody polypeptide of claim 1, wherein the amino acid sequence of the first, variable domain is at least 96% identical to the amino acid sequence of BMS2h-572-633 (SEQ ID NO: 274).

4. The antibody polypeptide of claim 1, wherein the amino acid sequence of the first variable domain is at least 97% identical to the amino acid sequence of BMS2h-572-633 (SEQ ID NO: 274).

5. The antibody polypeptide of claim 1, wherein the amino acid sequence of the first variable domain is at least 98% identical to the amino acid sequence of BMS2h-572-633 (SEQ ID NO: 274).

6. The antibody polypeptide of claim 1, wherein the amino acid sequence of the first variable domain is at least 99% identical to the amino acid sequence of BMS2h-572-633 (SEQ ID NO: 274).

7. The antibody polypeptide of claim 1, wherein first variable domain comprises the amino acid sequence of: BMS2h-572-11 (SEQ ID NO: 226), BMS2h-572-12 (SEQ ID NO: 227), BMS2h-572-14 (SW ID NO: 229), BMS2h-572-6 (SEQ ID NO: 243), BMS2h-572-601 (SEQ ID NO: 244), BMS2h-572-602 (SEQ ID NO: 245), BMS2h-572-603 (SEQ ID NO: 246), BMS2h-572-603 (SEQ ID NO: 247), BMS2h-572-606 (SEQ ID NO: 249), BMS2h-572-607 (SEQ ID NO: 250), BMS2h-572-608 (SEQ ID NO: 251), BMS2h-572-609 (SEQ ID NO: 252), BMS2h-572-610 (SEQ ID NO: 253), BMS2h-572-611 (SEQ ID NO: 254), BMS2h-572-612 (SEQ ID NO: 255), BMS2h-572-61.3 (SEQ ID NO: 256), BMS2h-572-614 (SEQ ID NO: 257), BMS2h-572-615 (SEQ ID NO: 258), BMS2h-572-616 (SEQ ID NO: 259 BMS2h-572-617 (SEQ ID NO: 260), BMS2h-572-618 (SEQ ID NO: 261), BMS2h-572-619 (SEQ ID NO: 262), BMS2h-572-620 (SEQ H) NO: 263), BMS2h-572-622 (SEQ ID NO: 265), BMS2h-572-623 (SEQ ID NO: 266), BMS2h-572-624 (SEQ ID NO: 267), BMS2h-572-625 (SEQ ID NO: 268), BMS2h-572-626 (SEQ ID NO: 269), BMS2h-572-627 (SEQ ID NO: 270), BMS2h-572-630 (SEQ ID NO: 271), BMS2h-572-631 (SEQ ID NO: 272), BMS2h-572-632 (SEQ ID NO: 273), BMS2h-572-634 (SEQ ID NO: 275), BMS2h-572-635 (SEQ ID NO: 276), or BMS2h-572-9 (SEQ ID NO: 279).

8. The antibody polypeptide of claim 1, wherein:
a) the CDR1 of the first variable domain has the same amino acid sequence as amino acids 31 to 35 of BMS2h-572-633 (SEQ ID NO: 274);
b) the CDR2 of the first variable domain has the same amino acid sequence as amino acids 51 to 66 of BMS2h-572-633 (SEQ ID NO: 274); and
c) the CDR3 of the first variable domain has the same amino acid sequence as amino acids 101 to 107 of BMS2h-572-633 (SEQ ID NO: 274).

9. The antibody polypeptide claim 1, wherein the first variable domain consists of the amino acid sequence of BMS2h-572-633 (SEQ ID NO: 274).

10. The antibody polypeptide of claim 9, wherein the antibody polypeptide is a domain antibody (dAb).

11. The antibody polypeptide of chum 1, wherein the antibody polypeptide is a fusion polypeptide comprising the first variable domain consisting of the amino acid sequence of BMS2h-572-633 (SEQ ID NO: 274) and an Fc domain.

12. The antibody polypeptide of claim 11, wherein the Fc domain comprises an IgG4 Fc domain.

13. The antibody polypeptide of claim 11, wherein the Fr domain comprises an IgG1 Fc domain.

14. The antibody polypeptide of claim 11, consisting of the amino acid sequence of SEQ ID NO: 355.

15. The antibody polypeptide of claim 1, wherein the antibody polypeptide further comprises a second variable domain that specifically binds a second antigen, wherein the second antigen is an antigen other than human CD40L.

16. The antibody polypeptide of claim 15, wherein the second antigen is a cluster of differentiation (CD) molecule or a Major Histocompatibility Complex (MHC) Class II molecule.

17. The antibody polypeptide of claim 15, wherein the second antigen is serum albumin (SA).

18. A pharmaceutical composition comprising a therapeutically-effective amount of the antibody polypeptide of claim 1 and a pharmaceutically acceptable carrier.

19. The pharmaceutical composition of claim 18, further comprising an immunosuppressive/immunomodulatory and/or anti-inflammatory agent.

20. The pharmaceutical composition of claim 18, wherein the antibody polypeptide is the antibody polypeptide of claim 9.

21. The pharmaceutical composition of claim 18, wherein the antibody polypeptide is the antibody of claim 14.

22. A method of antagonizing CD40L activity in a patient with an immune disease in need of such treatment, comprising administering to the patient a therapeutically effective amount of the antibody polypeptide of claim 1 to antagonize CD40L activity in the patient.

23. The method of claim 22, wherein the antibody polypeptide is the antibody polypeptide of claim 9.

24. A method of claim 22, wherein the antibody polypeptide is the antibody polypeptide of claim 14.

25. The method of claim 22, wherein the antibody polypeptide is administered in combination with an immunosuppressive/immunomodulatory and/or inflammatory agent.

26. The method of claim 22, wherein the immune disease is an autoimmune disease or a graft-related disease.

27. The method of claim 26, wherein the immune disease is a graft-related disease.

28. The method of claim 27, wherein the graft-related disease comprises solid organ, tissue and/or cell transplant rejection.

29. The method of claim 27, wherein the graft-related disease is graft versus host disease (GVHD).

30. The method of claim 27, wherein the graft-related disease is an acute transplant rejection.

31. The method of claim 27, wherein the graft-related disease is a chronic transplant rejection.

32. The method of claim 27, wherein the antibody polypeptide is co-administered with a CTLA4 mutant molecule.

33. The method of claim 32, wherein the CTLA4 mutant molecule is L104EA29Y-Ig (belatacept).

34. The method of claim 22, wherein the immune disease is selected from the group consisting of Addison's disease, allergies, ankylosing; spondylitis, asthma, atherosclerosis, autoimmune diseases of the ear, autoimmune diseases of the eye, autoimmune hepatitis, autoimmune parotitis, colitis, coronary heart disease, Crohn's disease, diabetes, including Type 1 and/or Type 2 diabetes, epidiymitis, glomerulonephritis, Graves' disease, Guillain-Barre syndrome, Hashimoto's disease, hemolytic anemia, idiopathic thrombocytopenic purpura, inflammatory bowel disease, immune response to recombinant drug products, systemic lupus erythematosus, male infertility, multiple sclerosis, myasthenia gravis, pemphigus, psoriasis, rheumatic fever, rheumatoid arthritis, sarcoidosis, scleroderma, Sjogren's syndrome, spondyloarthropathies, thyroiditis, transplant rejection, vasculitis, AIDS, atopic allergy, bronchial asthma, eczema, leprosy, schizophrenia, inherited depression, chronic fatigue syndrome, Alzheimer's disease, Parkinson's disease, myocardial infarction, stroke, autism, epilepsy, Arthus's phenomenon, anaphylaxis, alcohol addiction, and drug addiction.

35. The method of claim 22, wherein the immune disease is idiopathic thrombocytopenic purpura.

* * * * *